(12) United States Patent
Inoue et al.

(10) Patent No.: US 7,932,250 B2
(45) Date of Patent: Apr. 26, 2011

(54) THIENOPYRAZOLE DERIVATIVE HAVING PDE7 INHIBITORY ACTIVITY

(75) Inventors: Hidekazu Inoue, Osaka (JP); Hidenobu Murafuji, Osaka (JP); Yasuhiro Hayashi, Osaka (JP)

(73) Assignee: Daiichi Sankyo Company, Limited, Toyko (JP)

( * ) Notice: Subject to any disclaimer, the term of this patent is extended or adjusted under 35 U.S.C. 154(b) by 389 days.

(21) Appl. No.: 11/630,757

(22) PCT Filed: Jul. 1, 2005

(86) PCT No.: PCT/JP2005/012208
§ 371 (c)(1),
(2), (4) Date: May 29, 2008

(87) PCT Pub. No.: WO2006/004040
PCT Pub. Date: Jan. 12, 2006

(65) Prior Publication Data
US 2009/0131413 A1    May 21, 2009

(30) Foreign Application Priority Data

Jul. 1, 2004    (JP) .................................. 2004-195836

(51) Int. Cl.
*A61K 31/5355*    (2006.01)
*A61K 31/496*    (2006.01)
*A61K 31/4436*    (2006.01)
*A61K 31/4162*    (2006.01)
*C07D 413/12*    (2006.01)
*C07D 413/14*    (2006.01)
*C07D 403/12*    (2006.01)
*C07D 491/113*    (2006.01)
*C07D 401/12*    (2006.01)
*C07D 487/04*    (2006.01)

(52) U.S. Cl. ............ 514/234.2; 514/253.09; 514/254.06; 514/278; 514/322; 514/338; 514/407; 544/140; 544/364; 544/371; 546/19; 546/199; 546/275.7; 548/360.5

(58) Field of Classification Search .................. 514/408; 548/360.5
See application file for complete search history.

(56) References Cited

U.S. PATENT DOCUMENTS

| | | | |
|---|---|---|---|
| 3,649,641 A * | 3/1972 | Kim et al. ................. | 548/359.5 |
| 6,022,307 A | 2/2000 | Salvati et al. | |
| 6,613,778 B1 | 9/2003 | Eggenweiler et al. | |
| 6,627,651 B1 | 9/2003 | Shiraishi et al. | |
| 6,737,436 B1 | 5/2004 | Eggenweiler et al. | |
| 7,268,128 B2 | 9/2007 | Inoue et al. | |
| 2005/0208582 A1 | 9/2005 | Ohi et al. | |
| 2005/0261339 A1 | 11/2005 | Ohi et al. | |
| 2006/0128707 A1 | 6/2006 | Inoue et al. | |
| 2006/0128728 A1 | 6/2006 | Inoue et al. | |
| 2007/0270419 A1 | 11/2007 | Inoue et al. | |
| 2009/0054397 A1 | 2/2009 | Ohi et al. | |

FOREIGN PATENT DOCUMENTS

| | | |
|---|---|---|
| DE | 199 50 647 | 4/2001 |
| WO | 97/27200 | 7/1997 |
| WO | 00/68203 | 11/2000 |
| WO | 01/32618 | 5/2001 |
| WO | 01/34601 | 5/2001 |
| WO | 01/74786 | 10/2001 |
| WO | 01/90101 | 11/2001 |
| WO | 01/98274 | 12/2001 |
| WO | 02/28847 | 4/2002 |
| WO | 02/30907 | 4/2002 |
| WO | 02/40450 | 5/2002 |
| WO | 02/066469 | 8/2002 |
| WO | 02/074754 | 9/2002 |
| WO | 02/079146 | 10/2002 |
| WO | 02/087513 | 11/2002 |
| WO | 02/088080 | 11/2002 |
| WO | 02/100403 | 12/2002 |
| WO | 02/102315 | 12/2002 |
| WO | 03/024962 | 3/2003 |
| WO | 03/029245 | 4/2003 |
| WO | 03/040096 | 5/2003 |
| WO | 03/097617 | 11/2003 |

(Continued)

OTHER PUBLICATIONS

Brown and Meth-Cohn (Tetrahedron Letters, No. 46, 1974, pp. 4069-4072, esp. p. 4072).*

(Continued)

*Primary Examiner* — Yong Chu
*Assistant Examiner* — Alicia L Otton
(74) *Attorney, Agent, or Firm* — Drinker Biddle & Reath LLP

(57) ABSTRACT

To provide thienopyrazole derivatives inhibiting PDE 7 selectively, and therefore, enhance cellular cAMP level. Consequently, the compound is useful for treating various kinds of disease such as allergic diseases, inflammatory diseases or immunologic diseases. The compound is thienopyrazole compound represented by the following formula (I):

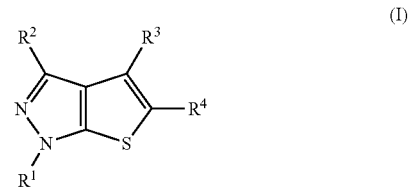

(I)

[wherein, especially, $R^1$ is a cyclohexyl, a cycloheptyl group or a tetrahydropyranyl group; $R^2$ is methyl; $R^3$ is a hydrogen atom; and $R^4$ is a group: —$CONR^5R^6$ (in which any one of $R^5$ and $R^6$ is a hydrogen atom)].

21 Claims, No Drawings

FOREIGN PATENT DOCUMENTS

| | | |
|---|---|---|
| WO | 03/099821 | 12/2003 |
| WO | 03/101968 | 12/2003 |

OTHER PUBLICATIONS

Kvitko et al. (Zhurnal Organicheskoi Khimii, vol. 5(8), 1969, pp. 1498-1503).*

Kvitko et al. (Khimiya Geterotsiklicheskikh Soedinenii, vol. 4, 1969, pp. 760-761).*

Ahluwalia, et. al. (Indian Journal of Chemistry, vol. 35B, Jul. 1996, pp. 715-717).*

Search Report dated Oct. 11, 2005 for International Application No. PCT/JP2005/012208 filed Jul. 1, 2005.

Barnes et al., "Synthesis and Structure—Activity Relationships of Guanine Analogues as Phosphodiesterase 7 (PDE7) Inhibitors," Bioorganic and Medicinal Chemistry Letters, No. 11, 2001, pp. 1081-1083.

Martínez et al., Benzyl Derivatives of 2,1,3-Benzo- and Benzothienol[3,2-α]thiadiazine 2,2-Dioxides: First Phosphodiesterase 7 Inhibitors, J. Med. Chem., No. 43, 2000, pp. 683-689.

Castro et al., "CoMFA of benzyl derivatives of 2,1,3-benzo and benzothieno[3,2-α]thiadiazine 2,2-dioxides: clues for the design of phosphodiesterase 7 inhibitors," Eur. J. Med. Chem., No. 36, 2001, pp. 333-338.

Bratenko et al., "4-Functionally Substituted 3-heterylpyrazoles: XII. 4-Chlorothieno[2,3-c]pyrazole-5-carbonyl Chlorides," Russian Journal of Organic Chemistry, vol. 39, No. 6, 2003, pp. 893-896.

Bakhite et al., "Synthesis and Antimicrobial Activity of Some New Pyrazoles and Thieno[2,3-c]Pyrazoles," Phosphorus, Sulfer and Silicon, 2000, vol. 157, pp. 107-122.

Zakharov et al., "Heterocyclic analogs of 3-hydroxybenzo[b]thiophene, Synthesis, tautomerism, and reactions of 4-hydroxy(amino)thieno[3,2-d] pyrazoles," Zhurnal Organicheskoi Khimii, 1973, 9(11): 2416-2421 (with partial English-language translation).

Kvitko et al., "Synthesis and some properties of 1-phenyl-3-methylthieno[2,3-b]pyrazole-5-carboxylic acid," Zhurnal Organicheskoi Khimii, 1969, 5(8): 1498-1503 (with partial English-language translation).

Wang et al., "A Novel Tandem Reaction for the Synthesis of Thieno[2,3-C]Pyrazole," Chinese Chemical Letters, vol. 10, No. 3, 1999, pp. 189-190.

Ahluwalia et al., "Novel synthesis of thieno[2, 3-c]pyrazoles and thieno[2,3-d]pyrimidines," Indian Journal of Chemistry, vol. 35B, Jul. 1996, pp. 715-717.

Alfred Brack "Uber kondensierte Pyrazolopyridine," Justus Liebigs Annalen Der Chemie, vol. 681, 1965, pp. 105-110. (German Language).

Supplementary European Search Report dated Jun. 2, 2009 issued in EP 05765241.4.

Chinese Office Action dated Feb. 6, 2009 issued in CN 200580021480.9 (w/English translation).

\* cited by examiner

THIENOPYRAZOLE DERIVATIVE HAVING PDE7 INHIBITORY ACTIVITY

CROSS REFERENCE TO RELATED APPLICATIONS

This application is a National Stage of International Application No. PCT/JP2005/012208, filed Jul. 1, 2005, and which claims benefit of Japanese Patent Application No. 2004-195836 filed Jul. 1, 2004, which are incorporated herein in their entirety.

TECHNICAL FIELD

The present invention relates to thienopyrazole derivatives, pharmaceutically acceptable salts and solvates thereof, having selective PDE 7 (phosphodiesterase VII) inhibiting effect. Further, the present invention relates to an intermediate compounds for preparing said thienopyrazole derivatives and a process for producing them. These compounds are effective compounds for treating various kinds of diseases such as allergic diseases, inflammatory diseases and immunological diseases.

BACKGROUND ART

Cyclic AMP (cAMP) or cyclic GMP (cGMP), which is an intracellular second messenger substance, is decomposed and inactivated by phosphodiesterases (PDE 1 to PDE 11). The PDE 7 selectively decomposes cAMP, and is characterized as an enzyme which is not inhibited by rolipram. Rolipram is a selective inhibitor of PDE 4, which decomposes cAMP similarly.

It is suggested that PDE 7 plays an important role for activating T cells (Beavo, et al., Science, 283, 848 (1999)), and is well known that activation of T-cell is concerned with the exacerbation of allergic diseases, inflammatory diseases or immunological diseases. These diseases are for example bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, sepsis, Crohn's disease, rejection reaction in transplantation, graft versus host disease (GVH disease), and restenosis after angioplasty [*J. Allergy Clin. Immunol.*, 2000 November; 106(5 Suppl.): S221-6; *Am. J. Respir. Crit. Care Med.*, 1996 February; 153(2): 629-32; *Am. J. Respir. Crit. Care Med.*, 1999 November; 160(5 Pt 2): S33-7; *Clin. Exp. Allergy*, 2000 Febuary; 30(2): 242-54; *Hosp. Med.*, 1998 July; 59(7): 530-3; *Int. Arch. Allergy Immunol.*, 1998 March; 115(3): 179-90; *J. Immunol.*, 1991 Feb. 15; 146(4): 1169-74; *Osteoarthritis Cartilage*, 1999 July; 7(4): 401-2; *Rheum. Dis. Clin. North Am.*, 2001 May; 27(2): 317-34; *J. Autoimmun.*, 2001 May; 16(3): 187-92; *Curr. Rheumatol. Rep.*, 2000 Febuary; 2(1): 24-31; *Trends Immunol.*, 2001 January; 22(1): 21-6; *Curr. Opin. Immunol.*, 2000 August; 12(4): 403-8; *Diabetes Care*, 2001 September; 24(9): 1661-7; *J. Neuroimmunol.*, 2000 Nov. 1; 111(1-2): 224-8; *Curr. Opin. Immunol.*, 1997 December; 9(6):793-9; *JAMA*, 1999 Sep. 15; 282(11):1076-82; *Semin. Cancer Biol.*, 1996 April; 7(2):57-64; *J. Interferon Cytokine Res.*, 2001 April; 21(4):219-21].

Therefore, it is considered that a compound having PDE 7 inhibiting effect is useful for treating various kinds of diseases such as allergic diseases, inflammatory diseases or immunological diseases concerned with T cells.

There has been proposed that many compounds selectively inhibit PDE 7. There can be mentioned the examples such as imidazopyridine derivatives (Patent Document 1), dihydropurine derivatives (Patent Document 2), pyrrole derivatives (Patent Document 3), benzothiopyranoimidazolone derivatives (Patent Document 4), heterocyclic compounds (Patent Document 5; Patent Document 6), quinazoline and pyridopyrimidine derivatives (Patent Document 7), spiro tricyclic compounds (Patent Document 8), thiazole and oxathiazole derivatives (Patent Document 9), sulfonamide derivatives (Patent Document 10), heterobiarylsulfonamide derivatives (Patent Document 11), dihydroisoquinoline derivatives (Patent Document 12), guanine derivatives (Non-Patent Document 1), benzothiadiazine derivatives and benzothienothiadiazine derivatives (Non-Patent Document 2, and Non-Patent Document 3). However, no curative medicines having PDE 7 inhibiting effect as main pharmacological mechanism have developed up to now.

Though some compounds having thienopyrazole skeleton have been known (Patent Documents 13-24; Non-Patent Documents 4-8), there is no suggestion that these compounds have PDE 7 inhibiting effect. Further, the method for producing the thienopyrazole derivatives of the present invention has been reported (Non-Patent Documents 9-11); however, the substituents on the thienopyrazole skeleton are different from those of the present invention.

Patent Document 1: International Patent Publication WO 01/34,601
Patent Document 2: International Patent Publication WO 00/68,203
Patent Document 3: International Patent Publication WO 01/32,618
Patent Document 4: DE Patent 19,950,647
Patent Document 5: International Patent Publications WO 02/88,080
Patent Document 6: International Patent Publications WO 02/87,513
Patent Document 7: International Patent Publication WO 02/102,315
Patent Document 8: International Patent Publication WO 02/74,754
Patent Document 9: International Patent Publication WO 02/28,847
Patent Document 10: International Patent Publication WO 01/98,274
Patent Document 11: International Patent Publication WO 01/74,786
Patent Document 12: International Patent Publication WO 02/40,450
Patent Document 13: International Patent Publication WO 02/100,403
Patent Document 14: International Patent Publication WO 02/79,146
Patent Document 15: International Patent Publication WO 02/66,469
Patent Document 16: International Patent Publication WO 01/90,101
Patent Document 17: U.S. Pat. No. 6,022,307
Patent Document 18: International Patent Publication WO 03/024,962
Patent Document 19: International Patent Publication WO 03/029,245
Patent Document 20: International Patent Publication WO 03/040,096
Patent Document 21: International Patent Publication WO 03/097,617

Patent Document 22: International Patent Publication WO 03/099,821

Patent Document 23: International Patent Publication WO 97/27,200

Patent Document 24: U.S. Pat. No. 3,649,641

Non-Patent Document 1: *Bioorg. Med. Chem. Lett.,* 11(2001), 1081

Non-Patent Document 2: *J. Med. Chem.,* 43(2000), 683

Non-Patent Document 3: *Eur. J. Med. Chem.,* 36(2001), 333

Non-Patent Document 4: *Russ. J. Org. Chem.,* 39(2003), 893

Non-Patent Document 5: *Aknos Consulting and Solutions GmbH Co., Catalog: Akos samples*

Non-Patent Document 6: *Phosphorus, sulfur and silicon and related Elements,* 157 (2000), 107

Non-Patent Document 7: *Zhurnal Organisheskoi Khimii.,* 9(1973), 2416

Non-Patent Document 8: *Zhurnal Organisheskoi Khimii.,* 5(1969), 1498

Non-Patent Document 9: *Phosphorus, sulfur and silicon and related Elements,* 157 (2000), 107

Non-Patent Document 10: *Chinese Chemical Letters,* 10(3), (1999). 189

Non-Patent Document 11: *Indian Journal of Chemistry, Section B: Organic Chemistry Including Medicinal Chemistry,* 35B(7), (1996), 715

DISCLOSURE OF INVENTION

The Problem to be Solved in the Invention

The purpose of the present invention is to provide novel compounds having PDE 7 inhibiting activity, and PDE 7 inhibitors containing said inhibitors as an active ingredient. Further, the present invention provides useful intermediate compounds for manufacturing the above-mentioned novel compounds.

The compounds of the present invention inhibit PDE 7 selectively, and therefore, enhance cellular cAMP level. Consequently, the compounds of the present invention are useful for treating various kinds of diseases such as allergic diseases, inflammatory diseases or immunological diseases by inhibiting the activation of T-cells.

For example, the compounds of the present invention are useful for treating or preventing the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, sepsis, Crohn's disease, rejection reaction in transplantation, GVH disease, restenosis after angioplasty.

Means to Solve the Problem

Through extensive investigations of researching compounds having the capabilities of inhibiting PDE 7, the present inventors discovered that the compounds having thienopyrazole skeleton in the molecule represented by the formula (I) mentioned below possess potent and selective PDE 7 inhibiting effect, and thus, completed the present invention.

Accordingly, as one aspect of the present invention, it is provided thienopyrazole compounds represented by the following formula (I):

[Formula 1]

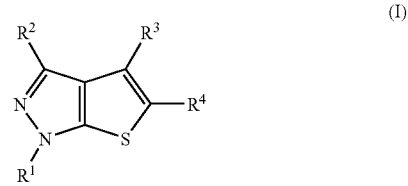

wherein:

$R^1$ is substituted or unsubstituted $C_3$-$C_8$ alkyl group, substituted or unsubstituted cycloalkyl group or substituted or unsubstituted heterocycloalkyl group;

$R^2$ is a hydrogen atom or substituted or unsubstituted $C_1$-$C_3$ alkyl group;

$R^3$ is a hydrogen atom, substituted or unsubstituted $C_1$-$C_3$ alkyl group, or a halogen atom;

$R^4$ is substituted or unsubstituted aryl group, substituted or unsubstituted heteroaryl group, or a group —$CONR^5R^6$ or —$CO_2R^7$;

$R^5$ and $R^6$ are, same or different from each other, a hydrogen atom; $C_1$-$C_6$ alkyl group which may be substituted by a halogen atom, substituted or unsubstituted aryl group, substituted or unsubstituted heteroaryl group, substituted or unsubstituted heterocycloalkyl group, substituted or unsubstituted cycloalkyl group, a group —$NR^7COR^8$, —$COR^8$, —$NR^9R^{10}$; substituted or unsubstituted cycloalkyl group; substituted or unsubstituted heterocycloalkyl group; substituted or unsubstituted aryl group; substituted or unsubstituted heteroaryl group; or substituted or unsubstituted heterocycloalkyl group in which the ring is formed together with the nitrogen atom binding $R^5$ and $R^6$;

$R^7$ is a hydrogen atom, or substituted or unsubstituted $C_1$-$C_3$ alkyl group;

$R^8$ is substituted or unsubstituted heterocycloalkyl group, or a a group —OH, —$OR^7$ or —$NR^9R^{10}$;

$R^9$ and $R^{10}$ are, same or different from each other, a hydrogen atom, substituted or unsubstituted $C_1$-$C_3$ alkyl group, substituted or unsubstituted heterocycloalkyl group; substituted or unsubstituted acyl group; a group —$SO_2R^7$, or substituted or unsubstituted heterocycloalkyl group in which the ring is formed together with the nitrogen atom binding $R^5$ and $R^6$;

or pharmaceutically acceptable salts.

Another aspect of the present invention, it is provided PDE 7 inhibiting composition containing the thienopyrazole compounds mentioned above, or pharmaceutically acceptable salts as an active ingredient.

Still another aspect of the present invention, it is provided a method for preparing the thienopyrazole compounds represented by the formula (I).

In particular, the method is comprised by chlorination of pyrazole-5-one derivative represented by the formula (VI):

[Formula 2]

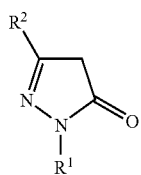
(VI)

wherein, $R^1$ and $R^2$ have the same meanings as defined above; and then, by an electrophilic substitution reaction of the resulting compound without separation to give the pyrazole derivative of the formula (IV):

[Formula 3]

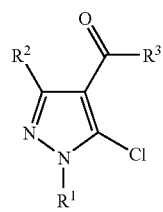
(IV)

wherein, $R^1$, $R^2$ and $R^3$ have the same meanings as defined above; then, by reacting the resulting pyrazole derivative of formula (IV) with the compound of the formula (III) in the presence of base:

[Formula 4]

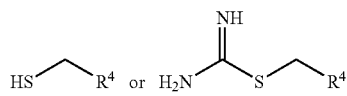
(III)

wherein, $R^4$ has the same meanings as defined above; to give the compound of the formula (II):

[Formula 5]

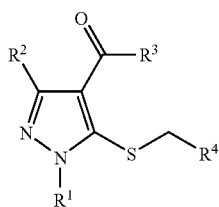
(II)

wherein, $R^1$, $R^2$, $R^3$ and $R^4$ have the same meanings as defined above; and then, by treating the resulting compound of formula (II) with base to give thienopyrazole compound of the formula (I):

[Formula 6]

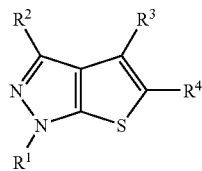
(I)

wherein, $R^1$, $R^2$, $R^3$ and $R^4$ have the same meanings as defined above.

Additionally, the intermediate compound of the formula (IV) can be obtained by electrophilic substitution reaction of chloropyrazole compound of the formula (V):

[Formula 7]

(V)

wherein, $R^1$ and $R^2$ have the same meanings as defined above.

Furthermore, the compound of the formula (I) can be obtained by one pot synthesis from the compound of the formula (IV) without separation of the intermediate compound of the formula (II). In particularly, it is provided the manufacturing method for the compound of the formula (I), in which $R^3$ is a hydrogen atom.

Effects of the Invention

The compounds of the present invention inhibit PDE 7 selectively, and therefore, the compounds of the present invention are useful for treating or preventing the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia sepsis, Crohn's disease, rejection reaction of transplantation, GVH disease, restenosis after angioplasty.

Further, the compounds of the formula (II) and (IV) are important intermediate compounds for synthesis of the present compound of formula (I), and therefore, by using these intermediates, the compounds of the present invention represented by the formula (I) can be obtained by simple and easy way.

BEST MODE FOR CARRYING OUT THE INVENTION

The present invention will now be explained more specifically as following.

The term "$C_n$-$C_m$ alkyl group" of the present invention includes a straight or a branched-chained alkyl group having n to m carbon atoms. The term "cycloalkyl group" means cycloalkyl group having 3 to 8 carbon atoms such as cyclopropyl, cyclobutyl, cyclopentyl, cyclohexyl, cycloheptyl, cyclooctyl and the like. The term "heterocycloalkyl group" may be 3 to 7 membered monocyclic or polycyclic heterocyclic group containing the same or different 1 to 4 hetero atom(s) such as oxygen, nitrogen or sulfur atom(s), and examples may include piperidinyl, pyrrolidinyl, piperazinyl, tetrahydrofuryl, tetrahydropyranyl, morpholinyl, azetidinyl, imidazolidinyl, oxazolidinyl, hexahydropyrrolidinyl, octahydroindolidinyl, octahydroquinolidinyl, octahydroindolyl, and oxo-derivatives thereof.

The "halogen atom" includes chlorine, fluorine, bromine and iodine. The term "aryl group" may be aromatic hydrocarbon group, which consists of mono-benzene ring, or binding or condensed benzene ring, such as phenyl, naphthyl, biphenyl and the like; and dicyclic or tricyclic group, which consists of benzene ring condensed with cycloalkyl or heterocyclic ring, such as 1,2,3,4-tetrahydronaphthalene, 2,3-dihydroindene, indoline, coumarone and the like.

The term "heteroaryl group" may be 5 to 7 membered monocyclic heteroaryl group or polycyclic heteroaryl group, and having 2 to 8 carbon atoms with 1 to 4 hetero atom(s) such as oxygen, nitrogen, sulfur atom(s), in which the polycyclic heteroaryl group has condensed ring system by the same or different nomocyclic heteroaryl or benzene ring each other; or polycyclic group which is consisted of heteroaryl group condensed with cycloalkyl or heterocycloalkyl ring.

The examples include pyrrole, furyl, thienyl, imidazolyl, thiazolyl, pyrazinyl, indolyl, indolinyl, quinolinyl, isoquinolinyl, tetrazolyl, pyridinyl, pyrazolyl, pyridazinyl, pyrimidinyl, benzothiophenyl, isoxazolyl, indazolyl, benzoimidazolyl, phthalazinyl, triazolyl, benzooxazolyl, benzothiazolyl, dihydrocyclopentapyridinyl, dihydro-pyrropyridinyl and the like.

Examples of suitable substituent of the present invention may include straight, branched-chained or cyclic $C_1$-$C_8$ alkyl group, which may be substituted by one or more methyl, ethyl, propyl, isopropyl, n-butyl, t-butyl, cyclohexyl, cycloheptyl, methoxymethyl, hydroxymethyl, trifluoromethyl, $C_1$-$C_3$ alkoxy group, halogen atom, and hydroxyl group; hydroxyl group; cyano group; substituted or unsubstituted alkoxy group such as methoxy, ethoxy group; amino group which may be substituted by $C_1$-$C_6$ alkyl group or acyl group such as amino, methylamino, ethylamino, dimethylamino, acylamino and the like; carboxylic group; substituted or unsubstituted ester group; phosphate group; sulfonic group; substituted or unsubstituted aryl group; substituted or unsubstituted heteroaryl group; saturated or unsaturated heterocycloalkyl group which may be substituted; substituted or unsubstituted carbamoyl group; substituted or unsubstituted amide group; substituted or unsubstituted thioamide group; halogen atom; nitro group; substituted or unsubstituted sulfone group; substituted or unsubstituted sulfonylamide group; oxo group; substituted or unsubstituted urea group; straight, branched-chained or cyclic alkenyl group such as ethenyl, propenyl, cyclohexenyl and the like.

Examples of suitable substituent of "$C_3$-$C_8$ alkyl group which may be substituted" in the group of $R^1$ may include hydroxyl group, halogen atom, alkoxy group and the like, and examples of suitable substituent of "cycloalkyl group which may be sunstituted" in the group of $R^1$ include hydroxyl group, alkoxy group, oxo group, $C_1$-$C_3$ alkyl group such as methyl group. Examples of suitable substituent of "heterocyclo alkyl group which may be substituted" in the group of $R^1$ may include $C_1$-$C_3$ alkyl group such as methyl group.

Examples of suitable substituent of "$C_1$-$C_3$ alkyl group which may be substituted" in the group $R^2$ may include hydroxyl group, alkoxy group, halogen atom such as fluorine atom. Further, examples of suitable substituent of $C_1$-$C_3$ alkyl group which may be substituted" in the group $R^3$ include hydroxyl group, alkoxy group, halogen atom such as fluorine atom.

Examples of suitable substituent of "aryl group which may be substituted" and "heteroaryl group which may be substituted" in the group $R^4$ may include hydroxyl group, halogen atom, heterocycloalkyl group which may be substituted by $C_1$-$C_6$ alkyl group.

Examples of suitable substituent of "cycloalkyl group which may be substituted" in the groups $R^5$ and $R^6$ may include hydroxyl group; oxo group; carboxyl group; carboxyl ester group; cyano group; $C_1$-$C_6$ alkyl group {in which said $C_1$-$C_6$ alkyl group may be substituted by $C_1$-$C_3$ alkoxyl group, hydroxyl group, amino group which may be substituted by $C_1$-$C_6$ alkyl group, arylsulfonyloxy group, heterocycloalkyl group (in which said heterocycloalkyl group may be substituted by hydroxyl group, $C_1$-$C_6$ alkyl group, oxo group or acetyl group)}; amide group (in which said amide group may be substituted by cycloalkyl group or $C_1$-$C_6$ alkyl group which may be substituted by hydroxyl group); heterocycloalkylamide group which may be substituted by $C_1$-$C_6$ alkyl group; heterocycloalkylamide group which may be substituted by hydroxyl group; amino group (in which said amino group may be substituted by $C_1$-$C_6$ alkyl group which may be substituted by $C_1$-$C_3$ alkoxy group and acyl group); heterocycloalkyl group {in which said heterocycloalkyl group may be substituted by $C_1$-$C_6$ alkyl group (in which said alkyl group may be substituted by hydroxyl group), oxo group, acyl group, hydroxyl group, amino group which may be substituted by $C_1$-$C_6$ alkyl group, amino group which may be substituted by acyl group, $C_1$-$C_3$ alkoxy group, alkoxycarbonyl group, carboxyl group, aminocarbonyl group which may be substituted by $C_1$-$C_6$ alkyl group, or sulfonyl group which may be substituted by $C_1$-$C_6$ alkyl group}.

Examples of suitable substituent of "heterocycloalkyl group which may be substituted" may include benzyl group; acyl group; oxo group; heterocycloalkyl group (in which said heterocycloalkyl group may be substituted by $C_1$-$C_6$ alkyl group, acyl group, sulfonyl group which may be substituted by $C_1$-$C_6$ alkyl group or alkoxycarbonyl group); $C_1$-$C_6$ alkyl group which may be substituted by carboxyl group or carboxylic ester group; amido group which may be substituted by $C_1$-$C_6$ alkyl group; heterocycloalkylamide group which may be substituted by $C_1$-$C_6$ alkyl group; sulfonyl group which may be substituted by $C_1$-$C_6$ alkyl group; sulfonamide group which may be substituted by $C_1$-$C_6$ alkyl group; cycloalkyl group which may be substituted by oxo or hydroxyl group; alkoxycarbonyl group, and the like.

Further, examples of suitable substituent of "aryl group which may be substituted" in the group of $R^5$ and $R^6$ may include halogen atom; nitro group; cyano group; acyl group; amino group which may be substituted by acyl group; amide group (in which said amide group may be substituted by $C_1$-$C_6$ alkyl group which may be substituted by $C_1$-$C_3$ alkoxy group or $C_1$-$C_6$ alkyl group which may be substitute by hydroxyl group); alkoxycarbonylamino group; alkoxycarbonyl group; alkoxy group (in which said alkoxy group may be substituted by carboxyl group, carboxylic ester group, or amide group); carbonyl group; carboxyl group; carboxylic ester group; carbamoyl group; sulfonic group; sulfonamide group; aminosulfonyl group; $C_1$-$C_6$ alkyl group (in which said alkyl group may be substituted by $C_1$-$C_3$ alkoxy group, hydroxyl group or hetrocycloalkyl group which may be substituted by $C_1$-$C_6$ alkyl group); heterocycloalkylamide group which may be substituted by $C_1$-$C_6$ alkyl group; heterocycloalkyl group which may be substituted by hydroxyl group; acetic acid group; acetic acid amide group; or heterocycloalkyl group (in which said heterocycloalkyl group may be substituted by hydroxyl group, oxo group, acyl group, $C_1$-$C_6$ alkyl group, amino group which may be substituted by $C_1$-$C_6$ alkyl group, amino group which may be substituted by acyl group, $C_1$-$C_3$ alkoxy group, alkoxycarbonyl group, and the like).

Examples of suitable substituent of "heteroaryl group which may be substituted" in the group of $R^5$ and $R^6$ may include halogen atom; acyl group; amide group {in which said amide group may be substituted by $C_1$-$C_6$ alkyl group (in which said alkyl group may be further substituted by amino group which may be substituted by $C_1$-$C_6$ alkyl group or hydroxyl group)}; cycloalkyl group which may be substituted by hydroxyl group; cycloheteroalkyl group which may be substituted by $C_1$-$C_6$ alkyl group or acyl group; heterocycloalkylamide group which may be substituted by $C_1$-$C_6$ alkyl group; heterocycloalkylamide group which may be substituted by hydroxyl group; oxo group; acylamino group; $C_1$-$C_6$ alkyl group (in which said alkyl group may be substituted by cycloheteroalkyl group which may be substituted by hydroxyl group, acyl group or cycloheteroalkyl group which may be substituted hydroxyl group); carboxyl group; carboxylic ester group; sulfonyl group; heterocycloalkyl group (in which said heterocycloalkyl group may be substituted by hydroxyl group, oxo group, acyl group, $C_1$-$C_6$ alkyl group, amino group which may be substituted by $C_1$-$C_6$ alkyl group, amino group which may be substituted by acyl group, $C_1$-$C_3$ alkoxy group, alkoxycarbonyl group, and the like).

Examples of suitable substituent of "substituted or unsubstituted heterocycloalkyl group which is formed said ring system together with nitrogen atom which they are bonded" may include acyl group; amide group; $C_1$-$C_6$ alkyl group or $C_1$-$C_3$ alkoxy group; carbonyl group; carboxyl group; carboxylic ester group; hydroxyl group; carbamoyl group; sulfonamide group; aminosulfonic group; oxo group; and the like.

Examples of suitable substituent of "$C_1$-$C_3$ alkyl group which may be substituted" in the group $R^7$ may include hydroxyl group, alkoxy group, halogen atom such as fluorine atom, and the like.

Examples of suitable substituent of "heterocycloalkyl group which may be substituted" in the group $R^8$ may include hydroxyl group, alkoxy group, oxo group, acyl group, $C_1$-$C_6$alkyl group, $C_1$-$C_3$alkoxy group, carboxyl group, amide group, and the like.

In the groups $R^9$ and $R^{10}$, examples of suitable substituent of "$C_1$-$C_3$ alkyl group which may be substituted" may include hydroxyl group, alkoxy group and the like. Further, examples of suitable substituent of "heterocycloalkyl group which may be substituted" may include $C_1$-$C_6$ alkyl group, hydroxyl group, alkoxy group, oxo group, acyl group and the like, and examples of suitable substituent of "acyl group which may be substituted" may include $C_1$-$C_6$ alkyl group, hydroxyl group, alkoxy group and the like.

Examples of suitable substituent of "substituted or unsubstituted heterocycloalkyl group which is formed said ring system together with nitrogen atom which they are bonded" include acyl group, amide group, $C_1$-$C_6$ alkyl group, $C_1$-$C_3$ alkoxy group, carbonyl group, carboxyl group, carboxylic ester group, hydroxyl group, carbamoyl group, sulfonamide group, aminosulfonic group, and the like.

Preferable compounds of the formula (I) of the present invention may include the compounds wherein $R^1$ is cyclohexyl group, cycloheptyl group or tetrahydropyranyl group; $R^2$ is methyl group; $R^3$ is a hydrogen atom; and $R^4$ is the group —$NR^5R^6$ (in which one of these $R^5$ and $R^6$ is a hydrogen atom).

It is understood that when the compounds of the formula (I) of the present invention exist in the tautomeric mixtures, each tautomeric isomers per se, as well as the mixture thereof. Furthermore, the radiolabelled compound of the formula (I) shall be included within the scope of the compounds of the present invention.

The compounds of the present invention may contain one or more asymmetric carbon atom and therefore, the compounds of the present invention may exist as optically isomer of (R)-form or (S)-form, racemic forms, as well as diastereomers. Further, the compounds of the present invention may exist as geometrical isomer such as (Z)-form or (E)-form due to the double bond in the substituent. Therefore, the compounds of the present invention should include these isomers per se as well as the isomeric mixtures thereof.

The compounds of the present invention may form acid additional salt thereof with various acids. Examples of the acid additional salt include the salts with inorganic acid such as hydrochloric acid, hydrobromic acid, hydroiodic acid, sulfuric acid, nitric acid, phosphoric acid, and the like; salts with organic acid such as formic acid, acetic acid, propionic acid, oxalic acid, malonic acid, succinic acid, fumaric acid, maleic acid, lactic acid, malic acid, citric acid, tartaric acid, benzoic acid, picric acid, methanesulfonic acid, toluenesulfonic acid, benzenesulfonic acid, trichloroacetic acid, trifluoroacetic acid, asparaginic acid, glutamic acid and the like.

The compounds of the present invention may form pharmaceutically acceptable salts by treating with various kinds of metal, especially alkali metal or alkali earth metal. These salts may include sodium salt, potassium salt, calcium salt and the like.

The following compounds are preferable thienopyrazole compounds of the formula (I) of the present invention.

Ethyl 1-cyclohexyl-3-methyl-1H-thieno[2,3-c]pyrazole-5-carboxylate;
N-Benzyl-1-cyclohexyl-3-methyl-1H-thieno[2,3-c]pyrazole-5-carboxamide;
1-Cyclohexyl-3-methyl-N-phenyl-1H-thieno[2,3-c]pyrazole-5-carboxamide;
N-{4-[Acetyl(methyl)amino]phenyl}-1-cyclohexyl-3-methyl-1H-thieno[2,3-c]pyrazole-5-carboxamide;
N-[4-(Acetylamino)-3-methoxyphenyl]-1-cyclohexyl-3-methyl-1H-thieno[2,3-c]pyrazole-5-carboxamide;
N-(1-Acetyl-2,3-dihydro-1H-indol-5-yl)-1-cyclohexyl-3-methyl-1H-thieno[2,3-c]pyrazole-5-carboxamide;
Ethyl 4-{[(1-cyclohexyl-3-methyl-1H-thieno[2,3-c]pyrazol-5-yl)-carbonyl]amino}phenylcarbamate;
tert-Butyl 5-{[(1-cyclohexyl-3-methyl-1H-thieno[2,3-c]pyrazol-5-yl)-carbonyl]amino}-1-indolinecarboxylate;
1-Cyclohexyl-N-(2,3-dihydro-1H-indol-5-yl)-3-methyl-1H-thieno[2,3-c]pyrazole-5-carboxamide;
1-Cyclohexyl-N-(1H-indol-5-yl)-3-methyl-1H-thieno[2,3-c]-pyrazole-5-carboxamide;
1-Cyclohexyl-3-methyl-N-[4-(4-morpholinyl)phenyl]-1H-thieno[2,3-c]pyrazole-5-carboxamide;
1-Cyclohexyl-3-methyl-N-(3-nitrophenyl)-1H-thieno[2,3-c]-pyrazole-5-carboxamide;
N-(3-Aminophenyl)-1-cyclohexyl-3-methyl-1H-thieno[2,3-c]-pyrazole-5-carboxamide;
N-[3-(Acetylamino)phenyl]-1-cyclohexyl-3-methyl-1H-thieno[2,3-c]pyrazole-5-carboxamide;
1-Cyclohexyl-3-methyl-N-{4-[(methylamino)carbonyl]phenyl}-1H-thieno[2,3-c]pyrazole-5-carboxamide;
1-Cyclohexyl-3-methyl-N-(1-propionyl-2,3-dihydro-1H-indol-5-yl)-1H-thieno[2,3-c]pyrazole-5-carboxamide;
Ethyl 5-{[(1-cyclohexyl-3-methyl-1H-thieno[2,3-c]pyrazol-5-yl)-carbonyl]amino}-1-indolinecarboxylate;

1-Cyclohexyl-N-(1-isobutyryl-2,3-dihydro-1H-indol-5-yl)-3-methyl-1H-thieno[2,3-c]pyrazole-5-carboxamide;
N-(1-Butyryl-2,3-dihydro-1H-indol-5-yl)-1-cyclohexyl-3-methyl-1H-thieno[2,3-c]pyrazole-5-carboxamide;
1-Cyclohexyl-N-[1-(2,2-dimethylpropanoyl)-2,3-dihydro-1H-indol-5-yl]-3-methyl-1H-thieno[2,3-c]pyrazole-5-carboxamide;
1-Cyclohexyl-3-methyl-N-(2-oxo-2,3-dihydro-1H-indol-5-yl)-1H-thieno[2,3-c]pyrazole-5-carboxamide;
N-[4-(Acetylamino)-3-chlorophenyl]-1-cyclohexyl-3-methyl-1H-thieno[2,3-c]pyrazole-5-carboxamide;
1-Cyclohexyl-N-{4-[(ethylamino)carbonyl]phenyl}-3-methyl-1H-thieno[2,3-c]pyrazole-5-carboxamide;
1-Cyclohexyl-N-[4-(methoxymethyl)phenyl]-3-methyl-1H-thieno[2,3-c]-pyrazole-5-carboxamide;
1-Cyclohexyl-N-[4-(hydroxymethyl)phenyl]-3-methyl-1H-thieno-[2,3-c]pyrazole-5-carboxamide;
1-Cyclohexyl-3-methyl-N-[4-(4-morpholinylcarbonyl)phenyl]-1H-thieno[2,3-c]pyrazole-5-carboxamide;
1-Cyclohexyl-3-methyl-N-{4-[(4-methyl-1-piperazinyl)carbonyl]-phenyl}-1H-thieno[2,3-c]pyrazole-5-carboxamide;
1-Cyclohexyl-3-methyl-N-{4-[(methylsulfonyl)amino]phenyl}-1H-thieno[2,3-c]pyrazole-5-carboxyamide;
1-Cyclohexyl-3-methyl-N-{4-[(methylamino)sulfonyl]phenyl}-1H-thieno[2,3-c]pyrazole-5-carboxamide;
N-{1-[(1-Cyclohexyl-3-methyl-1H-thieno[2,3-c]pyrazol-5-yl)-carbonyl]-2,3-dihydro-1H-indol-5-yl}acetamide;
1-Cyclohexyl-3-methyl-N-{4-[(4-methyl-1-piperazinyl)sulfonyl]-phenyl}-1H-thieno[2,3-c]pyrazole-5-carboxamide;
1-Cyclohexyl-N-(4-{[(2-methoxyethyl)amino]carbonyl}phenyl)-3-methyl-1H-thieno[2,3-c]pyrazole-5-carboxamide;
N-(4-Acetylphenyl)-1-cyclohexyl-3-methyl-1H-thieno[2,3-c]-pyrazole-5-carboxamide;
1-Cyclohexyl-N-{4-[(dimethylamino)carbonyl]phenyl}-3-methyl-1H-thieno[2,3-c]pyrazole-5-carboxamide;
Ethyl 4-{[(1-cyclohexyl-3-methyl-1H-thieno[2,3-c]pyrazol-5-yl)-carbonyl]amino}benzoate;
4-{[(1-Cyclohexyl-3-methyl-1H-thieno[2,3-c]pyrazol-5-yl)carbonyl]-amino}benzoic acid;
1-Cyclohexyl-N-(2-methoxy-4-nitrophenyl)-3-methyl-1H-thieno-[2,3-c]pyrazole-5-carboxamide;
N-(4-Amino-2-methoxyphenyl)-1-cyclohexyl-3-methyl-1H-thieno-[2,3-c]pyrazole-5-carboxamide;
N-[4-(Acetylamino)-2-methoxyphenyl]-1-cyclohexyl-3-methyl-1H-thieno[2,3-c]pyrazole-5-carboxamide;
1-Cyclohexyl-N-{4-[(isopropylamino)carbonyl]phenyl}-3-methyl-1H-thieno[2,3-c]pyrazole-5-carboxamide;
1-Cyclohexyl-N-(4-{[(2-hydroxyethyl)amino]carbonyl}phenyl)-3-methyl-1H-thieno[2,3-c]pyrazole-5-carboxamide;
N-[6-(Acetylamino)-3-pyridinyl]-1-cyclohexyl-3-methyl-1H-thieno[2,3-c]pyrazole-5-carboxamide;
1-Cyclohexyl-N-(4-methoxyphenyl)-3-methyl-1H-thieno[2,3-c]-pyrazole-5-carboxamide;
1-Cyclohexyl-N-cyclopentyl-3-methyl-1H-thieno[2,3-c]pyrazole-5-carboxamide;
N,1-Dicyclohexyl-3-methyl-1H-thieno[2,3-c]pyrazole-5-carboxamide;
N-{4-[(tert-butylamino)carbonyl]phenyl}-1-cyclohexyl-3-methyl-1H-thieno[2,3-c]pyrazole-5-carboxamide;
1-Cyclohexyl-N-{5-[(isopropylamino)carbonyl]-2-pyridinyl}-3-methyl-1H-thieno[2,3-c]pyrazole-5-carboxamide;
1-Cyclohexyl-N-[4-(formylamino)phenyl]-3-methyl-1H-thieno[2,3-c]-pyrazole-5-carboxamide;
tert-Butyl 4-[(4-{[(1-cyclohexyl-3-methyl-1H-thieno[2,3-c]pyrazol-5-yl)carbonyl]amino}phenyl)sulfonyl]-1-piperazinecarboxylate;
1-Cyclohexyl-3-methyl-N-[4-(1-piperazinylsulfonyl)phenyl]-1H-thieno[2,3-c]pyrazole-5-carboxamide;
1-Cyclohexyl-3-methyl-N-[4-(4-morpholinylsulfonyl)phenyl]-1H-thieno[2,3-c]pyrazole-5-carboxamide;
1-Cyclohexyl-3-methyl-N-[4-(methylsulfonyl)phenyl]-1H-thieno-[2,3-c]pyrazole-5-carboxamide;
1-Cyclohexyl-N-[1-(cyclopropylcarbonyl)-2,3-dihydro-1H-indol-5-yl]-3-methyl-1H-thieno[2,3-c]pyrazole-5-carboxamide;
1-Cyclohexyl-3-methyl-N-[1-(methylsulfonyl)-2,3-dihydro-1H-indol-5-yl]-1H-thieno[2,3-c]pyrazole-5-carboxamide;
N-(1-Acetyl-1H-indol-5-yl)-1-cyclohexyl-3-methyl-1H-thieno[2,3-c]-pyrazole-5-carboxamide;
1-Cyclohexyl-N-cyclopropyl-3-methyl-1H-thieno[2,3-c]pyrazole-5-carboxamide;
N-(1-Benzyl-4-piperidinyl)-1-cyclohexyl-3-methyl-1H-thieno[2,3-c]-pyrazole-5-carboxamide;
1-Cyclohexyl-3-methyl-N-(4-piperidinyl)-1H-thieno[2,3-c]pyrazole-5-carboxamide;
N-(1-Acetyl-4-piperidinyl)-1-cyclohexyl-3-methyl-1H-thieno-[2,3-c]pyrazole-5-carboxamide;
Ethyl (4-{[(1-cyclohexyl-3-methyl-1H-thieno[2,3-c]pyrazol-5-yl)-carbonyl]amino}phenoxy)acetate;
(4-{[(1-Cyclohexyl-3-methyl-1H-thieno[2,3-c]pyrazol-5-yl)-carbonyl]amino}phenoxy)acetic acid;
1-Cyclohexyl-3-methyl-N-{4-[2-(methylamino)-2-oxoethoxy]phenyl}-1H-thieno[2,3-c]pyrazole-5-carboxamide;
Ethyl (4-{[(1-cyclohexyl-3-methyl-1H-thieno[2,3-c]pyrazol-5-yl)-carbonyl]amino}phenyl)acetate;
(4-{[(1-Cyclohexyl-3-methyl-1H-thieno[2,3-c]pyrazol-5-yl)-carbonyl]amino}phenyl)acetic acid;
1-Cyclohexyl-3-methyl-N-{4-[2-(methylamino)-2-oxoethyl]phenyl}-1H-thieno[2,3-c]pyrazole-5-carboxamide;
tert-Butyl 4-(4-{[(1-cyclohexyl-3-methyl-1H-thieno[2,3-c]pyrazol-5-yl)carbonyl]amino}phenyl)-1-piperazinecarboxylate;
1-Cyclohexyl-3-methyl-N-[4-(1-piperazinyl)phenyl]-1H-thieno-[2,3-c]pyrazole-5-carboxamide;
N-[4-(4-Acetyl-1-piperazinyl)phenyl]-1-cyclohexyl-3-methyl-1H-thieno[2,3-c]pyrazole-5-carboxamide;
1-Cyclohexyl-N-(trans-4-hydroxycyclohexyl)-3-methyl-1H-thieno-[2,3-c]pyrazole-5-carboxamide;
1-Cyclohexyl-3-methyl-N-(4-oxocyclohexyl)-1H-thieno[2,3-c]-pyrazole-5-carboxamide;
1-Cyclohexyl-3-methyl-N-{4-[2-(4-methyl-1-piperazinyl)-2-oxoethoxy]phenyl}-1H-thieno[2,3-c]pyrazole-5-carboxamide;
1-Cyclohexyl-N-{4-[2-(dimethylamino)-2-oxoethoxy]phenyl}-3-methyl-1H-thieno[2,3-c]pyrazole-5-carboxamide;
2-{4-[4-{[(1-Cyclohexyl-3-methyl-1H-thieno[2,3-c]pyrazol-5-yl)-carbonyl]amino}phenyl]sulfonyl}-1-piperazinyl}ethyl acetate;
1-Cyclohexyl-N-(4-{[4-(2-hydroxyethyl)-1-piperazinyl]sulfonyl}-phenyl)-3-methyl-1H-thieno[2,3-c]pyrazole-5-carboxamide;
N-[trans-4-(Acetylamino)cyclohexyl]-1-cyclohexyl-3-methyl-1H-thieno[2,3-c]pyrazole-5-carboxamide;
1-Cyclohexyl-N,3-dimethyl-1H-thieno[2,3-c]pyrazole-5-carboxamide;
Ethyl 1-cyclopentyl-3-methyl-1H-thieno[2,3-c]pyrazole-5-carboxylate;
N-[4-(Acetylamino)phenyl]-1-cyclopentyl-3-methyl-1H-thieno[2,3-c]-pyrazole-5-carboxamide;

Ethyl 1-cycloheptyl-3-methyl-1H-thieno[2,3-c]pyrazole-5-carboxylate;
N-[4-(Acetylamino)phenyl]-1-cycloheptyl-3-methyl-1H-thieno-[2,3-c]pyrazole-5-carboxamide;
1-Cyclohexyl-N,3-dimethyl-N-phenyl-1H-thieno[2,3-c]pyrazole-5-carboxamide;
1-Cyclohexyl-3-methyl-N-(4-pyridinyl)-1H-thieno[2,3-c]pyrazole-5-carboxamide;
1-Cyclohexyl-3-methyl-N-(3-pyridinyl)-1H-thieno[2,3-c]pyrazole-5-carboxamide;
1-Cyclohexyl-3-methyl-N-(4-nitrophenyl)-1H-thieno[2,3-c]pyrazole-5-carboxamide;
N-(4-Aminophenyl)-1-cyclohexyl-3-methyl-1H-thieno[2,3-c]pyrazole-5-carboxamide;
N-[4-(Acetylamino)pheny]-1-cyclohexyl-3-methyl-1H-thieno[2,3-c]-pyrazole-5-carboxamide;
1-Cyclohexyl-N-{4-[(methoxyacetyl)amino]phenyl}-3-methyl-1H-thieno[2,3-c]pyrazole-5-carboxamide;
Methyl 5-{[(1-cyclohexyl-3-methyl-1H-thieno[2,3-c]pyrazol-5-yl)-carbonyl]amino}-2-pyridinecarboxylate;
5-{[(1-Cyclohexyl-3-methyl-1H-thieno[2,3-c]pyrazol-5-yl)carbonyl]-aminol}-2-pyridinecarboxylic acid;
1-Cyclohexyl-3-methyl-N-{6-[(methylamino)carbonyl]-3-pyridinyl}-1H-thieno[2,3-c]pyrazole-5-carboxamide;
1-Cyclohexyl-N-{6-[(dimethylamino)carbonyl]-3-pyridinyl}-3-methyl-1H-thieno[2,3-c]pyrazole-5-carboxamide;
1-Cyclohexyl-3-methyl-N-[4-(4-methyl-1-piperazinyl)phenyl]-1H-thieno[2,3-c]pyrazole-5-carboxamide;
1-Cyclohexyl-3-methyl-N-[4-(4-methyl-1-piperazinyl)phenyl]-1H-thieno[2,3-c]pyrazole-5-carboxamide methanesulfonate;
N-(4-Cyanophenyl)-1-cyclohexyl-3-methyl-1H-thieno[2,3-c]pyrazole-5-carboxamide;
1-Cyclohexyl-3-methyl-N-[6-(4-methyl-1-piperazinyl)-3-pyridinyl]-1H-thieno[2,3-c]pyrazole-5-carboxamide;
1-Cyclohexyl-3-methyl-N-{3-[(4-methyl-1-piperazinyl)sulfonyl]-phenyl}-1H-thieno[2,3-c]pyrazole-5-carboxamide;
1-Cyclohexyl-3-methyl-N-{3-[(methylamino)sulfonyl]phenyl}-1H-thieno[2,3-c]pyrazole-5-carboxamide;
1-Cycloheptyl-3-methyl-N-[4-(4-methyl-1-piperazinyl)phenyl]-1H-thieno[2,3-c]pyrazole-5-carboxamide;
1-Cyclohexyl-3-methyl-N-[3-(4-methyl-1-piperazinyl)phenyl]-1H-thieno[2,3-c]pyrazole-5-carboxamide;
1-Cyclohexyl-N-[4-(4-hydroxy-1-piperidinyl)phenyl]-3-methyl-1H-thieno[2,3-c]pyrazole-5-carboxamide;
N-[4-(Acetylamino)-3-methoxyphenyl]-1-cycloheptyl-3-methyl-1H-thieno[2,3-c]pyrazole-5-carboxamide;
1-Cyclohexyl-N-(3,5-dichloro-4-pyridinyl)-3-methyl-1H-thieno-[2,3-c]pyrazole-5-carboxamide;
5-(4-Bromophenyl)-1-cyclohexyl-3-methyl-1H-thieno[2,3-c]pyrazole;
1-Cyclohexyl-3-methyl-5-[4-(4-methyl-1-piperazinyl)phenyl]-1H-thieno[2,3-c]pyrazole;
1-Cyclohexyl-3-methyl-5-[4-(4-methyl-1,4-diazepam-1-yl)phenyl]-1H-thieno[2,3-c]pyrazole;
1-Cyclohexyl-N-{3-fluoro-4-[(2-hydroxyethyl)(methyl)amino]phenyl}-3-methyl-1H-thieno[2,3-c]pyrazole-5-carboxamide;
1-Cyclohexyl-N-{3-fluoro-4-[(2-hydroxyethyl)(methyl)amino]phenyl}-3-methyl-1H-thieno[2,3-c]pyrazole-5-carboxamide HCl salt;
Ethyl cis-4-{[(1-cyclohexyl-3-methyl-1H-thieno[2,3-c]pyrazol-5-yl)carbonyl]amino}cyclohexanecarboxylate;
cis-4-{[(1-Cyclohexyl-3-methyl-1H-thieno[2,3-c]pyrazol-5-yl)-carbonyl]amino}cyclohexanecarboxylic acid;
1-Cyclohexyl-N-[cis-4-(hydroxymethyl)cyclohexyl]-3-methyl-1H-thieno[2,3-c]pyrazole-5-carboxamide;
Methyl trans-4-({[(1-cyclohexyl-3-methyl-1H-thieno[2,3-c]pyrazol-5-yl)carbonyl]amino)methyl}cyclohexanecarboxylate;
1-Cyclohexyl-N-{[trans-4-(hydroxymethyl)cyclohexyl]methyl}-3-methyl-1H-thieno[2,3-c]pyrazole-5-carboxamide;
tert-Butyl trans-4-({[(1-cyclohexyl-3-methyl-1H-thieno[2,3-c]-pyrazol-5-yl)carbonyl]amino}cyclohexylcarbamate;
N-(trans-4-Aminocyclohexyl)-1-cyclohexyl-3-methyl-1H-thieno[2,3-c-pyrazole-5-carboxamide;
1-Cyclohexyl-3-methyl-N-[trans-4-(4-morpholinyl)cyclohexyl]-1H-thieno[2,3-c]pyrazole-5-carboxamide;
1-Cyclohexyl-3-methyl-N-(4-piperidinyl)-1H-thieno[2,3-c]pyrazole-5-carboxamide;
1-Cyclohexyl-3-methyl-N-(1-tetrahydroro-2H-pyran-4-yl-4-piperidinyl)-1H-thieno[2,3-c]pyrazole-5-carboxamide;
1-Cyclohexyl-N-[1-(1,4-diazaspiro[4.5]decan-8-yl)-4-piperidinyl]-3-methyl-1H-thieno[2,3-c]pyrazole-5-carboxamide;
1-Cyclohexyl-3-methyl-N-[1-(4-oxocyclohexyl)-4-piperidinyl]-1H-thieno[2,3-c]pyrazole-5-carboxamide;
1-Cyclohexyl-N-[1-(trans-4-hydroxycyclohexyl)-4-piperidinyl]-3-methyl-1H-thieno[2,3-c]pyrazole-5-carboxamide;
tert-Butyl 4-(4-{[(1-cyclohexyl-3-methyl-1H-thieno[2,3-c]pyrazol-5-yl)carbonyl]amino}phenyl)-1-piperidinecarboxylate;
1-Cyclohexyl-3-methyl-N-[4-(4-piperidinyl)phenyl]-1H-thieno-[2,3-c]pyrazole-5-carboxamide;
1-Cyclohexyl-3-methyl-N-[4-(1-methyl-4-piperidinyl)phenyl]-1H-thieno[2,3-c]pyrazole-5-carboxamide;
1-Cyclohexyl-N-[4-(4-ethyl-1-piperazinyl)-3-fluorophenyl]-3-methyl-1H-thieno[2,3-c]pyrazole-5-carboxamide;
1-Cyclohexyl-N-[3-fluoro-4-(4-methyl-1,4-diazepam-1-yl)phenyl]-3-methyl-1H-thieno[2,3-c]pyrazole-5-carboxamide;
Ethyl 4-{[(1-cyclohexyl-3-methyl-1H-thieno[2,3-c]pyrazol-5-yl)-carbonyl]amino}-2-methoxybenzoate;
4-{[(1-Cyclohexyl-3-methyl-1H-thieno[2,3-c]pyrazol-5-yl)carbonyl]-amino}-2-methoxybenzoic acid;
1-Cyclohexyl-N-{3-methoxy-4-[(4-methyl-1-piperazinyl)carbonyl]-phenyl}-3-methyl-1H-thieno[2,3-c]pyrazole-5-carboxamide;
1-Cyclohexyl-N-[3-methoxy-4-(4-morpholinylcarbonyl)phenyl]-3-methyl-1H-thieno[2,3-c]pyrazole-5-carboxamide;
1-Cyclohexyl-N-{4-[(4-hydroxy-1-piperidinyl)carbonyl]-3-methoxyphenyl}-3-methyl-1H-thieno[2,3-c]pyrazole-5-carboxamide;
1-Cyclohexyl-N-(4-{[(2-hydroxyethyl)amino]carbonyl}-3-methoxy-phenyl)-3-methyl-1H-thieno[2,3-c]pyrazole-5-carboxamide;
1-Cyclohexyl-N-(3-methoxy-4-{[(2-methoxyethyl)amino]carbonyl}-phenyl)-3-methyl-1H-thieno[2,3-c]pyrazole-5-carboxamide;
1-Cyclohexyl-N-{3-methoxy-4-[(methylamino)carbonyl]phenyl}-3-methyl-1H-thieno[2,3-c]pyrazole-5-carboxamide;
1-Cyclohexyl-N-{4-[(dimethylamino)carbonyl]-3-methoxyphenyl}-3-methyl-1H-thieno[2,3-c]pyrazole-5-carboxamide;
1-Cyclohexyl-N-[3-fluoro-4-(4-methyl-1-piperazinyl)phenyl]-3-methyl-1H-thieno[2,3-c]pyrazole-5-carboxamide;

N-[3-Chloro-4-(4-methyl-1-piperazinyl)phenyl]-1-cyclohexyl-3-methyl-1H-thieno[2,3-c]pyrazole-5-carboxamide;

1-cyclohexyl-N-[4-(1,4-dioxa-8-azaspiro[4.5]deca-8-yl)-3-fluorophenyl]-3-methyl-1H-thieno[2,3-c]pyrazole-5-carboxamide;

1-Cyclohexyl-N-[3-fluoro-4-(4-oxo-1-piperidinyl)phenyl]-3-methyl-1H-thieno[2,3-c]pyrazole-5-carboxamide;

1-Cyclohexyl-N-[3-fluoro-4-(4-hydroxy-1-piperidinyl)phenyl]-3-methyl-1H-thieno[2,3-c]pyrazole-5-carboxamide;

N-[3-Chloro-4-(1,4-dioxa-8-azaspiro[4.5]deca-8-yl)phenyl]-1-cyclohexyl-3-methyl-1H-thieno[2,3-c]pyrazole-5-carboxamide;

N-[3-Chloro-4-(4-oxo-1-piperidinyl)phenyl]-1-cyclohexyl-3-methyl-1H-thieno[2,3-c]pyrazole-5-carboxamide;

N-[3-Chloro-4-(4-hydroxy-1-piperidinyl)phenyl]-1-cyclohexyl-3-methyl-1H-thieno[2,3-c]pyrazole-5-carboxamide;

1-Cyclohexyl-N-{3-fluoro-4-[4-(methylamino)-1-piperidinyl]phenyl}-3-methyl-1H-thieno[2,3-c]pyrazole-5-carboxamide;

tert-Butyl 1-(2-chloro-4-{[(1-cyclohexyl-3-methyl-1H-thieno[2,3-c]-pyrazol-5-yl)carbonyl]amino}phenyl)-4-piperidinyl(methyl)carbamate;

N-{3-Chloro-4-[4-(methylamino)-1-piperidinyl]phenyl}-1-cyclohexyl-3-methyl-1H-thieno[2,3-c]pyrazole-5-carboxamide;

1-Cyclohexyl-3-methyl-N-[trans-4-(4-methyl-1-piperazinyl)-cyclohexyl]-1H-thieno[2,3-c]pyrazole-5-carboxamide;

1-Cyclohexyl-3-methyl-N-{trans-4-(4-methyl-1,4-diazapam-1-yl)-cyclohexyl}-1H-thieno[2,3-c]pyrazole-5-carboxamide;

1-Cyclohexyl-N-[trans-4-(4-methoxy-1-piperidinyl)cyclohexyl]-3-methyl-1H-thieno[2,3-c]pyrazole-5-carboxamide;

Benzyl 4-(trans-4-{[(1-cyclohexyl-3-methyl-1H-thieno[2,3-c]pyrazol-5-yl)carbonyl]amino}cyclohexyl)-1,4-diazepam-1-carboxylate;

1-Cyclohexyl-N-[trans-4-(1,4-diazepam-1-yl)cyclohexyl]-3-methyl-1H-thieno[2,3-c]pyrazole-5-carboxamide;

N-[trans-4-(4-Acetyl-1,4-diazepam-1-yl)cyclohexyl]-1-cyclohexyl-3-methyl-1H-thieno[2,3-c]pyrazole-5-carboxamide;

1-Cyclohexyl-N-{trans-4-[(2-methoxyethyl)(methyl)amino]cyclohexyl}-3-methyl-1H-thieno[2,3-c]pyrazole-5-carboxamide;

1-Cyclohexyl-N-{cis-4-[(2-methoxyethyl)(methyl)amino]cyclohexyl}-3-methyl-1H-thieno[2,3-c]pyrazole-5-carboxamide;

1-Cyclohexyl-N-[trans-4-(1,4-dioxa-8-azaspiro[4.5]deca-8-yl)-cyclohexyl]-3-methyl-1H-thieno[2,3-c]pyrazole-5-carboxamide;

1-Cyclohexyl-3-methyl-N-[trans-4-(4-oxo-1-piperidinyl)cyclohexyl]-1H-thieno[2,3-c]pyrazole-5-carboxamide;

1-Cyclohexyl-N-[trans-4-(4-hydroxy-1-piperidinyl)cyclohexyl]-3-methyl-1H-thieno[2,3-c]pyrazole-5-carboxamide;

1-Cyclohexyl-N-{trans-4-[(2R,6S)-2,6-dimethylmorpholinyl]cyclohexyl}-3-methyl-1H-thieno[2,3-c]pyrazole-5-carboxamide;

1-Cyclohexyl-N-{cis-4-[(2R,6S)-2,6-dimethylmorpholinyl]cyclohexyl}-3-methyl-1H-thieno[2,3-c]pyrazole-5-carboxamide;

1-Cyclohexyl-3-methyl-N-{trans-4-[4-(methylamino)-1-piperidinyl]-cyclohexyl}-1H-thieno[2,3-c]pyrazole-5-carboxamide;

N-(trans-4-{4-[Acetyl(methyl)amino]-1-piperidinyl}cyclohexyl)-1-cyclohexyl-3-methyl-1H-thieno[2,3-c]pyrazole-5-carboxamide;

1-Cyclohexyl-N-{trans-4-[4-(dimethylamino)-1-piperidinyl]cyclohexyl}-3-methyl-1H-thieno[2,3-c]pyrazole-5-carboxamide;

tert-Butyl 1-(trans-4-{[(1-cyclohexyl-3-methyl-1H-thieno[2,3-c]-pyrazol-5-yl)carbonyl]amino}cyclohexyl)-4-piperidinylcarbamate;

tert-Butyl 1-(cis-4-{[(1-cyclohexyl-3-methyl-1H-thieno[2,3-c]-pyrazol-5-yl)carbonyl]amino}cyclohexyl)-4-piperidinylcarbamate;

N-[trans-4-(4-Amino-1-piperidinyl)cyclohexyl]-1-cyclohexyl-3-methyl-1H-thieno[2,3-c]pyrazole-5-carboxamide;

N-[cis-4-(4-Amino-1-piperidinyl)cyclohexyl]-1-cyclohexyl-3-methyl-1H-thieno[2,3-c]pyrazole-5-carboxamide;

tert-Butyl 4-(trans-4-{[(1-cyclohexyl-3-methyl-1H-thieno[2,3-c]-pyrazol-5-yl)carbonyl]amino}cyclohexyl)-1-piperazinecarboxylate;

tert-Butyl 4-(cis-4-{[(1-cyclohexyl-3-methyl-1H-thieno[2,3-c]-pyrazol-5-yl)carbonyl]amino}cyclohexyl)-1-piperazinecarboxylate;

1-Cyclohexyl-3-methyl-N-[trans-4-(1-piperazinyl)cyclohexyl]-1H-thieno[2,3-c]pyrazole-5-carboxamide;

1-Cyclohexyl-3-methyl-N-[cis-4-(1-piperazinyl)cyclohexyl]-1H-thieno[2,3-c]pyrazole-5-carboxamide;

N-[trans-4-(4-Acetyl-1-piperazinyl)cyclohexyl]-1-cyclohexyl-3-methyl-1H-thieno[2,3-c]pyrazole-5-carboxamide;

1-Cyclohexyl-N-[3-fluoro-4-(4-methyl-1,4-diazapam-1-yl)phenyl]-3-methyl-1H-thieno[2,3-c]pyrazole-5-carboxamide;

Ethyl 3-methyl-1-tetrahydro-2H-pyran-4-yl-1H-thieno[2,3-c]-pyrazole-5-carboxamide;

3-Methyl-1-tetrahydro-2H-pyran-4-yl-1H-thieno[2,3-c]pyrazole-5-carboxylic acid;

3-Methyl-N-[4-(4-methyl-1-piperazinyl)phenyl]-1-tetrahydro-2H-pyran-4-yl-1H-thieno[2,3-c]pyrazole-5-carboxamide;

N-[3-Fluoro-4-(4-methyl-1-piperazinyl)phenyl]-3-methyl-1-tetrahydro-2H-pyran-4-yl-1H-thieno[2,3-c]pyrazole-5-carboxamide;

1-Cyclohexyl-3-methyl-N-[4-(4-morpholinylmethyl)phenyl]-1H-thieno[2,3-c]pyrazole-5-carboxamide;

1-Cyclohexyl-N-{4-[2-(dimethylamino)ethyl]phenyl}-3-methyl-1H-thieno[2,3-c]pyrazole-5-carboxamide;

1-Cyclohexyl-3-methyl-N-{4-[2-(4-morpholinyl)ethyl]phenyl}-1H-thieno[2,3-c]pyrazole-5-carboxamide;

1-Cyclohexyl-3-methyl-N-{4-[(3-methyl-2,5-dioxo-1-imidazolidinyl)-methyl]phenyl}-1H-thieno[2,3-c]pyrazole-5-carboxamide;

1-Cyclohexyl-3-methyl-N-[4-(3-methyl-2,5-dioxo-1-imidazolidinyl)-phenyl]-1H-thieno[2,3-c]pyrazole-5-carboxamide;

Methyl trans-4-{[(1-cyclohexyl-3-methyl-1H-thieno[2,3-c]pyrazol-5-yl)carbonyl]amino}cyclohexanecarboxylate;

4-{[(1-Cyclohexyl-3-methyl-1H-thieno[2,3-c]pyrazole-5-yl)carbonyl]-amino}cyclohexanecarboxylic acid;

1-Cyclohexyl-N-[4-(hydroxymethyl)cyclohexyl]-3-methyl-1H-thieno-[2,3-c]pyrazole-5-carboxamide;

1-Cyclohexyl-3-methyl-N-{4-[(4-methyl-1-piperazinyl)carbonyl]-cyclohexyl}-1H-thieno[2,3-c]pyrazole-5-carboxamide;

1-Cyclohexyl-N-{4-[(dimethylamino)carbonyl]cyclohexyl}-3-methyl-1H-thieno[2,3-c]pyrazole-5-carboxamide;
N-(4-Cyanocyclohexyl)-1-cyclohexyl-3-methyl-1H-thieno-[2,3-c]pyrazole-5-carboxamide;
tert-Butyl 2-{[(1-cyclohexyl-3-methyl-1H-thieno[2,3-c]pyrazol-5-yl)carbonyl]amino}ethyl(methyl)carbamate;
1-Cyclohexyl-3-methyl-N-[2-(methylamino)ethyl]-1H-thieno-[2,3-c]pyrazole-5-carboxamide;
N-{2-[Acetyl(methyl)amino]ethyl}-1-cyclohexyl-3-methyl-1H-thieno[2,3-c]pyrazole-5-carboxamide;
1-Cyclohexyl-3-methyl-N-{2-[methyl(methylsulfonyl)amino]ethyl}-1H-thieno[2,3-c]pyrazole-5-carboxamide;
Ethyl (4-{[(1-cyclohexyl-3-methyl-1H-thieno[2,3-c]pyrazol-5-yl)-carbonyl]amino}-1-piperidinyl)acetate;
(4-{[(1-Cyclohexyl-3-methyl-1H-thieno[2,3-c]pyrazol-5-yl)carbonyl]-amino}-1-piperidinyl)acetic acid;
Ethyl 2-(4-{[(1-cyclohexyl-3-methyl-1H-thieno[2,3-c]pyrazol-5-yl)-carbonyl]aminol}-1-piperidinyl)-2-methylpropanoate;
2-(4-{[(1-Cyclohexyl-3-methyl-1H-thieno[2,3-c]pyrazol-5-yl)-carbonyl]amino}-1-piperidinyl)-2-methylpropanoic acid;
1-Cyclohexyl-N-[2-(5,5-dimethyl-2,4-dioxo-1,3-oxazolidin-3-yl)-ethyl]-3-methyl-1H-thieno[2,3-c]pyrazole-5-carboxamide;
1-Cyclohexyl-3-methyl-N-{2-[methyl(4-morpholinylcarbonyl)amino]-ethyl}-1H-thieno[2,3-c]pyrazole-5-carboxamide;
1-Cyclohexyl-N-{2-[[(dimethylamino)carbonyl](methyl)amino]ethyl}-3-methyl-1H-thieno[2,3-c]pyrazole-5-carboxamide;
Methyl 2-{[(1-cyclohexyl-3-methyl-1H-thieno[2,3-c]pyrazol-5-yl)-carbonyl]amino}ethyl(methyl)carbamate;
1-Cyclohexyl-N-{2-[(methoxyacetyl)(methyl)amino]ethyl}-3-methyl-1H-thieno[2,3-c]pyrazole-5-carboxamide;
1-Cyclohexyl-N-{2-[glycoloyl(methyl)amino]ethyl}-3-methyl-1H-thieno[2,3-c]pyrazole-5-carboxamide;
1-Cyclohexyl-N-(4-{[(2-hydroxyethyl)(methyl)amino]carbonyl}cyclohexyl)-3-methyl-1H-thieno[2,3-c]pyrazole-5-carboxamide;
Methyl (1S,3S)-3-{[(1-cyclohexyl-3-methyl-1H-thieno[2,3-c]pyrazol-5-yl)carbonyl]amino}cyclopentanecarboxylate;
(1S,3S)-3-{[(1-Cyclohexyl-3-methyl-1H-thieno[2,3-c]pyrazol-5-yl)-carbonyl]amino}cyclopentanecarboxylic acid;
1-Cyclohexyl-3-methyl-N-[2-(4-methyl-2,3-dioxo-1-piperazinyl)-ethyl]-1H-thieno[2,3-c]pyrazole-5-carboxamide;
1-Cyclohexyl-N-{(1S,3S)-3-[(dimethylamino)carbonyl]cyclopentyl}-3-methyl-1H-thieno[2,3-c]pyrazole-5-carboxamide;
Methyl (1R,3R)-3-{[(1-cyclohexyl-3-methyl-1H-thieno[2,3-c]pyrazol-5-yl)carbonyl]amino}cyclopentanecarboxylate;
(1R,3R)-3-{[(1-Cyclohexyl-3-methyl-1H-thieno[2,3-c]pyrazol-5-yl)-carbonyl]amino}cyclopentanecarboxylic acid;
1-Cyclohexyl-N-{(1R,3R)-3-[(dimethylamino)carbonyl]cyclopentyl}-3-methyl-1H-thieno[2,3-c]pyrazole-5-carboxamide;
1-Cyclohexyl-N-{1-[(dimethylamino)carbonyl]-4-piperidinyl}-3-methyl-1H-thieno[2,3-c]pyrazole-5-carboxamide;
1-Cyclohexyl-3-methyl-N-[4-(4-morpholinylcarbonyl)cyclohexyl]-1H-thieno[2,3-c]pyrazole-5-carboxamide;
1-Cyclohexyl-3-methyl-N-{4-[(methylamino)carbonyl]cyclohexyl}-1H-thieno[2,3-c]pyrazole-5-carboxamide;
1-Cyclohexyl-N-{4-[(cyclopropylamino)carbonyl]cyclohexyl}-3-methyl-1H-thieno[2,3-c]pyrazole-5-carboxamide;
1-Cyclohexyl-N-{4-[(4-hydroxy-1-piperidinyl)carbonyl]cyclohexyl}-3-methyl-1H-thieno[2,3-c]pyrazole-5-carboxamide;
1-Cyclohexyl-N-{1-[(dimethylamino)sulfonyl]-4-piperidinyl}-3-methyl-1H-thieno[2,3-c]pyrazole-5-carboxamide;
tert-Butyl 4-{[(1-cyclohexyl-3-methyl-1H-thieno[2,3-c]pyrazol-5-yl)carbonyl]amino}-1-piperidinecarboxylate;
1-Cyclohexyl-3-methyl-N-(4-piperidinyl)-1H-thieno[2,3-c]pyrazole-5-carboxamide;
N-[(3S)-1-Benzylpyrrolidinyl]-1-cyclohexyl-3-methyl-1H-thieno[2,3-c]pyrazole-5-carboxamide;
1-Cyclohexyl-3-methyl-N-[(3S)-pyrrolidinyl]-1H-thieno[2,3-c]-pyrazole-5-carboxamide;
1-Cyclohexyl-N-{(3S)-1-[(dimethylamino)carbonyl]pyrrolidinyl}-3-methyl-1H-thieno[2,3-c]pyrazole-5-carboxamide;
1-Cyclohexyl-N-{4-[(2,5-dioxo-1-imidazolidinyl)methyl]cyclohexyl}-3-methyl-1H-thieno[2,3-c]pyrazole-5-carboxamide;
Ethyl 1-[(1-cyclohexyl-3-methyl-1H-thieno[2,3-c]pyrazol-5-yl)-carbonyl]-4-piperidinecarboxylate;
1-[(1-Cyclohexyl-3-methyl-1H-thieno[2,3-c]pyrazol-5-yl)carbonyl]-4-piperidinecarboxylic acid;
1-[(1-Cyclohexyl-3-methyl-1H-thieno[2,3-c]pyrazol-5-yl)carbonyl]-N-methyl-4-piperidinecarboxamide;
Ethyl (3S)-1-[(1-cyclohexyl-3-methyl-1H-thieno[2,3-c]pyrazol-5-yl)-carbonyl]-3-piperidinecarboxylate;
N-[(6S,7aS)-1,3-Dioxohexahydro-1H-pyrrolo[1,2-c]imidazol-6-yl]-1-cyclohexyl-3-methyl-1H-thieno[2,3-c]pyrazole-5-carboxamide;
N-[(6S,7aS)-2-Methyl-1,3-dioxohexahydro-1H-pyrrolo[1,2-c]imidazol-6-yl]-1-cyclohexyl-3-methyl-1H-thieno[2,3-c]pyrazole-5-carboxamide;
{1-[(1-Cyclohexyl-3-methyl-1H-thieno[2,3-c]pyrazol-5-yl)carbonyl]-3-piperidinyl}methanol;
N-{4-[(Dimethylamino)carbonyl]phenyl}-3-methyl-1-tetrahydro-2H-pyran-4-yl-1H-thieno[2,3-c]pyrazole-5-carboxamide;
1-Cyclohexyl-3-methyl-N-[6-(2-oxo-1-imidazolidinyl)-3-pyridinyl]-1H-thieno[2,3-c]pyrazole-5-carboxamide;
1-Cyclohexyl-N-[(1S,3S)-3-(hydroxymethyl)cyclopentyl]-3-methyl-1H-thieno[2,3-c]pyrazole-5-carboxamide;
1-Cyclohexyl-N-{(1S,3S)-3-[(2,5-dioxo-1-imidazolidinyl)methyl]-cyclopentyl}-3-methyl-1H-thieno[2,3-c]pyrazole-5-carboxamide;
1-Cyclohexyl-N-[4-(2,5-dioxo-1-imidazolidinyl)phenyl]-3-methyl-1H-thieno[2,3-c]pyrazole-5-carboxamide;
3-Methyl-N-[4-(3-methyl-2,5-dioxo-1-imidazolidinyl)phenyl]-1-tetrahydro-2H-pyran-4-yl-1H-thieno[2,3-c]pyrazole-5-carboxamide;
3-Methyl-N-[6-(2-oxo-1-imidazolidinyl)-3-pyridinyl]-1-tetrahydro-2H-pyran-4-yl-1H-thieno[2,3-c]pyrazole-5-carboxamide;
1-Cyclohexyl-N-{4-[(3R)-3-hydroxypyrrolidinyl]phenyl}-3-methyl-1H-thieno[2,3-c]pyrazole-5-carboxamide;
1-Cyclohexyl-N-{3-fluoro-4-[(3R)-3-hydroxypyrrolidinyl]phenyl}-3-methyl-1H-thieno[2,3-c]pyrazole-5-carboxamide;
1-Cyclohexyl-N-{3-[(4-hydroxy-1-piperidinyl)sulfonyl]phenyl}-3-methyl-1H-thieno[2,3-c]pyrazole-5-carboxamide;
N-{4-[4-{[tert-Butyl(dimethyl)silyl]oxy}-1-piperidinyl]sulfonyl}-phenyl}-1-cyclohexyl-3-methyl-1H-thieno[2,3-c]pyrazole-5-carboxamide;

1-Cyclohexyl-N-{4-[(4-hydroxy-1-piperidinyl)sulfonyl]phenyl}-3-methyl-1H-thieno[2,3-c]pyrazole-5-carboxamide;

1-Cyclohexyl-N-[4-(2-hydroxyethyl)phenyl]-3-methyl-1H-thieno[2,3-c]pyrazole-5-carboxamide;

N-[3-Fluoro-4-(4-hydroxy-1-piperidinyl)phenyl]-3-methyl-1-tetrahydro-2H-pyran-4-yl-1H-thieno[2,3-c]pyrazole-5-carboxamide;

1-Cyclohexyl-3-methyl-N-[4-(4-methyl-1-piperazinyl)-3-(trifluoromethyl)phenyl]-1H-thieno[2,3-c]pyrazole-5-carboxamide;

1-Cyclohexyl-3-methyl-N-[4-(2-oxo-1,3-oxazolidin-3-yl)cyclohexyl]-1H-thieno[2,3-c]pyrazole-5-carboxamide;

1-Cyclohexyl-3-methyl-N-[4-(2-oxo-1-imidazolidinyl)cyclohexyl]-1H-thieno[2,3-c]pyrazole-5-carboxamide;

4-[(4-{[(1-Cyclohexyl-3-methyl-1H-thieno[2,3-c]pyrazol-5-yl)-carbonyl]amino}cyclohexyl)amino]-4-oxobutanoic acid;

1-Cyclohexyl-N-[4-(2,5-dioxo-1-pyrrolidinyl)cyclohexyl]-3-methyl-1H-thieno[2,3-c]pyrazole-5-carboxamide;

1-Cyclohexyl-N-[4-(1,1-dioxide-2-isothiazolidinyl)cyclohexyl]-3-methyl-1H-thieno[2,3-c]pyrazole-5-carboxamide;

Benzyl [{[(4-{[(1-cyclohexyl-3-methyl-1H-thieno[2,3-c]pyrazol-5-yl)-carbonyl]amino}cyclohexyl)amino]carbonyl}(methyl)amino]acetate;

1-Cyclohexyl-3-methyl-N-[4-(3-methyl-2,5-dioxo-1-imidazolidinyl)-cyclohexyl]-1H-thieno[2,3-c]pyrazole-5-carboxamide;

1-Cyclohexyl-3-methyl-N-[2-(3-methyl-2,5-dioxo-1-imidazolidinyl)-ethyl]-1H-thieno[2,3-c]pyrazole-5-carboxamide;

1-Cyclohexyl-3-methyl-N-[3-(3-methyl-2,5-dioxo-1-imidazolidinyl)-propyl]-1H-thieno[2,3-c]pyrazole-5-carboxamide;

1-Cyclohexyl-N-[4-({[(2-hydroxyethyl)(methyl)amino]carbonyl}amino)-cyclohexyl]-3-methyl-1H-thieno[2,3-c]pyrazole-5-carboxamide;

1-Cyclohexyl-3-methyl-N-[4-(3-methyl-2-oxo-1-imidazolidinyl)-cyclohexyl]-1H-thieno[2,3-c]pyrazole-5-carboxamide;

Ethyl 3-{[(1-cyclohexyl-3-methyl-1H-thieno[2,3-c]pyrazol-5-yl)-carbonyl]amino}propanoate;

N-[(1-Cyclohexyl-3-methyl-1H-thieno[2,3-c]pyrazol-5-yl)carbonyl]-β-alanine;

tert-Butyl {[(1-cyclohexyl-3-methyl-1H-thieno[2,3-c]pyrazol-5-yl)-carbonyl]amino}acetate;

{[(1-Cyclohexyl-3-methyl-1H-thieno[2,3-c]pyrazol-5-yl)carbonyl]-amino}acetic acid;

1-Cyclohexyl-3-methyl-N-[3-(4-morpholinyl)-3-oxopropyl]-1H-thieno[2,3-c]pyrazole-5-carboxamide;

tert-Butyl 2-{[(1-cyclohexyl-3-methyl-1H-thieno[2,3-c]pyrazol-5-yl)-carbonyl]amino}ethylcarbamate;

N-(2-Aminoethyl)-1-cyclohexyl-3-methyl-1H-thieno[2,3-c]pyrazole-5-carboxamide;

1-Cyclohexyl-N-[3-(dimethylamino)-3-oxopropyl]-3-methyl-1H-thieno[2,3-c]pyrazole-5-carboxamide;

1-Cyclohexyl-3-methyl-N-{3-[methyl(1-methyl-4-piperidinyl)amino]-3-oxopropyl}-1H-thieno[2,3-c]pyrazole-5-carboxamide;

1-Cyclohexyl-N-[3-(4-hydroxy-1-piperidinyl)-3-oxopropyl]-3-methyl-1H-thieno[2,3-c]pyrazole-5-carboxamide;

1-Cyclohexyl-3-methyl-N-[2-(4-morpholinyl)-2-oxoethyl]-1H-thieno[2,3-c]pyrazole-5-carboxamide;

1-Cyclohexyl-N-[2-(dimethylamino)-2-oxoethyl]-3-methyl-1H-thieno[2,3-c]pyrazole-5-carboxamide;

1-Cyclohexyl-3-methyl-N-[2-(4-methyl-1-piperazinyl)-2-oxoethyl]-1H-thieno[2,3-c]pyrazole-5-carboxamide;

1-Cyclohexyl-N-[2-(4-hydroxy-1-piperidinyl)-2-oxoethyl]-3-methyl-1H-thieno[2,3-c]pyrazole-5-carboxamide;

1-Cyclohexyl-3-methyl-N-[3-(4-methyl-1-piperazinyl)-3-oxopropyl]-1H-thieno[2,3-c]pyrazole-5-carboxamide;

1-Cyclohexyl-3-methyl-N-{2-[methyl(1-methyl-4-piperidinyl)amino]-2-oxoethyl}-1H-thieno[2,3-c]pyrazole-5-carboxamide;

1-Cyclohexyl-3-methyl-N-[2-(2-oxo-1,3-oxazolidin-3-yl)ethyl]-1H-thieno[2,3-c]pyrazole-5-carboxamide;

1-Cyclohexyl-N-[2-(1,1-dioxide-2-isothiazolidinyl)ethyl]-3-methyl-1H-thieno[2,3-c]pyrazole-5-carboxamide;

1-Cyclohexyl-N-[2-({[(2-hydroxyethyl)(methyl)amino]carbonyl}amino)-ethyl]-3-methyl-1H-thieno[2,3-c]pyrazole-5-carboxamide;

1-Cyclohexyl-3-methyl-N-[2-(3-methyl-2-oxo-1-imidazolidinyl)ethyl]-1H-thieno[2,3-c]pyrazole-5-carboxamide;

Ethyl 4-{[(1-cyclohexyl-3-methyl-1H-thieno[2,3-c]pyrazol-5-yl)-carbonyl]amino}butanoate;

4-{[(1-Cyclohexyl-3-methyl-1H-thieno[2,3-c]pyrazol-5-yl)carbonyl]-amino}butanoic acid;

1-Cyclohexyl-N-[2-(2,5-dioxo-1-imidazolidinyl)ethyl]-3-methyl-1H-thieno[2,3-c]pyrazole-5-carboxamide;

1-Cyclohexyl-N-[4-(dimethylamino)-4-oxobutyl]-3-methyl-1H-thieno[2,3-c]pyrazole-5-carboxamide;

1-Cyclohexyl-3-methyl-N-[2-(3,4,4-trimethyl-2,5-dioxo-1-imidazolidinyl)ethyl]-1H-thieno[2,3-c]pyrazole-5-carboxamide;

1-Cyclohexyl-N-[2-(2,4-dioxo-1,3-thiazolidin-3-yl)ethyl]-3-methyl-1H-thieno[2,3-c]pyrazole-5-carboxamide;

1-Cyclohexyl-N-[1-(hydroxymethyl)cyclopropyl]-3-methyl-1H-thieno[2,3-c]pyrazole-5-carboxamide;

1-Cyclohexyl-3-methyl-N-{1-[(3-methyl-2,5-dioxo-1-imidazolidinyl)-methyl]cyclopropyl}-1H-thieno[2,3-c]pyrazole-5-carboxamide;

Methyl [(2-{[(1-cyclohexyl-3-methyl-1H-thieno[2,3-c]pyrazol-5-yl)-carbonyl]amino}ethyl)amino]acetate;

Methyl [(aminocarbonyl)(2-{[(1-cyclohexyl-3-methyl-1H-thieno-[2,3-c]pyrazol-5-yl)carbonyl]amino}ethyl)amino]acetate;

1-Cyclohexyl-N-[2-(2,4-dioxo-1-imidazolidinyl)ethyl]-3-methyl-1H-thieno[2,3-c]pyrazole-5-carboxamide;

1-Cyclohexyl-N-[2-(4,4-dimethyl-2,5-dioxo-1-imidazolidinyl)ethyl]-3-methyl-1H-thieno[2,3-c]pyrazole-5-carboxamide;

1-Cyclohexyl-3-methyl-N-[2-(5-methyl-1,1-dioxide-1,2,5-thiadiazolidin-2-yl)ethyl]-1H-thieno[2,3-c]pyrazole-5-carboxamide;

1-Cyclohexyl-N-[2-(3-ethyl-2,4-dioxo-1-imidazolidinyl)ethyl]-3-methyl-1H-thieno[2,3-c]pyrazole-5-carboxamide;

1-Cyclohexyl-3-methyl-N-[2-(3-methyl-2,4-dioxo-1-imidazolidinyl)-ethyl]-1H-thieno[2,3-c]pyrazole-5-carboxamide;

1-Cyclohexyl-N-[(1S)-2-hydroxy-1-methylethyl]-3-methyl-1H-thieno[2,3-c]pyrazole-5-carboxamide;

1-Cyclohexyl-N-[(1S)-2-(2,5-dioxo-1-imidazolidinyl)-1-methylethyl]-3-methyl-1H-thieno[2,3-c]pyrazole-5-carboxamide;

N-[(3R)-1-Benzylpyrrolidinyl]-1-cyclohexyl-3-methyl-1H-thieno[2,3-c]pyrazole-5-carboxamide;

1-Cyclohexyl-3-methyl-N-[(3R)-pyrrolidinyl]-1H-thieno[2,3-c]pyrazole-5-carboxamide;

1-Cyclohexyl-N-{(3R)-1-[(dimethylamino)carbonyl]pyrrolidinyl}-3-methyl-1H-thieno[2,3-c]pyrazole-5-carboxamide;

1-Cyclohexyl-N-[(1R)-2-hydroxy-1-methylethyl]-3-methyl-1H-thieno[2,3-c]pyrazole-5-carboxamide;
1-Cyclohexyl-N-[(1R)-2-(2,5-dioxo-1-imidazolidinyl)-1-methylethyl]-3-methyl-1H-thieno[2,3-c]pyrazole-5-carboxamide;
1-Cyclohexyl-N-[(2S)-2-hydroxypropyl]-3-methyl-1H-thieno[2,3-c]-pyrazole-5-carboxamide;
1-Cyclohexyl-N-[(2R)-2-(2,5-dioxo-1-imidazolidinyl)propyl]-3-methyl-1H-thieno[2,3-c]pyrazole-5-carboxamide;
1-Cyclohexyl-N-[(2R)-2-hydroxypropyl]-3-methyl-1H-thieno[2,3-c]pyrazole-5-carboxamide;
1-Cyclohexyl-N-[(2S)-2-(2,5-dioxo-1-imidazolidinyl)propyl]-3-methyl-1H-thieno[2,3-c]pyrazole-5-carboxamide;
1-Cyclohexyl-N-[(1R)-1-(hydroxymethyl)propyl]-3-methyl-1H-thieno[2,3-c]pyrazole-5-carboxamide;
1-Cyclohexyl-N-{(1R)-1-[(2,5-dioxo-1-imidazolidinyl)methyl]propyl}-3-methyl-1H-thieno[2,3-c]pyrazole-5-carboxamide;
1-Cyclohexyl-N-[(1R)-1-(hydroxymethyl)-2-methylpropyl]-3-methyl-1H-thieno[2,3-c]pyrazole-5-carboxamide;
1-Cyclohexyl-N-{(1R)-1-[(2,5-dioxo-1-imidazolidinyl)methyl]-2-methylpropyl}-3-methyl-1H-thieno[2,3-c]pyrazole-5-carboxamide;
tert-Butyl 2-{[(1-cyclohexyl-3-methyl-1H-thieno[2,3-c]pyrazol-5-yl)-carbonyl]amino}-2-methylpropylcarbamate;
N-(2-Amino-1,1-dimethylethyl)-1-cyclohexyl-3-methyl-1H-thieno[2,3-c]pyrazole-5-carboxamide;
1-Cyclohexyl-N-[2-(2,5-dioxo-1-imidazolidinyl)-1,1-dimethylethyl]-3-methyl-1H-thieno[2,3-c]pyrazole-5-carboxamide;
N-(3-Amino-2,2-dimethylpropyl)-1-cyclohexyl-3-methyl-1H-thieno[2,3-c]pyrazole-5-carboxamide;
1-Cyclohexyl-N-[3-(2,5-dioxo-1-imidazolidinyl)-2,2-dimethylpropyl]-3-methyl-1H-thieno[2,3-c]pyrazole-5-carboxamide;
(±)-1-Cyclohexyl-N-[trans-2-(hydroxymethyl)cyclopropyl]-3-methyl-1H-thieno[2,3-c]pyrazole-5-carboxamide;
N-[4-(4-Hydroxy-1-piperidinyl)phenyl]-3-methyl-1-tetrahydro-2H-pyran-4-yl-1H-thieno[2,3-c]pyrazole-5-carboxamide;
1-Cyclohexyl-3-methyl-N-[4-(3-oxo-1-piperazinyl)phenyl]-1H-thieno[2,3-c]pyrazole-5-carboxamide;
3-Methyl-N-[4-(3-oxo-1-piperazinyl)phenyl]-1-tetrahydro-2H-pyran-4-yl-1H-thieno[2,3-c]pyrazole-5-carboxamide;
Methyl 3-{[(1-cyclohexyl-3-methyl-1H-thieno[2,3-c]pyrazol-5-yl)-carbonyl]amino}benzoate;
3-{[(1-Cyclohexyl-3-methyl-1H-thieno[2,3-c]pyrazol-5-yl)carbonyl]-amino}benzoic acid;
1-Cyclohexyl-N-{3-[(dimethylamino)carbonyl]phenyl}-3-methyl-1H-thieno[2,3-c]pyrazole-5-carboxamide;
1-Cyclohexyl-3-methyl-N-[3-(4-morpholinylcarbonyl)phenyl]-1H-thieno[2,3-c]pyrazole-5-carboxamide;
Methyl trans-4-{[(3-methyl-1-tetrahydro-2H-pyran-4-yl-1H-thieno-[2,3-c]pyrazol-5-yl)carbonyl]amino}cyclohexanecarboxylate;
trans-4-{[(3-Methyl-1-tetrahydro-2H-pyran-4-yl-1H-thieno[2,3-c]-pyrazol-5-yl)carbonyl]amino}cyclohexanecarboxylic acid;
N-{trans-4-[(Dimethylamino)carbonyl]cyclohexyl}-3-methyl-1-tetrahydro-2H-pyran-4-yl-1H-thieno[2,3-c]pyrazole-5-carboxamide;
3-Methyl-N-[trans-4-(4-morpholinylcarbonyl)cyclohexyl]-1-tetrahydro-2H-pyran-4-yl-1H-thieno[2,3-c]pyrazole-5-carboxamide;
N-{trans-4-[(4-Hydroxy-1-piperidinyl)carbonyl]cyclohexyl}-3-methyl-1-tetrahydro-2H-pyran-4-yl-1H-thieno[2,3-c]pyrazole-5-carboxamide;
3-Methyl-N-{trans-4-[(4-methyl-1-piperazinyl)carbonyl]cyclohexyl}-1-tetrahydro-2H-pyran-4-yl-1H-thieno[2,3-c]pyrazole-5-carboxamide;
1-Cyclohexyl-3-methyl-N-[3-(4-morpholinyl)propyl]-1H-thieno[2,3-c]pyrazole-5-carboxamide;
1-Cyclohexyl-3-methyl-N-[2-(4-morpholinyl)ethyl]-1H-thieno[2,3-c]pyrazole-5-carboxamide;
1-Cyclohexyl-3-methyl-N-[2-(1-piperidinyl)ethyl]-1H-thieno[2,3-c]pyrazole-5-carboxamide;
N-[trans-4-(Hydroxymethyl)cyclohexyl]-3-methyl-1-tetrahydro-2H-pyran-4-yl-1H-thieno[2,3-c]pyrazole-5-carboxamide;
(trans-4-{[(3-Methyl-1-tetrahydro-2H-pyran-4-yl-1H-thieno[2,3-c]-pyrazol-5-yl)carbonyl]amino}cyclohexyl)methyl p-toluenesulfonate;
3-Methyl-N-[trans-4-(4-morpholinylmethyl)cyclohexyl]-1-tetrahydro-2H-pyran-4-yl-1H-thieno[2,3-c]pyrazole-5-carboxamide;
N-{trans-4-[(Dimethylamino)methyl]cyclohexyl}-3-methyl-1-tetrahydro-2H-pyran-4-yl-1H-thieno[2,3-c]pyrazole-5-carboxamide;
N-{trans-4-[(4-Acetyl-1-piperazinyl)methyl]cyclohexyl}-3-methyl-1-tetrahydro-2H-pyran-4-yl-1H-thieno[2,3-c]pyrazole-5-carboxamide;
N-{3-[(Dimethylamino)sulfonyl]phenyl}-3-methyl-1-tetrahydro-2H-pyran-4-yl-1H-thieno[2,3-c]pyrazole-5-carboxamide;
3-Methyl-N-[3-(methylsulfonyl)phenyl]-1-tetrahydro-2H-pyran-4-yl-1H-thieno[2,3-c]pyrazole-5-carboxamide;
N-{3-[(2-{[tert-Butyl(dimethyl)silyl]oxy}ethyl)sulfonyl]phenyl}-3-methyl-1-tetrahydro-2H-pyran-4-yl-1H-thieno[2,3-c]pyrazole-5-carboxamide;
N-[3-{(2-Hydroxyethyl)sulfonyl]phenyl}-3-methyl-1-tetrahydro-2H-pyran-4-yl-1H-thieno[2,3-c]pyrazole-5-carboxamide;
3-Methyl-N-[trans-4-(4-morpholinyl)cyclohexyl]-1-tetrahydro-2H-pyran-4-yl-1H-thieno[2,3-c]pyrazole-5-carboxamide;
1-Cyclohexyl-N-[6-(4-hydroxy-1-piperidinyl)-3-pyridinyl]-3-methyl-1H-thieno[2,3-c]pyrazole-5-carboxamide;
1-Cyclohexyl-N-[2,3-difluoro-4-(4-hydroxy-1-piperidinyl)phenyl]-3-methyl-1H-thieno[2,3-c]pyrazole-5-carboxamide;
1-Cyclohexyl-N-[4-(4-hydroxy-1-piperidinyl)-3-methylphenyl]-3-methyl-1H-thieno[2,3-c]pyrazole-5-carboxamide;
N-[3-cyano-4-(4-hydroxy-1-piperidinyl)phenyl]-1-cyclohexyl-3-methyl-1H-thieno[2,3-c]pyrazole-5-carboxamide;
Methyl 5-{[(1-cyclohexyl-3-methyl-1H-thieno[2,3-c]pyrazol-5-yl)-carbonyl]amino}-2-(4-hydroxy-1-piperidinyl)benzoate;
5-{[(1-Cyclohexyl-3-methyl-1H-thieno[2,3-c]pyrazol-5-yl)carbonyl]-amino}-2-(4-hydroxy-1-piperidinyl)benzoic acid;
N-[6-(4-Hydroxy-1-piperidinyl)-3-pyridinyl]-3-methyl-1-tetrahydro-2H-pyran-4-yl-1H-thieno[2,3-c]pyrazole-5-carboxamide;
3-Methyl-1-tetrahydro-2H-pyran-4-yl-N-(1-tetrahydro-2H-pyran-4-yl-4-piperidinyl)-1H-thieno[2,3-c]pyrazole-5-carboxamide;
1-Cyclohexyl-N-{6-[(4-hydroxy-1-piperidinyl)carbonyl]-3-pyridinyl}-3-methyl-1H-thieno[2,3-c]pyrazole-5-carboxamide;

1-Cyclohexyl-N-(6-{[(2-hydroxyethyl)amino]carbonyl}-3-pyridinyl)-3-methyl-1H-thieno[2,3-c]pyrazole-5-carboxamide;

1-Cyclohexyl-3-methyl-N-{6-[(4-methyl-1-piperazinyl)carbonyl]-3-pyridinyl}-1H-thieno[2,3-c]pyrazole-5-carboxamide;

1-Cyclohexyl-N-[6-({[2-(dimethylamino)ethyl]amino}carbonyl)-3-pyridinyl)-3-methyl-1H-thieno[2,3-c]pyrazole-5-carboxamide;

1-Cyclohexyl-N-(6-{[(trans-4-hydroxycyclohexyl)amino]carbonyl}-3-pyridinyl]-3-methyl-1H-thieno[2,3-c]pyrazole-5-carboxamide;

1-Cyclohexyl-3-methyl-N-{6-[(4-methyl-1,4-diazepam-1-yl)carbonyl]-3-pyridinyl}-1H-thieno[2,3-c]pyrazole-5-carboxamide;

tert-Butyl 4-{[(3-methyl-1-tetrahydro-2H-pyran-4-yl-1H-thieno[2,3-c]-pyrazol-5-yl)carbonyl]aminol}-1-piperidinecarboxylate;

3-Methyl-N-(4-piperidinyl)-1-tetrahydro-2H-pyran-4-yl-1H-thieno-[2,3-c]pyrazole-5-carboxamide;

N-{1-[(Dimethylamino)carbonyl]-4-piperidinyl}-3-methyl-1-tetrahydro-2H-pyran-4-yl-1H-thieno[2,3-c]pyrazole-5-carboxamide;

tert-Butyl 4-{4-{[(3-methyl-1-tetrahydro-2H-pyran-4-yl-1H-thieno[2,3-c]pyrazol-5-yl)carbonyl]amino}piperidin-1-yl}-1-piperidinecarboxylate;

3-Methyl-N-(piperidin-4-yl-4-piperidinyl)-1-tetrahydro-2H-pyran-4-yl-1H-thieno[2,3-c]pyrazole-5-carboxamide;

3-Methyl-N-(1-acetylpiperidin-4-yl-4-piperidinyl)-1-tetrahydro-2H-pyran-4-yl-1H-thieno[2,3-c]pyrazole-5-carboxamide;

3-Methyl-N-(1-methanesulfonylpiperidin-4-yl-4-piperidinyl)-1-tetrahydro-2H-pyran-4-yl-1H-thieno[2,3-c]pyrazole-5-carboxamide;

tert-Butyl 4-(trans-4-{[(3-methyl-1-tetrahydro-2H-pyran-4-yl-1H-thieno[2,3-c]pyrazol-5-yl)carbonyl]amino}cyclohexyl)-1-piperazine-carboxylate;

tert-Butyl 4-(cis-4-{[(3-methyl-1-tetrahydro-2H-pyran-4-yl-1H-thieno[2,3-c]pyrazol-5-yl)carbonyl]amino}cyclohexyl)-1-piperazine-carboxylate;

3-Methyl-N-[trans-4-(1-piperazinyl)cyclohexyl]-1-tetrahydro-2H-pyran-4-yl-1H-thieno[2,3-c]pyrazole-5-carboxamide;

3-Methyl-N-[cis-4-(1-piperazinyl)cyclohexyl]-1-tetrahydro-2H-pyran-4-yl-1H-thieno[2,3-c]pyrazole-5-carboxamide;

N-[trans-4-(4-Acetyl-1-piperazinyl)cyclohexyl]-3-methyl-1-tetrahydro-2H-pyran-4-yl-1H-thieno[2,3-c]pyrazole-5-carboxamide;

3-Methyl-N-{trans-4-[4-(methylsulfonyl)-1-piperazinyl]cyclohexyl}-1-tetrahydro-2H-pyran-4-yl-1H-thieno[2,3-c]pyrazole-5-carboxamide;

N-[cis-4-(4-Acetyl-1-piperazinyl)cyclohexyl]-3-methyl-1-tetrahydro-2H-pyran-4-yl-1H-thieno[2,3-c]pyrazole-5-carboxamide;

3-Methyl-N-[1-(4-morpholinylcarbonyl)-4-piperidinyl]-1-tetrahydro-2H-pyran-4-yl-1H-thieno[2,3-c]pyrazole-5-carboxamide;

3-Methyl-N-{1-[(4-methyl-1-piperazinyl)carbonyl]-4-piperidinyl}-1-tetrahydro-2H-pyran-4-yl-1H-thieno[2,3-c]pyrazole-5-carboxamide;

N-(trans-4-Hydroxycyclohexyl)-3-methyl-1-tetrahydro-2H-pyran-4-yl-1H-thieno[2,3-c]pyrazole-5-carboxamide;

3-Methyl-N-(4-oxocyclohexyl)-1-tetrahydro-2H-pyran-4-yl-1H-thieno[2,3-c]pyrazole-5-carboxamide;

N-[trans-4-(cis-2,6-Dimethylmorpholinyl)cyclohexyl]-3-methyl-1-tetrahydro-2H-pyran-4-yl-1H-thieno[2,3-c]pyrazole-5-carboxamide;

N-[cis-4-(cis-2,6-Dimethylmorpholinyl)cyclohexyl]-3-methyl-1-tetrahydro-2H-pyran-4-yl-1H-thieno[2,3-c]pyrazole-5-carboxamide;

1-Cyclohexyl-N-[6-(hydroxymethyl)-3-pyridinyl]-3-methyl-1H-thieno[2,3-c]pyrazole-5-carboxamide;

Methyl 5-{[(3-methyl-1-tetrahydro-2H-pyran-4-yl-1H-thieno[2,3-c]-pyrazol-5-yl)carbonyl]amino}-2-pyridinecarboxylate;

5-{[(3-Methyl-1-tetrahydro-2H-pyran-4-yl-1H-thieno[2,3-c]-pyrazol-5-yl)carbonyl]amino}-2-pyridinecarboxylic acid;

N-(6-{[(trans-4-Hydroxycyclohexyl)amino]carbonyl}-3-pyridinyl)-3-methyl-1-tetrahydro-2H-pyran-4-yl-1H-thieno[2,3-c]pyrazole-5-carboxamide;

N-[6-({[2-(Dimethylamino)ethyl]amino}carbonyl)-3-pyridinyl]-3-methyl-1-tetrahydro-2H-pyran-4-yl-1H-thieno[2,3-c]pyrazole-5-carboxamide;

3-Methyl-N-(6-{[(1-methyl-4-piperidinyl)amino]carbonyl}-3-pyridinyl)-1-tetrahydro-2H-pyran-4-yl-1H-thieno[2,3-c]pyrazole-5-carboxamide;

N-(6-{[(1-Acetyl-4-piperidinyl)amino]carbonyl}-3-pyridinyl)-3-methyl-1-tetrahydro-2H-pyran-4-yl-1H-thieno[2,3-c]pyrazole-5-carboxamide;

1-Cyclohexyl-3-methyl-N-[6-(4-morpholinylmethyl)-3-pyridinyl]-1H-thieno[2,3-c]pyrazole-5-carboxamide;

1-Cyclohexyl-N-{6-[(4-hydroxy-1-piperidinyl)methyl]-3-pyridinyl}-3-methyl-1H-thieno[2,3-c]pyrazole-5-carboxamide;

N-{6-[(4-Acetyl-1-piperazinyl)methyl]-3-pyridinyl}-1-cyclohexyl-3-methyl-1H-thieno[2,3-c]pyrazole-5-carboxamide;

3-Methyl-N-[trans-4-(4-methyl-2-oxo-1-piperazinyl)cyclohexyl]-1-tetrahydro-2H-pyran-4-yl-1H-thieno[2,3-c]pyrazole-5-carboxamide;

1-Cyclohexyl-3-methyl-N-[trans-4-(4-methyl-2-oxo-1-piperazinyl)-cyclohexyl]-1H-thieno[2,3-c]pyrazole-5-carboxamide;

3-Methyl-N-[trans-4-(3-oxo-1-piperazinyl)cyclohexyl]-1-tetrahydro-2H-pyran-4-yl-1H-thieno[2,3-c]pyrazole-5-carboxamide;

3-Methyl-N-[cis-4-(3-oxo-1-piperazinyl)cyclohexyl]-1-tetrahydro-2H-pyran-4-yl-1H-thieno[2,3-c]pyrazole-5-carboxamide;

3-Methyl-N-[trans-4-(4-methyl-3-oxo-1-piperazinyl)cyclohexyl]-1-tetrahydro-2H-pyran-4-yl-1H-thieno[2,3-c]pyrazole-5-carboxamide;

3-Methyl-N-[cis-4-(4-methyl-3-oxo-1-piperazinyl)cyclohexyl]-1-tetrahydro-2H-pyran-4-yl-1H-thieno[2,3-c]pyrazole-5-carboxamide;

Ethyl 1-(trans-4-{[(3-methyl-1-tetrahydro-2H-pyran-4-yl-1H-thieno-[2,3-c]pyrazol-5-yl)carbonyl]amino}cyclohexyl)-4-piperidinecarboxylate;

Ethyl 1-(cis-4-{[(3-methyl-1-tetrahydro-2H-pyran-4-yl-1H-thieno-[2,3-c]pyrazol-5-yl)carbonyl]amino}cyclohexyl)-4-piperidinecarboxylate;

N-{trans-4-[4-(Hydroxymethyl)-1-piperidinyl]cyclohexyl}-3-methyl-1-tetrahydro-2H-pyran-4-yl-1H-thieno[2,3-c]pyrazole-5-carboxamide;

N-{cis-4-[4-(Hydroxymethyl)-1-piperidinyl]cyclohexyl}-3-methyl-1-tetrahydro-2H-pyran-4-yl-1H-thieno[2,3-c]pyrazole-5-carboxamide;

N-[trans-4-(4-Hydroxy-1-piperidinyl)cyclohexyl]-3-methyl-1-tetrahydro-2H-pyran-4-yl-1H-thieno[2,3-c]pyrazole-5-carboxamide;

N-(cis-4-{4-[(Dimethylamino)carbonyl]-1-piperidinyl}cyclohexyl)-3-methyl-1-tetrahydro-2H-pyran-4-yl-1H-thieno[2,3-c]pyrazole-5-carboxamide;

1-(trans-4-{[(3-Methyl-1-tetrahydro-2H-pyran-4-yl-1H-thieno[2,3-c]-pyrazol-5-yl)carbonyl]amino}cyclohexyl)-4-piperidinecarboxylic acid;

N-(trans-4-{4-[(Dimethylamino)carbonyl]-1-piperidinyl}cyclohexyl)-3-methyl-1-tetrahydro-2H-pyran-4-yl-1H-thieno[2,3-c]pyrazole-5-carboxamide;

Ethyl 3-methyl-1-tetrahydro-2H-pyran-3-yl-1H-thieno[2,3-c]pyrazole-5-carboxylate;

3-Methyl-1-tetrahydro-2H-pyran-3-yl-1H-thieno[2,3-c]pyrazole-5-carboxylic acid;

3-Methyl-N-[trans-4-(4-morpholinyl)cyclohexyl]-1-tetrahydro-2H-pyran-3-yl-1H-thieno[2,3-c]pyrazole-5-carboxamide;

N-[trans-4-(4-Ethyl-3-oxo-1-piperazinyl)cyclohexyl]-3-methyl-1-tetrahydro-2H-pyran-4-yl-1H-thieno[2,3-c]pyrazole-5-carboxamide;

N-[cis-4-(4-Ethyl-3-oxo-1-piperazinyl)cyclohexyl]-3-methyl-1-tetrahydro-2H-pyran-4-yl-1H-thieno[2,3-c]pyrazole-5-carboxamide;

N-{trans-4-[(4-Ethyl-3-oxo-1-piperazinyl)methyl]cyclohexyl}-3-methyl-1-tetrahydro-2H-pyran-4-yl-1H-thieno[2,3-c]pyrazole-5-carboxamide;

3-Methyl-N-{trans-4-[(4-methyl-3-oxo-1-piperazinyl)methyl]-cyclohexyl}-1-tetrahydro-2H-pyran-4-yl-1H-thieno[2,3-c]pyrazole-5-carboxamide;

3-Methyl-N-[4-(4-methyl-2-oxo-1-piperazinyl)phenyl]-1-tetrahydro-2H-pyran-4-yl-1H-thieno[2,3-c]pyrazole-5-carboxamide;

The compounds represented by the formula (I) of the present invention may be prepared by the following methods.

[Formula 8]

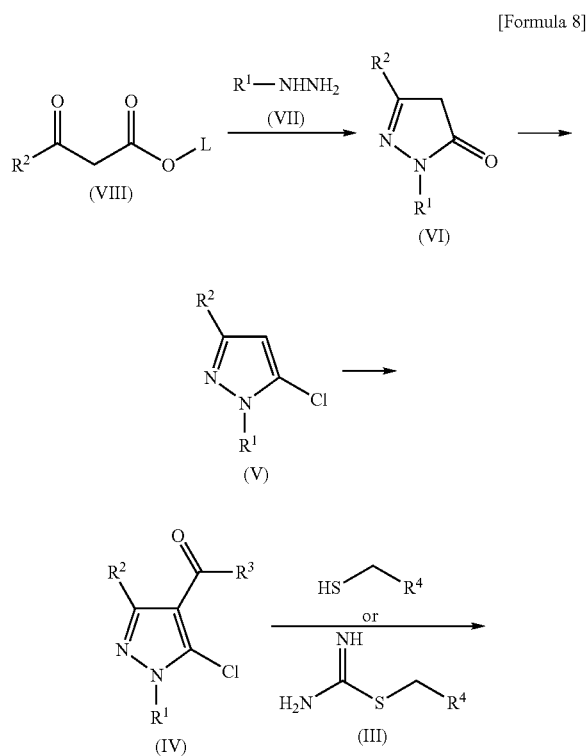

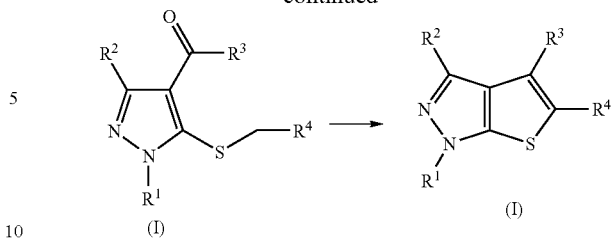

(wherein, $R^1$, $R^2$, $R^3$ and $R^4$ have same meanings mentioned above; L is $C_1$-$C_3$ lower alkyl group)

First, the compound (VI) obtained from the compound (VIII) by reacting with $R^1NHNH_2$ (VII) in accordance with the known method (e.g., International Patent Publication WO 03/053,975). Namely, the compound (VIII) is reacted with 1 to 2 equivalents, preferably about 1 equivalent of the compound (VII) in the solvent or absent of the solvent at room temperature to 120° C. The solvent to be used in the reaction is inorganic acid aqueous solution such as hydrochloric acid or sulfuric acid; aromatic carbon hydrate such as benzene or toluene; organic acid such as acetic acid; ethers such as 1,4-dioxane or tetrahydrofuran; halogenated hydrocarbons such as dichloromethane; alcohols such as methanol or ethanol; or the mixture solvent there of.

After the reaction is completed, the reaction mixture is neutralized and the mixture is extracted with an organic solvent, which is nonmiscible solvent with water, and the organic layer is washed sequentially with water and saturated saline solution. Then, the compound (VI) can be obtained by removal of the solvent. This compound (VI) can be purified by recrystallization, if necessary.

The starting compounds (VII) and (VIII) to be used in this reaction can be commercially available or can be known compounds (e.g., J. Org. Chem., 1981, 46, 5414-5415). Further, the compounds (VII) can be used as salt with acidic compounds, such as hydrochloric acid salt or acetic acid salt.

Then, the resulting compound (VI) is converted to the compound (V) in accordance with the common method. Namely, the reaction can be conducted by reacting the compound (VI) with 1 to 6 equivalents of halogenating reagent such as phosphorous oxychloride or thionyl chloride in aromatic hydrocarbon solvent such as benzene or toluene, or the absence of the solvent, at room temperature to refluxing temperature of the solvent for 1 to 12 hours. After the reaction is completed, the compound (V) can be obtained by removal of the solvent.

The obtained compound (V) is converted, without further purification, to the compound (IV) by an electrophilic substitution reaction. For example, the compound, (V) in which $R^3$ is a hydrogen atom, can be obtained by Vilsmeier reaction with the reaction reagent prepared from 1 to 5 equivalents of phosphorus oxychloride, in the amide solvent such as N,N-dimethylformamide. The reaction is carried out at room temperature to 120° C. for 1 to 12 hours.

After the reaction is completed, inorganic base aqueous solution such as sodium hydroxide aqueous solution is added to the reaction mixture and the mixture is extracted with an organic solvent, which is nonmiscible solvent with water, and the organic layer is washed sequentially with water and saturated saline solution. Then, the compound (IV) can be obtained by removal of the solvent. This compound (IV) can be purified by column chromatography or recrystallization, if necessary.

Further, the compound (IV) can be converted directly from the compound (IV) by Vilsmeier reaction in single process, or one-pot synthesis reaction without separation of the intermediate compound (V). Namely, the compound (VI) is treated with 2 to 5 equivalents of phosphorous oxychloride without using the reaction solvent at room temperature to 120° C. to obtain the compound (V) in the reaction mixture. Then, to this reaction mixture containing the resulting compound (V) is added formamide solvents such as N,N-dimethylformamide at 0° C. to 120° C., and the Vilsmeier reaction is carried out at room temperature to 120° C. for 1 to 24 hours.

After the reaction is completed, inorganic base aqueous solution such as sodium hydroxide aqueous solution is added to the reaction mixture and the mixture is extracted with an organic solvent, which is nonmiscible solvent with water, and the organic layer is washed sequentially with water and saturated saline solution. Then, the compound (IV) can be obtained by removal of the solvent. This compound (IV) can be purified by column chromatography or recrystallization, if necessary.

Then, the obtained compound (IV) is converted to the compound (II). The reaction is carried out by treating the compound (IV) with 1 to 1.5 equivalents of the compound (III), in the solvent at room temperature to 80° C. for 0.5 to 8 hours. The solvent to be used in this reaction is polar solvent such as acetonitrile or N,N-dimethylformamide; ethers such as 1,4-dioxane or tetrahydrofuran; halogenated hydrocarbons such as dichloromethane; alcohols such as methanol or ethanol; or the mixture solvent thereof. In this reaction, the compound (III) is previously treated with base such as potassium carbonate, sodium hydride, potassium tert-butoxide, sodium methylate or sodium hydroxide.

After the reaction is completed, water is added to the reaction mixture and the mixture is extracted with an organic solvent, which is nonmiscible solvent with water, and the organic layer is washed sequentially with water and saturated saline solution. Then, the compound (II) can be obtained by removal of the solvent. This compound (II) can be purified by column chromatography or recrystallization, if necessary.

Then, the obtained compound (II) is converted to the compound (I) of the present invention by ring formation reaction.

The reaction condition of this ring formation may vary depending on the variety of the group $R^4$. When the group $R^4$ is the group: $-CO_2R^7$, the compound (I) can be obtained from the compound (II) by treating with 1 to 1.5 equivalents of the base such as potassium carbonate, sodium hydride, sodium methylate or sodium hydroxide in the solvent at 0° C. to 80° C. for 0.5 to 24 hours. The solvent to be used in this reaction is polar solvent such as acetonitrile or N,N-dimethylformamide; ethers such as 1,4-dioxane or tetrahydrofuran; halogenated hydrocarbons such as dichloromethane; alcohols such as methanol or ethanol; or the mixture solvent there of.

After the reaction is completed, water is added to the reaction mixture and the mixture is extracted with an organic solvent, which is nonmiscible solvent with water, and the organic layer is washed sequentially with water and saturated saline solution. Then, the compound (I) can be obtained by removal of the solvent. This compound (I) can be purified by column chromatography, if necessary.

Further, when the group $R^4$ is the group: $-CO_2R^7$, the compound (I) can be obtained from the compound (IV), without the separation of the compound (II) in the corresponding stepwise reaction.

When the group $R^4$ is an aryl group which may be substituted or a heteroaryl group which may be substituted, the compound (I) can be obtained from the compound (II) by treating with 1 to 3 equivalents of the strong base such as lithium diisopropylamide or lithium bis(trimethylsilyl)amide in the ethers such as diethylether or tetrahydrofuran.

After the reaction is completed, water is added to the reaction mixture and the mixture is extracted with an organic solvent, which is nonmiscible solvent with water, and the organic layer is washed sequentially with water and saturated saline solution, then, the organic solvent is removed off. The resulting residue is dissolved in alcohols such as methanol or ethanol, and the acid such as hydrochloric acid is added to the mixture, and then, the mixture is stirred at room temperature to 60° C. to obtain the compound (I).

After the reaction is completed, water is added to the reaction mixture and the mixture is extracted with an organic solvent, which is nonmiscible solvent with water, and the organic layer is washed sequentially with water and saturated saline solution. Then, the compound (I) can be obtained by removal of the solvent. This compound (I) can be purified by column chromatography or recrystallization, if necessary.

In the case of the group $R^4$ is the group: $-CONR^5R^6$, first, the compound (I) in which the group $R^4$ is $-CO_2R^7$ obtained by the method described above, is converted to the compound (I) in which the group $R^4$ is $-CO_2H$. This convertion reaction is the hydrolysis reaction of ester compound, and can be carried out in the several manners. For example, the hydrolysis reaction can be carried out in the presence of the base such as sodium hydroxide, in the solvent at room temperature to refluxing temperature of the solvent. The solvent to be used in the reaction may be alcohols such as methanol or ethanol; water; or the mixture solvent thereof. After the reaction is completed, the reaction mixture is condensed, and the mixture is neutralized by adding hydrochloric acid to obtain the compound (I) in which the group $R^4$ is $-CO_2H$.

Then, the resulting compound (I) in which the group $R^4$ is $-CO_2H$ is converted to the compound in which the group $R^4$ is $-CONR^5R^6$ by amidation reaction in accordance with the several known methods. For example, the compound (I) in which the group $R^4$ is $-CO_2H$ is converted to the corresponding acid chloride by treating with the halogenating reagent such as phosphorous oxychloride or thionyl chloride. Then, the obtained acid chloride is treated with the amine compound $HNR^5R^6$ in the presence of base catalyst such as triethylamine in solvent at 0° C. to room temperature. The solvent to be used in the reaction may be halogenated hydrocarbons such as dichloromethane; aromoatic hydrocarbons such as toluene or benzene; ethers such as diethylether or tetrahydrofurane; or the mixture solvent thereof.

After the reaction is completed, the reaction mixture is diluted with the organic solvent, which is nonmiscible solvent with water, and the organic layer is washed sequentially with water and saturated saline solution. Then, the compound (I) in which the group $R^4$ is $-CONR^5R^6$ can be obtained by removal of the solvent. This compound can be purified by column chromatography or recrystallization, if necessary.

All reaction mentioned above are well known, and the reagents to be used or the reaction conditions to be applied can be easily established in accordance with the standard text book and the examples mentioned later. Further, the other methods or modified methods for obtaining the compound (I) of the present invention can be easily selected by the person skilled in this field.

EXAMPLES

The present invention is illustrated in more detail by way of the following Biological Test, Examples, and Manufacturing Examples.

The synthesis of the compounds of the present invention and intermediate compounds to be used in the synthesis are illustrated in the Examples and Manufacturing Examples mentioned later. Further, the physicochemical data and chemical structure of the compounds and intermediate compounds obtained by the Examples and Manufacturing Examples are summarized in the Tables mentions later.

The compound numbers in the Examples are identical to those in the Tables.

It is to be noted that the present invention is not limited by those Examples in any way.

Biological Test 1:

Methods for Evaluating the PDE 7 Inhibiting Effect

The PDE 7 (phosphodiesterase VII) inhibiting effect of the compounds of the present invention was performed by the following method, which was modified assay method described in *Biochemical. Pharmacol.* 48(6), 1219-1223 (1994).

(1) The active fraction of PDE 7 (phosphodiesterase VII) was obtained. That is, MOLT-4 (obtainable from ATCC as ATCC No. CRL-1582), which was cell line of human acute lymphoblastic lymphoma T cells, was incubated in RPMI1640 culture medium containing 10% fetal bovine serum to obtain $5 \times 10^8$ MOLT-4 cells. The cells were collected by centrifugation and suspended with 10 mL of buffer solution A [25 mM of tris-HCl, 5 mM of 2-mercaptoethnol, 2 mM of benzamidine, 2 mM of EDTA, 0.1 mM of 4-(2-aminoethyl)benzensulfonyl hydrochloride; pH 7.5], then homogenized by Polytron® homogenizer. The homogenate were centrifuged under 25,000×G for 10 minutes at 4° C. The supernatant was separated and thus obtained supernatant was further centrifuged under 100,000×G for 60 minutes at 4° C., and then filtrated with 0.2 µm filter to obtain the soluble fraction.

(2) The obtained soluble fraction was filled in equilibrium HiTrap Q column (5 mL×2) with buffer solution A, and phosphodiesterase fractions were eluted by 300 mL of buffer solution A with linear gradient from 0 to 0.8 M NaCl concentration. 5 mL each of 60 eluents were collected, and each eluents were examined for cyclic AMP metabolic activities of phosphodiesterase. The fraction eluting with about 350 mM NaCl concentration parts, where metabolic activities were not inactivated by 10 µM of rolipram (selective inhibitor for phosphodiesterase IV) and 10 µM of milrinone (selective inhibitor for phosphodiesterase III), were collected as storage solution for using to test PDE 7 inhibiting effect.

(3) The tested compound having desired concentration was reacted in the solution of 20 mM tris-HCl (pH7.5), 1 mM of $MgCl_2$, 100 µM of EDTA, 330 µg/mL of bovine serum albumin, 4 µg/mL of 5'-nucleotidase, 0.1 µCi of $^3$H-CAMP (0.064 µM of cAMP), 10 µM of rolipram in storage solution of PDE 7 for 2 hours at 25° C. After the reaction, suspension of Sephadex®-QAE in 10 mM of HEPES-Na (pH 7.0) was added to the reaction mixture, and the mixture was left at rest for 5 minutes. Further, Sephadex®-QAE was added to the obtained supernatant and the mixture was left at rest for 5 minutes, then, the radioactivity of the solution was measured.

(4) $IC_{50}$ was calculated as 50% inhibiting concentration of the metabolic activities of phosphodiesterase VII of the tested compound.

The compounds of the present invention selectively inhibit PDE 7 and their selectivities are more than 10 times compared to other phosphodiesterase. Therefore, it is expected that the side effect of the compounds of the present invention caused by other isozyme to be less.

For example, the selectivity against PDE 4 (phosphodiesterase IV) of the compounds of the present invention was affirmed by means of the following Biological Test.

Biological Test 2:

Methods for Evaluating the PDE 4 Inhibiting Effect

The PDE 4 (phosphodiesterase IV) inhibiting effect of the compounds of the present invention was performed by the following method, which was modified assay method described in *Biochemical. Pharmacol.* 48(6), 1219-1223 (1994).

(1) The active fraction of PDE 4 (phosphodiesterase IV) was obtained. That is, the livers obtained from three Balb/c mice (male, 12 weeks: obtainable from CLEA Japan, Inc.) were suspended with 30 mL of buffer solution B [20 mM of bis-tris, 5 mM of 2-mercaptoethnol, 2 mM of benzamidine, 2 mM of EDTA, 0.1 mM of 4-(2-aminoethyl)benzensulfonyl hydrochloride, 50 mM of sodium acetate; pH 6.5], then homogenized by Polytron® homogenizer. The homogenate were centrifuged under 25,000×G for 10 minutes at 4° C. The supernatant was separated and thus obtained supernatant was further centrifuged under 100,000×G for 60 minutes at 4° C., and then filtrated with 0.2 µm filter to obtain the soluble fraction.

(2) The obtained soluble fraction was filled in equilibrium DEAE sepharose column (1×10 cm) with buffer solution B, and phosphodiesterase fractions were eluted by 120 mL of buffer solution B with linear gradient from 0.05 to 1M sodium acetate concentration. 5 mL each of 24 eluents were collected, and each eluents were examined for cyclic AMP metabolic activities of phosphodiesterase. The fraction eluting with about 620 mM of sodium acetate concentration parts, where metabolic activities were inactivated by 3 µM of rolipram (selective inhibitor for phosphodiesterase IV), were collected as storage solution to test PDE 4 inhibiting effect.

(3) The tested compound having desired concentration was reacted in the solution of 20 mM tris-HCl (pH 7.5), 1 mM of $MgCl_2$, 100 µM of EDTA, 330 µg/mL of bovine serum albumin, 4 µg/mL of 5'-nucleotidase, 0.1 µCi of $^3$H-cAMP (0.064 µM of cAMP), and storage solution of PDE 4 for 2 hours at 25° C. After the reaction, suspension of Sephadex®-QAE in 10 mM of HEPES-Na (pH 7.0) was added to the reaction mixture, and the mixture was left at rest for 5 minutes. Further, Sephadex®-QAE was added to the obtained supernatant and the mixture was left at rest for 5 minutes, then, the radioactivity of the solution was measured.

(4) $IC_{50}$ was calculated as 50% inhibiting concentration of the metabolic activities of phosphodiesterase IV of the tested compound.

As the results of the mentioned above Biological Test 2, the $IC_{50}$ of the compounds of PDE 4 inhibiting effect of the present invention was more than 10 times weaker than that of PDE 7 inhibiting effect.

In the following Tables 1 to 4, the $IC_{50}$ values of PDE 7 inhibiting activities and PDE 4 inhibiting activities were summarized.

TABLE 1

| Compound No. | PD7 IC$_{50}$/μM | PDE4 IC$_{50}$/μM |
| --- | --- | --- |
| 10 | 0.027 | 1.8 |
| 11 | 0.019 | 2 |
| 12 | 0.053 | 5 |
| 14 | 0.088 | 3.7 |
| 16 | 0.034 | 2.2 |
| 20 | 0.033 | >30 |
| 21 | 0.084 | 2.5 |
| 23 | 0.083 | 4.8 |
| 25 | 0.098 | 6.5 |
| 26 | 0.044 | 3 |
| 28 | 0.05 | 30 |
| 32 | 0.095 | 2.5 |
| 36 | 0.04 | 25 |
| 37 | 0.028 | 2 |
| 38 | 0.033 | 5 |
| 39 | 0.014 | 3.5 |
| 40 | 0.075 | 15 |
| 41 | 0.05 | 12 |
| 45 | 0.05 | 12 |
| 46 | 0.03 | 2 |
| 47 | 0.032 | 3.5 |
| 51 | 0.075 | 9.5 |
| 53 | 0.055 | 3.5 |
| 58 | 0.036 | 3.6 |
| 59 | 0.08 | 7 |
| 60 | 0.065 | 6.5 |
| 67 | 0.023 | 3.5 |
| 70 | 0.025 | 4.7 |
| 72 | 0.01 | 1.2 |
| 73 | 0.012 | 1 |
| 74 | 0.05 | 7 |
| 76 | 0.02 | 2 |
| 77 | 0.02 | 2 |
| 79 | 0.06 | — |
| 80 | 0.06 | 2.5 |
| 94 | 0.058 | >30 |
| 99 | 0.099 | 5 |
| 100 | 0.037 | >30 |

TABLE 2

| Compound No. | PDE7 IC$_{50}$/μM | PDE4 IC$_{50}$/μM |
| --- | --- | --- |
| 101 | 0.03 | 1.3 |
| 102 | 0.085 | 5.5 |
| 104 | 0.058 | 1.5 |
| 106 | 0.009 | 1.2 |
| 107 | 0.017 | 2 |
| 109 | 0.015 | 1 |
| 110 | 0.075 | 5.5 |
| 111 | 0.01 | >30 |
| 112 | 0.008 | 1.2 |
| 114 | 0.021 | 1.5 |
| 115 | 0.04 | 1.5 |
| 125 | 0.075 | 4 |
| 132 | 0.088 | 10 |
| 133 | 0.009 | 1.8 |
| 135 | 0.053 | 7.4 |
| 141 | 0.022 | 1.6 |
| 142 | 0.014 | 2 |
| 147 | 0.085 | 3 |
| 149 | 0.065 | 2 |
| 150 | 0.045 | 0.7 |
| 152 | 0.085 | 3 |
| 155 | 0.01 | 1.5 |
| 156 | 0.055 | 2 |
| 159 | 0.035 | 1.6 |
| 162 | 0.07 | 2 |
| 163 | 0.014 | 0.9 |
| 165 | 0.02 | 0.65 |
| 166 | 0.016 | 1.5 |
| 167 | 0.015 | 1 |
| 168 | 0.022 | 1.5 |

TABLE 2-continued

| Compound No. | PDE7 IC$_{50}$/μM | PDE4 IC$_{50}$/μM |
| --- | --- | --- |
| 170 | 0.022 | 1.3 |
| 171 | 0.037 | 1.7 |
| 172 | 0.048 | 9.4 |
| 176 | 0.02 | 1.7 |
| 177 | 0.013 | 1.6 |
| 179 | 0.0031 | 0.75 |
| 180 | 0.01 | 1.4 |
| 181 | 0.0086 | 0.86 |
| 184 | 0.0068 | 1.1 |
| 188 | 0.0065 | 0.7 |
| 190 | 0.0035 | 1.7 |
| 191 | 0.0089 | 0.98 |
| 196 | 0.09 | 7.5 |
| 197 | 0.079 | 4.4 |

TABLE 3

| Compound No. | PDE7 IC$_{50}$/μM | PDE4 IC$_{50}$/μM |
| --- | --- | --- |
| 199 | 0.056 | 5.8 |
| 200 | 0.016 | 1.9 |
| 201 | 0.018 | 2.2 |
| 202 | 0.033 | 2.4 |
| 203 | 0.0061 | 1.4 |
| 205 | 0.091 | 14 |
| 206 | 0.05 | 3.8 |
| 207 | 0.024 | 2.4 |
| 208 | 0.025 | 3.8 |
| 209 | 0.077 | 7.4 |
| 225 | 0.018 | 2 |
| 227 | 0.056 | 10 |
| 228 | 0.051 | 5.8 |
| 230 | 0.023 | 7 |
| 234 | 0.013 | 2.1 |
| 235 | 0.017 | 2.8 |
| 236 | 0.02 | 2.7 |
| 237 | 0.0078 | — |
| 238 | 0.0078 | 2.7 |
| 239 | 0.015 | 2.6 |
| 240 | 0.041 | — |
| 246 | 0.051 | 6.6 |
| 247 | 0.0065 | 1.4 |
| 255 | 0.089 | 12 |
| 256 | 0.002 | 0.81 |
| 257 | 0.068 | 8.3 |
| 258 | 0.015 | 4.7 |
| 260 | 0.037 | 4.5 |
| 261 | 0.028 | 1.9 |
| 262 | 0.028 | 3.8 |
| 263 | 0.054 | 3.5 |
| 264 | 0.081 | 6.3 |
| 266 | 0.07 | 11 |
| 268 | 0.088 | 4.8 |
| 270 | 0.015 | 1.8 |
| 271 | 0.0089 | 2.1 |
| 273 | 0.014 | 1.6 |
| 274 | 0.0099 | 1.7 |
| 276 | 0.004 | 1.2 |
| 277 | 0.032 | 7.8 |
| 280 | 0.017 | 1.9 |
| 302 | 0.06 | 6.1 |
| 305 | 0.066 | 6.8 |
| 313 | 0.09 | 12 |
| 316 | 0.097 | 15 |
| 317 | 0.067 | 12 |

TABLE 4

| Compound No. | PDE7 IC$_{50}$/μM | PDE4 IC$_{50}$/μM |
|---|---|---|
| 323 | 0.071 | 6.3 |
| 325 | 0.034 | 4 |
| 331 | 0.029 | 4.9 |
| 339 | 0.02 | 5.1 |
| 340 | 0.054 | 28 |
| 341 | 0.005 | 1.8 |
| 342 | 0.028 | 4.6 |
| 349 | 0.078 | 2.8 |
| 358 | 0.071 | 11 |
| 360 | 0.057 | 7.9 |
| 365 | 0.041 | 3.9 |
| 366 | 0.049 | 3.6 |
| 367 | 0.02 | 2.3 |
| 368 | 0.026 | 2.9 |
| 369 | 0.024 | 7.6 |
| 370 | 0.0087 | 4.1 |
| 371 | 0.017 | 3.6 |
| 372 | 0.011 | 4 |
| 373 | 0.0045 | 3.4 |
| 375 | 0.0072 | 0.93 |
| 378 | 0.044 | 2.5 |
| 379 | 0.013 | 1.2 |
| 380 | 0.056 | 1.5 |
| 381 | 0.022 | 0.67 |
| 382 | 0.025 | 0.62 |
| 383 | 0.074 | 2.4 |
| 395 | 0.019 | 1.4 |
| 396 | 0.022 | 0.9 |
| 402 | 0.019 | 7.3 |
| 404 | 0.032 | 3.5 |
| 412 | 0.043 | 4.9 |
| 413 | 0.05 | 2.5 |
| 414 | 0.035 | 2.8 |
| 415 | 0.093 | 5.1 |
| 416 | 0.017 | 1.3 |
| 417 | 0.063 | 7 |
| 419 | 0.029 | 5.7 |
| 423 | 0.072 | 8.1 |
| 425 | 0.09 | 13 |
| 428 | 0.05 | 9.7 |
| 436 | 0.03 | 7.2 |
| 440 | 0.097 | 28 |

The compounds of the present invention inhibit PDE 7 selectively, and therefore, enhance cellular cAMP level. Consequently, the compounds of the present invention are useful for treating various kinds of diseases such as allergic diseases, inflammatory diseases or immunological diseases. For example, the compounds of the present invention are useful for treating or preventing the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, sepsis, Crohn's disease, rejection for organ transplantation, GVH disease, and restenosis after angioplasty.

The compounds of the present invention can be used for preparation of the pharmaceutical composition or PDE 7 inhibitor. As an active ingredient, one or more compounds may be administered in the appropriated formulation. The formulation for oral administration may include for example, capsules, granules, fine granules, syrups, dry syrups or the like; the formulation for parenteral administration may include, for example injectable solution, suppository formulation such as rectal suppository or vaginal suppository, nasal administration such as sprays, or percutaneous absorption formulation such as ointment and tapes, and the like.

The administration dose may vary depending on the various kinds of factors. These factors may be the condition of the patients, the severity of the diseases, ages, existence of a complication, as well as formulation. A usual recommended daily dose for oral administration is within the range of 0.1-1,000 mg/day/adult, preferably 0.1-500 mg/day/adult, and more preferably 1-100 mg/day/adult. In the case of parenteral administration, a usual recommended daily dose is within the range of ⅒ to ½ based on dose of oral administration. These doses can be adjusted depending on age, as well as the patient's condition.

The toxicological properties of the compounds of the present invention is low, therefore, the compounds of the present invention is expected to have high safety margin.

Examples and Manufacturing Examples

The compounds of the present invention and intermediate compounds used for the synthesis of the compounds of the present invention are illustrated in the following Manufacturing Examples and Examples. The physicochemical data and chemical structure of the compounds are summarized in the Tables mentions later. The compound numbers in the Examples and Manufacturing Examples are identical to those in the Tables.

Manufacturing Example 1 tert-Butyl 5-nitro-1-indolinecarboxylate

To a solution of 500 mg (3.05 mmol) of 5-nitroindoline in 10 mL of anhydrous dichloromethane was added 798 mg (3.65 mmol) of di-tert-butyl dicarbonate under ice cooling, and the mixture was stirred for 1.5 hours. Then, to this mixture was added catalytic amount of 4-dimethylamiopyridine and the mixture was stirred for 1 hour at room temperature. Water was added to the reaction mixture and the mixture was extracted with dichloromethane. The organic layer was washed with saturated saline solution and dried over with anhydrous sodium sulfate. The solvent was removed under reduced pressure and the resulting residue was purified by silica gel column chromatography (eluent:hexane/ethyl acetate=6/1) to give 800 mg (99%) of the title compound.

Manufacturing Example 2 tert-Butyl 5-amino-1-indolinecarboxylate 80 mg of 10% palladium-carbon was added to a solution of 760 mg (2.88 mmol) of the compound obtained in the Manufacturing Example 1 in 60 mL of methanol, and the reaction atmosphere was exchanged to hydrogen gas atmosphere. Then, the mixture was stirred for 30 minutes at room temperature and filtrated by Celite®. The filtrate was removed under reduced pressure to give 670 mg (99%) of the title compound.

Manufacturing Example 3 tert-Butyl 5-(acetylamino)-1-indolinecarboxylate

To a solution of 300 mg (1.28 mmol) of the compound obtained in the Manufacturing Example 2 in 10 mL of anhydrous dichloromethane were added 191 μL (2.69 mmol) of acetyl chloride and 375 μL (2.69 mmol) of triethylamine, and the mixture was stirred for 1 hour at room temperature. Then, water was added to the reaction mixture and the mixture was extracted with dichloromethane. The organic layer was dried over with anhydrous sodium sulfate and removed under reduced pressure. The resulting residue was purified by silica gel column chromatography (eluent:hexane/ethyl acetate=1/1 to 1/2) to give 370 mg (quantitative) of the title compound.

Manufacturing Example 4

N-(2,3-Dihydro-1H-indol-5-yl)acetamide HCl salt

A mixture solution of 330 mg (1.19 mmol) of the compound obtained in the Manufacturing Example 3 in 15 mL of 4M-HCl/dioxane was stirred for 1.5 hours at room temperature. Then, diethylether was added to the reaction mixture and the resulting precipitates were collected to give 173 mg (68%) of the title compound.

Manufacturing Example 5

6-Amino-N-isopropylnicotinamide

To a solution of 300 mg (2.17 mmol) of 6-aminonicotinic acid in 50 mL of chloroform were added 370 μL (4.34 mmol) of isopropylamine, 4 mL of anhydrous propanephosphonic acid (25 wt % solution in ethyl acetate) and 1.4 mL (10 mmol) of triethylamin, and the mixture was stirred for 6 hours at room temperature. Then, saturated sodium bicarbonate aqueous solution was added to the reaction mixture, and the mixture was extracted with dichloromethane. The organic layer was washed with saturated saline solution and dried over with anhydrous sodium sulfate. The solvent was removed under reduced pressure and the residue was purified by silica gel column chromatography (eluent:dichloromethane/methanol=10/1 to 5/1) to give 30 mg (8%) of the title compound.

Manufacturing Example 6

1-(Methylsulfonyl)-5-nitroindoline

To a solution of 300 mg (1.83 mmol) of 5-nitroindoline in 20 mL of dichloromethane were added 141 μL (2.74 mmol) of methanesulfonyl chloride and 382 μL (2.74 mmol) of triethylamine, and the mixture was stirred for 2 hours at room temperature. 141 μL (2.74 mmol) of methanesulfonyl chloride and 255 μL (1.83 mmol) of triethylamine were further added to the reaction mixture, and the mixture was stirred for 2 hours at room temperature. Then, water was added to the reaction mixture and the mixture was extracted with dichloromethane. The organic layer was washed with saturated saline solution and dried over with anhydrous sodium sulfate. The solvent was removed under reduced pressure and the residue was treated with diethyl ether, then, the precipitates were collected by filtration to give 410 mg (92%) of the title compound.

Manufacturing Example 7

1-(Methylsulfonyl)-5-indolineamine

The title compound 150 mg (58%) was obtained in a manner similar to the Manufacturing Example 2 by use of the compound obtained in the Manufacturing Example 6, instead of the compound obtained in the Manufacturing Example 1.

Manufacturing Example 8

2-{4-[(4-Nitrophenyl)sulfonyl]-1-piperazinyl}ethanol

To a solution of 415 μL (3.38 mmol) of 1-piperazineethanol in 20 mL of dichloromethane were added 500 mg (2.26 mmol) of 4-nitrobenzenesulfonyl chloride and 472 μL (3.38 mmol) of triethylamine under ice cooling, and the mixture was stirred for 30 minutes at the same temperature. The reaction mixture was diluted with dichloromethane and the organic layer was washed with water, saturated sodium bicarbonate aqueous solution and saturated saline solution and then, dried over with anhydrous sodium sulfate. The solvent was removed under reduced pressure and the residue was purified by silica gel column chromatography (eluent:dichloromethane/methanol=30/1) to give 670 mg (94%) of the title compound.

Manufacturing Example 9

2-{4-[(4-Nitrophenyl)sulfonyl]-1-piperazinyl}ethyl acetate

The title compound 175 mg (77%) was obtained in a manner similar to the Manufacturing Example 3 by use of the compound obtained in the Manufacturing Example 8, instead of the compound obtained in the Manufacturing Example 2.

Manufacturing Example 10

2-{4-(4-Aminophenyl)sulfonyl}-1-piperazinyl}ethyl acetate

The title compound 130 mg (95%) was obtained in a manner similar to the Manufacturing Example 2 by use of the compound obtained in the Manufacturing Example 9, instead of the compound obtained in the Manufacturing Example 1.

Manufacturing Example 11 tert-Butyl trans-4-(acetylamino)cyclohexylcarbamate

The title compound 130 mg (68%) was obtained in a manner similar to the Manufacturing Example 3 by use of tert-butyl trans-4-amino-cyclohexylcarbamate, instead of the compound obtained in the Manufacturing Example 2.

Manufacturing Example 12

N-(trans-4-Aminocyclohexyl)acetamide trifluoroacetic acid salt

To a solution of 220 mg (0.86 mmol) of the compound obtained in the Manufacturing Example 11 in 8 mL Of dichloromethane was added 8 mL of trifluoroacetic acid at room temperature, and the mixture was stirred for 30 minutes at the same temperature. The reaction mixture was condensed and the residue was treated with diethylether. The resulting precipitates were collected by filtration to give 194 mg (84%) of the title compound.

Manufacturing Example 13

2-Methoxy-N-(4-nitrophenyl)acetamide

To a mixture solution of 384 μL (5.0 mmol) of methoxyacetic acid and 691 mg (5.0 mmol) of p-nitroaniline in 10 mL of dichloromethane were added 1.53 mg (5.5 mmol) of 2-chloro-1,3-dimethylimidazoliumhexafluorophosphate and 1.53 mL (111.0 mmol) of triethylamine, and the mixture was refluxed for 7 hours. Then, the reaction mixture was extracted with ethyl acetate, the extract was washed with water and saturated saline solution, then, dried over with anhydrous sodium sulfate. The solvent was removed under reduced pressure and the residue was purified by silica gel column chromatography (eluent:hexane/ethyl acetate=2/1) to give 750 mg (71%) of the title compound.

Manufacturing Example 14

N-(4-Aminophenyl)-2-methoxyacetamide

The title compound 604 mg (86%) was obtained in a manner similar to the Manufacturing Example 2 by use of the compound obtained in the Manufacturing Example 13, instead of the compound obtained in the Manufacturing Example 1.

Manufacturing Example 15

6-(4-Methyl-1-piperazinyl)-3-pyridinylamine

The title compound 536 mg (quantitative) was obtained in a manner similar to the Manufacturing Example 2 by use of 1-methyl-4-(5-nitro-2-pyridinyl)piperazine, instead of the compound obtained in the Manufacturing Example 1.

Manufacturing Example 16

1-Methyl-4-[(3-nitrophenyl)sulfonyl]piperazine

To a solution of 500 mg (2.26 mmol) of 3-nitrobenzenesulfonyl chloride in 30 mL of dichloromethane were added 275 μL (2.48 mmol) of N-methylpiperazine and 786 μL (5.64 mmol) of triethylamine, and the mixture was stirred for 1 hour at room temperature. The reaction mixture was extracted with dichloromethane and the organic layer was washed with water and saturated saline solution, and then, dried over with anhydrous sodium sulfate. The solvent was removed under reduced pressure and the residue was treated with diethyl ether to give 510 mg (79%) of the title compound.

Manufacturing Example 17

3-[(4-Methyl-1-piperazinyl)sulfonyl]aniline

The title compound 350 mg (98%) was obtained in a manner similar to the Manufacturing Example 2 by use of the compound obtained in the Manufacturing Example 16, instead of the compound obtained in the Manufacturing Example 1.

Manufacturing Example 18

2-[2-Fluoro(methyl)-4-nitroanilino]ethanol

To a solution of 554 μL (5.0 mmol) of 3,4-difluoronitrobenzene in 10 mL of dimethyl sulfoxide were added 1.38 mg (10.0 mmol) of potassium carbonate and 803 μL (10.0 mmol) of 2-methylaminoetanol, and the mixture was stirred for 1.5 hours at 100° C. The reaction mixture was cooled to room temperature and extracted with ethyl acetate, then, the extract was washed with water and saturated saline solution. After dried over with anhydrous sodium sulfate, the solvent was removed under reduced pressure ant the residue was purified by silica gel column chromatography (eluent:hexane/ethyl acetate=1/1) to give 1.06 g (99%) of the title compound.

Manufacturing Example 19

2-(4-Amino-2-fluoromethylanilino)ethanol

The title compound 900 mg (quantitative) was obtained in a manner similar to the Manufacturing Example 2 by use of the compound obtained in the Manufacturing Example 18, instead of the compound obtained in the Manufacturing Example 1.

Manufacturing Example 20 tert-Butyl 4-(4-nitrophenyl)-1-piperidinecarboxylate

To a solution of 4.84 g (30 mmol) of 4-phenylpiperidine in 30 mL of conc. sulfuric acid was added gradually a solution of 1.26 mL of fuming nitric acid in 5 mL of conc. sulfuric acid under ice cooling, and after addition, the reaction mixture was warmed up to room temperature. Then, the reaction mixture was poured into 200 g of ice and sodium hydroxide aqueous solution was added slowly until the mixture to be alkalified. The mixture was extracted with chloroform and the organic layer was dried over with anhydrous sodium sulfate. The solvent removed under reduced pressure. Then, 2.18 g (10 mmol) of di-tert-butyl dicarbonate was added to a solution of the resulting residue in 20 mL of dichloromethane, and the mixture was stirred for 1 hour at room temperature. The mixture was concentrated and the residue was purified by silica gel column chromatography (eluent:dichloromethane/methanol=40/1) to give 0.78 g (8%) of the title compound.

Manufacturing Example 21 tert-Butyl 4-(4-aminophenyl)-1-piperidinecarboxylate

The title compound 392 mg (57%) was obtained in a manner similar to the Manufacturing Example 2 by use of the compound obtained in the Manufacturing Example 20, instead of the compound obtained in the Manufacturing Example 1.

Manufacturing Example 22

1-Ethyl-4-(2-fluoro-4-nitrophenyl)piperazine

The title compound 2.33 g (92%) was obtained in a manner similar to the Manufacturing Example 18 by use of N-ethylpiperazine instead of 2-methylaminoethanol.

Manufacturing Example 23

1-(2-Fluoro-4-nitrophenyl)-4-methyl-1,4-diazepam

The title compound 2.21 g (87%) was obtained in a manner similar to the Manufacturing Example 18 by use of N-methylhomopiperazine, instead of 2-methylaminoethanol.

Manufacturing Example 24

4-(4-Ethyl-1-piperazinyl)-3-fluoroaniline

The title compound 1.85 g (94%) was obtained in a manner similar to the Manufacturing Example 2 by use of the compound obtained in the Manufacturing Example 22, instead of the compound obtained in the Manufacturing Example 1.

Manufacturing Example 25

1-(2-Fluoro-4-nitrophenyl)-4-methylpiperazine

To a solution of 3.9 mL (35 mmol) of 3,4-difluoronitrobenzene in 60 mL of dimethyl sulfoxide were added 9.7 mL (87.5 mmol) of N-methylpiperazine and 12.1 g (87.5 mmol) of potassium carbonate, and the mixture was refluxed for 5 hours at 100° C. The reaction mixture was cooled to room temperature and poured into 500 mL of ice water, and the resulting precipitates were collected. The collected precipitates were dissolved in 2M-HCl aqueous solution and washed with ether. The aqueous layer was neutralized with 4M-NaOH aqueous solution to give the precipitates. The precipitates were collected to give 5.71 g (68%) of the title compound.

Manufacturing Example 26

3-Fluoro-4-(4-methyl-1-piperazinyl)aniline

The title compound 2.76 g (quantitative) was obtained in a manner similar to the Manufacturing Example 2 by use of the compound obtained in the Manufacturing Example 25, instead of the compound obtained in the Manufacturing Example 1.

Manufacturing Example 27

8-(2-Fluoro-4-nitrophenyl)-1,4-dioxa-8-azaspiro[4.5]decane

The title compound 2.82 g (quantitative) was obtained in a manner similar to the Manufacturing Example 25 by use of 1,4-dioxa-8-azaspiro[4.5]decane, instead of N-methylpiperazine.

Manufacturing Example 28

4-(1,4-Dioxa-8-azaspiro[4.5]deca-8-yl)-3-fluoroaniline

To a solution of 2.0 g (7.09 mmol) of the compound obtained in the Manufacturing Example 27 in 30 mL of methanol was added 200 mg of platinum on sulfide carbon, and the reaction atmosphere was changed to hydrogen gas atmosphere. Then, the mixture was stirred for 5 hours at normal pressures and temperature. The reaction mixture was filtrated by Celite®, and the filtrate was removed under reduced pressure. The residue was purified by silica gel column chromatography (eluent:hexane/ethyl acetate=3/1 to 1/1) to give 1.71 g (96%) of the title compound.

Manufacturing Example 29

8-(2-Chloro-4-nitrophenyl)-1,4-dioxa-8-azaspiro[4.5]decane

The title compound 3.05 g (quantitative) was obtained in a manner similar to the Manufacturing Example 25 by use of 3,4-dichloronitrobenzene and 1,4-dioxa-8-azaspiro[4.5]decane, instead of 3,4-difluoronitorobenzene and N-methylpiperazine, respectively.

Manufacturing Example 30

3-Chloro-4-(1,4-dioxa-8-azaspiro[4.5]decan-8-yl)aniline

The title compound 1.84 g (85%) was obtained in a manner similar to the Manufacturing Example 28 by use of the compound obtained in the Manufacturing Example 29, instead of the compound obtained in the Manufacturing Example 27.

Manufacturing Example 31

3-Fluoro-4-(4-methyl-1,4-diazapam-1-yl)aniline

The title compound 1.85 g (94%) was obtained in a manner similar to the Manufacturing Example 2 by use of the compound obtained in the Manufacturing Example 23, instead of the compound obtained in the Manufacturing Example 1.

Manufacturing Example 32

4-[2-(4-Morpholinyl)ethyl]aniline

The title compound 2.17 g (quantitative) was obtained in a manner similar to the Manufacturing Example 2 by use of 4-[2-(4-morpholinyl)-ethyl]nitrobenzene, instead of the compound obtained in the Manufacturing Example 1.

Manufacturing Example 33

1-Methyl-3-(4-nitrobenzyl)-2,4-imidazodinedione

To a mixture solution of 685 mg (6.0 mmol) of 1-methylhydantoin in 10 mL of N,N-dimethylformamide and 10 mL of tetrahydrofuran was added 240 mg (6.9 mmol) of sodiumhydride (60% oily) at room temperature, and the mixture was stirred for 30 minutes at the same temperature. Then, 1.08 g (5.0 mmol) of p-nitrobenzyl bromide was added to the reaction mixture, and the mixture was stirred for over night at room temperature. Water was added to the reaction mixture and the mixture was extracted with ethyl acetate. The organic layer was dried over with anhydrous sodium sulfate and the solvent was removed under reduced pressure to give 1.38 g (quantitative) of the title compound.

Manufacturing Example 34

3-(4-Aminobenzyl)-1-methyl-2,4-imidazolidinedione

To a mixture solution of 1.33 g (5.34 mmol) of the compound obtained in the Manufacturing Example 33 in 12 mL of ethanol and 6 mL of conc. hydrochloric acid was added 5.41 g (24.01 mmol) of tin chloride (II) dehydrate at room temperature, and the mixture was stirred for 2 hours at 75° C. The reaction mixture was cooled to room temperature, alkalized by adding of 4N-sodium hydroxide aqueous solution and treated with chloroform. The mixture was filtered with Celite®, and chloroform layer was separated and dried over with anhydrous sodium sulfate. The solvent was removed under reduced pressure to give 1.148 g (98%) of the title compound.

Manufacturing Example 35 tert-Butyl trans-4-cyanocyclohexylcarbamate

To a solution of 765 mg (4.99 mmol) of trans-4-cyanocyclohexane carboxylic acid in 10 mL of tert-butanol was added 766 µL (5.49 mmol) of triethylamine and 1.13 mL (5.24 mmol) of diphenylphosphorylazide at room temperature, and the mixture was refluxed for 6 hours. After the reaction mixture was cooled to room temperature, ethyl acetate was added to this mixture and the organic layer was washed with saturated sodium bicarbonate aqueous solution, then, dried over with anhydrous sodium sulfate. The solvent was removed under reduced pressure and the residue was purified by silica gel column chromatography (eluent:hexane/ethyl acetate=2/1) to give 608 mg (54%) of the title compound.

Manufacturing Example 36 trans-4-Aminocyclohexane carbonitrile HCl salt

The title compound 361 mg (90%) was obtained in a manner similar to the Manufacturing Example 4 by use of the compound obtained in the Manufacturing Example 35, instead of the compound obtained in the Manufacturing Example 3.

Manufacturing Example 37

1-(2-Aminoethyl)-4-methyl-2,3-piperazinedione HCl salt

To a solution of 3.60 g (11.95 mmol) of 2-[2-(4-methyl-2,3-dioxo-1-piperazinyl)ethyl]phthalimide in 30 mL of ethanol was added 695 µL (14.34 mmol) of hydrazine monohydrate and the mixture was stirred at 40° C. for over night. The reaction mixture was cooled to room temperature, then, 25 mL of water and 6 mL of 6N—HCl were added to this mixture and the mixture was stirred for 5 hours at room temperature. After removed off the insoluble substances by filtration, the filtrate was concentrated and the residue was re-crystallized by 2% water-ethanol solution to give 2.12 g (85%) of the title compound.

Manufacturing Example 38 tert-Butyl 1-[(dimethylamino)carbonyl]-4-piperidinylcarbamate

To a solution of 500 mg (2.50 mmol) of tert-butyl 4-piperidinyl-carbamate in 20 mL of dichloromethane was added 522 µL (3.74 mmol) of triethylamine and 276 µL (3.00 mmol) of dimethylaminocarbonyl chloride and the mixture was stirred for 2 hours at room temperature. Then, the mixture was treated with ethyl acetate and the organic layer was washed with water and saturated saline solution, and then, dried over with anhydrous sodium sulfate. The solvent was removed under reduced pressure to give 636 mg (94%) of the title compound.

Manufacturing Example 39

4-Amino-N,N-dimethyl-1-piperidinecarboxamide HCl salt

The title compound 571 mg (quantitative) was obtained in a manner similar to the Manufacturing Example 4 by use of the compound obtained in the Manufacturing Example 38, instead of the compound obtained in the Manufacturing Example 3.

Manufacturing Example 40 tert-Butyl 1-[(dimethylamino)sulfonyl]-4-piperidine-carbamate

To a solution of 412 mg (2.06 mmol) of tert-butyl 4-piperidinyl-carbamate in 20 mL of dichloromethane were added 430 µL (3.09 mmol) of triethylamine and 265 µL (2.47 mmol) of dimethylsulfamoyl chloride and the mixture was stirred for 2 hours at room temperature. Then, the mixture was treated with ethyl acetate and the organic layer was washed with water and saturated saline solution, and then, dried over with anhydrous sodium sulfate. The solvent was removed under reduced pressure and the residue was purified by silica gel column chromatography (eluent:dichloromethane/methanol=40/1) to give 536 mg (85%) of the title compound.

Manufacturing Example 41

4-Amino-N,N-dimethyl-1-piperidinesulfonamide HCl salt

The title compound 0.42 g (quantitative) was obtained in a manner similar to the Manufacturing Example 4 by use of the compound obtained in the Manufacturing Example 40, instead of the compound obtained in the Manufacturing Example 3.

Manufacturing Example 42

Methyl (2S,4S)-4-[tert-butoxycarbonyl]amino]-2-pyrrolidinecarboxylate

The title compound 4.70 g (96%) was obtained in a manner similar to the Manufacturing Example 2 by using methyl (2S,4S)-1-benzyloxycarbonyl-4-tert-butoxycarbonylami-nopyrrolidine-2-carboxylate, instead of the compound obtained in the Manufacturing Example 1.

Manufacturing Example 43

Methyl (2S,4S)-1-(aminocarbonyl)-4-[(tert-butoxycarbonyl)amino]-2-pyrrolidinecarboxylate To a solution of 4.60 g (18.83 mmol) of the compound obtained in the Manufacturing Example 42 in 80 mL of dioxane and 80 mL of water were added 2.29 g (28.55 mmol) of potassium isocyanate and 3.23 mL (56.49 mmol) of acetic acid, and the mixture was stirred for 17 hour at room temperature. Then, the mixture was treated with ethyl acetate and the organic layer was washed with water and saturated saline solution, and then, dried over with anhydrous sodium sulfate. The solvent was removed under reduced pressure and the residue was purified by silica gel column chromatography (eluent:dichloromethane/methanol=20/1) to give 2.32 g (43%) of the title compound.

Manufacturing Example 44 tert-Butyl (6S,7aS)-1,3-dioxohexahydro-1H-pyrrolo [1,2-c]imidazol-6-ylcarbamate

To a solution of 2.21 g (7.69 mmol) of the compound obtained in the Manufacturing Example 43 in 150 mL of methanol was added gradually 615 mg (15.38 mmol) of sodium hydride (60% oily) and the mixture was stirred for 30 minutes at room temperature. After condensed the reaction mixture, ethyl acetate and diluted hydrochloric acid were added to this mixture. The organic layer was separated and dried over with anhydrous sodium sulfate, and the solvent removed under reduced pressure to give 1.8 g (92%) of the title compound.

Manufacturing Example 45

(6S,7aS)-6-Aminotetrahydro-1H-pyrrolo[1,2-c]imidazole-1,3(2H)-dione HCl salt

The title compound 1.18 g (91%) was obtained in a manner similar to the Manufacturing Example 4 by use of the compound obtained in the Manufacturing Example 44, instead of the compound obtained in the Manufacturing Example 3.

Manufacturing Example 46

1-(5-Amino-2-pyridinyl)-2-imidazolidinone

The title compound 730 mg (quantitative) was obtained in a manner similar to the Manufacturing Example 2 by use of 1-(5-nitro-2-pyridinyl)-2-imidazolidinone, instead of the compound obtained in the Manufacturing Example 1.

Manufacturing Example 47

3-(4-Aminophenyl)-2,4-imidazolidinedione

The title compound 179 mg (69%) was obtained in a manner similar to the Manufacturing Example 2 by use of 3-(4-nitrophenyl)-2,4-imidazolidinedione, instead of the compound obtained in the Manufacturing Example 1.

Manufacturing Example 48

3-(4-Aminophenyl)-1-methyl-2,4-imidazolidinedione

The title compound 413 mg (95%) was obtained in a manner similar to the Manufacturing Example 2 by use of 3-(4-nitrophenyl)-1-methyl-2,4-imidazolidinedione, instead of the compound obtained in the Manufacturing Example 1.

Manufacturing Example 49

(3R)-1-(4-Aminophenyl)-3-pyrrolidinol

The title compound 1.98 g (quantitative) was obtained in a manner similar to the Manufacturing Example 2 by use of (3R)-1-(4-nitrophenyl)-3-pyrrolidinol, instead of the compound obtained in the Manufacturing Example 1.

Manufacturing Example 50

(3R)-1-(2-Fluoro-4-nitrophenyl)-3-pyrrolidinol

The title compound 2.19 g (65%) was obtained in a manner similar to the Manufacturing Example 18 by use of (R)-3-pyrrolidinol, instead of 2-methylaminoethanol.

Manufacturing Example 51

(3R)-1-(4-Amino-2-fluorophenyl)-3-pyrrolidinol

The title compound 1.81 g (99%) was obtained in a manner similar to the Manufacturing Example 2 by use of the compound obtained in the Manufacturing Example 50, instead of the compound obtained in the Manufacturing Example 1.

Manufacturing Example 52

1-[(3-Nitrophenyl)sulfonyl]-4-piperidinol

The title compound 1.91 g (49%) was obtained in a manner similar to the Manufacturing Example 16 by use of 4-hydroxypiperidine, instead of N-methylpiperazine.

Manufacturing Example 53

1-[(3-Aminophenyl)sulfonyl]-4-piperidinol

The title compound 1.56 g (52%) was obtained in a manner similar to the Manufacturing Example 2 by use of the compound obtained in the Manufacturing Example 52, instead of the compound obtained in the Manufacturing Example 1.

Manufacturing Example 54

1-[(4-Nitrophenyl)sulfonyl]-4-piperidinol

The title compound 1.91 g (49%) was obtained in a manner similar to the Manufacturing Example 8 by use of 4-hydroxypiperidine, instead of 1-piperazineethanol.

Manufacturing Example 55

4-{[tert-Butyl(dimethyl)silyl]oxy}-1-[(4-nitrophenyl)sulfonyl]-piperidine

To a solution of 1.5 g (5.24 mmol) of the compound obtained in the Manufacturing Example 54 in 60 mL of dichloromethane was added 1.32 mL (5.76 mmol) of tert-butyldimethylsilyl trifluorate at 0° C., and the mixture was stirred overnight at room temperature. After the reaction, the reaction mixture was washed with water and the organic layer was dried over with anhydrous sodium sulfate. The solvent was removed under reduced pressure and the residue was purified by silica gel column chromatography (eluent:hexane/ethyl acetate=5/1) to give 2.04 g (97%) of the title compound.

Manufacturing Example 56

4-[(4-{[tert-Butyl(dimethyl)silyl]oxy}-1-piperidinyl)sulfonyl]-aniline

The title compound 1.67 g (98%) was obtained in a manner similar to the Manufacturing Example 2 by use of the compound obtained in the Manufacturing Example 55, instead of the compound obtained in the Manufacturing Example 1.

Manufacturing Example 57

1-Methyl-4-[4-nitro-2-(trifluoromethyl)phenyl]piperazine

The title compound 2.28 g (82%) was obtained in a manner similar to the Manufacturing Example 25 by use of 2-fluoro-5-nitrobenzotrifluoride, instead of 3,4-difluoronitrobenzene.

Manufacturing Example 58

4-(4-Methyl-1-piperidinyl)-3-(trifluoromethyl)phenylamine

The title compound 1.96 g (99%) was obtained in a manner similar to the Manufacturing Example 2 by use of the compound obtained in the Manufacturing Example 57, instead of the compound obtained in the Manufacturing Example 1.

Manufacturing Example 59

2-[2-(5-Methyl-1,1-dioxide-1,2,5-thiadiazolidin-2-yl)ethyl]-1H-isoindole-1,3(2H)-dione To a solution of 686 mg (5.04 mmol) of 2-methyl-1,2,5-thiadiazolidine 1,1-dioxide in 10 mL of N,N-dimethylformamide was added 212 mg (5.30 mmol) of sodium hydride (60% oily) at room temperature, and the mixture was stirred for 1 hour at the same temperature. Then, 1.41 g (5.54 mmol) of N-(2-bromoethyl)phthalimide was added to the reaction mixture, and the mixture was stirred for 1.5 hours at 75° C. After the reaction, water was addedtothereactionmixtureandsolventwasremovedunderreducedpressure. The resulting residue was treated with water and extracted with dichloromethane and the organic layer was washed with water and saturated saline solution, then, dried over with anhydrous sodium sulfate. The solvent was removed under reduced pressure and the residue was purified by silica gel column chromatography (eluent:hexane/ethyl acetate=1/5), and solidified by treating with ethyl acetate/ether to give 526 mg (34%) of the title compound.

Manufacturing Example 60

2-(5-Methyl-1-1-dioxide-1,2,5-thiadiazolidin-2-yl)ethanamine HCl salt

To a suspension of 500 mg (1.62 mmol) of the compound obtained in the Manufacturing Example 59 in 5 mL of ethanol was added 94 µL (1.94 mmol) of hydrazine monohydrate, and the mixture was stirred for 6 hours at 70° C. Then, insoluble substances were removed off by filtration and the filtrate was removed under reduced pressure, and 5 mL of water and 1.5 mL of 6M-HCl aqueous solution were added to the residue. Then, the mixture was stirred for 6 hours at room temperature and insoluble substances were removed off by filtration and the filtrate was removed under reduced pressure. The resulting residue was recrystallized from ethanol to give 287 mg (82%) of the title compound.

Manufacturing Example 61

1-(2-Fluoro-4-nitrophenyl)-4-piperidinol

To a solution of 4.77 g (30.0 mmol) of 3,4-difluoronitrobenzene in 100 mL of N,N-dimethylformamide were added 5.33 g (40.0 mmol) of potassium carbonate and 3.03 g (30.0 mmol) of 4-hydroxypiperidine and the mixture was stirred for 1 hour at 120° C. After the reaction mixture was cooled to room temperature, the reaction mixture was diluted with chloroform and insoluble substances were removed off by filtration. The filtrate was condensed and the residue was purified by silica gel column chromatography (eluent:hexane/ethyl acetate=1.5/1) to give 3.1 g (43%) of the title compound.

Manufacturing Example 62

1-(4-Amino-2-fluorophenyl)-4-piperidinol

To a solution of 2.95 g (12.28 mmol) of the compound obtained in the Manufacturing Example 61 in 100 mL of ethanol was added 600 mg of 5%-palladium carbon, and the atmosphere was exchanged to hydrogen atmosphere. The mixture was stirred for 2 hours at room temperature and filtered. The filtrate was removed under reduced pressure to give 2.48 g (96%) of the title compound.

Manufacturing Example 63 tert-Butyl trans-4-(4-morpholinyl)cyclohexylcarbamate

To a solution of 21.43 g (0.1 mol) of tert-butyl N-(trans-4-aminocyclohexyl) carbamate in 250 mL of N,N-dimethylformamide were added 16.76 mL (0.12 mol) of bis (2-bromoethyl)ether and 34.85 mL (0.25 mol) of triethylamine, and the mixture was stirred for 6 hours at 70° C. Then solvent was removed under reduced pressure and the residue was treated with ethyl acetate. The organic layer was washed with sodium carbonate aqueous solution and saturated saline solution, then, dried over with anhydrous sodium sulfate. The solvent was removed under reduced pressure and the residue was purified by silica gel column chromatography (eluent:chloroform alone to chloroform/methanol=30/1) to give 19.92 g (70%) of the title compound.

Manufacturing Example 64 trans-4-(4-Morpholinyl)cyclohexylamine di-HCl salt

To a solution of 18.53 g (65.16 mmol) of the compound obtained in the Manufacturing Example 63 in 65 mL of chloroform was added 130 mL of 4N—HCl/ethyl acetate solution, and the mixture was stirred for 3 hours at room temperature. The reaction mixture was treated with 200 mL of diethyl ether and separated precipitates were collected to give 16.22 g (97%) of the title compound.

Manufacturing Example 65

4-(4-Nitrophenyl)-2-piperazinone

To a solution of 1.275 g (9.04 mmol) of 4-fluoronitrobenzene in 30 mL of N,N-dimethylformamide were added 1.87 g (13.56 mmol) of potassium carbonate and 905 mg (9.04 mmol) of piperazine-2-one, and the mixture was stirred for 1 hour at 130° C. and for 1 hour at 140° C. The reaction mixture was cooled to room temperature and diluted with chloroform, then, insoluble substances were removed off by filtration. The filtrate was condensed under reduced pressure and the resulting solid was washed with ethanol to give 859 mg (43%) of the title compound.

Manufacturing Example 66

4-(4-Aminophenyl)-2-piperadinone

The title compound 640 mg (89%) was obtained in a manner similar to the Manufacturing Example 2 by use of the compound obtained in the Manufacturing Example 65, instead of the compound obtained in the Manufacturing Example 1.

Manufacturing Example 67

3-Amino-N,N-dimethylbenzenesulfonamide

The title compound 2.55 g (99%) was obtained in a manner similar to the Manufacturing Example 2 by use of N,N-dimethyl-3-nitrobenzene-sulfonamide, instead of the compound obtained in the Manufacturing Example 1.

Manufacturing Example 68

3-[(2-{[tert-Butyl(dimethyl)siliyl]oxy}ethyl)sulfonyl]nitrobenzene

To a solution of 955 mg (4.13 mmol) of 3-[(2-hydroxyethyl) sulfonyl]-nitrobenzene in 30 mL of dichloromethane were added 747 mg (4.96 mmol) of tert-butyldimethylsilyl chloride and 10 mg of 4-dimethylaminopyridine, and the mixture was stirred for over night at room temperature. Then, the reaction mixture was diluted with dichloromethane and the organic layer was washed with water and dried over anhydrous sodium sulfate. The solvent was removed under reduced pressure and the residue was purified by silica gel column chromatography (eluent:hexane/ethyl acetate=4/1 to 2/1) to give 1.27 g (89%) of the title compound.

Manufacturing Example 69

3-[(2-tert-Butyl(dimethyl)silyl)oxy]ethyl) sulfonyl}aniline

The title compound 856 mg (94%) was obtained in a manner similar to the Manufacturing Example 2 by use of the compound obtained in the Manufacturing Example 68, instead of the compound obtained in the Manufacturing Example 1.

Manufacturing Example 70

2-[(2-Hydroxyethyl)(methyl)amino]-N-(4-nitrophenyl)acetamide

To a suspension of 2.946 g (13.73 mmol) of 2-chloro-N-(4-nitrophenyl)acetamide in 30 mL of ethanol was added 3.31 mL (41.18 mmol) of 2-(methylamino)ethanol and the mixture was refluxed for 4 hours. After the reaction mixture was cooled to room temperature and condensed, then, the residue was treated with ethyl acetate. The organic layer was washed with water and dried over with anhydrous sodium sulfate. The solvent was removed under reduced pressure and the residue was purified by silica gel column chromatography (eluent: dichloromethane/methanol=40/1) to give 2.05 g (59%) of the title compound.

Manufacturing Example 71

4-Methyl-1-(4-nitrophenyl)-2-piperazinone

To a solution of 1.48 g (5.84 mmol) of the compound obtained in the Manufacturing Example 70 in 50 mL of tetrahydrofuran were added 1.75 mL (7.01 mmol) of tri-n-butylphosphine and 1.21 g (7.01 mmol) of 1,1'-azobis-(N,N-dimethylformamide), and the mixture was stirred for 4 hours at room temperature. Water was added to the reaction mixture and the mixture was extracted with ethyl acetate. The organic layer was washed with saturated saline solution and dried over with anhydrous sodium sulfate. The solvent was removed under reduced pressure and the residue was purified by silica gel column chromatography to give 738 mg (54%) of the title compound.

Manufacturing Example 72

1-(4-Aminophenyl)-4-methyl-2-piperazinone

The title compound 545 mg (quantitative) was obtained in a manner similar to the Manufacturing Example 2 by use of the compound obtained in the Manufacturing Example 71, instead of the compound obtained in the Manufacturing Example 1.

Manufacturing Example 73

1-(5-Nitro-2-pyridinyl)-4-piperidinol

To a suspension of 11.0 g (6.3 mmol) of 2-chloro-5-nitro-pyridine in 20 mL of n-propanol was added 1.9 g (18.9 mmol) of 4-hydroxypiperidine, and the mixture was stirred for 1.5 hours at 100° C. After cooling the reaction mixture, the solvent was removed under reduced pressure, and the residue was purified by silica gel column chromatography (eluent: dichloromethane/methanol=50/1) to give 1.37 g (97%) of the title compound.

Manufacturing Example 74

1-(5-Amino-2-pyridinyl)-4-piperidinol

To a suspension of 1.35 g (6.04 mmol) of the compound obtained in the Manufacturing Example 73 in 18 mL of ethanol and 3 mL of water were added 1.3 g of reduced iron and 0.25 mL of conc. hydrochloric acid, and the mixture was stirred for 2 hours at 90° C. After cooling the reaction mixture, the mixture was filtrated by Celite® and filtrate was condensed under reduced pressure. The resulting residue was purified by silica gel column chromatography (eluent:dichloromethane/methanol=10/1) to give 601 mg (51%) of the title compound.

Manufacturing Example 75

1-(2,3-Difluoro-4-nitrophenyl)-4-piperidinol

To a solution of 1.72 mL (15 mmol) of 2,3,4-trifluorobenzene in N,N-dimethylformamide were added 1.01 g (10 mmol) of 4-hydroxypiperidine and 2.3 mL (20 mmol) of 2,6-lutidine, and the mixture was stirred for 24 hours at room temperature. The solvent was removed under reduced pressure, and saturated sodium bicarbonate aqueous solution was added to the residue and the mixture was extracted with ethyl acetate. The organic layer was washed with water and saturated saline solution, and dried over with anhydrous sodium sulfate. The solvent was removed under reduced pressure and the residue was purified by silica gel column chromatography (eluent:hexane/ethyl acetate=2/1 to ethyl acetate alone) to give 1.82 g (70%) of the title compound.

Manufacturing Example 76

1-(4-Amino-2,3-difluorophenyl)-4-piperidinol

The title compound 1.23 g (78%) was obtained in a manner similar to the Manufacturing Example 74 by use of the compound obtained in the Manufacturing Example 75, instead of the compound obtained in the Manufacturing Example 73.

Manufacturing Example 77

1-(2-Methyl-4-nitrophenyl)-4-piperidinol

To a solution of 1.55 g (10 mmol) of 2-fluoro-5-nitrotoluene in 35 mL of N,N-dimethylformamide were added 1.01 g (10 mmol) of 4-hydroxypiperidine and 1.8 g (13 mmol) of potassium carbonate, and the mixture was stirred for 2 hours at 120° C. The reaction mixture was poured into ice and the mixture was extracted with ethyl acetate. The organic layer was washed with water and saturated saline solution, and dried over with anhydrous sodium sulfate. The solvent was removed under reduced pressure and the residue was purified by silica gel column chromatography (eluent:hexane/ethyl acetate=1/1) to give 1.5 g (63%) of the title compound.

Manufacturing Example 78

1-(4-Amino-2-methylphenyl)-4-piperidinol

The title compound 1.2 g (quantitative) was obtained in a manner similar to the Manufacturing Example 2 by use of the compound obtained in the Manufacturing Example 77, instead of the compound obtained in the Manufacturing Example 1.

Manufacturing Example 79

2-(4-Hydroxy-1-piperidinyl)-5-nitrobenzonitrile

The title compound 2.0 g (81%) was obtained in a manner similar to the Manufacturing Example 77 by use of 2-fluoro-5-nitrobenzonitrile, instead of 2-fluoro-5-nitrotoluene.

Manufacturing Example 80

5-Amino-2-(4-hydroxy-1-piperidinyl)benzonitrile

To a suspension of 11.0 g (4.04 mmol) of the compound obtained in the Manufacturing Example 79 in 10 mL of water were added 790 mg (14.14 mmol) of iron and 130 mg (2.42 mmol) of ammonium chloride, and the mixture was refluxed for 3 hours. After the reaction mixture was cooled to room temperature, water was added to the reaction mixture, and the mixture was extracted with chloroform. The organic layer was washed with water and saturated saline solution, and dried over with anhydrous sodium sulfate. The solvent was removed under reduced pressure and the residue was purified by silica gel column chromatography (eluent:hexane/ethyl acetate=1/1 to 1/4) to give 327 mg (37%) of the title compound.

Manufacturing Example 81

Methyl 2-(4-hydroxy-1-piperidinyl)-5-nitrobenzoate

The title compound 2.30 g (98%) was obtained in a manner similar to the Manufacturing Example 77 by use of methyl 2-fluoro-5-nitrobenzoate, instead of 2-fluoro-5-nitrotoluene.

Manufacturing Example 82

Methyl 5-amino-2-(4-hydroxy-1-piperidinyl)benzoate

The title compound 1.83 g (91%) was obtained in a manner similar to the Manufacturing Example 2 by use of the compound obtained in the Manufacturing Example 81, instead of the compound obtained in the Manufacturing Example 1.

Manufacturing Example 83 tert-Butyl 1-tetrahydro-2H-pyran-4-yl-4-piperidinylcarbamate

To a suspension of 9.5 g (184 mmol) of tert-butyl piperidin-4-yl carbamate in 200 mL of 1,2-dichloroethane were added 4.4 mL (47.4 mmol) of tetrahydro-4H-pyran-4-one and 1.0 mL of acetic acid, and the mixture was stirred for 30 minute. The reaction mixture was cooled to 0° C., and to this mixture was added 15 g (71.1 mmol) of sodium triacetoxyborohydride and the mixture was stirred for 4 hours at room temperature, then, 5.0 g (23.6 mmol) of sodium triacetoxyborohydride was further added to the mixture and the mixture was stirred for 64 hours at room temperature. Saturated sodium bicarbonate aqueous solution was added to the reaction mixture, and the mixture was extracted with dichloromethane. The organic layer was washed with water and saturated saline solution, and dried over with anhydrous sodium sulfate. The solvent was removed under reduced pressure and the residue was purified by silica gel column chromatography (eluent: hexane/ethyl acetate=2/1) to give 11.54 g (86%) of the title compound.

Manufacturing Example 84

1-Tetrahydro-2H-pyran-4-yl-4-piperidineamine di-HCl salt

The title compound 10.8 g (quantitative) was obtained in a manner similar to the Manufacturing Example 4 by use of the compound obtained in the Manufacturing Example 83, instead of the compound obtained in the Manufacturing Example 3.

Manufacturing Example 85 tert-Butyl 4-(4-{[(benzyloxy)carbonyl]amino}cyclohexyl)-1-piperazine-carboxylate The title compound 4.0 g (96%) was obtained in a manner similar to the Manufacturing Example 83 by use of benzyl 4-oxocyclohexylcarbamate and tert-butyl 1-piperazinecarbamate, instead of tetrahydro-4H-pyran-4-one and tert-butyl piperidin-4-ylcarbamate, respectively.

Manufacturing Example 86 tert-Butyl 4-(4-aminocyclohexy)-1-piperazinecarboxylate

The title compound 2.6 g (quantitative) was obtained in a manner similar to the Manufacturing Example 2 by use of the compound obtained in the Manufacturing Example 85, instead of the compound obtained in the Manufacturing Example 1.

Manufacturing Example 87

(5-Amino-2-pyridinyl)methanol di-HCl salt

The title compound 686 mg (78%) was obtained in a manner similar to the Manufacturing Example 4 by use of tert-butyl 6-(hydroxylmethyl)pyridin-3-ylcarbamate, instead of the compound obtained in the Manufacturing Example 3.

Manufacturing Example 88 tert-Butyl trans-4-[(chloroacetyl)amino]cyclohexylcarbamate

The title compound 604 mg (89%) was obtained in a manner similar to the Manufacturing Example 3 by use of tert-butyl trans-4-aminocyclohexylcarbamate and chloroacetyl chloride, instead of the compound obtained in the Manufacturing Example 2 and acetyl chloride, respectively.

Manufacturing Example 89 tert-Butyl trans-4-({[(2-hydroxyethyl)(methyl) amino]acetyl}amino)-cyclohexylcarbamate To a suspension of 560 mg (1.93 mml) of the compound obtained in the Manufacturing Example 88 in 5 mL of ethanol was added 464 μL (5.78 mmol) of 2-(methylamino) ethanol and the mixture was refluxed for 1 hour. After cooling, the solvent was removed under reduced pressure and water was added to the residue, and the mixture was extracted with dichloromethane. The organic layer was washed with water and saturated saline solution, and dried over with anhydrous sodium sulfate. The solvent was removed under reduced pressure and the residue was purified by recrystallization (isopropanol) to give 391 mg (61%) of the title compound.

Manufacturing Example 90 tert-Butyl trans-4-(4-methyl-2-oxo-1-piperazinyl) cyclohexylcarbamate 589 mg (5.25 mmol) of potassium t-butoxide was added to a suspension solution of 560 mg (1.7 mmol) of the compound obtained in the Manufacturing Example 89 in 10 mL of tetrahydrofuran, and a solution of 499 mg (2.62 mmol) of p-toluenesulfonyl chloride in 5 mL of tetrahydrofuran was added to this mixture, then, the mixture was stirred for 2 hours at 0° C. 499 mg (2.62 mmol) of p-toluenesulfonyl chloride and 589 mg (5.25 mmol) of potassium t-butoxide were further added to the reaction mixture, and the mixture was stirred for 30 minutes at room temperature. Water was added to the reaction mixture and the mixture was extracted with chloroform. The organic layer was washed with water and saturated saline solution, and dried over with anhydrous sodium sulfate. The solvent was removed and the residue was purified by silica gel column chromatography (eluent:dichloromethane/methanol=10/1) to give 398 mg (75%) of the title compound.

Manufacturing Example 91

1-(trans-4-Aminocyclohexyl)-4-methyl-2-piperazinone di-HCl salt

The title compound 349 mg (quantitative) was obtained in a manner similar to the Manufacturing Example 4 by use of the compound obtained in the Manufacturing Example 90, instead of the compound obtained in the Manufacturing Example 3.

Manufacturing Example 92

Ethyl 1-(4-{[(benzyloxy)carbonyl] amino}cyclohexyl)-4-piperidinecarboxylate

The title compound 2.6 g (67%) was obtained in a manner similar to the Manufacturing Example 83 by use of benzyl 4-oxocyclohexylcarbamate and ethyl isonipecocotinate, instead of tetrahydro-4H-pyran-4-one and tert-butyl piperidin-4-ylcarbamate, respectively.

Manufacturing Example 93

Ethyl 1-(4-aminocyclohexyl)-4-pirepidinecarboxylate

The title compound 1.58 g (quantitative) was obtained in a manner similar to the Manufacturing Example 2 by use of the compound obtained in the Manufacturing Example 92, instead the compound obtained in the Manufacturing Example 1.

Manufacturing Example 94

Ethyl 1-(4-nitrophenyl)-4-pirepidinol

To a solution of 14.1 g (0.10 mol) of 4-fluoronitrobenzene in 200 mL of N,N-dimethylformamide were added 20.73 (0.15 mol) of potassium carbonate and 10.1 g (0.10 mol) of 4-hydroxypiperidine and the mixture was stirred for 1 hour at 140° C. The reaction mixture was cooled to room temperature and the mixture was treated with chloroform, then insoluble substances were removed off by filtration. The filtrate was condensed and the residue was recrystallized from ethanol to give 17.27 g (78%) of the title compound.

Manufacturing Example 95

1-(Aminophenyl)-4-piperidinol

To a solution of 17.09 g (76.95 mmol) of the compound obtained in the Manufacturing Example 94 in 300 mL of methanol was added 2.0 g of 5%-palladium-carbon, and the atmosphere was exchanged to hydrogen atmosphere. The mixture was stirred for over night at room temperature and the mixture was filtrated. The filtrate was removed under reduced pressure to give 13.04 g (88%) of the title compound.

Example 1

2-Cyclohexyl-5-methyl-2,4-dihydro-3H-pyrazol-3-one

A mixture solution of 39.88 g (0.265 mol) of cyclohexylhydazine HCl salt in 28.57 mL (0.265 mol) of methyl acetoacetate was heated for 1 hour at 120° C. After the reaction mixture was cooled to room temperature, dichloromethane was added to this mixture and the mixture was neutralized by 2N-NaOH aqueous solution. The organic layer was dried over with anhydrous sodium sulfate and the solvent was removed under reduced pressure. The resulting residue was treated with hexane to give crystalline and the crystalline was collected by filtration to give 33.84 g (71%) of the title compound.

Example 2

5-Chloro-1-cyclohexyl-3-methyl-1H-pyrazole

A mixture of 13.5 g (74.9 mmol) of the compound obtained in the Example 1 and 13.5 mL of phosphorus oxychloride was heated for 2 hours at 110° C. Then, the reaction mixture was cooled to room temperature and condensed under reduced pressure. The residue was extracted with ethyl acetate, and the extract was washed with saturated sodium bicarbonate aqueous solution and saturated saline solution, then, dried over with anhydrous sodium sulfate. The solvent removed under reduced pressure to give 9.84 g (66%) of the title compound.

Example 3-1

5-Chloro-1-cyclohexyl-3-methyl-1H-pyrazole-4-carboaldehyde

To a solution of 9.84 g (49.52 mmol) of the compound obtained in the Example 2 in 50 mL of N,N-dimethylformamide was added 11.5 mL (123.8 mmol) of phosphorous oxychloride under ice cooling, and the mixture was stirred for 30 minutes at room temperature and for 1 hour at 80° C. Then, the reaction mixture was cooled to room temperature and condensed under reduced pressure. The residue was extracted with ethyl acetate and the extract was washed with saturated sodium bicarbonate aqueous solution and saturates saline solution, then, dried over with anhydrous sodium sulfate. The solvent was removed under reduced pressure and the residue was purified by silica gel column chromatography (eluent: hexane/ethyl acetate=10/1) to give 8.73 g (76%) of the title compound.

Example 3-2

5-Chloro-1-cyclohexyl-3-methyl-1H-pyrazole-4-carboaldehyde

A mixture of 10 g (0.61 mol) of the compound obtained in the Example 1 and 216 mL (2.32 mol) of phosphorus oxychloride was heated and stirred for 2 hours at 110° C. Then, the reaction mixture was cooled to room temperature and added gradually to 630 mL of cooled N,N-dimethylformamide. After adding, the mixture was stirred for 30 minutes at room temperature and for 5 hours at 80° C. The reaction mixture was cooled to room temperature, and the mixture was poured slowly into ice. Chloroform was added to this mixture and pH of the mixture was adjusted to about 4 by 4N-NaOH aqueous solution (about 2.3 L). The organic layer was separated and water layer was extracted with chloroform. The combined organic layer was washed with water and saturated saline solution, then, dried over with anhydrous sodium sulfate. The solvent was removed under reduced pressure and the residue was purified by silica gel column chromatography (eluent:ethyl acetate/hexane=1/10 to 1/7) to give 100.8 g (73%) of the title compound.

Example 4

Ethyl [(1-cyclohexyl-4-formyl-3-methyl-1H-pyrazol-5-yl)sulfanil]-acetate

To a solution of 8.0 g (35.3 mmol) of the compound obtained in the Example 3 in 100 mL of acetonitrile were added 4.84 mL (44.1 mmol) of ethyl thioglycolate and 7.32 g (52.93 mmol) of potassium carbonate, and the mixture was refluxed for 4 hours. Then, 1.93 mL (17.64 mmol) of ethyl thioglycolate and 2.43 g (17.64 mmol) of potassium carbonate were further added to the reaction mixture and the mixture was refluxed for 2 hours. After the reaction mixture was cooled to room temperature and condensed under reduced pressure. The residue was extracted with ethyl acetate and the extract was washed with water and saturated saline solution, then, dried over with anhydrous sodium sulfate. The solvent was removed under reduced pressure and the residue was purified by silica gel column chromatography (eluent:hexane/ethyl acetate=4/1) to give 8.09 g (74%) of the title compound.

Example 5-1

Ethyl 1-cyclohexyl-3-methyl-1H-thieno[2,3-c]pyrazole-5-carboxylate

To a solution of 7.95 g (25.61 mmol) of the compound obtained in the Example 4 in 100 mL of N,N-dimethylformamide were added 5.31 g (38.42 mmol) of potassium carbonate and 677 mg (2.56 mmol) of 18-crown-6, and the mixture was heated for 2 hours at 120° C. to 130° C. After cooling the reaction mixture to room temperature, the mixture was extracted with ethyl acetate, and the extract was washed with water and saturated saline solution, then, dried over with anhydrous sodium sulfate. The solvent was removed under reduced pressure and the residue was purified by silica gel column chromatography (eluent:hexane/acetone=15/1) to give 2.2 g (29%) of the title compound.

Example 5-2

Ethyl 1-cyclohexyl-3-methyl-1H-thieno[2,3-c]pyrazole-5-carboxylate

To a solution of 63.4 mL (0.578 mmol) of ethyl thioglycolate in 1 L of tetrahydrofuran was added gradually 23 g (0.578 mol) of sodium hydride (60% oily) under ice cooling, and the mixture was stirred for 1 hour at room temperature. The reaction mixture was cooled with ice water, and a solution of 100.8 g (0.444 mol) of the compound obtained in the Example 3 in 400 mL of tetrahydrofuran was added gradually to this reaction mixture during 45 minutes, and the mixture was stirred for 2 hours at room temperature. Then, the reaction mixture was cooled with ice water, and 23 g (0.578 mol) of sodium hydride (60% oily) was added gradually to this reaction mixture, and the mixture was stirred for 30 minutes at 0° C. After the reaction, the reaction mixture was poured slowly into ice/ethyl acetate solution, and the organic layer was separated. The water layer was extracted with ethyl acetate, and the combined organic layer was washed with water and saturated saline solution, then dried over with anhydrous sodium sulfate. The solvent was removed under reduced pressure and the residue was purified by silica gel column chromatography (eluent:ethyl acetate/hexane=1/8 to 1/5) to give 104.7 g (81%) of the title compound.

Example 6

1-Cyclohexyl-3-methyl-1H-thieno[2,3-c]pyrazole-5-carboxylic acid

To a solution of 11.89 g (40.66 mmol) of the compound obtained in the Example 5 in 100 mL of ethanol was added 44.7 mL (44.7 mmol) of 1N sodium hydroxide solution, and the mixture was heated for 1 hour at 60° C. Then, the reaction mixture was cooled to room temperature and condensed under reduced pressure. Water and diethyl ether were added to the residue and the water layer was separated. 23 mL of 2N—HCl aqueous solution was added to the water layer, and the resulting precipitates were collected to give 10.38 g (97%) of the title compound.

Example 7

N-Benzyl-1-cyclohexyl-3-methyl-1H-thieno[2,3-c]pyrazole-5-carboxamide

To a suspension of 60 mg (0.23 mmol) of the compound obtained in the Example 6 in 2 mL of dichloromethane was added 33 μL (0.45 mmol) of thionyl chloride, and the mixture was stirred for 8 hours at 80° C. Then, the solvent was removed under reduced pressure to give the corresponding acid chloride intermediate compound.

Next, 27 μL (0.25 mmol) of benzylamine and 79 μL of triethylamine were added to the solution of the above acid chloride intermediate compound in 2 mL of anhydrous dichloromethane under ice-cooling, and the mixture was stirred for 1.5 hours at room temperature. Then, water was added to the reaction mixture and the mixture was extracted with dichloromethane. The organic layer was dried over with anhydrous sodium sulfate and removed under reduced pressure. The residue was purified by silica gel column chromatography (eluent:hexane/ethyl acetate=4/1 to 3/1) to give 75 mg (94%) of the title compound.

Example 8

1-Cyclohexyl-3-methyl-N-phenyl-1H-thieno[2,3-c]pyrazole-5-carboxamide

The title compound 65 mg (84%) was obtained in a manner similar to the Example 7 by use of aniline, instead of benzylamine.

Example 9

N-{4-[Acetyl(methyl)amino]phenyl}-1-cyclohexyl-3-methyl-1H-thieno[2,3-c]pyrazole-5-carboxamide The title compound 89 mg (82%) was obtained in a manner similar to the Example 7 by use of N-(4-aminophenyl)-N-methylacetamide, instead of benzylamine.

Example 10

N-[4-(Acetylamino)-3-methoxyphenyl]-1-cyclohexyl-3-methyl-1H-thieno[2,3-c]pyrazole-5-carboxamide The title compound 73 mg (65%) was obtained in a manner similar to the Example 7 by use of N-(4-amino-3-methoxyphenyl)acetamide, instead of benzylamine.

Example 11

N-(1-Acetyl-2,3-dihydror-1H-indol-5-yl)-1-cyclohexyl-3-methyl-1H-thieno[2,3-c]pyrazole-5-carboxamide The title compound 30 mg (27%) was obtained in a manner similar to the Example 7 by use of 1-acetyl-2,3-dihydro-1H-indol-5-ylamine, instead of benzylamine.

Example 12

Ethyl 4-{[(1-cyclohexyl-3-methyl-1H-thieno[2,3-c]pyrazol-5-yl)-carbonyl]amino}phenylcarbamate The title compound 101 mg (89%) was obtained in a manner similar to the Example 7 by use of ethyl 4-aminophenylcarbamate, instead of benzylamine.

Example 13 tert-Butyl 5-{[(1-cyclohexyl-3-methyl-1H-thieno[2,3-c]pyrazol-5-yl)carbonyl]amino}-1-indolinecarboxylate The title compound 133 mg (92%) was obtained in a manner similar to the Example 7 by use of the compound obtained in the Manufacturing Example 2, instead of benzylamine.

Example 14

1-Cyclohexyl-N-(2,3-dihydro-1H-indol-5-yl)-3-methyl-1H-thieno[2,3-c]pyrazole-5-carboxamide HCl salt The title compound 68 mg (99%) was obtained in a manner similar to the Manufacturing Example 4 by use of the compound obtained in the Example 13, instead of the compound obtained in the Manufacturing Example 3.

Example 15

1-Cyclohexyl-N-(1H-indol-5-yl)-3-methyl-1H-thieno[2,3-c]pyrazole-5-carboxamide

The title compound 95 mg (95%) was obtained in a manner similar to the Example 7 by use of 5-aminoindole, instead of benzylamine.

Example 16

1-Cyclohexyl-3-methyl-N-[4-(4-morpholinyl)phenyl]-1H-thieno[2,3-c]pyrazole-5-carboxamide The title compound 85 mg (89%) was obtained in a manner similar to the Example 7 by use of 4-(4-morpholinyl) aniline, instead of benzylamine.

Example 17

1-Cyclohexyl-3-methyl-N-(3-nitrophenyl)-1H-thieno[2,3-c]pyrazole-5-carboxamide

The title compound 175 mg (60%) was obtained in a manner similar to the Example 7 by use of 3-nitroaniline, instead of benzylamine.

Example 18

N-(3-Aminophenyl)-1-cyclohexyl-3-methyl-1H-thieno[2,3-c]pyrozole-5-carboxamide

The title compound 142 mg (quantitative) was obtained in a manner similar to the Manufacturing Example 2 by use of the compound obtained in the Example 17, instead of the compound obtained in the Manufacturing Example 1.

Example 19

N-[3-(Acetylamino)phenyl]-1-cyoclohexyl-3-methyl-1H-thieno[2,3-c]pyrazole-5-carboxamide To a solution of 60 mg (0.17 mmol) of the compound obtained in the Example 18 in 4 mL of anhydrous tetrahydrofuran were added 25 µL (0.35 mmol) of acetyl chloride and 50 µL (0.35 mmol) of triethylamine under ice cooling, and the mixture was stirred for 2 hour at room temperature. Then, water was added to the reaction mixture and the mixture was extracted with ethyl acetate. The organic layer was dried over with anhydrous sodium sulfate and removed under reduced pressure. The residue was purified by silica gel column chromatography (eluent:hexane/ethyl acetate=2/1 to 1/2) to give 15 mg (22%) of the title compound.

Example 20

1-Cyclohexyl-3-methyl-N-{4-(methylamino)carbonyl}phenyl}-1H-thieno[2,3-c]pyrazole-5-carboxamide The title compound 37 mg (41%) was obtained in a manner similar to the Example 7 by use of 4-amino-N-methylbenzamide, instead of benzylamine.

Example 21

1-Cyclohexyl-3-methyl-N-(1-propionyl-2,3-dihydro-1H-indol-5-yl)-1H-thieno[2,3-c]pyrazole-5-carboxamide The title compound 47 mg (75%) was obtained in a manner similar to the Example 19 by use of the compound obtained in the Example 14 and propionyl chloride, instead of using the compound obtained in the Example 18 and acetyl chloride, respectively.

Example 22

Ethyl 5-{[(1-Cyclohexyl-3-methyl-1H-thieno[2,3-c]pyrazol-5-yl)-carbonyl]amino}-1-indolinecarboxylate The title compound 62 mg (82%) was obtained in a manner similar to the Example 19 by use of the compound obtained in the Example 14 and ethyl chlorocarbonate, instead of the compound obtained in the Example 18 and acetyl chloride, respectively.

Example 23

1-Cyclohexyl-N-(1-isobutyl-2,3-dihydro-1H-indol-5-yl)-3-methyl-1H-thieno[2,3-c]pyrazole-5-carboxamide The title compound 68 mg (89%) was obtained in a manner similar to the Example 19 by use of the compound obtained in the Example 14 and isobutyryl chloride, instead of the compound obtained in the Example 18 and acetyl chloride, respectively.

Example 24

N-(1-Butyryl-2,3-dihydro-1H-indol-5-yl)-1-cyclohexyl-3-methyl-1H-thieno[2,3-c]pyrazole-5-carboxamide The title compound 66 mg (87%) was obtained in a manner similar to the Example 19 by use of the compound obtained in the Example 14 and n-butyryl chloride, instead of the compound obtained in the Example 18 and acetyl chloride, respectively.

Example 25

1-Cyclohexyl-N-[1-(2,2-dimethylpropanoyl)-2,3-dihydro-1H-indol-5-yl]-3-methyl-1H-thieno[2,3-c]pyrazole-5-carboxamide The title compound 59 mg (76%) was obtained in a manner similar to the Example 19 by use of the compound obtained in the Example 14 and propanoyl chloride, instead of the compound obtained in the Example 18 and acetyl chloride, respectively.

Example 26

1-Cyclohexyl-3-methyl-N-(2-oxo-2,3-dihydro-1H-indol-5-yl)-1H-thieno[2,3-c]pyrazole-5-carboxamide The title compound 60 mg (58%) was obtained in a manner similar to the Example 7 by use of 5-amino-1,3-dihydro-2H-indol-2-one, instead of benzylamine.

Example 27

N-[4-(Acetylamino)-3-chlorophenyl]-1-cyclohexyl-3-methyl-1H-thieno[2,3-c]pyrazole-5-carboxamide The title compound 28 mg (43%) was obtained in a manner similar to the Example 7 by use of N-(4-amino-2-chlorophenyl)acetamide, instead of benzylamine.

Example 28

1-Cyclohexyl-N-{4-[(ethylamino)carbonyl]phenyl}-3-methyl-1H-thieno[2,3-c]pyrazole-5-carboxamide The title compound 30 mg (32%) was obtained in a manner similar to the Example 7 by use of 4-amino-N-ethylbenzamide, instead of benzylamine.

Example 29

1-Cyclohexyl-N-[4-(methoxymethyl)phenyl]-3-methyl-1H-thieno[2,3-c]pyrazole-5-carboxamide The title compound 62 mg (70%) was obtained in a manner similar to the Example 7 by use of 4-(methoxymethyl)aniline, instead of benzylamine.

Example 30

1-Cyclohexyl-N-[4-(hydroxymethyl)phenyl]-3-methyl-1H-thieno[2,3-c]pyrazole-5-carboxamide The title compound 65 mg (76%) was obtained in a manner similar to the Example 7 by use of (4-aminophenyl)methanol, instead of benzylamine.

Example 31

1-Cyclohexyl-3-methyl-N-[4-(morpholinylcarbonyl)
phenyl]-1H-thieno[2,3-c]pyrazole-5-carboxamide The title compound 88 mg (90%) was obtained in a manner similar to the Example 7 by use of 4-(4-morpholinylcarbonyl) aniline, instead of benzylamine.

Example 32

1-Cyclohexyl-3-methyl-N-{4-[(4-methyl-1-piperazinyl)carbonyl]-phenyl}-1H-thieno[2,3-c]pyrazole-5-carboxamide The title compound 57 mg (53%) was obtained in a manner similar to the Example 7 by use of 4-[(4-methyl-1-piperazinyl)carbonyl]aniline, instead of benzylamine.

Example 33

1-Cyclohexyl-3-methyl-N-{4-[(methylsulfonyl)
amino]phenyl}-1H-thieno[2,3-c]pyrazole-5-carboxamide The title compound 33 mg (33%) was obtained in a manner similar to the Example 7 by use of N-(4-aminophenyl)methanesulfonamide, instead of benzylamine.

Example 34

1-Cyclohexyl-3-methyl-N-{4-[(methylamino)sulfonyl]phenyl}-1H-thieno[2,3-c]pyrazole-5-carboxamide The title compound 22 mg (22%) was obtained in a manner similar to the Example 7 by use of 4-amino-N-methylbenzenesulfonamide, instead of benzylamine.

Example 35

N-{1-[(1-Cyclohexyl-3-methyl-1H-thieno[2,3-c]
pyrazol-5-yl)carbonyl]-2,3-dihydro-1H-indol-5-
yl}acetamide The title compound 76 mg (80%) was obtained in a manner similar to the Example 7 by use of the compound obtained in the Manufacturing Example 4, instead of benzylamine.

Example 36

1-Cyclohexyl-3-methyl-N-{4-[(4-methyl-1-piperazinyl)sulfonyl]-phenyl}-1H-thieno[2,3-c]pyrazole-5-carboxamide The title compound 36 mg (32%) was obtained in a manner similar to the Example 7 by use of 4-[(4-methyl-1-piperazinyl)sulfonyl]aniline, instead of benzylamine.

Example 37

1-Cyclohexyl-N-(4-{[(2-methoxyethyl)amino]
carbonyl}phenyl)-3-methyl-1H-thieno[2,3-c]pyrazole-5-carboxamide The title compound 50 mg (50%) was obtained in a manner similar to the Example 7 by use of 4-amino-N-(2-methoxyethyl)benzamide, instead of benzylamine.

Example 38

N-(4-Acetylphenyl)-1-cyclohexyl-3-methyl-1H-
thieno[2,3-c]pyrazole-5-carboxamide The title compound 54 mg (62%) was obtained in a manner similar to the Example 7 by use of p-aminoacetophenone, instead of benzylamine.

Example 39

1-Cyclohexyl-N-{4-[(dimethylamino)carbonyl]phenyl}-3-methyl-1H-thieno[2,3-c]pyrazole-5-carboxamide The title compound 86 mg (92%) was obtained in a manner similar to the Example 7 by use of 4-amino-N,N-dimethylbenzamide, instead of benzylamine.

Example 40

Ethyl 4-{[(1-cyclohexyl-3-methyl-1H-thieno[2,3-c]
pyrazol-5-yl)-carbonyl]amino}benzoate The title compound 80 mg (51%) was obtained in a manner similar to the Example 7 by use of ethyl 4-aminobenzoate, instead of benzylamine.

Example 41

4-{[(1-Cyclohexyl-3-methyl-1H-thieno[2,3-c]pyrazol-5-yl)carbonyl]-amino}benzoic Acid To a solution of 55 mg (0.13 mmol) of the compound obtained in the Example 40 in 8 mL of ethanol was added 134 μL of 1M sodium hydroxide solution, and the mixture was stirred for 1 hour at room temperature. Then, 20 mL of water was added to the reaction mixture and the water layer was washed with ethyl acetate. The water layer was neutralized by adding of 1M-HCl solution, and the resulting precipitates were collected to give 33 mg (65%) of the title compound.

Example 42

1-Cyclohexyl-N-(2-methoxy-4-nitrophenyl)-3-methyl-1H-thieno[2,3-c]pyrazole-5-carboxamide The title compound 73 mg (31%) was obtained in a manner similar to the Example 7 by use of 2-methoxy-4-nitroaniline, instead of benzylamine.

Example 43

N-(4-Amino-2-methoxyphenyl)-1-cyclohexyl-3-
methyl-1H-thieno[2,3-c]pyrazole-5-carboxamide The title compound 22 mg (37%) was obtained in a manner similar to the Manufacturing Example 2 by use of the compound obtained in the Example 42, instead of the compound obtained in the Manufacturing Example 1.

Example 44

N-[4-(Acetylamino)-2-methoxyphenyl]-1-cyclohexyl-3-methyl-1H-thieno[2,3-c]pyrazole-5-carboxamide The title compound 27 mg (49%) was obtained in a manner similar to the Manufacturing Example 3 by use of the compound obtained in the Example 43, instead of the compound obtained in the Manufacturing Example 2.

Example 45

1-Cyclohexyl-N-{4-[(isopropylamino)carbonyl]phenyl}-3-methyl-1H-thieno[2,3-c]pyrazole-5-carboxamide The title compound 47 mg (49%) was obtained in a manner similar to the Example 7 by use of 4-amino-N-isopropylbenzamide, instead of benzylamine.

Example 46

1-Cyclohexyl-N-(4-{[(2-hydroxyethyl)amino]carbonyl}phenyl)-3-methyl-1H-thieno[2,3-c]pyrazole-5-carboxamide The title compound 93 mg (72%) was obtained in a manner similar to the Example 7 by use of 4-amino-N-(2-hydroxyethyl)benzamide, instead of benzylamine.

Example 47

N-[6-(Acetylamino)-3-pyridinyl]-1-cyclohexyl-3-methyl-1H-thieno[2,3-c]pyrazole-5-carboxamide The title compound 33 mg (37%) was obtained in a manner similar to the Example 7 by use of N-(5-amino-2-pyridinyl)acetamide, instead of benzylamine.

Example 48

1-Cyclohexyl-N-(4-methoxyphenyl)-3-methyl-1H-thieno[2,3-c]pyrazole-5-carboxamide The title compound 81 mg (96%) was obtained in a manner similar to the Example 7 by use of p-anisidine, instead of benzylamine.

Example 49

1-Cyclohexyl-N-cyclopentyl-3-methyl-1H-thieno[2,3-c]pyrazole-5-carboxamide

The title compound 65 mg (85%) was obtained in a manner similar to the Example 7 by use of cyclopentylamine, instead of benzylamine.

Example 50

N,1-Dicyclohexyl-3-methyl-1H-thieno[2,3-c]pyrazole-5-carboxamide

The title compound 82 mg (quantitative) was obtained in a manner similar to the Example 7 by use of cyclohexylamine, instead of benzylamine.

Example 51

N-{4-[(tert-Butylamino)carbonyl]phenyl}-1-cyclohexyl-3-methyl-1H-thieno[2,3-c]pyrazole-5-carboxamide The title compound 89 mg (89%) was obtained in a manner similar to the Example 7 by use of 4-amino-N-(tert-butyl)benzamide, instead of benzylamine.

Example 52

1-Cyclohexyl-N-{5-[(isopropylamino)carbonyl]-2-pyridinyl}-3-methyl-1H-thieno[2,3-c]pyrazole-5-carboxamide The title compound 13 mg (20%) was obtained in a manner similar to the Example 7 by use of the compound obtained in the Manufacturing Example 5, instead of benzylamine.

Example 53

1-Cyclohexyl-N-[4-(fromylamino)phenyl]-3-methyl-1H-thieno[2,3-c]pyrazole-5-carboxamide The title compound 11 mg (19%) was obtained in a manner similar to the Example 7 by use of 4-aminophenylformamide, instead of benzylamine.

Example 54 tert-Butyl 4-[(4-{[(1-cyclohexyl-3-methyl-1H-thieno[2,3-c]pyrazol-5-yl)carbonyl]amino}phenyl)sulfonyl]-1-piperazinecarboxylate The title compound 71 mg (32%) was obtained in a manner similar to the Example 7 by use of tert-butyl 4-[(4-aminophenyl)sulfonyl]-1-piperazinecarboxylate, instead of benzylamine.

Example 55

1-Cyclohexyl-3-methyl-N-[4-(1-piperazinylsulfonyl)phenyl]-1H-thieno[2,3-c]pyrazole-5-carboxamide HCl salt The title compound 30 mg (61%) was obtained in a manner similar to the Manufacturing Example 4 by use of the compound obtained in the Example 54, instead of the compound obtained in the Manufacturing Example 3.

Example 56

1-Cyclohexyl-3-methyl-N-[4-(4-morpholinylsulfonyl)phenyl]-1H-thieno[2,3-c]pyrazole-5-carboxamide The title compound 14 mg (12%) was obtained in a manner similar to the Example 7 by use of 4-(4-morpholinylsulfonyl)aniline, instead of benzylamine.

Example 57

1-Cyclohexyl-3-methyl-N-[4-(methylsulfonyl)phenyl]-1H-thieno[2,3-c]pyrazole-5-carboxamide The title compound 41 mg (43%) was obtained in a manner similar to the Example 7 by use of 4-(methylsulfonyl) aniline, instead of benzylamine.

Example 58

1-Cyclohexyl-N-[1-(cyclopropylcarbonyl)-2,3-dihydro-1H-indol-5-yl]-3-methyl-1H-thieno[2,3-c]pyrazole-5-carboxamide The title compound 42 mg (49%) was obtained in a manner similar to the Example 19 by use of the compound obtained in the Example 14 and cyclopropanecarbonyl chloride, instead of the compound obtained in the Example 18 and acetyl chloride, respectively.

Example 59

1-Cyclohexyl-3-methyl-N-[1-(methylsulfonyl)-2,3-dihydro-1H-indol-5-yl]-1H-thieno[2,3-c]pyrazole-5-carboxamide The title compound 106 mg (quantitative) was obtained in a manner similar to the Example 7 by use of the compound obtained in the Manufacturing Example 7, instead of benzylamine.

Example 60

N-(1-Acetyl-1H-indol-5-yl)-1-cyclohexyl-3-methyl-1H-thieno[2,3-c]pyrazole-5-carboxamide The title compound 94 mg (97%) was obtained in a manner similar to the Example 7 by use of 1-acetyl-1H-indole-5-amine, instead of benzylamine.

Example 61

1-Cyclohexyl-N-cyclopropyl-3-methyl-1H-thieno[2,3-c]pyrazole-5-carboxamide

The title compound 67 mg (96%) was obtained in a manner similar to the Example 7 by use of cyclopropylamine, instead of benzylamine.

Example 62

N-(1-Benzyl-4-piperidinyl)-1-cyclohexyl-3-methyl-1H-thieno[2,3-c]pyrazole-5-carboxamide The title compound 200 mg (81%) was obtained in a manner similar to the Example 7 by use of 1-benzyl-4-piperidinylamine, instead of benzylamine.

Example 63

1-Cyclohexyl-3-methyl-N-(4-piperidinyl)-1H-thieno[2,3-c]pyrazole-5-carboxamide HCl salt To a solution of 180 mg (0.42 mol) of the compound obtained in the Example 62 in 4 mL of 1,2-dichloroethane was added 50 μL of 1-chloroethyl chloroformate, and the mixture was refluxed for 2 hours. Then, the reaction mixture was cooled to room temperature and condensed under reduced pressure. The residue was dissolved in 6 mL of methanol and the mixture was refluxed for 3 hours. After the reaction mixture was cooled to room temperature, the solvent was removed under reduced pressure. The residue was washed with ethyl acetate and the resulting precipitates were collected to give 109 mg (69%) of the title compound.

Example 64

N-(1-Acetyl-4-piperidinyl)-1-cyclohexyl-3-methyl-1H-thieno[2,3-c]pyrazole-5-carboxamide The title compound 40 mg (78%) was obtained in a manner similar to the Manufacturing Example 3 by use of the compound obtained in the Example 63, instead of the compound obtained in the Manufacturing Example 2.

Example 65

Ethyl (4-{[(1-cyclohexyl-3-methyl-1H-thieno[2,3-c]pyrazol-5-yl)-carbonyl]amio}phenoxy)acetate The title compound 320 mg (96%) was obtained in a manner similar to the Example 7 by use of ethyl (4-aminophenoxy)acetate, instead of benzylamine.

Example 66

(4-{[(1-Cyclohexyl-3-methyl-1H-theino[2,3-c]pyrazol-5-yl)carbonyl]-amino}phenoxy)acetic acid The title compound 268 mg (95%) was obtained in a manner similar to the Example 41 by use of the compound obtained in the Example 65, instead of the compound obtained in the Example 40.

Example 67

1-Cyclohexyl-3-methyl-N-{[(4-[2-(methylamino)-2-oxoethoxy]phenyl)-1H-thieno[2,3-c]pyrazole-5-carboxamide The title compound 24 mg (39%) was obtained in a manner similar to the Manufacturing Example 5 by use of the compound obtained in the Example 66 and methylamine (30%-methanol solution), instead of 6-aminonicotic acid and isopropylamine, respectively.

Example 68

Ethyl 4-{[(1-cyclohexyl-3-methyl-1H-thieno[2,3-c]pyrazol-5-yl)-carbonyl]amino}phenyl)acetate The title compound 223 mg (93%) was obtained in a manner similar to the Example 7 by use of ethyl(4-aminophenyl)acetate, instead of benzylamine.

Example 69

(4-{[(1-Cyclohexyl-3-methyl-1H-thieno[2,3-c]pyrazol-5-yl)carbonyl]-amino}phenyl)acetic acid The title compound 157 mg (84%) was obtained in a manner similar to the Example 41 by use of the compound obtained in the Example 68, instead of the compound obtained in the Example 40.

Example 70

1-Cyclohexyl-3-methyl-N-{4-[2-(methylamino)-2-oxoethyl]phenyl}-1H-thieno[2,3-c]pyrazole-5-carboxamide The title compound 31 mg (50%) was obtained in a manner similar to the Manufacturing Example 5 by use of the compound obtained in the Example 69 and methylamine (30%-methanol solution), instead of 6-aminonicotic acid and isopropylamine, respectively.

Example 71 tert-Butyl 4-(4-{[(1-cyclohexyl-3-methyl-1H-thieno[2,3-c]pyrazol-5-yl)carbonyl]amino}phenyl)-1-piperazinecarboxylate The title compound 158 mg (quantitative) was obtained in a manner similar to the Example 7 by use of tert-buty 4-(4-aminophenyl)-1-piperazine-carboxylate, instead of benzylamine.

Example 72

1-Cyclohexyl-3-methyl-N-[4-(1-piperazinyl)phenyl]-1H-thieno[2,3-c]pyrazole-5-carboxamide HCl salt The title compound 108 mg (88%) was obtained in a manner similar to the Manufacturing Example 4 by use of the compound obtained in the Example 71, instead of the compound obtained in the Manufacturing Example 3.

Example 73

N-[4-(4-Acetyl-1-piperazinyl)phenyl]-1-cyclohexyl-3-methyl-1H-thieno[2,3-c]pyrazole-5-carboxamide The title compound 32 mg (63%) was obtained in a manner similar to the Manufacturing Example 3 by use of the compound obtained in the Example 72, instead of the compound obtained in the Manufacturing Example 2.

Example 74

1-Cyclohexyl-N-(trans-4-hydroxycyclohexyl)-3-methyl-1H-thieno[2,3-c]pyrazole-5-carboxamide The title compound 82 mg (quantitative) was obtained in a manner similar to the Example 7 by use of trans-4-aminocyclohexanol, instead of benzylamine.

Example 75

1-Cyclohexyl-3-methyl-N-(4-oxocyclohexyl)-1H-thieno[2,3-c]pyrazole-5-carboxamide To a solution of 4.0 g (11.1 mmol) of the compound obtained in the Example 74 in 200 mL of dichloromethane was added 5.0 g (13.3 mmol) of pyridinium dichromate, and the mixture was stirred for 6 hours at room temperature. Then, 5.0 g (13.3 mmol) of pyridinium dichromate was further added to the reaction mixture and the mixture was stirred for 18 hours. The reaction mixture was filtrated with Celite® and the filtrate was removed under reduced pressure. The residue was purified by silica gel column chromatography (eluent: dichloromethane/methanol=40/1) to give the 2.6 g (65%) of the title compound.

Example 76

1-Cyclohexyl-3-methyl-N-{4-[2-(4-methyl-1-piperazinyl)-2-oxoethoxy]-phenyl}-1H-thieno[2,3-c]pyrazole-5-carboxamide The title compound 65 mg (90%) was obtained in a manner similar to the Manufacturing Example 5 by use of the compound obtained in the Example 66 and N-methylpiperazine, instead of 6-aminonicotic acid and isopropylamine, respectively.

Example 77

1-Cyclohexyl-N-{4-[2-(dimethylamino)-2-oxoethoxy]phenyl}-3-methyl-1H-thieno[2,3-c]pyrazole-5-carboxamide The title compound 43 mg (67%) was obtained in a manner similar to the Manufacturing Example 5 by use of the compound obtained in the Example 66 and dimethylamine HCl salt, instead of 6-aminonicotic acid and isopropylamine, respectively.

Example 78

2-{4-[(4-{[(1-Cyclohexyl-3-methyl-1H-thieno[2,3-c]pyrazol-5-yl)-carbonyl]amino}phenyl)sulfonyl]-1-piperazinyl}ethyl acetate The title compound 60 mg (28%) was obtained in a manner similar to the Example 7 by use of the compound obtained in the Manufacturing Example 10, instead of benzylamine.

Example 79

1-Cyclohexyl-N-(4-{[4-(2-hydroxyethyl)-1-piperazinyl]sulfonyl}-phenyl)-3-methyl-1H-thieno[2,3-c]pyrazole-5-carboxamide To a solution of 45 mg (0.08 mmol) of the compound obtained in the Example 78 in 41 mL of ethanol was added 86 μL of 1M sodium hydroxide aqueous solution, and the mixture was stirred for 1 hour at room temperature. Then, water was added to the reaction mixture and the mixture was extracted with ethyl acetate. The organic layer was washed with saturated saline solution and dried over with anhydrous sodium sulfate. The solvent was removed under reduced pressure and the residue was purified by silica gel column chromatography (eluent:dichloromethane/methanol=20/1) to give 31 mg (74%) of the title compound.

Example 80

N-[trans-4-(Acetylamino)cyclohexyl]-1-cyclohexyl-3-methyl-1H-thieno[2,3-c]pyrazole-5-carboxamide The title compound 28 mg (30%) was obtained in a manner similar to the Example 7 by use of the compound obtained in the Manufacturing Example 12, instead of benzylamine.

Example 81

1-Cyclohexyl-N,3-dimethyl-1H-thieno[2,3-c]pyrazole-5-carboxamide

The title compound 58 mg (92%) was obtained in a manner similar to the Example 7 by use of methylamine HCl salt, instead of benzylamine.

Example 82

2-Cyclopentyl-5-methyl-2,4-dihydro-3H-pyrazole-3-one

The title compound 9.70 g (80%) was obtained in a manner similar to the Example 1 by use of cyclopentylhydrazine HCl salt, instead of cyclohexylhydrazine HCl salt.

Example 83

5-Chloro-1-cyclopentyl-3-methyl-1H-pyrazole

The title compound 4.5 g (81%) was obtained in a manner similar to the Example 2 by use of the compound obtained in the Example 82, instead of the compound obtained in the Example 1.

Example 84

5-Chloro-1-cyclopentyl-3-methyl-1H-pyrazole-4-carboaldehyde

The title compound 4.0 g (79%) was obtained in a manner similar to the Example 3-1 by use of the compound obtained in the Example 83, instead of the compound obtained in the Example 2.

Example 85

Ethyl [(1-cyclopentyl-4-formyl-3-methyl-1H-pyrazol-5-yl)sulfanil]-acetate

The title compound 1.9 g (36%) was obtained in a manner similar to the Example 4 by use of the compound obtained in the Example 84, instead of the compound obtained in the Example 3.

Example 86

Ethyl 1-cyclopentyl-3-methyl-1H-thieno[2,3-c]pyrazole-5-carboxylate

The title compound 1.47 g (87%) was obtained in a manner similar to the Example 5-1 by use of the compound obtained in the Example 85, instead of the compound obtained in the Example 4.

Example 87

1-Cyclopentyl-3-methyl-1H-thieno[2,3-c]pyrazole-5-carboxylic acid

The title compound 0.49 g (68%) was obtained in a manner similar to the Example 6 by use of the compound obtained in the Example 86, instead of the compound obtained in the Example 5.

Example 88

N-[4-(Acetylamino)phenyl]-1-cyclopentyl-3-methyl-1H-thieno[2,3-c]pyrazole-5-carboxamide The title compound 88 mg (72%) was obtained in a manner similar to the Example 7 by use of N-(4-aminophenyl)acetamide and the compound obtained in the Example 87, instead of benzylamine and the compound obtained in the Example 6 respectively.

Example 89

2-Cycloheptyl-5-methyl-2,4-dihydro-3H-pyrazole-3-one

The title compound 16.27 g (52%) was obtained in a manner similar to the Example 1 by use of cycloheptylhydrazine HCl salt, instead of using cyclohexylhydrazine HCl salt.

Example 90

5-Chloro-1-cycloheptyl-3-methyl-1H-pyrazole

The title compound 6.92 g (79%) was obtained in a manner similar to the Example 2 by use of the compound obtained in the Example 89, instead of the compound obtained in the Example 1.

Example 91

5-Chloro-1-cycloheptyl-3-methyl-1H-pyrazole-4-carboaldehyde

The title compound 6.47 g (84%) was obtained in a manner similar to the Example 3-1 by use of the compound obtained in the Example 90, instead of the compound obtained in the Example 2.

Example 92

Ethyl 1-cycloheptyl-3-methyl-1H-thieno[2,3-c]pyrazole-5-carboxylate

To a solution of 6.4 g (26.6 mmol) of the compound obtained in the Example 91 in 100 mL of acetonitrile were added 3.06 mL (27.9 mmol) of ethyl thioglycolate and 7.72 g (55.88 mmol) of potassium carbonate, and the mixture was refluxed for 23 hours. Then, 3.06 mL (27.9 mmol) of ethyl thioglycolate was further added ant the mixture was refluxed for 3 hours. After cooling the reaction mixture to room temperature, the mixture was condensed and the residue was extracted with dichloromethane. The organic layer was washed with water and saturated saline solution, then, dried over with anhydrous sodium sulfate. The solvent was removed under reduced pressure, and the residue was purified by silica gel column chromatography (eluent:hexane/acetone=20/1) to give 2.46 g (30%) of the title compound.

Example 93

1-Cycloheptyl-3-methyl-1H-thieno[2,3-c]pyrazole-5-carboxylic acid

The title compound 1.40 g (67%) was obtained in a manner similar to the Example 6 by use of the compound obtained in the Example 92, instead of the compound obtained in the Example 5.

Example 94

N-[4-(Acetylamino)phenyl]-1-cycloheptyl-3-methyl-1H-thieno[2,3-c]pyrazole-5-carboxamide The title compound 71 mg (60%) was obtained in a manner similar to the Example 7 by use of N-(4-aminophenyl)acetamide and the compound obtained in the Example 93, instead of benzylamine and the compound obtained in the Example 6, respectively.

Example 95

1-Cyclohexyl-N,3-dimethyl-N-phenyl-1H-thieno[2,3-c]pyrazole-5-carboxamide

The title compound 103 mg (96%) was obtained in a manner similar to the Example 7 by use of N-methylaniline, instead of benzylamine.

Example 96

1-Cyclohexyl-3-methyl-N-(4-pyridinyl)-1H-thieno[2,3-c]pyrazole-5-carboxamide

The title compound 80 mg (96%) was obtained in a manner similar to the Example 7 by use of 4-aminopyridine, instead of benzylamine.

Example 97

1-Cyclohexyl-3-methyl-N-(3-pyridinyl)-1H-thieno[2,3-c]pyrazole-5-carboxamide

The title compound 48 mg (57%) was obtained in a manner similar to the Example 7 by use of 3-aminopyridine, instead of benzylamine.

Example 98

1-Cyclohexyl-3-methyl-N-(4-nitrophenyl)1H-thieno[2,3-c]pyrazole-5-carboxamide

To a suspension of 170 mg (0.643 mmol) of the compound obtained in the Example 6 in 3 mL of 1,2-dichloroethane was added 94 μL (1.29 mmol) of thionyl chloride, and the mixture was stirred for 1.5 hours at 90° C. After cooling the reaction mixture to room temperature, and the solvent was removed under the reduced pressure to give the corresponding acid chloride intermediate compound.
Then, to a solution of 170 mg (0.643 mmol) of 4-nitroaniline in 4 mL of tetrahydrofuran was added 77 mg (60% oily; 1.93 mmol) of sodium borohydride, and the mixture was stirred for 10 minutes at room temperature. Next, a solution of the above acid chloride in 3 mL of tetrahydrofuran was added to this mixture, and the mixture was stirred for 30 minutes at room temperature. Water was added to the reaction mixture and the mixture was extracted with ethyl acetate. The organic layer was washed with saturated saline solution and dried over with anhydrous sodium sulfate. The solvent was removed under reduced pressure and the resulting solid was washed with methanol to give 150 mg (61%) of the title compound.

Example 99

N-(4-Aminophenyl)-1-cyclohexyl-3-methyl-1H-thieno[2,3-c]pyrazole-5-carboxamide

The title compound 142 mg (quantitative) was obtained in a manner similar to the Manufacturing Example 2 by use of the compound obtained in the Example 98, instead of the compound obtained in the Manufacturing Example 1.

Example 100

N-[4-(Acetylamino)phenyl]-1-cyclohexyl-3-methyl-1H-thieno[2,3-c]pyrazole-5-carboxamide The title compound 10 mg (24%) was obtained in a manner similar to the Example 19 by use of the compound obtained in the Example 99, instead of the compound obtained in the Example 18.

Example 101

1-Cyclohexyl-N-{4-[(methoxyacetyl)amino]phenyl}-3-methyl-1H-thieno[2,3-c]pyrazole-5-carboxamide The title compound 92 mg (88%) was obtained in a manner similar to the Example 7 by use of the compound obtained in the Manufacturing Example 14, instead of benzylamine.

Example 102

Methyl 5-{[(1-Cyclohexyl-3-methyl-1H-thieno[2,3-c]pyrazol-5-yl)-carbonyl]amino}-2-pyridinecarboxylate The title compound 98 mg (43%) was obtained in a manner similar to the Example 7 by use of methyl 5-amino-2-pyridinecarboxylate, instead of benzylamine.

Example 103

5-{[(1-Cyclohexyl-3-methyl-1H-thieno[2,3-c]pyrazol-5-yl)carbonyl]-amino}-2-pyridinecarboxylic Acid The title compound 160 mg (87%) was obtained in a manner similar to the Example 41 by use of the compound obtained in the Example 102, instead of the compound obtained in the Example 40.

Example 104

1-Cyclohexyl-3-methyl-N-{6-[(methylamino)carbonyl]-3-pyridinyl}-1H-thieno[2,3-c]pyrazole-5-carboxamide The title compound 44 mg (77%) was obtained in a manner similar to the Manufacturing Example 5 by use of the compound obtained in the Example 103 and methylamine (30%-methanol solution), instead of 6-aminonicotic acid and isopropylamine, respectively.

Example 105

1-Cyclohexyl-N-{6-[(dimethylamino)carbonyl]-3-pyridinyl}-3-methyl-1H-thieno[2,3-c]pyrazole-5-carboxamide The title compound 50 mg (85%) was obtained in a manner similar to the Manufacturing Example 5 by use of the compound obtained in the Example 103 and dimethylamine HCl salt, instead of 6-aminonicotic acid and isopropylamine, respectively.

Example 106

1-Cyclohexyl-3-methyl-N-[4-(4-methyl-1-piperazinyl)phenyl]-1H-thieno[2,3-c]pyrazole-5-carboxamide The title compound 76 mg (77%) was obtained in a manner similar to the Example 7 by use of 4-(4-methyl-1-piperazinyl)aniline, instead of benzylamine.

Example 107

1-Cyclohexyl-3-methyl-N-[4-(4-methyl-1-piperazinyl)phenyl]-1H-thieno[2,3-c]pyrazole-5-carboxamide methanesulfonate To a suspension of 563 mg (1.287 mmol) of the compound obtained in the Example 106 in 5.6 mL of methanol was added 85.6 µL (1.319 mmol) of methanesulfonic acid at 50° C., and the mixture was refluxed. Then, the reaction mixture was gradually cooled to 0° C. and the resulting precipitates were collected to give 452 mg (66%) of the title compound.

Example 108

N-(4-Cyanophenyl)-1-cyclohexyl-3-methyl-1H-thieno[2,3-c]pyrazole-5-carboxamide

The title compound 300 mg (quantitative) was obtained in a manner similar to the Example 7 by use of 4-cyanoaniline, instead of benzylamine.

Example 109

1-Cyclohexyl-3-methyl-N-[6-(4-methyl-1-piperazinyl)-3-pyridinyl]-1H-thieno[2,3-c]pyrazole-5-carboxamide di-HCl salt 1-Cyclohexyl-3-methyl-N-[6-(4-methyl-1-piperazinyl)-3-pyridinyl]-1H-thieno[2,3-c]pyrazole-5-carboxamide 235 mg (79%) was obtained in a manner similar to the Example 7 by use of 4-cyanoaniline, instead of benzylamine. Next, to a solution of 132 mg (0.301 mmol) of the above free base compound in 2 mL of methanol was added 166 µL of 4N—HCl/dioxane, and the mixture was diluted with diethyl ether. The resulting precipitates were collected to give 140 mg (91%) of the title compound.

Example 110

1-Cyclohexyl-3-methyl-N-{3-[(4-methyl-1-piperazinyl)sulfonyl]-phenyl}-1H-thieno[2,3-c]pyrazole-5-carboxamide HCl salt 1-Cyclohexyl-3-methyl-N-{3-[(4-methyl-1-piperazinyl)sulfonyl]-phenyl}-1H-thieno[2,3-c]pyrazole-5-carboxamide 133 mg (87%) was obtained in a manner similar to the Example 7 by use of the compound obtained in the Manufacturing Example 17, instead of benzylamine. Next, to a solution of 133 mg (0.265 mmol) of the above free base compound in 3 mL of methanol was added 80 µL of 4N—HCl/dioxane, and the mixture was diluted with diethyl ether. The resulting precipitates were collected to give 138 mg (97%) of the title compound.

Example 111

1-Cyclohexyl-3-methyl-N-{3-[(methylamino)sulfonyl]phenyl}-1H-thieno[2,3-c]pyrazole-5-carboxamide The title compound 45 mg (34%) was obtained in a manner similar to the Example 7 by use of 3-amino-N-methylbenzenesulfonamide, instead of benzylamine.

Example 112

1-Cycloheptyl-3-methyl-N-[(4-(4-methyl-1-piperazinyl)phenyl)-1H-thieno[2,3-c]pyrazole-5-carboxamide The title compound 89 mg (78%) was obtained in a manner similar to the Example 106 by use of the compound obtained in the Example 93, instead of the compound obtained in the Example 6.

Example 113

1-Cyclohexyl-3-methyl-N-[(3-(4-methyl-1-piperazinyl)phenyl)-1H-thieno[2,3-c]pyrazole-5-carboxamide The title compound 106 mg (80%) was obtained in a manner similar to the Example 7 by use of 3-(4-methyl-1-piperazinyl)aniline, instead of benzylamine.

Example 114

1-Cyclohexyl-N-[(4-(4-hydroxy-1-piperidinyl)phenyl)-3-methyl-1H-thieno[2,3-c]pyrazole-5-carboxamide To a suspension of 4.1 g (15.51 mmol) of the compound obtained in the Example 6 in 50 mL of 1,2-dichloroethane was added 2.26 mL (31.02 mmol) of thionyl chloride, and the mixture was refluxed for 1.5 hours. After cooling of the reaction and the solvent was removed under reduced pressure to give the corresponding acid chloride intermediate compound.

Then, 3.04 g (15.82 mmol) of the compound obtained in the Manufacturing Example 95 and 4.32 mL (31.02 mmol) of triethylamine were added to a solution of the above acid chloride intermediate compound in 150 mL of anhydrous dichloromethane under ice cooling, and the mixture was stirred for 20 hours at room temperature. Water was added to the reaction mixture, and the mixture was extracted with dichloromethane. The organic layer was dried over with anhydrous sodium sulfate and the solvent was removed under reduced pressure. The residue was purified by silica gel column chromatography (eluent:dichloromethane/methanol=40/1 to 30/1) to give 7.5 g (83%) of the title compound.

Example 115

N-[4-(Acetylamino)-3-methoxyphenyl]-1-cyclohep-tyl-3-methyl-1H-thieno[2,3-c]pyrazole-5-carboxamide The title compound 160 mg (59%) was obtained in a manner similar to the Example 10 by use of the compound obtained in the Example 93, instead of the compound obtained in the Example 6.

Example 116

1-Cyclohexyl-N-(3,5-dichloro-4-pyridinyl)-3-methyl-1H-thieno[2,3-c]pyrazole-5-carboxamide The title compound 342 mg (88%) was obtained in a manner similar to the Example 98 by use of 4-amino-3,5-dichloropyridine, instead of 4-nitoraniline.

Example 117

5-[(4-Bromobenzyl)sulfanil]-1-cyclohexyl-3-methyl-1H-pyrazole-4-carboaldehyde

To a solution of 1.2 g (5.29 mmol) of the compound obtained in the Example 3 in 21 mL of ethanol were added 2.07 g (6.35 mmol) of S-(4-bromobenzyl) isothiourea hydrobromic acid salt and 10.6 mL of 2N-sodium hydroxide solution, and the mixture was refluxed for 2 hours. After the reaction mixture was cooled to room temperature, the mixture was condensed and the residue was diluted with ethyl acetate. The organic layer was washed with saturated saline solution and dried over with anhydrous sodium sulfate. The solvent was removed under reduced pressure and the residue was purified by silica gel column chromatography (eluent:hexane/ethyl acetate=7/1) to give 1.723 g (82%) of the title compound.

Example 118

5-(4-Bromophenyl)-1-cyclohexyl-3-methyl-1H-thieno[2,3-c]pyrazole

To a solution of 1.623 g (4.13 mmol) of the compound obtained in the Example 117 in 30 mL of tetrahydrofuran was added gradually a solution of 10.3 mL (10.3 mmol) of 1M lithium bis(trimethylsilyl)amide in tetrahydrofuran at −78° C., and the mixture was stirred for 30 minutes at the same temperature. Then, the reaction mixture was warmed slowly to 0° C. during 1 hour, and water was added to the reaction mixture. The mixture was extracted with dichloromethane and the organic layer was dried over with anhydrous sodium sulfate. The solvent was removed under reduced pressure and 15 mL of ethanol and 10 mL of 4N—HCl/dioxane were added to the residue and the mixture was stirred for 30 minutes at room temperature and for 30 minutes at 60° C. Then, the reaction mixture was cooled to room temperature and condensed under reduced pressure. The residue was diluted with ethyl acetate and the organic layer was washed with saturated sodium bicarbonate aqueous solution, then, dried over with anhydrous sodium sulfate. The solvent was removed under reduced pressure and the residue was purified by silica gel column chromatography (eluent:hexane/ethyl acetate=8/1) to give 717 mg (46%) of the title compound.

Example 119

1-Cyclohexyl-3-methyl-5-[4-(4-methyl-1-piperazinyl)phenyl]-1H-thieno[2,3-c]pyrazole To a solution of 175 mg (0.466 mmol) of the compound obtained in the Example 118 in 30 mL of toluene were added 115 μL (1.40 mmol) of N-methylpiperazine, 89.6 mg (0.933 mmol) of sodium tert-butoxide, 5.2 mg (0.023 mmol) of palladium acetate (II) and 9.4 mg (0.0466 mmol) of tri-tert-butyl-phosphine, and the mixture was refluxed for 5 hours. After the mixture was cooled to room temperature, ethyl acetate was added to the mixture and the organic layer was washed with water and saturated saline solution, then, dried over with anhydrous sodium sulfate. The solvent was removed under reduced pressure and the residue was purified by silica gel column chromatography (eluent:dichloromethane/methanol=40/1) to give 158 mg (86%) of the title compound.

Example 120

1-Cyclohexyl-3-methyl-5-[4-(4-methyl-1-piperazinyl)phenyl]-1H-thieno[2,3-c]pyrazole methanesulfanate The title compound 143 mg (94%) was obtained in a manner similar to the Example 107 by use of the compound obtained in the Example 119, instead of the compound obtained in the Example 106.

Example 121

1-Cyclohexyl-3-methyl-5-[4-(4-methyl-1,4-diazepam-1-yl)phenyl]-1H-thieno[2,3-c]pyrazole The title compound 124 mg (65%) was obtained in a manner similar to the Example 119 by use of N-methylhomopiperazine, instead of N-methylpiperazine.

Example 122

1-Cyclohexyl-N-(2-hydroxypropyl)-3-methyl-1H-thoieno[2,3-c]pyrazole-5-carboxamide The title compound 82 mg (78%) was obtained in a manner similar to the Example 7 by use of 2-aminoethanol, instead of benzylamine.

Example 123

1-Cyclohexyl-N-(3-hydroxypropyl)-3-methyl-1H-thieno[2,3-c]pyrazole-5-carboxamide The title compound 103 mg (94%) was obtained in a manner similar to the Example 7 by use of 3-amino-1-propanol, instead of benzylamine.

Example 124

1-Cyclohexyl-N-{3-fluoro-4-[(2-hydroxyethyl)(methyl)amino]phenyl}-3-methyl-1H-thieno[2,3-c]pyrazole-5-carboxamide The title compound 99 mg (68%) was obtained in a manner similar to the Example 7 by use of the compound obtained in the Manufacturing Example 19, instead of benzylamine.

Example 125

1-Cyclohexyl-N-{3-fluoro-4-[(2-hydroxyethyl)(methyl)amino]phenyl}-3-methyl-1H-thieno[2,3-c]pyrazole-5-carboxamide HCl salt To a solution of 91 mg (0.211 mmol) of the compound obtained in the Example 124 in 2 mL of diethyl ether and 1 mL of ethyl acetate was added 63 μL (0.25 mmol) of 4N—HCl/1,4-dioxane, and 3 mL of diethyl ether was further added to the mixture. The resulting precipitates were collected to give 86 mg (87%) of the title compound.

Example 126

Ethyl cis-4-{[(1-cyclohexyl-3-methyl-1H-thieno[2,3-c]pyrazol-5-yl)-carbonyl]amino}cyclohexanecarboxylate The title compound 365 mg (92%) was obtained in a manner similar to the Example 7 by use of ethyl cis-4-aminocyclohexanecarboxylate, instead of benzylamine.

Example 127 cis-4-{[(1-Cyclohexyl-3-methyl-1H-thieno[2,3-c]pyrazol-5-yl)-carbonyl]amino}cyclohenxanecarboxylic acid The title compound 123 mg (88%) was obtained in a manner similar to the Example 41 by use of the compound obtained in the Example 126, instead of the compound obtained in the Example 40.

Example 128

1-Cyclohexyl-N-[cis-4-(hydroxymethyl)cyclohexyl]-3-methyl-1H-thieno[2,3-c]pyrazole-5-carboxamide To a solution of 185 mg (0.433 mmol) of the compound obtained in the Example 126 in 6 mL of tetrahydrofuran were added 56 mg (1.33 mmol) of lithium chloride and 50 mg (1.33 mmol) of sodium borohydride, and the mixture was stirred for 14 hours at room temperature. Then, ethyl acetate was added to the mixture and the organic layer was washed with water and saturated saline solution, then, dried over with anhydrous sodium sulfate. The solvent was removed under reduced pressure and the residue was purified by silica gel column chromatography (eluent:hexane/ethyl acetate=1/3) to give 110 mg (66%) of the title compound.

Example 129

Methyl trans-4-({[(1-cyclohexyl-3-methyl-1H-thoieno[2,3-c]pyrazol-5-yl)carbonyl]amino}methyl)cyclohexanecarboxylate The title compound 605 mg (96%) was obtained in a manner similar to the Example 7 by use of ethyl trans-4-aminocyclohexanecarboxylate hydrochloric acid salt, instead of benzylamine.

Example 130

1-Cyclohexyl-N-methyl{[trans-4-(hydroxymethyl)cyclohexyl]methyl}-3-methyl-1H-thieno[2,3-c]pyrazole-5-carboxamide The title compound 150 mg (80%) was obtained in a manner similar to the Example 128 by use of the compound obtained in the Example 129, instead of the compound obtained in the Example 126.

Example 131 tert-Butyl trans-4-{[(1-cyclohexyl-3-methyl-1H-thieno[2,3-c]pyrazol-5-yl)carbonyl]amino}cyclohexylcarbamate The title compound 90 mg (quantitative) was obtained in a manner similar to the Example 7 by use of tert-butyl trans-4-aminocyclohexyl-carbamate, instead of benzylamine.

Example 132

N-(trans-4-Aminocyclohexyl)-1-cyclohexyl-3-methyl-1H-thieno[2,3-c]pyrazole-5-carboxamide To a solution of 890 mg (1.93 mmol) of the compound obtained in the Example 131 in 5 mL of N,N-dimethylformamide was added 9.66 mL of 4N—HCl/dioxane, and the mixture was stirred for 3 hours at room temperature. Then, the mixture was diluted with dichloromethane and 50 mL of 1N-sodium hydroxide solution was added to the mixture. The organic layer was dried over with anhydrous sodium sulfate and the solvent was removed under reduced pressure. The residue was purified by alkaline silica gel column chromatography (eluent:chloroform/methanol=60/1) to give 495 mg (71%) of the title compound.

Example 133

1-Cyclohexyl-3-methyl-N-[trans-4-(4-morpholinyl)cyclohexyl]-1H-thieno[2,3-c]pyrazole-5-carboxamide To a solution of 120 mg (0.333 mmol) of the compound obtained in the Example 132 in 8 mL of N,N-dimethylformamide were added 46.8 μL (0.333 mmol) of bis(2-chloroethyl)ether, 116 μL (0.832 mmol) of triethylamine, 50 mg (0.333 mmol) of sodium iodide, and 6.5 μL (0.333 mmol) of 15-crown-5, and the mixture was stirred for 24 hours at 100° C. After the reaction mixture was cooled to room temperature, the mixture was extracted with ethyl acetate and the organic layer was washed with saturated sodium bicarbonate aqueous solution and saturated saline solution, then, dried over with anhydrous sodium sulfate. The solvent was removed under reduced pressure and the residue was purified by silica gel column chromatography (eluent:chloroform/methanol=20/1) to give 22 mg (15%) of the title compound.

Example 134

1-Cyclohexyl-3-methyl-N-(4-piperidinyl)-1H-thieno[2,3-c]pyrazole-5-carboxamide

Saturated sodium bicarbonate solution and ethyl acetate were added to the compound obtained in the Example 63, and the organic layer was dried over with anhydrous sodium sulfate. The solvent was removed and the residue was purified by alkaline silica gel column chromatography (eluent:chloroform/methanol=60/1) to give 411 mg (60%) of the title compound.

Example 135

1-Cyclohexyl-3-methyl-N-(1-tetrahydro-2H-pyran-4-yl-4-piperidinyl)-1H-thieno[2,3-c]pyrazole-5-carboxamide To a solution of 150 mg (0.433 mmol) of the compound obtained in the Example 134 in 8 mL of dichloromethane were added 44 μL (0.476 mmol) of tetrahydro-4-pyranone and 128 mg (0.606 mmol) of sodium triacetoxyborohydride, and the mixture was stirred for 24 hours at room temperature. Then, saturated sodium bicarbonate solution was added to the reaction mixture and the mixture was extracted with dichloromethane. The organic layer was washed with water and saturated saline solution, then, dried over with anhydrous sodium sulfate. The solvent was removed under reduced pressure and the residue was purified by silica gel column chromatography (eluent:dichloromethane/methanol=20/1) to give 70 mg (38%) of the title compound.

Example 136

1-Cyclohexyl-N-[1-(1,4-diazaspiro[4.5]decan-8-yl)-4-piperazdinyl]-3-methyl-1H-thieno[2,3-c]pyrazole-5-carboxamide The title compound 180 mg (92%) was obtained in a manner similar to the Example 135 by use of 1,4-cyclohexanedione monoethyleneketal, instead of tetrahydro-4-pyranone.

Example 137

1-Cyclohexyl-3-methyl-N-[1-(4-oxocyclohexyl)-4-piperidinyl]-1H-thieno[2,3-c]pyrazole-5-carboxamide To a solution of 153 mg (0.314 mmol) of the compound obtained in the Example 136 in 3 mL of acetone and 1 mL of water was added 71.8 mg (0.377 mmol) of p-toluenesulfonic acid monohydrate, and the mixture was refluxed for 2 days. Then, saturated sodium bicarbonate aqueous solution was added to the reaction mixture and the mixture was extracted with dichloromethane. The organic layer was dried over with anhydrous sodium sulfate and removed under reduced pressure to give 120 mg (86%) of the title compound.

Example 138

1-Cyclohexyl-N-[1-(trans-4-hydroxycyclohexyl)-4-piperidinyl]-3-methyl-1H-thieno[2,3-c]pyrazole-5-carboxamide To a solution of 109 mg (0.246 mmol) of the compound obtained in the Example 137 in 8 mL of ethanol was added 14.0 mg (0.369 mmol) of sodium borohydride, and the mixture was stirred for 1 hour at 0° C. Then, dichloromethane was added to the reaction mixture and the organic layer was washed with water, then, dried over with anhydrous sodium sulfate. The solvent was removed under reduced pressure and the residue was purified by silica gel column chromatography (eluent:dichloromethane/methanol=20/1) to give 67 mg (61%) of the title compound.

Example 139 tert-Butyl 4-(4-{[(1-cyclohexyl-3-methyl-1H-thieno[2,3-c]pyrazol-5-yl)carbonyl]amino}phenyl)-1-piperidinecarboxylate The title compound 649 mg (quantitative) was obtained in a manner similar to the Example 7 by use of the compound obtained in the Manufacturing Example 21, instead of benzylamine.

Example 140

1-Cyclohexyl-3-methyl-N-[4-(4-piperidinyl)phenyl]-1H-thieno[2,3-c]pyrazole-5-carboxamide To a solution of 584 mg (1.12 mmol) of the compound obtained in the Example 139 in 3 mL of dichloromethane was added 0.86 mL (11.2 mmol) of trifluoroacetic acid at room temperature, and the mixture was stirred for 1.5 hours at the same temperature. Then, the mixture was extracted with dichloromethane and the organic layer was washed with 2N sodium hydroxide solution and then, dried over with anhydrous sodium sulfate. The solvent was removed under reduced pressure and the residue was purified by silica gel column chromatography (eluent:dichloromethane/methanol=100/1) to give 437 mg (92%) of the title compound.

Example 141

1-Cyclohexyl-3-methyl-N-[4-(4-piperidinyl)phenyl]-1H-thieno[2,3-c]pyrazole-5-carboxamide HCl salt The title compound 94 mg (86%) was obtained in a manner similar to the Example 125 by use of the compound obtained in the Example 140, instead of the compound obtained in the Example 124.

Example 142

1-Cyclohexyl-3-methyl-N-[4(1-methyl-4-piperidinyl)phenyl]-1H-thieno[2,3-c]pyrazole-5-carboxamide To a solution of 174 mg (0.4412 mmol) of the compound obtained in the Example 140 in 5 mL of chloroform were added 31 μL (0.494 mmol) of methyl iodide and 86 μL (0.618 mmol) of triethylamine, and the mixture was stirred for 2 hours at room temperature. Then, saturated sodium bicarbonate aqueous solution was added to the reaction mixture and the mixture was extracted with dichloromethane. The organic layer was dried over with anhydrous sodium sulfate and removed under reduced pressure. The residue was purified by alkaline silica gel column chromatography (eluent:dichloromethane/methanol=40/1) to give 46 mg (26%) of the title compound.

Example 143

1-Cyclohexyl-N-[4-(4-ethyl-1-piperazinyl)-3-fluorophenyl]-3-methyl-1H-thieno[2,3-c]pyrazole-5-carboxamide The title compound 90 mg (42%) was obtained in a manner similar to the Example 7 by use of the compound obtained in the Manufacturing Example 24, instead of benzylamine.

Example 144

1-Cyclohexyl-N-[3-fluoro-4-(4-methyl-1,4-diazepam-1-yl)phenyl]-3-methyl-1H-thieno[2,3-c]pyrazole-5-carboxamide The title compound 161 mg (76%) was obtained in a manner similar to the Example 7 by use of the compound obtained in the Manufacturing Example 31, instead of benzylamine.

Example 145

Ethyl 4-{[(1-cyclohexyl-3-methyl-1H-thieno[2,3-c]pyrazol-5-yl)-carbonyl]amino-2-methoxybenzoate The title compound 401 mg (80%) was obtained in a manner similar to the Example 7 by use of ethyl 4-amino-2-methoxybenzoate, instead of benzylamine.

Example 146

4-{[(1-Cyclohexyl-3-methyl-1H-thieno[2,3-c]pyrazol-5-yl)carbonyl]-amino}-2-methoxybenzoic acid The title compound 242 mg (59%) was obtained in a manner similar to the Example 41 by use of the compound obtained in the Example 145, instead of the compound obtained in the Example 40.

Example 147

1-Cyclohexyl-N-{3-methoxy-4-[(4-methyl-1-piperazinyl)carbonyl]-phenyl}-3-methyl-1H-thieno[2,3-c]pyrazole-5-carboxamide HCl Salt To a solution of 200 mg (0.48 mmol) of the compound obtained in the Example 146 in 3 mL of anhydrous dichloromethane were added 64 μL (0.58 mmol) of N-methylpiperazine and 111 mg (0.58 mmol) of 1-ethyl-3-(3-dimethylaminopropyl) carbodiimide HCl salt, and the mixture was stirred for 3 hours at room temperature. Then, saturated sodium bicarbonate aqueous solution was added to the reaction mixture and the mixture was extracted with dichloromethane. The organic layer was washed with water and saturated saline solution and dried over with anhydrous sodium sulfate. The solvent was removed under reduced pressure and the residue was purified by silica gel column chromatography (eluent:dichloromethane/methanol=20/1 to 10/1). The obtained crude crystalline was dissolved in 4M-HCl/dioxane and the solvent was removed under reduced pressure. The obtained solid was collected to give 124 mg (49%) of the title compound.

Example 148

1-Cyclohexyl-N-[3-methoxy-4-(4-morpholinylcarbonyl)phenyl]-3-methyl-1H-thieno[2,3-c]pyrazole-5-carboxamide The title compound 76 mg (79%) was obtained in a manner similar to the Example 147 by use of morpholine, instead of N-methylpiperazine.

Example 149

1-Cyclohexyl-N-{4-[(4-hydroxy-1-piperidinyl)carbonyl]phenyl}-3-methoxyphenyl}-3-methyl-1H-thieno[2,3-c]pyrazole-5-carboxamide The title compound 68 mg (69%) was obtained in a manner similar to the Example 147 by use of 4-hydroxypiperidine, instead of N-methylpiperazine.

Example 150

1-Cyclohexyl-N-(4-{[(2-hydroxyethyl)amino]carbonyl}-3-methoxy-phenyl)-3-methyl-1H-thieno[2,3-c]pyrazole-5-carboxamide The title compound 53 mg (58%) was obtained in a manner similar to the Example 147 by use of 2-aminoethanol, instead of N-methylpiperazine.

Example 151

1-Cyclohexyl-N-(3-methoxy-4-{[(2-methoxyethyl)amino]carbonyl}-phenyl)-3-methyl-1H-thieno[2,3-c]pyrazole-5-carboxamide The title compound 73 mg (78%) was obtained in a manner similar to the Example 147 by use of 2-methoxyethylamine, instead of N-methylpiperazine.

Example 152

1-Cyclohexyl-N-{3-methoxy-4-[(methylamino)carbonyl]phenyl}-3-methyl-1H-thieno[2,3-c]pyrazole-5-carboxamide The title compound 31 mg (36%) was obtained in a manner similar to the Example 147 by use of methylamine HCl salt, instead of N-methylpiperazine.

Example 153

1-Cyclohexyl-N-{4-[(dimethylamino)carbonyl]-3-methoxyphenyl}-3-methyl-1H-thieno[2,3-c]pyrazole-5-carboxamide The title compound 70 mg (80%) was obtained in a manner similar to the Example 147 by use of dimethylamine HCl salt, instead of N-methyl-piperazine.

Example 154

1-Cyclohexyl-N-[3-fluoro-4-(4-methyl-1-piperazinyl)phenyl]-3-methyl-1H-thieno[2,3-c]pyrazole-5-carboxamide The title compound 136 mg (79%) was obtained in a manner similar to the Example 7 by use of the compound obtained in the Manufacturing Example 26, instead of benzylamine.

Example 155

1-Cyclohexyl-N-[3-fluoro-4-(4-methyl-1-piperazinyl)phenyl]-3-methyl-1H-thieno[2,3-c]pyrazole-5-carboxamide methanesulfonic acid salt A suspension of 100 mg (0.22 mmol) of the compound obtained in the Example 154 in 2 mL of methanol was heated at 50° C., and to this suspension was added 14 mL (0.22 mmol) of methanesulfonic acid, then, the mixture was refluxed for 10 minutes. The reaction mixture was cooled gradually and the appeared precipitates were collected to give 68 mg (56%) of the title compound.

Example 156

N-[3-Chloro-4-(4-methyl-1-piperizinyl)phenyl]-1-cyclohexyl-3-methyl-1H-thieno[2,3-c]pyrazole-5-carboxamide The title compound 169 mg (95%) was obtained in a manner similar to the Example 7 by use of 3-chloro-4-(4-methyl-1-piperazinyl)aniline, instead of benzylamine.

Example 157

1-Cyclohexyl-N-[4-(1,4-dioxa-8-azaspiro[4.5]decan-8-yl)-3-fluoro-phenyl]-3-methyl-1H-thieno[2,3-c]pyrazole-5-carboxamide The title compound 546 mg (96%) was obtained in a manner similar to the Example 7 by use of the compound obtained in the Manufacturing Example 28, instead of benzylamine.

Example 158

1-Cyclohexyl-N-[3-fluoro-4-(4-oxo-1-piperidinyl)phenyl]-3-methyl-1H-thieno[2,3-c]pyrazole-5-carboxamide To a solution of 500 mg (1.00 mmol) of the compound obtained in the Example 157 in a mixture solution of 20 mL of toluene and 2 mL of water was added 229 mg (1.20 mmol) of p-toluenesulfonic acid monohydrate, and the mixture was refluxed for 8 hours. Then, the reaction mixture was cooled to room temperature and condensed under reduced pressure. Saturated sodium bicarbonate aqueous solution was added to the residue and the mixture was extracted with ethyl acetate. The organic layer was washed with water and saturated saline solution, and then, dried over with anhydrous sodium sulfate. The solvent was removed under reduced pressure to give 460 mg (quantitative) of the title compound.

Example 159-1

1-Cyclohexyl-N-[3-fluoro-4-(4-hydroxy-1-piperidinyl)phenyl]-3-methyl-1H-thieno[2,3-c]pyrazole-5-carboxamide To a suspension of 150 mg (0.33 mmol) of the compound obtained in the Example 158 in anhydrous methanol was added 15 mg (0.39 mmol) of sodium borohydride under ice cooling, and the mixture was stirred for 3 hours at the same temperature and for 2 hours at room temperature. Then, acetone was added to the reaction mixture and the solvent was removed under reduced pressure. The residue was diluted with ethyl acetate and the organic layer was washed with water and saturated saline solution. The solvent was removed under reduced pressure and the residue was purified by silica gel column chromatography (eluent:hexane/ethyl acetate=1/2 to 0/1) to give 114 mg (76%) of the title compound.

Example 159-2

To a suspension of 900 mg (3.40 mmol) of the compound obtained in 15 mL of 1,2-dichloroethane was added 497 μL (6.81 mmol) of thionyl chloride, and the mixture was refluxed for 1.5 hours. After cooling the reaction mixture, the solvent removed under reduced pressure to give acid chloride intermediate compound.

Then, 752 mg (3.57 mmol) of the compound obtained in the Manufacturing Example 62 and 949 μL (6.81 mmol) of triethylamine were added to a solution of acid chloride intermediate compound obtained above in 40 mL of anhydrous dichloromethane, and the mixture was stirred for 6 hours at room temperature. Water was added to the reaction mixture and the mixture was extracted with dichloromethane. The organic layer was dried over with anhydrous sodium sulfate, and the solvent was removed under reduced pressure. The resulting residue was recrystallized from ethanol to give 0.86 g (55%) of the title compound.

Example 160

N-[3-Chloro-4-(1,4-dioza-8-azaspiro[4.5]decan-8-yl)phenyl]-1-cyclohexyl-3-methyl-1H-thieno[2,3-c]pyrazole-5-carboxamide The title compound 565 mg (96%) was obtained in a manner similar to the Example 7 by use of the compound obtained in the Manufacturing Example 30, instead of benzylamine.

Example 161

N-[3-Chloro-4-(4-oxo-1-piperidinyl)phenyl]-1-cyclohexyl-3-methyl-1H-thieno[2,3-c]pyrazole-5-carboxamide The title compound 282 mg (61%) was obtained in a manner similar to the Example 158 by use of the compound obtained in the Example 160, instead of the compound obtained in the Example 157.

Example 162

N-[3-Chloro-4-(4-hydroxy-1-piperidinyl)phenyl]-1-cyclohexyl-3-methyl-1H-thieno[2,3-c]pyrazole-5-carboxamide The title compound 90 mg (90%) was obtained in a manner similar to the Example 159-1 by use of the compound obtained in the Example 161, instead of the compound obtained in the Example 158.

Example 163

1-Cyclohexyl-N-{3-fluoro-4-[4-(methylamino)-1-piperidinyl]phenyl}-3-methyl-1H-thieno[2,3-c]pyrazole-5-carboxamide To a suspension of 150 mg (0.33 mmol) of the compound obtained in the Example 158 in 3 mL of 1,2-dichloroethane were added 68 μL (0.66 mmol) of trimethylamine (30%-ethanol solution), 20 μL of acetic acid and 105 mg (0.50 mmol) of sodium triacetoxyborohydride, and the mixture was stirred for 18 hours at room temperature. Then, saturated sodium bicarbonate solution was added to the reaction mixture and the mixture was extracted with dichloromethane. The organic layer was washed with water and saturated saline solution, and then, dried over with anhydrous sodium sulfate. The solvent was removed under reduced pressure and the residue was purified by alkaline silica gel column chromatography (eluent:dichloromethane/methanol=20/1) to give 148 mg (97%) of the title compound.

Example 164 tert-Butyl 1-(2-chloro-4-{[(1-cyclohexyl-3-methyl-3-1H-thieno[2,3-c]-pyrazol-5-yl)carbonyl]amino}phenyl)-4-piperidinyl(methyl)carbamate To a suspension of 200 mg (0.43 mmol) of the compound obtained in the Example 161 in 3 mL of 1,2-dichloroethane were added 88 μL (0.85 mmol) of trimethylamine (30%-ethanol solution), 15 μL of acetic acid and 135 mg (0.64 mmol) of sodium triacetoxyborohydride, and the mixture was stirred for 4 hours at room temperature. Then, saturated sodium bicarbonate solution was added to the reaction mixture and the mixture was extracted with dichloromethane. The organic layer was washed with water and saturated saline solution, the dried over with anhydrous sodium sulfate. The solvent was removed under reduced pressure and the residue was dissolved in 4 mL of dichloromethane. To this mixture were added 186 mg (0.85 mmol) of tert-butyldicarbonate and 0.14 mL (1.02 mmol) of triethylamine, and the mixture was stirred for 1 hour at room temperature. Water was added to the reaction mixture and the mixture was extracted with dichloromethane. The organic layer was washed with water and saturated saline solution and dried over with anhydrous sodium sulfate. The solvent was removed under reduced pressure and the residue was purified by silica gel column chromatography (eluent:hexane/ethyl acetate=1/1) to give 236 mg (95%) of the title compound.

Example 165

N-{3-Chloro-4-[4-(methylamino)-1-piperidinyl]phenyl}-1-cyclohexyl-3-methyl-1H-thieno[2,3-c]pyrazole-5-carboxamide To a solution of 211 mg (0.36 mmol) of the compound obtained in the Example 164 in 3 mL of dichloromethane was added 1.5 mL of trifluoroacetic acid, and the mixture was stirred for 1.5 hours at room temperature. After removal of the solvent under reduced pressure, water was added to the residue and the mixture was extracted with chloroform. The organic layer was washed with water and saturated saline solution and dried over with anhydrous sodium sulfate. The solvent was removed under reduced pressure and the residue was purified by alkaline silica gel column chromatography (eluent=dichloromethane/methanol=40/1) to give 116 mg (66%) of the title compound.

Example 166

1-Cyclohexyl-3-methyl-N-[trans-4-(4-methyl-1-piperazinyl)-cyclohexyl]-1H-thieno[2,3-c]pyrazole-5-carboxamide To a solution of 150 mg (0.42 mmol) of the compound obtained in the Example 75 in 3 mL of dichloromethane were added 93 μL (0.84 mmol) of N-methylpiperazine, 15 μL of acetic acid and 133 mg (0.63 mmol) of sodium triacetoxyborohydride, and the mixture was stirred for 3 hours at room temperature. Then, saturated sodium bicarbonate solution was added to the reaction mixture and the mixture was extracted with dichloromethane. The organic layer was washed with water and saturated saline solution, then, dried over with anhydrous sodium sulfate. The solvent was removed under reduced pressure and the residue was purified by alkaline silica gel column chromatography (eluent:ethyl acetate) to give 103 mg (56%) of the title compound.

Example 167

1-Cyclohexyl-3-methyl-N-[trans-4-(4-methyl-1,4-diazepam-1-yl)-cyclohexyl]-1H-thieno[2,3-c]pyrazole-5-carboxamide The title compound 101 mg (53%) was obtained in a manner similar to the Example 166 by use of N-methylhomopiperazine, instead of N-methylpiperazine.

Example 168

1-Cyclohexyl-N-[trans-4-(4-methoxyl-1-piperidinyl)cyclohexyl]-3-methyl-1H-thieno[2,3-c]pyrazole-5-carboxamide The title compound 30 mg (20%) was obtained in a manner similar to the Example 166 by use of 4-methoxypiperidine p-toluenesulfonic acid salt, instead of N-methylpiperazine.

Example 169

Benzyl 4-(trans-4-{[(1-cyclohexyl-3-methyl-1H-thieno[2,3-c]-pyrazol-5-yl)carbonyl]amino}cyclohexyl)-1,4-diazepam-1-carboxylate The title compound 252 mg (78%) was obtained in a manner similar to the Example 166 by use of benzyl 1-homopiperazinecarboxylate, instead of N-methylpiperazine.

Example 170

1-Cyclohexyl-N-[trans-4-(1,4-diazepam-1-yl)cyclohexyl]-3-methyl-1H-thieno[2,3-c]pyrazole-5-carboxamide A mixture solution of 219 mg (0.38 mmol) of the compound obtained in the Example 169 in 3 mL of 30%-HBr/acetic acid was stirred for 3 hours at room temperature. Then, the reaction mixture was neutralized by 4M-sodium hydroxide aqueous solution and the mixture was extracted with dichloromethane. The organic layer was washed with water and saturated saline solution and dried over with anhydrous sodium sulfate. The solvent was removed under reduced pressure and the residue was purified by alkaline silica gel column chromatography (eluent:dichloromethane/methanol=30/1) to give 126 mg (75%) of the title compound.

Example 171

N-[trans-4-(4-Acetyl-1,4-diazepam-1-yl)cyclohexyl]-1-cyclohexyl-3-methyl-1H-thieno[2,3-c]pyrazole-5-carboxamide The title compound 96 mg (99%) was obtained in a manner similar to the Manufacturing Example 3 by use of the compound obtained in the Example 170 and acetic anhydride, instead of the compound obtained in the Manufacturing Example 2 and acetyl chloride, respectively.

Example 172

1-Cyclohexyl-N-{trans-4-[(2-methoxyethyl)(methyl)amino]cyclohexyl}-3-methyl-1H-thieno[2,3-c]pyrazole-5-carboxamide The title compound 131 mg (73%) was obtained in a manner similar to the Example 166 by use of N-(2-methoxylethyl)methylamine, instead of N-methylpiperazine.

Example 173

1-Cyclohexyl-N-{cis-4-[(2-methoxyethyl)(methyl)amino]cyclohexyl}-3-methyl-1H-thieno[2,3-c]pyrazole-5-carboxamide The title compound 34 mg (19%) was obtained as by-product in the Example 172.

Example 174

1-Cyclohexyl-N-[trans-4-(1,4-dioxa-8-azaspiro[4.5]decan-8-yl)-cyclohexyl]-3-methyl-1H-thieno[2,3-c]pyrazole-5-carboxamide The title compound 664 mg (98%) was obtained in a manner similar to the Example 166 by use of 1,4-dioxa-8-azaspiro[4.5]decane, instead of N-methylpiperazine.

Example 175

1-Cyclohexyl-3-methyl-N-[trans-4-(4-oxo-1-piperidinyl)cyclohexyl]-1H-thieno[2,3-c]pyrazole-5-carboxamide A mixture of 384 mg (0.79 mmol) of the compound obtained in the Example 174 in 6 mL of 6M-HCl aqueous solution was stirred for 9 days at room temperature. Then, the reaction mixture was neutralized by saturated sodium bicarbonate aqueous solution and the mixture was extracted with chloroform. The organic layer was washed with water and saturated saline solution, and dried over with anhydrous sodium sulfate. The solvent was removed under reduced pressure to give 317 mg (91%) of the title compound.

Example 176

1-Cyclohexyl-N-[trans-4-(4-hydroxy-1-piperidinyl)cyclohexyl]-3-methyl-1H-thieno[2,3-c]pyrazole-5-carboxamide The title compound 102 mg (quantitative) was obtained in a manner similar to the Example 159 by use of the compound obtained in the Example 175, instead of the compound obtained in the Example 158.

Example 177

1-Cyclohexyl-N-{trans-4-[(2R,6S)-2,6-dimethylmorpholinyl]cyclohexyl}-3-methyl-1H-thieno[2,3-c]pyrazole-5-carboxamide The title compound 126 mg (66%) was obtained in a manner similar to the Example 166 by use of cis-2,6-dimethylmorpholine, instead of N-methylpiperazine.

Example 178

1-Cyclohexyl-N-{cis-4-[(2R,6S)-2,6-dimethylmorpholinyl]cyclohexyl}-3-methyl-1H-thieno[2,3-c]pyrazole-5-carboxamide The title compound 50 mg (26%) was obtained as by-product in the Example 177.

Example 179

1-Cyclohexyl-3-methyl-N-{trans-4-[4-(methylamino)-1-piperidinyl]-cyclohexyl}-1H-thieno[2,3-c]pyrazole-5-carboxamide The title compound 182 mg (89%) was obtained in a manner similar to the Example 166 by use of the compound obtained in the Example 175 and methylamine (30% ethanol solution), instead of the compound obtained in the Example 75 and N-methylpiperazine, respectively.

Example 180

N-(trans-4-{4-[Acetyl(methyl)amino]-1-piperidinyl}cyclohexyl)-1-cyclohexyl-3-methyl-1H-thieno[2,3-c]pyrazole-5-carboxamide The title compound 35 mg (72%) was obtained in a manner similar to the Manufacturing Example 3 by use of the compound obtained in the Example 179 and acetic anhydride, instead of the compound obtained in the Manufacturing Example 2 and acetyl chloride, respectively.

Example 181

1-Cyclohexyl-N-{trans-4-[4-(dimethylamino)-1-piperidinyl]-cyclohexyl}-3-methyl-1H-thieno[2,3-c]pyrazole-5-carboxamide To a mixture solution of 70 mg (0.15 mmol) of the compound obtained in the Example 179 in 2 mL of ethanol and 2 mL of water were added 30 mg of paraformaldehyde and 1 mL of formic acid, and the mixture was refluxed for 6 hours. Further 30 mg of paraformaldehyde and 1 mL of formic acid were added to the reaction mixture, and the mixture was refluxed for 18 hours. Then, the reaction mixture was cooled to room temperature and neutralized with saturated sodium bicarbonate aqueous solution, and extracted with dichloromethane. The organic layer was washed with water and saturated saline solution, and dried over with anhydrous sodium sulfate. The solvent was removed under reduced pressure and the residue was recrystallized from ethyl acetate to give 32 mg (44%) of the title compound.

Example 182 tert-Butyl 1-(trans-4-{[(1-cyclohexyl-3-methyl-1H-thieno[2,3-c]-pyrazol-5-yl)carbonyl]amino}cyclohexyl)-4-piperidinylcarbamate The title compound 176 mg (58%) was obtained in a manner similar to the Example 166 by use of tert-butyl 4-piperidinecarbamate, instead of N-methylpiperazine.

Example 183 tert-Butyl 1-(cis-4-{[(1-cyclohexyl-3-methyl-1H-thieno[2,3-c]-pyrazol-5-yl)carbonyl]amino}cyclohexyl)-4-piperidinylcarbamate The title compound 94 mg (31%) was obtained as by-product in the Example 182.

Example 184

N-[trans-4-(4-Amino-1-piperidinyl)cyclohexyl]-1-cyclohexyl-3-methyl-1H-thieno[2,3-c]pyrazole-5-carboxamide The title compound 82 mg (60%) was obtained in a manner similar to the Example 165 by use of the compound obtained in the Example 182, instead of the compound obtained in the Example 164.

Example 185

N-[cis-4-(4-Amino-1-piperidinyl)cyclohexyl]-1-cyclohexyl-3-methyl-1H-thieno[2,3-c]pyrazole-5-carboxamide The title compound 63 mg (95%) was obtained in a manner similar to the Example 165 by use of the compound obtained in the Example 183, instead of the compound obtained in the Example 164.

Example 186 tert-Butyl 4-(trans-4-{[(1-cyclohexyl-3-methyl-1H-thieno[2,3-c]-pyrazol-5-yl)carbonyl]amino}cyclohexyl)-1-piperazinecarboxylate The title compound 218 mg (74%) was obtained in a manner similar to the Example 166 by use of tert-butyl 1-piperazinecarboxylate, instead of N-methylpiperazine.

Example 187 tert-Butyl 4-(cis-4-{[(1-cyclohexyl-3-methyl-1H-thieno[2,3-c]-pyrazol-5-yl)carbonyl]amino}cyclohexyl)-1-piperazinecarboxylate The title compound 72 mg (14%) was obtained as by-product in the Example 186.

Example 188

1-Cyclohexyl-3-methyl-N-[trans-4-(1-piperazinyl)cyclohexyl]-1H-thieno[2,3-c]pyrazole-5-carboxamide The title compound 146 mg (86%) was obtained in a manner similar to the Example 165 by use of the compound obtained in the Example 186, instead of the compound obtained in the Example 164.

Example 189

1-Cyclohexyl-3-methyl-N-[cis-4-(1-piperazinyl)cyclohexyl]-1H-thieno[2,3-c]pyrazole-5-carboxamide The title compound 51 mg (97%) was obtained in a manner similar to the Example 165 by use of the compound obtained in the Example 187, instead of the compound obtained in the Example 164.

Example 190

N-[trans-4-(4-Acetyl-1-piperazinyl)cyclohexyl]-1-cyclohexyl-3-methyl-1H-thieno[2,3-c]pyrazole-5-carboxamide The title compound 81 mg (95%) was obtained in a manner similar to the Manufacturing Example 3 by use of the compound obtained in the Example 188, instead of the compound obtained in the Manufacturing Example 2.

Example 191

1-Cyclohexyl-N-[3-fluoro-4-(4-methyl-1,4-diazepam-1-yl)phenyl]-3-methyl-1H-thieno[2,3-c]pyrazole-5-carboxamide hemifumarate To a solution of 143 mg (0.305 mmol) of the compound obtained in the Example 144 in 2 mL of ethanol was added 38.9 mg (0.335 mmol) of fumaric acid, and the resulting precipitates were collected to give 139 mg (86%) of the title compound.

Example 192

5-Methyl-2-tetrahydro-2H-pyran-4-yl-2,4-dihydro-3H-pyrazole-3-one

The title compound 6.93 g (58%) was obtained in a manner similar to the Example 1 by use of 4-tetrahydropyranylhydrazine, instead of cyclohexylhydrazine HCl salt.

Example 193

5-Chloro-3-methyl-1-tetrahydro-2H-pyran-4-yl-1H-pyrazole-4-carboaldehyde

A mixture solution of 6.87 g (3.77 mmol) of the compound obtained in the Example 192 and 14.1 mL (150.8 mmol) of phosphorous oxychloride was stirred for 1 hour at 110° C. After the reaction mixture was cooled to room temperature, this mixture was added gradually to ice-cooled 40 mL of N,N-dimethylformamide, and the mixture was stirred for 1 hour at room temperature and for 3 hours at 90° C. Then, the reaction mixture was cooled with ice and diluted with ethyl acetate, and pH of the reaction mixture was adjusted to 4 by adding 2N-NaOH aqueous solution. The mixture was extracted with ethyl acetate and the organic layer was washed with saturated saline solution and then, dried over with anhydrous sodium sulfate. The solvent was removed under reduced pressure and the residue was purified by silica gel column chromatography (eluent:hexane/ethyl acetate=2/1) to give 4.64 g (54%) of the title compound.

Example 194

Ethyl 3-methyl-1-tetrahydro-2H-pyran-4-yl-1H-thieno[2,3-c]pyrazole-5-carboxylate To a solution of 16.54 mL (0.151 mol) of ethyl thioglycolate in 300 mL of tetrahydrofuran was added 6.03 g (0.151 mol) of sodium hydride (60% oily) in small portions, and the mixture was stirred for 3 minutes. Then, 31.36 g (0.137 mol) of the compound obtained in the Example 193 was added to this mixture at once, and the mixture was stirred for 1 hour. Further, 6.03 g (0.151 mol) of sodium hydride (60% oily) was added to this mixture in small portions at 0° C., and the mixture was stirred for 1 hour. The reaction mixture was diluted with ethyl acetate and the organic layer was washed with water and saturated saline solution, and dried over with anhydrous sodium sulfate. The solvent was removed under reduced pressure and the residue was purified by silica gel column chromatography (eluent:hexane/ethyl acetate=3/1 to 2/1) to give 30.1 g (76%) of the title compound.

Example 195

3-Methyl-1-tetrahydro-2H-pyran-4-yl-1H-thieno[2,3-c]pyrazole-5-carboxylic acid

The title compound 4.26 g (99%) was obtained in a manner similar to the Example 6 by use of the compound obtained in the Example 194, instead of the compound obtained in the Example 5.

Example 196

3-Methyl-N-[4-(4-methyl-1-piperazinyl)phenyl]-1-tetrahydro-2H-pyran-4-yl-1H-thieno[2,3-c]pyrazole-5-carboxamide The title compound 166 mg (84%) was obtained in a manner similar to the Example 7 by use of 4-(4-methyl-1-piperazinyl)aniline and the compound obtained in Example 194, instead of benzylamine and the compound obtained in the Example 6, respectively.

Example 197

N-[3-Fluoro-4-(4-methyl-1-piperazinyl)phenyl]-3-methyl-1-tetrahydro-2H-pyran-4-yl-1H-thieno[2,3-c]pyrazole-5-carboxamide The title compound 214 mg (83%) was obtained in a manner similar to the Example 7 by use of [3-fluoro-4-(4-methyl-1-piperazinyl)]aniline and the compound obtained in Example 195, instead of benzylamine and the compound obtained in the Example 6, respectively.

Example 198

1-Cyclohexyl-3-methyl-N-[4-(4-morpholinylmethyl)phenyl]-1H-thieno[2,3-c]pyrazole-5-carboxamide The title compound 173 mg (87%) was obtained in a manner similar to the Example 7 by use of 4-(4-morpholinylmethyl)aniline, instead of benzylamine.

Example 199

1-Cyclohexyl-3-methyl-N-[4-(4-morpholinylmethyl)phenyl]-1H-thieno[2,3-c]pyrazole-5-carboxamide fumarate 41.7 mg (0.59 mmol) of fumaric acid was added to a mixture of 150 mg (0.432 mmol) of the compound obtained in the Example 198 in 1 mL of ethanol, and 2 mL of diethyl ether was further added to the mixture. Then, the mixture was stirred for over night and appeared precipitates were collected by filtration to give 112 mg (59%) of the title compound.

Example 200

1-Cyclohexyl-N-{4-[2-(dimethylamino)ethyl]phenyl}-3-methyl-1H-thieno[2,3-c]pyrazole-5-carboxamide The title compound 83 mg (75%) was obtained in a manner similar to the Example 7 by use of 4-[(2-dimethylamino)ethyl]aniline, instead of benzylamine.

Example 201

1-Cyclohexyl-3-methyl-N-{4-[2-(4-morpholinyl)ethyl]phenyl}-1H-thieno[2,3-c]pyrazole-5-carboxamide The title compound 140 mg (68%) was obtained in a manner similar to the Example 7 by use of the compound obtained in the Example 32, instead of benzylamine.

Example 202

1-Cyclohexyl-3-methyl-N-{4-[(3-methyl-2,5-dioxo-1-imidazolidinyl)-methyl]phenyl}-1H-thieno[2,3-c]pyrazole-5-carboxamide The title compound 185 mg (88%) was obtained in a manner similar to the Example 7 by use of the compound obtained in the Example 34, instead of benzylamine.

Example 203

1-Cyclohexyl-3-methyl-N-[4-(3-methyl-2,5-dioxo-1-imidazolidinyl)-phenyl]-1H-thieno[2,3-c]pyrazole-5-carboxamide The title compound 116 mg (57%) was obtained in a manner similar to the Example 7 by use of 4-(3-methyl-2,5-dioxo-1-imidazolidinyl) aniline, instead of benzylamine.

Example 204

Methyl trans-4-{[(1-cyclohexyl-3-methyl-1H-thieno[2,3-c]pyrazol-5-yl)carbonyl]amino}cyclohexane carboxylate The title compound 2.18 g (95%) was obtained in a manner similar to the Example 7 by use of methyl trans-4-aminocyclohexanecarboxylate, instead of benzylamine.

Example 205

4-{[(1-Cyclohexyl-3-methyl-1H-thieno[2,3-c]pyrazol-5-yl)carbonyl]-amino}cyclohexane carboxylic acid The title compound 1.48 g (quantitative) was obtained in a manner similar to the Example 41 by use of the compound obtained in the Example 204, instead of the compound obtained in the Example 40.

Example 206

1-Cyclohexyl-N-[4-(hydroxymethyl)cyclohexyl]-3-methyl-1H-thieno[2,3-c]pyrazole-5-carboxamide To a solution of 200 mg (0.496 mmol) of the compound obtained in the Example 204 in 5 mL of tetrahydrofuran was added 43 mg (1.98 mmol) of lithium borohydride, and the mixture was stirred for 1.5 hours under heating at 70° C. The reaction mixture was cooled to room temperature and water was added to the mixture and mixture was extracted with dichloromethane. The organic layer was dried over with anhydrous sodium sulfate and the solvent was removed under reduced pressure. The resulting residue was recrystallized from isopropanol/hexane (1/1) to give 76 mg (41%) of the title compound.

Example 207

1-Cyclohexyl-3-methyl-N-{4-[(4-methyl-1-piperazinyl)carbonyl]-cyclohexyl}-1H-thieno[2,3-c]pyrazole-5-carboxamide To a solution of 200 mg (0.513 mmol) of the compound obtained in the Example 205 in 5 mL of dichloromethane and 1 mL of N,N-dimethylformamide were added 51.3 µL (0.462 mmol) of N-methylpiperazine and 750 mg of PS carbodiimide (Argonaut Co.), and the mixture was stirred for over night at room temperature. The reagent removed off by filtration and the filtrate was condensed to give 36 mg (15%) of the title compound.

Example 208

1-Cyclohexyl-N-{4-[(dimethylamino)carbonyl]cyclohexyl}-3-methyl-1H-thieno[2,3-c]pyrazole-5-carboxamide The title compound 18 mg (8%) was obtained in a manner similar to the Example 207 by use of 2M-dimethylamine in tetrahydrofuran, instead of N-methylpiperazine.

Example 209

N-(4-Cyanocyclohexyl)-1-cyclohexyl-3-methyl-1H-thieno[2,3-c]-pyrazole-5-carboxamide The title compound 189 mg (84%) was obtained in a manner similar to the Example 7 by use of the compound obtained in the Example 36, instead of benzylamine.

Example 210 tert-Butyl 2-{[(1-cyclohexyl-3-methyl-1H-thieno[2,3-c]pyrazol-5-yl)-carbonyl]amino}ethyl(methyl)carbamate The title compound 1.89 g (99%) was obtained in a manner similar to the Example 7 by use of [2-(N-Boc-N-methyl)amino]ethylamine, instead of benzylamine.

Example 211

1-Cyclohexyl-3-methyl-N-[2-(methylamino)ethyl]-1H-thieno[2,3-c]-pyrazole-5-carboxamide 2HCl Salt The title compound 1.71 g (quantitative) was obtained in a manner similar to the Manufacturing Example 4 by use of the compound obtained in the Example 210, instead of the compound obtained in the Manufacturing Example 3.

Example 212

N-{2-[Acetyl(methyl)amino]ethyl}-1-cyclohexyl-3-methyl-1H-thieno[2,3-c]pyrazole-5-carboxamide To a solution of 150 mg (0.381 mmol) of the compound obtained in the Example 211 in 5 mL of dichloromethane were added 54 µL (0.572 mmol) of acetic anhydride and 123 µL (1.53 mmol) of pyridine, and the mixture was stirred for 1 hour at room temperature. Then, 54 µL (0.572 mmol) of acetic anhydride and 123 µL (1.53 mmol) of pyridine were further added to the reaction mixture, and the mixture was stirred for 1 hour at room temperature. Water was added to the reaction mixture and the mixture was extracted with dichloromethane, and the organic layer was dried over with anhydrous sodium sulfate. The solvent was removed under reduced pressure, and the residue was purified by silica gel column chromatography (eluent:dichloromethane/methanol=30/1) to give 120 mg (87%) of the title compound.

Example 213

1-Cyclohexyl-3-methyl-N-{2-[methyl(methylsulfonyl)amino]ethyl}-1H-thieno[2,3-c]pyrazole-5-carboxamide HCl Salt To a solution of 150 mg (0.381 mmol) of the compound obtained in the Example 211 in 5 mL of dichloromethane were added 44 µL (0.572 mmol) of methanesulfonyl chloride and 212 µL (1.53 mmol) of triethylamine, and the mixture was stirred for 1 hour at room temperature. After the reaction, water was added to the reaction mixture and the mixture was extracted with dichloromethane. The organic layer was dried over with anhydrous sodium sulfate and the solvent was removed under reduced pressure. The resulting residue was purified by silica gel column chromatography (eluent:dichloromethane/methanol=40/1), and the eluate was treated with 4N—HCl/dioxane to give 128 mg (77%) of the title compound.

Example 214

Ethyl (4-{[(1-cyclohexyl-3-methyl-1H-thieno[2,3-c]pyrazol-5-yl)-carbonyl]amino}-1-piperidinyl)acetate To a solution of 250 mg (0.722 mol) of the compound obtained in the Example 134 in 6 mL of dichloromethane were added 88 µL (0.794 mmol) of ethyl bromoacetate and 151 µL (1.082 mmol) of triethylamine, and the mixture was stirred for 3 days at room temperature. Then, water was added to the reaction mixture and the mixture was extracted with dichloromethane. The organic layer was dried over with anhydrous sodium sulfate and the solvent was removed under reduced pressure. The resulting residue was purified by silica gel column chromatography (eluent:dichloromethane/methanol=40/1) to give 237 mg (76%) of the title compound.

Example 215

(4-{[(1-Cyclohexyl-3-methyl-1H-thieno[2,3-c]pyrazol-5-yl)carbonyl]-amino}-1-piperidinyl)acetic acid The title compound 176 mg (86%) was obtained in a manner similar to the Example 41 by use of the compound obtained in the Example 214, instead of the compound obtained in the Example 40.

Example 216

Ethyl 2-(4-{[(1-cyclohexyl-3-methyl-1H-thieno[2,3-c]pyrazol-5-yl)-carbonyl]amino}-1-piperidinyl)-2-methylpropanoate To a solution of 252 mg (0.727 mmol) of the compound obtained in the Example 134 in 5 mL of N,N-dimethylformamide were added 128 µL (0.873 mmol) of ethyl 2-bromoisobutyrate and 152 µL (1.09 mmol) of triethylamine, and the mixture was stirred for over night at 70° C. Then, water was added to the reaction mixture and the mixture was extracted with dichloromethane. The organic layer was dried over with anhydrous sodium sulfate and the solvent was removed under reduced pressure. The resulting residue was purified by silica gel column chromatography (eluent:dichloromethane/methanol=40/1) to give 115 mg (34%) of the title compound.

Example 217

2-(4-{[(1-Cyclohexyl-3-methyl-1H-thieno[2,3-c]pyrazol-5-yl)-carbonyl]amino}-1-piperidinyl)-2-methylpropanoic Acid The title compound 65 mg (69%) was obtained in a manner similar to the Example 41 by use of the compound obtained in the Example 216, instead of the compound obtained in the Example 40.

Example 218

N-[4-(4-Hydroxy-1-piperidinyl)phenyl]-3-methyl-1-tetrahydro-2H-pyran-4-yl-1H-thieno[2,3-c]pyrazole-5-carboxamide The title compound 198 mg (90%) was obtained in a manner similar to the Example 7 by use of 1-(4-aminophenyl)-4-piperidinol and the compound obtained in the Example 195, instead of benzylamine and the compound obtained in the Example 6, respectively.

Example 219

1-Cyclohexyl-N-[2-(5,5-dimethyl-2,4-dioxo-1,3-oxazolidin-3-yl)-ethyl]-3-methyl-1H-thieno[2,3-c]pyrazole-5-carboxamide To a solution of 150 mg (0.488 mol) of the compound obtained in the Example 122 in 5 mL of tetrahydrofuran were added 75.6 mg (0.586 mmol) of 5,5-dimethyloxazolidine-dione, 154 mg (0.586 mmol) of triphenylphsophine and 267 µL (0.586 mmol) of diethyl azodicarboxylate (40% toluene solution), and the mixture was stirred for 2 hours at room temperature. After the reaction, water was added to the reaction mixture and the mixture was extracted with dichloromethane. The organic layer was dried over with anhydrous sodium sulfate and the solvent was removed under reduced pressure. The resulting residue was purified by silica gel column chromatography (eluent:dichloromethane/acetone=2/1 for first trial, and hexane/ethyl acetate=2/1 for second trial) to give 133 mg (65%) of the title compound.

Example 220

1-Cyclohexyl-3-methyl-N-{[methyl(4-morpholinylcarbonyl)amino]ethyl}-1H-thieno[2,3-c]pyrazole-5-carboxamide The title compound 164 mg (99%) was obtained in a manner similar to the Example 214 by use of the compound obtained in the Example 211 and 4-morpholinylcarbonyl chloride, instead of the compound obtained in the Example 134 and ethyl bromoacetate, respectively.

Example 221

1-Cyclohexyl-N-{2-[[(dimethylamino)carbonyl](methyl)amino]ethyl}-3-methyl-1H-thieno[2,3-c]pyrazole-5-carboxamide The title compound 119 mg (80%) was obtained in a manner similar to the Example 214 by use of the compound obtained in the Example 211 and dimethylaminocarbonyl chloride, instead of the compound obtained in the Example 134 and ethyl bromoacetate, respectively.

Example 222

Methyl 2-{[(1-cyclohexyl-3-methyl-1H-thieno[2,3-c]pyrazol-5-yl)-carbonyl]amino}ethyl(methyl)carbamate To a solution of 150 mg (0.381 mmol) of the compound obtained in the Example 211 in 5 mL of dichloromethane and 5 mL of water were added 158 mg (1.14 mmol) of potassium carbonate and 44 µL (0.572 mmol) of ethyl chlorocarbonate, and the mixture was stirred for over night at room temperature. Then, water was added to the reaction mixture and the mixture was extracted with dichloromethane. The organic layer was dried over with anhydrous sodium sulfate and the solvent was removed under reduced pressure. The resulting residue was purified by silica gel column chromatography (eluent:dichloromethane/methanol=40/1) to give 120 mg (83%) of the title compound.

Example 223

1-Cyclohexyl-N-{2-[(methoxyacetyl)(methyl)amino]ethyl}-3-methyl-1H-thieno[2,3-c]pyrazole-5-carboxamide The title compound 124 mg (83%) was obtained in a manner similar to the Example 214 by use of the compound obtained in the Example 211 and methoxyacetyl chloride, instead of the compound obtained in the Example 134 and ethyl bromoacetate, respectively.

Example 224

1-Cyclohexyl-N-{2-[glycoloyl(methyl)amino]ethyl}-3-methyl-1H-thieno[2,3-c]pyrazole-5-carboxamide To a solution of 150 mg (0.381 mmol) of the compound obtained in the Example 211 in 6 mL of dichloromethane were added 34.8 mg (0.458 mmol) of hydroxyacetic acid, 186 μL (1.335 mmol) of triethylamine, 61.8 mg (0.458 mmol) of N-hydroxybenzotriazole and 80.4 mg (0.419 mmol) of 1-ethyl-3-(3'-di-methylaminopropyl)carbodiimide, and the mixture was stirred for 3 hours at room temperature. Then, water was added to the reaction mixture and the mixture was extracted with dichloromethane. The organic layer was dried over with anhydrous sodium sulfate and the solvent was removed under reduced pressure. The resulting residue was purified by silica gel column chromatography (eluent:dichloromethane/methanol=40/1) to give 87 mg (60%) of the title compound.

Example 225

1-Cyclohexyl-N-(4-{[(2-hydroxyethyl)(methyl)amino]carbonyl}-cyclohexyl)-3-methyl-1H-thieno[2,3-c]pyrazole-5-carboxamide The title compound 128 mg (74%) was obtained in a manner similar to the Example 224 by use of the compound obtained in the Example 205 and 2-N-methylaminoethanol, instead of the compound obtained in the Example 211 and hydroxyacetic acid, respectively.

Example 226

Methyl (1S,3S)-3-{[(1-cyclohexyl-3-methyl-1H-thieno[2,3-c]pyrazol-5-yl)carbonyl]amino}cyclopentanecarboxylate The title compound 565 mg (97%) was obtained in a manner similar to the Example 7 by use of methyl (1S,3S)-3-aminocyclopentanecarboxylate, instead of benzylamine.

Example 227

(1S,3S)-3-{[(1-Cyclohexyl-3-methyl-1H-thieno[2,3-c]pyrazol-5-yl)-carbonyl]amino}cyclopentanecarboxylic Acid The title compound 542 mg (quantitative) was obtained in a manner similar to the Example 41 by use of the compound obtained in the Example 226, instead of the compound obtained in the Example 40.

Example 228

1-Cyclohexyl-3-methyl-N-[2-(4-methyl-2,3-dioxo-1-piperazinyl)ethyl]-1H-thieno[2,3-c]pyrazole-5-carboxamide The title compound 88 mg (35%) was obtained in a manner similar to the Example 7 by use of the compound obtained in the Example 37, instead of benzylamine.

Example 229

1-Cyclohexyl-N-{(1S,3S)-3-[(dimethylamino)carbonyl]cyclopentyl}-3-methyl-1H-thieno[2,3-c]pyrazole-5-carboxamide The title compound 176 mg (91%) was obtained in a manner similar to the Example 224 by use of the compound obtained in the Example 227 and 2M-dimethylamine tetrahydrofuran solution, instead of the compound obtained in the Example 211 and hydroxyacetic acid, respectively.

Example 230

1-Cyclohexyl-N-{(1S,3S)-3-[(dimethylamino)carbonyl]cyclopentyl}-3-methyl-1H-thieno[2,3-c]pyrazole-5-carboxamide HCl Salt The title compound 137 mg (84%) was obtained in a manner similar to the Example 125 by using the compound obtained in the Example 229, instead of the compound obtained in the Example 124.

Example 231

Methyl (1R,3R)-3-{[(1-cyclohexyl-3-methyl-1H-thieno[2,3-c]pyrazol-5-yl)carbonyl]amino}cyclopentanecarboxylate The title compound 772 mg (99%) was obtained in a manner similar to the Example 7 by use of methyl (1R,3R)-3-aminocyclopentanecarboxylate, instead of benzylamine.

Example 232

(1R,3R)-3-{[(1-Cyclohexyl-3-methyl-1H-thieno[2,3-c]pyrazol-5-yl)-carbonyl]amino}cyclopentanecarboxylic acid The title compound 822 mg (quantitative) was obtained in a manner similar to the Example 41 by use of the compound obtained in the Example 231, instead of the compound obtained in the Example 40.

Example 233

1-Cyclohexyl-N-{(1R,3R)-3-[(dimethylamino)carbonyl]cyclopentyl}-3-methyl-1H-thieno[2,3-c]pyrazole-5-carboxamide The title compound 153 mg (79%) was obtained in a manner similar to the Example 224 by use of the compound obtained in the Example 232 and 2M-dimethylamine tetrahydrofuran solution, instead of the compound obtained in the Example 211 and hydroxyacetic acid, respectively.

Example 234

1-Cyclohexyl-N-{(1R,3R)-3-[(dimethylamino)carbonyl]cyclopentyl}-3-methyl-1H-thieno[2,3-c]pyrazole-5-carboxamide HCl Salt The title compound 80 mg (54%) was obtained in a manner similar to the Example 125 by use of the compound obtained in the Example 233, instead of the compound obtained in the Example 124.

Example 235

1-Cyclohexyl-N-{1[(dimethylamino)carbonyl]-4-piperidinyl}-3-methyl-1H-thieno[2,3-c]pyrazole-5-carboxamide The title compound 241 mg (95%) was obtained in a manner similar to the Example 7 by use of the compound obtained in the Manufacturing Example 39, instead of benzylamine.

Example 236

1-Cyclohexyl-3-methyl-N-[4-(4-morpholinylcarbonyl)cyclohexyl]-1H-thieno[2,3-c]pyrazole-5-carboxamide The title compound 236 mg (96%) was obtained in a manner similar to the Example 224 by use of the compound obtained in the Example 205 and morpholine, instead of the compound obtained in the Example 211 and hydroxyacetic acid, respectively.

Example 237

1-Cyclohexyl-3-methyl-N-{4-[(methylamino)carbonyl]cyclohexyl}-1H-thieno[2,3-c]pyrazole-5-carboxamide The title compound 122 mg (79%) was obtained in a manner similar to the Example 224 by use of the compound obtained in the Example 205 and methylamine (30% ethanol solution), instead of the compound obtained in the Example 211 and hydroxyacetic acid, respectively.

Example 238

1-Cyclohexyl-N-{4-[(cyclopropylamino)carbonyl]cyclohexyl}-3-methyl-1H-thieno[2,3-c]pyrazole-5-carboxamide HCl Salt The title compound 115 mg (64%) was obtained in a manner similar to the Example 224 by use of the compound obtained in the Example 205 and cyclopropylamine, instead of the compound obtained in the Example 211 and hydroxyacetic acid, respectively.

Example 239

1-Cyclohexyl-N-{4-[(4-hydroxy-1-piperidinyl)carbonyl]cyclohexyl}-3-methyl-1H-thieno[2,3-c]pyrazole-5-carboxamide The title compound 157 mg (86%) was obtained in a manner similar to the Example 224 by use of the compound obtained in the Example 205 and 4-hydroxypiperidine, instead of the compound obtained in the Example 211 and hydroxyacetic acid, respectively.

Example 240

1-Cyclohexyl-N-{1-[(dimethylamino)sulfonyl]-4-piperidinyl}-3-methyl-1H-thieno[2,3-c]pyrazole-5-carboxamide The title compound 257 mg (99%) was obtained in a manner similar to the Example 7 by use of the compound obtained in the Manufacturing Example 41, instead of benzylamine.

Example 241 tert-Butyl 4-{[(1-cyclohexyl-3-methyl-1H-thieno[2,3-c]pyrazol-5-yl)-carbonyl]amino}-1-piperidinecarboxylate The title compound 2.57 g (98%) was obtained in a manner similar to the Example 7 by use of 4-amino-1-Boc-piperidine, instead of benzylamine.

Example 242

1-Cyclohexyl-3-methyl-N-(4-piperidinyl)-1H-thieno[2,3-c]pyrazole-5-carboxamide di-HCl Salt The title compound 2.29 g (97%) was obtained in a manner similar to the Manufacturing Example 4 by using the compound obtained in the Example 241, instead of the compound obtained in the Manufacturing Example 3.

Example 243

N-[(3S)-1-Benzylpyrrolidinyl]-1-cyclohexyl-3-methyl-1H-thieno[2,3-c]pyrazole-5-carboxamide The title compound 2.32 g (97%) was obtained in a manner similar to the Example 7 by use of (3S)-1-benzyl-3-aminopyrrolidine, instead of benzylamine.

Example 244

1-Cyclohexyl-3-methyl-N-[(3S)-pyrrolidinyl]-1H-thieno[2,3-c]-pyrazole-5-carboxamide To a solution of 2.26 g (5.35 mmol) of the compound obtained in the Example 243 in 50 mL of 1,2-dichloroethane was added 721 µL (6.68 mmol) of 1-chloroethyl chloroformate, and the mixture was refluxed for 2 hours. Then, 289 µL (2.67 mmol) of 1-chloroethyl chloroformate was further added to this mixture and the mixture was refluxed for 1 hour under stirring. The solvent was removed under reduced pressure and 50 mL of methanol was added to the residue, and the mixture was refluxed for 30 minutes. The solvent was removed under reduced pressure and the residue was treated with saturated sodium bicarbonate aqueous solution, and the mixture was extracted with dichloromethane. The organic layer was dried over with anhydrous sodium sulfate, and the solvent was removed under reduced pressure. The residue was purified by silica gel column chromatography (eluent: dichloromethane/methanol=20/1) to give 0.83 g (47%) of the title compound.

Example 245

1-Cyclohexyl-N-{(3S)-1-[(dimethylamino)carbonyl]pyrrolidinyl}-3-methyl-1H-thieno[2,3-c]pyrazole-5-carboxamide The title compound 155 mg (85%) was obtained in a manner similar to the Example 214 by use of the compound obtained in the Example 244 and dimethylaminocarbonyl chloride, instead of the compound obtained in the Example 134 and ethyl bromoacetate, respectively.

Example 246

1-Cyclohexyl-N-{(3S)-1-[(dimethylamino)carbonyl]pyrrolidinyl}-3-methyl-1H-thieno[2,3-c]pyrazole-5-carboxamide HCl Salt The title compound 155 mg (85%) was obtained in a manner similar to the Example 125 by use of the compound obtained in the Example 245, instead of the compound obtained in the Example 124.

Example 247

1-Cyclohexyl-N-{4-[(2,5-dioxo-1-imidazolidinyl)methyl]cyclohexyl}-3-methyl-1H-thieno[2,3-c]pyrazole-5-carboxamide To a solution of 136 mg (0.362 mmol) of the compound obtained in the Example 206 in 10 mL of tetrahydrofuran were added 72 mg (0.724 mmol) of hydantoin, 135 µL (0.543 mmol) of tri-n-butylphosphine and 1,1'-azobis (N,N-dimethylformamide), and the mixture was stirred for 3 hours at 60° C. The reaction mixture was cooled to room temperature, treated with water, and extracted with ethyl acetate. The organic layer was dried over with anhydrous sodium sulfate and removed under reduced pressure. The residue was purified by silica gel column chromatography (eluent:ethyl acetate) to give 96 mg (58%) of the title compound.

Example 248

Ethyl 1-[(1-cyclohexyl-3-methyl-1H-thieno[2,3-c]pyrazol-5-yl)-carbonyl]-4-piperidinecarboxylate The title compound 2.73 g (98%) was obtained in a manner similar to the Example 7 by using ethyl isonipecotic acid, instead of benzylamine.

Example 249

1-[(1-Cyclohexyl-3-methyl-1H-thieno[2,3-c]pyrazol-5-yl)carbonyl]-4-piperidinecarboxylic acid The title compound 1.1 g (99%) was obtained in a manner similar to the Example 41 by use of the compound obtained in the Example 248, instead of the compound obtained in the Example 40.

Example 250

1-[(1-Cyclohexyl-3-methyl-1H-thieno[2,3-c]pyrazol-5-yl)carbonyl]-N-methyl-4-piperidinecarboxamide The title compound 195 mg (94%) was obtained in a manner similar to the Example 224 by use of methylamine (30% ethanol solution) and the compound obtained in the Example 249, instead of the compound obtained in the Example 211 and hydroxyacetic acid, respectively.

Example 251

Ethyl (3S)-1-[(1-cyclohexyl-3-methyl-1H-thieno[2,3-c]pyrazol-5-yl)-carbonyl]-3-piperidinecarboxylate The title compound 2.29 g (quantitative) was obtained in a manner similar to the Example 7 by use of ethyl (R)-nipecotic acid, instead of benzylamine.

Example 252

N-[(6S,7aS)-1,3-Dioxohexahydro-1H-pyrrolo[1,2-c]imidazol-6-yl]-1-cyclohexyl-3-methyl-1H-thieno[2,3-c]pyrazole-5-carboxamide The title compound 595 mg (74%) was obtained in a manner similar to the Example 7 by use of the compound obtained in the Manufacturing Example 45, instead of benzylamine.

Example 253

N-[(6S,7aS)-2-Methyl-1,3-dioxohexahydro-1H-pyrrolo[1,2-c]imidazol-6-yl]-1-cyclohexyl-3-methyl-1H-thieno[2,3-c]pyrazole-5-carboxamide HCl Salt To a solution of 150 mg (0.374 mmol) of the compound obtained in the Example 252 in 10 mL of tetrahydrofuran were added 30 µL (0.747 mmol) of methanol, 122 mg (0.476 mmol) of triphenylphosophine and 213 µL (0.467 mmol) of diethylazodicarboxylate (40% toluene solution), and the mixture was stirred for 1 hour at room temperature. Then, the solvent was removed under reduced pressure and the residue was purified by silica gel column chromatography (eluent: hexane/acetone=2/1 for first trial; dichloromethane/ethyl acetate=1/1 for second trial), and obtained product was converted to the HCl salt by treating with 100 µL of 4N—HCl/dioxane solution and recrystallized from methanol-ethanol (1/1) to give 23 mg (15%) of the title compound.

Example 254

(±)-{1-[(1-Cyclohexyl-3-methyl-1H-thieno[2,3-c]pyrazol-5-yl)-carbonyl]-3-piperidinyl}methanol The title compound 595 mg (74%) was obtained in a manner similar to the Example 7 by use of (±)-3-hydroxymethylpiperidine, instead of benzylamine.

Example 255

N-{4-[(Dimethylamino)carbonyl]phenyl}-3-methyl-1-tetrahydro-2H-pyran-4-yl-1H-thieno[2,3-c]pyrazole-5-carboxamide The title compound 123 mg (80%) was obtained in a manner similar to the Example 7 by use of 4-(dimethylaminocarbonyl)aniline, instead of benzylamine.

Example 256

1-Cyclohexyl-3-methyl-N-[6-(2-oxo-1-imidazolidinyl)-3-pyridinyl]-1H-thieno[2,3-c]pyrazole-5-carboxamide The title compound 199 mg (83%) was obtained in a manner similar to the Example 7 by use of the compound obtained in the Manufacturing Example 46, instead of benzylamine.

Example 257

1-Cyclohexyl-N-[(1S,3S)-3-(hydroxymethyl)cyclopentyl]-3-methyl-1H-tieno[2,3-c]pyrazole-5-carboxamide The title compound 462 mg (quantitative) was obtained in a manner similar to the Example 206 by use of the compound obtained in the Example 226, instead of the compound obtained in the Example 204.

Example 258

1-Cyclohexyl-N-{(1S,3S)-3-[(2,5-dioxo-1-imidazolidinyl)methyl]-cyclopentyl}-3-methyl-1H-thieno[2,3-c]pyrazole-5-carboxamide The title compound 74 mg (40%) was obtained in a manner similar to the Example 247 by use of the compound obtained in the Example 257, instead of the compound obtained in the Example 206.

Example 259

1-Cyclohexyl-N-[4-(2,5-dioxo-1-imidazolidinyl)phenyl]-3-methyl-1H-thieno[2,3-c]pyrazole-5-carboxamide The title compound 54 mg (27%) was obtained in a manner similar to the Example 7 by use of the compound obtained in the Manufacturing Example 47, instead of benzylamine.

Example 260

3-Methyl-N-[4-(3-methyl-2,5-dioxo-1-imidazolidinyl)phenyl]-1-tetrahydro-2H-pyran-4-yl-1H-thieno[2,3-c]pyrazole-5-carboxamide The title compound 104 mg (61%) was obtained in a manner similar to the Example 7 by use of the compound obtained in the Manufacturing Example 48 and the compound obtained in the Example 195, instead of benzylamine and the compound obtained in the Example 6, respectively.

Example 261

3-Methyl-N-[6-(2-oxo-1-imidazolidinyl)-3-piperidinyl]-1-tetrahydro-2H-pyran-4-yl-1H-thieno[2,3-c]pyrazole-5-carboxamide The title compound 101 mg (63%) was obtained in a manner similar to the Example 7 by use of the compound obtained in the Manufacturing Example 46 and the compound obtained in the Example 195, instead of benzylamine and the compound obtained in the Example 6, respectively.

Example 262

1-Cyclohexyl-N-{4-[(3R)-3-hydroxypyrrolidinyl]phenyl}-3-methyl-1H-thieno[2,3-c]pyrazole-5-carboxamide The title compound 308 mg (64%) was obtained in a manner similar to the Example 7 by use of the compound obtained in the Manufacturing Example 49, instead of benzylamine.

Example 263

1-Cyclohexyl-N-{3-fluoro-4-[(3R)-3-hydroxypyrrolidinyl]phenyl}-3-methyl-1H-thieno[2,3-c]pyrazole-5-carboxamide The title compound 397 mg (79%) was obtained in a manner similar to the Example 7 by use of the compound obtained in the Manufacturing Example 51, instead of benzylamine.

Example 264

1-Cyclohexyl-N-{3-[(4-hydroxy-1-piperidinyl)sulfonyl]phenyl}-3-methyl-1H-thieno[2,3-c]pyrazole-5-carboxamide The title compound 80 mg (35%) was obtained in a manner similar to the Example 7 by use of the compound obtained in the Manufacturing Example 53, instead of benzylamine.

Example 265

N-{4-[4-{[tert-Butyl(dimethyl)silyl]oxy}-1-piperidinyl]sulfonyl}-phenyl}-1-cyclohexyl-3-methyl-1H-thieno[2,3-c]pyrazole-5-carboxamide The title compound 243 mg (69%) was obtained in a manner similar to the Example 7 by use of the compound obtained in the Manufacturing Example 56, instead of benzylamine.

Example 266

1-Cyclohexyl-N-{4-[(4-hydroxy-1-piperidinyl)sulfonyl]phenyl}-3-methyl-1H-thieno[2,3-c]pyrazole-5-carboxamide To a solution of 231 mg (0.374 mmol) of the compound obtained in the Example 265 in 5 mL of tetrahydrofuran was added 562 µL (0.562 mmol) of tetrabutylammoniumfluoride (1M-tetrahydrofuran solution), and the mixture was stirred for over night at room temperature. Then, the reaction mixture was treated with ethyl acetate, and the organic layer was washed with water, saturated saline solution and then, dried over with anhydrous sodium sulfate. The solvent was removed under reduced pressure and the residue was purified by silica gel column chromatography (eluent:hexane/ethyl acetate=1/2) to give 176 mg (94%) of the title compound.

Example 267

1-Cyclohexyl-N-[4-(2-hydroxyethyl)phenyl]-3-methyl-1H-thieno[2,3-c]pyrazole-5-carboxamide The title compound 139 mg (64%) was obtained in a manner similar to the Example 7 by use of 4-aminophenethylalcohol, instead of benzylamine.

Example 268

N-[3-Fluoro-4-(4-hydroxy-1-piperidinyl)phenyl]-3-methyl-1-tetrahydro-2H-pyran-4-yl-1H-thieno[2,3-c]pyrazole-5-carboxamide The title compound 161 mg (96%) was obtained in a manner similar to the Example 7 by use of the compound obtained in the Manufacturing Example 62 and the compound obtained in the Example 195, instead of benzylamine and the compound obtained in the Example 6, respectively.

Example 269

1-Cyclohexyl-3-methyl-N-[4-(4-methyl-1-piperazinyl)-3-(trifluoromethyl)phenyl]-1H-thieno[2,3-c]pyrazole-5-carboxamide The title compound 229 mg (80%) was obtained in a manner similar to the Example 7 by use of the compound obtained in the Manufacturing Example 58, instead of benzylamine.

Example 270

1-Cyclohexyl-3-methyl-N-[trans-4-(2-oxo-1,3-oxazolidin-3-yl)-cyclohexyl]-1H-thieno[2,3-c]pyrazole-5-carboxamide To a suspension of 150 mg (0.416 mmol) of the compound obtained in the Example 132 in 2.5 mL of tetrahydrofuran were added 52 µL (0.50 mmol) of 2-chloroethyl chloroformate and 87 µL (0.624 mmol) of triethylamine, and the mixture was stirred for 3 hours at room temperature. Saturated sodium bicarbonate aqueous solution was added to the reaction mixture and the mixture was extracted with chloroform. The organic layer was washed with water and saturated saline solution and dried over with anhydrous sodium sulfate. The solvent was removed under reduced pressure to give urethane intermediate compound.

Next, to a mixture solution of the urethane intermediate compound obtained above in 2 mL of ethanol and 4 mL of tetrahydrofuran was added 2 mL of 4M-NaOH aqueous solution, and the mixture was stirred for 40 hours at room temperature. The solvent was removed under reduced pressure and the residue was treated with water, and the mixture was extracted with chloroform. The organic layer was washed with water and saturated saline solution and dried over with anhydrous sodium sulfate. The solvent was removed under reduced pressure and the residue was purified by silica gel column chromatography (eluent:chloroform/methanol=10/1) to give 180 mg (quantitative) of the title compound.

Example 271

1-Cyclohexyl-3-methyl-N-[trans-4-(2-oxo-1-imidazolidinyl)-cyclohexyl]-1H-thieno[2,3-c]pyrazole-5-carboxamide To a suspension of 150 mg (0.416 mmol) of the compound obtained in the Example 132 in 4 mL of tetrahydrofuran was added 71 µL (0.832 mmol) of 2-chloroethylsocyanate, and the mixture was stirred for 3.5 hours at room temperature. 2 mL of 1M-NaOH aqueous solution was added to the reaction mixture, and the mixture was stirred. Then, further 5 mL of 4M-NaOH aqueous solution and 15 mL of tetrahydrofuran were added to the mixture, and the mixture was stirred for 2 hours. Next, 5 µL of 15-crown-5 was added to the reaction mixture and the mixture was further stirred for 43 hours at room temperature, then, 5 mL of ethanol was added to the reaction mixture and stirred for 6 hours at 80° C. The solvent was removed under reduced pressure and the residue was treated with water. The mixture was extracted with chloroform and the organic layer was washed with water and saturated saline solution, then, dried over with anhydrous sodium sulfate. The solvent was removed under reduced pressure and the residue was purified by silica gel column chromatography (eluent:chloroform/methanol=10/1) to give 106 mg (55%) of the title compound.

Example 272

4-[(trans-4-{[(1-Cyclohexyl-3-methyl-1H-thieno[2,3-c]pyrazol-5-yl)-carbonyl]amino}cyclohexyl)amino]-4-oxobutanoic acid To a suspension of 150 mg (0.416 mmol) of the compound obtained in the Example 132 in 5 mL of xylene was added 62 mg (0.624 mmol) of succinic anhydride, and the mixture was refluxed for 5 hours. The solvent was removed under reduced pressure and the residue was treated with ether. The appeared precipitates were collected to give 178 mg (93%) of the title compound.

Example 273

1-Cyclohexyl-N-[trans-4-(2,5-dioxo-1-pyrrolidinyl)cyclohexyl]-3-methyl-1H-thieno[2,3-c]pyrazole-5-carboxamide A mixture of 141 mg (0.306 mmol) of the compound obtained in the Example 272, 2 mL of acetic anhydride and 33 mg of sodium acetate was stirred for 3 hours at 60° C. and for 14 hours at 80° C., then, 2 mL of acetic anhydride was further added to the reaction mixture, and the mixture was stirred for 6 hours at 100° C. After the reaction, ice water was added to the reaction mixture and the mixture was neutralized by adding saturates sodium bicarbonate aqueous solution, and extracted with chloroform. The organic layer was washed with water and saturated saline solution, and dried over with anhydrous sodium sulfate. The solvent was removed under reduced pressure and the residue was treated with ethanol to give 59 mg (49%) of the title compound.

Example 274

1-Cyclohexyl-N-[trans-4-(1,1-dioxide-2-isothiazolidinyl)cyclohexyl]-3-methyl-1H-thieno[2,3-c]pyrazole-5-carboxamide To a solution of 150 mg (0.416 mmol) of the compound obtained in the Example 132 in 10 mL of dichloromethane were added 87 µL (0.624 mmol) of triethylamine and 61 µL (0.50 mmol) of 3-chloropropanesulfonyl chloride, and the mixture was stirred for 1.5 hours at room temperature. Water was added to the reaction mixture and the mixture was extracted with chloroform. The organic layer was washed with water and saturated saline solution and dried over with anhydrous sodium sulfate. The solvent was removed under reduced pressure to give sulfonamide intermediate compound.

Next, to a mixture solution of the sulfonamide intermediate compound obtained above in 5 mL of ethanol was added 2 mL of 4M-NaOH aqueous solution, and the mixture was stirred for 1.5 hours at room temperature and for 3 hours at 80° C. The reaction mixture was cooled and treated with water, and then, extracted with chloroform. The organic layer was washed with water and saturated saline solution and dried over with anhydrous sodium sulfate. The solvent was removed under reduced pressure and the residue was recrystallized from ethanol to give 112 mg (58%) of the title compound.

Example 275

Benzyl [{[(trans-4-{[(1-cyclohexyl-3-methyl-1H-thieno[2,3-c]pyrazol-5-yl)carbonyl]amino}cyclohexyl)amino]carbonyl}(methyl)amino]acetate To a solution of 200 mg (0.555 mmol) of the compound obtained in the Example 132 in 4 mL of tetrahydrofuran were added 66 mg (0.22 mmol) of tri-phosgene and 232 μL (1.66 mmol) of triethylamine, and the mixture was stirred for 1 hour at room temperature. Then, 195 mg (0.55 mmol) of p-toluene sulfonic acid sarcosine benzyl ester and 77 μL (0.555 mmol) of triethylamine were added to the reaction mixture, and the mixture was stirred for 5 hours at room temperature. Water was added to the reaction mixture and the mixture was extracted with chloroform, and the organic layer was washed with water and saturated saline solution, then, dried over with anhydrous sodium sulfate. The solvent was removed under reduced pressure and the residue was purified by silica gel column chromatography (eluent:chloroform/methanol=15/1) to give 227 mg (72%) of the title compound.

Example 276

1-Cyclohexyl-3-methyl-N-[trans-4-(3-methyl-2,5-dioxo-1-imidazolidinyl)cyclohexyl]-1H-thieno[2,3-c]pyrazole-5-carboxamide To a solution of 207 mg (0.366 mmol) of the compound obtained in the Example 275 in 5 mL of ethanol was added 0.5 mL of 6M-HCl aqueous solution and the mixture was refluxed for 4 hours. After the reaction, the mixture was neutralized by adding saturated sodium bicarbonate aqueous solution, and extracted with chloroform. The organic layer was washed with water and saturated saline solution and dried over with anhydrous sodium sulfate. The solvent was removed under reduced pressure and the residue was purified by silica gel column chromatography (eluent:chloroform/methanol=15/1) to give 169 mg (quantitative) of the title compound.

Example 277

1-Cyclohexyl-3-methyl-N-[2-(3-methyl-2,5-dioxo-1-imidazolidinyl)-ethyl]-1H-thieno[2,3-c]pyrazole-5-carboxamide To a solution of 150 mg (0.487 mmol) of the compound obtained in the Example 122 and 55.6 mg (0.487 mmol) of 1-methylhydantoin 4 mL of tetrahydrofuran were added 12 μL (0.487 mmol) of n-butylphosphine and 83.8 mg (0.487 mmol) of 1,1'-azobis(N,N-dimethylformamide), and the mixture was stirred for 5 hours at room temperature. The reaction mixture was treated with water and extracted with chloroform. The organic layer was washed with water and saturated saline solution, and dried over with anhydrous sodium sulfate. The solvent was removed under reduced pressure and the residue was purified by silica gel column chromatography (eluent:ethyl acetate) to give 113 mg (58%) of the title compound.

Example 278

1-Cyclohexyl-3-methyl-N-[3-(3-methyl-2,5-dioxo-1-imidazolidinyl)-propyl]-1H-thieno[2,3-c]pyrazole-5-carboxamide The title compound 147 mg (75%) was obtained in a manner similar to the Example 277 by use of the compound obtained in the Example 123, instead of the compound obtained in the Example 122.

Example 279

1-Cyclohexyl-N-[trans-4-({[(2-hydroxyethyl)(methyl)amino]carbonyl}-aminocyclohexyl]-3-methyl-1H-thieno[2,3-c]pyrazole-5-carboxamide To a suspension of 200 mg (0.555 mmol) of the compound obtained in the Example 132 in 4 mL of tetrahydrofuran were added 66 mg (0.22 mmol) of triphosgene and 232 μL (1.66 mmol) of triethylamine and the mixture was stirred for 1 hour at room temperature. Then, 54 μL (0.66 mmol) of 2-(methylamino) ethanol was added to the reaction mixture and the mixture was stirred for 3 hours at room temperature. The reaction mixture was treated with water and extracted with chloroform, washed with water and saturated saline solution, and then, dried over with anhydrous sodium sulfate. The solvent was removed under reduced pressure and the residue was purified by silica gel column chromatography (eluent:chloroform/methanol=15/1) to give 190 mg (74%) of the title compound.

Example 280

1-Cyclohexyl-3-methyl-N-[trans-[4-(3-methyl-2-oxo-1-imidazolidinyl)-cyclohexyl]-1H-thieno[2,3-c]pyrazole-5-carboxamide To a suspension of 187 mg (0.519 mmol) of the compound obtained in the Example 279 in 6 mL of tetrahydrofuran was added 140 mg (1.25 mmol) of potassium tert-butoxide and the mixture was cooled to 0° C. Then, a solution of 119 mg (0.623 mmol) of p-toluenesulfonyl chloride in 2 mL of tetrahydrofuran was added gradually to the reaction mixture and the mixture was stirred for 30 minutes at room temperature. The reaction mixture was treated with water and extracted with chloroform. The organic layer was washed with water and saturated saline solution and dried over with anhydrous sodium sulfate. The solvent was removed under reduced pressure and the residue was purified by silica gel column chromatography (eluent:chloroform/methanol=20/1) to give 115 mg (64%) of the title compound.

Example 281

Ethyl 3-{[(1-cyclohexyl-3-methyl-1H-thieno[2,3-c]pyrazol-5-yl)-carbonyl]amino}propanoate The title compound 716 mg (98%) was obtained in a manner similar to the Example 7 by use of β-alanine ethyl ester HCl salt, instead of benzylamine.

Example 282

N-[(1-Cyclohexyl-3-methyl-1H-thieno[2,3-c]pyrazole-5-yl)carbonyl]-β-alanine

The title compound 620 mg (99%) was obtained in a manner similar to the Example 41 by use of the compound obtained in the Example 281, instead of the compound obtained in the Example 40.

Example 283 tert-Butyl {[(1-cyclohexyl-3-methyl-1H-thieno[2,3-c]pyrazol-5-yl)-carbonyl]amino}acetate The title compound 663 mg (88%) was obtained in a manner similar to the Example 7 by use of glycine tert-butyl ester HCl salt, instead of benzylamine.

Example 284

{[(1-Cyclohexyl-3-methyl-1H-thieno[2,3-c]pyrazol-5-yl)carbonyl]-amino}acetic acid A mixture solution of 637 mg (1.68 mmol) of the compound obtained in the Example 283 and 5 mL of 4M-HCl/dioxane was stirred for 5 hours at room temperature, and after the reaction, the solvent was removed under reduced pressure. The residue was treated with water and extracted with chloroform, and the organic layer was washed with water and saturated saline solution, then, dried over with anhydrous sodium sulfate. The solvent was removed under reduced pressure to give 556 mg (quantitative) of the title compound.

Example 285

1-Cyclohexyl-3-methyl-N-[3-(4-morphonyl)-3-oxopropyl]-1H-thieno[2,3-c]pyrazole-5-carboxamide A suspension solution of 85 mg (0.253 mmol) of the compound obtained in the Example 282, 246 mg (0.337 mmol) of PS-carbodiimide (Argonaut Co.), and 39 mg (0.287 mmol) of 1-hydroxybenzotriazole in 4 mL of dichloromethane was stirred for 10 minutes at room temperature. To the reaction mixture was added 20 μL (0.228 mmol) of morpholine, and the mixture was stirred for 20 hours at room temperature. Then, 267 mng (0.861 mmol) of MP-carbonate (Argonaut Co.) was added to the reaction mixture and the mixture was stirred for 3 hours at room temperature. The reaction mixture was filtrated and the filtrate was condensed under reduced pressure. The residue was recrystallized from ethyl acetate/hexane to give 80 mg (78%) of the title compound.

Example 286 tert-Butyl 2-{[(1-cyclohexyl-3-methyl-1H-thieno[2,3-c]pyrazol-5-yl)-carbonyl]amino}ethylcarbamate The title compound 2.23 g (97%) was obtained in a manner similar to the Example 7 by use of N-(2-aminomethyl) carbamic acid tert-butyl ester, instead of benzylamine.

Example 287

N-(2-Aminoethyl)-1-cyclohexyl-3-methyl-1H-thieno[2,3-c]pyrazole-5-carboxamide

To a solution of 2.18 g (5.36 mmol) of the compound obtained in the Example 286 in 20 mL of dichloromethane was added 5 mL of 4M-HCl/dioxane, and the mixture was stirred for 18 hours at room temperature. After reaction, the solvent was removed under reduced pressure and the residue was neutralized with saturated sodium bicarbonate aqueous solution, and extracted with chloroform. The organic layer was washed with water and saturated saline solution, then, dried over with anhydrous sodium sulfate. The solvent was removed under reduced pressure and the residue was treated with ethanol to give 670 mg (41%) of the title compound.

Example 288

1-Cyclohexyl-N-[3-(dimethylamino)-3-oxopropyl]-3-methyl-1H-thieno[2,3-c]pyrazole-5-carboxamide The title compound 52 mg (57%) was obtained in a manner similar to the Example 285 by use of 2.0M-dimethylamine/tetrahydrofuran, instead of morpholine.

Example 289

1-Cyclohexyl-3-methyl-N-{3-[methyl(1-methyl-4-piperidinyl)amino]-3-oxopropyl}-1H-thieno[2,3-c]pyrazole-5-carboxamide The title compound 79 mg (70%) was obtained in a manner similar to the Example 285 by use of 1-methyl-4-(methylamino)piperidine, instead of morpholine.

Example 290

1-Cyclohexyl-N-[3-(4-hydroxy-1-piperidinyl)-3-oxopropyl]-3-methyl-1H-thieno[2,3-c]pyrazole-5-carboxamide The title compound 74 mg (70%) was obtained in a manner similar to the Example 285 by use of 4-hydroxypiperidine, instead of morpholine.

Example 291

1-Cyclohexyl-3-methyl-N-[2-(4-morpholinyl)-2-oxoethyl]-1H-thieno[2,3-c]pyrazole-5-carboxamide The title compound 62 mg (63%) was obtained in a manner similar to the Example 285 by use of the compound obtained in the Example 284, instead of the compound obtained in the Example 282.

Example 292

1-Cyclohexyl-N-[2-(dimethylamino)-2-oxoethyl]-3-methyl-1H-thieno[2,3-c]pyrazole-5-carboxamide The title compound 63 mg (71%) was obtained in a manner similar to the Example 285 by use of the compound obtained in the Example 284 and 2.0M-dimethylamine/tetrahydrofuran, instead of the compound obtained in the Example 282 and morpholine, respectively.

Example 293

1-Cyclohexyl-3-methyl-N-[2-(4-methyl-1-piperazinyl)-2-oxoethyl]-1H-thieno[2,3-c]pyrazole-5-carboxamide The title compound 68 mg (67%) was obtained in a manner similar to the Example 285 by use of the compound obtained in the Example 284 and N-methylpiperazine, instead of the compound obtained in the Example 282 and morpholine, respectively.

Example 294

1-Cyclohexyl-N-[2-(4-hydroxy-1-piperidinyl)-2-oxoethyl]-3-methyl-1H-thieno[2,3-c]pyrazole-5-carboxamide The title compound 75 mg (73%) was obtained in a manner similar to the Example 285 by use of the compound obtained in the Example 284 and 4-hydroxypiperidine, instead of the compound obtained in the Example 282 and morpholine, respectively.

Example 295

1-Cyclohexyl-3-methyl-N-[3-(4-methyl-1-piperazinyl)-3-oxopropyl]-1H-thieno[2,3-c]pyrazole-5-carboxamide The title compound 84 mg (80%) was obtained in a manner similar to the Example 285 by use of N-methylpiperazine, instead of morpholine.

Example 296

1-Cyclohexyl-3-methyl-N-{3-[4-methyl-1-piperidinyl]-3-oxopropyl}-1H-thieno[2,3-c]pyrazole-5-carboxamide fumarate The title compound 41 mg (41%) was obtained in a manner similar to the Example 191 by use of the compound obtained in the Example 295, instead of the compound obtained in the Example 144.

Example 297

1-Cyclohexyl-3-methyl-N-{2-[methyl(1-methyl-4-piperidinyl)amino]-2-oxoethyl}-1H-thieno[2,3-c]pyrazole-5-carboxamide The title compound 81 mg (74%) was obtained in a manner similar to the Example 285 by use of the compound obtained in the Example 284 and 1-methyl-4-(methylamino) piperidine, instead of the compound obtained in the Example 282 and morpholine, respectively.

Example 298

1-Cyclohexyl-3-methyl-N-{2-[methyl(1-methyl-4-piperidinyl)amino-2-oxoethyl}-1H-thieno[2,3-c]pyrazole-5-carboxamide fumarate The title compound 74 mg (79%) was obtained in a manner similar to the Example 191 by use of the compound obtained in the Example 297, instead of the compound obtained in the Example 144.

Example 299

1-Cyclohexyl-3-methyl-N-[2-(2-oxo-1,3-oxazolidin-3-yl)ethyl]-1H-thieno[2,3-c]pyrazole-5-carboxamide To a suspension of 150 mg (0.490 mmol) of the compound obtained in the Example 287 in 3 mL of tetrahydrofuran were added 102 µL (0.735 mmol) of triethylamine and 61 µL (0.590 mmol) of 2-chloroethyl chloroformate, and the mixture was stirred for 2 hours at room temperature. Then, 210 mg (1.08 mmol) of 28%-sodium methoxide/methanol solution was added to the reaction mixture and the mixture was stirred for 2 hours at room temperature, and further 130 mg (0.674 mmol) of 28%-sodium methoxide/methanol solution was added to the reaction mixture and the resulting mixture was stirred for 15 hours at room temperature. Then, the reaction mixture was treated with water and extracted with chloroform. The organic layer was washed with water and saturated saline solution, then, dried over with anhydrous sodium sulfate. The solvent was removed under reduced pressure and the residue was recrystallized from ethyl acetate to give 107 mf (58%) of the title compound.

Example 300

1-Cyclohexyl-N-[2-(1,1-dioxide-2-isothiazolidinyl) ethyl]-3-methyl-1H-thieno[2,3-c]pyrazole-5-carboxamide The title compound 125 mg (62%) was obtained in a manner similar to the Example 274 by use of the compound obtained in the Example 287, instead of the compound obtained in the Example 132.

Example 301

1-Cyclohexyl-N-[2-({[(2-hydroxyethyl)(methyl) amino]carbonyl}amino)-ethyl]-3-methyl-1H-thieno[2,3-c]pyrazole-5-carboxamide The title compound 160 mg (60%) was obtained in a manner similar to the Example 279 by use of the compound obtained in the Example 287, instead of the compound obtained in the Example 132.

Example 302

1-Cyclohexyl-3-methyl-N-[2-(3-methyl-2-oxo-1-imidazolidinyl)ethyl]-1H-thieno[2,3-c]pyrazole-5-carboxamide The title compound 110 mg (80%) was obtained in a manner similar to the Example 280 by use of the compound obtained in the Example 301, instead of the compound obtained in the Example 279.

Example 303

Ethyl 4-{[(1-cyclohexyl-3-methyl-1H-thieno[2,3-c]pyrazol-5-yl)-carbonyl]amino}butanoate The title compound 763 mg (67%) was obtained in a manner similar to the Example 7 by use of ethyl 4-aminobutyrate HCl salt, instead of benzylamine.

Example 304

4-{[(1-Cyclohexyl-3-methyl-1H-thieno[2,3-c]pyrazol-5-yl)carbonyl]-amino}butanoic acid The title compound 690 mg (quantitative) was obtained in a manner similar to the Example 41 by use of the compound obtained in the Example 303, instead of the compound obtained in the Example 40.

Example 305

1-Cyclohexyl-N-[2-(2,5-dioxo-1-imidazolidinyl)
ethyl]-3-methyl-1H-thieno[2,3-c]pyrazole-5-car-
boxamide The title compound 98 mg (67%) was obtained in a manner similar to the Example 7 by use of 3-(2-aminoethyl)-2,4-imidazolidinedione, instead of benzylamine.

Example 306

1-Cyclohexyl-N-[4-(dimethylamino)-4-oxobutyl]-3-
methyl-1H-thieno[2,3-c]pyrazole-5-carboxamide The title compound 101 mg (85%) was obtained in a manner similar to the Example 285 by use of the compound obtained in the Example 304 and 2.0M-dimethylamine/tetrahydrofuran solution, instead of the compound obtained in the Example 282 and morpholine, respectively.

Example 307

1-Cyclohexyl-3-methyl-N-[2-(3,4,4-trimethyl-2,5-
dioxo-1-imidazolidinyl)ethyl]-1H-thieno[2,3-c]pyra-
zole-5-carboxamide To a solution of 150 mg (0.487 mmol) of the compound obtained in the Example 122 in 5 mL of tetrahydrofuran were added 90 mg (0.634 mmol) of 1,5,5-trimethylhydantoin, 166 mg (0.634 mmol) of triphenylphosphine and 289 µL (0.634 mmol) of 40%-diethyl azodicarboxylate/toluene solution, and the mixture was stirred for 30 minutes at room temperature. After the reaction, the reaction mixture was treated with water and extracted with dichloromethane. The organic layer was washed with water and saturated saline solution, then, dried over with anhydrous sodium sulfate. The solvent was removed under reduced pressure and the residue was purified by silica gel column chromatography (eluent:hexane/ethyl acetate=1/2) to give 146 mg (69%) of the title compound.

Example 308

1-Cyclohexyl-N-[2-(2,4-dioxo-1,3-thiazolidine-3-yl)
ethyl]-3-methyl-1H-thieno[2,3-c]pyrazole-5-car-
boxamide The title compound 106 mg (53%) was obtained in a manner similar to the Example 307 by use of 2,4-thiazolidinedione, instead of 1,5,5-trimethylhydantoin.

Example 309

1-Cyclohexyl-N-[1-(hydroxymethyl)cyclopropyl]-3-
methyl-1H-thieno[2,3-c]pyrazole-5-carboxamide The title compound 766 mg (93%) was obtained in a manner similar to the Example 7 by use of (1-aminocyclopropyl)methanol, instead of benzylamine.

Example 310

1-Cyclohexyl-3-methyl-N-{1-[(3-methyl-2,5-dioxo-
1-imidazolidinyl)-methyl]cyclopropyl}-1H-thieno[2,
3-c]pyrazole-5-carboxamide The title compound 111 mg (58%) was obtained in a manner similar to the Example 307 by use of the compound obtained in the Example 309 and 1-methylhydantoin, instead of the compound obtained in the Example 122 and 1,5,5-trimethylhydantoin, respectively.

Example 311

Methyl [(2-{[(1-cyclohexyl-3-methyl-1H-thieno[2,3-
c]pyrazol-5-yl)-carbonyl]amino}ethyl)amino]acetate To a solution of 170 mg (0.555 mmol) of the compound obtained in the Example 287 in 5 mL of acetonitrile were added 52.5 µL (0.555 mmol) of methyl bromoacetate and 153 mg (1.11 mmol) of potassium carbonate, and the mixture was refluxed for 3 hours. The reaction mixture was cooled and filtrated. The filtrate was treated with water and extracted with ethyl acetate. The organic layer was washed with water and saturated saline solution, then, dried over with anhydrous sodium sulfate. The solvent was removed under reduced pressure and the residue was purified by silica gel column chromatography (eluent:dichloromethane/methanol=20/1 to 10/1) to give 93 mg (44%) of the title compound.

Example 312

Methyl [(aminocarbonyl)(2-{[(1-cyclohexyl-3-me-
thyl-1H-thieno-[2,3-c]pyrazol-5-yl)carbonyl]
amino}ethyl)amino]acetate To a solution of 78.8 mg (0.208 mmol) of the compound obtained in the Example 311 in 1.5 mL of dioxane and 1.5 mL of water were added 25.3 mg (0.312 mmol) of potassium cyanate and 36 µL of acetic acid, and the mixture was stirred for 1.5 hours at room temperature. The reaction mixture was treated with water and extracted with ethyl acetate. The organic layer was washed with water and saturated saline solution, then, dried over with anhydrous sodium sulfate. The solvent was removed under reduced pressure and the residue was purified by silica gel column chromatography (eluent: ethyl acetate/methanol=20/1 to 10/1) to give 73 mg (84%) of the title compound.

Example 313

1-Cyclohexyl-N-[2-(2,4-dioxo-1-imidazolidinyl)
ethyl]-3-methyl-1H-thieno[2,3-c]pyrazole-5-car-
boxamide To a solution of 68 mg (0.161 mmol) of the compound obtained in the Example 312 in 6 mL of methanol was added 13 mg (60% oily; 0.323 mmol) of sodiumhydride, and the mixture was stirred for 1.5 hour at room temperature. The solvent was removed and the residue was treated with water and extracted with ethyl acetate. The organic layer was washed with water and saturated saline solution, and then, dried over with anhydrous sodium sulfate. The solvent was removed under reduced pressure and the residue was recrystallized from ethanol to give 20 mg (32%) of the title compound.

Example 314

1-Cyclohexyl-N-[2-(4,4-dimethyl-2,5-dioxo-1-imi-
dazolidinyl)ethyl]-3-methyl-1H-thieno[2,3-c]pyra-
zole-5-carboxamide The title compound 195 mg (96%) was obtained in a manner similar to the Example 307 by use of 5,5-dimethylhydantoin, instead of 1,5,5-trimethylhydantoin.

Example 315

1-Cyclohexyl-3-methyl-N-[2-(5-methyl-1,1-dioxide-1,2,5-thiadiazolidin-2-yl)ethyl]-1H-thieno[2,3-c]pyrazole-5-carboxamide The title compound 227 mg (94%) was obtained in a manner similar to the Example 7 by use of the compound obtained in the Manufacturing Example 60, instead of benzylamine.

Example 316

1-Cyclohexyl-N-[2-(3-ethyl-2,4-dioxo-1-imidazolidinyl)ethyl]-3-methyl-1H-thieno[2,3-c]pyrazole-5-carboxamide The title compound 84 mg (65%) was obtained in a manner similar to the Example 307 by use of the compound obtained in the Example 313 and ethanol, instead of 1,5,5-trimethylhydantoin and the compound obtained in the Example 122, respectively.

Example 317

1-Cyclohexyl-3-methyl-N-[2-(3-methyl-2,4-dioxo-1-imidazolidinyl)-ethyl]-1H-thieno[2,3-c]pyrazole-5-carboxamide The title compound 82 mg (66%) was obtained in a manner similar to the Example 307 by use of the compound obtained in the Example 313 and methanol, instead of 1,5,5-trimethylhydantoin and the compound obtained in the Example 122, respectively.

Example 318

1-Cyclohexyl-N-[(1S)-2-hydroxy-1-methylethyl]-3-methyl-1H-thieno[2,3-c]pyrazole-5-carboxamide The title compound 170 mg (56%) was obtained in a manner similar to the Example 7 by use of (S)-(+)-2-amino-1-propanol, instead of benzylamine.

Example 319

1-Cyclohexyl-N-[(1S)-2-(2,5-dioxo-1-imidazolidinyl)-1-methylethyl]-3-methyl-1H-thieno[2,3-c]pyrazole-5-carboxamide The title compound 46 mg (24%) was obtained in a manner similar to the Example 307 by use of the compound obtained in the Example 318 and hydantoin, instead of the compound obtained in the Example 122 and 1,5,5-trimethylhydantoin, respectively.

Example 320

N-[(3R)-1-Benzylpyrrolidinyl]-1-cyclohexyl-3-methyl-1H-thieno[2,3-c]pyrazole-5-carboxamide The title compound 2.32 g (97%) was obtained in a manner similar to the Example 7 by use of (3R)-(−)-1-benzyl-3-aminopyrrolidine, instead of benzylamine.

Example 321

1-Cyclohexyl-3-methyl-N-[(3R)-pyrrolidinyl]-1H-thieno[2,3-c]-pyrazole-5-carboxamide To a solution of 2.28 g (5.40 mmol) of the compound obtained in the Example 320 in 15 mL of dichloromethane was added gradually 1.16 mL (10.8 mmol) of 1-chloroethyl formate at 0° C., and the mixture was stirred for 1 hour at the same temperature and for 2 hours at room temperature. The solvent was removed under reduced pressure and 25 mL of ethanol was added to the residue, then, the mixture was refluxed for 2.5 hours. After cooling, the solvent was removed under reduced pressure, and the residue was treated with 6M-HCl aqueous solution. Water layer was washed with ether, and neutralized by 4M-NaOH aqueous solution, and extracted with dichloromethane. The organic layer was washed with water and saturated saline solution, then, dried over with anhydrous sodium sulfate. The solvent was removed under reduced pressure and the residue was purified by alkaline silica gel column chromatography (eluent:dichloromethane/methanol=50/1 to 30/1) to give 1.06 g (59%) of the title compound.

Example 322

1-Cyclohexyl-N-{(3R)-1-[(dimethylamino)carbonyl]pyrrolidinyl}-3-methyl-1H-thieno[2,3-c]pyrazole-5-carboxamide To a solution of 150 mg (0.451 mmol) of the compound obtained in the Example 321 in 5 mL of dichloromethane were added 50 µL (0.541 mmol) of N,N-dimethylcarbamoyl chloride and 94 µL of (0.677 mmol) of triethylamine, and the mixture was stirred for 4 hours at room temperature. The reaction mixture was treated with saturated sodium bicarbonate aqueous solution and extracted with dichloromethane. The organic layer was washed with water and saturated saline solution, then, dried over with anhydrous sodium sulfate. The solvent was removed under reduced pressure and the residue was purified by alkaline silica gel column chromatography (eluent:dichloromethane/methanol=30/1 to 10/1) to give 177 mg (97%) of the title compound.

Example 323

1-Cyclohexyl-N-{(3R)-1-[(dimethylamino)carbonyl]pyrrolidinyl}-3-methyl-1H-thieno[2,3-c]pyrazole-5-carboxamide HCl salt 0.11 mL (0.44 mmol) of 4M-HCl/ethyl acetate was added to a solution of 150 mg (0.372 mmol) of the title compound in 1 mL of ethyl acetate, and the mixture was treated with ether, then, stirred for 2 hours. The precipitates were collected to give 152 mg (93%) of the title compound.

Example 324

1-Cyclohexyl-N-[(1R)-2-hydroxy-1-methylethyl]-3-methyl-1H-thieno[2,3-c]pyrazole-5-carboxamide The title compound 357 mg (98%) was obtained in a manner similar to the Example 7 by use of (R)-(−)-2-amino-1-propanol, instead of benzylamine.

Example 325

1-Cyclohexyl-N-[(1R)-2-(2,5-dioxo-1-imidazolidinyl)-1-methylethyl]-3-methyl-1H-thieno[2,3-c]pyrazole-5-carboxamide The title compound 67 mg (18%) was obtained in a manner similar to the Example 307 by use of the compound obtained in the Example 324 and hydantoin, instead of the compound obtained in the Example 122 and 1,5,5-trimethylhydantoin, respectively.

Example 326

1-Cyclohexyl-N-[(2S)-2-hydroxypropyl]-3-methyl-1H-thieno[2,3-c]-pyrazole-5-carboxamide The title compound 343 mg (94%) was obtained in a manner similar to the Example 7 by use of (S)-(−)-1-amino-2-propanol, instead of benzylamine.

Example 327

1-Cyclohexyl-N-[(2R)-2-(2,5-dioxo-1-imidazolidinyl)propyl]-3-methyl-1H-thieno[2,3-c]pyrazole-5-carboxamide The title compound 57 mg (15%) was obtained in a manner similar to the Example 307 by use of the compound obtained in the Example 326 and hydantoin, instead of the compound obtained in the Example 122 and 1,5,5-trimethylhydantoin, respectively.

Example 328

1-Cyclohexyl-N-[(2R)-2-hydroxypropyl]-3-methyl-1H-thieno[2,3-c]-pyrazole-5-carboxamide The title compound 338 mg (93%) was obtained in a manner similar to the Example 7 by use of (R)-(+)-1-amino-2-propanol, instead of benzylamine.

Example 329

1-Cyclohexyl-N-[(2S)-2-(2,5-dioxo-1-imidazolidinyl)propyl]-3-methyl-1H-thieno[2,3-c]pyrazole-5-carboxamide The title compound 42 mg (11%) was obtained in a manner similar to the Example 307 by use of the compound obtained in the Example 328 and hydantoin, instead of the compound obtained in the Example 122 and 1,5,5-trimethylhydantoin, respectively.

Example 330

1-Cyclohexyl-N-[(1R)-1-(hydroxymethyl)propyl]-3-methyl-1H-thieno[2,3-c]pyrazole-5-carboxamide The title compound 355 mg (94%) was obtained in a manner similar to the Example 7 by use of (R)-(−)-2-mino-1-butanol, instead of benzylamine.

Example 331

1-Cyclohexyl-N-{(1R)-1-[(2,5-dioxo-1-imidazolidinyl)methyl]propyl}-3-methyl-1H-thieno[2,3-c]pyrazole-5-carboxamide The title compound 66 mg (18%) was obtained in a manner similar to the Example 307 by use of the compound obtained in the Example 330 and hydantoin, instead of the compound obtained in the Example 122 and 1,5,5-trimethylhydantoin, respectively.

Example 332

1-Cyclohexyl-N-[(1R)-1-(hydroxymethyl)-2-methylpropyl]-3-methyl-1H-thieno[2,3-c]pyrazole-5-carboxamide The title compound 392 mg (99%) was obtained in a manner similar to the Example 7 by use of D-valinol, instead of benzylamine.

Example 333

1-Cyclohexyl-N-{(1R)-1-[(2,5-dioxo-1-imidazolidinyl)methyl]-2-methylpropyl}-3-methyl-1H-thieno[2,3-c]pyrazole-5-carboxamide The title compound 97 mg (22%) was obtained in a manner similar to the Example 307 by use of the compound obtained in the Example 332 and hydantoin, instead of the compound obtained in the Example 122 and 1,5,5-trimethylhydantoin, respectively.

Example 334 tert-Butyl 2-{[(1-cyclohexyl-3-methyl-1H-thieno[2,3-c]pyrazol-5-yl)-carbonyl]amino}-2-methylpropyl-carbamate The title compound 493 mg (quantitative) was obtained in a manner similar to the Example 7 by use of tert-butyl 2-amino-2-methylpropyl-carbamate, instead of benzylamine.

Example 335

N-(2-Amino-1,1-dimethylethyl)-1-cyclohexyl-3-methyl-1H-thieno[2,3-c]pyrazole-5-carboxamide A mixture solution of 470 mg (1.08 mmol) of the compound obtained in the Example 334 in 2 mL of 4M-HCl/dioxane was stirred for 3 hours at room temperature. Then, the solvent was removed under reduced pressure and the residue was treated with ether and the resultant precipitates were collected. The collected precipitates were dissolved in water and the mixture was neutralized with saturated sodium bicarbonate aqueous solution, and extracted with dichloromethane. The organic layer was washed with water and saturated saline solution and dried over with anhydrous sodium sulfate. The solvent was removed under reduced pressure to give 344 mg (92%) of the title compound.

Example 336

1-Cyclohexyl-N-[2-(2,5-dioxo-1-imidazolidinyl)-1,
1-dimethylethyl]-3-methyl-1H-thieno[2,3-c]pyra-
zole-5-carboxamide To a solution of 304 mg (0.882 mmol) of the compound obtained in the Example 335 in 5 mL of ethanol was added gradually a solution of 114 mg (0.882 mmol) of ethyl isocyanatoacetate in 5 mL of ethanol, and the mixture was stirred for 3 hours at room temperature. The solvent was removed under reduced pressure and the residue was dissolved in 5 mL of ethanol, then, 5 mL of 6M-HCl aqueous solution was added to the mixture. The mixture was refluxed for 3 hours, and the solvent was removed under reduced pressure. The residue was neutralized with saturated sodium bicarbonate aqueous solution and the mixture was extracted with ethyl acetate. The organic layer was washed with water and saturated saline solution and then, dried over with anhydrous sodium sulfate. The solvent was removed under reduced pressure and the residue was purified by silica gel column chromatography (eluent:ethyl acetate) to give 336 mg (91%) of the title compound.

Example 337

1-Cyclohexyl-N-[2-(2,5-dioxo-1-imidazolidinyl)-1,
1-dimethylethyl]-3-methyl-1H-thieno[2,3-c]pyra-
zole-5-carboxamide HCl Salt The title compound 227 mg (70%) was obtained in a manner similar to the Example 323 by use of the compound obtained in the Example 336, instead of the compound obtained in the Example 322.

Example 338

N-(3-Amino-2,2-dimethylpropyl)-1-cyclohexyl-3-
methyl-1H-thieno[2,3-c]pyrazole-5-carboxamide The title compound 162 mg (41%) was obtained in a manner similar to the Example 7 by use of 2,2-dimethyl-1,3-propanediamine, instead of benzylamine.

Example 339

1-Cyclohexyl-N-[3-(2,5-dioxo-1-imidazolidinyl)-2,
2-dimethylpropyl]-3-methyl-1H-thieno[2,3-c]pyra-
zole-5-carboxamide The title compound 123 mg (72%) was obtained in a manner similar to the Example 336 by use of the compound obtained in the Example 338, instead of the compound obtained in the Example 335.

Example 340

(±)-1-Cyclohexyl-N-[trans-2-(hydroxymethyl)cyclo-
propyl]-3-methyl-1H-thieno[2,3-c]pyrazole-5-car-
boxamide The title compound 280 mg (42%) was obtained in a manner similar to the Example 7 by use of (±)-trans-(2-aminocyclopropyl)methanol, instead of benzylamine.

Example 341

1-Cyclohexyl-3-methyl-N-[4-(3-oxo-1-piperazinyl)
phenyl]-1H-thieno[2,3-c]pyrazole-5-carboxamide The title compound 215 mg (87%) was obtained in a manner similar to the Example 7 by use of the compound obtained in the Manufacturing Example 66, instead of benzylamine.

Example 342

3-Methyl-N-[4-(3-oxo-1-piperazinyl)phenyl]-1-tet-
rahydro-2H-pyran-4-yl-1H-thieno[2,3-c]pyrazole-5-
carboxamide The title compound 152 mg (77%) was obtained in a manner similar to the Example 7 by use of the compound obtained in the Manufacturing Example 66 and the compound obtained in the Example 195, instead of benzylamine and the compound obtained in the Example 6, respectively.

Example 343

Methyl 3-{[(1-cyclohexyl-3-methyl-1H-thieno[2,3-c]
pyrazol-5-yl)-carbonyl]amino}benzoate The title compound 1.78 g (95%) was obtained in a manner similar to the Example 7 by use of methyl m-aminobenzoate, instead of benzylamine.

Example 344

3-{[(1-Cyclohexyl-3-methyl-1H-thieno[2,3-c]pyra-
zol-5-yl)carbonyl]-amino}benzoic acid The title compound 1.67 g (quantitative) was obtained in a manner similar to the Example 41 by use of the compound obtained in the Example 343, instead of the compound obtained in the Example 40.

Example 345

1-Cyclohexyl-N-{3-[(dimethylamino)carbonyl]phe-
nyl}-3-methyl-1H-thieno[2,3-c]pyrazole-5-carboxa-
mide The title compound 145 mg (90%) was obtained in a manner similar to the Example 224 by use of the compound obtained in the Example 344 and 2M-dimethylamine/tetrahydrofuran solution, instead of the compound obtained in the Example 211 and hydroxyacetic acid, respectively.

Example 346

1-Cyclohexyl-3-methyl-N-[3-(4-morpholinylcarbo-
nyl)phenyl]-1H-thieno[2,3-c]pyrazole-5-carboxam-
ide The title compound 167 mg (94%) was obtained in a manner similar to the Example 224 by use of the compound obtained in the Example 344 and morpholine, instead of the compound obtained in the Example 211 and hydroxyacetic acid, respectively.

Example 347

Methyl trans-4-{[(3-methyl-1-tetrahydro-2H-pyran-4-yl-1H-thieno-[2,3-c]pyrazol-5-yl)carbonyl]amino}cyclohexanecarboxylate The title compound 605 mg (99%) was obtained in a manner similar to the Example 7 by use of methyl trans-4-aminocyclohexanecarboxylate HCl salt and the compound obtained in the Example 195, instead of benzylamine and the compound obtained in the Example 6, respectively.

Example 348 trans-4-{[(3-Methyl-1-tetrahydro-2H-pyran-4-yl-1H-thieno[2,3-c]-pyrazol-5-yl)carbonyl]amino}cyclohexanecarboxylic acid The title compound 540 mg (98%) was obtained in a manner similar to the Example 41 by use of the compound obtained in the Example 347, instead of the compound obtained in the Example 40.

Example 349

N-{trans-4-[(Dimethylamino)carbonyl]cyclohexyl}-3-methyl-1-tetrahydro-2H-pyran-4-yl-1H-thieno[2,3-c]pyrazole-5-carboxamide The title compound 117 mg (91%) was obtained in a manner similar to the Example 224 by use of the compound obtained in the Example 348 and 2M-dimethylamine/tetrahydrofuran solution, instead of the compound obtained in the Example 211 and hydroxyacetic acid, respectively.

Example 350

3-Methyl-N-[trans-4-(4-morpholinylcarbonyl)cyclohexyl]-1-tetrahydro-2H-pyran-4-yl-1H-thieno[2,3-c]pyrazole-5-carboxamide The title compound 132 mg (93%) was obtained in a manner similar to the Example 224 by use of the compound obtained in the Example 348 and morpholine, instead of the compound obtained in the Example 211 and hydroxyacetic acid, respectively.

Example 351

N-{trans-4-[(4-Hydroxy-1-piperidinyl)carbonyl]cyclohexyl}-3-methyl-1-tetrahydro-2H-pyran-4-yl-1H-thieno[2,3-c]pyrazole-5-carboxamide The title compound 137 mg (94%) was obtained in a manner similar to the Example 224 by use of the compound obtained in the Example 348 and 4-hydroxypiperidine, instead of the compound obtained in the Example 211 and hydroxyacetic acid, respectively.

Example 352

3-Methyl-N-{trans-4-[(4-methyl-1-piperazinyl)carbonyl]cyclohexyl}-1-tetrahydro-2H-pyran-4-yl-1H-thieno[2,3-c]pyrazole-5-carboxamide The title compound 97 mg (76%) was obtained in a manner similar to the Example 224 by use of the compound obtained in the Example 348 and 1-methylpiperazine, instead of the compound obtained in the Example 211 and hydroxyacetic acid, respectively.

Example 353

1-Cyclohexyl-3-methyl-N-[3-(4-morpholinyl)propyl]-1H-thieno[2,3-c]pyrazole-5-carboxamide The title compound 199 mg (90%) was obtained in a manner similar to the Example 7 by use of N-(3-aminopropyl)morpholine, instead of benzylamine.

Example 354

1-Cyclohexyl-3-methyl-N-[2-(4-morpholinyl)ethyl]-1H-thieno[2,3-c]pyrazole-5-carboxamide The title compound 174 mg (82%) was obtained in a manner similar to the Example 7 by use of N-(2-aminoethyl)morpholine, instead of benzylamine.

Example 355

1-Cyclohexyl-3-methyl-N-[2-(1-piperidinyl)ethyl]-1H-thieno[2,3-c]pyrazole-5-carboxamide The title compound 148 mg (70%) was obtained in a manner similar to the Example 7 by use of N-(2-aminoethyl)piperidine, instead of benzylamine.

Example 356

N-[trans-4-(Hydroxymethyl)cyclohexyl]-3-methyl-1-tetrahydro-2H-pyran-4-yl-1H-thieno[2,3-c]pyrazole-5-carboxamide The title compound 628 mg (96%) was obtained in a manner similar to the Example 206 by use of the compound obtained in the Example 347, instead of the compound obtained in the Example 204.

Example 357

(trans-4-{[(3-Methyl-1-tetrahydro-2H-pyran-4-yl-1H-thieno[2,3-c]-pyrazol-5-yl)carbonyl]amino}cyclohexyl)methyl p-toluenesulfonate To a suspension solution of 510 mg (1.35 mmol) of the compound obtained in the Example 356 in 20 mL of dichloromethane and 20 mL of chloroform were added 270 mg (1.42 mmol) of p-toluenesulfonyl chloride and 131 μL (1.62 mmol) of pyridine, and the mixture was stirred for over night at room temperature. Then, further 270 mg (1.42 mmol) of p-toluenesulfonyl chloride and 131 μL (1.62 mmol) of pyridine were added twice to the reaction mixture at 50° C., and the mixture was stirred for over night. Further, 270 mg (1.42 mmol) of p-toluenesulfonyl chloride, 131 μL (1.62 mmol) of pyridine and 226 μL (1.62 mmol) of triethylamine were added twice to the reaction mixture, and the mixture was stirred for over night. Then, the reaction mixture was washed with water and dried over with anhydrous sodium sulfate. The solvent was removed under reduced pressure and the residue was purified by silica gel column chromatography (eluent:hexane/ethyl acetate=1/1 to ethyl acetate only) to give 402 mg (56%) of the title compound.

Example 358

3-Methyl-N-[trans-4-(4-morpholinylmethyl)cyclohexyl]-1-tetrahydro-2H-pyran-4-yl-1H-thieno[2,3-c]pyrazole-5-carboxamide To a solution of 120 mg (0.226 mmol) of the compound obtained in the Example 357 in 5 mL of N,N-dimethylformamide was added 79 μL (0.903 mmol) of morpholine, and the mixture was stirred for 12 hours at 100° C. Then, the reaction mixture was cooled to room temperature, and treated with 20 mL of ethylacetate. The organic layer was washed with water and saturated saline solution, and dried over with anhydrous sodium sulfate. The solvent was removed under reduced pressure and the residue was purified by silica gel column chromatography (eluent:dichloromethane/methanol=40/1) to give 52 mg (52%) of the title compound.

Example 359

N-{trans-4-[(Dimethylamino)methyl]cyclohexyl}-3-methyl-1-tetrahydro-2H-pyran-4-yl-1H-thieno[2,3-c]pyrazole-5-carboxamide The title compound 92 mg (quantitative) was obtained in a manner similar to the Example 358 by use of 2M-dimethylamine/tetrahydrofuran solution, instead of morpholine.

Example 360

N-{trans-4-[(4-Acetyl-1-piperazinyl)methyl]cyclohexyl}-3-methyl-1-tetrahydro-2H-pyran-4-yl-1H-thieno[2,3-c]pyrazole-5-carboxamide The title compound 82 mg (87%) was obtained in a manner similar to the Example 358 by use of 1-acetylpiperazine, instead of morpholine.

Example 361

N-{3-[(Dimethylamino)sulfonyl]phenyl}-3-methyl-1-tetrahydro-2H-pyran-4-yl-1H-thieno[2,3-c]pyrazole-5-carboxamide The title compound 133 mg (66%) was obtained in a manner similar to the Example 7 by use of the compound obtained in the Manufacturing Example 67 and the compound obtained in the Example 195, instead of benzylamine and the compound obtained in the Example 6, respectively.

Example 362

3-Methyl-N-[3-(methylsulfonyl)phenyl]-1-tetrahydro-2H-pyran-4-yl-1H-thieno[2,3-c]pyrazole-5-carboxamide The title compound 74 mg (39%) was obtained in a manner similar to the Example 7 by use of 3-methylsulfonylaniline HCl salt and the compound obtained in the Example 195, instead of benzylamine and the compound obtained in the Example 6, respectively.

Example 363

N-{3-[(2-{[tert-Butyl(dimethyl)silyl]oxy}ethyl)sulfonyl]phenyl}-3-methyl-1-tetrahydro-2H-pyran-4-yl-1H-thieno[2,3-c]pyrazole-5-carboxamide The title compound 135 mg (53%) was obtained in a manner similar to the Example 7 by use of the compound obtained in the Manufacturing Example 68 and the compound obtained in the Example 195, instead of benzylamine and the compound obtained in the Example 6, respectively.

Example 364

N-[3-[(2-Hydroxyethyl)sulfonyl]phenyl]-3-methyl-1-tetrahydro-2H-pyran-4-yl-1H-thieno[2,3-c]pyrazole-5-carboxamide The title compound 61 mg (60%) was obtained in a manner similar to the Example 266 by use of the compound obtained in the Example 363, instead of the compound obtained in the Example 265.

Example 365

1-Cyclohexyl-N-[3-fluoro-4-(4-hydroxy-1-piperidinyl)phenyl]-3-methyl-1H-thieno[2,3-c]pyrazole-5-carboxamide dimethanesulfonate A mixture solution of 456.5 mg (1.00 mmol) of the compound obtained in the Example 159 and 142.8 μL (2.20 mmol) of methanesulfonic acid in 4 mL of ethanol was condensed under reduced pressure. The residue was treated with 5 mL of ethanol and the residue was solved in the solution by heating and refluxing. Then, 2 mL of isopropyl ether was added and the mixture was cooled gradually to room temperature. The resulting precipitates were collected by filtration to give 383 mg (59%) of the title compound.

Example 366

1-Cyclohexyl-N-[3-fluoro-4-(4-hydroxy-1-piperidinyl)phenyl]-3-methyl-1H-thieno[2,3-c]pyrazole-5-carboxamide p-toluenesulfonate To a solution of 228.3 mg (0.50 mmol) of the compound obtained in the Example 159 in 2 mL of ethanol was added 104.6 mg (0.55 mmol) of p-toluenesulfonic acid monohydrate at 50° C., and the mixture was condensed under reduced pressure. Then, 1.5 mL of isopropanol was added to the residue and the residue was solved in the mixture by heating at 70° C., and the mixture was cooled gradually to room temperature. The resulting precipitates were collected by filtration to give 281 mg (89%) of the title compound.

Example 367

1-Cyclohexyl-N-[4-(4-hydroxy-1-piperidinyl)phenyl]-3-methyl-1H-thieno[2,3-c]pyrazole-5-carboxamide methanesulfonate To a solution of 438.6 mg (1.00 mmol) of the compound obtained in the Example 114 in 4 mL of ethanol was added 71.4 µL (1.10 mmol) of methanesulfonic acid, and further 0.8 mL of ethyl acetate was added to the mixture. After refluxing the mixture, then, the mixture was cooled gradually to room temperature. The resulting precipitates were collected by filtration to give 424 mg (79%) of the title compound.

Example 368

1-Cyclohexyl-N-[4-(4-hydroxy-1-piperidinyl)phenyl]-3-methyl-1H-thieno[2,3-c]pyrazole-5-carboxamide p-toluenesulfonate To a suspension of 219.3 mg (0.50 mmol) of the compound obtained in the Example 114 in 3 mL of ethanol was added 104.6 mg (0.55 mmol) of p-toluenesulfonic acid monohydrate, and the mixture was refluxed. Then, the separated precipitates were dissolved by adding 0.6 mL of water and the mixture was cooled gradually to 0° C. The resulting precipitates were collected by filtration to give 244 mg (80%) of the title compound.

Example 369

3-Methyl-N-[trans-4-(4-morpholinyl)cyclohexyl]-1-tetrahydro-2H-pyran-4-yl-1H-thieno[2,3-c]pyrazole-5-carboxamide To a suspension of 120 mg (0.45 mmol) of the compound obtained in the Example 195 in 2 mL of 1,2-dichloroethane was added 66 µL (0.90 mmol) of thionyl chloride and the mixture was refluxed for 2 hours. After cooling the reaction mixture and the solvent removed under reduced pressure to give acid chloride intermediate compound.
314 µL (2.25 mmol) of triethylamine and 139 mg (0.54 mmol) of the compound obtained in the Manufacturing Example 64 were added to the solution of the acid chloride intermediate compound in 5 mL of anhydrous dichloromethane, and the mixture was stirred for 3 hours at room temperature. The reaction mixture was treated with saturated sodium bicarbonate aqueous solution and extracted with dichloromethane. The organic layer was washed with water and saturated saline solution, then, dried over with anhydrous sodium sulfate. The solvent was removed under reduced pressure and the residue was purified by silica gel column chromatography (eluent:dichloromethane/methanol=20/1 to 10/1) to give 172 mg (88%) of the title compound.

Example 370

1-Cyclohexyl-N-[6-(4-hydroxy-1-piperidinyl)-3-pyridinyl]-3-methyl-1H-thieno[2,3-c]pyrazole-5-carboxamide The title compound 216 mg (quantitative) was obtained in a manner similar to the Example 7 by use of the compound obtained in the Manufacturing Example 74, instead of benzylamine.

Example 371

1-Cyclohexyl-N-[2,3-difluoro-4-(4-hydroxy-1-piperidinyl)phenyl]-3-methyl-1H-thieno[2,3-c]pyrazole-5-carboxamide The title compound 177 mg (82%) was obtained in a manner similar to the Example 7 by use of the compound obtained in the Manufacturing Example 76, instead of benzylamine.

Example 372

1-Cyclohexyl-N-[4-(4-hydroxy-1-piperidinyl)-3-methylphenyl]-3-methyl-1H-thieno[2,3-c]pyrazole-5-carboxamide The title compound 189 mg (92%) was obtained in a manner similar to the Example 7 by use of the compound obtained in the Manufacturing Example 78, instead of benzylamine.

Example 373

N-[3-Cyano-4-(4-hydroxy-1-piperidinyl)phenyl]-1-cyclohexyl-3-methyl-1H-thieno[2,3-c]pyrazole-5-carboxamide The title compound 209 mg (99%) was obtained in a manner similar to the Example 7 by use of the compound obtained in the Manufacturing Example 80, instead of benzylamine.

Example 374

Methyl 5-{[(1-cyclohexyl-3-methyl-1H-thieno[2,3-c]pyrazol-5-yl)-carbonyl]amino}-2-(4-hydroxy-1-piperidinyl)benzoate The title compound 224 mg (99%) was obtained in a manner similar to the Example 7 by use of the compound obtained in the Manufacturing Example 82, instead of benzylamine.

Example 375

5-{[(1-Cyclohexyl-3-methyl-1H-thieno[2,3-c]pyrazol-5-yl)carbonyl]-amino}-2-(4-hydroxy-1-piperidinyl)benzoic acid The title compound 167 mg (81%) was obtained in a manner similar to the Example 41 by use of the compound obtained in the Example 374, instead of the compound obtained in the Example 40.

Example 376

N-[6-(4-Hydroxy-1-piperidinyl)-3-pyridinyl]-3-methyl-1-tetrahydro-2H-pyran-4-yl-1H-thieno[2,3-c]pyrazole-5-carboxamide The title compound 202 mg (quantitative) was obtained in a manner similar to the Example 369 by use of the compound obtained in the Manufacturing Example 74, instead of the compound obtained in the Manufacturing Example 64.

Example 377

3-Methyl-1-tetrahydro-2H-pyran-4-yl-N-(1-tetrahydro-2H-pyran-4-yl-4-piperidinyl)-1H-thieno[2,3-c]pyrazole-5-carboxamide The title compound 187 mg (96%) was obtained in a manner similar to the Example 369 by use of the compound

Example 378

1-Cyclohexyl-N-{6-[(4-hydroxy-1-piperidinyl)carbonyl]-3-pyridinyl}-3-methyl-1H-thieno[2,3-c]pyrazole-5-carboxamide To a suspension of 100 mg (0.26 mmol) of the compound obtained in the Example 103 in 5 mL of anhydrous dichloromethane were added 39.4 mg (0.39 mmol) of 4-hydroxypiperidine, 53 mg (0.39 mmol) of 1-hydroxy-benzotriazole, 74.8 mg (0.39 mmol) of 1-ethyl-3-(3-dimethylamino-propyl)carbodiimide HCl salt and 72.5 µL (0.52 mmol) of triethylamine, and the mixture was stirred for 17 hours at room temperature. The reaction mixture was treated with saturated sodium bicarbonate aqueous solution, and extracted with dichloromethane. The organic layer was washed with water and saturated saline solution, then, dried over with anhydrous sodium sulfate. The solvent was removed under reduced pressure and the residue was purified by silica gel column chromatography (eluent:dichloromethane/methanol=10/1) to give 102 mg (84%) of the title compound.

Example 379

1-Cyclohexyl-N-(6-{[(2-hydroxyethyl)amino]carbonyl}-3-pyridinyl)-3-methyl-1H-thieno[2,3-c]pyrazole-5-carboxamide The title compound 76 mg (68%) was obtained in a manner similar to the Example 378 by use of 2-aminoethanol, instead of 4-hydroxypiperidine.

Example 380

1-Cyclohexyl-3-methyl-N-{6-[(4-methyl-1-piperazinyl)carbonyl]-3-pyridinyl}-1H-thieno[2,3-c]pyrazole-5-carboxamide The title compound 87 mg (72%) was obtained in a manner similar to the Example 378 by use of N-methylpiperazine, instead of 4-hydroxypiperidine.

Example 381

1-Cyclohexyl-N-[6-({[2-(dimethylamino)ethyl]amino}carbonyl-3-pyridinyl)-3-methyl-1H-thieno[2,3-c]pyrazole-5-carboxamide The title compound 71 mg (60%) was obtained in a manner similar to the Example 378 by use of N,N-dimethylethylenediamine, instead of 4-hydroxypiperidine.

Example 382

1-Cyclohexyl-N-(6-{[(trans-4-hydroxycyclohexyl)amino]carbonyl}-3-pyridinyl)-3-methyl-1H-thieno[2,3-c]pyrazole-5-carboxamide The title compound 50 mg (39%) was obtained in a manner similar to the Example 378 by use of trans-4-aminocyclohexanaol, instead of 4-hydroxypiperidine.

Example 383

1-Cyclohexyl-3-methyl-N-{6-[(4-methyl-1,4-diazepam-1-yl)carbonyl]-3-pyridinyl}-1H-thieno[2,3-c]pyrazole-5-carboxamide The title compound 105 mg (84%) was obtained in a manner similar to the Example 378 by use of N-methylhomopiperazine, instead of 4-hydroxypiperidine.

Example 384 tert-Butyl 4-{[(3-methyl-1-tetrahydro-2H-pyran-4-yl-1H-thieno[2,3-c]-pyrazol-5-yl)carbonyl]amino}-1-piperidinecarboxylate The title compound 1.86 g (92%) was obtained in a manner similar to the Example 369 by use of 4-amino-1-Boc-piperidine, instead of the compound obtained in the Manufacturing Example 64.

Example 385

3-Methyl-N-(4-piperidinyl)-1-tetrahydro-2H-pyran-4-yl-1H-thieno-[2,3-c]pyrazole-5-carboxamide A mixture solution of 1.81 g (4.03 mmol) of the compound obtained in the Example 384 in 10 mL of 4M-HCl/dioxane was stirred for 30 minutes at room temperature and for 2 hours at 60° C. After cooling the reaction mixture, the solvent was removed under reduced pressure and the residue was treated with saturated sodium bicarbonate aqueous solution, then, the mixture was extracted with chloroform. The organic layer was washed with water and saturated saline solution and then, dried over with anhydrous sodium sulfate. The solvent was removed under reduced pressure to give 1.22 g (87%) of the title compound.

Example 386

N-{1-[(Dimethylamino)carbonyl]-4-piperidinyl}-3-methyl-1-tetrahydro-2H-pyran-4-yl-1H-thieno[2,3-c]pyrazole-5-carboxamide The title compound 132 mg (91%) was obtained in a manner similar to the Example 322 by use of the compound obtained in the Example 385, instead of the compound obtained in the Example 321.

Example 387 tert-Butyl 4-{4-{[(3-methyl-1-tetrahydro-2H-pyran-4-yl-1H-thieno-[2,3-c]pyrazol-5-yl)carbonyl]amino}piperidin-1-yl}-1-piperidinecarboxylate To a suspension of 220 mg (0.63 mmol) of the compound obtained in the Example 385 in 5 mL of 1,2-dichloroethane were added 15 µL of acetic acid and 151 mg (0.757 mmol) of 1-Boc-4-piperidone, and the mixture was stirred for 30 minutes at room temperature. Then, 200 mg (0.95 mmol) of sodium triacetoxyborohydride was added to the reaction mixture, and the mixture was stirred for 6 hours at room temperature. The reaction mixture was treated with saturated sodium bicarbonate aqueous solution and extracted with dichloromethane. The organic layer was washed with water and saturated saline solution, then, dried over with anhydrous sodium sulfate. The solvent was removed under reduced pressure and the residue was purified by silica gel column chromatography (eluent:dichloromethane/methanol=10/1) to give 230 mg (69%) of the title compound.

Example 388

3-Methyl-N-(piperidin-4-yl-4-piperidinyl)-1-tetrahydro-2H-pyran-4-yl-1H-thieno[2,3-c]pyrazole-5-carboxamide The title compound 165 mg (98%) was obtained in a manner similar to the Example 385 by use of the compound obtained in the Example 387, instead of the compound obtained in the Example 384.

Example 389

3-Methyl-N-(1-acetylpiperidin-4-yl-4-piperidinyl)-1-tetrahydro-2H-pyran-4-yl-1H-thieno[2,3-c]pyrazole-5-carboxamide The title compound 51 mg (62%) was obtained in a manner similar to the Manufacturing Example 3 by use of the compound obtained in the Example 388, instead of the compound obtained in the Manufacturing Example 2.

Example 390

3-Methyl-N-(1-methanesulfonylpiperidin-4-yl-4-piperidinyl)-1-tetrahydro-2H-pyran-4-yl-1H-thieno[2,3-c]pyrazole-5-carboxamide The title compound 68 mg (77%) was obtained in a manner similar to the Manufacturing Example 3 by use of the compound obtained in the Example 388 and methanesulfonyl chloride, instead of the compound obtained in the Manufacturing Example 2 and acetyl chloride, respectively.

Example 391 tert-Butyl 4-(trans-4-{[(3-methyl-1-tetrahydro-2H-pyran-4-yl-1H-thieno[2,3-c]pyrazol-5-yl)carbonyl]amino}cyclohexyl)-1-piperazine-carboxylate The title compound 456 mg (46%) was obtained in a manner similar to the Example 369 by use of the compound obtained in the Manufacturing Example 86, instead of the compound obtained in the Manufacturing Example 64.

Example 392 tert-Butyl 4-(cis-4-{[(3-methyl-1-tetrahydro-2H-pyran-4-yl-1H-thieno[2,3-c]pyrazol-5-yl)carbonyl]amino}cyclohexyl)-1-piperazine-carboxylate 523 mg (52%) of the title compound was obtained as by-product in the Example 391.

Example 393

3-Methyl-N-[trans-4-(1-piperazinyl)cyclohexyl]-1-tetrahydro-2H-pyran-4-yl-1H-thieno[2,3-c]pyrazole-5-carboxamide di-HCl Salt A mixture of 419 mg (0.817 mmol) of the compound obtained in the Example 391 in 3 mL of 4M-HCl/dioxane and 1 mL of methanol was stirred for 5 hours at room temperature. The solvent was removed under reduced pressure and the residue was treated with ethanol. The resulting precipitates were collected by filtration to give 343 mg (83%) of the title compound.

Example 394

3-Methyl-N-[cis-4-(1-piperazinyl)cyclohexyl]-1-tetrahydro-2H-pyran-4-yl-1H-thieno[2,3-c]pyrazole-5-carboxamide di-HCl Salt The title compound 234 mg (51%) was obtained in a manner similar to the Example 393 by use of the compound obtained in the Example 392, instead of the compound obtained in the Example 391.

Example 395

N-[trans-4-(4-Acetyl-1-piperazinyl)cyclohexyl]-3-methyl-1-tetrahydro-2H-pyran-4-yl-1H-thieno[2,3-c]pyrazole-5-carboxamide The title compound 100 mg (70%) was obtained in a manner similar to the Manufacturing Example 3 by use of the compound obtained in the Example 388 and acetic anhydride, instead of the compound obtained in the Manufacturing Example 2 and acetyl chloride, respectively.

Example 396

3-Methyl-N-{trans-4-[4-(methylsulfonyl)-1-piperazinyl]cyclohexyl}-1-tetrahydro-2H-pyran-4-yl-1H-thieno[2,3-c]pyrazole-5-carboxamide The title compound 109 mg (71%) was obtained in a manner similar to the Manufacturing Example 3 by use of the compound obtained in the Example 393 and methanesulfonyl chloride, instead of the compound obtained in the Manufacturing Example 2 and acetyl chloride, respectively.

Example 397

N-[cis-4-(4-Acetyl-1-piperazinyl)cyclohexyl]-3-methyl-1-tetrahydro-2H-pyran-4-yl-1H-thieno[2,3-c]pyrazole-5-carboxamide The title compound 113 mg (66%) was obtained in a manner similar to the Manufacturing Example 3 by use of the compound obtained in the Example 394 and acetic anhydride, instead of the compound obtained in the Manufacturing Example 2 and acetyl chloride, respectively.

Example 398

3-Methyl-N-[1-(4-morpholinylcarbonyl)-4-piperidinyl]-1-tetrahydro-2H-pyran-4-yl-1H-thieno[2,3-c]pyrazole-5-carboxamide The title compound 109 mg (69%) was obtained in a manner similar to the Manufacturing Example 3 by use of the compound obtained in the Example 385 and 4-morpholinyl chloride, instead of the compound obtained in the Manufacturing Example 2 and acetyl chloride, respectively.

Example 399

3-Methyl-N-{1-[(4-methyl-1-piperazinyl)carbonyl]-4-piperidinyl}-1-tetrahydro-2H-pyran-4-yl-1H-thieno[2,3-c]pyrazole-5-carboxamide The title compound 92 mg (56%) was obtained in a manner similar to the Manufacturing Example 3 by use of the compound obtained in the Example 385 and 4-methyl-1-piperazinecarbonyl chloride HCl salt, instead of the compound obtained in the Manufacturing Example 2 and acetyl chloride, respectively.

Example 400

N-(trans-4-Hydroxycyclohexyl)-3-methyl-1-tetrahydro-2H-pyran-4-yl-1H-thieno[2,3-c]pyrazole-5-carboxamide The title compound 843 mg (52%) was obtained in a manner similar to the Example 396 by use of trans-4-aminocyclohexanol, instead of the compound obtained in the Manufacturing Example 64.

Example 401

3-Methyl-N-(4-oxocyclohexyl)-1-tetrahydro-2H-pyran-4-yl-1H-thieno[2,3-c]pyrazole-5-carboxamide To a solution of 828 mg (2.28 mmol) of the compound obtained in the Example 400 in 30 mL of dichloromethane were added 983 mg (4.56 mmol) of pyridinium chlorochromate and 2 g of Molecular sieves 4A, and the mixture was stirred for 4 hours at room temperature. The reaction mixture was filtrated by Celite®, and the filtrate was removed under reduced pressure. The residue was purified by silica gel column chromatography (eluent:dichloromethane/ethyl acetate) and further purified by silica gel column chromatography (eluent:ethyl acetate) to give 668 mg (81%) of the title compound.

Example 402

N-[trans-4-(cis-2,6-Dimethylmorpholinyl)cyclohexyl]-3-methyl-1-tetrahydro-2H-pyran-4-yl-1H-thieno[2,3-c]pyrazole-5-carboxamide To a solution of 150 mg (0.415 mmol) of the compound obtained in the Example 401 in 3 mL of 1,2-dichloroethane were added 103 µL (0.83 mmol) of cis-2,6-dimethylmorpholine and 15 µL of acetic acid, and the mixture was stirred for 30 minutes at room temperature. Then, 132 mg (0.623 mmol) of sodium triacetoxyborohydride was added to the reaction mixture and the mixture was stirred for 4 hours at room temperature. The reaction mixture was treated with saturated sodium bicarbonate aqueous solution and extracted with dichloromethane. The organic layer was washed with water and saturated saline solution, then, dried over with anhydrous sodium sulfate. The organic layer was removed under reduced pressure and the residue was purified by alkaline silica gel column chromatography (eluent:ethyl acetate/hexane=1/1) to give 132 mg (69%) of the title compound.

Example 403

N-[cis-4-(cis-2,6-Dimethylmorpholinyl)cyclohexyl]-3-methyl-1-tetrahydro-2H-pyran-4-yl-1H-thieno[2,3-c]pyrazole-5-carboxamide The title compound 46 mg (24%) was obtained in the Example 402 as by-product.

Example 404

1-Cyclohexyl-N-[6-(hydroxymethyl)-3-pyridinyl]-3-methyl-1H-thieno[2,3-c]pyrazole-5-carboxamide The title compound 215 mg (58%) was obtained in a manner similar to the Example 7 by use of the compound obtained in the Manufacturing Example 87, instead of benzylamine.

Example 405

Methyl 5-{[(3-methyl-1-tetrahydro-2H-pyran-4-yl-1H-thieno[2,3-c]-pyrazol-5-yl)carbonyl]amino}-2-pyridinecarboxylate To a suspension of 700 mg (2.63 mmol) of the compound obtained in the Example 195 in 6 mL of 1,2-dichloroethane was added 384 µL (5.26 mmol) of thionyl chloride, and the mixture was refluxed for 2 hours. After reaction mixture was cooled, the solvent was removed under reduced pressure to give acid chloride intermediate compound.

Then, to a solution of the acid chloride intermediate compound obtained above in 8 mL of pyridine was added 400 mg (2.63 mmol) of methyl 5-amino-2-pyridinecarboxylate, and the mixture was stirred for 2 hours at room temperature. The reaction mixture was treated with saturated sodium bicarbonate aqueous solution and extracted with dichloromethane. The organic layer was washed with water and saturated saline solution, then, dried over with anhydrous sodium sulfate. The solvent was removed under reduced pressure and the residue was purified by silica gel column chromatography (eluent: ethyl acetate) to give 956 mg (91%) of the title compound.

Example 406

5-{[(3-Methyl-1-tetrahydro-2H-pyran-4-yl-1H-thieno[2,3-c]pyrazol-5-yl)carbonyl]amino}-2-pyridinecarboxylic acid To a solution of 923 mg (2.30 mmol) of the compound obtained in the Example 405 in 5 mL of methanol was added 5 mL of 1M-NaOH aqueous solution, and the mixture was stirred for 1.5 hours at 60° C. After cooling the reaction mixture, the solvent was removed under reduced pressure and the residue was neutralized by adding 2.5 mL of 2M-HCl aqueous solution. The resulting precipitates were collected to give 870 mg (98%) of the title compound.

Example 407

N-(6-{[(trans-4-Hydroxycyclohexyl)amino]carbonyl}-3-pyridinyl)-3-methyl-1-tetrahydro-2H-pyran-4-yl-1H-thieno[2,3-c]pyrazole-5-carboxamide The title compound 118 mg (94%) was obtained in a manner similar to the Example 378 by use of the compound obtained in the Example 406 and trans-4-aminocyclohexanol, instead of the compound obtained in the Example 103 and 4-hydroxypiperidine, respectively.

Example 408

N-[6-({[2-(Dimethylamino)ethyl]amino}carbonyl)-3-pyridinyl]-3-methyl-1-tetrahydro-2H-pyran-4-yl-1H-thieno[2,3-c]pyrazole-5-carboxamide The title compound 108 mg (91%) was obtained in a manner similar to the Example 378 by use of the compound obtained in the Example 406 and N,N-dimethylethylenediamine, instead of the compound obtained in the Example 103 and 4-hydroxypiperidine, respectively.

Example 409

3-Methyl-N-(6-{[(1-methyl-4-piperidinyl)amino]carbonyl}-3-pyridinyl)-1-tetrahydro-2H-pyran-4-yl-1H-thieno[2,3-c]pyrazole-5-carboxamide The title compound 35.6 mg (36%) was obtained in a manner similar to the Example 378 by use of the compound obtained in the Example 406 and 4-amino-1-methylpiperidine, instead of the compound obtained in the Example 103 and 4-hydroxypiperidine, respectively.

Example 410

N-(6-{[(1-Acetyl-4-piperidinyl)amino]carbonyl}-3-pyridinyl)-3-methyl-1-tetrahydro-2H-pyran-4-yl-1H-thieno[2,3-c]pyrazole-5-carboxamide The title compound 109 mg (82%) was obtained in a manner similar to the Example 378 by use of the compound obtained in the Example 406 and 4-amino-1-acetylpiperidine, instead of the compound obtained in the Example 103 and 4-hydroxypiperidine, respectively.

Example 411

1-Cyclohexyl-3-methyl-N-[6-(4-morpholinylmethyl)-3-pyridinyl]-1H-thieno[2,3-c]pyrazole-5-carboxamide To a suspension of 120 mg (0.324 mmol) of the compound obtained in the Example 404 in 3 mL of ethyl acetate were added 90 μL (0.648 mmol) of triethylamine and 38 μL (0.486 mmol) of methanesulfonyl chloride, and the mixture was stirred for 30 minutes at room temperature. The reaction mixture was treated with ethyl acetate, and the organic layer was washed with saturated sodium bicarbonate aqueous solution, water and saturated saline solution, respectively, then, dried over with anhydrous sodium sulfate. Sodium sulfate was removed off by filtration, and the filtrate was treated with 1 mL of 4M-HCl/dioxane, and the solvent was removed to give (5-{[(1-cyclohexyl-3-methyl-1H-thieno[2,3-c]pyrazole-5-yl)carbonyl]amino}-2-pyridinyl)methyl methanesulfonate HCl salt as the intermediate compound.

To a suspension of the intermediate compound obtained above in 3 mL of acetonitrile were added 162 mg (1.17 mmol) of potassium carbonate, 28.8 μL (0.33 mmol) of morpholine and 5.8 mg (0.035 mmol) of potassium iodide, and then, the mixture was stirred for 2 hours at 70° C. and for 15 hours at room temperature. Then, the reaction mixture was treated with water and extracted with ethyl acetate. The organic layer was washed with water and saturated saline solution, and dried over with anhydrous sodium sulfate. The solvent was removed under reduced pressure and the residue was purified by silica gel column chromatography (eluent:dichloromethane/methanol=10/1) to give 114 mg (80%) of the title compound.

Example 412

1-Cyclohexyl-3-methyl-N-[6-(4-morpholinylmethyl)-3-pyridinyl]-1H-thieno[2,3-c]pyrazole-5-carboxamide methanesulfonate To a solution of 100 mg (0.227 mmol) of the compound obtained in the Example 411 in 2 mL of ethanol was added 14.8 μL of methanesulfonic acid and the solvent was removed. The residue was recrystallized from isopropanol to give 77 mg (63%) of the title compound.

Example 413

1-Cyclohexyl-N-{6-[(4-hydroxy-1-piperidinyl)methyl]-3-pyridinyl}-3-methyl-1H-thieno[2,3-c]pyrazole-5-carboxamide The title compound 104 mg (71%) was obtained in a manner similar to the Example 411 by use of 4-hydroxypiperidine, instead of morpholine.

Example 414

N-{6-[(4-Acetyl-1-piperazinyl)methyl]-3-pyridinyl}-1-cyclohexyl-3-methyl-1H-thieno[2,3-c]pyrazole-5-carboxamide The title compound 102 mg (66%) was obtained in a manner similar to the Example 411 by use of 1-acetylpiperazine, instead of morpholine.

Example 415

3-Methyl-N-[trans-4-(4-methyl-2-oxo-1-piperazinyl)cyclohexyl]-1-tetrahydro-2H-pyran-4-yl-1H-thieno[2,3-c]pyrazole-5-carboxamide The title compound 124 mg (72%) was obtained in a manner similar to the Example 369 by use of the compound obtained in the Manufacturing Example 91, instead of the compound obtained in the Manufacturing Example 64.

Example 416

1-Cyclohexyl-3-methyl-N-[trans-4-(4-methyl-2-oxo-1-piperazinyl)-cyclohexyl]-1H-thieno[2,3-c]pyrazole-5-carboxamide The title compound 130 mg (75%) was obtained in a manner similar to the Example 7 by use of the compound obtained in the Manufacturing Example 91, instead of benzylamine.

Example 417

3-Methyl-N-[trans-4-(3-oxo-1-piperazinyl)cyclohexyl]-1-tetrahydro-2H-pyran-4-yl-1H-thieno[2,3-c]pyrazole-5-carboxamide The title compound 115 mg (62%) was obtained in a manner similar to the Example 402 by use of 2-piperazine, instead of cis-2,6-dimethyl-morpholine.

Example 418

3-Methyl-N-[cis-4-(3-oxo-1-piperazinyl)cyclohexyl]-1-tetrahydro-2H-pyran-4-yl-1H-thieno[2,3-c]pyrazole-5-carboxamide The title compound 43 mg (23%) was obtained in the Example 471, as by-product.

Example 419

3-Methyl-N-[trans-4-(4-methyl-3-oxo-1-piperazinyl)cyclohexyl]-1-tetrahydro-2H-pyran-4-yl-1H-thieno[2,3-c]pyrazole-5-carboxamide To a suspension of 150 mg (0.415 mmol) of the compound obtained in the Example 401 in 3 mL of 1,2-dichloroethane were added 125 mg (0.83 mmol) of 1-methyl-2-piperazinone HCl salt, 15 μL of acetic acid, and 82 mg (1.0 mmol) of sodium acetate, and the mixture was stirred for 30 minutes at room temperature. Then, 132 mg (0.623 mmol) of sodium triacetoxyborohydride was added to the reaction mixture, and the mixture was stirred for 1 hour at room temperature. The reaction mixture was diluted by saturated sodium bicarbonate aqueous solution and extracted with dichloromethane. The organic layer was washed with water and saturated saline solution, then, dried over with anhydrous sodium sulfate. The solvent was removed under reduced pressure and the residue was purified by silica gel column chromatography (eluent: dichloromethane/methanol=10/1) to give 131 mg (69%) of the title compound.

Example 420

3-Methyl-N-[cis-4-(4-methyl-3-oxo-1-piperazinyl)cyclohexyl]-1-tetrahydro-2H-pyran-4-yl-1H-thieno[2,3-c]pyrazole-5-carboxamide The title compound 21 ng (11%) was obtained in the Example 419, as by-product.

Example 421

Ethyl 1-(trans-4-{[(3-methyl-1-tetrahydro-2H-pyran-4-yl-1H-thieno-[2,3-c]pyrazol-5-yl)carbonyl]amino}cyclohexyl)-4-piperidinecarboxylate The title compound 690 mg (37%) was obtained in a manner similar to the Example 369 by use of the compound obtained in the manufacturing Example 93, instead of the compound obtained in the Manufacturing Example 64.

Example 422

Ethyl 1-(cis-4-{[(3-methyl-1-tetrahydro-2H-pyran-4-yl-1H-thieno-[2,3-c]pyrazol-5-yl)carbonyl]amino}cyclohexyl)-4-piperidinecarboxylate The title compound 10.10 g (58%) was obtained in the Example 421, as by-product.

Example 423

N-{trans-4-[4-(Hydroxymethyl)-1-piperidinyl]cyclohexyl}-3-methyl-1-tetrahydro-2H-pyran-4-yl-1H-thieno[2,3-c]pyrazole-5-carboxamide The title compound 59 mg (54%) was obtained in a manner similar to the Example 206 by use of the compound obtained in the Example 421, instead of the compound obtained in the Example 204.

Example 424

N-{cis-4-[4-(Hydroxymethyl)-1-piperidinyl]cyclohexyl}-3-methyl-1-tetrahydro-2H-pyran-4-yl-1H-thieno[2,3-c]pyrazole-5-carboxamide The title compound 61 mg (55%) was obtained in a manner similar to the Example 206 by use of the compound obtained in the Example 422, instead of the compound obtained in the Example 204.

Example 425

N-[trans-4-(4-Hydroxy-1-piperidinyl)cyclohexyl]-3-methyl-1-tetrahydro-2H-pyran-4-yl-1H-thieno[2,3-c]pyrazole-5-carboxamide The title compound 76 mg (42%) was obtained in a manner similar to the Example 402 by use of 4-hydroxypiperidine, instead of cis-2,6-di-methylmorpholine.

Example 426

N-(cis-4-{4-[(Dimethylamino)carbonyl]-1-piperidinyl}cyclohexyl)-3-methyl-1-tetrahydro-2H-pyran-4-yl-1H-thieno[2,3-c]pyrazole-5-carboxamide A mixture solution of 400 mg (0.795 mmol) of the compound obtained in the Example 422 in 8 mL of 6M-HCl aqueous solution was refluxed for 2.5 hours. After cooling the reaction mixture, the solvent was removed under reduced pressure to give 1-(cis-4-{[(3-methyl-1-tetrahydro-2H-pyran-4-yl-1H-thieno[2,3-c]pyrazol-5-yl)carbonyl]amino}cyclohexyl)-4-piperidinecarboxylic acid HCl salt as intermediate compound.

Then, to a suspension of the intermediate compound obtained above in dichloromethane were added 0.60 mL (1.2 mmol) of 2M-dimethylamine/tetrahydrofuran, 229 mg (1.19 mmol) of 1-ethyl-3-(3-dimethylaminopropyl)-carbodiimide HCl salt, 746 μL (5.35 mmol) of triethylamine and 182 mg (1.19 mmol) of 1-hydroxybenzotriazole, and the mixture was stirred for 95 hours at room temperature. The saturated sodium bicarbonate aqueous solution was added to the reaction mixture, and the mixture was extracted with dichloromethane. The organic layer was washed water and saturated saline solution, then, dried over with anhydrous sodium sulfate. The solvent was removed under reduced pressure and the residue was purified by alkaline silica gel column chromatography (eluent:ethyl acetate) to give 196 mg (49%) of the title compound.

Example 427

1-(trans-4-{[(3-Methyl-1-tetrahydro-2H-pyran-4-yl-1H-thieno[2,3-c]-pyrazol-5-yl)carbonyl]amino}cyclohexyl)-4-piperidinecarboxylic acid HCl salt A mixture solution of 400 mg (0.795 mmol) of the compound obtained in the Example 421 in 6M-HCl aqueous solution was stirred for 2 hours at 70° C. The solvent was removed to give 465 mg (quantitative) of the title compound.

Example 428

N-(trans-4-{4-[(Dimethylamino)carbonyl]-1-piperidinyl}cyclohexyl)-3-methyl-1-tetrahydro-2H-pyran-4-yl-1H-thieno[2,3-c]pyrazole-5-carboxamide The title compound 195 mg (78%) was obtained in a manner similar to the Example 378 by use of the compound obtained in the Example 427 and 2M-dimethylamine/tetrahydrofuran, instead of the compound obtained in the Example 103 and 4-hydroxypiperidine, respectively.

Example 429

N'-(Dihydro-2H-pyran-3(4H)-ilidene)benzohydrazide

To a solution of 3.48 g (34.1 mmol) of tetrahydro-2H-pyran-3-ol in 350 mL of dichloromethane were added 11.1 g (51.2 mmol) of pyridinium chlorochromate, 3.16 g (38.5 mmol) of sodium acetate, and 30 g of molecular sieve 4A, and the mixture was stirred for 4 hours at room temperature. Then, the reaction mixture was filtrated by Celite® and the filtrate was condensed under reduced pressure. The residue was purified by silica gel column chromatography (eluent:hexane/ethyl acetate=2/1) to give dihydro-2H-pyran-3(4H)-one as intermediate compound.

A mixture solution of the intermediate compound obtained above and 4.6 g (34.1 mmol) of benzoylhydrazine in 20 mL of methanol was stirred for 4 hours at 60° C. After cooling the reaction mixture, the solvent was removed and the residue was purified by silica gel column chromatography (eluent: dichloromethane/methanol=30/1) to give 1.75 g (24%) of the title compound.

Example 430

N'-Tetrahydro-2H-pyran-3-ylbenzohydrazide

To a solution of 1.64 g (7.51 mmol) of the compound obtained in the Example 429 in methanol was added 257 mg (6.76 mmol) of sodium borohydride at 0° C., and the mixture was stirred for 3 hours at the same temperature. The solvent was removed and the residue was treated with water and the mixture was extracted with dichloromethane. The organic layer was washed with water and saturated saline solution, then, dried over with anhydrous sodium sulfate. The solvent was removed and the residue was purified by silica gel column chromatography (eluent:dichloromethane/methanol=30/1) to give 1.46 g (88%) of the title compound.

Example 431

5-Methyl-2-tetrahydro-2H-pyran-3-yl-2,4-dihydro-3H-pyrazol-3-one

To a solution of 1.44 g (6.53 mmol) of the compound obtained in the Example 430 in 10 mL of water was added 20 mL of conc. HCl, and the mixture was stirred for 24 hours at 100° C. After cooling the reaction mixture, the insoluble substances were removed off by filtration, and the filtrate was condensed to give 1-(tetrahydro-2H-pyran-3-yl)hydrazine HCl salt as intermediate compound.

A mixture of the intermediate compound obtained above and 705 μL (6.53 mmol) of methyl acetoacetate was stirred for 2 hours at 110° C. The reaction mixture was cooled and diluted with water and ethyl acetate, then, neutralized by 1M-NaOH aqueous solution. The solvent was removed and the residue was purified by silica gel column chromatography (eluent:dichloromethane/methanol=20/1) to give 793 mg (67%) of the title compound.

Example 432

5-Chloro-3-methyl-1-tetrahydro-2H-pyran-3-yl-1H-pyrazole-4-carboaldehyde

The title compound 452 mg (47%) was obtained in a manner similar to the Example 193 by use of the compound obtained in the Example 431, instead of the compound obtained in the Example 192.

Example 433

Ethyl 3-methyl-1-tetrahydro-2H-pyran-3-yl-1H-thieno[2,3-c]pyrazole-5-carboxylate To a solution of 259 μL (2.36 mmol) of ethyl thioglycolate in 4 mL of tetrahydrofuran was added 94 mg (2.36 mmol) of sodium borohydride (60% oily) at 0° C., and the mixture was stirred for 30 minutes at room temperature. Then, the reaction mixture was cooled to 0° C. and 415 mg (1.81 mmol) of the compound obtained in the Example 432 in 4 mL of tetrahydrofuran was added gradually to this mixture, and the mixture was stirred for 2 hours at room temperature. Then, the reaction mixture was cooled to 0° C. and 94 mg (2.36 mmol) of sodium borohydride (60% oily) was added to this mixture, and the mixture was stirred for 30 minutes at room temperature. The reaction mixture was treated with ice water and extracted with ethyl acetate. The organic layer was washed with water and saturated saline solution, then, dried over with anhydrous sodium sulfate. The solvent was removed under reduced pressure and the residue was purified by silica gel column chromatography (eluent:hexane/ethyl aceteta=3/1) to give 413 mg (78%) of the title compound.

Example 434

3-Methyl-1-tetrahydro-2H-pyran-3-yl-1H-thieno[2,3-c]pyrazole-5-carboxylic acid

The title compound 320 mg (89%) was obtained in a manner similar to the Example 6 by use of the compound obtained in the Example 433, instead of the compound obtained in the Example 5.

Example 435

3-Methyl-N-[trans-4-(4-morpholinyl)cyclohexyl]-1-tetrahydro-2H-pyran-3-yl-1H-thieno[2,3-c]pyrazole-5-carboxamide The title compound 185 mg (95%) was obtained in a manner similar to the Example 369 by use of the compound obtained in the Example 434, instead of the compound obtained in the Example 195.

Example 436

N-[trans-4-(4-Ethyl-3-oxo-1-piperazinyl)cyclohexyl]-3-methyl-1-tetrahydro-2H-pyran-4-yl-1H-thieno[2,3-c]pyrazole-5-carboxamide The title compound 140 mg (71%) was obtained in a manner similar to the Example 419 by use of 1-ethyl-2-piperazinone HCl salt, instead of 1-methyl-2-piperazinone HCl salt.

Example 437

N-[cis-4-(4-Ethyl-3-oxo-1-piperazinyl)cyclohexyl]-3-methyl-1-tetrahydro-2H-pyran-4-yl-1H-thieno[2,3-c]pyrazole-5-carboxamide The title compound 41 mg (21%) was obtained in the Example 436, as by-product.

Example 438

N-{trans-4-[(4-Ethyl-3-oxo-1-piperazinyl)methyl]cyclohexyl}-3-methyl-1-tetrahydro-2H-pyran-4-yl-1H-thieno[2,3-c]pyrazole-5-carboxamide To a solution of 150 mg (0.282 mmol) of the compound obtained in the Example 357 in 3 mL of N,N-dimethylformamide were added 93 mg (0.564 mmol) of 1-ethyl-2-piperazinone HCl salt, and 236 μL (1.7 mmol) of triethylamine, and the mixture was stirred for 5 hours at 100° C. Then, 43 mg (0.282 mmol) of sodium iodide was added to the reaction mixture and the mixture was stirred for 40 hours at 100° C. Further, 100 mg (0.61 mmol) of 1-ethyl-2-piperazinone HCl salt and 50 mg (0.33 mmol) of sodium iodide were added to the reaction mixture, and the mixture was stirred for 15 minutes at 120° C. using microwave. After the reaction, water was added to the reaction mixture and the mixture was extracted with dichloromethane. The organic layer was washed with water and saturated saline solution, then, dried over with anhydrous sodium sulfate. The solvent was removed under reduced pressure and the residue was purified by silica gel column chromatography (eluent:dichloromethane/methanol=20/1 to 15/1), and further alkaline silica gel column chromatography (eluent:ethyl acetate) to give 63 mg (46%) of the title compound.

Example 439

3-Methyl-N-{trans-4-[(4-methyl-3-oxo-1-piperazinyl)methyl]-cyclohexyl}-1-tetrahydro-2H-pyran-4-yl-1H-thieno[2,3-c]pyrazole-5-carboxamide The title compound 24 mg (18%) was obtained in a manner similar to the Example 438 by use of 1-methyl-2-piperazinone HCl salt, instead of 1-ethyl-2-piperazinone HCl salt.

Example 440

3-Methyl-N-[4-(4-methyl-2-oxo-1-piperazinyl)phenyl]-1-tetrahydro-2H-pyran-4-yl-1H-thieno[2,3-c]pyrazole-5-carboxamide The free base of the title compound was obtained in a manner similar to the Example 7 by use of the compound obtained in the Manufacturing Example 72 and the compound obtained in the Example 195, instead of benzylamine and the compound obtained in the Example 6, respectively. Then, 30.7 μL (0.473 mmol) of methanesulfonic acid was added to a solution of the free base of the compound obtained above in 2.5 mL of isopropanol, and the mixture was refluxed. The reaction mixture was cooled to room temperature and the resultant precipitates were collected to give 206 mg (83%) of the title compound.

Chemical structure and physicochemical data of the compounds obtained by the above-mentioned Manufacturing Examples and Examples are summarized in the following Tables.

TABLE 5

| Manufacturing Exmple No. | Chemical Structure | Properties m.p. (° C.) (recryst. solvent) | $^1$H-NMR | MS(FAB) $(M + 1)^+$ |
|---|---|---|---|---|
| 1 | O$_2$N—indoline-BOC | pale yellow cryst. 98-100 | CDCl$_3$ 1.58 (9H, s), 3.17 (2H, t, J = 8.8 Hz), 4.09 (2H, t, J = 8.8 Hz), 7.76-7.82 (1H, m), 8.00-8.02 (1H, m), 8.10 (1H, m) | 265 |
| 2 | H$_2$N—indoline-BOC | brown oil | CDCl$_3$ 1.53 (9H, s), 3.00 (2H, t, J = 8.6 Hz), 3.45 (2H, brs), 3.88-3.98 (2H, m), 6.45-6.56 (2H, m), 7.58-7.65 (1H, m) | 234 |
| 3 | AcNH—indoline-BOC | colorless cryst. 134-138 | CDCl$_3$ 1.57 (9H, s), 2.15 (3H, s), 3.08 (2H, t, J = 8.7 Hz), 3.91-4.05 (2H, m), 6.90-7.11 (2H, m), 7.50-7.71 (1H, m) | 277 |
| 4 | AcNH—indoline-NH·HCl | pale pink cryst. 195-210 | DMSO 2.06 (3H, s), 3.18 (2H, t, J = 7.8 Hz), 3.70 (2H, t, J = 7.8 Hz), 7.35-7.38 (1H, m), 7.50-7.53 (1H, m), 7.76-7.78 (1H, m), 10.24 (1H, brs), 11.18 (2H, brs) | 177 |

TABLE 6

| Manufacturing Exmple No. | Chemical Structure | Properties m.p. (° C.) (recryst. solvent) | ¹H-NMR | MS(FAB) (M + 1)⁺ |
|---|---|---|---|---|
| 5 | H₂N-pyridine-C(O)NH-iPr | colorless cryst. 247-249 | DMSO 1.13 (6H, d, J = 6.6 Hz), 3.99-4.09 (1H, m), 6.38-6.41 (3H, m), 7.79 (1H, dd, J = 2.3 and 8.6 Hz), 7.84 (1H, d, J = 7.6 Hz), 8.43 (1H, d, J = 2.3 Hz) | 180 |
| 6 | O₂N-indoline-N-SO₂Me | pale yellow 190-192 | CDCl₃ 2.99 (3H, s), 3.26 (2H, t, J = 8.6 Hz), 4.13(2H, t, J = 8.6 Hz), 7.47 (1H, d, J = 8.9 Hz), 8.07-8.09 (1H, m), 8.13-8.16 (1H, m) | 243 |
| 7 | H₂N-indoline-N-SO₂Me | yellow crys. 117-118 | CDCl₃ 2.79 (3H, s), 3.05 (2H, t, J = 8.3 Hz), 3.57(2H, brs), 3.94 (2H, t, J = 8.3 Hz), 6.53 (1H, dd, J = 2.2 and 8.4 Hz), 6.58-6.60 (1H, m), 7.21 (1H, d, J = 8.4 Hz) | 212 |
| 8 | O₂N-C₆H₄-SO₂-piperazine-CH₂CH₂OH | pale yellow cryst. 146-148 | CDCl₃ 2.22 (1H, t, J = 5.3 Hz), 2.56 (2H, t, J = 5.3 Hz), 2.59-2.63 (4H, m), 3.08-3.13 (4H, m), 2.56-2.61 (2H, m), 7.94-7.97 (2H, m), 8.39-8.42 (2H, m) | 316 |

TABLE 7

| Manufacturing Exmple No. | Chemical Structure | Properties m.p. (° C.) (recryst. solvent) | ¹H-NMR | MS(FAB) (M + 1)⁺ |
|---|---|---|---|---|
| 9 | O₂N-C₆H₄-SO₂-piperazine-CH₂CH₂OAc | pale yellow cryst. 114-116 | CDCl₃ 2.02 (3H, s), 2.55-2.69 (6H, m), 3.04-3.15 (4H, m), 4.13 (2H, t, J = 5.7 Hz), 7.94 (2H, dd, J = 1.8 and 7.0 Hz), 8.39 (2H, dd, J = 1.8 and 7.0 Hz) | 358 |
| 10 | H₂N-C₆H₄-SO₂-piperazine-CH₂CH₂OAc | colorless cryst. 109-112 | CDCl₃ 2.03 (3H, s), 2.53-2.68 (6H, m), 2.94-3.07 (4H, m), 4.07-4.19 (4H, m), 6.67-6.70 (2H, m), 7.51-7.54 (2H, m) | 328 |
| 11 | AcNH-cyclohexyl-NHBOC | colorless cryst. 210 (dec.) | CDCl₃ 1.12-1.28 (4H, m), 1.44 (9H, s), 1.92-2.05 (4H, m), 1.95 (3H, s), 3.33-3.45 (1H, m), 3.68-3.78 (1H, m), 4.32-4.42 (1H, m), 5.21-5.29 (1H, m) | 257 |
| 12 | AcNH-cyclohexyl-NH₂·CF₃COOH | colorless cryst. 230 (dec.) | MeOH 1.26-1.55 (4H, m), 1.91 (3H, s), 1.94-2.11 (4H, m), 3.01-3.12 (1H, m), 3.55-3.67 (1H, m), 7.99 (1H, d, J = 6.8 Hz) | 157 |

TABLE 8

| Manufacturing Exmple No. | Chemical Structure | Properties m.p. (° C.) (recryst. solvent) | $^1$H-NMR | MS(FAB) (M + 1)$^+$ |
|---|---|---|---|---|
| 13 | (4-nitrophenyl NHC(O)CH$_2$OMe) | yellow solid 107-110 | CDCl$_3$ 3.53 (3H, s), 4.06 (2H, m), 7.77 (2H, d, J = 9.1 Hz), 8.22 (2H, d, J = 9.1 Hz), 8.56 (1H, brs) | 211 |
| 14 | (4-aminophenyl NHC(O)CH$_2$OMe) | brown solid 82-83 | CDCl$_3$ 3.49 (3H, s), 3.61 (2H, brs), 3.99 (2H, s), 6.66 (2H, d, J = 8.6 Hz), 7.33 (2H, d, J = 8.6 Hz), 8.06 (1H, brs) | 181 |
| 15 | (5-amino-2-(4-methylpiperazin-1-yl)pyridine) | brown solid 73-78 | CDCl$_3$ 2.34 (3H, s), 2.51-2.56 (4H, m), 3.29 (2H, brs), 3.38-3.43 (4H, m), 6.57 (1H, d, J = 8.8 Hz), 6.98 (1H, dd, J = 3.0 and 8.8 Hz), 7.79 (1H, d, J = 3.0 Hz) | 193 |
| 16 | (3-nitrophenyl sulfonyl-4-methylpiperazine) | pale yellow solid 104-105 | CDCl$_3$ 2.28 (3H, s), 2.48-2.53 (4H, m), 3.08-3.13 (4H, m), 7.73-7.80 (1H, m), 8.07-8.12 (1H, m), 8.44-8.49 (1H, m), 8.60-6.62 (1H, m) | 286 |

TABLE 9

| Manufacturing Exmple No. | Chemical Structure | Properties m.p. (° C.) (recryst. solvent) | $^1$H-NMR | MS(FAB) (M + 1)$^+$ |
|---|---|---|---|---|
| 17 | (3-aminophenyl sulfonyl-4-methylpiperazine) | colorless solid 141-142 | CDCl$_3$ 2.27 (3H, s), 2.45-2.50 (4H, m), 3.01-3.06 (4H, m), 3.89 (2H, brs), 6.82-6.87 (1H, m), 7.00-7.03 (1H, m), 7.08-7.12 (1H, m), 7.24-7.27 (1H, m) | 256 |
| 18 | (2-fluoro-4-nitro-N-methyl-N-(2-hydroxyethyl)aniline) | yellow solid 49-50 | CDCl$_3$ 3.13 (3H, s), 3.58-3.64 (2H, m), 3.87-3.93 (2H, m), 6.80-6.86 (1H, m), 7.89 (1H, dd, J = 1.5 and 14.3 Hz), 7.95-8.00 (1H, m) | 215 |

TABLE 9-continued

| Manufacturing Exmple No. | Chemical Structure | Properties m.p. (° C.) (recryst. solvent) | ¹H-NMR | MS(FAB) (M + 1)⁺ |
|---|---|---|---|---|
| 19 | 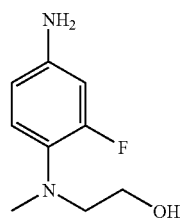 | brown oil | CDCl₃ 2.73 (3H, s), 3.06-3.11 (2H, m), 3.59 (2H, brs), 3.88-3.93 (2H, m), 6.37-6.454 (2H, m), 6.88-6.95 (1H, m) | 185 |
| 20 | 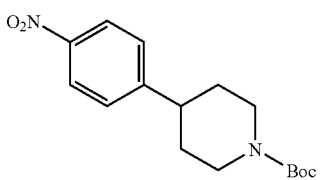 | ywllow oil | CDCl₃ 1.47 (9H, s), 1.57-1.70 (2H, m), 1.78-1.90 (2H, m), 2.70-2.86 (3H, m), 4.20-4.32 (2H, m), 7.34 (2H, d, J = 8.7 Hz), 8.15 (2H, d, J = 8.7 Hz) | 307 |

TABLE 10

| Manufacturing Exmple No. | Chemical Structure | Properties m.p. (° C.) (recryst. solvent) | ¹H-NMR | MS(FAB) (M + 1)⁺ |
|---|---|---|---|---|
| 21 | 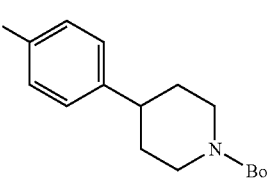 | pale yellow solid 109-112 | CDCl₃ 1.46 (9H, s), 1.51-1.61 (2H, m), 1.72-1.79 (2H, m), 2.47-2.57 (1H, m), 2.70-2.81 (2H, m), 3.56 (2H, brs), 4.14-4.26 (1H, m), 6.63 (2H, d, J = 8.4 Hz), 6.97 (2H, d, J = 8.3 Hz) | 277 |
| 22 | 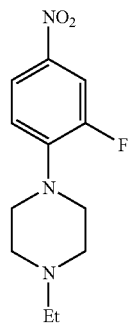 | yellow solid 64-65 | CDCl₃ 1.12 (3H, t, J = 7.2 Hz), 2.47 (2H, q, J = 7.2 Hz), 2.58-2.63 (4H, m), 3.29-3.34 (4H, m), 6.89 (1H, dd, J = 8.8 and 8.8 Hz), 7.88 (1H, dd, J = 2.6 and 13.2 Hz), 7.95-8.00 (1H, m) | 254 |
| 23 | 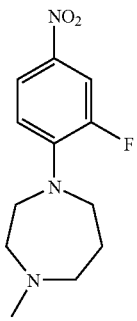 | yellow solid 49-50 | CDCl₃ 2.00-2.07 (2H, m), 2.39 (3H, s), 2.58-2.63 (2H, m), 2.73-2.79 (2H, m), 3.54-3.60 (2H, m), 3.61-3.66 (2H, m), 6.68-6.74 (1H, m), 7.83-7.94 (2H, m) | 254 |

TABLE 10-continued

| Manufacturing Exmple No. | Chemical Structure | Properties m.p. (° C.) (recryst. solvent) | ¹H-NMR | MS(FAB) (M + 1)⁺ |
|---|---|---|---|---|
| 24 | (4-(4-ethylpiperazin-1-yl)-3-fluoroaniline) | pale yellow solid 58-60 | CDCl$_3$ 1.11 (3H, t, J = 7.2 Hz), 2.46 (2H, q, J = 7.2 Hz), 2.57-2.64 (4H, m), 2.97-3.03 (4H, m), 3.51 (2H, brs), 6.35-6.45 (2H, m), 7.77-7.84 (1H, m) | 224 |

TABLE 11

| Manufacturing Exmple No. | Chemical Structure | Properties m.p. (° C.) (recryst. solvent) | ¹H-NMR | MS(FAB) (M + 1)⁺ |
|---|---|---|---|---|
| 25 | (1-(2-fluoro-4-nitrophenyl)-4-methylpiperazine) | pale yellow solid 71-71.5 | CDCl$_3$ 2.36 (3H, s), 2.57-2.64 (4H, m), 3.30-3.38 (4H, m), 6.88-6.94 (1H, m), 7.90 (1H, dd, J = 2.5 and 13.2 Hz), 7.98 (1H, dd, J = 2.5 and 9.0 Hz) | 240 |
| 26 | (3-fluoro-4-(4-methylpiperazin-1-yl)aniline) | pale reddish brown solid 93-94.5 | CDCl$_3$ 2.34 (3H, s), 2.51-2.69 (4H, m), 2.96-3.09 (4H, m), 3.53 (2H, brs), 6.37-6.48 (2H, m), 6.78-6.87 (1H, m) | 210 |
| 27 | (8-(2-fluoro-4-nitrophenyl)-1,4-dioxa-8-azaspiro[4.5]decane) | pale yellow solid 129-131 (AcOEt/hexane) | CDCl$_3$ 1.84-1.92 (4H, m), 3.38-3.47 (4H, m), 4.01 (4H, s), 6.89-6.97 (1H, m), 7.90 (1H, dd, J = 2.6 and 13.1 Hz), 7.97 (1H, dd, J = 2.6 and 8.8 Hz) | 284 |
| 28 | (4-(1,4-dioxa-8-azaspiro[4.5]decan-8-yl)-3-fluoroaniline) | colorless solid 100.5-101.5 (EtOH) | CDCl$_3$ 1.83-1.92 (4H, m), 3.01-3.09 (4H, m), 3.53 (2H, brs), 3.99 (4H, s), 6.37-6.47 (2H, m), 6.79-6.88 (1H, m) | 253 |

TABLE 12

| Manufacturing Exmple No. | Chemical Structure | Properties m.p. (° C.) (recryst. solvent) | ¹H-NMR | MS(FAB) (M + 1)⁺ |
|---|---|---|---|---|
| 29 | 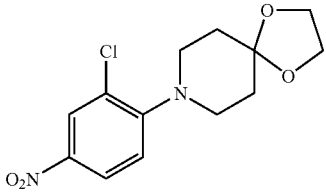 | yellow solid 121-122 (AcOEt/hexane) | CDCl₃ 1.89-1.98 (4H, m), 3.27-3.34 (4H, m), 4.02 (4H, s), 7.05 (1H, d, J = 8.9 Hz), 8.08 (1H, dd, J = 2.7 and 8.9 Hz), 8.25 (1H, d, J = 2.7 Hz) | 299 |
| 30 | 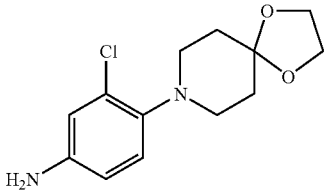 | pale yellow solid 139.5-140.5 (EtOH) | CDCl₃ 1.83-1.92 (4H, m), 2.97-3.04 (4H, m), 3.52 (2H, brs), 4.00 (4H, s), 6.54 (1H, dd, J = 2.6 and 8.5 Hz), 6.74 (1H, d, J = 2.6 Hz), 6.91 (1H, d, J = 8.5 Hz) | 269 |
| 31 | 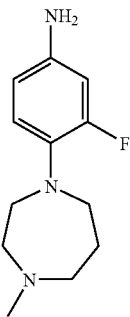 | reddish brown solid 40-42 | CDCl₃ 1.90-1.97 (2H, m), 2.39 (3H, s), 2.65-2.75 (4H, m), 3.23-3.30 (4H, m), 3.43 (2H, brs), 6.32-6.42 (2H, m), 6.72-6.78 (1H, m) | 224 |
| 32 | 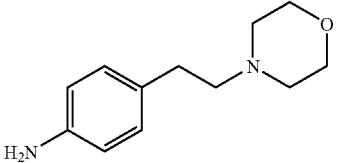 | pale brown solid | CDCl₃ 2.46-2.56 (6H, m), 2.66-2.73 (2H, m), 3.58 (2H, brs), 3.70-3.76 (4H, m), 6.59-6.65 (2H, m), 6.96-7.02 (2H, m) | 207 |

TABLE 13

| Manufacturing Exmple No. | Chemical Structure | Properties m.p. (° C.) (recryst. solvent) | ¹H-NMR | MS(FAB) (M + 1)⁺ |
|---|---|---|---|---|
| 33 | 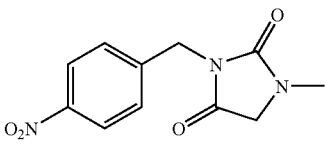 | pale yellow viscous solid | CDCl₃ 3.02 (3H, s), 3.92 (2H, s), 4.74 (2H, s), 7.54-7.59 (2H, m), 8.15-8.20 (2H, m) | 250 |
| 34 | 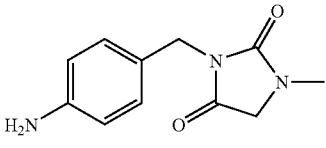 | pale yellow viscous solid | CDCl₃ 2.96 (3H, s), 3.65 (2H, brs), 3.82 (2H, s), 4.53 (2H, s), 6.57-6.62 (2H, m), 7.22-7.27 (2H, m) | 220 |
| 35 | 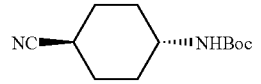 | pale yellow solid | CDCl₃ 1.10-1.22 (2H, m), 1.44 (9H, s), 1.61-1.73 (2H, m), 2.04-2.15 (4H, m), 2.36-2.45 (1H, m), 3.46 (1H, br), 4.38 (1H, br) | 225 |

TABLE 13-continued

| Manufacturing Exmple No. | Chemical Structure | Properties m.p. (° C.) (recryst. solvent) | ¹H-NMR | MS(FAB) (M + 1)⁺ |
|---|---|---|---|---|
| 36 | 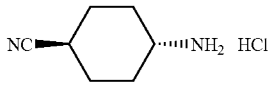 | colorless solid | DMSO-$d_6$ 1.27-1.40 (2H, m), 1.51-1.65 (2H, m), 1.90-1.98 (2H, m), 2.03-2.11 (2H, m), 2.67 (1H, tt, J = 3.7 and 11.7 Hz), 2.94-3.07 (1H, m), 8.06 (3H, br) | 125 |

TABLE 14

| Manufacturing Exmple No. | Chemical Structure | Properties m.p. (° C.) (recryst. solvent) | ¹H-NMR | MS(FAB) (M + 1)⁺ |
|---|---|---|---|---|
| 37 | 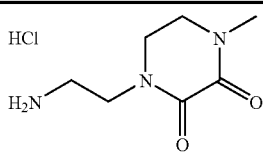 | colorless solid | $D_2O$ 3.06 (3H, brs), 3.25-3.32 (2H, m), 3.67-3.99 (6H, m) | 172 |
| 38 | 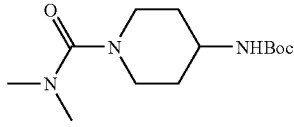 | colorless solid | $CDCl_3$ 1.29-1.40 (2H, m), 1.45 (9H, s), 1.89-1.96 (2H, m), 2.88 (6H, s), 2.82-2.88 (2H, m), 3.57-3.65 (3H, m), 4.43 (1H, br) | 272 |
| 39 | 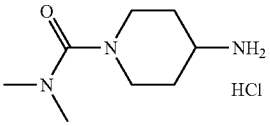 | colorless foamy solid | DMSO-$d_6$ 1.39-1.51 (2H, m), 1.83-1.92 (2H, m), 2.50 (3H, s), 2.68-2.78 (2H, m), 2.72 (3H, s), 3.08-3.21 (1H, m), 3.51-3.59 (2H, m) | 172 |
| 40 | 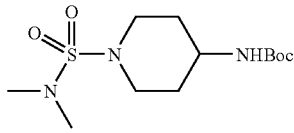 | colorless solid | $CDCl_3$ 1.39-1.49 (2H, m), 1.44 (9H, s), 1.93-2.02 (2H, m), 2.81 (6H, s), 2.88-2.89 (2H, m), 3.50-3.68 (3H, m), 4.46 (1H, br) | 308 |

TABLE 15

| Manufacturing Exmple No. | Chemical Structure | Properties m.p. (° C.) (recryst. solvent) | ¹H-NMR | MS(FAB) (M + 1)⁺ |
|---|---|---|---|---|
| 41 | 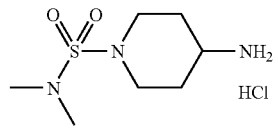 | colorless solid | DMSO-$d_6$ 1.45-1.56 (2H, m), 1.88-1.96 (2H, m), 2.74 (6H, s), 2.86-2.96 (2H, m), 3.11-3.21 (1H, m), 3.56-3.62 (2H, m), 8.02 (3H, br) | 208 |
| 42 | 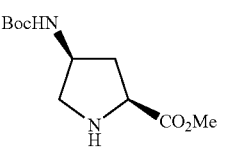 | colorless solid | $CDCl_3$ 1.43 (9H, s), 1.80-1.87 (1H, m), 2.41 (1H, ddd, J = 7.2, 9.4 and 14.7 Hz), 2.92-2.99 (1H, m), 3.12 (1H, dd, J = 5.7 and 11.0 Hz), 3.76 (3H, s), 3.82 (1H, dd, J = 4.8 and 9.4 Hz), 4.12 (1H, br), 4.92 (1H, br) | 245 |

TABLE 15-continued

| Manufacturing Exmple No. | Chemical Structure | Properties m.p. (° C.) (recryst. solvent) | ¹H-NMR | MS(FAB) (M + 1)⁺ |
|---|---|---|---|---|
| 43 | BocHN—pyrrolidine—CO₂Me, N-C(O)NH₂ | colorless solid | CDCl₃ 1.44 (9H, s), 1.97-2.06 (1H, m), 2.47 (1H, ddd, J = 6.5, 9.5 and 13.9 Hz), 3.33-3.39 (1H, m), 3.70 (1H, dd, J = 6.0 and 9.9 Hz), 3.79 (3H, s), 4.36-4.46 (1H, m), 4.43 (1H, dd, J = 2.7 and 9.5 Hz), 4.60 (2H, brs), 5.52-5.58 (1H, m) | 288 |
| 44 | BocHN—bicyclic pyrrolidinyl hydantoin | colorless solid | CDCl₃ 1.45 (9H, s), 1.80-2.65 (2H, br), 3.25-4.80 (5H, br) | 256 |

TABLE 16

| Manufacturing Exmple No. | Chemical Structure | Properties m.p. (° C.) (recryst. solvent) | ¹H-NMR | MS(FAB) (M + 1)⁺ |
|---|---|---|---|---|
| 45 | H₂N—bicyclic pyrrolidinyl hydantoin · HCl | colorless solid | D₂O 1.94-2.04 (1H, m), 2.70-2.78 (1H, m), 3.64-3.75 (2H, m), 3.76 (1H, s), 4.25-4.34 (1H, m), 4.51 (1H, dd, J = 7.3 and 10.5 Hz) | 156 |
| 46 | H₂N-pyridinyl-imidazolidinone | pale reddish brown solid | CDCl₃ 3.42-3.58 (4H, m), 4.07-4.14 (2H, m), 4.58 (1H, br), 7.06 (1H, dd, J = 2.9 and 8.9 Hz), 7.79 (1H, dd, J = 0.7 and 2.9 Hz), 8.04 (1H, dd, J = 0.7 and 8.9 Hz) | 179 |
| 47 | H₂N-phenyl-hydantoin | pale brown solid | DMSO-d₆ 3.99 (2H, s), 5.24 (2H, brs), 6.57 (2H, dd, J = 2.0 and 6.6 Hz), 6.89 (1H, dd, J = 2.0 and 6.6 Hz), 8.10 (1H, brs) | 192 |
| 48 | H₂N-phenyl-N-methyl-hydantoin | pale brown solid | DMSO-d₆ 2.89 (3H, s), 4.04 (2H, s), 5.27 (2H, brs), 6.55-6.60 (2H, m), 6.86-6.91 (2H, m) | 206 |

TABLE 17

| Manufacturing Exmple No. | Chemical Structure | Properties m.p. (° C.) (recryst. solvent) | ¹H-NMR | MS(FAB) (M + 1)⁺ |
| --- | --- | --- | --- | --- |
| 49 | H₂N-phenyl-pyrrolidine-OH | reddish brown solid | CDCl₃ 1.98-2.06 (1H, m), 2.13-2.24 (1H, m), 3.18-3.50 (6H, m), 4.52-4.58 (1H, m), 6.45-6.51 (1H, m), 6.64-6.70 (1H, m) | 179 |
| 50 | O₂N-(F)phenyl-pyrrolidine-OH | brown solid (EtOH) | DMSO-d₆ 1.86-2.05 (2H, m), 3.38-3.45 (1H, m), 3.55-3.74 (3H, m), 4.36-4.42 (1H, m), 5.05 (1H, d, J = 3.5 Hz), 6.74-6.80 (1H, m), 7.89-7.97 (2H, m) | 227 |
| 51 | H₂N-(F)phenyl-pyrrolidine-OH | purple oil | CDCl₃ 1.90-1.99 (1H, m), 2.14-2.25 (1H, m), 3.06-3.27 (2H, m), 3.35-3.56 (2H, m), 4.47-4.52 (1H, m), 6.36-6.48 (2H, m), 6.57-6.64 (1H, m) | 197 |
| 52 | O₂N-phenyl-SO₂-piperidine-OH | pale brown solid | DMSO-d₆ 1.38-1.48 (2H, m), 1.70-1.78 (2H, m), 2.78-2.85 (2H, m), 3.19-3.26 (2H, m), 3.50-3.58 (1H, m), 4.69 (1H, d, J = 4.0 Hz), 7.93-7.99 (1H, m), 8.17-8.21 (1H, m), 8.36-8.38 (1H, m), 8.54-8.58 (1H, m) | 287 |

TABLE 18

| Manufacturing Exmple No. | Chemical Structure | Properties m.p. (° C.) (recryst. solvent) | ¹H-NMR | MS(FAB) (M + 1)⁺ |
| --- | --- | --- | --- | --- |
| 53 | H₂N-phenyl-SO₂-piperidine-OH | colorless solid | DMSO-d₆ 1.39-1.48 (2H, m), 1.69-1.77 (2H, m), 2.65-2.73 (2H, m), 3.06-3.15 (2H, m), 3.50-3.58 (1H, m), 4.65 (1H, d, J = 3.8 Hz), 5.61 (2H, brs), 6.76-6.84 (2H, m), 6.89-6.92 (1H, m), 7.20-7.26 (1H, m) | 257 |
| 54 | O₂N-phenyl-SO₂-piperidine-OH | colorless solid | DMSO-d₆ 1.38-1.48 (2H, m), 1.71-1.79 (2H, m), 2.81-2.88 (2H, m), 3.18-3.26 (2H, m), 3.52-3.59 (1H, m), 4.68 (1H, d, J = 4.0 Hz), 8.00-8.05 (2H, m), 8.42-8.47 (2H, m) | 287 |
| 55 | O₂N-phenyl-SO₂-piperidine-OTBDMS | colorless solid | CDCl₃ −0.01 (6H, s), 0.77 (9H, s), 1.59-1.68 (2H, m), 1.77-1.87 (2H, m), 3.07-3.15 (2H, m), 3.17-3.24 (2H, m), 3.82-3.89 (1H, m), 7.93-7.98 (2H, m), 8.37-8.42 (2H, m) | 401 |

TABLE 18-continued

| Manufacturing Example No. | Chemical Structure | Properties m.p. (° C.) (recryst. solvent) | ¹H-NMR | MS(FAB) (M + 1)⁺ |
|---|---|---|---|---|
| 56 | H₂N–C₆H₄–SO₂–N(piperidine)–OTBDMS | colorless solid | CDCl₃ −0.01 (6H, s), 0.80 (9H, s), 1.56-1.65 (2H, m), 1.75-1.84 (2H, m), 2.89-2.96 (2H, m), 3.12-3.19 (2H, m), 3.72-3.78 (1H, m), 4.10 (2H, br), 6.68-6.73 (2H, m), 7.52-7.57 (2H, m) | 371 |

TABLE 19

| Manufacturing Exmple No. | Chemical Structure | Properties m.p. (° C.) (recryst. solvent) | ¹H-NMR | MS(FAB) (M + 1)⁺ |
|---|---|---|---|---|
| 57 | O₂N–C₆H₃(CF₃)–N(N-methylpiperazine) | yellow solid 56.5-57.5 | CDCl₃ 2.36 (3H, s), 2.52-2.64. (4H, m), 3.11-3.22 (4H, m), 7.27 (1H, d, J = 9.1 Hz), 8.31 (1H, dd, J = 2.6 and 9.1 Hz), 8.50 (1H, d, J = 2.6 Hz) | 290 |
| 58 | H₂N–C₆H₃(CF₃)–N(N-methylpiperazine) | reddish brown solid 123-125 | CDCl₃ 2.32 (3H, s), 2.40-2.60 (4H, m), 2.80-2.89 (4H, m), 3.69 (2H, brs), 6.78 (1H, dd, J = 2.7 and 8.5 Hz), 6.89 (1H, d, J = 2.7 Hz), 7.19 (1H, d, J = 8.5 Hz) | 260 |
| 59 | phthalimide-CH₂CH₂-N(thiadiazolidine-S,S-dioxide)-N-methyl | colorless solid 154-156.5 | CDCl₃ 2.66 (3H, s), 3.28 (2H, t, J = 6.5 Hz), 3.35-3.42 (2H, m), 3.51 (2H, t, J = 6.5 Hz), 3.88-3.95 (2H, m), 7.69-7.76 (2H, m), 7.82-7.89 (2H, m) | 310 |
| 60 | H₂N–CH₂CH₂–N(thiadiazolidine-S,S-dioxide)-N-methyl · HCl | colorless solid 142-145 (EtOH) | DMSO-d₆ 2.63 (3H, s), 2.98-3.03 (2H, m), 3.17-3.43 (6H, m), 8.02 (3H, brs) | 180 (free) |

TABLE 20

| Manufacturing Example No. | Chemical Structure | properties m.p. (° C.) (recryst. solvent) | ¹H-NMR | MS(FAB) (M + 1)⁺ |
|---|---|---|---|---|
| 61 | O₂N–C₆H₃(F)–N(piperidine)–OH | yellow solid 53-57 | CDCl₃ 1.69-1.79 (2H, m), 2.01-2.09 (2H, m), 3.05-3.15 (2H, m), 3.55-3.64 (2H, m), 3.91-4.00 (1H, m), 6.89-6.96 (1H, m), 7.87-8.04 (2H, m) | 241 |
| 62 | H₂N–C₆H₃(F)–N(piperidine)–OH | pale reddish brown solid 112-116 | CDCl₃ 1.58 (1H, br), 1.71-1.81 (2H, m), 1.98-2.06 (2H, m), 2.71-2.81 (2H, m), 3.17-3.25 (2H, m), 3.53 (2H, br), 3.77-3.86 (1H, m), 6.37-6.47 (2H, m), 6.79-6.86 (1H, m) | 211 |

TABLE 20-continued

| Manufacturing Example No. | Chemical Structure | properties m.p. (° C.) (recryst. solvent) | ¹H-NMR | MS(FAB) (M + 1)⁺ |
|---|---|---|---|---|
| 63 | BocHN-cyclohexyl-N-morpholine | pale yellow solid 147-149 | CDCl₃ 1.05-1.16 (2H, m), 1.24-1.40 (2H, m), 1.43 (9H, s), 1.88-1.97 (2H, m), 2.02-2.10 (2H, m), 2.16 (1H, tt, J = 3.5 and 11.4 Hz), 2.50-2.56 (4H, m), 3.37 (1H, br), 3.67-3.72 (4H, m), 4.36 (1H, br) | 285 |
| 64 | H₂N-cyclohexyl-N-morpholine · 2HCl | colorless solid >250 | DMSO-d₆ 1.32-1.48 (2H, m), 1.51-1.66 (2H, m), 2.03-2.12 (2H, m), 2.17-2.26 (2H, m), 2.90-3.20 (4H, m), 3.33-3.41 (2H, m), 3.82-3.99 (4H, m), 8.10-8.28 (3H, m), 11.17-11.46 (1H, m) | 185 |

TABLE 21

| Manufacturing Example No. | Chemical Structure | properties m.p. (° C.) (recryst. solvent) | ¹H-NMR | MS(FAB) (M + 1)⁺ |
|---|---|---|---|---|
| 65 | O₂N-phenyl-N-piperazinone | pale brown solid 195-199 | DMSO-d₆ 3.32-3.37 (2H, m), 3.62-3.67 (2H, m), 3.98 (2H, s), 6.96-7.02 (2H, m), 8.06-8.12 (2H, m), 8.26 (1H, brs) | 222 |
| 66 | H₂N-phenyl-N-piperazinone | pale brown solid | CDCl₃ 3.28-3.33 (2H, m), 3.45-3.51 (2H, m), 3.74 (2H, s), 6.00 (1H, brs), 6.65-6.71 (2H, m), 6.77-6.83 (2H, m), | 192 |
| 67 | H₂N-phenyl-SO₂-N(CH₃)₂ | pale purple solid 151-154 | CDCl₃ 2.71 (6H, s), 3.91 (2H, br), 6.84-6.88 (1H, m), 7.05-7.07 (1H, m), 7.11-7.16 (1H, m), 7.28-7.33 (1H, m) | 201 |
| 68 | O₂N-phenyl-SO₂-CH₂CH₂-OTBDMS | colorless solid 87-88 | CDCl₃ −0.08 (6H, s), 0.72 (9H, s), 3.43 (2H, t, J = 5.6 Hz), 4.07 (2H, t, J = 5.6 Hz), 7.74-7.80 (1H, m), 8.24-8.28 (1H, m), 8.47-8.52 (1H, m), 8.77-8.79 (1H, m) | 346 |

TABLE 22

| Manufacturing Example No. | Chemical Structure | properties m.p. (° C.) (recryst. solvent) | ¹H-NMR | MS(FAB) (M + 1)⁺ |
|---|---|---|---|---|
| 69 | H₂N-phenyl-SO₂-CH₂CH₂-OTBDMS | colorless viscous solid | CDCl₃ −0.01 (6H, s), 0.81 (9H, s), 3.33 (2H, t, J = 6.6 Hz), 3.94 (2H, br), 3.98 (2H, t, J = 6.6 Hz), 6.85-6.91 (1H, m), 7.15-7.17 (1H, m), 7.22-7.32 (2H, m) | 316 |

TABLE 22-continued

| Manufacturing Example No. | Chemical Structure | properties m.p. (° C.) (recryst. solvent) | $^1$H-NMR | MS(FAB) (M + 1)$^+$ |
|---|---|---|---|---|
| 70 | O$_2$N-C$_6$H$_4$-NH-C(O)-CH$_2$-N(CH$_3$)-CH$_2$CH$_2$-OH | pale yellow solid | CDCl$_3$ 1.77 (1H, brs), 2.48 (3H, s), 2.70 (2H, t, J = 5.0 Hz), 3.27 (2H, s), 3.80 (2H, brs), 7.78-7.84 (2H, m), 8.28-8.34 (2H, m), 9.97 (1H, brs) | 254 |
| 71 | O$_2$N-C$_6$H$_4$-(4-methyl-3-oxopiperazin-1-yl) | pale yellow solid 100-101 | CDCl$_3$ 2.42 (3H, s), 2.83 (2H, t, J = 5.3 Hz), 3.32 (2H, s), 3.79 (2H, t, J = 5.3 Hz), 7.53-7.59 (2H, m), 8.24-8.30 (2H, m) | 236 |
| 72 | H$_2$N-C$_6$H$_4$-(4-methyl-3-oxopiperazin-1-yl) | colorless solid 158-160 | CDCl$_3$ 2.39 (3H, s), 2.74-2.79 (2H, m), 3.25 (2H, s), 3.61-3.74 (4H, m), 6.66-6.73 (2H, m), 7.00-7.07 (2H, m) | 208 |

TABLE 23

| Manufacturing Example No. | Chemical Structure | properties m.p. (° C.) (recryst. solvent) | $^1$H-NMR | MS(FAB) (M + 1)$^+$ |
|---|---|---|---|---|
| 73 | O$_2$N-pyridin-2-yl-(4-hydroxypiperidin-1-yl) | yellow solid 149-151 | CDCl$_3$ 1.56-1.70 (2H, m), 1.93-2.06 (2H, m), 3.44-3.58 (2H, m), 4.00-4.09 (1H, m), 4.11-4.22 (2H, m), 6.60 (1H, d, J = 9.6 Hz), 8.19 (1H, dd, J = 2.8 and 9.6 Hz), 9.03 (1H, d, J = 2.8 Hz) | 224 |
| 74 | H$_2$N-pyridin-2-yl-(4-hydroxypiperidin-1-yl) | reddish brown solid 140-140 | CD$_3$OD 1.50-1.61 (2H, m), 1.88-1.96 (2H, m), 2.88-2.97 (2H, m), 3.70-3.81 (3H, m), 6.73 (1H, d, J = 8.8 Hz), 7.10 (1H, dd, J = 2.7 and 8.8 Hz), 7.70 (1H, d, J = 2.7 Hz) | 194 |
| 75 | 2,3-difluoro-4-nitrophenyl-(4-hydroxypiperidin-1-yl) | yellow solid 90.5-91.5 | CDCl$_3$ 1.66-1.80 (2H, m), 1.97-2.11 (2H, m), 3.09-3.23 (2H, m), 3.53-3.71 (2H, m), 3.91-4.06 (1H, m), 6.61-6.72 (1H, m), 7.79-7.90 (1H, m) | 259 |
| 76 | 2,3-difluoro-4-aminophenyl-(4-hydroxypiperidin-1-yl) | pale yellow solid 148-150 | CD$_3$OD 1.62-1.73 (2H, m), 1.90-2.00 (2H, m), 2.69-2.79 (2H, m), 3.12-3.21 (2H, m), 3.65-3.74 (1H, m), 6.52 (1H, dt, J = 2.2 and 8.9 Hz), 6.65 (1H, dt, J = 2.2 and 8.8 Hz) | 229 |

TABLE 24

| Manufacturing Example No. | Chemical Structure | properties m.p. (° C.) (recryst. solvent) | $^1$H-NMR | MS(FAB) (M + 1)$^+$ |
|---|---|---|---|---|
| 81 | O$_2$N-C$_6$H$_3$(CO$_2$Me)-(4-hydroxypiperidin-1-yl) | pale yellow oil | CDCl$_3$ 1.69-1.80 (2H, m), 1.99-2.10 (2H, m), 3.08-3.19 (2H, m), 3.45-3.56 (2H, m), 3.93 (3H, s), 3.94-4.004 (1H, m), 6.98 (1H, d, J = 9.3 Hz), 8.19 (1H, dd, J = 2.8 and 9.3 Hz), 8.60 (1H, d, J = 2.8 Hz) | 281 |

TABLE 24-continued

| Manufacturing Example No. | Chemical Structure | properties m.p. (° C.) (recryst. solvent) | ¹H-NMR | MS(FAB) (M + 1)⁺ |
|---|---|---|---|---|
| 82 | H₂N–(phenyl with CO₂Me)–N(piperidine-OH) | pale yellow solid 123-124.5 | CDCl₃ 1.47-1.53 (1H, m), 1.67-1.78 (2H, m), 1.95-2.02 (2H, m), 2.70-2.79 (2H, m), 3.10-3.19 (2H, m), 3.50-3.63 (2H, m), 3.74-3.83 (1H, m), 3.88 (3H, s), 6.75 (1H, dd, J = 2.9 and 8.6 Hz), 6.91-6.98 (1H, m), 7.03 (1H, d, J = 2.9 Hz) | 251 |
| 83 | Boc-HN–(piperidine)–N–(tetrahydropyran) | colorress solid 142-145 (EtOH) | CDCl₃ 1.33-1.49 (2H, m), 1.44 (9H, s), 1.52-1.63 (2H, m), 1.70-1.79 (2H, m), 1.90-1.99 (2H, m), 2.19-2.28 (2H, m), 2.44 (1H, tt, J = 3.8 and 11.4 Hz), 2.83-2.92 (2H, m), 3.36 (2H, dt, J = 1.9 and 11.9 Hz), 3.41-3.50 (1H, m), 3.99-4.05 (2H, m), 4.39-4.48 (1H, m) | 285 |
| 84 | H₂N–(piperidine)–N–(tetrahydropyran) · 2HCl | colorless solid | DMSO-d₆ 1.67-1.80 (2H, m), 1.95-2.20 (6H, m), 2.93-3.09 (2H, m), 3.23-3.39 (4H, m), 3.45-3.57 (2H, m), 3.90-4.02 (2H, m), 8.40-8.68 (3H, m), 10.95-11.22 (1H, m) | 185 (free) |

TABLE 25

| Manufacturing Example No. | Chemical Structure | properties m.p. (° C.) (recryst. solvent) | ¹H-NMR | MS(FAB) (M + 1)⁺ |
|---|---|---|---|---|
| 81 | O₂N–(phenyl with CO₂Me)–N(piperidine-OH) | pale yellow oil | CDCl₃ 1.69-1.80 (2H, m), 1.99-2.10 (2H, m), 3.08-3.19 (2H, m), 3.45-3.56 (2H, m), 3.93 (3H, s), 3.94-4.004 (1H, m), 6.98 (1H, d, J = 9.3 Hz), 8.19 (1H, dd, J = 2.8 and 9.3 Hz), 8.60 (1H, d, J = 2.8 Hz) | 281 |
| 82 | H₂N–(phenyl with CO₂Me)–N(piperidine-OH) | pale yellow solid 123-124.5 | CDCl₃ 1.47-1.53 (1H, m), 1.67-1.78 (2H, m), 1.95-2.02 (2H, m), 2.70-2.79 (2H, m), 3.10-3.19 (2H, m), 3.50-3.63 (2H, m), 3.74-3.83 (1H, m), 3.88 (3H, s), 6.75 (1H, dd, J = 2.9 and 8.6 Hz), 6.91-6.98 (1H, m), 7.03 (1H, d, J = 2.9 Hz) | 251 |
| 83 | Boc-HN–(piperidine)–N–(tetrahydropyran) | colorress solid 142-145 (EtOH) | CDCl₃ 1.33-1.49 (2H, m), 1.44 (9H, s), 1.52-1.63 (2H, m), 1.70-1.79 (2H, m), 1.90-1.99 (2H, m), 2.19-2.28 (2H, m), 2.44 (1H, tt, J = 3.8 and 11.4 Hz), 2.83-2.92 (2H, m), 3.36 (2H, dt, J = 1.9 and 11.9 Hz), 3.41-3.50 (1H, m), 3.99-4.05 (2H, m), 4.39-4.48 (1H, m) | 285 |
| 84 | H₂N–(piperidine)–N–(tetrahydropyran) · 2HCl | colorless solid | DMSO-d₆ 1.67-1.80 (2H, m), 1.95-2.20 (6H, m), 2.93-3.09 (2H, m), 3.23-3.39 (4H, m), 3.45-3.57 (2H, m), 3.90-4.02 (2H, m), 8.40-8.68 (3H, m), 10.95-11.22 (1H, m) | 185 (free) |

50

TABLE 26

| Manufacturing Example No. | Chemical Structure | properties m.p. (° C.) (recryst. solvent) | ¹H-NMR | MS(FAB) (M + 1)⁺ |
|---|---|---|---|---|
| 85 | Cbz-HN–(cyclohexyl)–N(piperazine)–N-Boc (cis, trans mixture) | pale yellow oil | CDCl₃ 1.08-1.92 (7H, m), 1.45 (9H, s), 2.03-2.12 (1H, m), 2.19-2.31 (1H, m), 2.42-2.53 (4H, m), 3.37-3.50 (4.5H, m), 3.74-3.83 (0.5H, m), 4.57-4.64 (0.5H, m), 4.83-4.91 (0.5H, m), 5.05-5.14 (2H, m), 7.29-7.41 (5H, m) | 418 |

TABLE 26-continued

| Manufacturing Example No. | Chemical Structure | properties m.p. (° C.) (recryst. solvent) | $^1$H-NMR | MS(FAB) (M + 1)$^+$ |
|---|---|---|---|---|
| 86 | cis, trans mixture | colorless oil | CDCl$_3$ 1.05-1.78 (6H, m), 1.45 and 1.46 (9H, each s), 1.82-1.98 (2H, m), 2.17-2.31 (1H, m), 2.43-2.68 (4.5H, m), 2.98-3.04 (0.5H, m), 3.37-3.47 (4H, m) | 284 |
| 87 | 2HCl | brown solid 145-148 | DMSO-d$_6$ 4.66 (2H, s), 7.60-7.70 (2H, m), 7.94 (1H, d, 2.4 Hz) | 125 (free) |
| 88 | 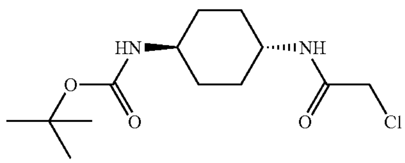 | colorless solid 215-217 (EtOH) | CDCl$_3$ 1.18-1.38 (4H, m), 1.44 (9H, s), 1.99-2.10 (4H, m), 3.39-3.51 (1H, m), 3.69-3.80 (1H, m), 4.03 (2H, s), 4.37-4.46 (1H, m), 6.35-6.42 (1H, m) | 291 |

TABLE 27

| Manufacturing Example No. | Chemical Structure | properties m.p. (° C.) (recryst. solvent) | $^1$H-NMR | MS(FAB) (M + 1)$^+$ |
|---|---|---|---|---|
| 89 | 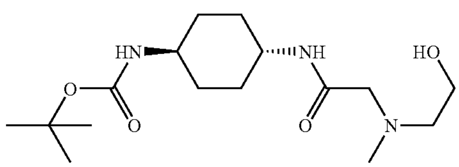 | colorless solid 161-163 (iso-PrOH) | CDCl$_3$ 1.17-1.37 (4H, m), 1.44 (9H, s), 1.92-2.13 (5H, m), 2.33 (3H, s), 2.58 (2H, t, J = 5.2 Hz), 3.06 (2H, s), 3.35-3.48 (1H, m), 3.69 (2H, t, J = 5.2 Hz), 3.71-3.80 (1H, m), 4.38-4.48 (1H, m), 7.09-7.16 (1H, m) | 330 |
| 90 | 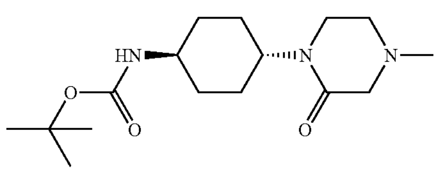 | pale brown solid 162.5-165 | CDCl$_3$ 1.21-1.37 (2H, m), 1.44 (9H, s), 1.48-1.60 (2H, m), 1.63-1.74 (2H, m), 2.01-2.10 (2H, m), 2.32 (3H, s), 2.59-2.65 (2H, m), 3.11 (2H, s), 3.20-3.27 (2H, m), 3.30-3.44 (1H, m), 4.38-4.50 (2H, m) | 312 |
| 91 | 2HCl | colorless solid | DMSO-d$_6$ 1.38-1.71 (6H, m), 1.98-2.09 (2H, m), 3.17 (3H, s), 2.90-3.01 (1H, m), 3.20-3.90 (6H, m), 4.11-4.22 (1H, m), 8.09-8.28 (3H, m), 11.92 (1H, brs) | 212 (free) |
| 92 | cis, trans mixture | colorless gum | CDCl$_3$ 1.06-1.97 (14H, m), 2.02-2.31 (5H, m), 2.81-2.98 (2H, m), 3.37-3.49 (0.4H, m), 3.74-3.87 (0.6H, m), 4.08-4.18 (2H, m), 4.53-4.62 (0.4H, m), 4.83-4.93 (0.6H, m), 5.04-5.19 (2H, m), 7.28-7.43 (5H, m) | 389 |

TABLE 28

| Manufacturing Example No. | Chemical Structure | properties m.p. (° C.) (recryst. solvent) | ¹H-NMR | MS(FAB) (M + 1)⁺ |
|---|---|---|---|---|
| 93 | 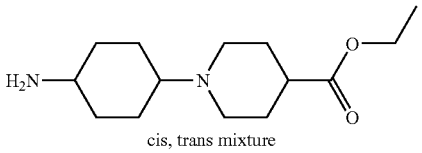<br>cis, trans mixture | colorless oil | CDCl₃ 1.05-1.19 (1H, m), 1.20-1.39(4H, m), 1.50-1.97 (12H, m), 2.12-2.32 (4H, m), 2.62 (0.4H, tt, J = 3.9 and 11.1 Hz), 2.74-3.00 (2H, m), 3.01-3.09 (0.6H, m), 4.08-4.19 (2H, m) | 255 |
| 94 | 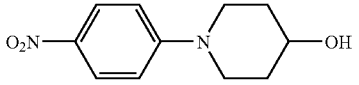 | yellow solid 106-107 (EtOH) | CDCl₃ 1.53-1.56 (1H, m), 1.62-1.72 (2H, m), 1.98-2.06 (2H, m), 3.21-3.29 (2H, m), 3.76-3.84 (2H, m), 3.97-4.06 (1H, m), 6.81-6.87 (2H, m), 8.10-8.16 (2H, m) | 223 |
| 95 | 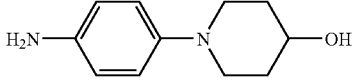 | pale purple solid 171-173 | CDCl₃ 1.45 (1H, br), 1.68-1.77 (2H, m), 1.98-2.06 (2H, m), 2.74-2.83 (2H, m), 3.32-3.40 (2H, m), 3.42 (2H, br), 3.76-3.85 (1H, m), 6.63-6.68 (2H, m), 6.81-6.86 (2H, m) | 193 |

TABLE 29

| Example No. | Chemical Structure | properties m.p. (° C.) (recryst. solvent) | ¹H-NMR | MS(FAB) (M + 1)⁺ |
|---|---|---|---|---|
| 1 | 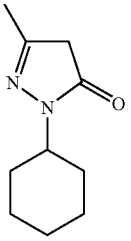 | colorless cryst. 147.6-150.4 | CDCl₃ 1.21-1.36 (1H, m), 1.39-1.52 (2H, m), 1.71-1.98 (7H, m), 2.09 (3H, s), 3.20 (2H, s) 3.95-4.02 (1H, m) | 181 |
| 2 | 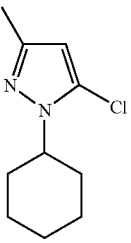 | pale brown oil | CDCl₃ 1.21-1.47 (3H, m), 1.65-1.75 (1H, m), 1.83-1.95 (6H, m), 2.23 (3H, s), 4.10-4.20 (1H, m), 5.95 (1H, s) | |
| 3 | 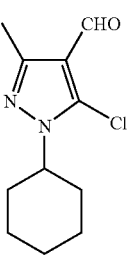 | colorless cryst. 86.0-87.6 | CDCl₃ 1.21-1.50 (3H, m), 1.71-1.79 (1H, m), 1.90-1.98 (6H, m), 2.46 (3H, s), 4.18-4.28 (1H, m), 9.88 (1H, s) | 227 |

TABLE 29-continued

| Example No. | Chemical Structure | properties m.p. (° C.) (recryst. solvent) | ¹H-NMR | MS(FAB) (M + 1)⁺ |
|---|---|---|---|---|
| 4 | [pyrazole with CHO, methyl, and N-cyclohexyl, S-CH₂-COOEt substituents] | colorless oil | CDCl₃ 1.21 (3H, t, J = 7.1 Hz), 1.22-1.50 (3H, m), 1.71-2.01 (7H, m), 2.48 (3H, s), 3.59 (2H, s), 4.12 (2H, q, J = 7.1 Hz), 4.58-4.60 (1H, m), 10.02 (1H, s) | 311 |

TABLE 30

| Example No. | Chemical Structure | properties m.p. (° C.) (recryst. solvent) | ¹H-NMR | MS(FAB) (M + 1)⁺ |
|---|---|---|---|---|
| 5 | [thieno[2,3-c]pyrazole with methyl, N-cyclohexyl, COOEt] | colorless oil | CDCl₃ 1.22-1.34 (1H, m), 1.38 (3H, t, J = 7.1 Hz), 1.38-1.52 (2H, m), 1.70-1.88 (3H, m), 1.89-1.98 (2H, m), 2.15-2.22 (2H, m), 2.45 (3H, s), 4.12-4.21 (1H, m), 4.35 (2H, q, J = 7.1 Hz), 7.70(1H, s) | 293 |
| 6 | [thieno[2,3-c]pyrazole with methyl, N-cyclohexyl, COOH] | colorless cryst. 231.5-235.0 | CDCl₃ 1.22-1.37 (1H, m), 1.39-1.51 (2H, m), 1.72-1.89 (3H, m), 1.91-1.98 (2H, m), 2.16-2.24 (2H, m), 2.47 (3H, s), 4.16-4.25 (1H, m), 7.79 (1H, s) | 265 |
| 7 | [thieno[2,3-c]pyrazole with methyl, N-cyclohexyl, CONHCH₂Ph] | colorless cryst. 128.4-130.1 | CDCl₃ 1.21-1.33 (1H, m), 1.38-1.51 (2H, m), 1.70-1.87 (3H, m), 1.89-1.95 (2H, m), 2.14-2.21 (2H, m), 2.42 (3H, s), 4.10-4.21 (1H, m), 4.63 (1H, d, J = 5.7 Hz), 6.11-6.17 (1H, m), 7.29-7.37 (6H, m) | 354 |
| 8 | [thieno[2,3-c]pyrazole with methyl, N-cyclohexyl, CONHPh] | colorless cryst 149.0-150.0 | CDCl₃ 1.24-1.35 (1H, m), 1.40-1.52 (2H, m), 1.72-1.99 (5H, m), 2.15-2.23 (2H, m), 2.47 (3H, s), 4.15-4.26 (1H, m), 7.12-7.16 (1H, m), 7.35-7.40 (2H, m), 7.47 (1H, s), 7.49-7.51 (3H, m) | 340 |

TABLE 31

| Example No. | Chemical Structure | properties m.p. (° C.) (recryst. solvent) | ¹H-NMR | MS(FAB) (M + 1)⁺ |
|---|---|---|---|---|
| 9 | 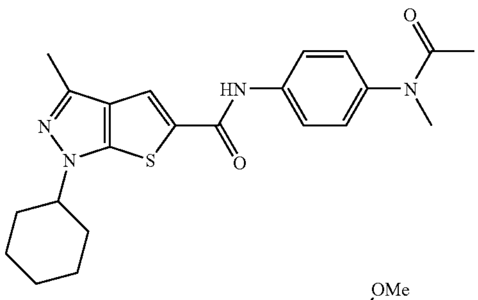 | colorless cryst. 221.8-224.2 | CDCl₃ 1.25-1.53 (3H, m), 1.74-1.96 (5H, m), 1.89 (3H, s), 2.19-2.23 (2H, m), 2.47 (3H, s), 3.26 (3H, s), 4.18-4.23 (1H, m), 7.17-7.20 (2H, m), 7.49 (1H, s), 7.64-7.67 (3H, m) | 411 |
| 10 | 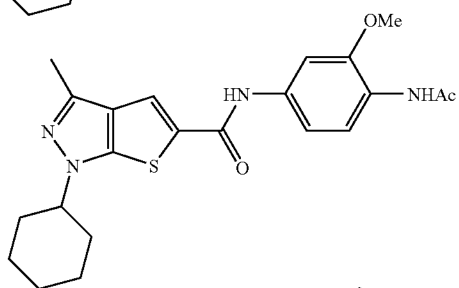 | colorless cryst. 241.5-242.8 | CDCl₃ 1.23-1.33 (1H, m), 1.40-1.52 (2H, m), 1.70-1.97 (5H, m), 2.17-2.23 (2H, m), 2.20 (3H, s), 2.46 (3H, s), 3.93 (3H, s), 4.13-4.20 (1H, m), 6.73-6.76 (1H, m), 7.46 (1H, s), 7.59-7.61 (1H, m), 7.67-7.69 (1H, m), 7.77-7.79 (1H, m), 8.30-8.34 (1H, m) | 427 |
| 11 | 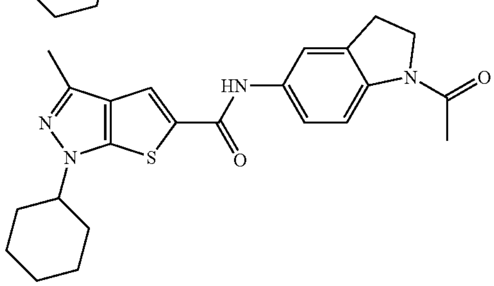 | colorless cryst. >270 | CDCl₃ 1.23-1.33 (1H, m), 1.40-1.52 (2H, m), 1.71-1.97 (5H, m), 2.15-2.22 (2H, m), 2.22 (3H, s), 2.46 (3H, s), 3.22 (2H, t, J = 8.5 Hz), 4.08 (2H, t, J = 8.5 Hz), 4.13-4.21 (1H, m), 7.05-7.08 (1H, m), 7.44 (1H, s), 7.53-7.55 (1H, m), 7.79 (1H, brs), 8.16-8.19 (1H, m) | 423 |
| 12 | 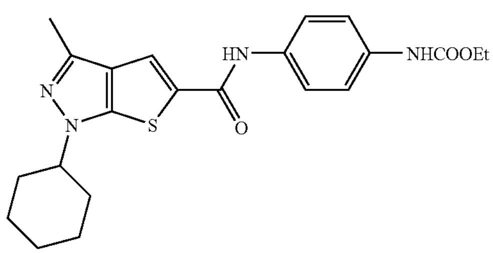 | colorless cryst. 195.9-197.9 | CDCl₃ 1.23-1.33 (1H, m), 1.31 (3H, t, J = 7.1 Hz), 1.41-1.54 (2H, m), 1.71-1.95 (5H, m), 2.15-2.22 (2H, m), 2.46 (3H, s), 4.15-4.22 (1H, m), 4.23 (2H, q, J = 7.1 Hz), 6.52(1H, brs), 7.36-7.38 (2H, m), 7.45 (1H, s), 7.52-755 (3H, m) | 427 |

TABLE 32

| Example No. | Chemical Structure | properties m.p. (° C.) (recryst. solvent) | ¹H-NMR | MS(FAB) (M + 1)⁺ |
|---|---|---|---|---|
| 13 | 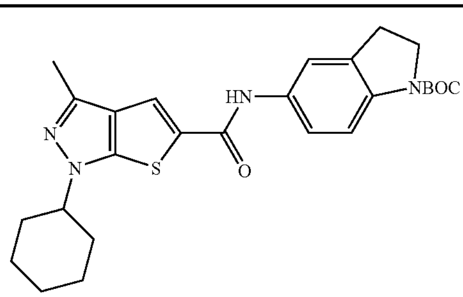 | colorless cryst/ 200.3-200.8 | CDCl₃ 1.23-1.32 (1H, m), 1.39-1.52 (2H, m), 1.53 (9H, s), 1.73-1.96 (5H, m), 2.16-2.24 (2H, m), 2.46 (3H, s), 3.10 (2H, t, J = 8.5 Hz), 3.99 (2H, t, J = 8.5 Hz), 4.15-4.22 (1H, m), 7.08-7.20 (1H, m), 7.44 (1H, s), 7.53 (1H, brs), 7.58-7.72 (1H, m) | 481 |

TABLE 32-continued

| Example No. | Chemical Structure | properties m.p. (° C.) (recryst. solvent) | ¹H-NMR | MS(FAB) (M + 1)⁺ |
|---|---|---|---|---|
| 14 | 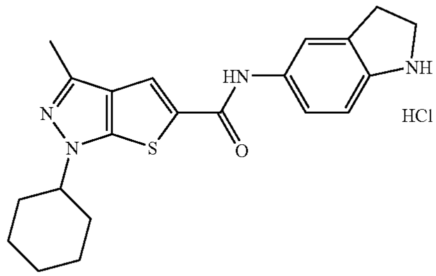 | colorless cryst. 268.3-271.2 | DMSO 1.23-1.33 (1H, m), 1.40-1.51 (2H, m), 1.66-1.90 (5H, m), 2.04-2.13 (2H, m), 2.40 (3H, s), 3.23 (2H, t, J = 7.7 Hz), 3.74 (2H, t, J = 7.7 Hz), 4.29-4.31 (1H, m), 7.41-7.45 (1H, m), 7.69-7.72 (1H, m), 7.90-7.92 (1H, m), 8.17 (1H, s), 10.49-10.51 (1H, m), 11.18 (1H, brs) | 381 |
| 15 | 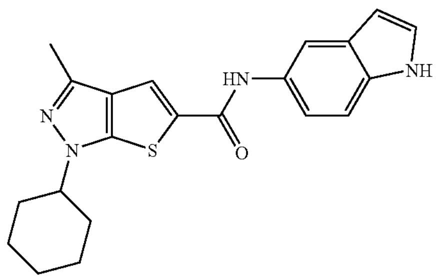 | pale brown cryst. 234.3-235.6 | CDCl₃ 1.23-1.32 (1H, m), 1.39-1.52 (2H, m), 1.72-1.98 (5H, m), 2.16-2.23 (2H, m), 2.46 (3H, s), 4.13-4.22 (1H, m), 6.53-6.55 (1H, m), 7.21-7.23 (1H, m), 7.31-7.38 (2H, m), 7.47 (1H, s), 7.67 (1H, brs), 7.89-7.91 (1H, m), 8.20 (1H, brs) | 379 |
| 16 | 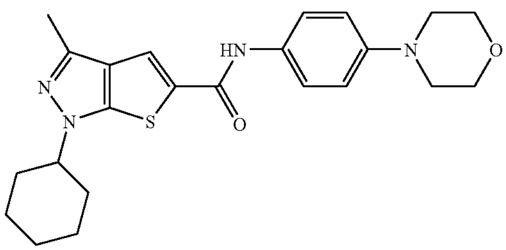 | pale yellow cryst. 216.9-218.4 | CDCl₃ 1.23-1.32 (1H, m), 1.40-1.52 (2H, m), 1.71-1.88 (3H, m), 1.90-1.98 (2H, m), 2.15-2.22 (2H, m), 2.46 (3H, s), 3.12-3.16 (4H, m), 3.85-3.88 (4H, m), 4.13-4.22 (1H, m), 6.90-6.93 (2H, m), 7.43 (1H, s), 7.47-7.51 (3H, m) | 424 |

TABLE 33

| Example No. | Chemical Structure | properties m.p. (° C.) (recryst. solvent) | ¹H-NMR | MS (FAB) (M + 1)⁺ |
|---|---|---|---|---|
| 17 | 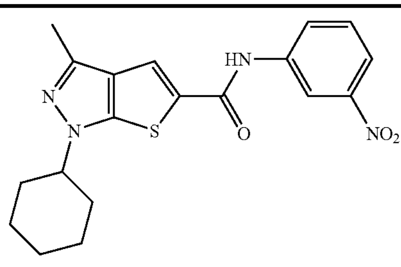 | pale yellow cryst. 193.1-194.8 | CDCl₃ 1.23-1.35 (1H, m), 1.40-1.52 (2H, m), 1.72-1.89 (3H, m), 1.90-1.98 (2H, m), 2.17-2.23 (2H, m), 2.48 (3H, s), 4.16-4.24 (1H, m), 7.51-7.57 (2H, m), 7.80 (1H, brs), 8.00 (1H, dd, J = 1.8 and 8.2 Hz), 8.07 (1H, dd, J = 1.8 and 8.2 Hz), 8.43 (1H, s) | 385 |
| 18 | 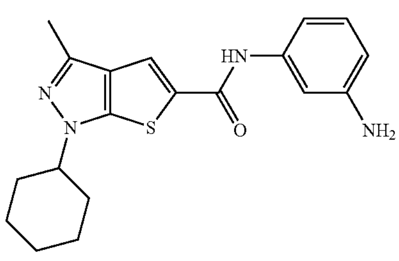 | yellow cryst. 150.0-153.8 | CDCl₃ 1.23-1.35 (1H, m), 1.39-1.55 (2H, m), 1.72-1.98 (5H, m), 2.16-2.23 (2H, m), 2.46 (3H, s), 3.49 (2H, brs), 4.15-4.24 (1H, m), 6.75-6.84 (2H, m), 7.06-7.09 (1H, m), 7.43-7.46 (2H, m), 7.60 (1H, brs) | 355 |

TABLE 33-continued

| Example No. | Chemical Structure | properties m.p. (° C.) (recryst. solvent) | ¹H-NMR | MS (FAB) (M + 1)⁺ |
|---|---|---|---|---|
| 19 | (structure) | pale yellow cryst. >270 | DMSO 1.20-1.31 (1H, m), 1.39-1.51 (2H, m), 1.65-1.88 (5H, m). 2.01-2.11 (2H, m), 2.05 (3H, s), 2.40 (3H, s), 4.18-4.26 (1H, m), 7.21-7.29 (2H, m), 7.39-7.42 (1H, m), 8.06-8.11 (2H, m), 9.93 (1H. brs), 10.21 (1H, brs) | 397 |
| 20 | (structure) | colorless cryst. >270 (EtOH) | DMSO 1.19-1.30 (1H, m), 1.37-1.50 (2H, m), 1.63-1.87 (5H, m), 2.04-2.11 (2H, m), 2.40 (3H, s), 2.78 (3H, d, J = 4.4 Hz), 4.16-4.22 (1H, m), 7.78-7.85 (4H, m), 8.10 (1H, s), 8.30-8.32 (1H, m), 10.38 (1H, brs) | 397 |

TABLE 34

| Example No. | Chemical Structure | properties m.p. (° C.) (recryst. solvent) | ¹H-NMR | MS (FAB) (M + 1)⁺ |
|---|---|---|---|---|
| 21 | (structure) | colorless cryst. 223.2-226.5 | CDCl₃ 1.25 (3H, t, J = 7.3 Hz), 1.23-1.35 (1H, m), 1.39-1.55 (2H, m), 1.72-1.89 (3H, m), 1.90-1.98 (2H, m), 2.18-2.24 (2H, m), 2.41-2.49 (2H, m), 2.46 (3H, s), 3.22 (2H, t, J = 8.5 Hz), 4.07 (2H, t, J = 8.5 Hz), 4.17-4.25 (1H, m), 7.06-7.09 (1H, m), 7.45 (1H, s), 7.59-7.61 (1H, m), 7.78-7.80 (1H, m), 8.19-8.22 (1H, m) | 437 |
| 22 | (structure) | pale yellow cryst. 155.0-159.0 | CDCl₃ 0.88 (3H, t, J = 6.8 Hz), 1.23-1.52 (3H, m), 1.73-1.98 (5H, m), 2.17-2.22 (2H, m), 2.45 (3H, s), 3.13 (2H, t, J = 8.6 Hz), 4.03 (2H, t, J = 8.6 Hz), 4.15-4.23 (1H, m), 4.22-4.37 (2H, m), 7.11-7.18 (1H, m), 7.45 (1H, s), 7.59 (1H, brs), 7.63-7.74 (1H, m), 7.75-7.89 (1H, m) | 453 |
| 23 | (structure) | colorless cryst. 192.8-196.6 | CDCl₃ 1.23 (6H, d, J = 6.7 Hz), 1.23-1.35 (1H, m), 1.38-1.52 (2H, m), 1.72-1.99 (5H, m), 2.17-2.22 (2H, m), 2.46 (3H, s), 2.74-2.83 (1H, m), 3.22 (2H, t, J = 8.4 Hz), 4.09-4.24 (1H, m), 4.15 (2H, t, J = 8.4 Hz), 7.05-7.09 (1H, m), 7.45 (1H, s), 7.59-7.61 (1H, m), 7.79-7.81 (1H, m), 8.22-8.25 (1H, m) | 451 |

TABLE 34-continued

| Example No. | Chemical Structure | properties m.p. (° C.) (recryst. solvent) | ¹H-NMR | MS (FAB) (M + 1)⁺ |
|---|---|---|---|---|
| 24 | 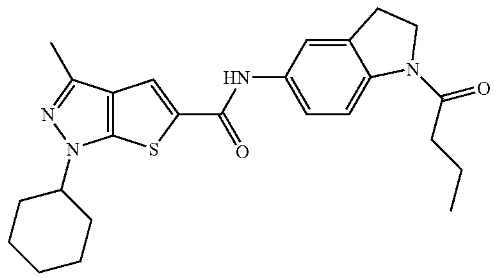 | colorless cryst. 179.9-183.1 | CDCl₃ 1.03 (3H, t, J = 7.3 Hz), 1.23-1.35 (1H, m), 1.38-1.52 (2H, m), 1.74-1.99 (7H, m), 2.18-2.24 (2H, m), 2.40 (2H, t, J = 7.3 Hz), 2.46 (3H, s), 3.21 (2H, t, J = 8.5 Hz), 4.08 (2H, t, J = 8.5 Hz), 4.12-4.27 (1H, m), 7.06-7.09 (1H, m), 7.45 (1H, s), 7.59-7.61 (1H, m), 7.79-7.81 (1H, m), 8.20-8.23 (1H, m) | 451 |

TABLE 35

| Example No. | Chemical Structure | properties m.p. (° C.) (recryst. solvent) | ¹H-NMR | MS (FAB) (M + 1)⁺ |
|---|---|---|---|---|
| 25 | 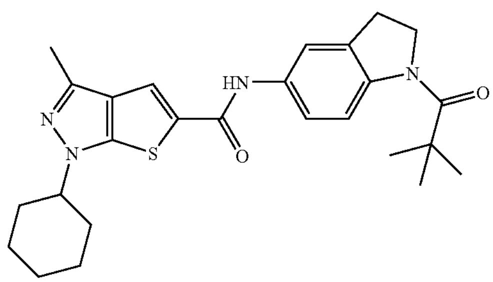 | colorless cryst. 162.8-167.3 | CDCl₃ 1.21-1.51 (3H, m), 1.38 (9H, s), 1.72-1.99 (5H, m), 2.18-2.22 (2H, m), 2.45 (3H, s), 3.15 (2H, t, J = 8.1 Hz), 4.12-4.27 (1H, m), 4.25 (2H, t, J = 8.1 Hz), 7.08(1H, dd, J = 2.1 and 8.7 Hz), 7.45 (1H, s), 7.62-7.65 (1H, m), 7.79-7.81 (1H, m), 8.19-8.22 (1H, m) | 465 |
| 26 | 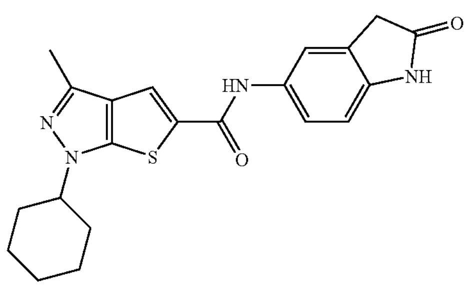 | pale yellow cryst. 171.8-176.3 | CDCl₃ 1.22-1.37 (1H, m), 1.39-1.52 (2H, m), 1.72-1.89 (3H, m), 1.90-1.99 (2H, m), 2.18-2.24 (2H, m), 2.46 (3H, s), 3.56 (2H, s), 4.14-4.22 (1H, m), 6.81-6.84 (1H, m), 7.28-7.31 (1H, m), 7.46 (1H, s), 7.50-7.52 (1H, m), 7.55-7.58 (1H, m), 7.62-7.64 (1H, m) | 395 |
| 27 | 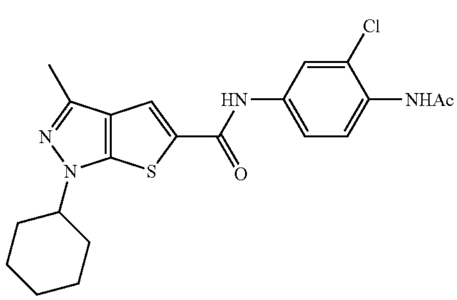 | vcolorless cryst. >270 EtOH | DMSO 1.19-1.30 (1H, m), 1.37-1.50 (2H, m), 1.63-1.88 (5H, m), 2.04-2.11 (2H, m), 2.08 (3H, s), 2.40 (3H, s), 4.19-4.28 (1H, m), 7.60-7.65 (2H, m), 7.96-7.98 (1H, m), 8.06 (1H, s), 9.49 (1H, brs), 10.36 (1H, brs) | 431 |

TABLE 35-continued

| Example No. | Chemical Structure | properties m.p. (° C.) (recryst. solvent) | $^1$H-NMR | MS (FAB) (M + 1)$^+$ |
|---|---|---|---|---|
| 28 | 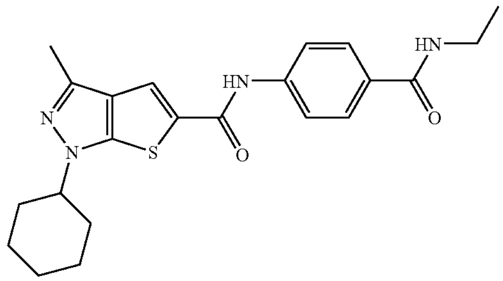 | colorless cryst. 262.2-263.8 EtOH | DMSO 1.12 (3H, t, J = 7.2 Hz), 1.21-1.30 (1H, m), 1.38-1.50 (2H, m), 1.63-1.88 (5H, m), 2.04-2.11 (2H, m), 2.40 (3H, s), 3.23-3.32 (2H, m), 4.19-4.28 (1H, m), 7.78-7.86 (4H, m), 8.11 (1H, s), 8.35-8.36 (1H, m), 10.46 (1H, brs) | 411 |

TABLE 36

| Example No. | Chemical Structure | properties m.p. (° C.) (recryst. solvent) | $^1$H-NMR | MS (FAB) (M + 1)$^+$ |
|---|---|---|---|---|
| 29 | 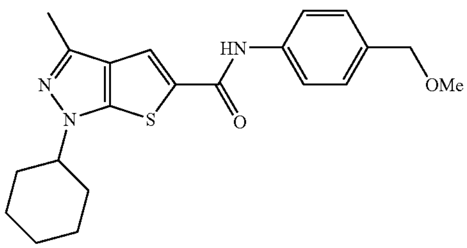 | pale yellow cryst. 135.2-136.3 | CDCl$_3$ 1.22-1.35 (1H, m), 1.39-1.52 (2H, m), 1.72-1.98 (5H, m), 2.16-2.22 (2H, m), 2.46 (3H, s), 3.39 (3H, s), 4.14-4.22 (1H, m), 4.44 (2H, s), 7.33-7.36 (2H, m), 7.47 (1H, s), 7.57-7.60 (3H, m) | 384 |
| 30 | 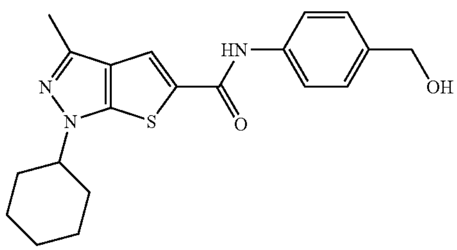 | pale yellow cryst. 190.0-191.9 | CDCl$_3$ 1.22-1.35 (1H, m), 1.39-1.51 (2H, m), 1.72-1.98 (5H, m), 2.17-2.22 (2H, m), 2.47 (3H, s), 4.12-4.22 (1H, m), 4.68 (2H, d, J = 5.1 Hz), 7.35-7.39 (2H, m), 7.48 (1H, s), 7.58-7.61 (2H, m), 7.64 (1H, brs) | 370 |
| 31 | 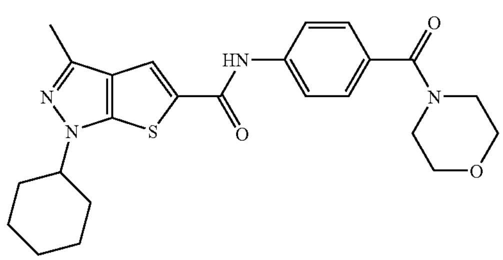 | colorless cryst. 246.5-248.3 | CDCl$_3$ 1.22-1.35 (1H, m), 1.39-1.51 (2H, m), 1.72-1.89 (3H, m), 1.90-1.98 (2H, m), 2.17-2.22 (2H, m), 2.47 (3H, s), 3.39-3.89 (8H, m), 4.13-4.25 (1H, m), 7.40-7.43 (2H, m), 7.55 (1H, s), 7.61-7.64 (2H, m), 7.85 (1H, brs) | 453 |
| 32 | 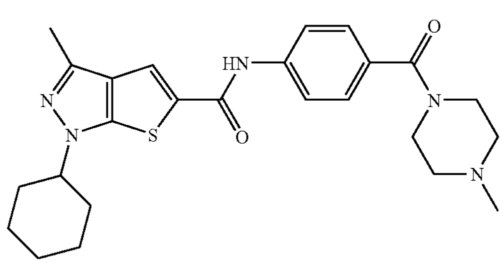 | colorless cryst. 193.2-196.0 | CDCl$_3$ 1.22-1.34 (1H, m), 1.39-1.51 (2H, m), 1.72-1.89 (3H, m), 1.90-1.98 (2H, m), 2.16-2.25 (2H, m), 2.38-2.56 (4H, m), 2.36 (3H, s), 2.47 (3H, s), 3.36-3.90 (4H, m), 4.15-4.25 (1H, m), 7.39-7.42 (2H, m), 7.56 (1H, s), 7.59-7.62 (2H, m), 7.91 (1H, brs) | 466 |

TABLE 37

| Example No. | Chemical Structure | properties m.p. (° C.) (recryst. solvent) | $^1$H-NMR | MS (FAB) (M + 1)$^+$ |
| --- | --- | --- | --- | --- |
| 33 | 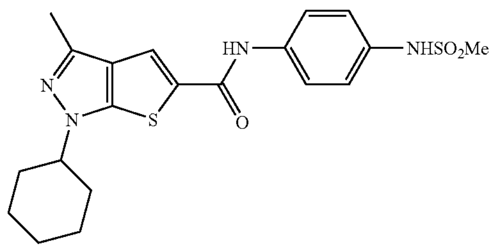 | colorless cryst. 240.0-243.1 EtOH | DMSO 1.17-1.30 (1H, m), 1.38-1.50 (2H, m), 1.62-1.88 (5H, m), 2.03-2.11 (2H, m), 2.40 (3H, s), 2.95 (3H, s), 4.17-4.25 (1H, m), 7.18-7.21 (2H, m), 7.66-7.69 (2H, m), 8.05 (1H, s), 9.60 (1H, brs), 10.23 (1H, brs) | 433 |
| 34 | 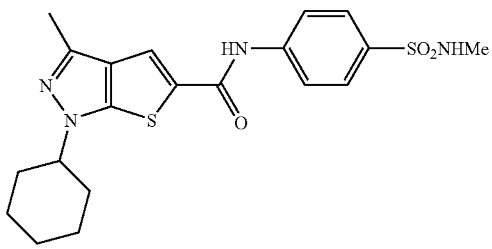 | pale yellow cryst. 338.7-240.0 AcOEt/hexane | CDCl$_3$ 1.20-1.31 (1H, m), 1.39-1.50 (2H, m), 1.63-1.89 (5H, m), 2.03-2.12 (2H, m), 2.41 (3H, s), 2.42 (3H, s), 4.19-4.29 (1H, m), 7.31-7.36 (1H, m), 7.75-7.78 (2H, m), 7.93-7.96 (2H, m), 8.13 (1H, s), 10.55 (1H, brs) | 433 |
| 35 | 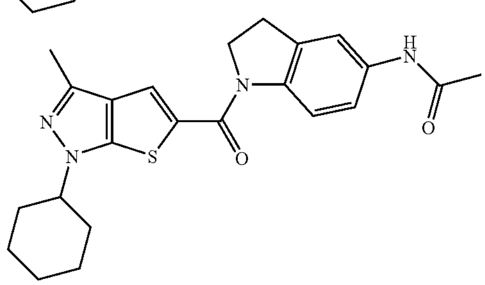 | colorless cryst. 203.9-207.1 EtOH | DMSO 1.18-1.31 (1H, m), 1.36-1.51 (2H, m), 1.61-1.89 (5H, m), 2.00-2.11 (2H, m), 2.03 (3H, s), 2.39 (3H, s), 3.22 (2H, t, J = 8.0 Hz), 4.15-4.26 (1H, m), 4.49 (2H, t, J = 8.0 Hz), 7.28-7.31 (1H, m), 7.60-7.62 (1H, m), 7.79 (1H, s), 7.95-7.98 (1H, m), 9.91 (1H, brs) | 423 |
| 36 | 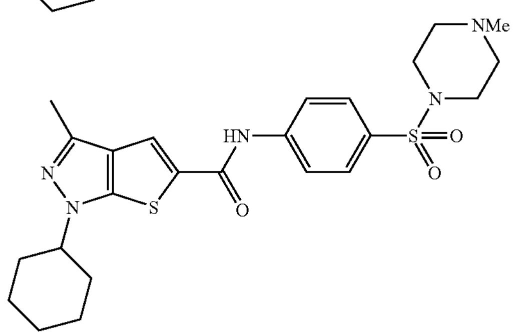 | colorless cryst. 223.5-225.0 | CDCl$_3$ 1.21-1.38 (1H, m), 1.41-1.55 (2H, m), 1.73-1.91 (3H, m), 1.91-2.00 (2H, m), 2.16-2.25 (2H, m), 2.27 (3H, s), 2.42-2.55 (4H, m), 3.00-3.12 (4H, m), 4.16-4.25 (1H, m), 7.52 (1H, s), 7.73-7.80 (5H, m) | 502 |

TABLE 38

| Example No. | Chemical Structure | properties m.p. (° C.) (recryst. solvent) | $^1$H-NMR | MS (FAB) (M + 1)$^+$ |
| --- | --- | --- | --- | --- |
| 37 | 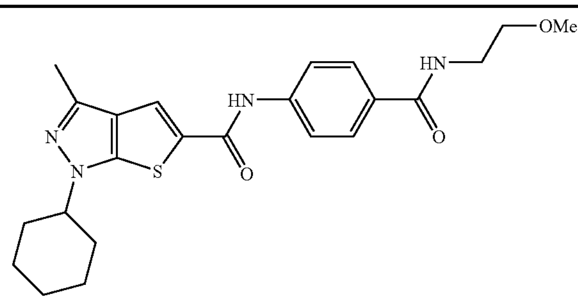 | colorless cryst. 203.2-205.8 | CDCl$_3$ 1.22-1.38 (1H, m), 1.40-1.53 (2H, m), 1.72-1.90 (3H, m), 1.91-1.99 (2H, m), 2.16-2.22 (2H, m), 2.40 (3H, s), 3.40 (3H, s), 3.55-3.60 (2H, m), 3.64-3.69 (2H, m), 4.15-4.25 (1H, m), 6.48-6.52 (1H, m), 7.52 (1H, s), 7.67-7.71 (2H, m), 7.78-7.81 (2H, m), 7.83 (1H, brs) | 441 |

TABLE 38-continued

| Example No. | Chemical Structure | properties m.p. (° C.) (recryst. solvent) | $^1$H-NMR | MS (FAB) (M + 1)$^+$ |
|---|---|---|---|---|
| 38 | 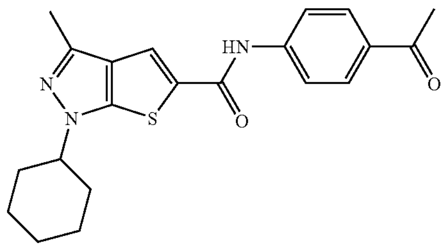 | colorless cryst. 177.8-179.4 | CDCl$_3$ 1.22-1.36 (1H, m), 1.40-1.53 (2H, m), 1.72-1.89 (3H, m), 1.91-1.99 (2H, m), 2.16-2.23 (2H, m), 2.47 (3H, s), 2.60 (3H, s), 4.15-4.25 (1H, m), 7.51 (1H, s) 7.71-7.74 (2H, m), 7.78 (1H, brs), 7.97-8.01 (2H, m) | 382 |
| 39 | 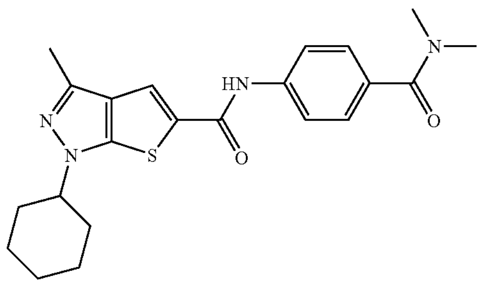 | colorless cryst. 239.0-243.8 | CDCl$_3$ 1.22-1.36 (1H, m), 1.40-1.52 (2H, m), 1.72-1.89 (3H, m), 1.90-1.99 (2H, m), 2.17-2.24 (2H, m), 2.47 (3H, s), 3.02 (3H, brs), 3.12 (3H, brs), 4.15-4.25 (1H, m), 7.37 (2H, dd, J = 1.8 and 8.5 Hz), 7.55 (2H, dd, J = 1.8 and 8.5 Hz), 7.64 (1H, s), 8.17 (1H, brs) | 411 |
| 40 | 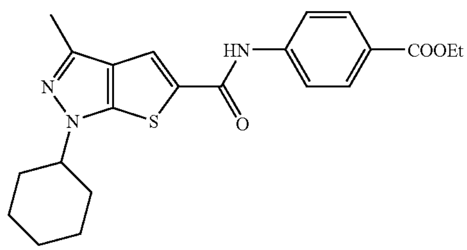 | colorless cryst. 159.5-163.3 | CDCl$_3$ 1.22-1.36 (1H, m), 1.40 (3H, t, J = 7.1 Hz), 1.40-1.52 (2H, m), 1.72-1.89 (3H, m), 1.90-1.99 (2H, m), 2.17-2.24 (2H, m), 2.47 (3H, s), 4.15-4.25 (1H, m), 4.37 (2H, q, J = 7.1 Hz), 7.50 (1H, s), 7.68-7.71 (2H, m), 7.74 (1H, brs), 8.04-8.08 (2H, m) | 412 |

TABLE 39

| Example No. | Chemical Structure | properties m.p. (° C.) (recryst. solvent) | $^1$H-NMR | MS (FAB) (M + 1)$^+$ |
|---|---|---|---|---|
| 41 | 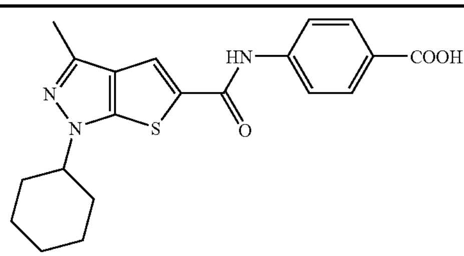 | colorless cryst. 265.9-268.8 | DMSO 1.18-1.31 (1H, m), 1.39-1.51 (2H, m), 1.62-1.89 (5H, m), 2.04-2.11 (2H, m), 2.41 (3H, s), 4.18-4.26 (1H, m), 7.84-7.87 (2H, m), 7.92-7.95 (2H, m), 8.13 (1H, s), 10.48 (1H, brs) | 384 |
| 42 | 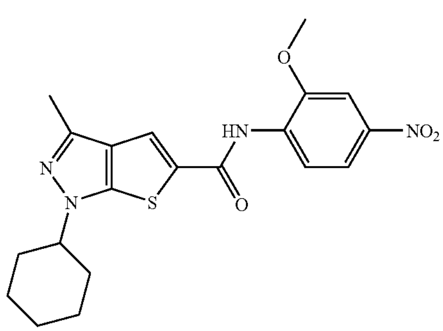 | colorless cryst. 215.8-216.8 | CDCl$_3$ 1.22-1.38 (1H, m), 1.40-1.52 (2H, m), 1.72-1.89 (3H, m), 1.90-1.99 (2H, m), 2.18-2.24 (2H, m), 2.50 (3H, s), 4.09 (3H, s), 4.15-4.25 (1H, m), 7.50 (1H, s), 7.81 (1H, d, J = 2.3 Hz), 7.97 (1H, dd, J = 2.3 and 9.0 Hz), 8.54 (1H, brs), 8.65 (1H, d, J = 9.0 Hz) | 415 |

TABLE 39-continued

| Example No. | Chemical Structure | properties m.p. (° C.) (recryst. solvent) | ¹H-NMR | MS (FAB) (M + 1)⁺ |
|---|---|---|---|---|
| 43 | 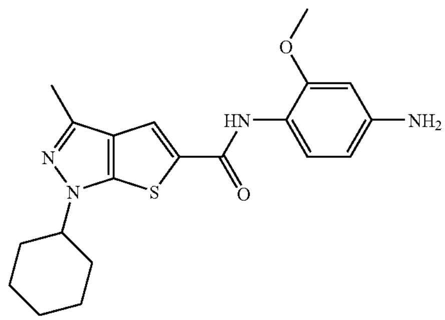 | yellow cryst. 102.2-105.0 | CDCl₃ 1.22-1.37 (1H, m), 1.39-1.52 (2H, m), 1.70-1.98 (5H, m), 2.17-2.23 (2H, m), 2.47 (3H, s), 3.62 (2H, brs), 3.90 (3H, s), 4.13-4.24 (1H, m), 6.30-6.35 (2H, m), 7.40 (1H, s), 8.06 (1H, brs), 8.12-8.15 (1H, m) | 384 (M+) |
| 44 | 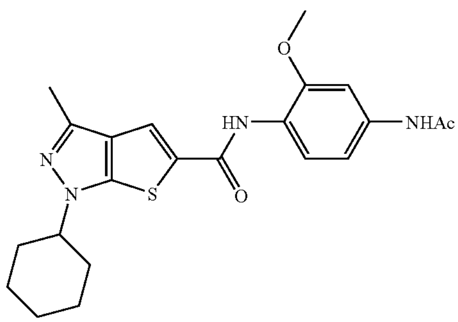 | pale yellow cryst. 263.1-265.3 EtOH | DMSO 1.18-1.31 (1H, m), 1.38-1.51 (2H, m), 1.63-1.88 (5H, m), 2.04-2.11 (2H, m), 2.05 (3H, s), 2.38 (3H, s), 3.79 (3H, s), 4.15-4.29 (1H, m), 7.08-7.11 (1H, m), 7.45-7.51 (2H, m), 8.02 (1H, s), 9.45 (1H, brs), 9.97 (1H, brs) | 427 |

TABLE 40

| Example No. | Chemical Structure | properties m.p. (° C.) (recryst. solvent) | ¹H-NMR | MS (FAB) (M + 1)⁺ |
|---|---|---|---|---|
| 45 | 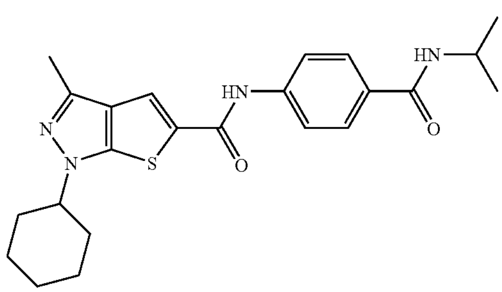 | ccolorless cryst. 255.7-259.5 EtOH | DMSO 1.16 (6H, d, J = 6.6 Hz), 1.18-1.31 (1H, m), 1.38-1.51 (2H, m), 1.63-1.88 (5H, m), 2.03-2.12 (2H, m), 2.41 (3H, s), 4.04-4.15 (1H, m), 4.19-4.28 (1H, m), 7.78-7.81 (2H, m), 7.84-7.87 (2H, m), 8.09 (1H, d, J = 7.4 Hz), 8.11 (1H, s), 10.39 (1H, brs) | 425 |
| 46 | 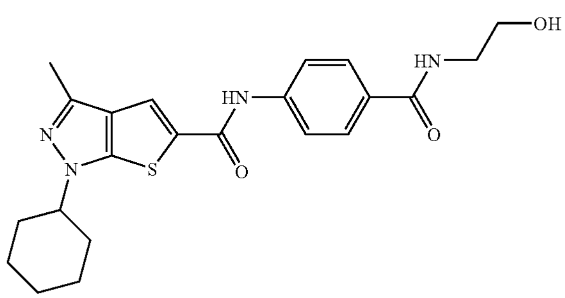 | colorless cryst. 194.2-196.0 | DMSO 1.20-1.33 (1H, m), 1.39-1.54 (2H, m), 1.65-1.95 (5H, m), 2.05-2.15 (2H, m), 2.41 (3H, s), 3.26-3.40 (2H, m), 3.49-3.59 (2H, m), 4.18-4.29 (1H, m), 4.69-4.73 (1H, m), 7.79-7.88 (4H, m), 8.11 (1H, s), 8.31-8.35 (1H, m), 10.40 (1H, brs) | 427 |

TABLE 40-continued

| Example No. | Chemical Structure | properties m.p. (° C.) (recryst. solvent) | ¹H-NMR | MS (FAB) (M + 1)⁺ |
|---|---|---|---|---|
| 47 | 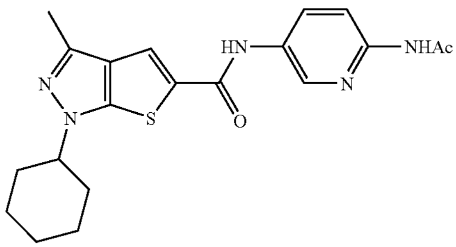 | colorless cryst. >270 EtOH | DMSO 1.19-1.33 (1H, m), 1.39-1.52 (2H, m), 1.63-1.90 (5H, m), 2.05-2.12 (2H, m), 2.08 (3H, s), 2.40 (3H, s), 4.18-4.28 (1H, m), 8.01-8.08 (2H, m), 8.04 (1H, s), 8.65-8.67 (1H, m), 10.36 (1H, brs), 10.45 (1H, brs) | 398 |
| 48 | 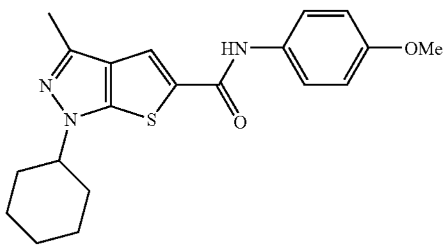 | colorless cryst. 133.5-136.0 | CDCl₃ 1.22-1.37 (1H, m), 1.39-1.52 (2H, m), 1.71-1.98 (5H, m), 2.16-2.23 (2H, m), 2.46 (3H, s), 3.81 (3H, s), 4.13-4.25 (1H, m), 6.91 (2H, dd, J = 2.1 and 6.9 Hz), 7.44 (1H, s), 7.49 (2H, dd, J = 2.1 and 6.9 Hz), 10.51 (1H, brs) | 370 |

TABLE 41

| Example No. | Chemical Structure | properties m.p. (° C.) (recryst. solvent) | ¹H-NMR | MS (FAB) (M + 1)⁺ |
|---|---|---|---|---|
| 49 | 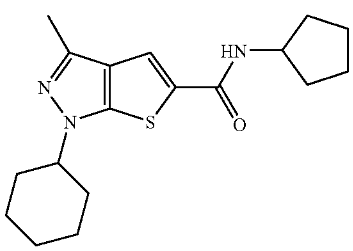 | colorless cryst. 161.0-164.2 | CDCl₃ 1.22-1.35 (1H, m), 1.39-1.54 (4H, m), 1.61-1.98 (9H, m), 2.04-2.21 (4H, m), 2.43 (3H, s), 4.13-4.22 (1H, m), 4.31-4.42 (1H, m), 5.80 (1H, d, J = 6.6 Hz), 7.29 (1H, s) | 332 |
| 50 | 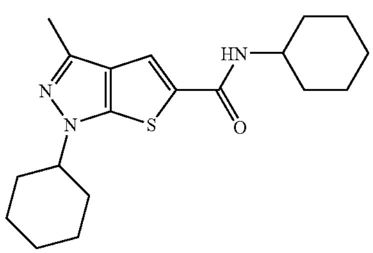 | colorless cryst. 184.0-185.8 | CDCl₃ 1.15-1.35 (4H, m), 1.37-1.52 (4H, m), 1.61-1.70 (1H, m), 1.71-1.98 (7H, m), 2.00-2.09 (2H, m), 2.14-2.21 (2H, m), 2.43 (3H, s), 3.88-3.98 (1H, m), 4.13-4.22 (1H, m), 5.73 (1H, d, J = 8.0 Hz), 7.30 (1H, s) | 346 |
| 51 | 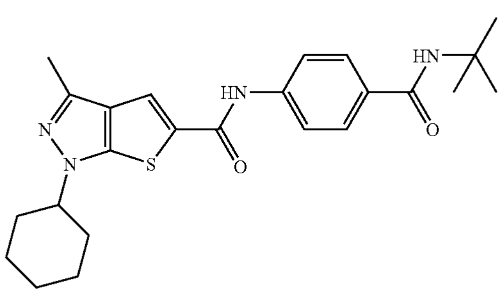 | colorless cryst. 256.0-257.3 | CDCl₃ 1.21-1.37 (1H, m), 1.40-1.52 (2H, m), 1.48 (9H, s), 1.71-1.89 (3H, m), 1.91-1.99 (2H, m), 2.18-2.25 (2H, m), 2.46 (3H, s), 4.15-4.22 (1H, m), 5.92 (1H, brs), 7.53 (1H, s), 7.63-7.66 (2H, m), 7.70-7.73 (2H, m), 7.85 (1H, brs) | 439 |

TABLE 41-continued

| Example No. | Chemical Structure | properties m.p. (° C.) (recryst. solvent) | ¹H-NMR | MS (FAB) (M + 1)⁺ |
|---|---|---|---|---|
| 52 | 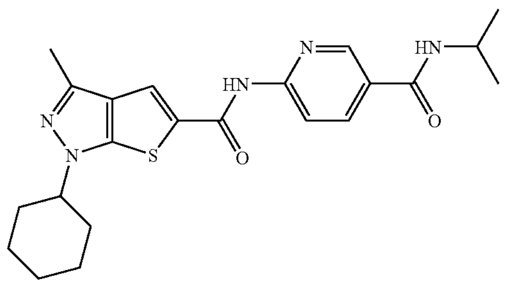 | colorless cryst. >270 | CDCl₃ 1.21-1.36 (1H, m), 1.29 (6H, d, J = 6.6 Hz), 1.40-1.52 (2H, m), 1.71-1.89 (3H, m), 1.91-1.99 (2H, m), 2.18-2.24 (2H, m), 2.47 (3H, s), 4.15-4.24 (1H, m), 4.28-4.35 (1H, m), 5.85 (1H, d, J = 7.6 Hz), 7.57 (1H, s), 8.08 (1H, dd, J = 2.2 and 8.7 Hz), 8.36 (1H, d, J = 8.7 Hz), 8.56 (1H, brs), 8.71-8.72 (1H, m) | 426 |

TABLE 42

| Example No. | Chemical Structure | properties m.p. (° C.) (recryst. solvent) | ¹H-NMR | MS (FAB) (M + 1)⁺ |
|---|---|---|---|---|
| 53 | 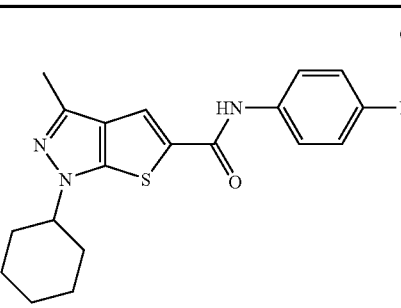 | pale brown cryst. 216.9-218.5 EtOH/Et₂O | DMSO 1.19-1.31 (1H, m), 1.39-1.52 (2H, m), 1.63-1.89 (5H, m), 2.05-2.11 (2H, m), 2.39 (3H, s), 4.18-4.27 (1H, m), 7.54-7.58 (2H, m), 7.64-7.68 (2H, m), 8.04 (1H, s), 8.24 (1H, brs), 10.14 (1H, brs), 10.21 (1H, brs) | 383 |
| 54 | 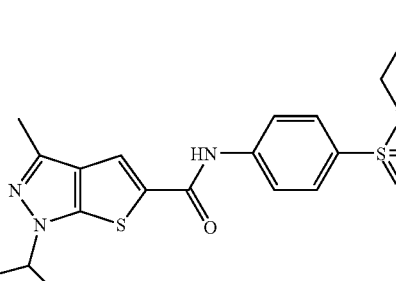 | colorless cryst. 226.0-227.8 | CDCl₃ 1.21-1.36 (1H, m), 1.41 (9H, s), 1.40-1.52 (2H, m), 1.71-1.89 (3H, m), 1.91-1.99 (2H, m), 2.18-2.25 (2H, m), 2.48 (3H, s), 2.97-3.01 (4H, m), 3.50-3.55 (4H, m), 4.18-4.27 (1H, m), 7.53 (1H, s), 7.73-7.76 (2H, m), 7.78-7.81 (2H, m), 7.82 (1H, brs) | 588 |
| 55 | 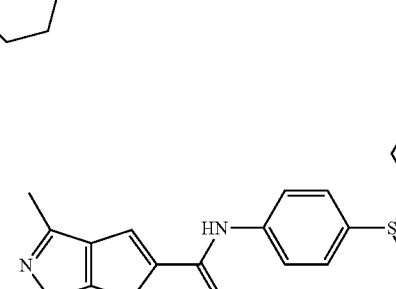 | colorless cryst. >270 | DMSO 1.19-1.31 (1H, m), 1.39-1.50 (2H, m), 1.63-1.89 (5H, m), 2.05-2.11 (2H, m), 2.41 (3H, s), 3.09-3.22 (8H, m), 4.19-4.30 (1H, m), 7.77-7.80 (2H, m), 8.05-8.08 (2H, m), 8.22 (1H, s), 8.84 (1H, brs), 10.74 (1H, brs) | 488 |

TABLE 42-continued

| Example No. | Chemical Structure | properties m.p. (° C.) (recryst. solvent) | ¹H-NMR | MS (FAB) (M + 1)⁺ |
|---|---|---|---|---|
| 56 | 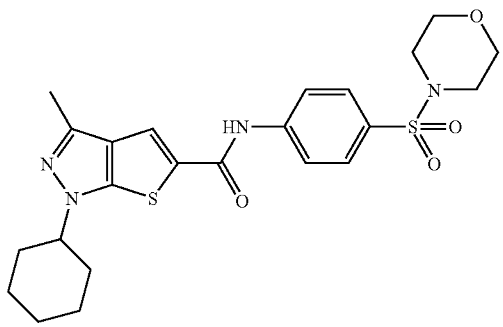 | colorless cryst. >270 | CDCl₃ 1.21-1.35 (1H, m), 1.39-1.51 (2H, m), 1.74-1.99 (5H, m), 2.17-2.26 (2H, m), 2.48 (3H, s), 3.00-3.03 (4H, m), 3.72-3.77 (4H, m), 4.18-4.26 (1H, m), 7.53 (1H, s), 7.71-7.83 (5H, m) | 489 |

TABLE 43

| Example No. | Chemical Structure | properties m.p. (° C.) (recryst. solvent) | ¹H-NMR | MS (FAB) (M + 1)⁺ |
|---|---|---|---|---|
| 57 | 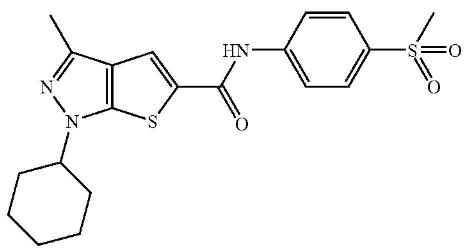 | colorless cryst. >270 | CDCl₃ 1.21-1.35 (1H, m), 1.37-1.51 (2H, m), 1.73-1.99 (5H, m), 2.17-2.26 (2H, m), 2.48 (3H, s), 3.06 (3H, s), 4.14-4.26 (1H, m), 7.54 (1H, s), 7.81-7.84 (3H, m), 7.93-7.96 (2H, m) | 418 |
| 58 | 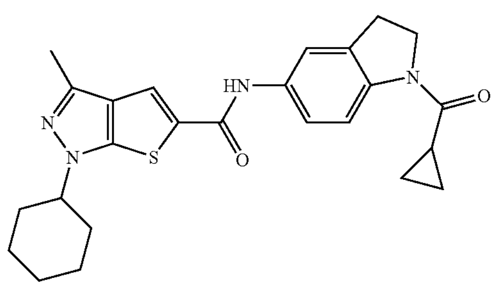 | colorless cryst. 217.7-219.9 EtOH | DMSO 0.80-0.91 (4H, m), 1.15-1.30 (1H, m), 1.39-1.50 (2H, m), 1.63-1.88 (5H, m), 1.90-1.99 (1H, m), 2.02-2.10 (2H, m), 2.39 (3H, s), 3.15-3.22 (2H, m), 4.18-4.35 (3H, m), 7.38-7.41 (1H, m), 7.67-7.69 (1H, m), 7.94-7.99 (1H, m), 8.03 (1H, s), 10.16 (1H, brs) | 449 |
| 59 | 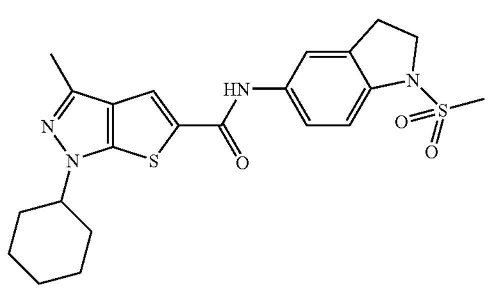 | colorless cryst. 132.8-137.4 | CDCl₃ 1.21-1.37 (1H, m), 1.39-1.53 (2H, m), 1.72-1.98 (5H, m), 2.17-2.23 (2H, m), 2.47 (3H, s), 2.86 (3H, s), 3.18 (2H, t, J = 8.4 Hz), 4.01 (2H, t, J = 8.4 Hz), 4.15-4.27 (1H, m), 7.14-7.18 (1H, m), 7.37-7.40 (1H, m), 7.47 (1H, s), 7.58 (1H, brs), 7.74 (1H, brs) | 459 |

TABLE 43-continued

| Example No. | Chemical Structure | properties m.p. (° C.) (recryst. solvent) | $^1$H-NMR | MS (FAB) (M + 1)$^+$ |
|---|---|---|---|---|
| 60 | 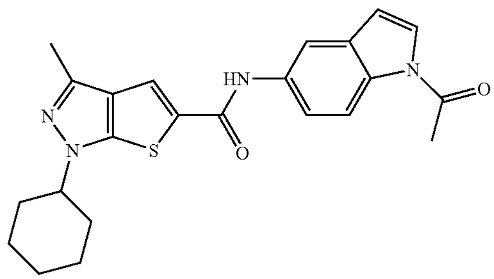 | colorless cryst. 213.1-217.5 | CDCl$_3$ 1.22-1.36 (1H, m), 1.40-1.52 (2H, m), 1.72-1.98 (5H, m), 2.18-2.23 (2H, m), 2.47 (3H, s), 2.64 (3H, s), 4.15-4.27 (1H, m), 6.63-6.64 (1H, m), 7.29 (1H, dd, J = 1.8 and 8.9 Hz), 7.42-7.44 (1H, m), 7.50 (1H, s), 7.75 (1H, brs), 8.10 (1H, d, J = 1.8 Hz), 8.38-8.42 (1H, m) | 421 |

TABLE 44

| Example No. | Chemical Structure | properties m.p. (° C.) (recryst. solvent) | $^1$H-NMR | MS (FAB) (M + 1)$^+$ |
|---|---|---|---|---|
| 61 | 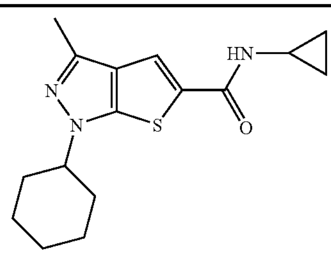 | colorless cryst. 178.9-181.5 | CDCl$_3$ 0.60-0.64 (2H, m), 0.82-0.89 (2H, m), 1.21-1.32 (1H, m), 1.38-1.50 (2H, m), 1.72-1.88 (3H, m), 1.89-1.95 (2H, m), 2.13-2.20 (2H, m), 2.42 (3H, s), 2.85-2.91 (1H, m), 4.12-4.20 (1H, m), 6.02 (1H, brs), 7.29 (1H, s) | 304 |
| 62 | 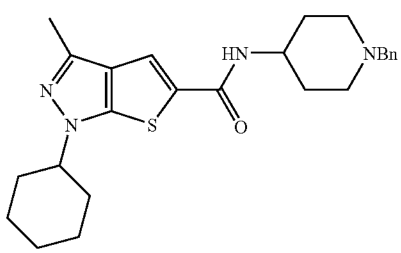 | colorless cryst. 170.2-172.2 | CDCl$_3$ 1.21-1.50 (5H, m), 1.70-1.95 (5H, m), 1.98-2.04 (2H, m), 2.12-2.23 (4H, m), 2.43 (3H, s), 2.84-2.90 (2H, m), 3.52 (2H, s), 3.91-4.02 (1H, m), 4.12-4.21 (1H, m), 5.73 (1H, d, J = 7.2 Hz), 7.26-7.33 (6H, m) | 437 |
| 63 | 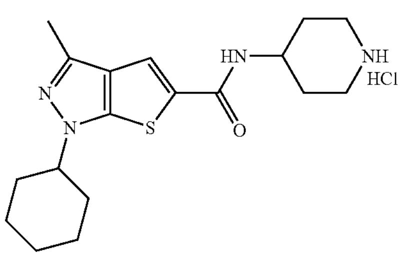 | colorless cryst. 164.1-167.3 | DMSO 1.17-1.30 (1H, m), 1.39-1.50 (2H, m), 1.64-1.87 (7H, m), 1.92-2.00 (2H, m), 2.02-2.10 (2H, m), 2.36 (3H, s), 2.95-3.01 (2H, m), 3.29-3.36 (2H, m), 3.96-4.05 (1H, m), 4.15-4.22 (1H, m), 7.88 (1H, s), 8.51 (1H, d, J = 7.5 Hz), 8.72 (1H, brs) | 347 |
| 64 | 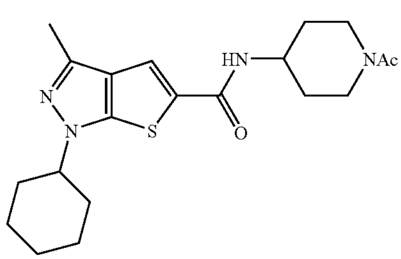 | colorless cryst. 249.2-250.8 | CDCl$_3$ 1.21-1.50 (5H, m), 1.71-1.88 (3H, m), 1.89-1.98 (2H, m), 2.01-2.07 (1H, m), 2.12 (3H, s), 2.14-2.21 (3H, m), 2.44 (3H, s), 2.72-2.80 (1H, m), 3.18-3.25 (1H, m), 3.79-3.88 (1H, m), 4.12-4.21 (2H, m), 4.59-4.66 (1H, m), 5.78 (1H, d, J = 7.7 Hz), 7.34 (1H, s) | 389 |

TABLE 45

| Example No. | Chemical Structure | properties m.p. (° C.) (recryst. solvent) | $^1$H-NMR | MS (FAB) $(M + 1)^+$ |
|---|---|---|---|---|
| 65 | (structure) | colorless cryst. 137.1-138.1 | CDCl$_3$ 1.25-1.34 (1H, m), 1.31 (3H, t, J = 7.1 Hz), 1.38-1.50 (2H, m), 1.71-1.88 (3H, m), 1.89-1.98 (2H, m), 2.16-2.22 (2H, m), 2.46 (3H, s), 4.15-4.22 (1H, m), 4.28 (2H, q, J = 7.1 Hz), 4.62 (2H, s), 6.90-6.94 (2H, m), 7.45 (1H, s), 7.49-7.53 (2H, m), 7.55 (1H, brs) | 442 |
| 66 | (structure) | colorless cryst. 181.0-182.6 | DMSO 1.18-1.30 (1H, m), 1.38-1.50 (2H, m), 1.64-1.90 (5H, m), 2.04-2.10 (2H, m), 2.39 (3H, s), 4.18-4.27 (1H, m), 4.64 (2H, s), 6.89-6.92 (2H, m), 7.59-7.62 (2H, m), 8.01 (1H, s), 10.13 (1H, brs) | 414 |
| 67 | (structure) | colorless cryst. 233.2-235.0 | CDCl$_3$ 1.25-1.35 (1H, m), 1.40-1.52 (2H, m), 1.72-1.98 (5H, m), 2.18-2.23 (2H, m), 2.46 (3H, s), 2.92 (3H, d, J = 5.0 Hz), 4.15-4.24 (1H, m), 4.49 (2H, s), 6.53-6.63 (1H, m), 6.92 (2H, dd, J = 2.1 and 6.9 Hz), 7.47 (1H, s), 7.53 (2H, dd, J = 2.1 and 6.9 Hz), 7.57 (1H, brs) | 427 |
| 68 | (structure) | colorless cryst. 149.3-151.2 | CDCl$_3$ 1.22-1.35 (1H, m), 1.26 (3H, t, J = 7.2 Hz), 1.38-1.53 (2H, m), 1.71-1.98 (5H, m), 2.15-2.22 (2H, m), 2.47 (3H, s), 3.60 (2H, s), 4.15-4.22 (1H, m), 4.16 (2H, q, J = 7.2 Hz), 7.27-7.30 (2H, m), 7.46 (1H, s), 7.54-7.57 (2H, m), 7.58 (1H, brs) | 426 |

TABLE 46

| Example No. | Chemical Structure | properties m.p. (° C.) (recryst. solvent) | $^1$H-NMR | MS (FAB) $(M + 1)^+$ |
|---|---|---|---|---|
| 69 | (structure) | colorless cryst. 233.2-234.7 | DMSO 1.18-1.30 (1H, m), 1.38-1.51 (2H, m), 1.61-1.89 (5H, m), 2.05-2.11 (2H, m), 2.40 (3H, s), 3.53 (2H, s), 4.18-4.29 (1H, m), 7.21-7.25 (2H, m), 7.63-7.66 (2H, m), 8.06 (1H, s), 10.20 (1H, brs) | 398 |

TABLE 46-continued

| Example No. | Chemical Structure | properties m.p. (° C.) (recryst. solvent) | ¹H-NMR | MS (FAB) (M + 1)⁺ |
|---|---|---|---|---|
| 70 | (3-methyl-1-cyclohexyl-thieno[2,3-c]pyrazole-5-carboxamide with N-(4-CH₂CONHMe-phenyl)) | colorless cryst. 257.3-258.8 | DMSO 1.18-1.32 (1H, m), 1.37-1.50 (2H, m), 1.61-1.89 (5H, m), 2.05-2.09 (2H, m), 2.39 (3H, s), 2.57 (3H, d, J = 4.6 Hz), 3.35 (2H, s), 4.19-4.27 (1H, m), 7.20-7.23 (2H, m), 7.61-7.64 (2H, m), 7.88-7.91 (1H, m), 8.06 (1H, s), 10.18 (1H, brs) | 411 |
| 71 | (3-methyl-1-cyclohexyl-thieno[2,3-c]pyrazole-5-carboxamide with N-(4-(4-BOC-piperazin-1-yl)phenyl)) | colorless cryst. 228.3-229.6 | CDCl₃ 1.24-1.35 (1H, m), 1.38-1.52 (2H, m), 1.49 (9H, s), 1.72-1.98 (5H, m), 2.15-2.21 (2H, m), 2.46 (3H, s), 3.09-3.12 (4H, m), 3.58-3.61 (4H, m), 4.12-4.25 (1H, m), 6.91-6.94 (2H, m), 7.44 (1H, s), 7.47-7.50 (2H, m), 7.53 (1H, brs) | 523 |
| 72 | (3-methyl-1-cyclohexyl-thieno[2,3-c]pyrazole-5-carboxamide with N-(4-(piperazin-1-yl)phenyl)) HCl | colorless cryst. 248.5-252.6 | DMSO 1.19-1.31 (1H, m), 1.38-1.51 (2H, m), 1.63-1.89 (5H, m), 2.04-2.10 (2H, m), 2.39 (3H, s), 3.19-3.22 (4H, m), 3.30-3.33 (4H, m), 4.05-4.15 (1H, m), 6.98-7.01 (2H, m), 7.61-7.64 (2H, m), 8.07 (1H, s), 9.08-9.15 (2H, m), 10.17 (1H, brs) | 424 |

TABLE 47

| Example No. | Chemical Structure | properties m.p. (° C.) (recryst. solvent) | ¹H-NMR | MS (FAB) (M + 1)⁺ |
|---|---|---|---|---|
| 73 | (3-methyl-1-cyclohexyl-thieno[2,3-c]pyrazole-5-carboxamide with N-(4-(4-acetyl-piperazin-1-yl)phenyl)) | colorless cryst. >270 EtOH | DMSO 1.18-1.32 (1H, m), 1.35-1.51 (2H, m), 1.65-1.90 (5H, m), 2.04 (3H, s), 2.05-2.11 (2H, m), 2.39 (3H, s), 3.02-3.13 (4H, m), 3.55-3.60 (4H, m), 4.15-4.28 (1H, m), 6.94-6.98 (2H, m), 7.56-4.59 (2H, m), 8.01 (1H, s), 10.07 (1H, brs) | 466 |
| 74 | (3-methyl-1-cyclohexyl-thieno[2,3-c]pyrazole-5-carboxamide with N-(trans-4-hydroxycyclohexyl)) | colorless cryst. 181.3-182.8 | CDCl₃ 1.22-1.52 (7H, m), 1.72-1.88 (3H, m), 1.89-1.98 (2H, m), 2.00-2.08 (2H, m), 2.10-2.22 (4H, m), 2.43 (3H, s), 3.60-3.71 (1H, m), 3.90-4.00 (1H, m), 4.12-4.21 (1H, m), 5.68 (1H, d, J = 7.8 Hz), 7.30 (1H, s) | 362 |

TABLE 47-continued

| Example No. | Chemical Structure | properties m.p. (° C.) (recryst. solvent) | ¹H-NMR | MS (FAB) (M + 1)⁺ |
|---|---|---|---|---|
| 75 | 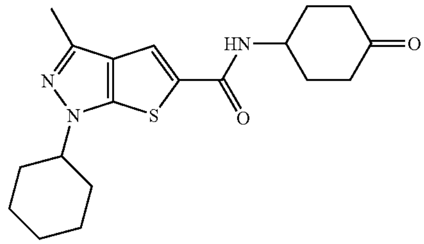 | colorless cryst. 177.2-178.5 | CDCl₃ 1.21-1.35 (1H, m), 1.39-1.50 (2H, m), 1.72-1.88 (5H, m), 1.90-1.98 (2H, m), 2.15-2.23 (2H, m), 2.32-2.60 (6H, m), 2.43 (3H, s), 4.14-4.22 (1H, m), 4.40-4.50 (1H, m), 5.86 (1H, d, J = 7.6 Hz), 7.35 (1H, s) | 360 |
| 76 | 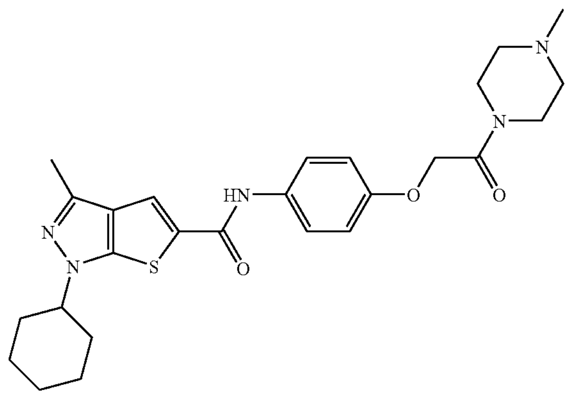 | colorless cryst. 117.2-121.2 | CDCl₃ 1.21-1.35 (1H, m), 1.40-1.52 (2H, m), 1.72-1.89 (3H, m), 1.90-1.98 (2H, m), 2.16-2.22 (2H, m), 2.30 (3H, s), 2.34-2.42 (4H, m), 2.46 (3H, s), 3.59-3.68 (4H, m), 4.14-4.25 (1H, m), 4.68 (2H, s), 6.93-6.97 (2H, m), 7.46 (1H, s), 7.49-7.52 (2H, m), 7.60 (1H, brs) | 496 |

TABLE 48

| Example No. | Chemical Structure | properties m.p. (° C.) (recryst. solvent) | ¹H-NMR | MS (FAB) (M + 1)⁺ |
|---|---|---|---|---|
| 77 | 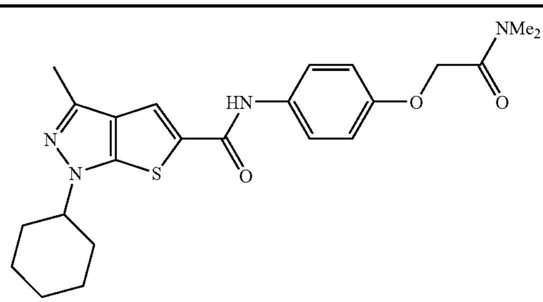 | colorless cryst. 178.2-180.8 | CDCl₃ 1.22-1.35 (1 H, m), 1.37-1.52 (2 H, m), 1.72 1.89 (3 H, m), 1.90-1.98 (2 H, m), 2.15-2.22 (2 H, m), 2.46 (3 H, s), 2.99 (3 H, s), 3.10 (3 H, s), 4.15-4.23 (1 H, m), 4.69 (2 H, s), 6.94-6.98 (2 H, m), 7.46 (1 H, s), 7.48 7.51 (2 H, m), 7.56 (1 H, brs) | 441 |
| 78 | 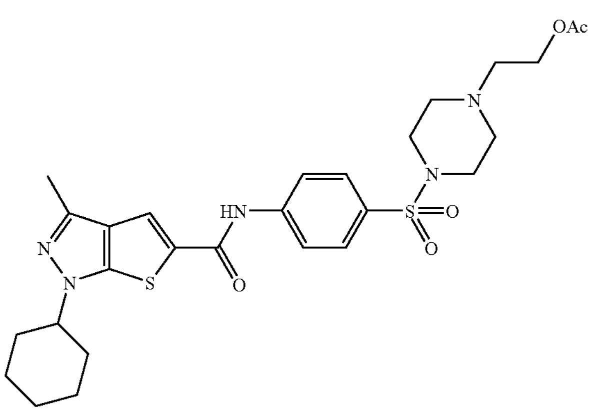 | colorless cryst. 202.2-203.8 | CDCl₃ 1.22-1.35 (1 H, m), 1.40-1.52 (2 H, m), 1.72-1.89 (3 H, m), 1.91-1.99 (2 H, m), 2.03 (3 H, s), 2.19-2.25 (2 H, m), 2.48 (3 H, s), 2.59-2.64 (6 H, m), 3.02 3.08 (4H, m), 4.13 (2 H, t, J = 5.7 Hz), 4.15-4.26 (1 H, m), 7.53 (1 H, s), 7.73-7.81 (4H, m), 7.84 (1 H, brs) | 574 |

TABLE 48-continued

| Example No. | Chemical Structure | properties m.p. (° C.) (recryst. solvent) | ¹H-NMR | MS (FAB) (M + 1)⁺ |
|---|---|---|---|---|
| 79 | 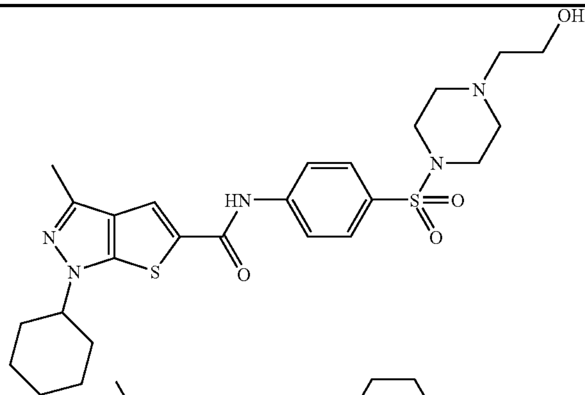 | colorless cryst. 141.4-145.8 | CDCl₃ 1.22-1.35 (1 H, m), 1.39-1.53 (2 H, m), 1.72 1.98 (5 H, m), 2.18-2.22 (2 H, m), 2.34 (1 H, brs), 2.48 (3 H, s), 2.52-2.58 (2 H, m), 2.60-2.63 (4 H, m), 3.03-3.09 (4 H, m), 3.58-3.61 (2 H, m), 4.17-4.26 (1 H, m), 7.54 (1 H, s), 7.74-7.82 (4 H, m), 7.84 (1 H, brs) | 532 |
| 80 | 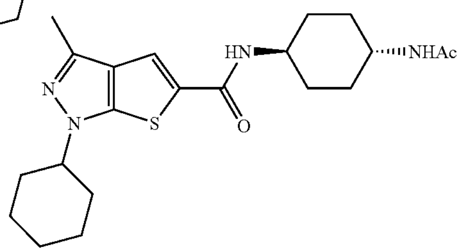 | colorless cryst. >270 EtOH | DMSO 1.17-1.50 (7 H, m), 1.63-1.90 (9 H, m), 1.78 (3 H, s), 2.00-2.08 (2 H, m), 2.35 (3 H, s), 3.41-3.57 (1 H, m), 3.60 3.72 (1 H, m), 4.12-4.24 (1 H, m), 7.73 (1 H, d, J = 7.6 Hz), 7.79 (1 H, s), 8.24 (1 H, d, J = 7.7 Hz) | 403 |

TABLE 49

| Example No. | Chemical Structure | properties m.p. (° C.) (recryst. solvent) | ¹H-NMR | MS (FAB) (M + 1)⁺ |
|---|---|---|---|---|
| 81 | 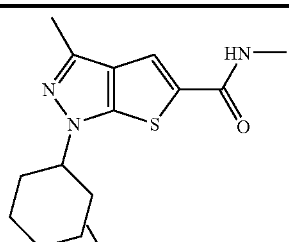 | colorless cryst. 217.5-218.3 | CDCl₃ 1.21-1.32 (1 H, m), 1.37-1.51 (2 H, m), 1.70 1.88 (3 H, m), 1.89-1.97 (2 H, m), 2.13-2.21 (2 H, m), 2.43 (3 H, s), 3.00 (3 H, d, J = 4.9 Hz), 4.10-4.21 (1 H, m), 5.85-5.93 (1 H, m), 7.30 (1 H, s) | 278 |
| 82 | 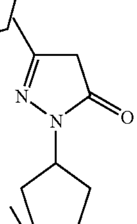 | colorless cryst. 125.1-127.8 | CDCl₃ 1.54-1.69 (2 H, m), 1.75-1.93 (6 H, m), 2.09 (3 H, s), 3.19 (2 H, s), 4.51-4.60 (1 H, m) | 167 |
| 83 | 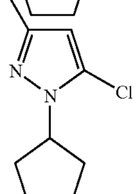 | brown oil | CDCl₃ 1.60-1.72 (2 H, m), 1.86-1.98 (2 H, m), 2.00 2.10 (4 H, m), 2.23 (3 H, s), 4.68-4.75 (1 H, m), 5.95 (1 H, s) | |
| 84 | 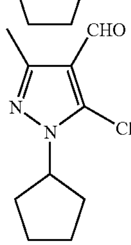 | colorless oil | CDCl₃ 1.65-1.75 (2 H, m), 1.92-2.02 (2 H, m), 2.14- 2.13 (4 H, m), 2.45 (3 H, s), 4.72-4.80 (1 H, m), 9.85 (1 H, s) | 213 |

TABLE 50

| Example No. | Chemical Structure | properties m.p. (° C.) (recryst. solvent) | ¹H-NMR | MS (FAB) (M + H)⁺ |
|---|---|---|---|---|
| 85 | [structure: pyrazole with cyclopentyl, methyl, CHO, and S-CH2-COOEt substituents] | colorless oil | CDCl₃ 1.20 (3 H, t, J = 7.1 Hz), 1.65-1.75 (2 H, m), 1.92-2.11 (6 H, m), 2.48 (3 H, s), 3.58 (2 H, s), 4.10 (2 H, q, J = 7.1 Hz), 5.17-5.22 (1 H, m), 10.01 (1 H, s) | 297 |
| 86 | [structure: thienopyrazole with cyclopentyl, methyl, COOEt] | colorless oil | CDCl₃ 1.38 (3 H, t, J = 7.1 Hz), 1.68-1.78 (2 H, m), 1.83-1.95 (2 H, m), 2.05-2.24 (4 H, m), 2.44 (3 H, s), 4.35 (2 H, q, J = 7.1 Hz), 4.66-4.72 (1 H, m), 7.69 (1 H, s) | 279 |
| 87 | [structure: thienopyrazole with cyclopentyl, methyl, COOH] | colorless cryst. 167.5-168.9 | CDCl₃ 1.68-1.80 (2 H, m), 1.84-1.96 (2 H, m), 2.08-2.25 (4 H, m), 2.47 (3 H, s), 4.66-4.75 (1 H, m), 7.80 (1 H, s) | 251 |
| 88 | [structure: thienopyrazole with cyclopentyl, methyl, C(O)NH-phenyl-NHAc] | colorless cryst. >270 EtOH | DMSO 1.62-1.72 (2 H, m), 1.75-1.85 (2 H, m), 1.94-2.04 (2 H, m), 2.02 (3 H, s), 2.09-2.19 (2 H, m), 2.40 (3 H, s), 4.70-4.79 (1 H, m), 7.52-7.55 (2 H, m), 7.60-7.63 (2 H, m), 8.03 (1 H, s), 9.88 (1 H, brs), 10.16 (1 H, brs) | 383 |

TABLE 51

| Example No. | Chemical Structure | properties m.p. (° C.) (recryst. solvent) | $^1$H-NMR | MS (FAB) (M + 1)$^+$ |
|---|---|---|---|---|
| 89 | (pyrazolone with methyl, N-cycloheptyl) | pale yellow cryst. 134.0-137.7 | CDCl$_3$ 1.45-1.71 (6 H, m), 1.72-1.97 (6 H, m), 2.09 (3 H, s), 3.16 (2 H, s), 4.154.21 (1 H, m), | 195 |
| 90 | (5-chloro-3-methyl-1-cycloheptyl pyrazole) | brown oil | CDCl$_3$ 1.48-1.72 (6 H, m), 1.78-188 (2 H, m), 1.91-2.00 (2 H, m), 2.01-2.11 (2 H, m), 2.23 (3 H, s), 4.30-4.38 (1 H, m), 5.93 (1 H, s) | |
| 91 | (4-CHO-5-chloro-3-methyl-1-cycloheptyl pyrazole) | colorless cryst. 75.0-76.3 | CDCl$_3$ 1.50-1.73 (6 H, m), 1.81-1.91 (2 H, m), 1.93-2.02 (2 H, m), 2.03-2.14 (2 H, m), 2.45 (3 H, s), 4.39-4.46 (1 H, m), 9.87 (1 H, s) | 241 |
| 92 | (thieno[2,3-c]pyrazole-COOEt, N-cycloheptyl) | colorless oil | CDCl$_3$ 1.38 (3 H, t, J = 7.1 Hz), 1.51-1.73 (6 H, m), 1.79-1.89 (2 H, m), 1.99-2.10 (2 H, m), 2.15-2.23 (2 H, m), 2.44 (3 H, s), 4.35 (2 H, q, J = 7.1 Hz), 4.32-4.42 (1 H, m), 7.69 (1 H, s) | 307 |

TABLE 52

| Example No. | Chemical Structure | properties m.p. (° C.) (recryst. solvent) | $^1$H-NMR | MS (FAB) (M + 1)$^+$ |
|---|---|---|---|---|
| 93 | (thieno[2,3-c]pyrazole-COOH, N-cycloheptyl) | colorless cryst. 239.8-241.4 | CDCl$_3$ 1.52-1.75 (6 H, m), 1.80-1.90 (2 H, m), 2.00-2.10 (2 H, m), 2.16-2.25 (2 H, m), 2.46 (3 H, s), 4.35-4.41 (1 H, m), 7.79 (1 H, s) | 278 |

TABLE 52-continued

| Example No. | Chemical Structure | properties m.p. (° C.) (recryst. solvent) | ¹H-NMR | MS (FAB) (M + 1)⁺ |
|---|---|---|---|---|
| 94 | 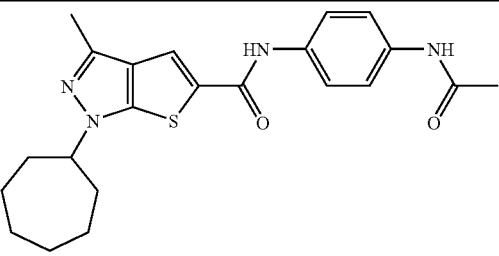 | colorless cryst. >270 EtOH | DMSO-$d_6$ 1.50-1.82 (8 H, m), 1.88-2.12 (4 H, m), 1.97 (3 H, s), 2.39 (3 H, s), 4.32-4.46 (1 H, m), 7.52-7.55 (2 H, m), 7.60-7.63 (2 H, m), 8.03 (1 H, s), 9.88 (1 H, brs), 10.15 (1 H, brs) | 411 |
| 95 | 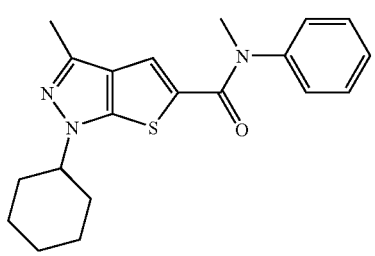 | colorless cryst. 157-159 | CDCl$_3$ 1.18-1.45 (3 H, m), 1.68-1.82 (3 H, m), 1.84-1.93 (2 H, m), 2.04-2.13 (2 H, m), 2.21 (3 H, s), 3.45 (3 H, s), 4.04-4.14 (1 H, m), 6.11 (1 H, s), 7.27-7.33 (2 H, m), 7.39-7.49 (3 H, m) | 354 |
| 96 | 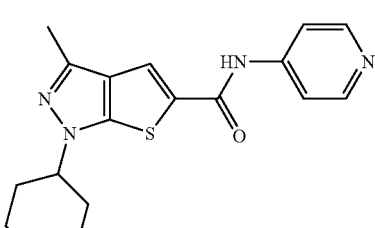 | colorless cryst. 223-224 | CDCl$_3$ 1.22-1.36 (1 H, m), 1.40-1.53 (2 H, m), 1.72-1.89 (3 H, m), 1.91-2.00 (2 H, m), 2.15-2.25 (2 H, m), 2.47 (3 H, s), 4.15-4.25 (1 H, m), 7.53 (1 H, s), 7.54-7.58 (2 H, m), 7.74 (1 H, brs), 8.53-8.58 (2 H, m) | 341 |

TABLE 53

| Example No. | Chemical Structure | properties m.p. (° C.) (recryst. solvent) | ¹H-NMR | MS (FAB) (M + 1)⁺ |
|---|---|---|---|---|
| 97 | 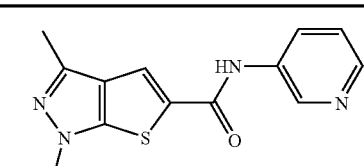 | colorless solid 178-180 | CDCl$_3$ 1.23-1.35 (1 H, m), 1.39-1.42 (2 H, m), 1.72-1.89 (3 H, m), 1.90-1.97 (2 H, m), 2.16-2.25 (2 H, m), 2.48 (3 H, s), 4.15-4.25 (1 H, m), 7.29-7.35 (1 H, m), 7.53 (1 H, s), 7.68 (1 H, brs), 8.24-8.29 (1 H, m), 8.38-8.42 (1 H, m), 8.63-8.66 (1 H, m) | 341 |
| 98 | 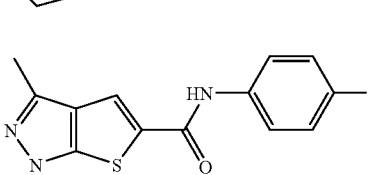 | pale yellow cryst. 210-212 | CDCl$_3$ 1.22-1.52 (3 H, m), 1.72-1.89 (3 H, m), 1.91-1.98 (2 H, m), 2.17-2.26 (2 H, m), 2.48 (3 H, s), 4.15-4.25 (1 H, m), 7.54 (1 H, s), 7.77-7.81 (2 H, m), 7.87 (1 H, brs), 8.24-2.29 (2 H, m) | 385 |

TABLE 53-continued

| Example No. | Chemical Structure | properties m.p. (° C.) (recryst. solvent) | ¹H-NMR | MS (FAB) (M + 1)⁺ |
|---|---|---|---|---|
| 99 | 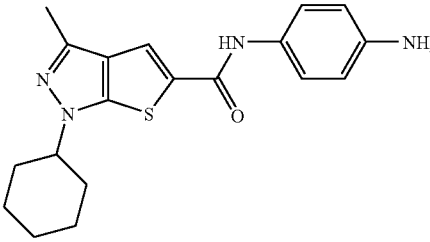 | pale yellow foamy solid | CDCl₃ 1.22-1.34 (1 H, m), 1.38-1.51 (2 H, m), 1.71-1.98 (5 H, m), 2.14-2.23 (2 H, m), 2.45 (3 H, s), 4.14-4.24 (1 H, m), 6.65-6.72 (2 H, m), 7.33-7.38 (2 H, m), 7.42 (1 H, s), 7.48 (1 H, s) | 355 |
| 100 | 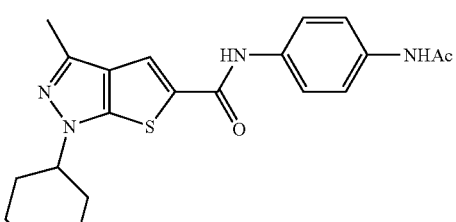 | colorless solid >300 | CDCl₃ 1.19-1.30 (1 H, m), 1.36-1.50 (2 H, m), 1.63-1.86 (5 H, m), 2.03 (3 H, s), 2.03-2.10 (2 H, m), 2.39 (3 H, s), 4.15-4.26 (1 H, m), 7.51-7.56 (2 H, m), 7.59-7.64 (2 H, m), 8.04 (1 H, s), 9.91 (1 H, brs), 10.18 (1 H, brs) | 397 |

TABLE 54

| Example No. | Chemical Structure | properties m.p. (° C.) (recryst. solvent) | ¹H-NMR | MS (FAB) (M + 1)⁺ |
|---|---|---|---|---|
| 101 | 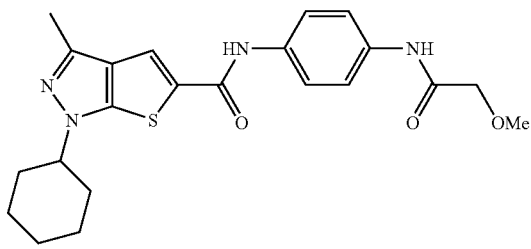 | pale yellow cryst. 233-236 | CDCl₃ 1.23-1.35 (1 H, m), 1.38-1.54 (2 H, m), 1.72-1.97 (5 H, m), 2.15-2.24 (2 H, m), 2.47 (3 H, s), 3.52 (3 H, s), 4.03 (2 H, s), 4.15-4.25 (1 H, m), 7.47 (1 H, s), 7.56-7.65 (4 H, m), 8.25 (1 H, brs) | 427 |
| 102 | 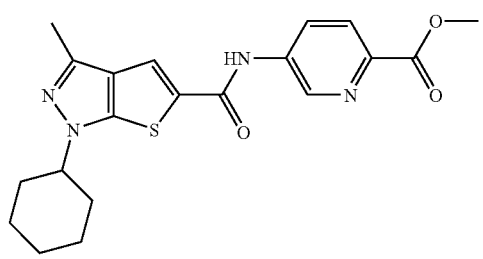 | colorless solid 120-123 | CDCl₃ 1.23-1.36 (1 H, m), 1.39-1.52 (2 H, m), 1.72-1.98 (5 H, m), 2.16-2.24 (2 H, m), 2.48 (3 H, s), 4.01 (3 H, s), 4.15-4.25 (1 H, m), 7.58 (1 H, s), 7.88 (1 H, brs), 8.18 (1 H, d, J = 8.6 Hz), 8.51 (1 H, dd, J = 2.6 and 8.6 Hz), 8.71 (1 H, d, J = 2.6 Hz) | 399 |
| 103 | 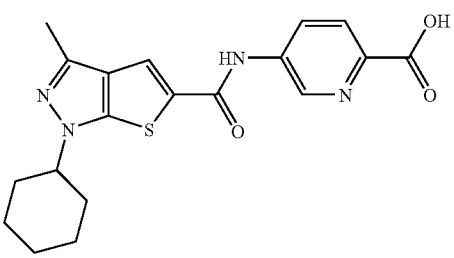 | pale yellow solid 161-166 | DMSO-d₆ 1.18-1.42 (1 H, m), 1.38-1.51 (2 H, m), 1.65-1.89 (5 H, m), 2.05-2.13 (2 H, m, 2.42 (3 H, s), 4.19-4.28 (1 H, m), 8.07 (1 H, d, J = 8.6 Hz), 8.14 (1 H, s), 8.35 (1 H, dd, J = 2.4 and 8.6 Hz), 8.99 (1 H, d, J = 2.4 Hz), 10.71 (1 H, brs) | 385 |

TABLE 54-continued

| Example No. | Chemical Structure | properties m.p. (° C.) (recryst. solvent) | $^1$H-NMR | MS (FAB) (M + 1)$^+$ |
|---|---|---|---|---|
| 104 | 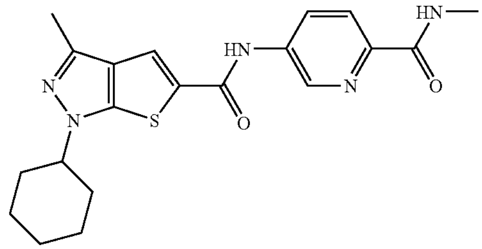 | colorless solid 255-257 | CDCl$_3$ 1.21-1.35 (1 H, m), 1.40-1.60 (2 H, m), 1.72-1.97 (5 H, m), 2.16-2.25 (2 H, m), 2.47 (3 H, s), 3.04 (3 H, d, J = 5.1 Hz), 4.15-4.25 (1 H, m), 7.55 (1 H, s), 7.79 (1 H, brs), 7.86-7.92 (2 H, m), 8.21-8.24 (2 H, m), 8.76 (1 H, brs) | 398 |

TABLE 55

| Example No. | Chemical Structure | properties m.p. (° C.) (recryst. solvent) | $^1$H-NMR | MS (FAB) (M + 1)$^+$ |
|---|---|---|---|---|
| 105 | 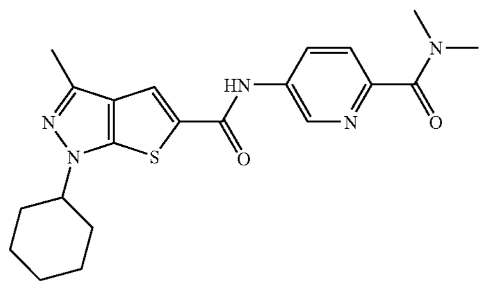 | colorless cryst. 243-245 | CDCl$_3$ 1.23-1.35 (1 H, m), 1.39-1.52 (2 H, m), 1.72-1.98 (5 H, m), 2.16-2.24 (2 H, m), 2.48 (3 H, s), 3.11 (3 H, s), 3.17 (3 H, s), 4.15-4.25 (1 H, m), 7.51 (1 H, d, J = 8.5 Hz), 7.78 (1 H, s), 8.00 (1 H, dd, J = 2.5 and 8.5 Hz), 8.57-8.60 (2 H, m) | 412 |
| 106 | 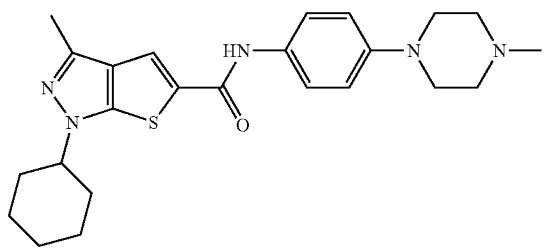 | yellow solid 206-208 | CDCl$_3$ 1.22-1.35 (1 H, m), 1.38-1.50 (2 H, m), 1.70-1.97 (5 H, m), 2.15-2.23 (2 H, m), 2.36 (3 H, s), 2.46 (3 H, s), 2.56-2.63 (4 H, m), 3.17-3.23 (4 H, m), 4.14-4.23 (1 H, m), 6.93 (2 H, d, J = 8.9 Hz), 7.44 (1 H, s), 7.47 (2 H, d, J = 8.9 Hz), 7.53 (1 H, brs) | 438 |
| 107 | MsOH | colorless cryst. 175 (dec.) (MeOH) | D$_2$O 1.05-1.18 (1 H, m), 1.25-1.39 (2 H, m), 1.48-1.69 (3 H, m), 1.73-1.83 (2 H, m), 1.93-2.01 (2 H, m), 2.31 (3 H, s), 2.86 (3 H, s), 2.96 (3 H, s), 3.25-3.55 (8 H, m), 3.90-4.00 (1 H, m), 6.96 (2 H, d, J = 8.6 Hz), 7.34 (1 H, d, J = 8.6 Hz), 7.50 (1 H, brs) | 438 |
| 108 | 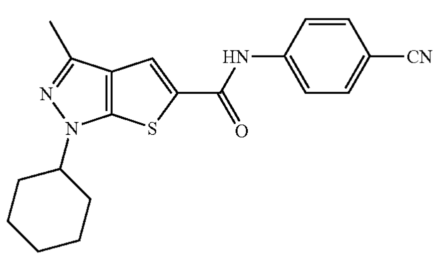 | colorless solid 98-103 | CDCl$_3$ 1.21-1.36 (1 H, m), 1.38-1.52 (2 H, m), 1.72-1.98 (5 H, m), 2.15-2.24 (2 H, m), 2.36 (3 H, s), 4.13-4.23 (1 H, m), 7.53 (1 H, s), 7.64 (2 H, d, J = 8.6 Hz), 7.75 (2 H, d, J = 8.6 Hz), 7.89 (1 H, brs) | 365 |

TABLE 56
| Example No. | Chemical Structure | properties m.p. (° C.) (recryst. solvent) | ¹H-NMR | MS (FAB) (M + 1)⁺ |
|---|---|---|---|---|
| 109 | 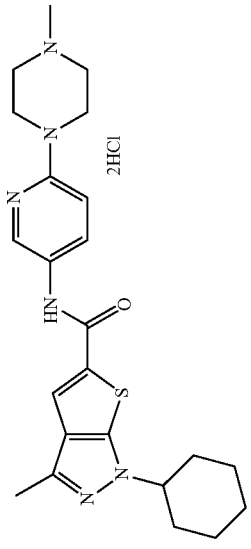 | colorless solid 250 (dept.) | D₂O 1.12-1.26 (1 H, m), 1.31-1.44 (2 H, m), 1.54-1.64 (3 H, m), 1.80-1.88 (2 H, m), 1.96-2.05 (2 H, m), 2.32 (3 H, s), 3.00 (3 H, s), 3.17-3.30 (2 H, m), 3.34-3.45 (2 H, m), 3.63-3.74 (2 H, m), 3.95-4.05 (1 H, m), 4.18-4.29 (2 H, m), 7.03 (1 H, d, J = 9.4 Hz), 7.55 (1 H, s), 7.82 (1 H, dd, J = 2.4 and 9.4 Hz), 8.25 (1 H, d, J = 2.4 Hz) | 439 |
| 110 | 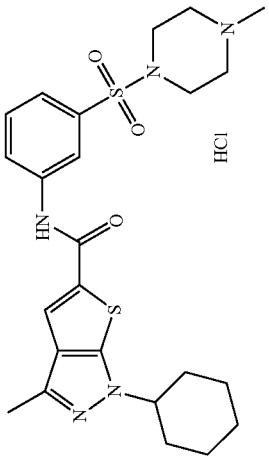 | colorless cryst. 164-170 | DMSO-d₆ 1.28-1.32 (1 H, m), 1.38-1.52 (2 H, m), 1.64-1.89 (5 H, m), 2.05-2.12 (2 H, m), 2.41 (3 H, s), 2.63-2.74 (2 H, m), 2.76 (3 H, s), 3.09-3.12 (2 H, m), 3.41-3.50 (2 H, m), 3.73-3.82 (2 H, m), 4.20-4.30 (1 H, m), 7.47-7.51 (1 H, m), 7.65-7.71 (1 H, m), 8.08-8.13 (1 H, m), 8.17 (1 H, s), 8.26-8.28 (1 H, m), 10.22 (1 H, brs), 10.68 (1 H, brs) | 502 |

TABLE 56-continued

| Example No. | Chemical Structure | properties m.p. (° C.) (recryst. solvent) | ¹H-NMR | MS (FAB) (M + 1)⁺ |
|---|---|---|---|---|
| 111 | (structure) | coloeless solid 255-256 | DMSO-d₆ 1.28-1.31 (1 H, m), 1.38-1.52 (2 H, m), 1.64-1.89 (5 H, m), 2.04-2.12 (2 H, m), 2.41 (3 H, s), 2.45 (3 H, s), 4.17-4.27 (1 H, m), 7.44 (1 H, brs), 7.47-7.51 (1 H, m), 7.55-7.61 (1 H, m), 7.99-8.04 (1 H, m), 8.11 (1 H, s), 8.22-8.26 (1 H, m), 10.51 (1 H, brs) | 433 |
| 112 | (structure) | pale yellow solid 203-205 | CDCl₃ 1.52-1.75 (6 H, m), 1.78-1.88 (2 H, m), 1.99-2.11 (2 H, m), 2.15-2.24 (2 H, m), 2.35 (3 H, s), 2.45 (3 H, s), 2.55-2.61 (4 H, m), 3.16-3.22 (4 H, m), 4.34-4.43 (1 H, m), 6.92 (2 H, d, J = 9.0 Hz), 7.43 (1 H, s), 7.46 (2 H, d, J = 9.0 Hz), 7.49 (1 H, brs) | 452 |

TABLE 57

| Example No. | Chemical Structure | properties m.p. (° C.) (recryst. solvent) | $^1$H-NMR | MS (FAB) $(M+1)^+$ |
|---|---|---|---|---|
| 113 | 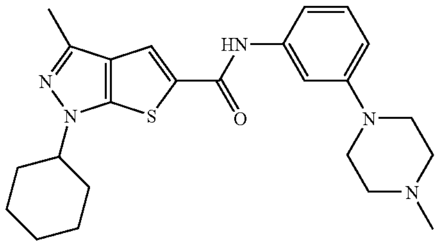 | colorless foamy solid | CDCl$_3$ 1.22-1.36 (1 H, m), 1.39-1.52 (2 H, m), 1.69-1.98 (5 H m), 2.15-2.24 (2 H, m), 2.35 (3 H, s), 2.46 (3 H, s), 2.53-2.59 (4 H, m), 3.21-3.27 (4 H, m), 4.13-4.23 (1 H, m), 6.67-6.72 (1 H, m), 6.88-6.93 (1 H, m), 7.19-7.25 (1 H, m), 7.40-7.43 (1 H, m), 7.45 (1 H, s), 7.45 (1 H, brs) | 438 |
| 114 | 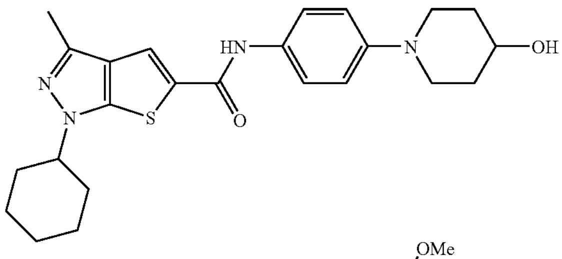 | yellow cryst. 165-167 (iPrOH) | DMSO-d$_6$ 1.18-1.32 (1 H, m), 1.37-1.53 (4 H, m), 1.64-1.88 (7 H, m), 2.03-2.10 (2 H, m), 2.39 (3 H, s), 2.75-2.84 (2 H, m), 3.45-3.52 (2 H, m), 3.56-3.65 (1 H, m), 4.16-4.26 (1 H, m), 4.65 (1 H, d, J = 4.2 Hz), 6.91 (2 H, d, J = 9.0 Hz), 7.52 (2 H, d, J = 9.0 Hz), 7.99 (1 H, s), 10.02 (1 H, brs) | 439 |
| 115 | 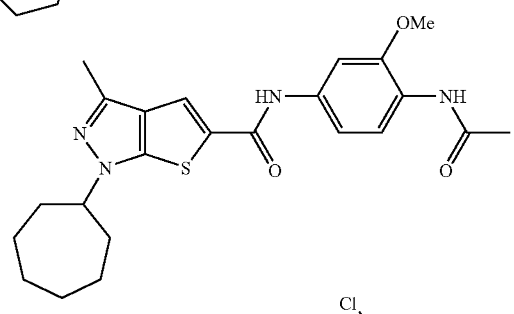 | colorless cryst. 205-207 (EtOH) | CDCl$_3$ 1.56-1.75 (6 H, m), 1.80-1.88 (2 H, m), 2.00-2.10 (2 H, m), 2.15-2.25 (5 H, m), 2.46 (3 H, s), 3.93 (3 H, s), 4.33-4.43 (1 H, m), 6.74 (1 H, dd, J = 2.2 and 8.7 Hz), 7.47 (1 H, s), 7.65 (1 H, brs), 7.70 (1 H, brs), 7.78 (1 H, d, J = 2.2 Hz), 8.31 (1 H, d, J = 8.7 Hz) | 441 |
| 116 | 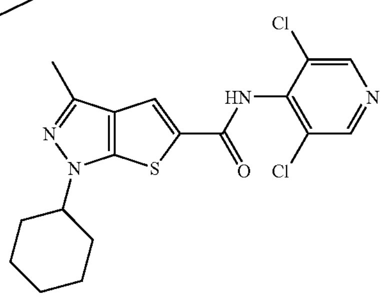 | colorles cryst. 201-202 (iPr$_2$O/EtOAc) | CDCl$_3$ 1.21-1.35 (1 H, m), 1.38-1.52 (2 H, m), 1.71-1.98 (5 H, m), 2.15-2.23 (2 H, m), 2.48 (3 H, s), 4.15-4.25 (1 H, m), 7.64 (1 H, s), 7.64 (1 H, brs), 8.55 (2 H, s) | 409 |

TABLE 58

| Example No. | Chemical Structure | properties m.p. (° C.) (recryst. solvent) | $^1$H-NMR | MS (FAB) $(M+1)^+$ |
|---|---|---|---|---|
| 117 | 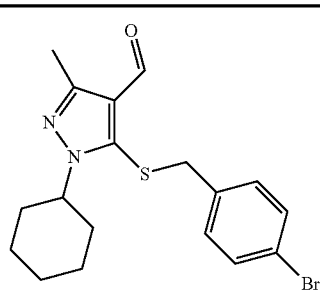 | colorless solid 93-96 | CDCl$_3$ 1.16-1.31 (4 H, m), 1.38-1.47 (2 H, m), 1.65-1.89 (4 H, m), 2.47 (3 H, s), 3.92 (3 H, s), 4.16-4.26 (1 H, m), 6.94 (2 H, d, J = 8.3 Hz), 7.38 (2 H, d, J = 8.3 Hz), 9.90 (1 H, s) | 393 |

TABLE 58-continued

| Example No. | Chemical Structure | properties m.p. (° C.) (recryst. solvent) | ¹H-NMR | MS (FAB) (M + 1)⁺ |
|---|---|---|---|---|
| 118 | 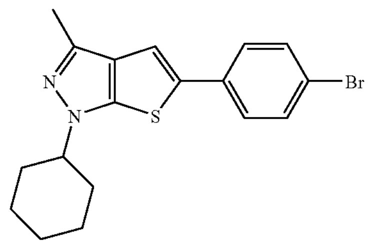 | colorless solid 118-120 | CDCl₃ 1.22-1.34 (1 H, m), 1.37-1.52 (2 H, m), 1.72-1.98 (5 H, m), 2.15-2.24 (2 H, m), 2.45 (3 H, s), 4.14-4.24 (1 H, m), 7.13 (1 H, s), 7.39-7.44 (2 H, m), 7.47-7.52 (2 H, m) | 375 |
| 119 | 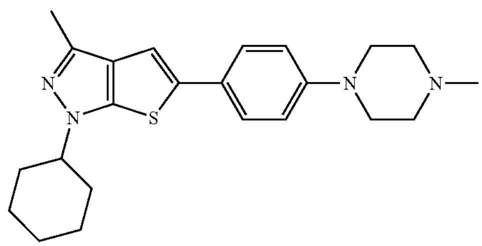 | pale yellow solid 182-183 | CDCl₃ 1.22-1.48 (3 H, m), 1.70-1.95 (5 H, m), 2.15-2.24 (2 H, m), 2.36 (3 H, s), 2.44 (3 H, s), 2.56-2.61 (4 H, m), 3.23-3.28 (4 H, m), 4.12-4.22 (1 H, m), 6.88-6.94 (2 H, m), 6.98 (1 H, s), 7.42-7.48 (2 H, m) | 395 |
| 120 | 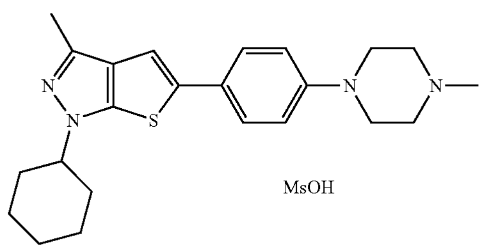 | colorless cryst. 210-214 (EtOH/Et₂O) | DMSO-d₆ 1.16-1.28 (1 H, m), 1.38-1.50 (2 H, m), 1.65-1.87 (5 H, m), 2.04-2.13 (2 H, m), 2.30 (3 H, s), 2.34 (3 H, s), 2.85-2.88 (3 H, m), 2.93-3.21 (4 H, m), 3.40-3.58 (2 H, m), 3.82-3.97 (2 H, m), 4.12-4.22 (1 H, m), 7.01-7.06 (2 H, m), 7.31 (1 H, s), 7.48-7.53 (2 H, m), 9.55 (1 H, brs) | 395 |

TABLE 59

| Example No. | Chemical Structure | properties m.p. (° C.) (recryst. solvent) | ¹H-NMR | MS (FAB) (M + 1)⁺ |
|---|---|---|---|---|
| 121 | 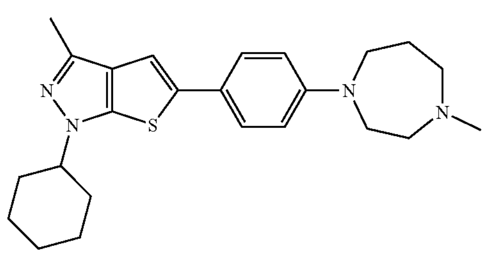 | pale yellow solid 112-114 | CDCl₃ 1.22-1.53 (3 H, m), 1.70-1.96 (5 H, m), 1.99-2.07 (2 H, m), 2.15-2.24 (2 H, m), 2.39 (3 H, s), 2.43 (3 H, s), 2.56-2.61 (2 H, m), 2.71-2.76 (2 H, m), 3.47-3.53 (2 H, m), 3.57-3.62 (2 H, m), 4.12-4.22 (1 H, m), 6.66-6.71 (2 H, m), 6.91 (1 H, s), 7.38-7.43 (2 H, m) | 409 |
| 122 | 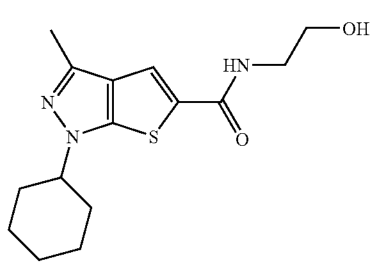 | colorless cryst. 127-129 | CDCl₃ 1.22-1.33 (1 H, m), 1.37-1.50 (2 H, m), 1.70-1.96 (5 H, m), 2.13-2.21 (2 H, m), 2.41-2.46 (1 H, brs), 2.44 (3 H, s), 3.59-3.65 (2 H, m), 3.81-3.87 (2 H, m), 4.18 (1 H, tt, J = 3.8 and 11.8 Hz), 6.36-6.44 (1 H, m), 7.36 (1 H, s) | 308 |

TABLE 59-continued

| Example No. | Chemical Structure | properties m.p. (° C.) (recryst. solvent) | $^1$H-NMR | MS (FAB) (M + 1)$^+$ |
|---|---|---|---|---|
| 123 | (structure) | colorless viscous solid | CDCl$_3$ 1.20-1.33 (1 H, m), 1.37-1.50 (2 H, m), 1.71-1.97 (7 H, m), 2.14-2.22 (2 H, m), 2.43 (3 H, s), 2.85-2.91 (1 H, m), 3.59-3.65 (2 H, m), 3.72-3.79 (2 H, m), 4.18 (1 H, tt, J = 3.8 and 11.8 Hz), 6.42-6.48 (1 H, m), 7.34 (1 H, s) | 322 |
| 124 | (structure) | pale yellow foamy solid | CDCl$_3$ 1.22-1.35 (1 H, m), 1.39-1.53 (2 H, m), 1.71-1.97 (5 H, m), 2.15-2.25 (3 H, m), 2.46 (3 H, s), 2.84 (3 H, s), 3.20-3.26 (2 H, m), 3.72-3.79 (2 H, m), 4.20 (1 H, tt, J = 3.8 and 11.8 Hz), 6.97-7.04 (1 H, m), 7.18 (1 H, dd, J = 1.9 and 8.6 Hz), 7.47 (1 H, s), 7.50 (1 H, dd, J = 2.3 and 13.8 Hz), 7.58 (1 H, brs) | 431 |

TABLE 60

| Example No. | Chemical Structure | properties m.p. (° C.) (recryst. solvent) | $^1$H-NMR | MS (FAB) (M + 1)$^+$ |
|---|---|---|---|---|
| 125 | (structure) HCl | colorless solid 112-125 | DMSO-d$_6$ 1.18-1.30 (1 H, m), 1.37-1.50 (2 H, m), 1.63-1.88 (5 H, m), 2.02-2.10 (2 H, m), 2.40 (3 H, s), 2.89 (3 H, s), 3.20-3.26 (2 H, m), 3.52-3.58 (2 H, m), 4.22 (1 H, tt. J = 3.8 and 11.7 Hz) 7.18-7.26 (1 H, m), 7.39-7.45 (1 H, m), 7.64 (1 H, dd, J = 2.0 and 15.3 Hz), 8.06 (1 H, s), 10.30 (1 H, brs) | 431 |
| 126 | (structure) | colorless foamy solid | CDCl$_3$ 1.22-1.34 (1 H, m), 1.28 (3 H, t, J = 7.1 Hz), 1.37-1.50 (2 H, m), 1.62-2.00 (13 H, m), 2.14-2.22 (2 H, m), 2.44 (3 H, s), 2.49-2.57 (1 H, m), 4.08-4.22 (2 H, m), 4.16 (2 H, q, J = 7.1 Hz), 5.84-5.90 (1 H, m), 7.32 (1 H, s) | 418 |

TABLE 60-continued

| Example No. | Chemical Structure | properties m.p. (° C.) (recryst. solvent) | $^1$H-NMR | MS (FAB) $(M + 1)^+$ |
|---|---|---|---|---|
| 127 | 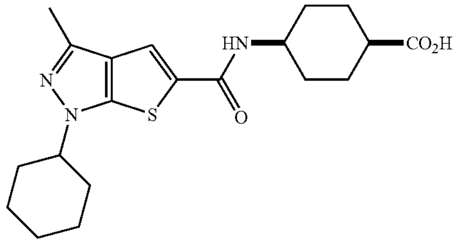 | colorless solid 212-213 | CDCl$_3$ 1.20-2.06 (16 H, m), 2.13-2.22 (2 H, m), 2.44 (3 H, s), 2.60-2.68 (1 H, m), 4.06-4.23 (2 H, m), 5.82-5.89 (1 H, m), 7.32 (1 H, s) | 390 |
| 128 | 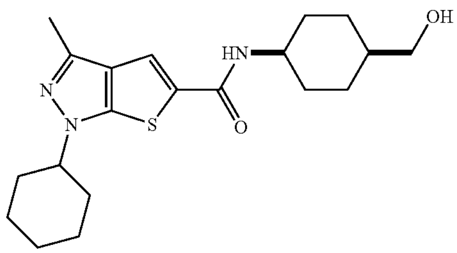 | colorless solid 150-153 | CDCl$_3$ 1.22-1.97 (17 H, m), 2.13-2.21 (2 H, m), 2.45 (3 H, s), 3.57-3.61 (2 H, m), 4.09-4.27 (2 H, m), 5.93-5.98 (1 H, m), 7.32 (1 H, s) | 376 |

TABLE 61

| Example No. | Chemical Structure | properties m.p. (° C.) (recryst. solvent) | $^1$H-NMR | MS (FAB) $(M + 1)^+$ |
|---|---|---|---|---|
| 129 | 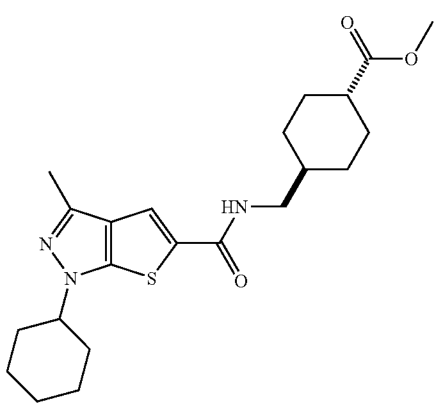 | colorless solid 147-148 | CDCl$_3$ 0.98-1.11 (2 H, m), 1.21-1.35 (1 H, m), 1.38-1.50 (4 H, m), 1.53-1.65 (1 H, m), 1.72-1.97 (7 H, m), 2.00-2.08 (2 H, m), 2.14-2.21 (2 H, m), 2.26 (1 H, tt, J = 3.6 and 12.2 Hz), 2.44 (3 H, s), 3.28-3.34 (2 H, m), 3.67 (3 H, s), 4.18 (1 H, tt, J = 3.8 and 11.8 Hz), 5.92-6.00 (1 H, m), 7.33 (1 H, s) | 418 |
| 130 | 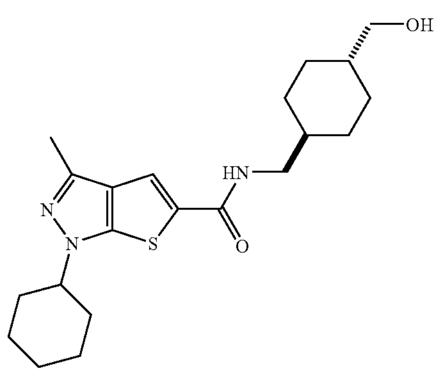 | colorless cryst. 101-104 (EtOAc) | CDCl$_3$ 0.92-1.10 (4 H, m), 1.21-1.34 (2 H, m), 1.36-1.55 (3 H, m), 1.70-1.97 (9 H, m), 2.13-2.21 (2 H, m), 2.44 (3 H, s), 3.28-3.34 (2 H, m), 3.46-3.51 (2 H, m), 4.18 (1 H, tt, J = 3.8 and 11.9 Hz), 5.92-6.00 (1 H, m), 7.33 (1 H, s) | 390 |

TABLE 61-continued

| Example No. | Chemical Structure | properties m.p. (° C.) (recryst. solvent) | ¹H-NMR | MS (FAB) (M + 1)⁺ |
|---|---|---|---|---|
| 131 | 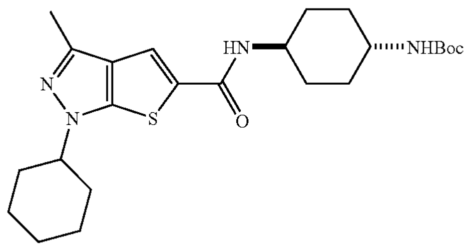 | colorless solid 265 (dec.) | CDCl₃ 1.21-2.22 (18 H, m), 1.45 (9 H, s), 2.43 (3 H, s), 3.37-3.53 (1 H, m), 3.87-3.97 (1 H, m), 4.17 (1 H, tt, J = 3.8 and 11.9 Hz), 4.37-4.45 (1 H, m), 5.66-5.72 (1 H, m), 7.31 (1 H, s) | 461 |
| 132 | 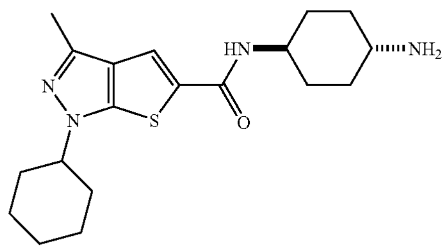 | colorless cryst. 154-156 (Et₂O) | CDCl₃ 1.20-1.98 (14 H, m), 2.05-2.23 (4 H, s), 2.44 (3 H, s), 2.65-2.74 (1 H, m), 3.86-3.96 (1 H, m), 4.18 (1 H, tt, J = 3.8 and 11.8 Hz), 5.64-5.69 (1 H, m), 7.30 (1 H, s) | 361 |

TABLE 62

| Example No. | Chemical Structure | properties m.p. (° C.) (recryst. solvent) | ¹H-NMR | MS (FAB) (M + 1)⁺ |
|---|---|---|---|---|
| 133 | 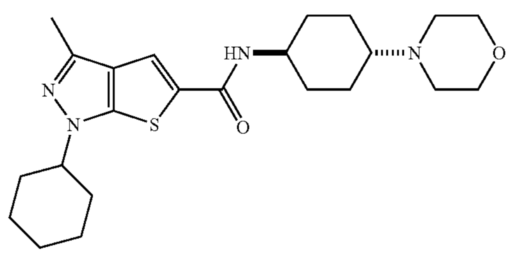 | colorless solid 211-214 | CDCl₃ 1.19-1.49 (7 H, m), 1.71-2.03 (7 H, m), 2.13-2.29 (5 H, m), 2.44 (3 H, s), 2.56-2.61 (4 H, m), 3.72-3.77 (4 H, m), 3.85-3.94 (1 H, m), 4.17 (1 H, tt, J = 3.9 and 11.8 Hz), 5.66-5.71 (1 H, m), 7.30 (1 H, s) | 431 |
| 134 | 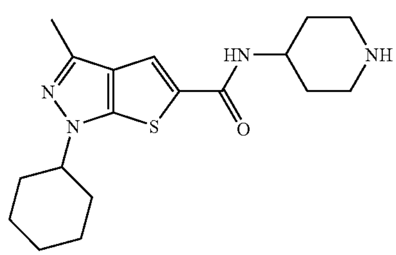 | colorless solid 184-187 | CDCl₃ 1.21-1.52 (5 H, m), 1.71-1.97 (5 H, m), 2.01-2.08 (2 H, m), 2.04-2.11 (2 H, m), 2.44 (3 H, s), 2.70-2.80 (2 H, m), 3.08-3.15 (2 H, m), 3.99-4.10 (1 H, m), 4.18 (1 H, tt, J = 3.9 and 11.8 Hz), 5.72-5.79 (1 H, m), 7.32 (1 H, s) | 347 |
| 135 | 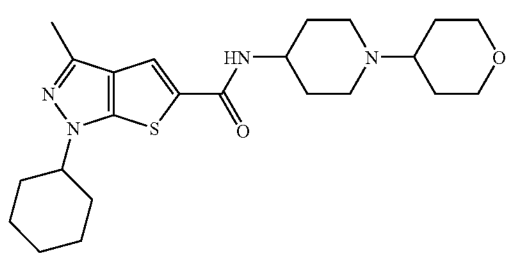 | colorless solid 207-208 | CDCl₃ 1.22-1.34 (1 H, m), 1.38-1.68 (6 H, m), 1.71-1.96 (7 H, m), 2.03-2.11 (2 H, m), 2.13-2.21 (2 H, m), 2.30-2.39 (2 H, m), 2.44 (3 H, s), 2.46-2.55 (1 H, m), 2.92-3.00 (2 H, m), 3.35-3.45 (2 H, m), 3.92-4.07 (3 H, m), 4.17 (1 H, tt, J = 3.8 and 11.8 Hz), 5.71-5.77 (1 H, m), 7.31 (1 H, s) | 431 |

TABLE 62-continued

| Example No. | Chemical Structure | properties m.p. (° C.) (recryst. solvent) | $^1$H-NMR | MS (FAB) $(M + 1)^+$ |
|---|---|---|---|---|
| 136 | 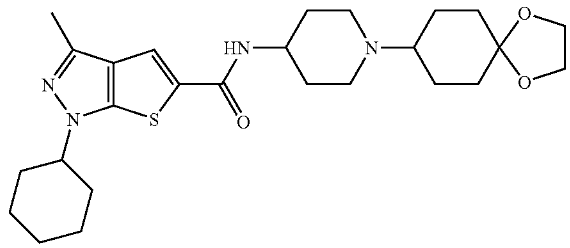 | colorless solid 217-220 | CDCl$_3$ 1.22-1.96 (18 H, m), 2.01-2.09 (2 H, m), 2.13-2.21 (2 H, m), 2.36-2.49 (3 H, m), 2.44 (3 H, s), 2.87-2.94 (2 H, m), 3.77-3.84 (1 H, m), 3.91-4.01 (8 H, m), 4.17 (1 H, tt, J = 3.8 and 11.8 Hz), 5.76-5.80 (1 H, m), 7.31 (1 H, s) | 487 |

TABLE 63

| Example No. | Chemical Structure | properties m.p. (° C.) (recryst. solvent) | $^1$H-NMR | MS (FAB) $(M + 1)^+$ |
|---|---|---|---|---|
| 137 | 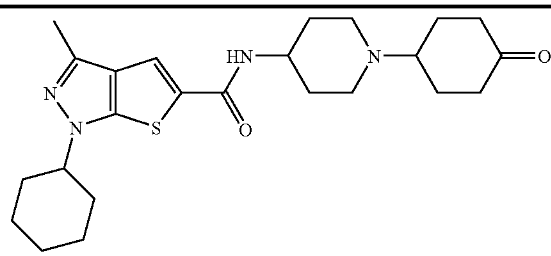 | colorless solid 207-210 | CDCl$_3$ 1.21-2.22(18 H, m), 2.28-2.54 (4 H, m), 2.44 (3 H, s), 2.58-2.66 (1 H, m), 2.72-2.82 (1 H, m), 2.93-3.01 (2 H, m), 3.93-4.02 (1 H, m), 4.18 (1 H, tt, J = 3.8 and 11.8 Hz), 5.73-5.79 (1 H, m), 7.32 (1 H, s) | 443 |
| 138 | 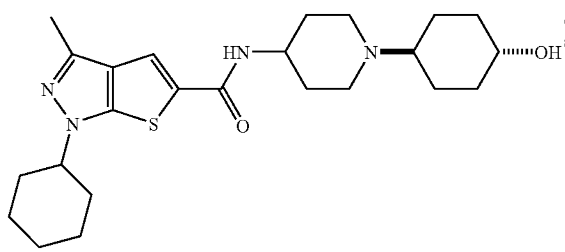 | colorless solid 150-160 | CDCl$_3$ 1.20-1.65 (8 H, m), 1.69-1.98 (8 H, m), 2.00-2.10 (4 H, m), 2.13-2.20 (2 H, m), 2.30-2.41 (3 H, m), 2.44 (3 H, s), 2.95-3.96 (2 H, m), 3.55-3.64 (1 H, m), 3.88-4.01 (1 H, m), 4.17 (1 H, tt, J = 3.8 and 11.8 Hz). 5.70-5.77 (1 H, m), 7.31 (1 H, s) | 445 |
| 139 | 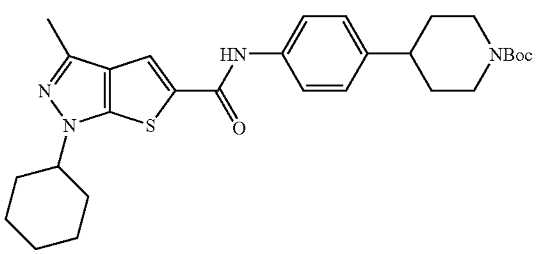 | colorless solid 197 (dec.) | CDCl$_3$ 1.22-1.33 (1 H, m), 1.37-1.64 (4 H, m), 1.48 (9 H, s), 1.70-1.96 (7 H, m), 2.15-2.21 (2 H, m), 2.45 (3 H, s), 2.57-2.67 (1 H, m), 2.72-2.84 (2 H, m), 4.12-4.30 (3 H, m), 7.18 (2 H, d, J = 8.5 Hz), 7.46 (1 H, s), 7.51 (2 H, d, J = 8.5 Hz), 7.63 (1 H, brs) | 523 |
| 140 | 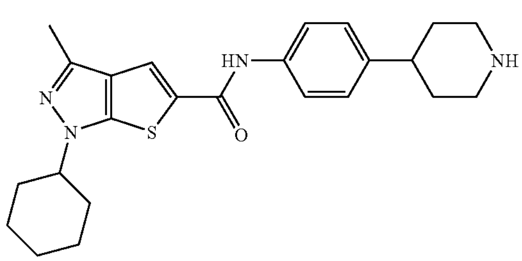 | pale yellow foamy solid | CDCl$_3$ 1.22-1.33 (1 H, m), 1.37-1.50 (2 H, m), 1.52-1.67 (1 H, m), 1.70-1.95 (8 H, m) 2.13-2.21 (2 H, m), 2.44 (3 H, s), 2.55-2.64 (1 H, m), 2.68-2.78 (2 H, m), 3.13-3.21 (2 H, m), 4.18 (1 H, tt, J = 3.8 and 11.8 Hz), 7.20 (2 H, d, J = 8.4 Hz), 7.45 (1 H, s), 7.50 (2 H, d, J = 8.4 Hz), 7.60 (1 H, brs) | 423 |

TABLE 64

| Example No. | Chemical Structure | properties m.p. (° C.) (recryst. solvent) | $^1$H-NMR | MS (FAB) (M + 1)$^+$ |
|---|---|---|---|---|
| 141 | 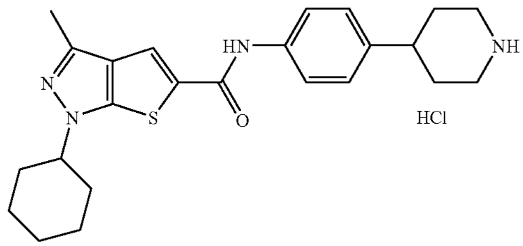 | colorless cryst. 270 (dec.) (EtOH/Et$_2$O) | DMSO-d$_6$ 1.14-1.28 (1 H, m), 1.35-1.48 (2 H, m), 1.59-1.93 (9 H, m), 1.99-2.07 (2 H, m), 2.47 (3 H, s), 2.74-2.84 (1 H, m), 2.90-3.01 (2 H, m), 3.26-3.36 (2 H, m), 4.18 (1 H, tt, J = 3.8 and 11.8 Hz), 7.18 (2 H, d, J = 8.5 Hz), 7.65 (2 H, d, J = 8.5 Hz), 8.06 (1 H, s), 8.42-8.58 (1 H, m), 8.63-8.77 (1 H, m), 10.21 (1 H, brs) | 423 |
| 142 | 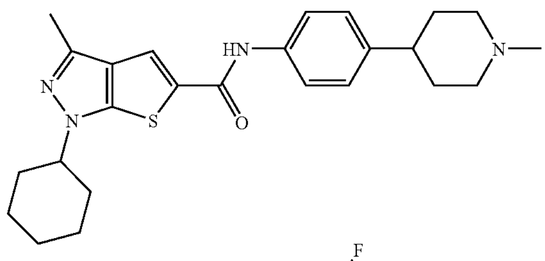 | colorless foamy solid | CDCl$_3$ 1.20-1.33 (1 H, m), 1.37-1.51 (2 H, m), 1.69-1.95 (9 H, m), 1.98-2.07 (2 H, m), 2.12-2.21 (2 H, m), 2.31 (3 H, s), 2.39-2.49 (1 H, m), 2.45 (3 H, s), 2.92-3.00 (2 H, m), 4.18 (1 H, tt, J = 3.8 and 11.8 Hz), 7.21 (2 H, d, J = 8.5 Hz), 7.44 (1 H, s), 7.50 (2 H, d, J = 8.5 Hz), 7.57 (1 H, brs) | 437 |
| 143 | 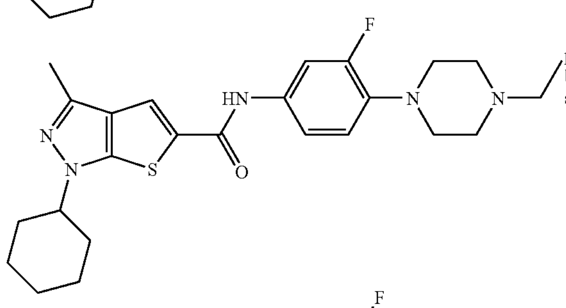 | pale brown solid 197-198 | CDCl$_3$ 1.12 (3 H, t, J = 7.3 Hz), 1.21-1.33 (1 H, m), 1.37-1.51 (2 H, m), 1.69-1.96 (5 H, m), 2.15-2.22 (2 H, m), 2.45 (3 H, s), 2.48 (2 H, q, J = 7.3 Hz), 2.58-2.66 (4 H, m), 3.07-3.14 (4 H, m), 4.18 (1 H, tt, J = 3.8 and 11.8 Hz), 6.89-6.97 (1 H, m), 7.15 (1 H, dd, J = 1.6 and 8.6 Hz), 7.43 (1 H, s), 7.46-7.53 (1 H, m), 7.51 (1 H, brs) | 470 |
| 144 | 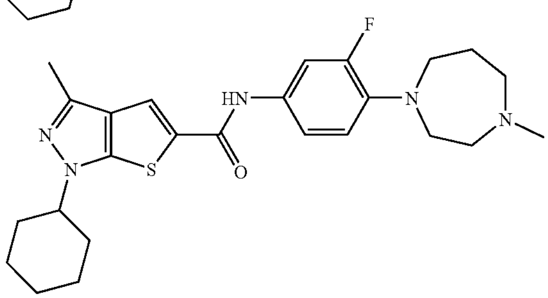 | brown foamy solid | CDCl$_3$ 1.21-1.33 (1 H, m), 1.37-1.50 (2 H, m), 1.69-2.04 (7 H, m), 2.12-2.21 (2 H, m), 2.39 (3 H, s), 2.44 (3 H, s), 2.62-2.67 (2 H, m), 2.73-2.78 (2 H, m), 3.35-3.44 (4 H, m), 4.17 (1 H, tt, J = 3.8 and 11.8 Hz), 6.76-6.83 (1 H, m), 7.09 (1 H, dd, J = 1.9 and 8.9 Hz), 7.43 (1 H, s), 7.48 (1 H, dd, J = 2.4 and 11.6 Hz), 7.42 (1 H, s), 7.51 (1 H, brs) | 470 |

TABLE 65

| Example No. | Chemical Structure | properties m.p. (° C.) (recryst. solvent) | $^1$H-NMR | MS (FAB) (M + 1)$^+$ |
|---|---|---|---|---|
| 145 | 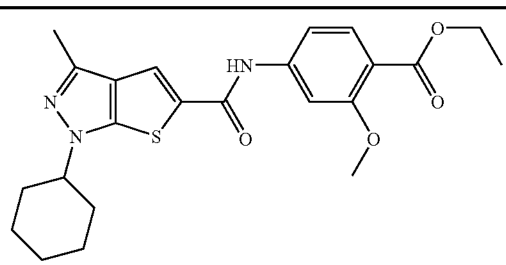 | colorless solid 216-218 (AcOEt/hexane) | CDCl$_3$ 1.21-1.52 (3 H, m), 1.38 (3 H, t, J = 7.1 Hz), 1.71-1.99 (5 H, m), 2.16-2.25 (2 H, m), 2.45 (3 H, s), 3.92 (3 H, s), 4.13-4.22 (1 H, m), 4.35 (2 H, q, J = 7.1 Hz), 6.95 (1 H, dd, J = 1.8 and 8.4 Hz), 7.52 (1 H, s), 7.72 (1 H, d, 1.8 Hz), 7.84 (1 H, d, J = 8.4 Hz), 7.92 (1 H, brs) | 442 |

TABLE 65-continued

| Example No. | Chemical Structure | properties m.p. (° C.) (recryst. solvent) | ¹H-NMR | MS (FAB) (M + 1)⁺ |
|---|---|---|---|---|
| 146 | 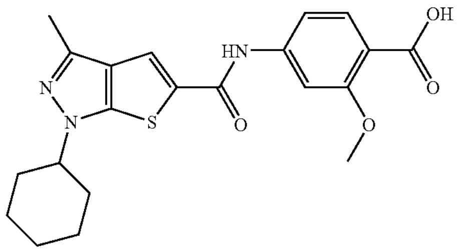 | colorless solid 223-224.5 (AcOEt) | DMSO-d₆ 1.15-1.30 (1 H, m), 1.38-1.51 (2 H, m), 1.62-1.90 (5 H, m), 2.02-2.13 (2 H, m), 2.41 (3 H, s), 3.83 (3 H, s), 4.17-4.29 (1 H, m), 7.43 (1 H, dd, J = 1.6 and 8.5 Hz), 7.59 (1 H, d, 1.6 Hz), 7.72 (1 H, d, J = 8.5 Hz), 8.12 (1 H, s), 10.41 (1 H, brs), 12.31 (1 H, brs) | 414 |
| 147 | 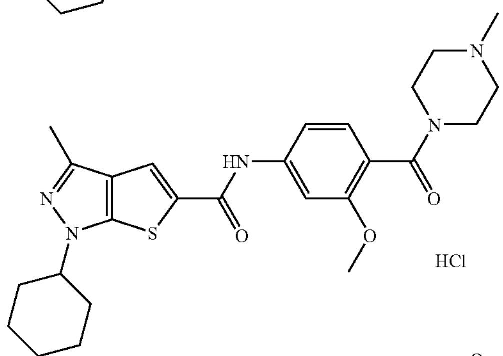 | colorless solid 193.5-198 | DMSO-d₆ 1.17-1.31 (1 H, m), 1.39-1.51 (2 H, m), 1.62-1.90 (5 H, m), 2.02-2.13 (2 H, m), 2.41 (3 H, s), 2.78 (3 H, s), 2.88-3.08 (2 H, m), 3.19-3.60 (5 H, m), 3.84 (3 H, s), 4.17-4.29 (1 H, m), 4.51-4.64 (1 H, m), 7.19-7.29 (1 H, m), 7.41-7.54 (1 H, m), 7.59-7.68 (1 H, m), 8.21 (1 H, s), 10.50 (1 H, brs), 11.20 (1 H, brs) | 496 |
| 148 | 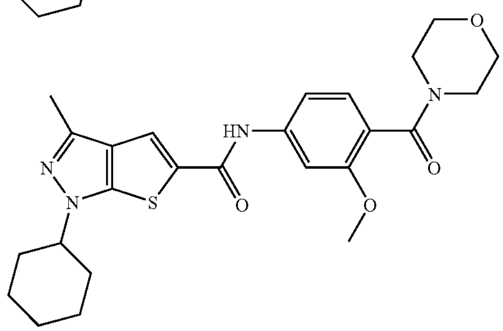 | colorless solid 188.5-190 (AcOEt/ hexane) | CDCl₃ 1.21-1.35 (1 H, m), 1.39-1.1.52 (2 H, m), 1.71-2.00 (5 H, m), 2.13-2.25 (2 H, m), 2.50 (3 H, s), 3.19-3.39 (2 H, m), 3.51-3.65 (2 H, m), 3.70-3.97 (4 H, m), 3.77 (3 H, s), 4.14-4.26 (1 H, m), 6.80 (1 H, dd, J = 1.8 and 8.1 Hz), 7.04 (1 H, d, J = 8.1 Hz), 7.37 (1 H, d, J = 1.7 Hz), 7.76 (1 H, s), 8.72 (1 H, brs) | 483 |

TABLE 66

| Example No. | Chemical Structure | properties m.p. (° C.) (recryst. solvent) | ¹H-NMR | MS (FAB) (M + 1)⁺ |
|---|---|---|---|---|
| 149 | 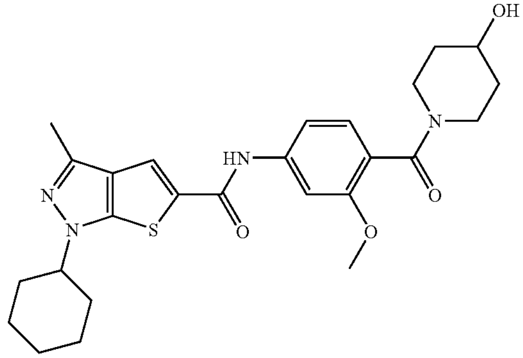 | colorless solid 242.5-245.5 | CDCl₃ 1.21-1.69 (6 H, m), 1.71-2.00 (7 H, m), 2.13-2.25 (2 H, m), 4.46 (3 H, s), 2.99-3.18 (1 H, m), 3.34-3.59 (2 H, m), 3.70-3.80 (3 H, m), 3.90-4.00 (1 H, m), 4.13-4.34 (2 H, m), 6.77-6.82 (1 H, m), 6.95-7.03 (1 H, m), 7.29-7.36 (1 H, m), 7.82 (1 H, s), 8.84 (1 H, brs) | 497 |

TABLE 66-continued

| Example No. | Chemical Structure | properties m.p. (° C.) (recryst. solvent) | ¹H-NMR | MS (FAB) (M + 1)⁺ |
|---|---|---|---|---|
| 150 | 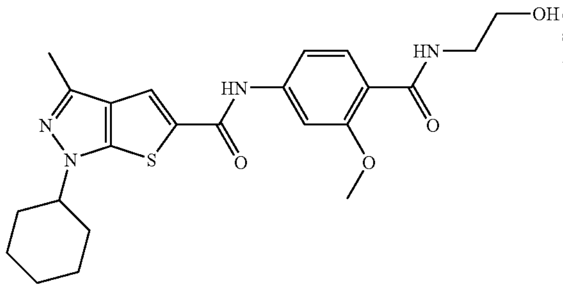 | colorless solid 243-245.5 | CDCl₃ 1.21-1.36 (1 H, m), 1.39-1.51 (2 H, m), 1.70-2.00 (5 H, m), 2.15-2.25 (2 H, m), 3.27 (1 H, brt, J = 5.2 Hz), 3.60-3.69 (2 H, m), 3.79-3.89 (2 H, m), 3.99 (3 H, s), 4.13-4.25 (1 H, m), 6.88 (1 H, dd, J = 1.8 and 8.5 Hz), 7.58 (1 H, s), 7.93 (1 H, d, J = 1.8 Hz), 8.13 (1 H, d, J = 8.5 Hz), 8.15 (1 H, brs), 8.26 (1 H, brt, 5.5 Hz) | 457 |
| 151 | 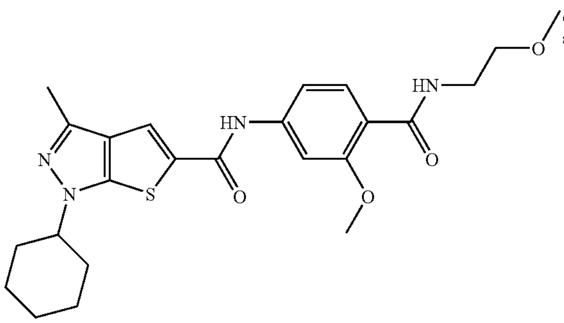 | colorless solid 187-188 | CDCl₃ 1.21-1.35 (1 H, m), 1.39-1.52 (2 H, m), 1.71-1.99 (5 H, m), 2.14-2.24 (2 H, m), 2.44 (3 H, s), 3.41 (3 H, s), 3.52-3.60 (2 H, m), 3.62-3.70 (2 H, m), 3.99 (3 H, s), 4.13-4.24 (1 H, m), 6.89 (1 H, dd, J = 1.5 and 8.5 Hz), 7.57 (1 H, s), 7.95 (1 H, d, J = 1.5 Hz), 8.11 (1 H, brs), 8.16 (1 H, d, J = 8.5 Hz), 8.19 (1 H, brt, 5.3 Hz) | 471 |
| 152 | 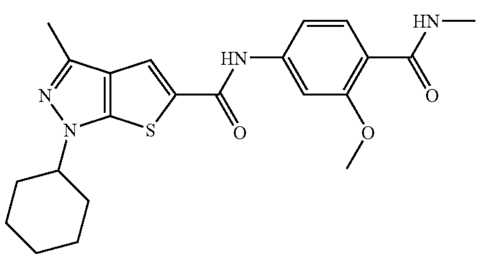 | colorless solid 279-281 (AcOEt) | CDCl₃ 1.22-1.36 (1 H, m), 1.39-1.52 (2 H, m), 1.71-1.99 (5 H, m), 2.14-2.23 (2 H, m), 2.45 (3 H, s), 3.01 (3 H, d, J = 4.8 Hz), 4.00 (3 H, s), 4.13-4.23 (1 H, m), 6.87 (1 H, dd, J = 1.8 and 8.5 Hz), 7.56 (1 H, s), 7.81 (1 H, brq, J = 4.8 Hz), 7.97 (1 H, d, J = 1.8 Hz), 8.04 (1 H, brs), 8.19 (1 H, d, J = 8.5 Hz) | 427 |

TABLE 67

| Example No. | Chemical Structure | properties m.p. (° C.) (recryst. solvent) | ¹H-NMR | MS (FAB) (M + 1)⁺ |
|---|---|---|---|---|
| 153 | 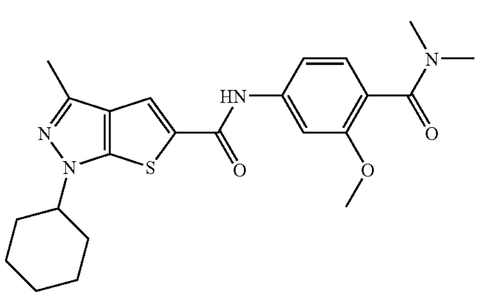 | colorless solid 216-218 (AcOEt) | CDCl₃ 1.21-1.37 (1 H, m), 1.39-1.52 (2 H, m), 1.70-1.98 (5 H, m), 2.15-2.25 (2 H, m), 2.47 (3 H, s), 2.87 (3 H, s), 3.16 (3 H, s), 3.73 (3 H, s), 4.13-4.24 (1 H, m), 6.79 (1 H, dd, J = 1.4 and 8.1 Hz), 6.98 (1 H, d, J = 8.1 Hz), 7.28 (1 H, d, J = 1.4 Hz), 7.88 (1 H, s), 8.98 (1 H, brs) | 441 |

TABLE 67-continued

| Example No. | Chemical Structure | properties m.p. (° C.) (recryst. solvent) | ¹H-NMR | MS (FAB) (M + 1)⁺ |
|---|---|---|---|---|
| 154 | 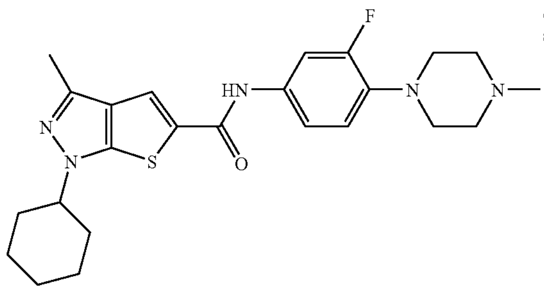 | colorless solid 169-172.5 (EtOH) | CDCl₃ 1.21-1.34 (1 H, m), 1.38-1.51 (2 H, m), 1.69-1.97 (5 H, m), 2.12-2.21 (2 H, m), 2.34 (3 H, s), 2.44 (3 H, s), 2.53-2.64 (4 H, m), 3.03-3.14 (4 H, m), 4.11-4.21 (1 H, m), 6.89-6.96 (1 H, m), 7.15 (1 H, dd J = 2.4 and 8.6 Hz), 7.43 (1 H, s), 7.49 (1 H, dd J = 2.4 and 14.0 Hz), 7.53 (1 H, brs) | 456 |
| 155 | 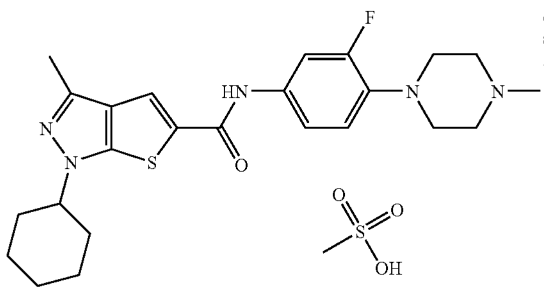 | colorless solid 270 (dec.) | DMSO-d₆ 1.15-1.29 (1 H, m), 1.34-1.49 (2 H, m), 1.60-1.88 (5 H, m), 1.99-2.09 (2 H, m), 2.30 (3 H, s), 2.37 (3 H, s), 2.84 (3 H, s), 2.90-3.62 (8 H, m), 4.13-4.27 (1 H, m), 7.08-7.14 (1 H, m), 7.39-7.45 (1 H, m), 7.62-7.71 (1 H, m), 8.02 (1 H, s), 9.56 (1 H, brs), 10.28 (1 H, brs) | 456 |
| 156 | 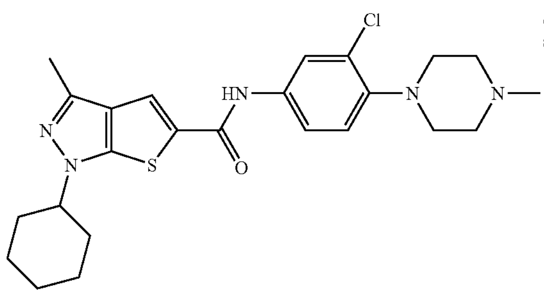 | colorless solid 114-118 (EtOH) | CDCl₃ 1.21-1.35 (1 H, m), 1.40-1.52 (2 H, m), 1.71-1.98 (5 H, m), 2.14-2.23 (2 H, m), 2.39 (3 H, s), 2.46 (3 H, s), 2.54-2.72 (4 H, m), 3.00-3.17 (4 H, m), 4.14-4.26 (1 H, m), 7.05 (1 H, d, J = 8.7 Hz), 7.43 (1 H, dd, J = 2.4 and 8.7 Hz), 7.46 (1 H, s), 7.57 (1 H, brs), 7.69 (1 H, d, J = 2.4 Hz) | 472 |

TABLE 68

| Example No. | Chemical Structure | properties m.p. (° C.) (recryst. solvent) | ¹H-NMR | MS (FAB) (M + 1)⁺ |
|---|---|---|---|---|
| 157 | 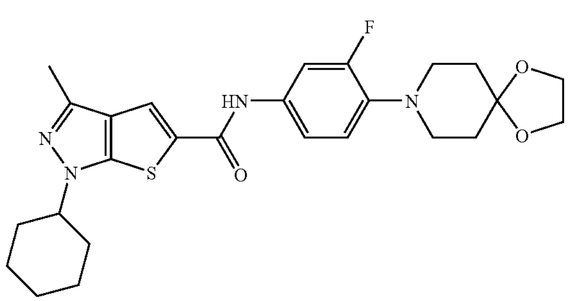 | colorless solid 188-189.5 (EtOH) | CDCl₃ 1.21-1.35 (1 H, m), 1.39-1.51 (2 H, m), 1.70-1.98 (9 H, m), 2.14-2.23 (2 H, m), 2.45 (3 H, s), 3.11-3.19 (4 H, m), 4.00 (4 H, s), 4.12-4.24 (1 H, m), 6.91-6.98 (1 H, m), 7.16 (1 H, dd, J = 2.4 and 8.6 Hz), 7.46 (1 H, s), 7.49 (1 H, dd, J = 2.4 and 13.9 Hz), 7.61 (1 H, brs) | 499 |

TABLE 68-continued

| Example No. | Chemical Structure | properties m.p. (° C.) (recryst. solvent) | ¹H-NMR | MS (FAB) (M + 1)⁺ |
|---|---|---|---|---|
| 158 | (structure) | colorless solid 198-199 (EtOH) | CDCl₃ 1.21-1.35 (1 H, m), 1.39-1.52 (2 H, m), 1.70-1.99 (5 H, m), 2.16-2.25 (2 H, m), 2.46 (3 H, s), 2.59-2.68 (4 H, m), 3.34-3.43 (4 H, m), 4.14-4.25 (1 H, m), 6.94-7.01 (1 H, m), 7.18-7.23 (1 H, m), 7.47 (1 H, s), 7.56 (1 H, dd, J = 2.4 and 13.7 Hz), 7.62 (1 H, brs) | 455 |
| 159 | (structure) | colorless solid 210-212 (EtOH) | CDCl₃ 1.21-1.34 (1 H, m), 1.39-1.52 (3 H, m), 1.70-1.98 (7 H, m), 2.00-2.09 (2 H, m), 2.16-2.24 (2 H, m), 2.46 (3 H, s), 2.79-2.89 (2 H, m), 3.29-3.39 (2 H, m), 3.81-3.91 (1 H, m), 4.13-4.24 (1 H, m), 6.91-7.00 (1 H, m), 7.17 (1 H, dd, J = 2.5 and 8.6 Hz), 7.46 (1 H, s), 7.48 (1 H, dd, J = 2.5 and 13.9 Hz), 7.58 (1 H, brs) | 457 |
| 160 | (structure) | colorless solid 230.5-232 (EtOH) | CDCl₃ 1.22-1.36 (1 H, m), 1.39-1.52 (2 H, m), 1.71-1.98 (9 H, m), 2.15-2.23 (2 H, m), 2.45 (3 H, s), 3.05-3.16 (4 H, m), 4.01 (4 H, s), 4.15-4.24 (1 H, m), 7.05 (1 H, d, J = 8.7 Hz), 7.44 (1 H, dd, J = 2.5 and 8.7 Hz), 7.46 (1 H, s), 7.58 (1 H, brs), 7.66 (1 H, d, J = 2.5 Hz) | 515 |

TABLE 69

| Example No. | Chemical Structure | properties m.p. (° C.) (recryst. solvent) | ¹H-NMR | MS (FAB) (M + 1)⁺ |
|---|---|---|---|---|
| 161 | (structure) | colorless solid 217.5-219 (EtOH) | CDCl₃ 1.21-1.37 (1 H, m), 1.40-1.52 (2 H, m), 1.71-1.99 (5 H, m), 2.15-2.24 (2 H, m), 2.46 (3 H, s), 2.60-2.70 (4 H, m), 3.29-3.38 (4 H, m), 4.13-4.26 (1 H, m), 7.05 (1 H, d, J = 8.7 Hz), 7.47 (1 H, dd, J = 2.5 and 8.7 Hz), 7.48 (1 H, s), 7.64 (1 H, brs), 7.73 (1 H, d, J = 2.5 Hz) | 471 |

TABLE 69-continued

| Example No. | Chemical Structure | properties m.p. (° C.) (recryst. solvent) | ¹H-NMR | MS (FAB) (M + 1)⁺ |
|---|---|---|---|---|
| 162 | 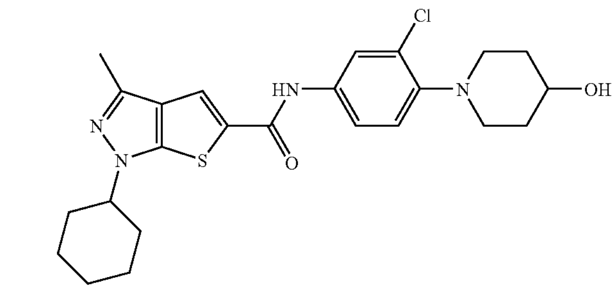 | colorless solid 153.5-156 (AcOEt/ hexane) | CDCl₃ 1.21-1.36 (1 H, m), 1.39-1.53 (3 H, m), 1.71-1.99 (7 H, m), 2.01-2.10 (2 H, m), 2.16-2.24 (2 H, m), 2.45 (3 H, s), 275-2.87 (2 H, m), 3.21-3.31 (2 H, m), 3.82-3.92 (1 H, m), 4.14-4.26 (1 H, m), 7.03 (1 H, d, J = 8.7 Hz), 7.44 (1 H, dd, J = 2.5 and 8.7 Hz), 7.47 (1 H, s), 7.63 (1 H, brs), 7.65 (1 H, d, J = 2.5 Hz) | 473 |
| 163 | 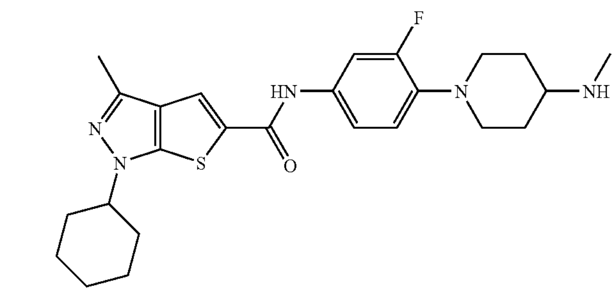 | colorless solid 174-176 (AcOEt/ hexane) | CDCl₃ 1.22-1.36 (1 H, m), 1.39-1.63 (4 H, m), 1.71-2.07 (7 H, m), 2.14-2.23 (2 H, m), 2.41-2.56 (1 H, m), 2.46 (3 H, s), 2.48 (3 H, s), 2.68-2.80 (2 H, m), 3.38-3.45 (2 H, m), 4.14-4.23 (1 H, m), 6.90-6.99 (1 H, m), 7.17 (1 H, dd, J = 2.4 and 8.6 Hz), 7.42-7.51 (2 H, m), 7.58 (1 H, brs) | 470 |
| 164 | 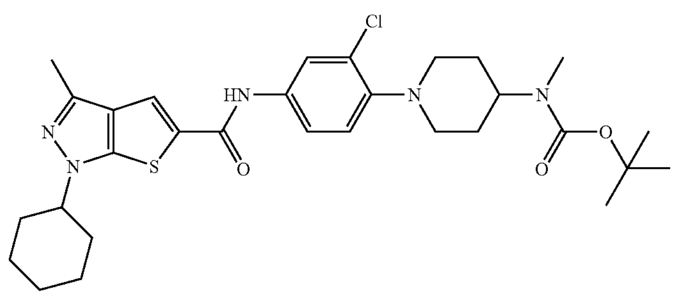 | colorless solid 99.5-106.5 | CDCl₃ 1.22-1.36 (1 H, m), 1.39-1.52 (2 H, m), 1.49 (9 H, s), 1.70-2.00 (9 H, m), 2.14-2.24 (2 H, m), 2.46 (3 H, s), 2.67-2.77 (2 H, m), 2.81 (3 H, s), 3.37-3.46 (2 H, m), 4.10-4.26 (2 H, m), 7.00-7.07 (1 H, m), 7.39-7.45 (1 H, m), 7.47 (1 H, s), 7.59-7.62 (1 H, m), 7.69 (1 H, brs) | 586 |

TABLE 70

| Example No. | Chemical Structure | properties m.p. (° C.) (recryst. solvent) | ¹H-NMR | MS (FAB) (M + 1)⁺ |
|---|---|---|---|---|
| 165 | 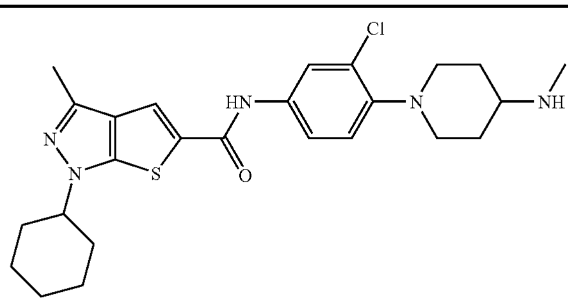 | colorless solid 112-121 | CDCl₃ 1.22-1.37 (1 H, m), 1.39-1.65 (4 H, m), 1.71-2.08 (7 H, m), 2.16-2.25 (2 H, m), 2.46 (3 H, s), 2.49 (3 H, s), 2.50-2.58 (1 H, m), 265-2.76 (2 H, m), 3.30-3.39 (2 H, m), 4.12-4.24 (1 H, m), 7.04 (1 H, d, J = 8.7 Hz), 7.45 (1 H, dd, J = 2.4 and 8.7 Hz), 7.46 (1 H, s), 7.56 (1 H, brs), 7.64 (1 H, d, J = 2.4 Hz) | 486 |

TABLE 70-continued

| Example No. | Chemical Structure | properties m.p. (° C.) (recryst. solvent) | ¹H-NMR | MS (FAB) (M + 1)⁺ |
|---|---|---|---|---|
| 166 | 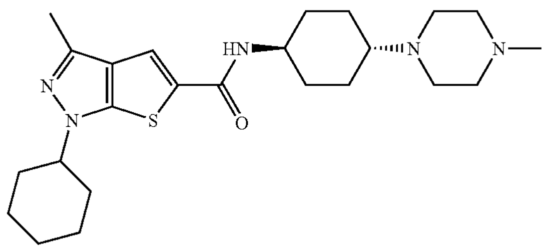 | colorless solid 230-233.5 (AcOEt) | CDCl₃ 1.17-1.32 (3 H, m), 1.36-1.49 (4 H, m), 1.69-2.00 (7 H, m), 2.10-2.20 (4 H, m), 2.22-2.30 (1 H, m), 2.27 (3 H, s), 2.37-2.70 (8 H, m), 2.41 (3 H, s), 3.81-3.92 (1 H, m), 4.09-4.21 (1 H, m), 5.62-5.69 (1 H, m), 7.28 (1 H, s) | 444 |
| 167 | 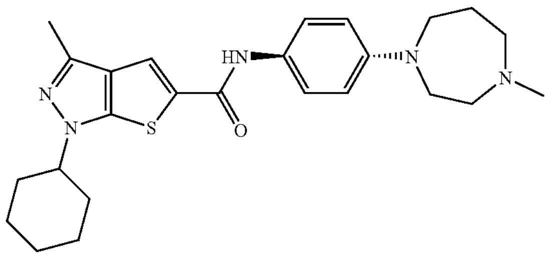 | colorless solid 195-199 (AcOEt) | CDCl₃ 1.17-1.32 (3 H, m), 1.36-1.50 (4 H, m), 1.69-1.95 (9 H, m), 2.09-2.20 (4 H, m), 2.34 (3 H, s), 2.41 (3 H, s), 2.42-2.50 (1 H, m), 2.52-2.62 (4 H, m), 2.71-2.80 (4 H, m), 3.80-3.91 (1 H, m), 4.10-4.20 (1 H, m), 5.61-5.69 (1 H, m), 7.28 (1 H, s) | 458 |
| 168 | 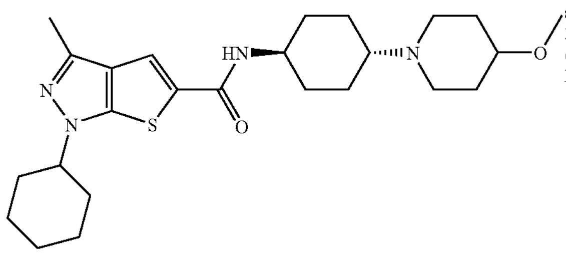 | colorless solid 204.5-207 (AcOEt/ hexane) | CDCl₃ 1.18-1.32 (3 H, m), 1.36-1.49 (4 H, m), 1.51-1.61 (2 H, m), 1.69-1.95 (9 H, m), 2.10-2.20 (4 H, m), 2.25-2.38 (3 H, m), 2.41 (3 H, s), 2.72-2.81 (2 H, m), 3.13-3.22 (1 H, m), 3.32 (3 H, s), 3.80-3.93 (1 H, m), 4.11-4.21 (1 H, m), 5.62-5.69 (1 H, m), 7.28 (1 H, s) | 459 |

TABLE 71

| Example No. | Chemical Structure | properties m.p. (° C.) (recryst. solvent) | ¹H-NMR | MS (FAB) (M + 1)⁺ |
|---|---|---|---|---|
| 169 | 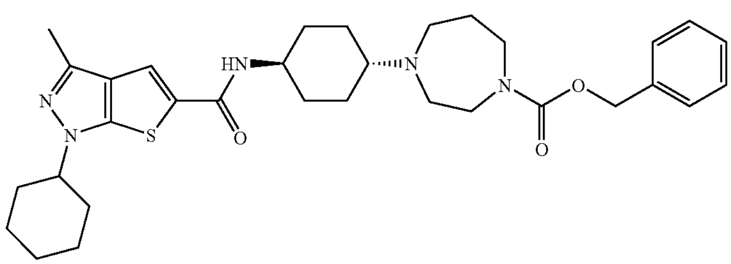 | colorless solid 61-63 | CDCl₃ 1.12-1.50 (7 H, m), 1.68-1.95 (9 H, m), 2.05-2.20 (4 H, m), 2.35-2.50 (1 H, m), 2.41 (3 H, s), 2.57-2.78 (4 H, m), 3.41-3.59 (4 H, m), 3.76-3.90 (1 H, m), 4.08-4.21 (1 H, m), 5.13 (2 H, s), 5.60-5.71 (1 H, m), 7.28-7.40 (6 H, m) | 578 |

TABLE 71-continued

| Example No. | Chemical Structure | properties m.p. (° C.) (recryst. solvent) | ¹H-NMR | MS (FAB) (M + 1)⁺ |
|---|---|---|---|---|
| 170 | 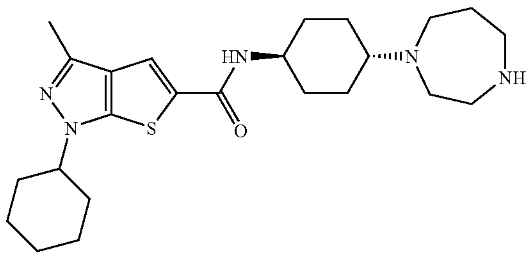 | colorless solid 115-120 | CDCl₃ 1.17-1.32 (3 H, m), 1.36-1.50 (4 H, m), 1.64-1.96 (9 H, m), 2.09-2.21 (4 H, m), 2.41 (3 H, s), 2.43-2.54 (1 H, m), 2.68-2.77 (4 H, m), 2.83-2.94 (4 H, m), 3.80-3.92 (1 H, m), 4.10-4.21 (1 H, m), 5.61-5.70 (1 H, m), 7.28 (1 H, s) | 444 |
| 171 | 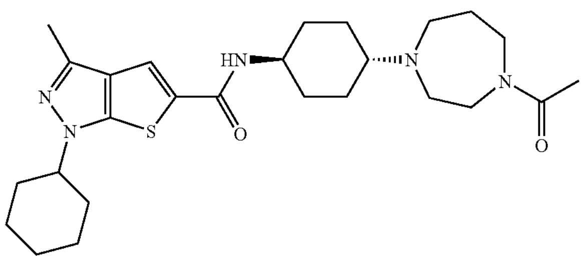 | colorless foamy solid | CDCl₃ 1.17-1.50 (7 H, m), 1.69-1.97 (9 H, m), 2.07 and 2.08 (total 3 H, each s), 2.10-2.21 (4 H, m), 2.41 (3 H, s), 2.44-2.54 (1 H, m), 2.61-2.69 (2 H, m), 2.71-2.79 (2 H, m), 3.41-3.52 (2 H, m), 3.55-3.12 (2 H, m), 3.79-3.92 (1 H, m), 4.11-4.21 (1 H, m), 5.64-5.72 (1 H, m), 7.28 (1 H, s) | 486 |
| 172 | 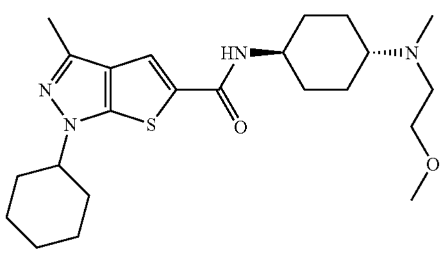 | colorless solid 142-143.5 (AcOEt/ hexane) | CDCl₃ 1.17-1.32 (3 H, m), 1.35-1.49 (4 H, m), 1.69-1.96 (7 H, m), 2.10-2.20 (4 H, m), 2.30 (3 H, s), 2.39-2.48 (1 H, m), 2.41 (3 H, s), 2.63 (2 H, t, J = 5.9 Hz), 3.35 (3 H, s), 3.45 (2 H, t, J = 5.9 Hz), 3.80-3.92 (1 H, m), 4.10-4.20 (1 H, m), 5.61-5.69 (1 H, m), 7.28 (1 H, s) | 433 |

TABLE 72

| Example No. | Chemical Structure | properties m.p. (° C.) (recryst. solvent) | ¹H-NMR | MS (FAB) (M + 1)⁺ |
|---|---|---|---|---|
| 173 | 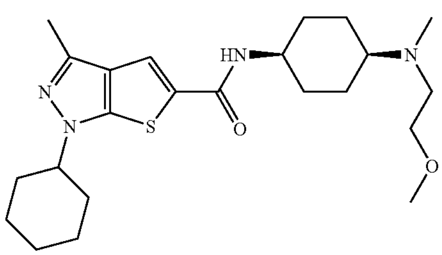 | colorless foamy solid | CDCl₃ 1.20-1.97 (16 H, m), 2.11-2.20 (2 H, m), 2.28-2.47 (1 H, m), 2.33 (3 H, s), 2.44 (3 H, s), 2.68 (2 H, t, J = 6.0 Hz), 3.35 (3 H, s), 3.47 (2 H, t, J = 6.0 Hz), 4.11-4.24 (2 H, m), 5.93-6.00 (1 H, m), 7.30 (1 H, s) | 433 |

TABLE 72-continued

| Example No. | Chemical Structure | properties m.p. (° C.) (recryst. solvent) | ¹H-NMR | MS (FAB) (M + 1)⁺ |
|---|---|---|---|---|
| 174 | 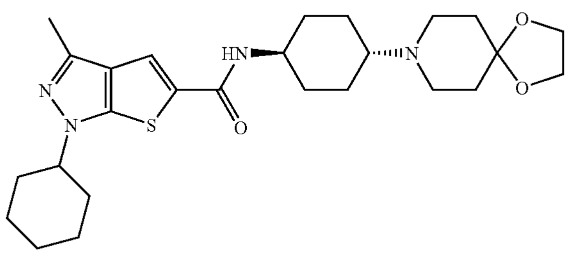 | colorless solid 222-224.5 (EtOH) | CDCl₃ 1.16-1.31 (3 H, m), 1.35-1.50 (4 H, m), 1.68-1.96 (11 H, m), 2.09-2.19 (4 H, m), 2.31-2.40 (1 H, m), 2.41 (3 H, s), 2.58-2.67 (4 H, m), 3.80-3.92 (1 H, m), 3.94 (4 H, s), 4.10-4.20 (1 H, m), 5.62-5.71 (1 H, m), 7.28 (1 H, s) | 487 |
| 175 | 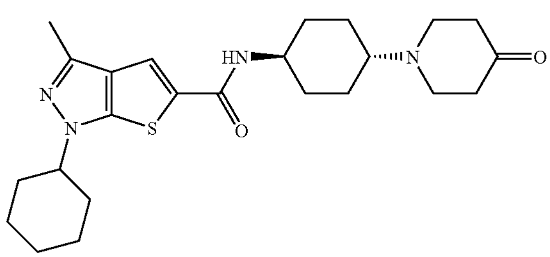 | colorless solid 197-199 (AcOEt) | CDCl₃ 1.19-1.32 (3 H, m), 1.36-1.52 (4 H, m), 1.69-2.00 (7 H, m), 2.10-2.23 (4 H, m), 2.36-2.56 (8 H, m), 2.79-2.89 (4 H, m), 3.82-3.95 (1 H, m), 4.10-4.20 (1 H, m), 5.66-5.76 (1 H, m), 7.29 (1 H, s) | 443 |
| 176 | 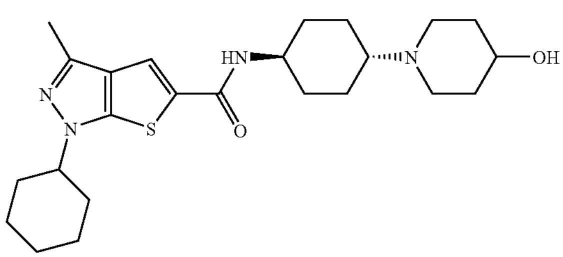 | colorless solid 200-202 (AcOEt) | CDCl₃ 1.18-1.31 (3 H, m), 1.36-1.97 (16 H, m), 2.10-2.20 (4 H, m), 2.27-2.38 (3 H, m), 2.41 (3 H, s), 2.75-2.85 (2 H, m), 3.61-3.71 (1 H, m), 3.80-3.92 (1 H, m), 4.10-4.20 (1 H, m), 5.64-5.73 (1 H, m), 7.28 (1 H, s) | 445 |

TABLE 73

| Example No. | Chemical Structure | properties m.p. (° C.) (recryst. solvent) | ¹H-NMR | MS (FAB) (M + 1)⁺ |
|---|---|---|---|---|
| 177 | 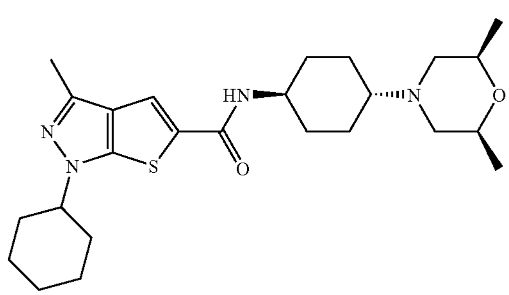 | colorless solid 226-228 (EtOH) | CDCl₃ 1.15 (6 H, d, J = 6.2 Hz), 1.17-1.32 (3 H, m), 1.34-1.50 (4 H, m), 1.69-1.99 (9 H, m), 2.11-2.27 (5 H, m), 2.41 (3 H, s), 2.68-2.78 (2 H, m), 3.59-3.69 (2 H, m), 3.81-3.93 (1 H, m), 4.11-4.20 (1 H, m), 5.63-5.70 (1 H, m), 7.28 (1 H, s) | 459 |

TABLE 73-continued

| Example No. | Chemical Structure | properties m.p. (° C.) (recryst. solvent) | ¹H-NMR | MS (FAB) (M + 1)⁺ |
|---|---|---|---|---|
| 178 | 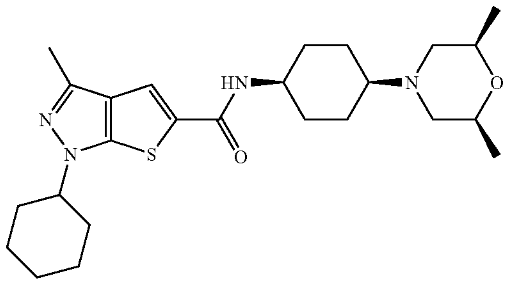 | colorless solid 199.5-200.5 (EtOH) | CDCl₃ 1.17 (6 H, d, J = 6.2 Hz), 1.20-1.33 (1 H, m), 1.36-1.50 (2 H, m), 1.53-1.96 (15 H, m), 2.09-2.20 (3 H, m), 2.43 (3 H, s), 2.80-2.89 (2 H, m), 3.60-3.70 (2 H, m), 4.10-4.22 (2 H, m), 5.89-5.96 (1 H, m), 7.30 (1 H, s) | 459 |
| 179 | 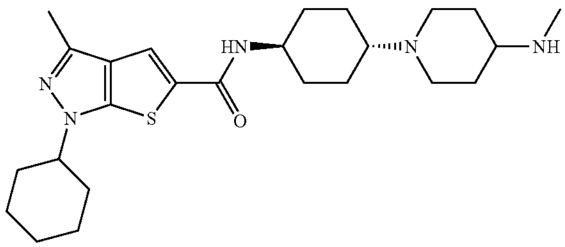 | colorless solid 201.5-203 (AcOEt/ hexane) | CDCl₃ 1.17-1.98 (18 H, m), 2.10-2.38 (8 H, m), 2.41 (6 H, s), 2.81-2.90 (2 H, m), 3.80-3.92 (1 H, m), 4.11-4.20 (1 H, m), 5.62-5.69 (1 H, m), 7.29 (1 H, s) | 458 |
| 180 | 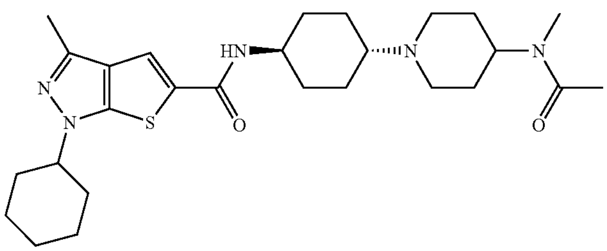 | colorless solid 253-255 (AcOEt/ EtOH) | CDCl₃ 1.18-1.31 (3 H, m), 1.35-1.50 (4 H, m), 1.57-2.00 (11 H, m), 2.07 and 2.10 (total 3 H, each s), 2.11-2.21 (4 H, m), 2.24-2.40 (3 H, m), 2.41 (3 H, s), 2.81 and 2.85 (total 3 H, each s), 2.90-3.01 (2 H, m), 3.41-3.51 (0.4 H, m), 3.81-3.94 (1 H, m), 4.10-4.21 (1 H, m), 4.41-4.52 (0.6 H, m), 5.67-5.74 (1 H, m), 7.29 (1 H, s) | 500 |

TABLE 74

| Example No. | Chemical Structure | properties m.p. (° C.) (recryst. solvent) | ¹H-NMR | MS (FAB) (M + 1)⁺ |
|---|---|---|---|---|
| 181 | 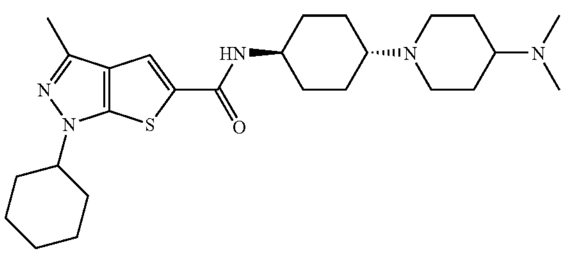 | colorless solid 204-208.5 (AcOEt) | CDCl₃ 1.18-1.33 (3 H, m), 1.36-1.50 (4 H, m), 1.55-1.99 (11 H, m), 2.10-2.20 (4 H, m), 2.23-2.48 (4 H, m), 2.38 (6 H, s), 2.41 (3 H, s), 2.95-3.05 (2 H, m), 3.80-3.92 (1 H, m), 4.10-4.20 (1 H, m), 5.68-5.74 (1 H, m), 7.29 (1 H, s) | 472 |

TABLE 74-continued

| Example No. | Chemical Structure | properties m.p. (° C.) (recryst. solvent) | ¹H-NMR | MS (FAB) (M + 1)⁺ |
|---|---|---|---|---|
| 182 | 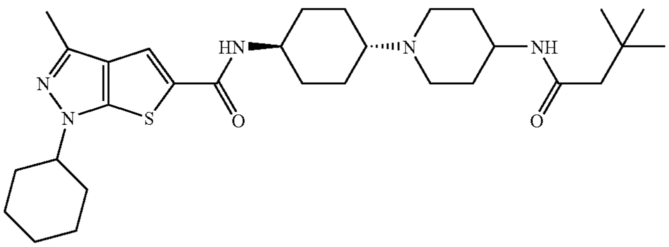 | colorless solid 215.5-224 | CDCl₃ 1.16-1.50 (9 H, m), 1.43 (9 H, s), 1.69-1.99 (9 H, m), 2.10-2.19 (4 H, m), 2.22-2.36 (3 H, m), 2.41 (3 H, s), 2.78-2.87 (2 H, m), 3.36-3.49 (1 H, m), 3.81-3.92 (1 H, m), 4.09-4.20 (1 H, m), 4.35-4.44 (1 H, m), 5.62-5.69 (1 H, m), 7.28 (1 H, s) | 544 |
| 183 | 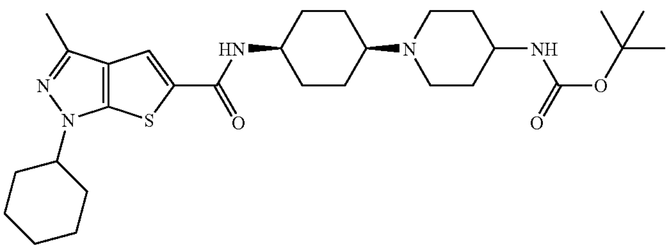 | colorless solid | CDCl₃ 1.20-2.00 (20 H, m), 1.44 (9 H, s), 2.11-2.28 (5 H, m), 2.43 (3 H, s), 2.40-2.49 (2 H, m), 3.38-3.51 (1 H, m), 4.11-4.22 (2 H, m), 4.33-4.46 (1 H, m), 5.90-5.97 (1 H, m), 7.30 (1 H, s) | 544 |
| 184 | 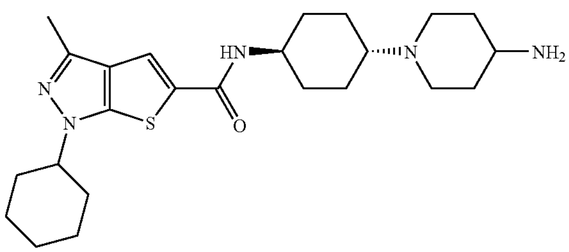 | colorless solid 219-221.5 (AcOEt/ hexane) | CDCl₃ 1.16-1.52 (9 H, m), 1.69-1.96 (9 H, m), 2.10-2.38 (7 H, m), 2.41 (3 H, s), 2.57-2.68 (1 H, m), 2.80-2.89 (2 H, m), 3.80-3.92 (1 H, m), 4.10-4.21 (1 H, m), 5.62-5.70 (1 H, m), 7.28 (1 H, s) | 444 |

TABLE 75

| Example No. | Chemical Structure | properties m.p. (° C.) (recryst. solvent) | ¹H-NMR | MS (FAB) (M + 1)⁺ |
|---|---|---|---|---|
| 185 | 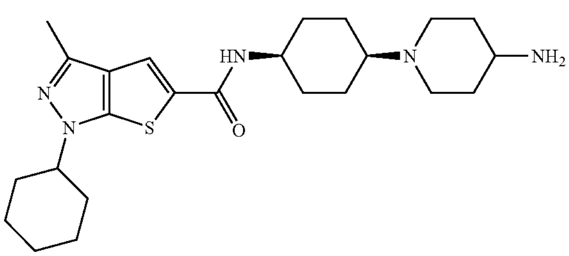 | colorless solid 83-86.5 | CDCl₃ 1.20-1.95 (20 H, m), 2.02-2.36 (5 H, s), 2.43 (3 H, s), 2.60-2.70 (1 H, m), 2.92-3.03 (2 H, m), 4.11-4.22 (2 H, m), 5.91-6.00 (1 H, m), 7.30 (1 H, s) | 444 |

TABLE 75-continued

| Example No. | Chemical Structure | properties m.p. (° C.) (recryst. solvent) | ¹H-NMR | MS (FAB) (M + 1)⁺ |
|---|---|---|---|---|
| 186 | 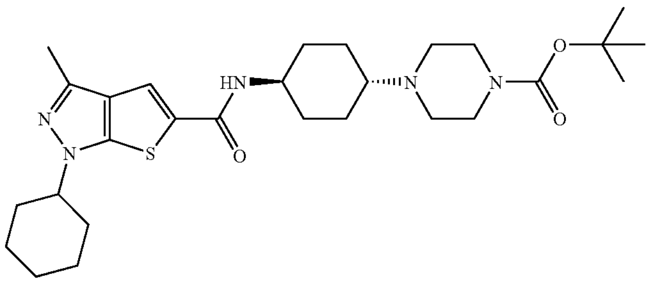 | colorless solid 190.5-193.5 | CDCl₃ 1.17-1.32 (3 H, m), 1.36-1.49 (4 H, m), 1.45 (9 H, s), 1.69-1.96 (7 H, m), 2.11-2.21 (4 H, m), 2.25-2.36 (1 H, m), 2.41 (3 H, s), 2.45-2.53 (4 H, m), 3.38-3.45 (4 H, m), 3.81-3.93 (1 H, m), 4.10-4.20 (1 H, m), 5.63-5.70 (1 H, m), 7.28 (1 H, s) | 530 |
| 187 | 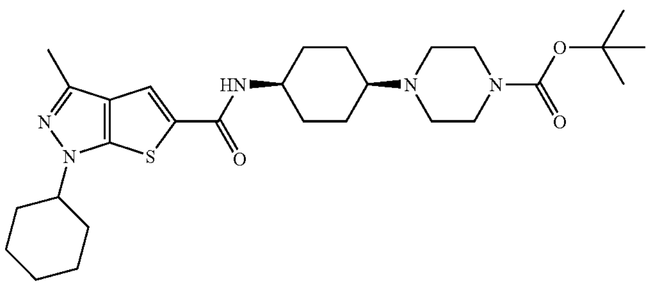 | colorless foamy solid | CDCl₃ 1.20-1.96 (16 H, m), 1.45 (9 H, s), 2.11-2.24 (3 H, m), 2.43 (3 H, s), 2.45-2.51 (4 H, m), 3.39-3.47 (4 H, m), 4.10-4.21 (2 H, m), 5.88-5.93 (1 H, m), 7.30 (1 H, s) | 530 |
| 188 | 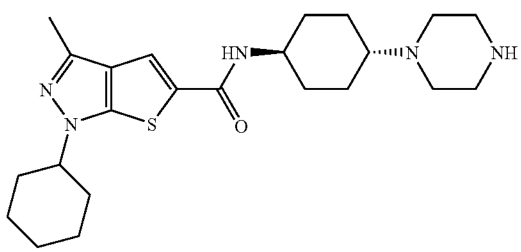 | colorless solid 180.5-182 (AcOEt) | CDCl₃ 1.18-1.32 (3 H, m), 1.34-1.49 (4 H, m), 1.69-1.99 (7 H, m), 2.10-2.19 (4 H, m), 2.20-2.29 (1 H, m), 2.41 (3 H, s), 2.48-2.58 (4 H, m), 2.82-2.91 (4 H, m), 3.80-3.93 (1 H, m), 4.10-4.20 (1 H, m), 5.63-5.70 (1 H, m), 7.28 (1 H, s) | 430 |

TABLE 76

| Example No. | Chemical Structure | properties m.p. (° C.) (recryst. solvent) | ¹H-NMR | MS (FAB) (M + 1)⁺ |
|---|---|---|---|---|
| 189 | 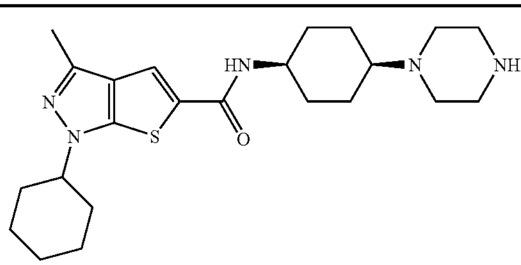 | colorless solid 161-164.5 | CDCl₃ 1.20-1.96 (16 H, m), 2.11-2.21 (3 H, m), 2.43 (3 H, s), 2.46-2.58 (4 H, m), 2.87-2.96 (4 H, m), 4.10-4.22 (2 H, m), 5.90-5.99 (1 H, m), 7.30 (1 H, s) | 430 |

TABLE 76-continued

| Example No. | Chemical Structure | properties m.p. (° C.) (recryst. solvent) | ¹H-NMR | MS (FAB) (M + 1)⁺ |
|---|---|---|---|---|
| 190 | 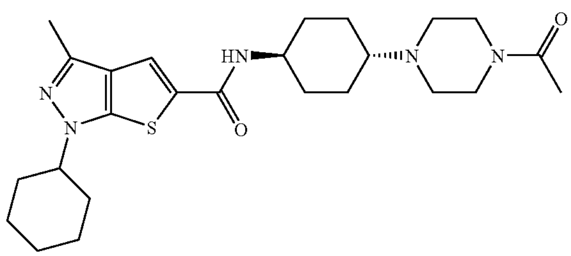 | colorless solid 242-243.5 (AcOEt/ EtOH) | CDCl₃ 1.18-1.32 (3 H, m), 1.35-1.50 (4 H, m), 1.69-1.96 (7 H, m), 2.07 (3 H, s), 2.11-2.21 (4 H, m), 2.27-2.38 (1 H, m), 2.41 (3 H, s), 2.49-2.59 (4 H, m), 3.40-3.47 (2 H, m), 3.57-3.63 (2 H, m), 3.81-3.93 (1 H, m), 4.10-4.21 (1 H, m), 5.64-5.71 (1 H, m), 7.28 (1 H, s) | 472 |
| 191 | 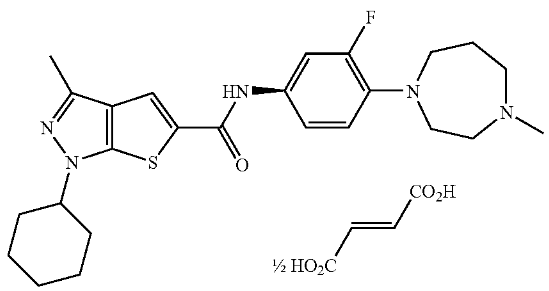 | pale brown solid 237 (dec.) | DMSO-d₆ 1.16-1.29 (1 H, m), 1.35-1.50 (2 H, m), 1.61-1.84 (5 H, m), 1.88-1.96 (2 H, m), 2.00-2.08 (2 H, m), 2.35 (3 H, s), 2.36 (3 H, s), 2.63-2.69 (2 H, m), 2.72-2.77 (2 H, m), 3.25-3.35 (4 H, m), 4.19 (1 H, tt, J = 3.8 and 11.7 Hz), 6.51 (1 H, s), 6.88-6.95 (1 H, m), 7.29 (1 H, dd, J = 2.0 and 8.8 Hz), 7.55 (1 H, dd, J = 2.3 and 15.7 Hz), 7.98 (1 H, s), 10.15 (1 H, brs) | 470 |
| 192 | 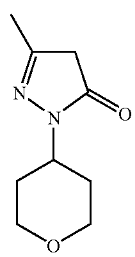 | colorless solid | CDCl₃ 1.64-1.73 (2 H, m), 2.00-2.10 (2 H, m), 2.10 (3 H, s), 3.22 (2 H, s), 3.43-3.52 (2 H, m), 4.02-4.09 (2 H, m), 4.23 (1 H, tt, J = 11.7 and 4.2 Hz) | 183 |

TABLE 77

| Example No. | Chemical Structure | properties m.p. (° C.) (recryst. solvent) | ¹H-NMR | MS (FAB) (M + 1)⁺ |
|---|---|---|---|---|
| 193 | 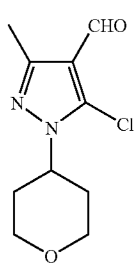 | colorless solid | CDCl₃ 1.80-1.88 (2 H, m), 2.22-2.35 (2 H, m), 2.46 (3 H, s), 3.50-3.58 (2 H, m), 4.09-4.15 (2 H, m), 4.48 (1 H, tt, J = 11.6 and 4.2 Hz), 9.89 (1 H, s) | 229 |

TABLE 77-continued

| Example No. | Chemical Structure | properties m.p. (° C.) (recryst. solvent) | ¹H-NMR | MS (FAB) (M + 1)⁺ |
|---|---|---|---|---|
| 194 | (3-methyl-1-(tetrahydro-2H-pyran-4-yl)-1H-thieno[2,3-c]pyrazole-5-carboxylic acid ethyl ester) | colorless solid 78-80 | CDCl₃ 1.38 (3 H, t, J = 7.1 Hz), 2.08-2.25 (4 H, m), 2.45 (3 H, s), 3.52-3.61 (2 H, m), 4.10-4.17 (2 H, m), 4.35 (2 H, q, J = 7.1 Hz), 4.38-4.47 (1 H, m), 7.71 (1 H, s) | 295 |
| 195 | (3-methyl-1-(tetrahydro-2H-pyran-4-yl)-1H-thieno[2,3-c]pyrazole-5-carboxylic acid) | colorless solid 240-242 | DMSO-d₆ 1.90-2.05 (4 H, m), 2.38 (3 H, s), 3.44-3.52 (2 H, m), 3.92-4.00 (2 H, m), 4.43-4.54 (1 H, m), 7.66 (1 H, s) | 267 |
| 196 | (3-methyl-N-(4-(4-methylpiperazin-1-yl)phenyl)-1-(tetrahydro-2H-pyran-4-yl)-1H-thieno[2,3-c]pyrazole-5-carboxamide) | colorless solid 107-109 (EtOH) | CDCl₃ 2.08-2.26 (4 H, m), 2.36 (3 H, s), 2.46 (3 H, s), 2.55-2.61 (4 H, m), 3.16-3.23 (4 H, m), 3.52-3.61 (2 H, m), 4.09-4.16 (2 H, m), 4.37-4.47 (1 H, m), 6.90-6.95 (2 H, m), 7.45 (1 H, s), 7.45-7.50 (2 H, m), 7.53 (1 H, brs) | 440 |

TABLE 78

| Example No. | Chemical Structure | properties m.p. (° C.) (recryst. solvent) |
|---|---|---|
| 197 | (N-(3-fluoro-4-(4-methylpiperazin-1-yl)phenyl)-3-methyl-1-(tetrahydro-2H-pyran-4-yl)-1H-thieno[2,3-c]pyrazole-5-carboxamide) | colorless solid 98-102 (EtOH) |

TABLE 78-continued
| | | |
|---|---|---|
| 198 | 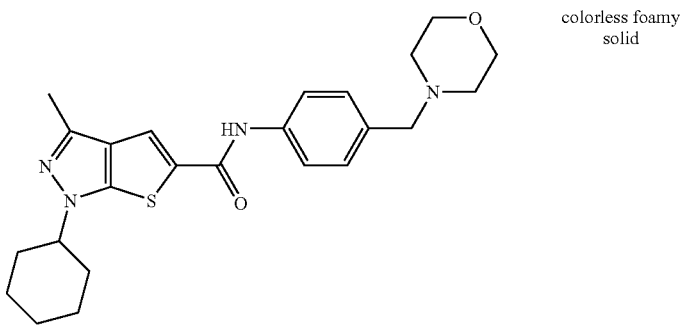 | colorless foamy solid |
| 199 | 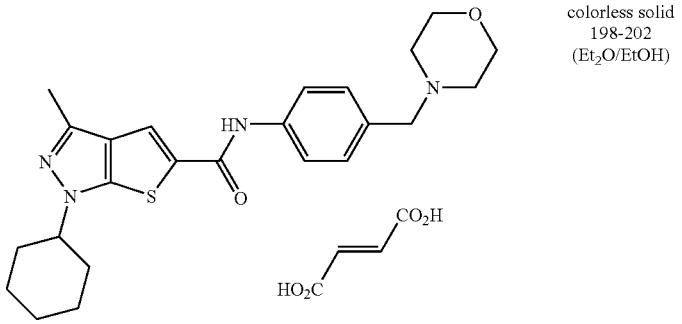 | colorless solid 198-202 (Et₂O/EtOH) |
| 200 | 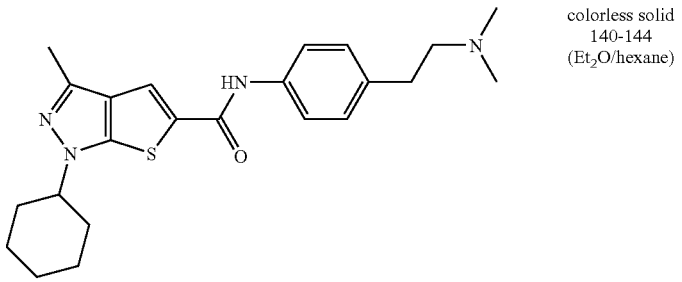 | colorless solid 140-144 (Et₂O/hexane) |
| Example No. | $^1$H-NMR | MS(FAB) $(M + 1)^+$ |
|---|---|---|
| 197 | CDCl₃ 2.07-2.25(4 H, m), 2.36(3 H, s), 2.46(3 H, s), 2.57-2.63(4 H, m), 3.06-3.12(4 H, m), 3.50-3.58(2 H, m), 4.08-4.15(2 H, m), 4.36-4.47(1 H, m), 6.89-6.96(1 H, m), 7.12-7.16(1 H, m), 7.45(1 H, s), 7.47-7.52(1 H, m), 7.52(1 H, brs) | 458 |
| 198 | CDCl₃ 1.23-1.36(1 H, m), 1.38-1.52(2 H, m), 1.72-1.98(5 H, m), 2.15-2.25(2 H, m), 2.41-2.47(4 H, m), 2.46(3 H, s), 3.48(2 H, s), 3.69-3.75(4 H, m), 4.19(1 H, tt, J = 3.8 and 11.8 Hz), 7.32(2 H, d, J = 8.4 Hz), 7.47(1 H, s), 7.54(2 H, d, J = 8.4 Hz), 7.65(1 H, brs) | 439 |
| 199 | DMSO-d₆ 1.16-1.31(1 H, m), 1.38-1.52(2 H, m), 1.62-1.86(5 H, m), 2.01-2.11(2 H, m), 2.31-2.39(4 H, m), 2.40(3 H, s), 3.44(2 H, s), 3.54-3.60(4 H, m), 4.22(1 H, tt, J = 3.8 and 11.6 Hz), 6.62(2 H, s), 7.27(2 H, d, J = 8.5 Hz), 7.67(2 H, d, J = 8.5 Hz), 8.06(1 H, s), 10.21(1 H, s) | 439 |
| 200 | CDCl₃ 1.21-1.33(1 H, m), 1.38-1.51(2 H, m), 1.71-1.96(5 H, m), 2.14-2.23(2 H, m), 2.31(6 H, m), 2.46(3 H, s), 2.50-2.56(2 H, m), 2.65-2.71(2 H, m), 4.19(1 H, tt, J = 3.9 and 11.8 Hz), 7.18-7.23(2 H, m), 7.46(1 H, s), 7.49-7.54(2 H, m), 7.58(1 H, brs) | 411 |

TABLE 79

| Example No. | Chemical Structure | properties m.p. (° C.) (recryst. solvent) |
|---|---|---|
| 201 | 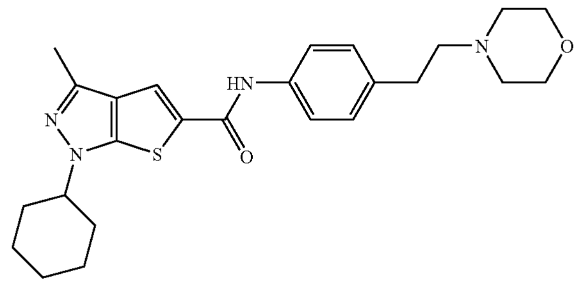 | colorless solid 162-164 |
| 202 | 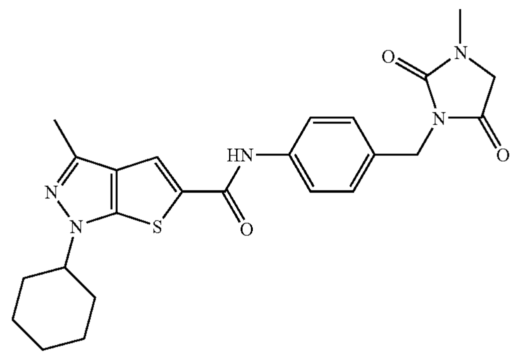 | colorless foamy solid 216-218 |
| 203 | 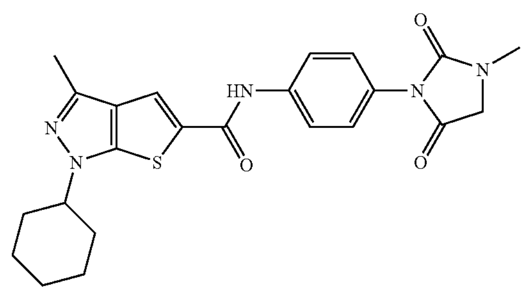 | colorless solid (AcOEt) |
| 204 | 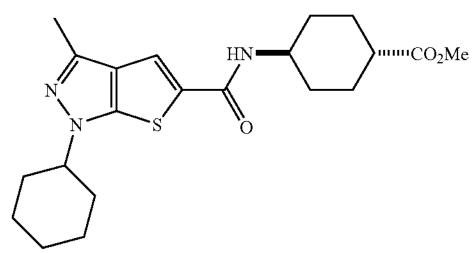 | colorless solid 153-156 |

| Example No. | ¹H-NMR | MS(FAB) (M + 1)⁺ |
|---|---|---|
| 201 | CDCl₃ 1.24-1.36(1 H, m), 1.39-1.52(2 H, m), 1.72-1.98(5 H, m), 2.15-2.24(2 H, m), 2.46(3 H, s), 2.49-2.55(4 H, m), 2.56-2.62(2 H, m), 2.76-2.83(2 H, m), 3.73-3.78(4 H, m), 4.19(1 H, tt, J = 3.9 and 11.8 Hz), 7.20(2 H, d, J = 8.4 Hz), 7.46(1 H, s), 7.51(2 H, d, J = 8.4 Hz), 7.61(1 H, brs) | 453 |
| 202 | CDCl₃ 1.24-1.35(1 H, m), 1.39-1.52(2 H, m), 1.72-1.99(5 H, m), 2.16-2.24(2 H, m), 2.46(3 H, s), 2.99(3 H, s), 3.86(2 H, s), 4.19(1 H, tt, J = 3.9 and 11.8 Hz), 4.63(2 H, 7.41-7.46(2 H, m), 7.47(1 H, s), 7.53-7.57(2 H, m), 7.63(1 H, brs) | 466 |
| 203 | CDCl₃ 1.22-1.53(3 H, m), 1.72-1.99(5 H, m), 2.16-2.24(2 H, m), 2.47(3 H, s), 3.10(3 H, s), 4.04(2 H, s), | 452 |

TABLE 79-continued

| | | |
|---|---|---|
| | 4.19(1 H, tt, J = 3.9 and 11.8 Hz), 7.36-7.42(2 H, m), 7.51(1 H, s), 7.66-7.72(2 H, m), 7.79(1 H, brs) | |
| 204 | CDCl$_3$ 1.18-1.33(3 H, m), 1.38-1.51(2 H, m), 1.55-1.67(2 H, m), 1.71-1.96(5 H, m), 2.03-2.22(6 H, m), 2.28(1 H, tt, J = 3.6 and 12.1 Hz), 2.43(3 H, s), 3.68(3 H, s), 3.88-4.00(1 H, m), 4.16(1 H, tt, J = 3.9 and 11.9 Hz), 5.69-5.75(1 H, m), 7.30(1 H, s) | 404 |

TABLE 80

| Example No. | Chemical Structure | properties m.p. (° C.) (recryst. solvent) |
|---|---|---|
| 205 | 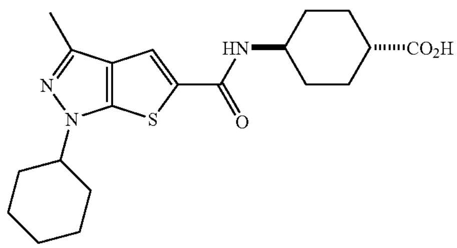 | colorless solid 280-288 |
| 206 | 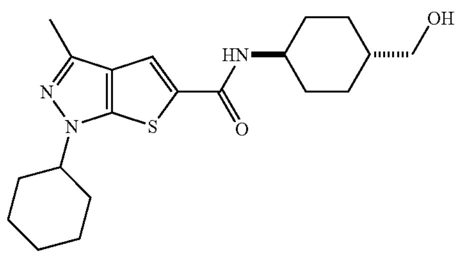 | colorless solid 180-182 |
| 207 | 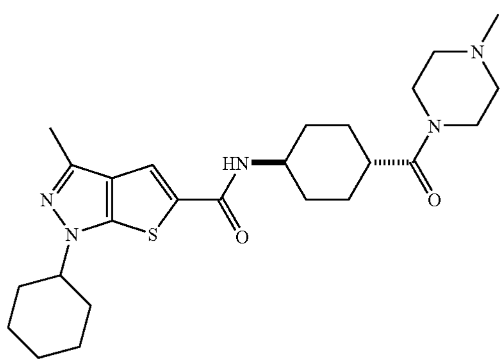 | colorless foamy solid |
| 208 | 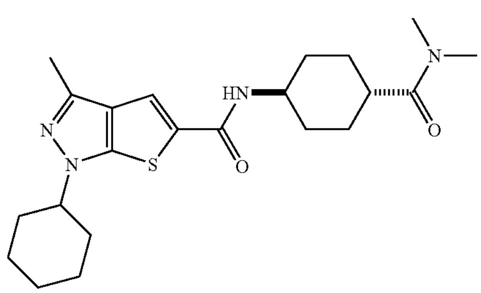 | colorless solid 224-228 |

| Example No. | $^1$H-NMR | MS(FAB) (M + 1)$^+$ |
|---|---|---|
| 205 | DMSO-d$_6$ 1.16-1.49(7 H, m), 1.62-2.08(11 H, m), 2.17(1 H, tt, J = 3.4 and 11.5 Hz), 2.35(3 H, s), 3.60- | 390 |

TABLE 80-continued

| | | |
|---|---|---|
| | 3.72(1 H, m), 4.18(1 H, tt, J = 3.8 and 11.5 Hz), 7.80(1 H, s), 8.26(1 H, d, J = 7.8 Hz), 12.12(1 H, brs) | |
| 206 | CDCl$_3$ 1.07-1.56(8 H, m), 1.70-1.95(7 H, m), 2.11-2.20(4 H, m), 2.43(3 H, s), 3.46-3.52(2 H, m), 3.85-3.97(1 H, m), 4.17(1 H, tt, J = 3.8 and 11.9 Hz), 5.66-5.72(1 H, m), 7.30(1 H, s) | 376 |
| 207 | CDCl$_3$ 1.19-1.35(3 H, m), 1.37-1.51(2 H, m), 1.69-1.96(9 H, m), 2.13-2.25(4 H, m), 2.32(3 H, s), 2.34-2.49(5 H, m), 2.43(3 H, s), 3.47-3.55(2 H, m), 3.60-3.67(2 H, m), 3.88-4.01(1 H, m), 4.17(1 H, tt, J = 3.9 and 11.9 Hz), 5.65-5.71(1 H, m), 7.31(1 H, s) | 472 |
| 208 | CDCl$_3$ 1.21-1.52(5 H, m), 1.67-1.96(9 H, m), 2.13-2.23(4 H, m), 2.43(3 H, s), 2.49(1 H, tt, J = 3.5 and 11.7 Hz), 2.95(3 H, s), 3.06(3 H, s), 3.90-4.02(1 H, m), 4.17(1 H, tt, J = 3.8 and 11.9 Hz), 5.64-5.70(1 H, m), 7.29(1 H, s) | 417 |

TABLE 81

| Example No. | Chemical Structure | properties m.p. (° C.) (recryst. solvent) |
|---|---|---|
| 209 | 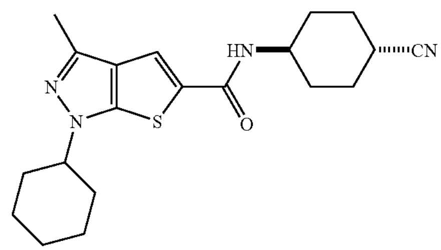 | colorless solid 134-136 |
| 210 | 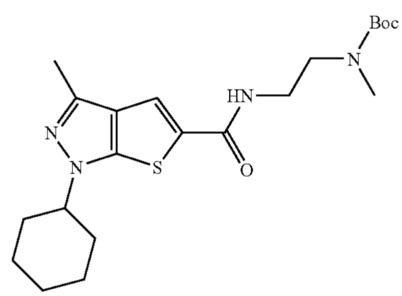 | colorless foamy solid |
| 211 | 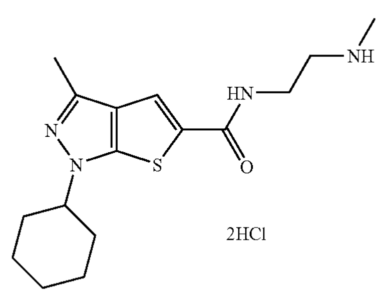 | colorless solid 130-142 |

TABLE 81-continued

| Example No. | ¹H-NMR | MS(FAB) (M + 1)⁺ |
|---|---|---|
| 209 | CDCl₃ 1.22-1.34(3 H, m), 1.37-1.51(2 H, m), 1.70-1.87(5 H, m), 1.89-1.96(2 H, m), 2.13-2.23(6 H, m), 2.40-2.49(1 H, m), 2.43(3 H, s), 3.92-4.02(1 H, m), 4.17(1 H, tt, J = 3.8 and 11.8 Hz), 5.66-5.72(1 H, m), 7.30(1 H, s) | 371 |
| 210 | CDCl₃ 1.21-1.33(1 H, m), 1.37-1.50(2 H, m), 1.47(9 H, s), 1.69-1.95(5 H, m), 2.12-2.21(2 H, m), 2.41(3 H, s), 2.92(3 H, s), 3.47-3.60(4 H, m), 4.17(1 H, tt, J = 3.8 and 11.8 Hz), 7.26-7.36(1 H, m), 7.34(1 H, s) | 421 |
| 211 | DMSO-d₆ 1.17-1.30(1 H, m), 1.37-1.50(2 H, m), 1.50-1.86(5 H, m), 2.02-2.10(2 H, m), 2.36(3 H, s), 2.56-2.61(2 H, m), 3.03-3.12(2 H, m), 3.51-3.57(1 H, m), 3.57(3 H, s), 4.20(1 H, tt, J = 3.8 and 11.6 Hz), 7.86(1 H, s), 8.72-8.87(3 H, m) | 321 |
| 212 | CDCl₃ 1.21-1.34(1 H, m), 1.37-1.49(2 H, m), 1.70-1.96(5 H, m), 2.12(3 H, s), 2.13-2.22(2 H, m), 2.44(3 H, s), 3.08(3 H, s), 3.58-3.71(4 H, m), 4.16(1 H, tt, J = 3.8 and 11.8 Hz), 7.30-7.37(1 H, m), 7.31(1 H, s) | 363 |

TABLE 82

| Example No. | Chemical Structure | properties m.p. (° C.) (recryst. solvent) |
|---|---|---|
| 213 | 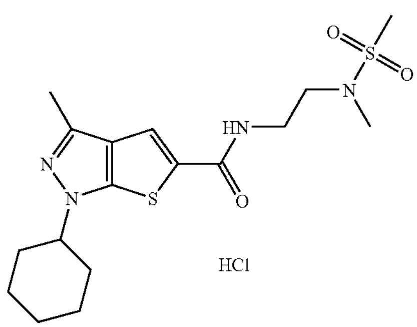 | colorless solid 120-130 |
| 214 | 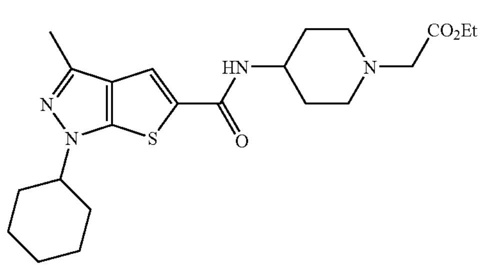 | colorless foamy solid |

TABLE 82-continued

| | | properties m.p. (° C.) (recryst. solvent) |
|---|---|---|
| 215 | 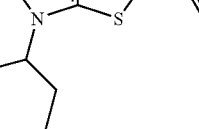 | colorless solid 230-236 |
| 216 | 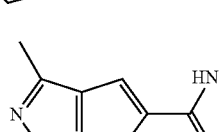 | pale yellow solid 156-158 |

| Example No. | $^1$H-NMR | MS(FAB) $(M + 1)^+$ |
|---|---|---|
| 213 | DMSO-$d_6$ 1.14-1.28(1 H, m), 1.35-1.48(2 H, m), 1.62-1.85(5 H, m), 2.01-2.08(2 H, m), 2.35(3 H, s), 2.81(3 H, s), 2.86(3 H, s), 3.18-3.23(2 H, m), 3.38-3.44(2 H, m), 4.19(1 H, tt, J = 3.8 and 11.5 Hz), 7.75(1 H, s), 8.62-8.68(1 H, m) | 399 |
| 214 | CDCl$_3$ 1.21-1.34(1 H, m), 1.28(3 H, t, J = 7.1 Hz), 1.38-1.51(2 H, m), 1.57-1.97(7 H, m), 2.01-2.08(2 H, m), 2.14-2.21(2 H, m), 2.36(2 H, dt, J = 2.3 and 11.6 Hz), 2.44(3 H, s), 2.93-3.00(2 H, m), 3.24(2 H, s), 3.94-4.04(1 H, m), 4.12-4.22(1 H, m), 4.19(2 H, q, J = 7.1 Hz), 5.72-5.77(1 H, m), 7.32(1 H, s) | 433 |
| 215 | DMSO-$d_6$ 1.16-130(1 H, m), 1.36-1.49(2 H, m), 1.61-1.88(7 H, m), 2.01-2.08(2 H, m), 2.36(3 H, s), 2.41-2.59(4 H, m), 3.07-3.14(2 H, m), 3.17-3.20(2 H, m), 3.73-3.84(1 H, m), 4.18(1 H, tt, J = 3.9 and 11.5 Hz), 7.83(1 H, s), 8.31-8.35(1 H, m) | 405 |
| 216 | CDCl$_3$ 1.21-1.34(1 H, m), 1.29(3 H, t, J = 7.1 Hz), 1.33(6 H, s), 1.37-1.69(4 H, m), 1.69-1.97(5 H, m), 2.01-2.08(2 H, m), 2.13-2.21(2 H, m), 2.31-2.41(2 H, m), 2.43(3 H, s), 2.92-2.99(2 H, m), 3.91-4.01(1 H, m), 4.12-4.22(1 H, m), 4.19(2 H, q, J = 7.1 Hz), 5.70-5.75(1 H, m), 7.30(1 H, s) | 461 |

TABLE 83

| Example No. | Chemical Structure | properties m.p. (° C.) (recryst. solvent) |
|---|---|---|
| 217 | 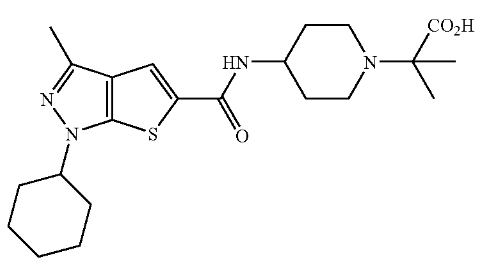 | colorless solid 251-256 |

TABLE 83-continued
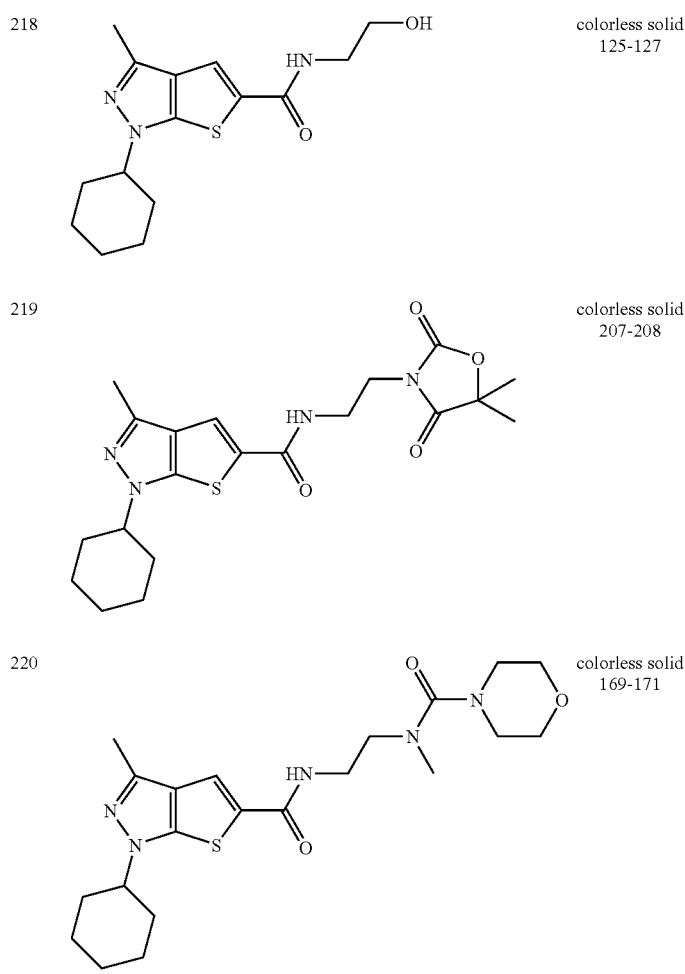
| Example No. | ¹H-NMR | MS(FAB) (M + 1)⁺ |
|---|---|---|
| 217 | DMSO-d₆ 1.16-1.30(1 H, m), 1.25(6 H, s), 1.34-1.51(2 H, m), 1.62-1.86(7 H, m), 1.92-1.99(2 H, m), 2.02-2.09(2 H, m), 2.36(3 H, s), 2.65-2.76(2 H, m), 3.13-3.20(2 H, m), 3.81-3.91(1 H, m), 4.19(1 H, tt, J = 3.7 and 11.5 Hz), 7.86(1 H, s), 8.34-8.39(1 H, m) | 433 |
| 218 | CDCl₃ 1.21-1.34(1 H, m), 1.38-1.50(2 H, m), 1.72-1.77(5 H, m), 2.14-2.22(2 H, m), 2.36-2.46(1 H, m), 2.44(3 H, s), 3.60-3.66(2 H, m), 3.83-3.88(2 H, m), 4.18(1 H, tt, J = 3.8 and 11.8 Hz), 6.36-6.44(1 H, m), 7.36(1 H, s) | 308 |
| 219 | CDCl₃ 1.21-1.34(1 H, m), 1.38-1.51(2 H, m), 1.57(6 H, s), 1.71-1.97(5 H, m), 2.12-2.20(2 H, m), 2.44(3 H, s), 3.72-3.77(2 H, m), 3.78-3.83(2 H, m), 4.16(1 H, tt, J = 3.8 and 11.8 Hz), 6.40-6.46(1 H, m), 7.31(1 H, s) | 419 |
| 220 | CDCl₃ 1.21-1.33(1 H, m), 1.37-1.48(2 H, m), 1.68-1.96(5 H, m), 2.11-2.21(2 H, m), 2.44(3 H, s), 2.94(3 H, s), 3.23-3.29(4 H, m), 3.47-3.52(2 H, m), 3.58-3.64(2 H, m), 3.66-3.71(4 H, m), 4.16(1 H, tt, J = 3.8 and 11.8 Hz), 7.34(1 H, s), 7.94-7.99(1 H, m) | 434 |

TABLE 84
| Example No. | Chemical Structure | properties m.p. (° C.) (recryst. solvent) |
|---|---|---|
| 221 | 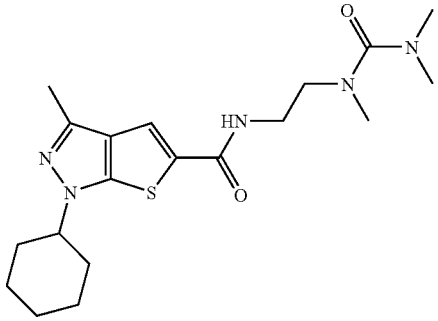 | colorless solid 103-105 (Et₂O/hexane) |
| 222 | 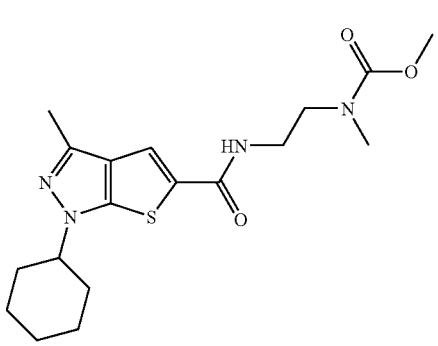 | colorless solid 109-113 (Et₂O/hexane) |
| 223 | 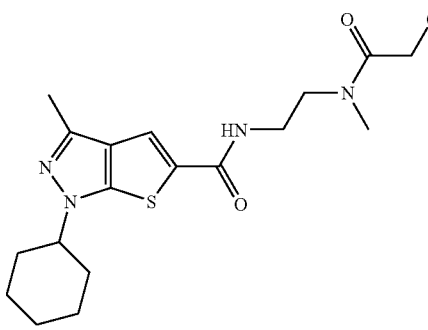 | colorless solid 136-137 (Et₂O/hexane) |
| 224 | 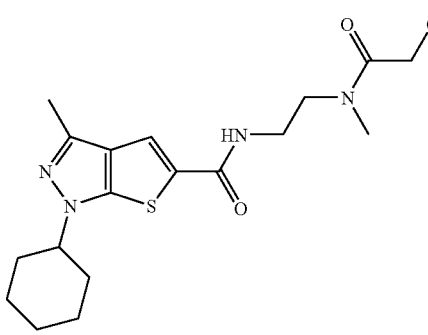 | colorless foamy solid |
| Example No. | ¹H-NMR | MS(FAB) (M + 1)⁺ |
|---|---|---|
| 221 | CDCl₃ 1.18-1.32(1 H, m), 1.36-1.50(2 H, m), 1.68-1.95(5 H, m), 2.12-2.20(2 H, m), 2.44(3 H, s), 2.86(6 H, s), 2.90(3 H, s), 3.44-3.49(2 H, s), 3.56-3.62(2 H, m), 4.16(1 H, tt, J = 3.8 and 11.8 Hz), 7.39(1 H, s), 8.37-8.43(1 H, m) | 392 |
| 222 | CDCl₃ 1.18-1.33(1 H, m), 1.36-1.50(2 H, m), 1.69-1.96(5 H, m), 2.12-2.20(2 H, m), 2.44(3 H, s), 2.96(3 H, brs), 3.46-3.64(4 H, s), 3.72(3 H, s), 4.17(1 H, tt, J = 3.8 | 379 |

TABLE 84-continued

| | | |
|---|---|---|
| | and 11.8 Hz), 6.05-6.15(0.2 H, m), 7.00-7.08(0.8 H, m), 7.32(1 H, s) | |
| 223 | CDCl$_3$ 1.18-1.33(1 H, m), 1.36-1.50(2 H, m), 1.69-1.96(5 H, m), 2.12-2.20(2 H, m), 2.44(3 H, s), 2.99(0.5 H, s), 3.06(2.5 H, s), 3.41(2.5 H, s), 3.44(0.5 H, s), 3.56-3.70(4 H, s), 4.10-4.21(3 H, m), 6.65-6.72(0.17 H, m), 7.12-7.18(0.83 H, m), 7.33(1 H, s) | 393 |
| 224 | CDCl$_3$ 1.21-1.34(1 H, m), 1.37-1.52(2 H, m), 1.70-1.96(5 H, m), 2.13-2.22(2 H, m), 2.43(0.3 H, s), 2.44(2.7 H, s), 2.97(2.7 H, s), 3.08(0.3 H, s), 3.38-3.74(5 H, s), 4.11-4.22(3 H, m), 6.17-6.24(0.1 H, m), 6.78-6.84(0.9 H, m), 7.29(0.9 H, s), 7.34(0.1 H, s) | 379 |

TABLE 85

| Example No. | Chemical Structure | properties m.p. (° C.) (recryst. solvent) |
|---|---|---|
| 225 | 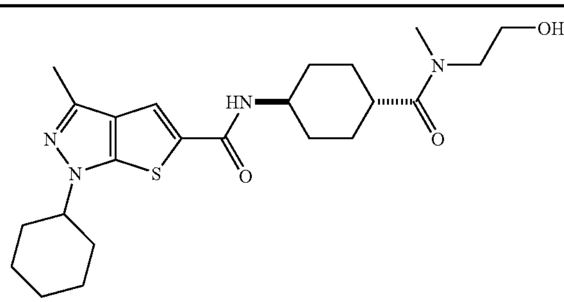 | colorless solid 190-194 |
| 226 | 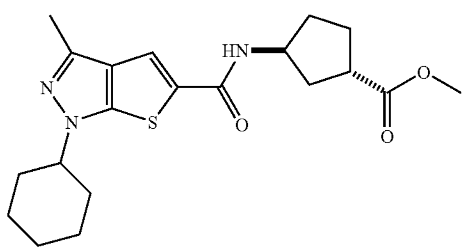 | colorless solid 190-194 |
| 227 | 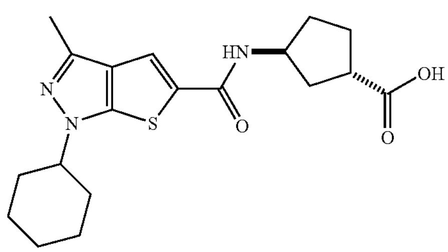 | colorless solid 164-167 |
| 228 | 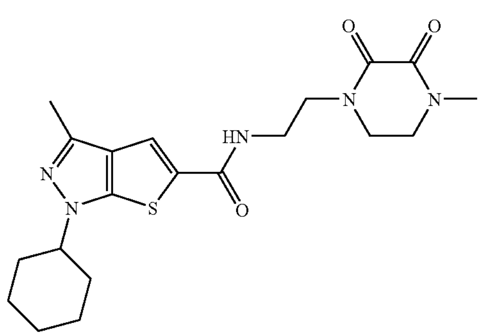 | colorless solid >300 |

TABLE 85-continued

| Example No. | $^1$H-NMR | MS(FAB) (M + 1)$^+$ |
|---|---|---|
| 225 | CDCl$_3$ 1.20-1.50(5 H, m), 1.66-1.96(9 H, m), 2.12-2.26(4 H, m), 2.43(3 H, s), 2.44-2.68(1 H, m), 2.96(0.6 H, s), 3.13(2.4 H, s), 3.48-3.59(2 H, m), 3.76-3.83(2 H, m), 3.91-4.03(1 H, m), 4.17(1 H, tt, J = 3.8 and 11.8 Hz), 5.68-5.74(1 H, m), 7.30(1 H, s) | 447 |
| 226 | CDCl$_3$ 1.21-1.33(1 H, m), 1.37-1.50(2 H, m), 1.54-1.64(1 H, m), 1.70-1.98(7 H, m), 2.05-2.40(5 H, m), 2.43(3 H, s), 2.92-3.02(1 H, m), 3.70(3 H, s), 4.17(1 H, tt, J = 3.8 and 11.8 Hz), 4.46-4.55(1 H, m), 5.77-5.84(1 H, m), 7.30(1 H, s) | 390 |
| 227 | DMSO-d$_6$ 1.16-1.31(1 H, m), 1.37-1.86(10 H, m), 1.93-2.08 (5 H, m), 2.35(3 H, s), 2.87-2.97(1 H, m), 4.18(1 H, tt, J = 3.8 and 11.7 Hz), 4.23-4.32(1 H, m), 7.81(1 H, s), 8.32-8.36(1 H, m), 12.14(1 H, brs) | 376 |
| 228 | DMSO-d$_6$ 1.16-1.29(1 H, m), 1.36-1.49(2 H, m), 1.62-1.86(5 H, m), 2.00-2.07(2 H, m), 2.35(3 H, s), 2.91(3 H, s), 3.39-3.58(8 H, m), 4.19(1 H, tt, J = 3.8 and 11.6 Hz), 7.69(1 H, s), 8.60-8.66(1 H, m) | 418 |

TABLE 86

| Example No. | Chemical Structure | properties m.p. (° C.) (recryst. solvent) |
|---|---|---|
| 229 | 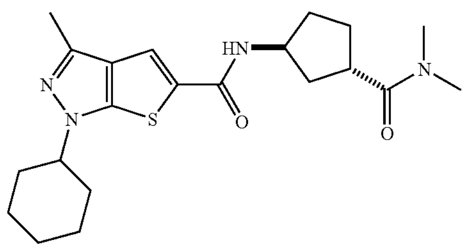 | colorless foamy solid |
| 231 | | colorless solid 75-90 |
| 231 | | colorless solid 95-101 |
| 232 | 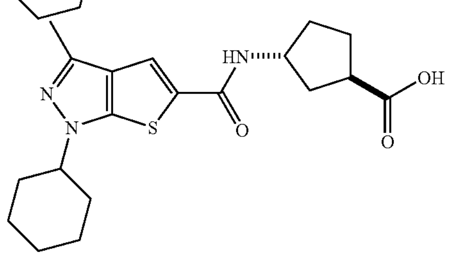 | colorless solid 165-168 |

TABLE 86-continued

| Example No. | ¹H-NMR | MS(FAB) (M + 1)⁺ |
|---|---|---|
| 229 | CDCl₃ 1.21-1.33(1 H, m), 1.38-1.51(2 H, m), 1.58-1.68(1 H, m), 1.70-2.05(8 H, m), 2.13-2.21(2 H, m), 2.23-2.40(2 H, m), 2.43(3 H, s), 2.96(3 H, s), 3.05(3 H, s), 3.12-3.22(1 H, m), 4.17(1 H, tt, J = 3.8 and 11.8 Hz), 4.43-4.52(1 H, m), 5.83-5.89(1 H, m), 7.31(1 H, s) | 403 |
| 231 | DMSO-d₆ 1.15-1.28(1 H, m), 1.36-1.48(2 H, m), 1.51-1.85(8 H, m), 1.92-2.07(5 H, m), 2.36(3 H, s), 2.83(3 H, s), 3.02(3 H, s), 3.18-3.29(1 H, m), 4.18(1 H, tt, J = 3.8 and 11.6 Hz), 4.22-4.32(1 H, m), 7.81(1 H, s), 8.30-8.35(1 H, m) | 403 |
| 231 | CDCl₃ 1.21-1.33(1 H, m), 1.37-1.50(2 H, m), 1.54-1.64(1 H, m), 1.70-1.98(7 H, m), 2.05-2.40(5 H, m), 2.43(3 H, s), 2.92-3.02(1 H, m), 3.70(3 H, s), 4.17(1 H, tt, J = 3.8 and 11.8 Hz), 4.46-4.55(1 H, m), 5.84-5.89(1 H, m), 7.31(1 H, s) | 390 |
| 232 | DMSO-d₆ 1.16-1.30(1 H, m), 1.37-1.86(10 H, m), 1.93-2.09(5 H, m), 2.35(3 H, s), 2.87-2.96(1 H, m), 4.19(1 H, tt, J = 3.8 and 11.7 Hz), 4.23-4.31(1 H, m), 7.81(1 H, s), 8.32-8.36(1 H, m), 12.14(1 H, brs) | 376 |

TABLE 87

| Example No. | Chemical Structure | properties m.p. (° C.) (recryst. solvent) |
|---|---|---|
| 233 | 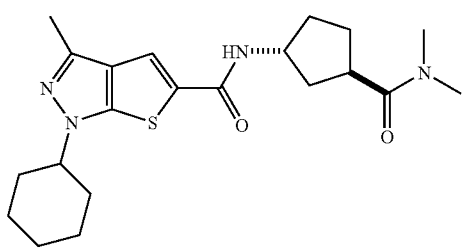 | colorless foamy solid |
| 234 | HCl | colorless solid 96-105 |
| 235 | 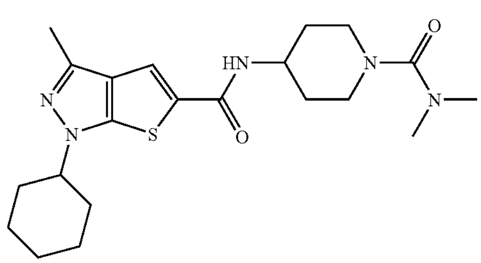 | colorless solid 210-212 |

TABLE 87-continued
| | | |
|---|---|---|
| 236 | 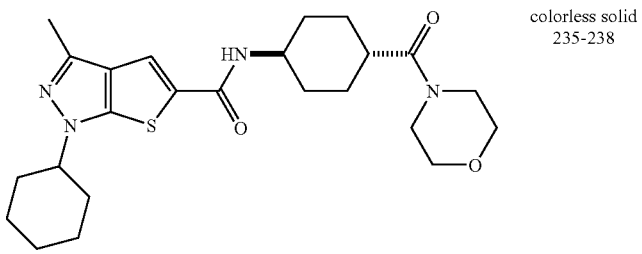 | colorless solid 235-238 |
| Example No. | ¹H-NMR | MS(FAB) (M + 1)⁺ |
|---|---|---|
| 233 | CDCl₃ 1.21-1.33(1 H, m), 1.38-1.51(2 H, m), 1.59-1.68(1 H, m), 1.70-2.04(8 H, m), 2.13-2.21(2 H, m), 2.23-2.40(2 H, m), 2.43(3 H, s), 2.96(3 H, s), 3.05(3 H, s), 3.12-3.22(1 H, m), 4.17(1 H, tt, J = 3.8 and 11.8 Hz), 4.42-4.52(1 H, m), 5.83-5.89(1 H, m), 7.30(1 H, s) | 403 |
| 234 | DMSO-d₆ 1.15-1.28(1 H, m), 1.36-1.48(2 H, m), 1.51-1.85(8 H, m), 1.92-2.07(5 H, m), 2.36(3 H, s), 2.83(3 H, s), 3.02(3 H, s), 3.18-3.29(1 H, m), 4.18(1 H, tt, J = 3.8 and 11.6 Hz), 4.22-4.31(1 H, m), 7.81(1 H, s), 8.30-8.35(1 H, m) | 403 |
| 235 | CDCl₃ 1.22-1.33(1 H, m), 1.38-1.56(4 H, m), 1.70-1.96 (5 H, m), 2.00-2.08(2 H, m), 2.14-2.22(2 H, m), 2.44(3 H, s), 2.84(6 H, s), 2.89-2.99(2 H, m), 3.65-3.73(2 H, m), 4.08-4.22(2 H, m), 5.78-5.84(1 H, m), 7.32(1 H, s) | 418 |
| 236 | CDCl₃ 1.20-1.35(3 H, m), 1.38-1.51(2 H, m), 1.72-1.97(9 H, m), 2.13-2.26(4 H, m), 2.43(3 H, s), 3.49-3.54(2 H, m), 3.60-3.72(6 H, m), 3.90-4.02(1 H, m), 4.17(1 H, tt, J = 3.8 and 11.8 Hz), 5.67-5.72(1 H, m), 7.30(1 H, s) | 459 |
TABLE 88
| Example No. | Chemical Structure | properties m.p. (° C.) (recryst. solvent) |
|---|---|---|
| 237 | 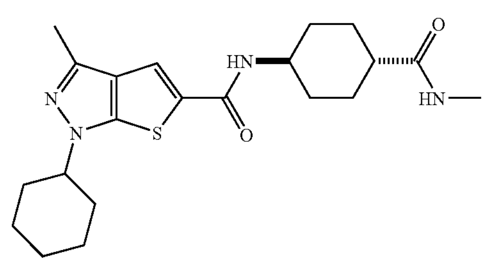 | colorless solid >300 |
| 238 | 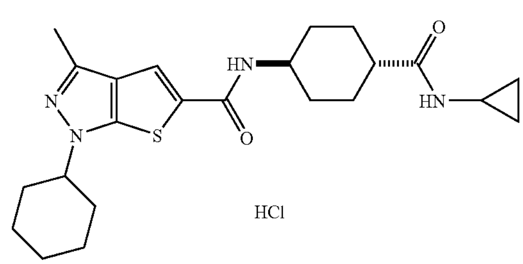 | colorless solid >300 |

TABLE 88-continued

| | | | |
|---|---|---|---|
| 239 | 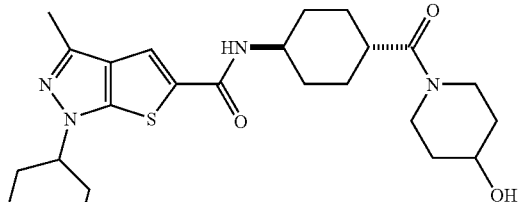 | colorless solid 260-263 | |
| 240 | 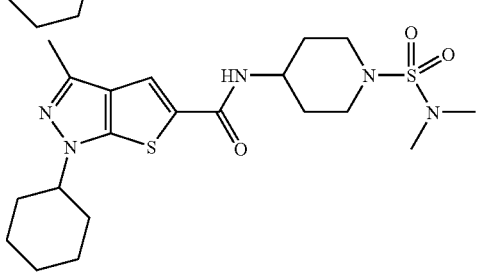 | colorless solid 230-231 | |

| Example No. | $^1$H-NMR | MS(FAB) $(M+1)^+$ |
|---|---|---|
| 237 | DMSO-d$_6$ 1.17-1.49(7 H, m), 1.63-1.92(9 H, m), 2.01-2.11(3 H, m), 2.35(3 H, s), 2.55(3 H, d, J = 4.5 Hz), 3.59-3.71(1 H, m), 4.18(1 H, tt, J = 3.8 and 11.6 Hz), 7.64-7.70(1 H, m), 7.79(1 H, s), 8.22-8.27(1 H, m) | 403 |
| 238 | DMSO-d$_6$ 0.33-0.39(2 H, m), 0.56-0.62(2 H, m), 1.16-1.49(7 H, m), 1.63-1.91(9 H, m), 1.96-2.08(3 H, m), 2.35(3 H, s), 2.57-2.63(1 H, m), 3.60-3.72(1 H, m), 4.13-4.22(1 H, m), 7.75-7.78(1 H, m), 7.78(1 H, s), 8.21-8.26(1 H, m) | 429 |
| 239 | CDCl$_3$ 1.21-1.34(3 H, m), 1.37-1.60(4 H, m), 1.68-1 H, m), 2.14-2.26(4 H, m), 2.43(3 H, s), 2.48(1 H, tt, J = 3.7 and 11.6 Hz), 3.15-3.31(2 H, m), 3.74-3.83(1 H, m), 3.91-4.02(2 H, m), 4.08-4.16(1 H, m), 4.17(1 H, tt, J = 3.8 and 11.8 Hz), 5.68-5.73(1 H, m), 7.30(1 H, s) | 473 |
| 240 | CDCl$_3$ 1.21-1.34(1 H, m), 1.38-1.51(2 H, m), 1.57-1.66(2 H, m), 1.72-1.97(5 H, m), 2.05-2.13(2 H, m), 2.15-2.23(2 H, m), 2.44(3 H, s), 2.83(6 H, s), 2.96-3.06(2 H, m), 3.72-3.80(2 H, m), 4.06-4.16(1 H, m), 4.18(1 H, tt, J = 3.8 and 11.8 Hz), 5.78-5.93(1 H, m), 7.34(1 H, s) | 454 |

TABLE 89

| Example No. | Chemical Structure | properties m.p. (° C.) (recryst. solvent) |
|---|---|---|
| 241 | 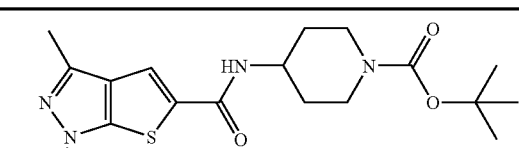 | colorless solid 83-87 |
| 242 | 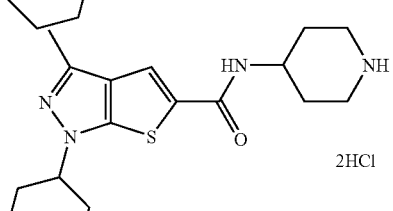 | pale yellow solid 153-160 |

TABLE 89-continued

| | | |
|---|---|---|
| 243 | [structure: 1-cyclohexyl-3-methyl-N-(1-benzylpyrrolidin-3-yl)-1H-thieno[2,3-c]pyrazole-5-carboxamide] | colorless foamy solid |
| 244 | [structure: 1-cyclohexyl-3-methyl-N-(pyrrolidin-3-yl)-1H-thieno[2,3-c]pyrazole-5-carboxamide] | colorless foamy solid |

| Example No. | $^1$H-NMR | MS(FAB) $(M + 1)^+$ |
|---|---|---|
| 241 | CDCl$_3$ 1.21-1.50(5 H, m), 1.47(9 H, s), 1.70-2.06(7 H, m), 2.13-2.21(2 H, m), 2.43(3 H, s), 2.80-2.96(2 H, m), 4.04-4.17(2 H, m), 4.18(1 H, tt, J = 3.9 and 11.8 Hz), 5.74-5.81(1 H, m), 7.33(1 H, s) | 447 |
| 242 | DMSO-d$_6$ 1.15-1.29(1 H, m), 1.36-1.49(2 H, m), 1.62-1 86(7 H, m), 1.91-1.99(2 H, m), 2.00-2.08(2 H, m), 2.36(3 H, s), 2.89-3.06(2 H, m), 3.26-3.35(2 H, m), 3.97-4.06(1 H, m), 4.19(1 H, tt, J = 3.8 and 11.6 Hz), 7.89(1 H, s), 8.50-8.55(1 H, m), 8.76(1 H, brs) | 347 |
| 243 | CDCl$_3$ 1.22-1.33(1 H, m), 1.38-1.50(2 H, m), 1.69-1.97(6 H, m), 2.13-2.22(2 H, m), 2.26-2.43(2 H, m), 2.44(3 H, s), 2.58-2.64(1 H, m), 2.72-2.77(1 H, m), 2.91-2.98(1 H, m), 3.64 and 3.65(total 2 H, each s), 4.17(1 H, tt, J = 3.8 and 11.8 Hz), 6.34-6.40(1 H, m), 7.26-7.38(6 H, m) | 423 |
| 244 | CDCl$_3$ 1.21-1.34(1 H, m), 1.38-1.50(2 H, m), 1.69-1.97(6 H, m), 2.10-2.28(3 H, m), 2.42(3 H, s), 2.90-3.02(2 H, m), 3.09-3.22(2 H, m), 4.17(1 H, tt, J = 3.8 and 11.8 Hz), 4.54-4.63(1 H, m), 6.33-6.39(1 H, m), 7.38(1 H, m) | 333 |

TABLE 90

| Example No. | Chemical Structure | properties m.p. (° C.) (recryst. solvent) |
|---|---|---|
| 245 | [structure: 1-cyclohexyl-3-methyl-N-[1-(dimethylcarbamoyl)pyrrolidin-3-yl]-1H-thieno[2,3-c]pyrazole-5-carboxamide] | colorless foamy solid |
| 246 | [structure: same as 245, HCl salt] | colorless solid 110-114 |

TABLE 90-continued

| 247 | [structure: 1-cyclohexyl-3-methyl-N-(trans-4-((2,5-dioxoimidazolidin-1-yl)methyl)cyclohexyl)-1H-thieno[2,3-c]pyrazole-5-carboxamide] | colorless solid 251-254 |
| --- | --- | --- |
| 248 | [structure: ethyl 1-((1-cyclohexyl-3-methyl-1H-thieno[2,3-c]pyrazol-5-yl)carbonyl)piperidine-4-carboxylate] | pale yellow oil |

| Example No. | ¹H-NMR | MS(FAB) $(M+1)^+$ |
| --- | --- | --- |
| 245 | CDCl₃ 1.21-1.34(1 H, m), 1.38-1.50(2 H, m), 1.71-1.96(5 H, m), 1.99-2.08(1 H, m), 2.12-2.23(3 H, m), 2.43(3 H, s), 2.89(6 H, s), 3.42-3.62(4 H, m), 4.17(1 H, tt, J = 3.9 and 11.8 Hz), 4.50-4.58(1 H, m), 6.60-6.65(1 H, m), 7.35(1 H, s) | 404 |
| 246 | DMSO-d₆ 1.16-1.30(1 H, m), 1.36-1.50(2 H, m), 1.62-1.91(6 H, m), 2.00-2.10(3 H, m), 2.35(3 H, s), 2.74(6 H, s), 3.21(1 H, dd, J = 5.4 and 10.6 Hz), 3.29-3.47(2 H, m), 3.55(1 H, dd, J = 7.6 and 10.6 Hz), 4.19(1 H, tt, J = 3.8 and 11.6 Hz), 4.28-4.36(1 H, m), 7.86(1 H, s), 8.50-8.55(1 H, m) | 404 |
| 247 | CDCl₃ 1.12-1.50(7 H, m), 1.69-1.96(8 H, m), 2.07-2.21(4 H, m), 2.43(3 H, s), 3.38-3.43(2 H, m), 3.85-3.95(1 H, m), 4.00(2 H, brs), 4.17(1 H, tt, J = 3.9 and 11.9 Hz), 5.21(1 H, brs), 5.63-5.69(1 H, m), 7.30(1 H, s) | 458 |
| 248 | CDCl₃ 1.21-1.33(1 H, m), 1.28(3 H, t, J = 7.1 Hz), 1.37-1.51(2 H, m), 1.70-2.06(9 H, m), 2.15-2.23(2 H, m), 2.44(3 H, s), 2.57-2.67(1 H, m), 3.14-3.24(2 H, m), 4.11-4.22(1 H, m), 4.17(2 H, q, J = 7.1 Hz), 4.35-4.45(2 H, m), 7.12(1 H, s) | 404 |

TABLE 91

| Example No. | Chemical Structure | properties m.p. (° C.) (recryst. solvent) |
| --- | --- | --- |
| 249 | [structure: 1-((1-cyclohexyl-3-methyl-1H-thieno[2,3-c]pyrazol-5-yl)carbonyl)piperidine-4-carboxylic acid] | colorless solid 94-96 |

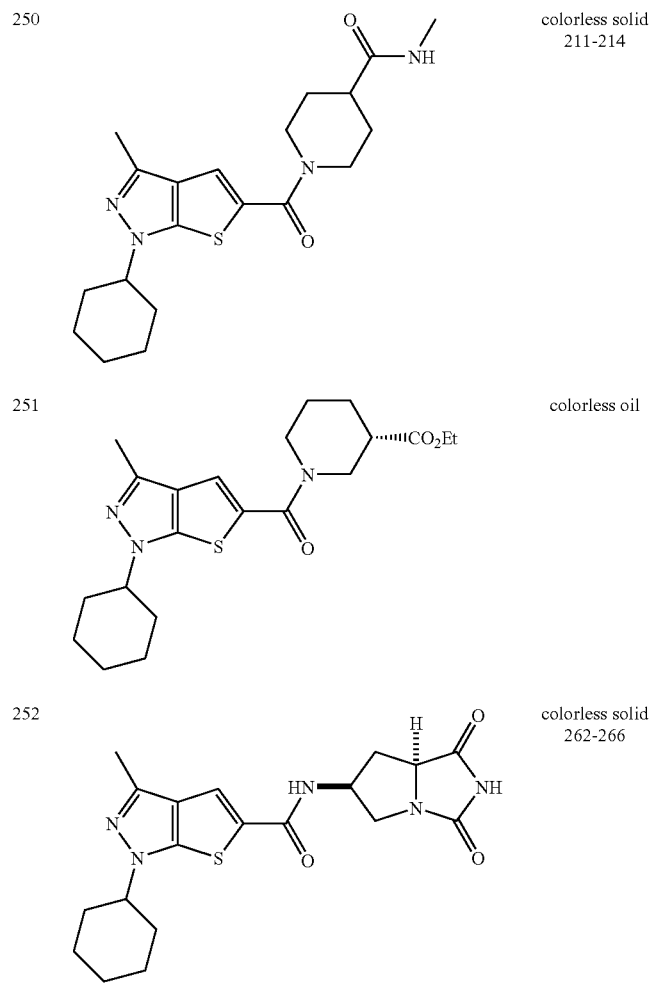
| Example No. | ¹H-NMR | MS(FAB) (M + 1)⁺ |
|---|---|---|
| 249 | CDCl₃ 1.20-1.33(1 H, m), 1.37-1.50(2 H, m), 1.70-1.96(7 H, m), 2.02-2.10(2 H, m), 2.12-2.20(2 H, m), 2.44(3 H, s), 2.65-2.75(1 H, m), 3.17-3.28(2 H, m), 4.18(1 H, tt, J = 3.8 and 11.9 Hz), 4.36-4.45(2 H, m), 7.13(1 H, s) | 376 |
| 250 | CDCl₃ 1.21-1.33(1 H, m), 1.37-1.51(2 H, m), 1.70-1.99(9 H, m), 2.12-2.22(2 H, m), 2.39(1 H, tt, J = 4.0 and 11.3 Hz), 2.44(3 H, s), 2.84(3 H, d, J = 4.8 Hz), 3.00-3.12(2 H, m), 4.17(1 H, tt, J = 3.8 and 11.8 Hz), 4.48-4.57(2 H, m), 5.46-5.55(1 H, m), 7.13(1 H, s) | 389 |
| 251 | CDCl₃ 1.20-1.32(1 H, m), 1.26(3 H, t, J = 7.1 Hz), 1.37-1.50(2 H, m), 1.55-1.66(1 H, m), 1.70-1.97(7 H, m), 2.10-2.20(3 H, m), 2.44(3 H, s), 2.53-2.63(1 H, m), 3.12-3.21(1 H, m), 3.27-3.38(1 H, m), 4.12-4.22(1 H, m), 4.15(2 H, q, J = 7.1 Hz), 4.25-4.34(1 H, m), 4.47-4.56(1 H, m), 7.16(1 H, s) | 404 |
| 252 | DMSO-d₆ 1.16-1.29(1 H, m), 1.36-1.50(2 H, m), 1.62-1.92(6 H, m), 2.01-2.09(2 H, m), 2.35(3 H, s), 2.35-2.45(1 H, m), 3.27-3.34(1 H, m), 3.55(1 H, dd, J = 5.5 and 11.3 Hz), 4.19(1 H, tt, J = 3.8 and 11.6 Hz), 4.24-4.30(1 H, m), 4.55-4.65(1 H, m), 7.73(1 H, s), 8.52-8.56(1 H, m), 10.90(1 H, brs) | 402 |

TABLE 92

| Example No. | Chemical Structure | properties m.p. (° C.) (recryst. solvent) |
|---|---|---|
| 253 | 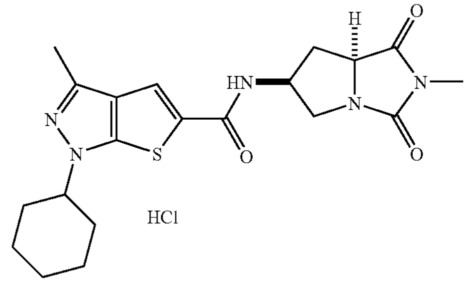 | colorless solid 221-223 |
| 254 | 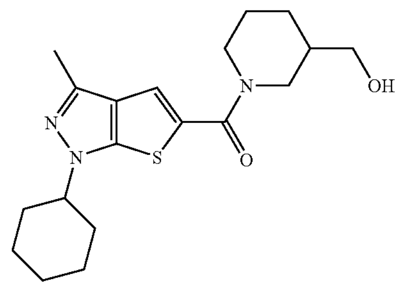 | pale yellow foamy solid |
| 255 | 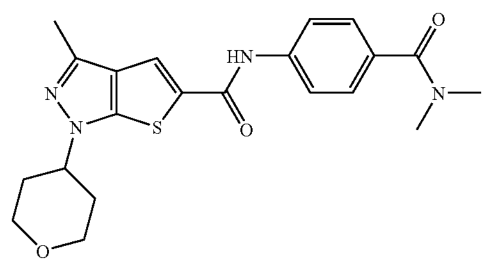 | colorless solid 247-248.5 |
| 256 | 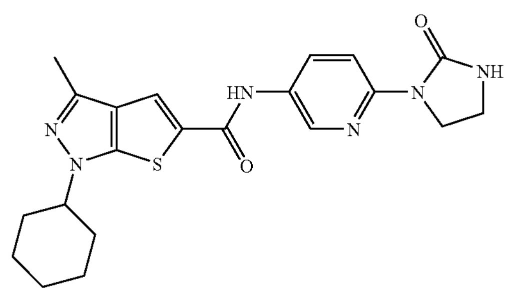 | colorless solid 148-150 |

| Example No. | ¹H-NMR | MS(FAB) $(M + 1)^+$ |
|---|---|---|
| 253 | DMSO-d$_6$ 1.16-1.28(1 H, m), 1.36-1.50(2 H, m), 1.62-1.91(6 H, m), 2.00-2.08(2 H, m), 2.35(3 H, s), 2.40-2.48(1 H, m), 2.87(3 H, s), 3.39(1 H, dd, J = 6.9 and 11.4 Hz), 3.58(1 H, tt, J = 5.4 and 11.4 Hz), 4.19(1 H, tt, J = 3.8 and 11.6 Hz), 4.33(1 H, t, J = 8.4 Hz), 4.56-4.64(1 H, m), 7.71(1 H, s), 8.51-8.56(1 H, m) | 416 |
| 254 | CDCl$_3$ 1.21-1.34(1 H, m), 1.37-1.49(3 H, m), 1.52-1.63(1 H, m), 1.70-1.97(8 H, m), 2.12-2.20(2 H, m), 2.43(3 H, s), 2.44-2.60(1 H, m), 3.26-3.61(4 H, m), 4.05-4.17(2 H, m), 4.17(1 H, tt, J = 3.8 and 11.9 Hz), 7.18(1 H, s) | 362 |
| 255 | CDCl$_3$ 2.11-2.27(4 H, m), 2.48(3 H, s), 2.97-3.16(6 H, m), 3.57(2 H, dt, J = 2.4 and 11.6 Hz), 4.11-4.18(2 H, m), 4.39-4.49(1 H, m), 7.36-7.41(2 H, m), 7.54-7.59(2 H, m), 7.65(1 H, s), 8.11(1 H, brs) | 413 |
| 256 | DMSO-d$_6$ 1.16-1.31(1 H, m), 1.37-1.51(2 H, m), 1.62-1.88(5 H,m), 2.03-2.12(2 H, m), 2.40(3 H, s), 3.37- | 425 |

TABLE 92-continued
3.43(2 H, m), 3.95-4.02(2 H, m), 4.22(1 H, tt, J = 3.8 and
11.5 Hz),7.15(1 H, brs), 8.00(1 H, dd, J = 2.6 and 9.1 Hz),
8.03(1 H, s), 8.16(1 H, d, J = 9.1 Hz), 8.59(1 H, d, J = 2.6 Hz),
10.3(1 H, brs)
TABLE 93
| Example No. | Chemical Structure | properties m.p. (° C.) (recryst. solvent) |
|---|---|---|
| 257 | 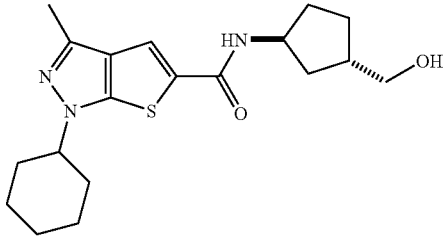 | colorless foamy solid |
| 258 | 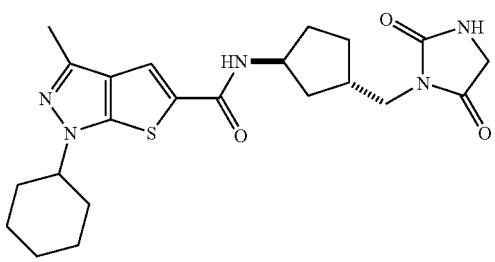 | colorless solid 183-185 (toluene) |
| 259 | 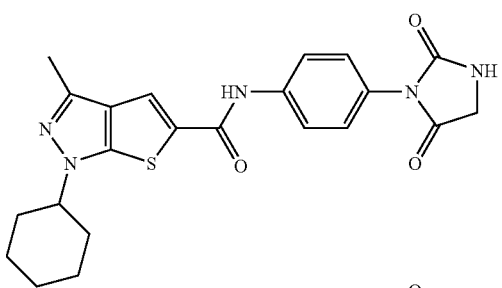 | colorless solid 218-222 |
| 260 | 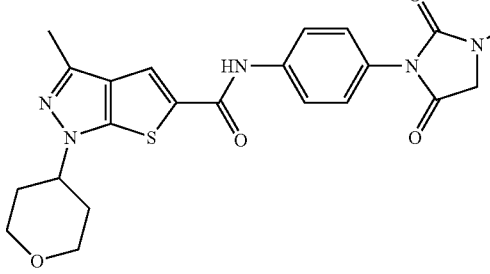 | colorless solid 204-206 |
| Example No. | $^1$H-NMR | MS(FAB) $(M + 1)^+$ |
|---|---|---|
| 257 | CDCl$_3$ 1.21-1.59(5 H, m), 1.67-2.00(8 H, m), 2.12-2.22(3 H, m), 2.28-2.38(1 H, m), 2.43(3 H, s), 3.56(2 H, d, J = 6.8 Hz), 4.17(1 H, tt, J = 3.8 and 11.9 Hz), 4.38-4.48(1 H, m), 5.82-5.86(1 H, m), 7.30(1 H, s) | 362 |
| 258 | CDCl$_3$ 1.20-1.58(6 H, m), 1.69-1.96(7 H, m), 2.12-2.30(3 H, m), 2.43(3 H, s), 2.49-2.61(1 H, m), 3.50-3.55(2 H, m), 3.98(2 H, s), 4.17(1 H, tt, J = 3.8 and 11.9 Hz), 4.43-4.53(1 H, m), 5.26(1 H, brs), 5.76-5.82(1 H, m), 7.29(1 H, s) | 444 |

TABLE 93-continued

| | | |
|---|---|---|
| 259 | CDCl$_3$ 1.21-1.33(1 H, m), 1.37-1.51(2 H, m), 1.70-1.97(5 H, m), 2.15-2.21(2 H, m), 2.43(3 H, s), 4.18(1 H, tt, J = 3.8 and 11.8 Hz), 4.63(2 H, s), 6.75-6.79(2 H, m), 7.13-7.17(2 H, m), 8.28(1 H, s) | 438 |
| 260 | CDCl$_3$ 2.11-2.27(4 H, m), 2.48(3 H, s), 3.10(3 H, s), 3.57(2 H, dt, J = 2.4 and 11.6 Hz), 4.05(2 H, s), 4.11-4.18(2 H, m), 4.37-4.48(1 H, m), 7.40-7.45(2 H, m), 7.50(1 H, s), 7.68(1 H, brs), 7.70-7.75(2 H, m) | 454 |

TABLE 94

| Example No. | Chemical Structure | properties m.p. (° C.) (recryst. solvent) |
|---|---|---|
| 261 | 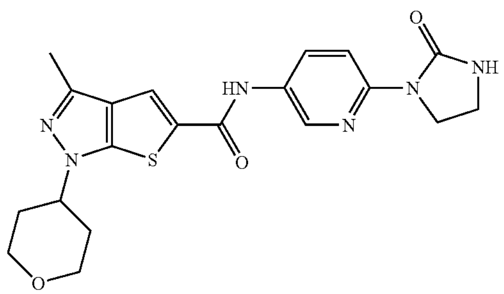 | pale brown solid 252-254 (EtOH) |
| 262 | 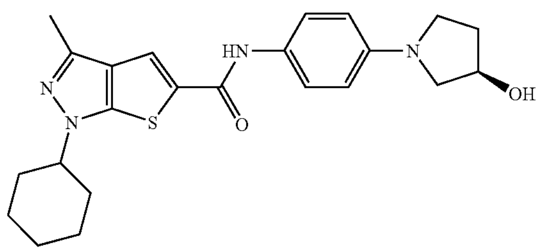 | pale yellow solid 164-166 (iso-PrOH) |
| 263 | 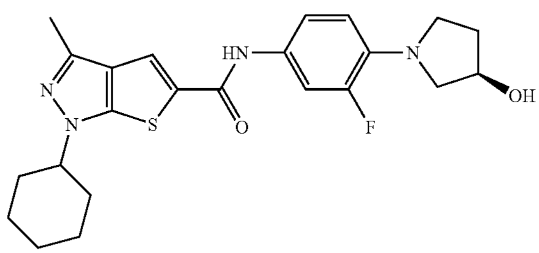 | pale yellow solid 167-168 (hexane/AcOEt) |
| 264 | 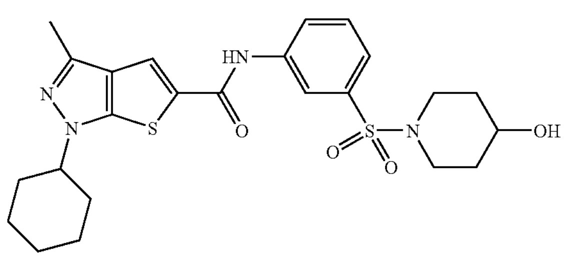 | colorless solid 216-218 |

| Example No. | $^1$H-NMR | MS(FAB) (M + 1)$^+$ |
|---|---|---|
| 261 | DMSO-d$_6$ 1.91-2.07(4 H, m), 2.41(3 H, s), 3.38-3.44(2 H, s), 3.51(2 H, dt, J = 2.4 and 11.6 Hz), 3.95-4.03(4 H, m), 4.47-4.57(1 H, m), 7.16(1 H, brs), 8.00(1 H, dd, J = 2.7 and 9.1 Hz), 8.05(1 H, s), 8.16(1 H, d, J = 9.1 Hz), 8.60(1 H, d, J = 2.7 Hz), 10.33(1 H, brs) | 427 |

TABLE 94-continued

| | | | |
|---|---|---|---|
| | 262 | CDCl$_3$ 1.22-1.35(1 H, m), 1.38-1.53(2 H, m), 1.70-1.97(5 H, m), 2.04-2.12(1 H, m), 2.15-2.25(3 H, m), 2.45(3 H, s), 3.25-3.41(2 H, m), 3.46-3.57(2 H, m), 4.19(1 H, tt, J = 3.9 and 11.8 Hz), 4.58-4.65(1 H, m), 6.53-6.59(2 H, m), 7.40-7.51 (4 H, m) | 425 |
| | 263 | CDCl$_3$ 1.22-1.35(1 H, m), 1.38-1.52(2 H, m), 1.71-2.05(7 H, m), 2.11-2.23(3 H, m), 2.45(3 H, s), 3.29-3.39(2 H, m), 3.57-3.68(2 H, m), 4.19(1 H, tt, J = 3.9 and 11.8 Hz), 4.52-4.58(1 H, m), 6.61-6.67(1 H, m), 7.10(1 H, dd, J = 2.2 and 8.7 Hz), 7.42(1 H, dd, J = 2.5 and 14.8 Hz), 7.44(1 H, s), 7.52(1 H, brs) | 443 |
| | 264 | CDCl$_3$ 1.23-1.67(5 H, m), 1.72-1.98(7 H, m), 2.15-2.23(2 H, m), 2.50(3 H, s), 2.85-2.95(2 H, m), 3.31-3.40(2 H, m), 3.72-3.80(1 H, m), 4.20(1 H, tt, J = 3.8 and 11.8 Hz), 7.49-7.57(2 H, m), 7.64(1 H, s), 7.93(1 H, d, J = 1.7 Hz), 8.11-8.17(1 H, m), 8.19(1 H, brs) | 503 |

TABLE 95

| Example No. | Chemical Structure | properties m.p. (° C.) (recryst. solvent) |
|---|---|---|
| 265 | 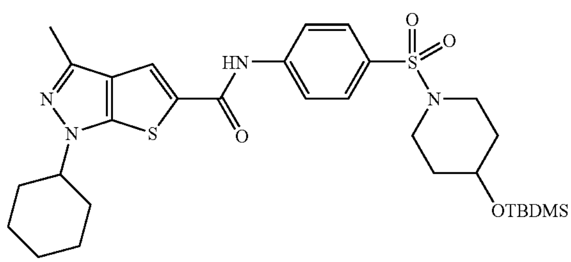 | colorless solid 226-228 |
| 266 | 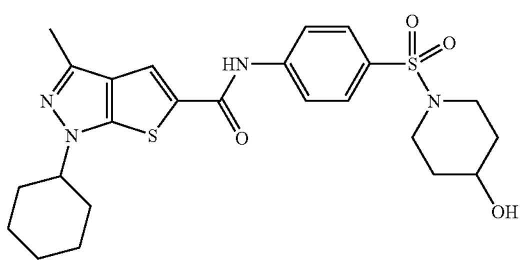 | colorless solid 229-233 |
| 267 | 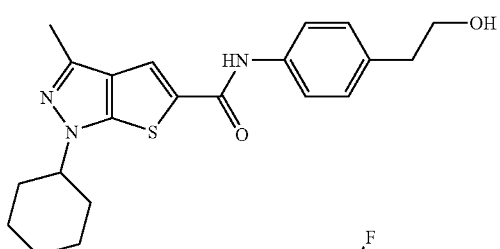 | colorless solid 162-165 |
| 268 | 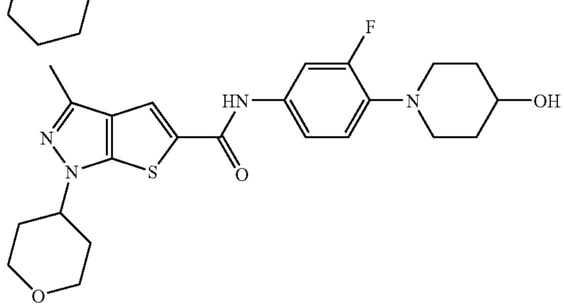 | pale yellow solid 211-213 |

TABLE 95-continued

| Example No. | ¹H-NMR | MS(FAB) (M + 1)⁺ |
|---|---|---|
| 265 | CDCl₃ −0.01(6 H, s), 0.80(9 H, s), 1.22-1.36(1 H, s), 1.40-1.68(4 H, m), 1.72-1.99(7 H, m), 2.16-2.26(2 H, m), 2.48(3 H, s), 2.97-3.05(2 H, m), 3.15-3.25(2 H, m), 3.75-3.81(1 H, m), 4.16-4.26(1 H, m), 7.53(1 H, s), 7.75-7.81(5 H, m) | 617 |
| 266 | CDCl₃ 1.24-1.55(4 H, m), 1.60-1.98(9 H, m), 2.18-2.25(2 H, s), 2.47(3 H, s), 2.85-2.93(2 H, m), 3.29-3.38(2 H, m), 3.75-3.82(1 H, m), 4.20(1 H, tt, J = 3.8 and 11.8 Hz), 7.54(1 H, s), 7.73-7.81(4 H, m), 7.84(1 H, brs) | 503 |
| 267 | CDCl₃ 1.22-1.35(1 H, m), 1.38-1.55(2 H, m), 1.72-1.98(5 H, s), 2.17-2.24(2 H, m), 2.46(3 H, s), 2.86(2 H, t, J = 6.5 Hz), 3.86(2 H, t, J = 6.5 Hz), 4.19(1 H, tt, J = 3.9 and 11.8 Hz), 7.23(2 H, d, J = 8.4 Hz), 7.47(1 H, s), 7.53(2 H, d, J = 8.4 Hz), 7.60(1 H, brs) | 384 |
| 268 | CDCl₃ 1.43-1.47(1 H, m), 1.72-1.82(2 H, m), 2.00-2.27(6 H, m), 2.47(3 H, s), 2.81-2.91(2 H, m), 3.30-3.37(2 H, m), 3.56(2 H, dt, J = 2.4 and 11.6 Hz), 3.83-3.91(1 H, m), 4.11-4.18(2 H, m), 4.38-4.48(1 H, m), 6.90-7.00(1 H, m), 7.16-7.21(1 H, m), 7.45(1 H, s), 7.47-7.52(1 H, m), 7.53(1 H, brs) | 459 |

TABLE 96

| Example No. | Chemical Structure | properties m.p. (° C.) (recryst. solvent) |
|---|---|---|
| 269 | 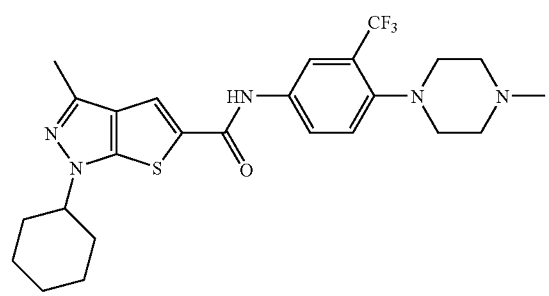 | colorless solid 205-206.5 (AcOEt/hexane) |
| 270 | 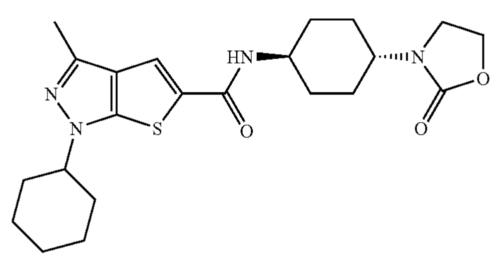 | colorless solid >300 (EtOH) |
| 271 | 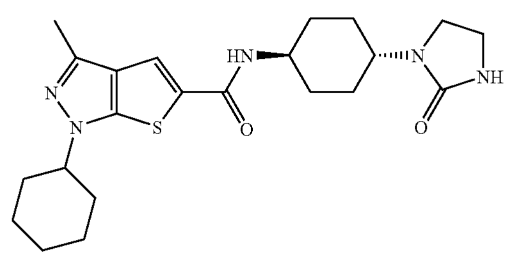 | colorless solid 290 (dec.) (EtOH) |

TABLE 96-continued

| | | | |
|---|---|---|---|
| 272 | [structure] | | colorless solid 268(dec.) |

| Example No. | ¹H-NMR | MS(FAB) (M + 1)⁺ |
|---|---|---|
| 269 | CDCl3 1.19-1.33(1 H, m), 1.38-1.50(2 H, m), 1.70-1.97(5 H, m), 2.12-2.21(2 H, m), 2.34(3 H, s), 2.45(3 H, s), 2.48-2.63(4 H, m), 2.88-2.96(4 H, m), 4.12-4.22(1 H, m), 7.37(1 H, d, J = 8.7 Hz), 7.48(1 H, s), 7.66(1 H, brs), 7.75(1 H, d, J = 2.5 Hz), 7.83(1 H, dd, J = 2.5 and 8.7 Hz) | 506 |
| 270 | CDCl₃ 1.21-1.34(1 H, m), 1.47-1.50(4 H, m), 1.54-1.67(2 H, m), 1.71-1.96(7 H, m), 2.13-2.22(4 H, m), 2.43(3 H, s), 3.51-3.59(2 H, m), 3.79(1 H, tt, J = 3.9 and 12.1 Hz), 3.89-4.01(1 H, m), 4.17(1 H, lt, J = 3.8 and 11.8 Hz), 4.32-4.38(2 H, m), 6.08-6.12(1 H, m), 7.44(1 H, s) | 431 |
| 271 | CDCl₃ 1.20-1.50(7 H, m), 1.70-1.97(5 H, m), 2.06-2.21(6 H, m), 2.43(3 H, s), 3.40-3.50(1 H, m), 3.79(2 H, t, J = 8.5 Hz), 3.88-3.99(1 H, m), 4.17(1 H, tt, J = 3.8 and 11.9 Hz), 4.25(2 H, t, J = 8.5 Hz), 5.69-5.77(1 H, m), 7.32(1 H, s) | 430 |
| 272 | CD₃OD 1.24-1.56(7 H, m), 1.72-2.03(9 H, m), 2.09-2.17(2 H, m), 2.42(3 H, s), 2.44(2 H, t, J = 7.0 Hz), 2.58(2 H, t, J = 7.0 Hz), 3.61-3.70(1 H, m), 3.77-3.86(1 H, m), 4.18(1 H, tt, J = 3.8 and 11.8 Hz), 7.66(1 H, s) | 461 |

TABLE 97

| Example No. | Chemical Structure | properties m.p. (° C.) (recryst. solvent) | ¹H-NMR | MS (FAB) (M + 1)⁺ |
|---|---|---|---|---|
| 273 | [structure] | pale brown solid >300 | CDCl₃ 1.21-1.51 (5 H, m), 1.61-1.97 (7 H, m), 2.12-2.24 (4 H, m), 2.37-2.49 (2H, m), 2.43 (3 H, s), 2.67 (4 H, s), 3.98-4.09 (2 H, m), 4.17 (1 H, tt, J = 3.8 and 11.8 Hz), 5.68-5.73 (1 H, m), 7.32 (1 H, s) | 443 |
| 274 | [structure] | colorless solid 279-280 (EtOH) | CDCl₃ 1.21-1.50 (5 H, m), 1.58-1.87 (7 H, m), 1.88-1.96 (2 H, m), 2.12-2.21 (4 H, m), 2.31-2.40 (2 H, m), 2.43 (3 H, s), 3.14 (2 H, t, J = 7.5 Hz), 3.29 (2 H, t, J = 6.7 Hz), 3.50 (1 H, tt, J = 3.8 and 11.8 Hz), 3.84-3.97 (1 H, m), 4.17 (1 H, tt, J = 3.8 and 11.8 Hz), 5.78-5.83 (1 H, m), 7.34 (1 H, s) | 465 |

TABLE 97-continued

| Example No. | Chemical Structure | properties m.p. (° C.) (recryst. solvent) | ¹H-NMR | MS (FAB) (M + 1)⁺ |
|---|---|---|---|---|
| 275 | 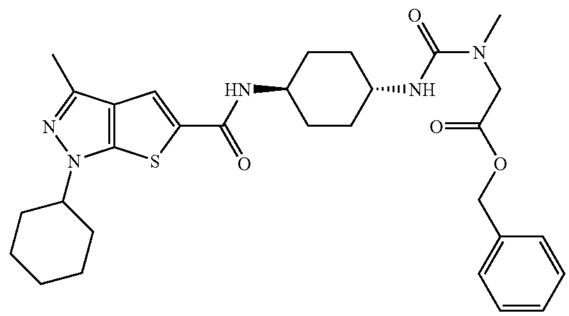 | colorless solid 251-254 | CDCl₃ 1.20-1.50 (7 H, m), 1.70-1.98 (5 H, m), 2.03-2.21 (6 H, m), 2.42 (3 H, s), 2.94 (3 H, s), 3.60-3.71 (1 H, m), 3.88-3.99 (1 H, m), 4.11 (2 H, s), 4.17 (1 H, tt, J = 3.8 and 11.8 Hz), 4.34-4.40 (1 H, m), 5.17 (2 H, s), 5.78-5.84 (1 H, m), 7.29-7.41 (6 H, s) | 566 |
| 276 | 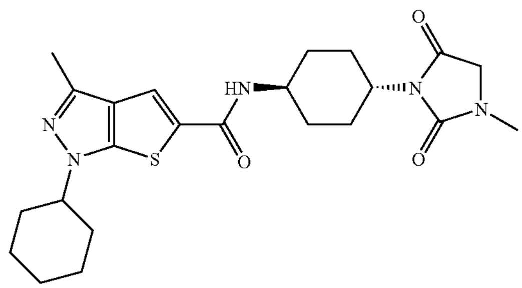 | colorless solid 274-276 (EtOH) | CDCl₃ 1.21-1.50 (5 H, m), 170-1.97 (7 H, m), 2.11-2.23 (4 H, m), 2.33-2.49 (2 H, m), 2.43 (3 H, s), 2.98 (3 H, s), 3.81 (2 H, s), 3.90-4.08 (2 H, m), 4.17 (1 H, tt, J = 3.9 and 11.9 Hz), 5.69-5.75 (1 H, m), 7.32 (1 H, s) | 458 |

TABLE 98

| Example No. | Chemical Structure | properties m.p. (° C.) (recryst. solvent) |
|---|---|---|
| 277 | 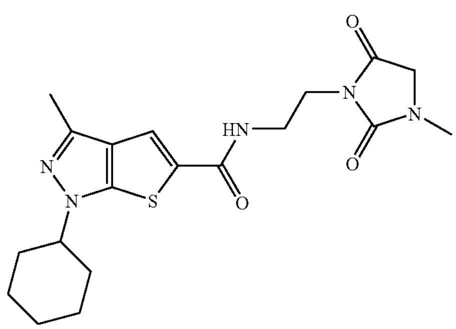 | colorless solid 156-157.5 (AcOEt/hexane) |
| 278 | 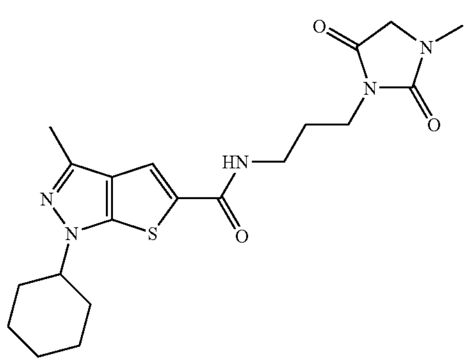 | colorless solid 170-171 (AcOEt) |

TABLE 98-continued

| | | properties m.p. (° C.) (recryst. solvent) |
|---|---|---|
| 279 | [structure: 1-cyclohexyl-3-methyl-thieno[2,3-c]pyrazole-5-carboxamide with trans-cyclohexyl-NH-C(O)-N(Me)-CH2CH2OH] | colorless solid >300 |
| 280 | [structure: 1-cyclohexyl-3-methyl-thieno[2,3-c]pyrazole-5-carboxamide with trans-cyclohexyl-N(3-methyl-2-oxoimidazolidin-1-yl)] | colorless solid 274-276.5 (EtOH) |

| Example No. | ¹H-NMR | MS(FAB) (M + 1)⁺ |
|---|---|---|
| 277 | CDCl₃ 1.21-1.33(1 H, m), 1.37-1.50(2 H, m), 1.69-1.97(5 H, m), 2.12-2.21(2 H, m), 2.45(3 H, s), 3.02(3 H, s), 3.61-3.69(2 H, m), 3.79-3.88(2 H, m), 3.93(2 H, s), 4.16(1 H, tt, J = 3.9 and 11.8 Hz), 6.98-7.06(1 H, m), 7.34(1 H, s) | 404 |
| 278 | CDCl₃ 1.21-1.33(1 H, m), 1.38-1.51(2 H, m), 1.70-1.98(7 H, m), 2.12-2.22(2 H, m), 2.45(3 H, s), 3.04(3 H, s), 3.38-3.46(2 H, m), 3.67(2 H, t, J = 6.0 Hz), 3.94(2 H, s), 4.17(1 H, tt, J = 3.9 and 11.8 Hz), 7.15-7.22(1 H, m), 7.43(1 H, s) | 418 |
| 279 | CDCl₃ 1.20-1.50(7 H, m), 1.69-1.96(5 H, m), 2.03-2.21(6 H, m), 2.41(3 H, s), 2.93(3 H, s), 3.44(2 H, t, J = 4.6 Hz), 3.49-3.53(1 H, m), 3.58-3.69(1 H, m), 3.72-3.80(2 H, m), 3.87-3.99(1 H, m), 4.16(1 H, tt, J = 3.9 and 11.8 Hz), 4.70-4.78(1 H, m), 5.88-5.95(1 H, m), 7.35(1 H, s) | 462 |
| 280 | CDCl₃ 1.20-1.68(7 H, m), 1.70-1.98(7 H, m), 2.09-2.22(4 H, m), 2.43(3 H, s), 2.79(3 H, s), 3.28(4 H, s), 3.79(1 H, tt, J = 3.9 and), 3.87-3.98(1 H, m), 4.17(1 H, tt, J = 3.9 and 11.8 Hz), 5.93-6.01(1 H, m), 7.36(1 H, s) | 444 |

TABLE 99

| Example No. | Chemical Structure | properties m.p. (° C.) (recryst. solvent) |
|---|---|---|
| 281 | [structure: 1-cyclohexyl-3-methyl-thieno[2,3-c]pyrazole-5-carboxamide-NH-CH2CH2-C(O)-O-ethyl] | colorless solid 98.5-99.5 |

TABLE 99-continued
| 282 | 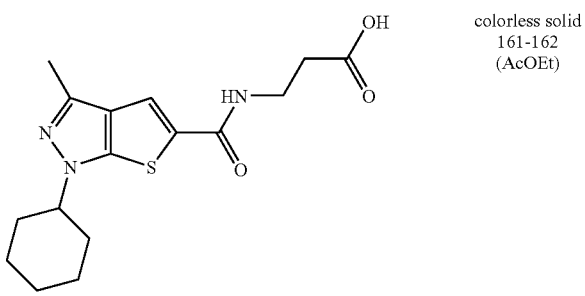 | colorless solid 161-162 (AcOEt) |
| 283 | 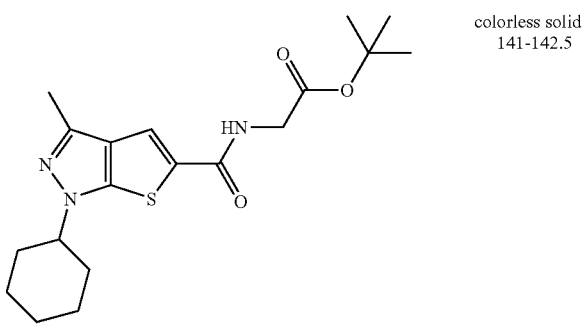 | colorless solid 141-142.5 |
| 284 | 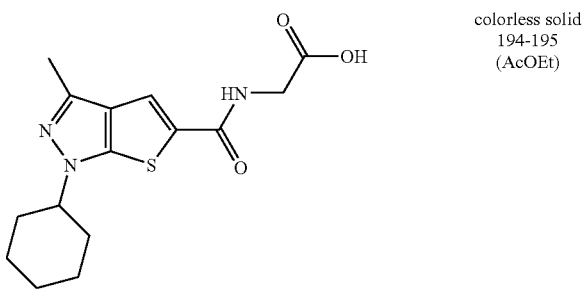 | colorless solid 194-195 (AcOEt) |
| Example No. | $^1$H-NMR | MS(FAB) $(M + 1)^+$ |
|---|---|---|
| 281 | CDCl$_3$ 1.21-1.35(1 H, m), 1.29(3 H, t, J = 7.1 Hz), 1.38-1.51(2 H, m), 1.70-1.98(5 H, m), 2.12-2.22(2 H, m), 2.44(3 H, s), 2.64(2 H, t, J = 6.0 Hz), 3.67-3.76(2 H, m), 4.11-4.25(1 H, m), 4.19(2 H, q, J = 7.1 Hz), 6.68-6.74(1 H, m), 7.37(1 H, s) | 364 |
| 282 | CDCl$_3$ 1.20-1.33(1 H, m), 1.38-1.50(2 H, m), 1.69-1.96(5 H, m), 2.10-2.20(2 H, m), 2.42(3 H, s), 2.72(2 H, t, J = 5.9 Hz), 3.68-3.74(2 H, m), 4.18(1 H, tt, J = 3.9 and 11.9 Hz), 6.68-6.74(1 H, m), 7.34(1 H, s) | 336 |
| 283 | CDCl$_3$ 1.21-1.50(3 H, m), 1.51(9 H, s), 1.71-1.97(5 H, m), 2.13-2.22(2 H, m), 2.44(3 H, s), 4.12(2 H, d, J = 4.8 Hz), 4.17(1 H, tt, J = 3.8 and 11.9 Hz), 6.43-6.49(1 H, m), 7.40(1 H, s) | 378 |
| 284 | CDCl$_3$ 1.20-1.33(1 H, m), 1.38-1.51(2 H, m), 1.70-1.98(5 H, m), 2.12-2.21(2 H, m), 2.44(3 H, s), 4.19(1 H, J = 3.9 and 11.9 Hz), 4.27(2 H, d, J = 5.1 Hz), 6.55-6.61(1 H, m), 7.45(1 H, s) | 322 |

TABLE 100
| Example No. | Chemical Structure | properties m.p. (° C.) (recryst. solvent) |
|---|---|---|
| 285 | 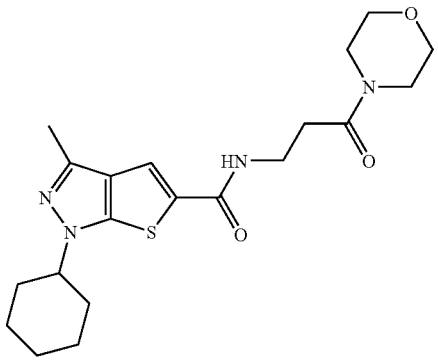 | colorless solid 138.5-139.5 (AcOEt/hexane) |
| 286 | 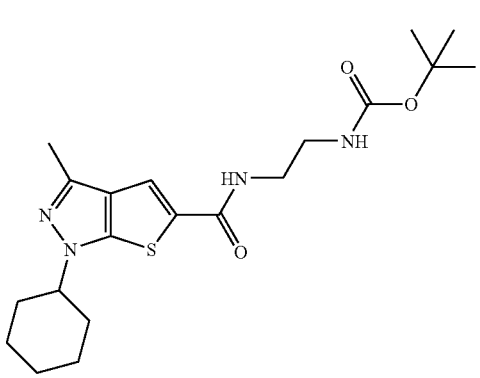 | colorless solid 183.5-185 |
| 287 | 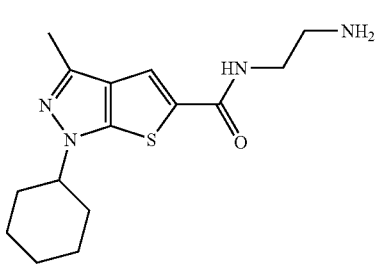 | colorless solid 157-158 |
| 288 | 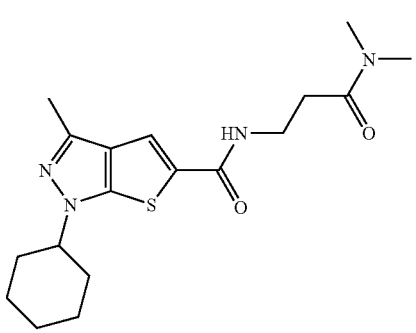 | colorless solid 154-155 (AcOEt) |
| Example No. | $^1$H-NMR | MS(FAB) $(M + 1)^+$ |
|---|---|---|
| 285 | CDCl$_3$ 1.21-1.33(1 H, m), 1.38-1.50(2 H, m), 1.70-1.98(5 H, m), 2.11-2.21(2 H, m), 2.43(3 H, s), 2.61(2 H, t, J = 5.5 Hz), 3.41-3.49(2 H, m), 3.60-3.71(6 H, m), 3.71-3.78(2 H, m), 4.17(1 H, tt, J = 3.9 and 11.8 Hz), 6.95-7.02(1 H, m), 7.32(1 H, s) | 405 |
| 286 | CDCl$_3$ 1.20-1.32(1 H, m), 1.37-1.51(2 H, m), 1.45(9 H, s), 1.70-1.96(5 H, m), 2.12-2.21(2 H, m), 2.42(3 H, s), 3.38-3.45(2 H, m), 3.50-3.56(2 H, m), 4.17(1 H, tt, J = 3.9 | 407 |

TABLE 100-continued

| | | |
|---|---|---|
| | and 11.8 Hz), 4.97-5.03(1 H, m), 7.09-7.16(1 H, m), 7.36(1 H, s) | |
| 287 | CDCl₃ 1.20-1.32(1 H, m), 1.37.1.37-1.52(2 H, m), 1.70-1.97(5 H, m), 2.12-2.21(2 H, m), 2.43(3 H, s), 2.94(2 H, t, J = 5.7 Hz), 3.45-3.52(2 H, m), 4.17(1 H, tt, J = 3.8 and 11.8 Hz), 6.53-6.61(1 H, m), 7.36(1 H, s) | 307 |
| 288 | CDCl₃ 1.21-1.33(1 H, m), 1.38-1.50(2 H, m), 1.69-1.96(5 H, m), 2.11-2.20(2 H, m), 2.43(3 H, s), 2.61(2 H, t, J = 5.4 Hz), 2.98(3 H, s), 3.00(3 H, s), 3.70-3.78(2 H, m), 4.16(1 H, tt, J = 3.9 and 11.9 Hz), 7.10-7.17(1 H, m), 7.33(1 H, s) | 363 |

TABLE 101

| Example No. | Chemical Structure | properties m.p. (° C.) (recryst. solvent) |
|---|---|---|
| 289 | 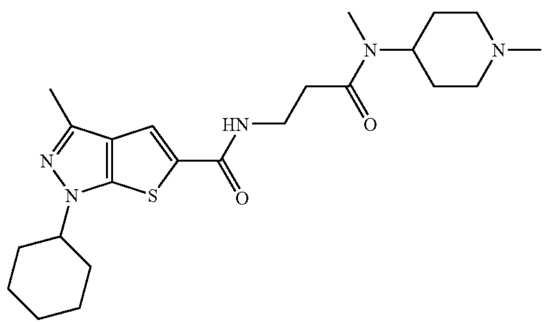 | colorless solid 164.5-168 (AcOEt/hexane) |
| 290 | 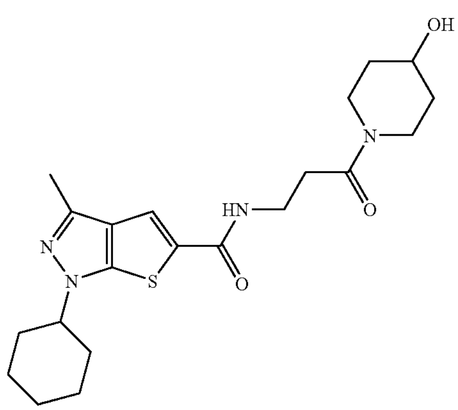 | colorless solid 173-175.5 (AcOEt) |
| 291 | 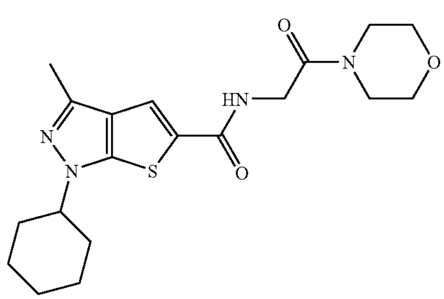 | colorless solid 214-215 (AcOEt) |

TABLE 101-continued

| | | |
|---|---|---|
| 292 | 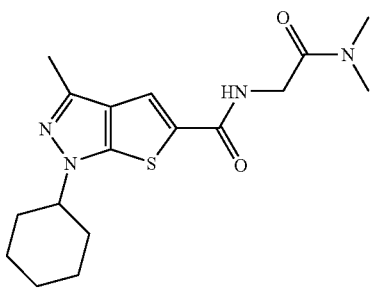 | colorless solid 130-131.5 |

| Example No. | ¹H-NMR | MS(FAB) (M + 1)⁺ |
|---|---|---|
| 289 | CDCl₃ 1.21-1.33(1 H, m), 1.37-1.50(2 H, m), 1.56-1.65(2 H, m), 1.70-2.20(11 H, m), 2.29 and 2.30(total 3 H, each s), 2.42 and 2.43(total 3 H, each s), 2.57-2.68(2 H, m), 2.83 and 2.85(total 3 H, each s), 2.89-2.99(2 H, m), 3.51(0.4 H, tt, J = 4.1 and 11.6 Hz), 3.70-3.79(2 H, m), 4.16(1 H, tt, J = 3.8 and 11.8 Hz), 4.47(0.6 H, tt, J = 4.2 and 12.2 Hz), 7.08-7.16(1 H, m), 7.32 and 7.33(total 1 H, each s) | 446 |
| 290 | CDCl₃ 1.21-1.34(1 H, m), 1.38-1.59(4 H, m), 1.69-1.98(7 H, m), 2.11-2.20(2 H, m), 2.43(3 H, s), 2.63(2 H, d, J = 5.5 Hz), 3.18-3.31(2 H, m), 3.65-3.78(3 H, m), 3.91-4.00(1 H, m), 4.01-4.21(2 H, m), 7.03-7.10(1 H, m), 7.33(1 H, s) | 419 |
| 291 | CDCl₃ 1.20-1.33(1 H, m), 1.38-1.52(2 H, m), 1.69-1.98(5 H, m), 2.13-2.23(2 H, m), 2.44(3 H, s), 3.43-3.52(2 H, m), 3.68-3.79(6 H, m), 4.18(1 H, tt, J = 3.9 and 11.8 Hz), 4.23(2 H, d, J = 3.9 Hz), 7.08-7.15(1 H, m), 7.44(1 H, s) | 391 |
| 292 | CDCl₃ 1.20-1.34(1 H, m), 1.38-1.51(2 H, m), 1.70-1.98(5 H, m), 2.13-2.22(2 H, m), 2.44(3 H, s), 3.04(3 H, s), 3.05(H, s), 4.18(1 H, tt, J = 3.9 and 11.8 Hz), 4.21(2 H, d, J = 3.9 Hz), 7.11-7.18(1 H, m), 7.44(1 H, s) | 349 |

TABLE 102

| Example No. | Chemical Structure | properties m.p. (° C.) (recryst. solvent) |
|---|---|---|
| 293 | 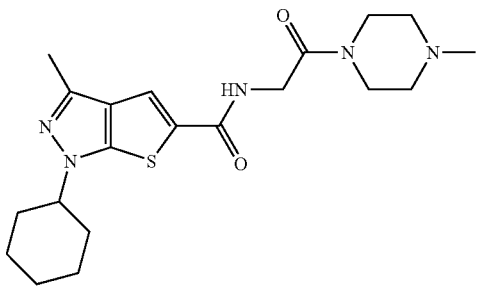 | colorless solid 157-159 |
| 294 | 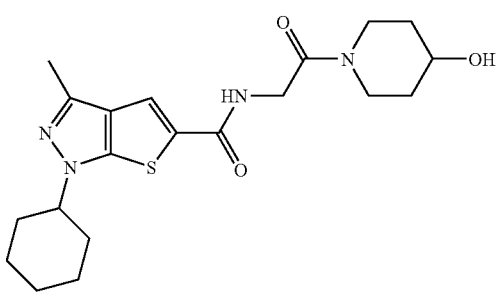 | colorless solid 175-176 |

TABLE 102-continued
295
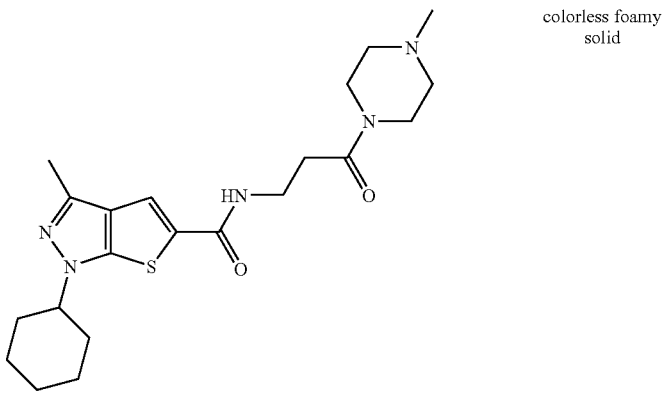
colorless foamy solid
296
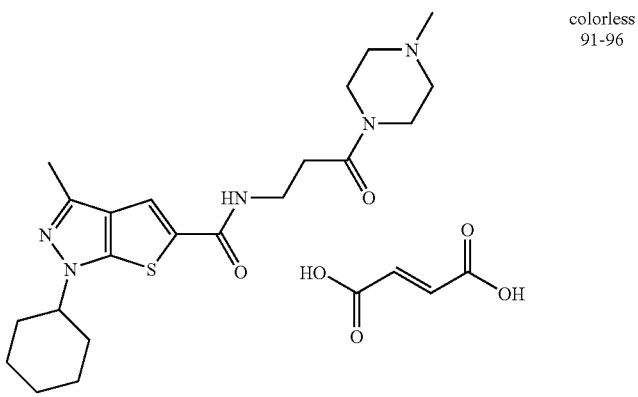
colorless
91-96
| Example No. | ¹H-NMR | MS(FAB) (M + 1)⁺ |
|---|---|---|
| 293 | CDCl₃ 1.20-1.34(1 H, m), 1.38-1.50(2 H, m), 1.70-1.98(5 H, m), 2.13-2.22(2 H, m), 2.33(3 H, s), 2.40-2.50(4 H, m), 2.44(3 H, s), 3.46-3.51(2 H, m), 3.69-3.75(2 H, m), 4.18(1 H, tt, J = 3.9 and 11.8 Hz), 4.22(2 H, d, J = 3.9 Hz), 7.10-7.16(1 H, m), 7.44(1 H, s) | 404 |
| 294 | CDCl₃ 1.20-1.33(1 H, m), 1.39-1.50(2 H, m), 1.53-1.64(3 H, m), 1.70-1.99(7 H, m), 2.15-2.21(2 H, m), 2.44(3 H, s), 3.21-3.31(1 H, m), 3.37-3.46(1 H, m), 3.66-3.74(1 H, m), 3.99-4.09(2 H, m), 4.18(1 H, tt, J = 3.9 and 11.8 Hz), 4.23(2 H, d, J = 3.9 Hz), 7.12-7.18(1 H, m), 7.44(1 H, s) | 405 |
| 295 | CDCl₃ 1.20-1.32(1 H, m), 1.38-1.50(2 H, m), 1.68-1.98(5 H, m), 2.11-2.21(2 H, m), 2.30(3 H, s), 2.36-2.51(4 H, m), 2.43(3 H, s), 2.61(2 H, t, J = 5.5 Hz), 3.42-3.51(2 H, m), 3.61-3.69(2 H, m), 3.70-3.80(2 H, m), 4.16(1 H, tt, J = 3.9 and 11.8 Hz), 7.00-7.09(1 H, m), 7.33(1 H, s) | 418 |
| 296 | CD₃OD 1.22-1.38(1 H, m), 1.43-1.59(2 H, m), 1.72-2.99(5 H, m), 2.09-2.18(2 H, m), 2.42(3 H, s), 2.63(3 H, s), 2.74(2 H, t, J = 6.7 Hz), 2.86-3.00(4 H, m), 3.62(2 H, t, J = 6.7 Hz), 3.70-3.80(4 H, m), 4.16(1 H, tt, J = 3.9 and 11.8 Hz), 6.72(2 H, s), 7.60(1 H, s) | 418 (free) |

TABLE 103

| Example No. | Chemical Structure | properties m.p. (° C.) (recryst. solvent) |
|---|---|---|
| 297 | 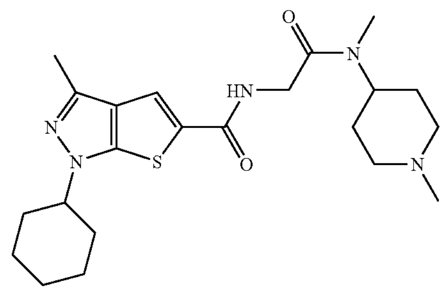 | colorless foamy solid |
| 298 | 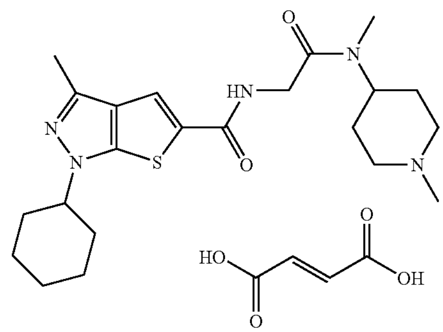 | colorless solid 107-116.5 |
| 299 | 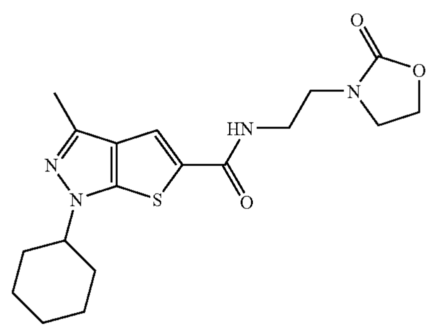 | colorless solid 182-183 (AcOEt) |
| 300 | 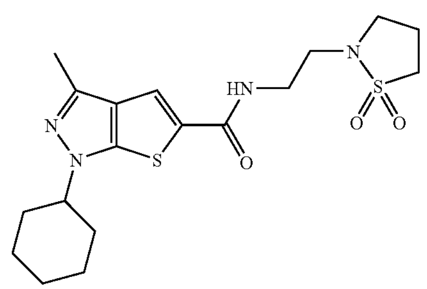 | colorless solid 158-160 (EtOH) |

| Example No. | $^1$H-NMR | MS(FAB) $(M + 1)^+$ |
|---|---|---|
| 297 | CDCl$_3$ 1.20-1.34(1 H, m), 1.38-1.50(2 H, m), 1.60-1.69(2 H, m), 1.72-2.21(11 H, m), 2.30 and 2.32(total 3 H, each s), 2.44(3 H, s), 2.88 and 2.92(total 3 H, each s), 2.90-2.99(2 H, m), 3.43-3.53(0.4 H, m), 4.12-4.28(3 H, m), 4.47(0.6 H, tt, J = 4.2 and 12.2 Hz), 7.14-7.27(1 H, m), 7.44 and 7.45(total 1 H, each s) | 432 |
| 298 | CD$_3$OD 1.23-1.38(1 H, m), 1.43-1.57(2 H, m), 1.71-2.21(11 H, m), 2.43(3 H, s), 2.83(3 H, s), 2.87 and 2.99(total 3 H, each s), 3.02-3.13(2 H, m), 3.49-3.58(2 H, m), 4.01-4.13(0.3 H, m), 4.15-4.24(1 H, m), 4.21 and 4.31(total 2 H, each s), 4.50-4.60(0.7 H, m), 6.70(2 H, s), 7.70(1 H, s) | 432(free) |

TABLE 103-continued

| 299 | CDCl₃ 1.20-1.33(1 H, m), 1.36-1.50(2 H, m), 1.69-1.98(5 H, m), 2.11-2.21(2 H, m), 2.43(3 H, s), 3.51-3.59(2 H, m), 3.64-3.76(4 H, m), 4.16(1 H, tt, J = 3.9 and 11.8 Hz), 4.33-4.42(2 H, m), 6.79-6.87(1 H, m), 7.37(1 H, s) | 377 |
| --- | --- | --- |
| 300 | CDCl₃ 1.20-1.33(1 H, m), 1.38-1.51(2 H, m), 1.69-1.96(5 H, m), 2.12-2.21(2 H, m), 2.37-2.48(2 H, m), 2.44(3 H, s), 3.21(2 H, t, J = 7.5 Hz), 3.34-3.42(4 H, m), 3.61-3.69(2 H, m), 4.17(1 H, tt, J = 3.9 and 11.8 Hz), 6.20-6.27(1 H, m), 7.40(1 H, s) | 411 |

TABLE 104

| Example No. | Chemical Structure | properties m.p. (° C.) (recryst. solvent) |
| --- | --- | --- |
| 301 | 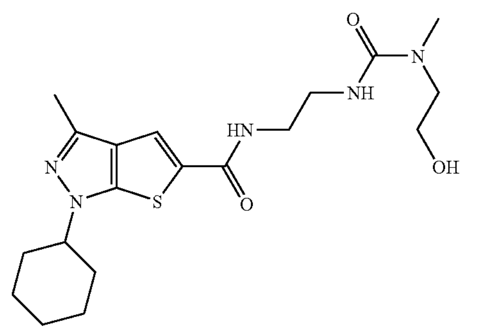 | colorless foamy solid |
| 302 | 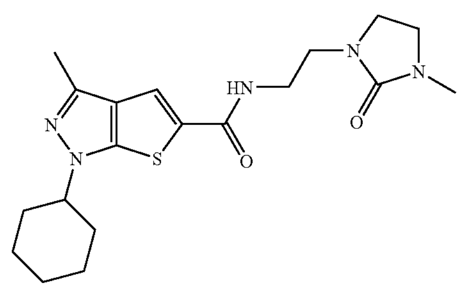 | colorless solid 182-183 (AcOEt) |
| 303 | 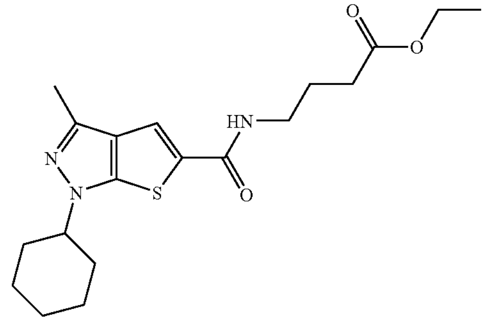 | colorless solid 110-111 |

TABLE 104-continued

| Example No. | ¹H-NMR | MS(FAB) (M + 1)⁺ |
|---|---|---|
| 301 | CDCl₃ 1.19-1.32(1 H, m), 1.37-1.50(2 H, m), 1.69-1.97(5 H, m), 2.09-2.11(2 H, m), 2.43(3 H, s), 2.92(3 H, s), 3.38-3.55(6 H, m), 3.61-3.67(1 H, m), 3.72-3.79(2 H, m), 4.16(1 H, tt, J = 3.9 and 11.8 Hz), 5.81-5.89(1 H, m), 7.43(1 H, s), 7.63-7.72(1 H, m) | 408 |
| 302 | CDCl₃ 1.21-1.33(1 H, m), 1.37-1.50(2 H, m), 1.69-1.97(5 H, m), 2.11-2.21(2 H, m), 2.44(3 H, s), 2.79(3 H, s), 3.31-3.49(6 H, m), 3.54-3.61(2 H, m), 4.16(1 H, tt, J = 3.8 and 11.8 Hz), 7.37-3.43(1 H, m), 7.38(1 H, s) | 390 |
| 303 | CDCl₃ 1.20-1.33(1 H, m), 1.96(3 H, t, J = 6.7 Hz), 1.38-1.51(2 H, m), 1.70-2.01(7 H, m), 2.12-2.21(2 H, m), 2.38-2.51(2 H, m), 2.44(3 H, s), 3.45-3.53(2 H, m), 4.10-4.22(3 H, m), 6.39-6.44(1 H, m), 7.32(1 H, s) | 378 |
| 304 | CDCl₃ 1.19-1.32(1 H, m), 1.37-1.51(2 H, m), 1.70-1.84(3 H, m), 1.88-2.01(4 H, m), 2.11-2.20(2 H, m), 2.28(3 H, s), 2.49(2 H, t, J = 6.4 Hz), 3.50-3.58(2 H, m), 4.18(1 H, tt, J = 3.8 and 11.9 Hz), 6.54-6.61(1 H, m), 7.30(1 H, s) | 350 |

(Example 304: colorless solid, 170-171 (AcOEt/benzene))

TABLE 105

| Example No. | Chemical Structure | properties m.p. (° C.) (recryst. solvent) |
|---|---|---|
| 305 | 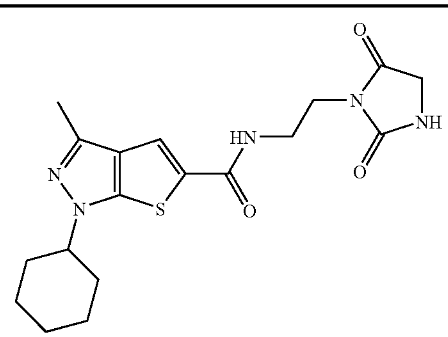 | colorless solid 233-234 (EtOH) |
| 306 | 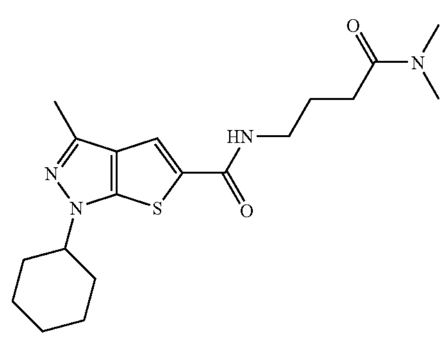 | colorless solid 114.5-116 (AcOEt/hexane) |

TABLE 105-continued

| | | |
|---|---|---|
| 307 | 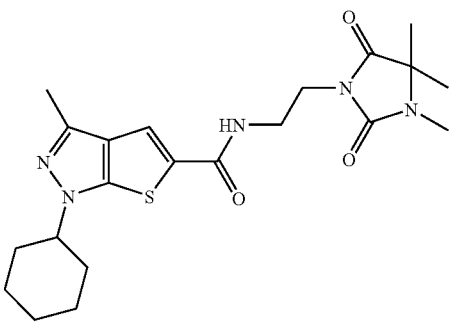 | colorless solid 162-163 (AcOEt/hexane) |
| 308 | 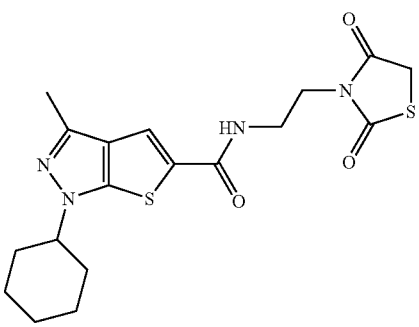 | colorless solid 168-169 (AcOEt) |

| Example No. | $^1$H-NMR | MS(FAB) $(M + 1)^+$ |
|---|---|---|
| 305 | DMSO-d$_6$ 1.16-1.30(1 H, m), 1.37-1.49(2 H, m), 1.62-1.87(5 H, m), 2.00-2.09(2 H, m), 2.35(3 H, s), 3.33-3.42(2 H, m), 3.46-3.52(3 H, m), 3.85(2 H, s), 4.18(1 H, tt, J = 3.8 and 11.6 Hz), 7.64(1 H, s), 8.03(1 H, s), 8.57-8.62(1 H, m) | 390 |
| 306 | CDCl$_3$ 1.20-1.33(1 H, m), 1.38-1.50(2 H, m), 1.70-1.96(5 H, m), 1.99-2.06(2 H, m), 2.11-2.20(2 H, m), 2.43(3 H, s), 2.48-2.53(2 H, m), 2.97(3 H, s), 3.02(3 H, s), 3.44-3.51(2 H, m), 4.16(1 H, tt, J = 3.9 and 11.8 Hz), 7.39(1 H, s), 7.49-7.56(1 H, m) | 377 |
| 307 | CDCl$_3$ 1.21-1.34(1 H, m), 1.38-1.50(2 H, m), 1.39(6 H, s), 1.69-1.97(5 H, m), 2.12-2.20(2 H, m), 2.45(3 H, s), 2.90(3 H, s), 3.62-3.69(2 H, m), 3.80-3.86(2 H, m), 4.16(1 H, tt, J = 3.8 and 11.8 Hz), 6.99-7.05(1 H, m), 7.34(1 H, s) | 432 |
| 308 | CDCl$_3$ 1.21-1.33(1 H, m), 1.37-1.51(2 H, m), 1.70-1.98(5 H,m), 2.12-2.20(2 H, m), 2.44(3 H, s), 3.66-3.72(2 H,m), 3.89-3.96(2 H, m), 4.16(1 H, tt, J = 3.9 and 11.8 Hz), 6.39-6.47(1 H, m), 7.29(1 H, s) | 407 |

TABLE 106

| Example No. | Chemical Structure | properties m.p. (° C.) (recryst. solvent) |
|---|---|---|
| 309 | 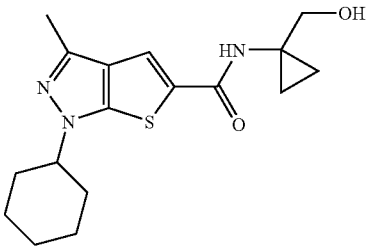 | colorless solid 173-174 (AcOEt/hexane) |

TABLE 106-continued
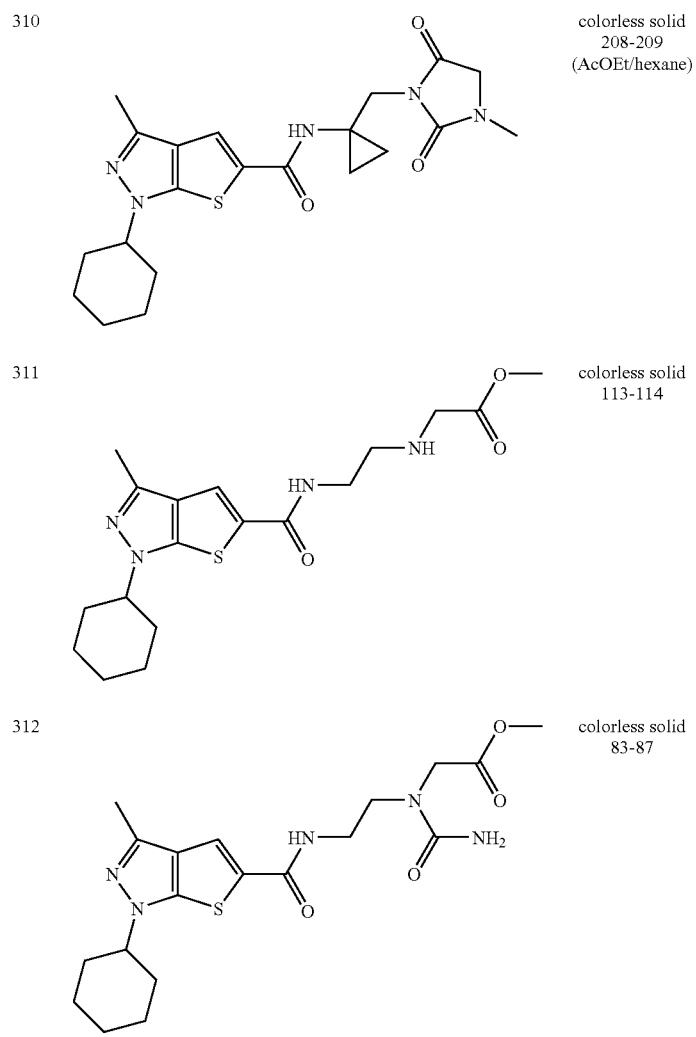
| 310 | | colorless solid 208-209 (AcOEt/hexane) |
| 311 | | colorless solid 113-114 |
| 312 | | colorless solid 83-87 |
| Example No. | ¹H-NMR | MS(FAB) (M + 1)⁺ |
|---|---|---|
| 309 | CDCl₃ 0.92-1.02(4 H, m), 1.20-1.32(1 H, m), 1.37-1.50(2 H, m), 1.70-1.84(3 H, m), 1.88-1.97(2 H, m), 2.11-2.20(2 H, m), 2.42(3 H, s), 3.70(2 H, d, J = 5.1 Hz), 3.92(1 H, t, J = 5.1 Hz), 4.16(1 H, tt, J = 3.9 and 11.8 Hz), 6.60(1 H, brs), 7.33(1 H, s) | 334 |
| 310 | CDCl₃ 0.98-1.14(4 H, m), 1.20-1.33(1 H, m), 1.38-1.50(2 H, m), 1.69-1.99(5 H, m), 2.11-2.21(2 H, m), 2.40(3 H, s), 2.99(3 H, s), 3.73(2 H, s), 3.87(2 H, s), 4.14(1 H, tt, J = 3.9 and 11.8 Hz), 6.53(1 H, brs), 7.27(1 H, | 430 |
| 311 | CDCl₃ 1.20-1.33(1 H, m), 1.39-1.51(2 H, m), 1.65-1.98(5 H, m), 2.12-2.21(2 H, m), 2.44(3 H, s), 2.86-2.92(2 H, m), 3.44-3.56(2 H, m), 3.47(2 H, s), 3.76(3 H, s), 4.14(1 H, tt, J = 3.8 and 11.8 Hz), 6.80-6.89(1 H, m), 7.40(1 H, s) | 379 |
| 312 | CDCl₃ 1.21-1.34(1 H, m), 1.38-1.50(2 H, m), 1.69-1.97(5 H, m), 2.12-2.21(2 H, m), 2.44(3 H, s), 3.48-3.64(4 H, m), 3.79(3 H, s), 4.06(2 H, s), 4.17(1 H, tt, J = 3.8 and 11.8 Hz), 4.93(2 H, brs), 7.31-7.42(1 H, m), 7.39(1 H, s) | 422 |

TABLE 107

| Example No. | Chemical Structure | properties m.p. (° C.) (recryst. solvent) |
|---|---|---|
| 313 | 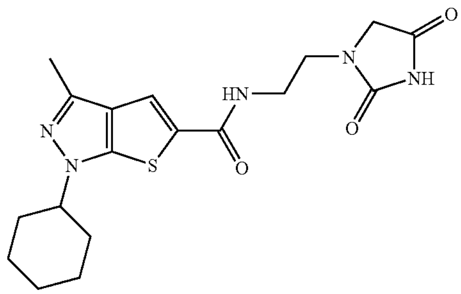 | colorless solid 233-235 (EtOH) |
| 314 | 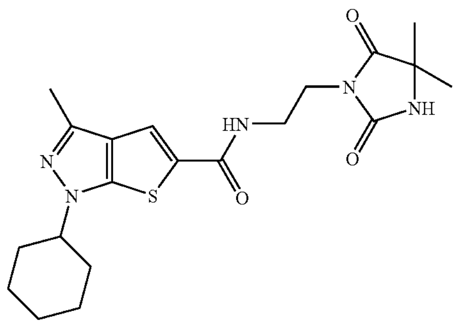 | colorless solid 207-2113 (EtOH) |
| 315 | 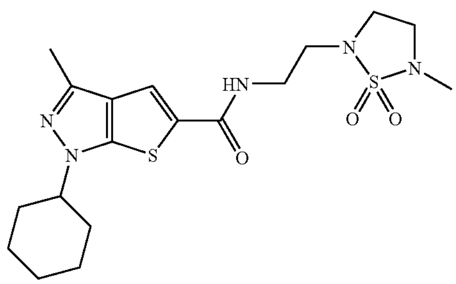 | colorless solid 149-150 (AcOEt/hexane) |
| 316 | 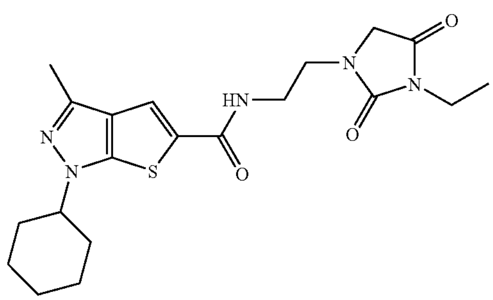 | colorless solid 148.5-150 (AcOEt/hexane) |

| Example No. | ¹H-NMR | MS(FAB) (M + 1)⁺ |
|---|---|---|
| 313 | CDCl₃ 1.20-1.32(1 H, m), 1.38-1.50(2 H, m), 1.70-1.98(5 H, m), 2.11-2.21(2 H, m), 2.42(3 H, s), 3.57-3.70(4 H, m), 4.07(2 H, s), 4.14(1 H, tt, J = 3.9 and 11.9 Hz), 6.62-6.70(1 H, m), 7.35(1 H, s), 7.97(1 H, brs) | 390 |
| 314 | CDCl₃ 1.20-1.32(1 H, m), 1.37-1.51(2 H, m), s), 1.69-1.96(5 H, m), 2.11-2.20(2 H, m), 2.44(3 H, s). 3.64-71(2 H, m), 3.79-3.85(2 H, m), 4.16(1 H, tt, J = 3.9 and 11.9 Hz), 5.51(1 H, brs), 6.89-6.96(1 H, m), 7.33(1 H, s) | 418 |
| 315 | CDCl₃ 1.21-1.33(1 H, m), 1.38-1.51(2 H, m), 1.70-1.98(5 H, m), 2.13-2.21(2 H, m), 2.44(3 H, s), 2.78(3 H, s), 3.31-3.48(6 H, m), 3.68-3.75(2 H, m), 4.17(1 H, tt, J = 3.8 and 11.9 Hz), 6.62-6.70(1 H, m), 7.38(1 H, s) | 426 |

TABLE 107-continued

| | | |
|---|---|---|
| 316 | CDCl$_3$ 1.13(3 H, t, J = 7.2 Hz), 1.20-1.33(1 H, m), 1.38-1.50(2 H, m), 1.70-1.98(5 H, m), 2.11-2.21(2 H, m), 2.44(3 H, s), 3.53(2 H, q, J = 7.2 Hz), 3.60-3.72(4 H, m), 3.99(2 H, s), 4.16(1 H, tt, J = 3.9 and 11.9 Hz), 6.57-6.65(1 H, m), 7.33(1 H, s) | 418 |

TABLE 108

| Example No. | Chemical Structure | properties m.p. (° C.) (recryst. solvent) |
|---|---|---|
| 317 | 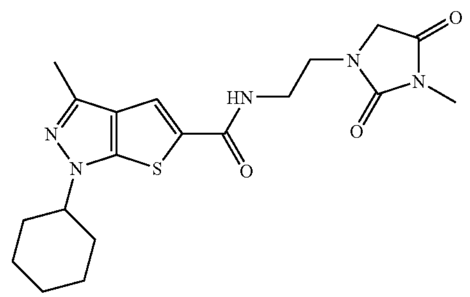 | colorless solid 154-155 (AcOEt/hexane) |
| 318 | 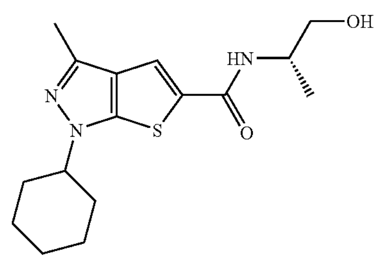 | colorless solid 152-153 (AcOEt/hexane) |
| 319 | 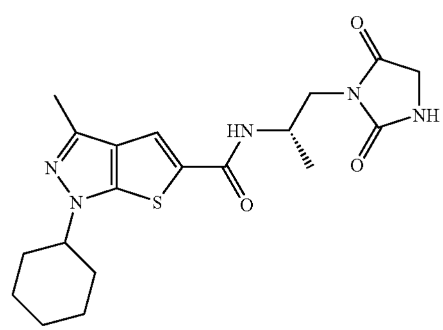 | colorless solid 172.5-175 (AcOEt/hexane) |
| 320 | 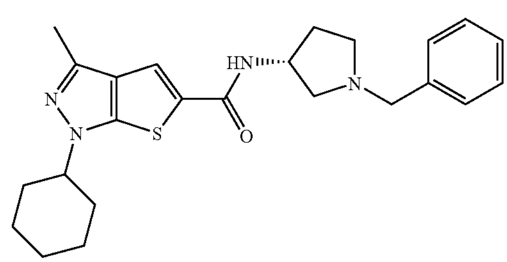 | colorless foamy solid |

| Example No. | $^1$H-NMR | MS(FAB) (M + 1)$^+$ |
|---|---|---|
| 317 | CDCl$_3$ 1.20-1.33(1 H, m), 1.37-1.50(2 H, m), 1.69-1.97(5 H, m), 2.11-2.21(2 H, m), 2.44(3 H, s), 2.99(3 H, s), 3.59-3.74(4 H, m), 4.01(2 H, s), 4.17(1 H, tt, J = 3.9 and 11.9 Hz), 6.57-6.67(1 H, m), 7.34(1 H, s) | 404 |

TABLE 108-continued

| | | |
|---|---|---|
| 318 | CDCl₃ 1.20-1.34(1 H, m), 1.30(3 H, d, J = 6.8 Hz), 1.38-1.50(2 H, m), 1.69-1.98(5 H, m), 2.12-2.21(2 H, m), 2.42(3 H, s), 2.75(1 H, t, J = 5.5 Hz), 3.61-3.68(2 H, m), 3.74-3.82(2 H, m), 4.17(1 H, tt, J = 3.9 and 11.9 Hz), 4.21-4.31(1 H, m), 6.13-6.21(1 H, m), 7.35(1 H, s) | 322 |
| 319 | CDCl₃ 1.20-1.34(1 H, m), 1.29(3 H, d, J = 6.8 Hz), 1.38-1.50(2 H, m), 1.69-1.96(5 H, m), 2.11-2.20(2 H, m), 2.43(3 H,s), 3.61-3.77(2 H, m), 3.96-4.08(2 H, m), 4.16(1 H, tt, J = 3.9 and 11.9 Hz), 4.36-4.48(1 H, m), 5.46(1 H, brs), 6.79-6.86(1 H, m), 7.32(1 H, s) | 404 |
| 320 | CDCl₃ 1.21-1.33(1 H, m), 1.38-1.50(2 H, m), 1.68-1.97(6 H, m), 2.11-2.21(2 H, m), 2.26-2.42(2 H, m), 2.44(3 H, s), 2.58-2.63(1 H, m), 2.70-2.78(1 H, m), 2.90-2.99(1 H, m), 3.59-3.69(2 H, m), 4.16(1 H, tt, J = 3.9 and 11.8 Hz), 4.59-4.69(1 H, m), 6.34-6.42(1 H, m), 7.23-7.40(6 H, m) | 423 |

TABLE 109

| Example No. | Chemical Structure | properties m.p.(° C.) (recryst. solvent) | ¹H-NMR | MS (FAB) (M + 1)⁺ |
|---|---|---|---|---|
| 321 | 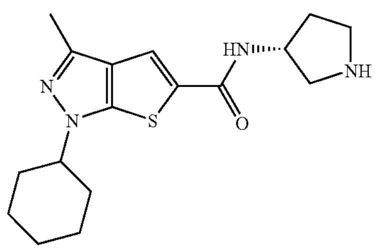 | colorless solid 119-123 | CDCl₃ 1.20-1.32(1 H, m), 1.37-1.50(2 H, m), 1.70-1.98(6 H, m), 2.11-2.31(3 H, m), 2.42(3 H, s), 2.93-3.04(2 H, m), 3.11-3.25(2 H, m), 4.16(1 H, tt, J = 3.9 and 11.9 Hz), 4.55-4.65(1 H, m), 6.48-6.55(1 H, m), 7.41(1 H, s) | 333 |
| 322 | 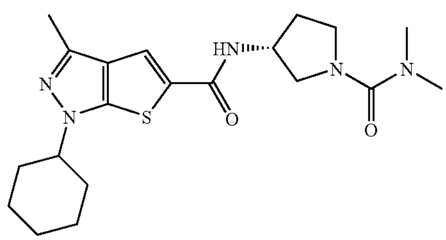 | colorless foamy solid | CDCl₃ 1.21-1.32(1 H, m), 1.37-1.50(2 H, m), 1.70-1.96(5 H, m), 1.98-2.08(1 H, m), 2.11-2.24(3 H, m), 2.43(3 H, s), 2.89(6 H, s), 3.41-3.62(4 H, m), 4.17(1 H, tt, J = 3.8 and 11.8 Hz), 4.50-4.59(1 H, m), 6.61-6.69(1 H, m), 7.35(1 H, s) | 404 |
| 323 | HCl | colorless solid 126-128 | DMSO-d₆ 1.16-1.29(1 H, m), 1.38-1.50(2 H, m), 1.61-1.91(6 H, m), 2.00-2.10(3 H, m), 2.35(3 H, s), 2.74(6 H,s ), 3.19-3.25(1 H, m), 3.30-3.49(2 H, m), 3.51-3.60(1 H, m), 4.19(1 H, tt, J = 3.8 and 11.6 Hz), 4.28-4.38(1 H, m), 7.88(1 H, s), 8.52-8.59(1 H, m) | 404 (free) |
| 324 | 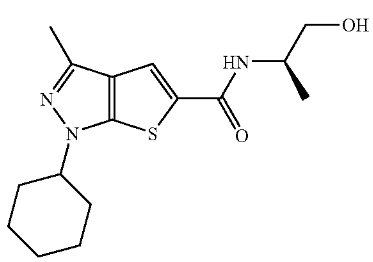 | colorless solid 146.5-148 | CDCl₃ 1.20-1.34(1 H, m), 1.30(3 H, d, J = 6.8 Hz), 1.38-1.50(2 H, m), 1.69-1.98(5 H, m), 2.12-2.21(2 H, m), 2.42(3 H, s), 2.68-2.73(1 H, m), 3.61-3.68(2 H, m), 3.74-3.82(2 H, m), 4.17(1 H, tt, J = 3.9 and 11.9 Hz), 4.21-4.31(1 H, m), 6.11-6.19(1 H, m), 7.35(1 H, s) | 322 |

TABLE 110

| Example No. | Chemical Structure | properties m.p.(° C.) (recryst. solvent) | ¹H-NMR | MS(FAB) (M + 1)⁺ |
|---|---|---|---|---|
| 325 | 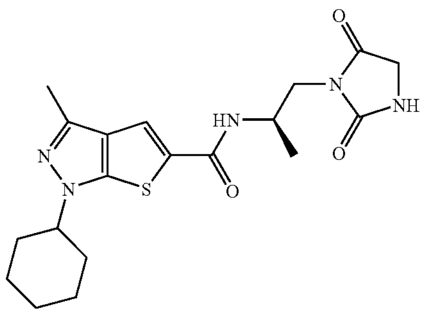 | colorless solid 170-173 | CDCl₃ 1.20-1.34(1 H, m), 1.29(3 H, d, J = 6.8 Hz), 1.38-1.50(2 H, m), 1.69-1.96(5 H, m), 2.11-2.20(2 H, m), 2.43(3 H, s), 3.61-3.77(2 H, m), 3.96-4.08(2 H, m), 4.16(1 H, tt, J = 3.9 and 11.9 Hz), 4.36-4.48(1 H, m), 5.44(1 H, brs), 6.79-6.86(1 H, m), 7.32(1 H, s) | 404 |
| 326 | 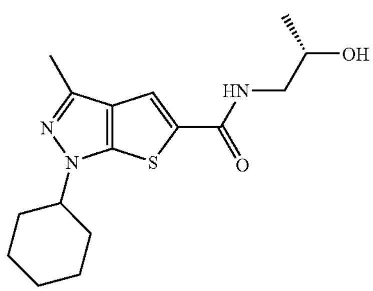 | colorless solid 116-117.5 | CDCl₃ 1.20-1.33(1 H, m), 1.26(3 H, d, J = 6.3 Hz), 1.38-1.51(2 H, m), 1.70-1.97(5 H, m), 2.12-2.21(2 H, m), 2.42(3 H, s), 2.49-2.54(1 H, m), 3.23-3.32(1 H, m), 3.61-3.70(1 H, m), 3.99-4.09(1 H, m), 4.17(1 H, tt, J = 3.9 and 11.8 Hz), 6.42-6.50(1 H, m), 7.37(1 H, s) | 322 |
| 327 | 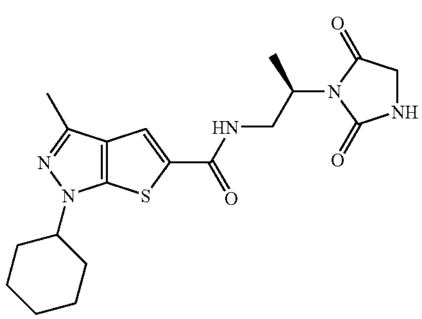 | colorless solid 213-215 | CDCl₃ 1.20-1.34(1 H, m), 1.38-1.50(2 H, m), 1.47(3 H, d, J = 7.1 Hz), 1.69-1.97(5 H, m), 2.12-2.20(2 H, m), 2.44(3 H, s), 3.37-3.44(1 H, m), 3.98(2 H, s), 4.10-4.23(2 H, m), 4.47-4.58(1 H, m), 5.42(1 H, brs), 7.10-7.18(1 H, m), 7.36(1 H, s) | 404 |
| 328 | 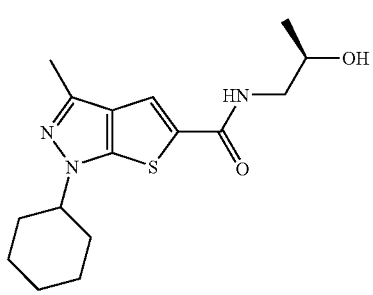 | colorless solid 115.5-117 | CDCl₃ 1.20-1.33(1 H, m), 1.26(3 H, d, J = 6.3 Hz), 1.38-1.51(2 H, m), 1.70-1.97(5 H, m), 2.12-2.21(2 H, m), 2.42(3 H, s), 2.44-2.49(1 H, m), 3.23-3.32(1 H, m), 3.61-3.70(1 H, m), 3.99-4.09(1 H, m), 4.17(1 H, tt, J = 3.9 and 11.8 Hz), 6.40-6.48(1 H, m), 7.37(1 H, s) | 322 |

TABLE 111

| Example No. | Chemical Structure | properties m.p.(° C.) (recryst. solvent) | ¹H-NMR | MS(FAB) (M + 1)⁺ |
|---|---|---|---|---|
| 329 | 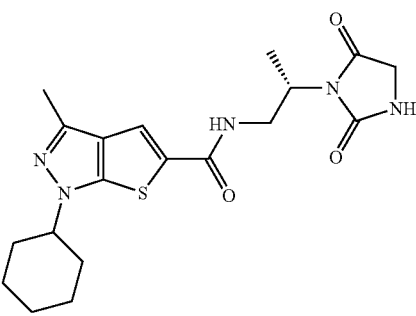 | colorless solid 214-216 (AcOEt/ hexane) | CDCl₃ 1.20-1.34(1 H, m), 1.38-1.50(2 H, m), 1.47(3 H, d, J = 7.1 Hz), 1.69-1.97(5 H, m), 2.12-2.20(2 H, m), 2.44(3 H, s), 3.37-3.44(1 H, m), 3.98(2 H, s), 4.10-4.23(2 H, m), 4.47-4.58(1 H, m), 5.46(1 H, brs), 7.12-7.20(1 H, m), 7.36(1 H, s) | 404 |
| 330 | 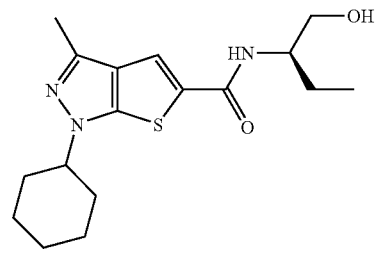 | colorless solid 147-149.5 | CDCl₃ 1.02(3 H, t, J = 7.5 Hz), 1.20-1.32(1 H, m), 1.38-1.51(2 H, m), 1.58-1.97(7 H, m), 2.12-2.21(2 H, m), 2.43(3 H, s), 2.51-2.59(1 H, m), 3.68-3.74(1 H, m), 3.78-3.83(1 H, m), 4.00-4.10(1 H, m), 4.17(1 H, tt, J = 3.8 and 11.9 Hz), 6.07-6.14(1 H, m), 7.36(1 H, s) | 336 |
| 331 | 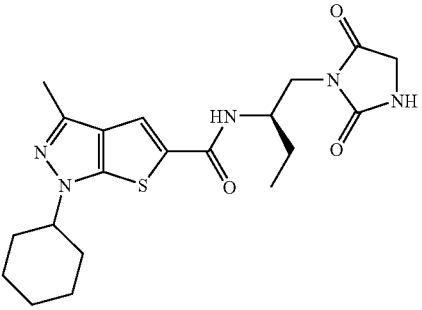 | colorless solid 180-183 | CDCl₃ 1.03(3 H, t, J = 7.5 Hz), 1.20-1.33(1 H, m), 1.37-1.50(2 H, m), 1.55-1.97(7 H, m), 2.11-2.19(2 H, m), 2.43(3 H, s), 3.62-3.77(2 H, m), 3.91-4.04(2 H, m), 4.16(1 H, tt, J = 3.8 and 11.8 Hz), 4.25-4.37(1 H, m), 5.45(1 H, brs), 6.53-6.60(1 H, m), 7.33(1 H, s) | 418 |
| 332 | 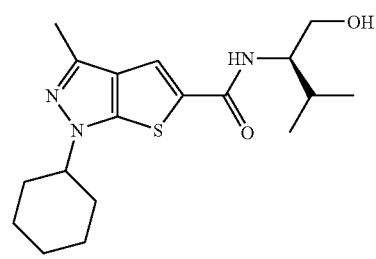 | colorless solid 148.5-149.5 | CDCl₃ 0.99-1.08(6 H, m), 1.19-1.32(1 H, m), 1.38-1.51(2 H, m), 1.70-2.07(6 H, m), 2.12-2.21(2 H, m), 2.43(3 H, s), 2.51-2.60(1 H, m), 3.77-3.83(2 H, m), 3.86-3.95(1 H, m), 4.17(1 H, tt, J = 3.9 and 11.8 Hz), 6.12-6.20(1 H, m), 7.56(1 H, s) | 350 |

TABLE 112

| Example No. | Chemical Structure | properties m.p.(° C.) (recryst. solvent) | ¹H-NMR | MS (FAB) (M + 1)⁺ |
|---|---|---|---|---|
| 333 | 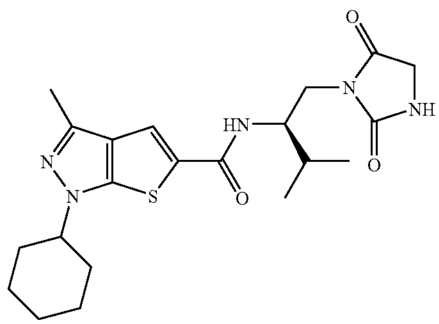 | colorless solid 180-184 | CDCl₃ 1.05(6 H, d, J = 6.8 Hz), 1.19-1.33(1 H, m), 1.38-1.51(2 H, m), 1.69-2.01(6 H, m), 2.10-2.20(2 H, m), 2.44(3 H, s), 3.59-3.80(2 H, m), 3.88-4.02(2 H, m), 4.11-4.31(2 H, m), 5.45(1 H, brs), 6.32-6.41(1 H, m), 7.34(1 H, s) | 432 |
| 334 | 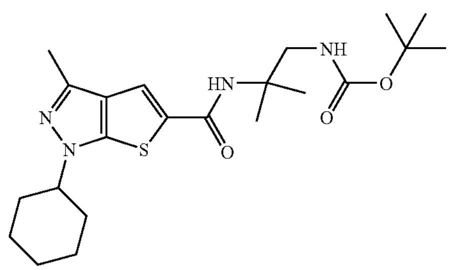 | colorless foamy solid | CDCl₃ 1.20-1.33(1 H, m), 1.38-1.53(2 H, m), 1.47(6 H, s), 1.50(9 H, s), 1.69-1.95(5 H, m), 2.11-2.20(2 H, m), 2.40(3 H, s), 3.22(2 H, d, J = 6.7 Hz), 4.16(1 H, tt, J = 3.9 and 11.8 Hz), 5.15-5.20(1 H, m), 7.36(1 H, s), 7.58(1 H, brs) | 435 |
| 335 | 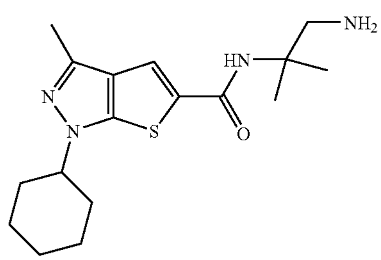 | colorless solid 134-136.5 | CDCl₃ 1.20-1.50(3 H, m), 1.43(6 H, s), 1.70-1.97(5 H, m), 2.11-2.20(2 H, m), 2.43(3 H, s), 2.83(2 H, s), 4.16(1 H, tt, J = 3.9 and 11.8 Hz), 6.70(1 H, brs), 7.28(1 H, s) | 335 |
| 336 | 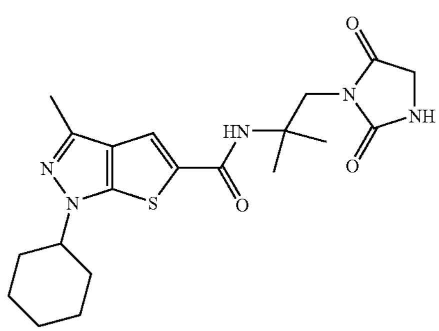 | colorless foamy solid | CDCl₃ 1.21-1.32(1 H, m), 1.38-1.51(2 H, m), 1.55(6 H, s), 1.69-1.96(5 H, m), 2.10-2.19(2 H, m), 2.44(3 H, s), 3.66(2 H, s), 4.10-4.20(3 H, m), 5.55(1 H, brs), 7.34(1 H, s), 7.74(1 H, brs) | 418 |

TABLE 113

| Example No. | Chemical Structure | properties m.p.(° C.) (recryst. solvent) |
|---|---|---|
| 337 | (structure: 1-cyclohexyl-3-methyl-N-(2-methyl-1-(2,5-dioxoimidazolidin-1-yl)propan-2-yl)thieno[2,3-c]pyrazole-5-carboxamide · HCl) | colorless solid 141.5-143 |
| 338 | (structure: N-(3-amino-2,2-dimethylpropyl)-1-cyclohexyl-3-methylthieno[2,3-c]pyrazole-5-carboxamide) | colorless solid 145-147 |
| 339 | (structure: 1-cyclohexyl-3-methyl-N-(2,2-dimethyl-3-(2,5-dioxoimidazolidin-1-yl)propyl)thieno[2,3-c]pyrazole-5-carboxamide) | colorless solid 180-182 |
| 340 | (structure: 1-cyclohexyl-3-methyl-N-((1R,2S)-2-(hydroxymethyl)cyclopropyl)thieno[2,3-c]pyrazole-5-carboxamide) | colorless solid 153-154 |

| Example No. | ¹H-NMR | MS(FAB) (M + 1)⁺ |
|---|---|---|
| 337 | DMSO-d₆ 1.18-1.31(1 H, m), 1.34-1.51(2 H, m), 1.35(6 H, s), 1.61-1.88(5 H, m), 2.00-2.09(2 H, m), 2.35(3 H, s), 3.62(2 H, s), 3.98(2 H, m), 4.18(1 H, tt, J = 3.8 and 11.5 Hz), 7.60(1 H, s), 8.01(1 H, s), 8.28(1 H, s) | 418(free) |
| 338 | CDCl₃ 0.97(5 H, s), 1.20-1.33(1 H, m), 1.39-1.53(2 H, m), 1.70-1.98(5 H, m), 2.12-2.21(2 H, m), 2.44(3 H, s), 2.72(2 H, s), 3.37(2 H, d, J = 5.2 Hz), 4.17(1 H, tt, J = 3.9 and 11.8 Hz), 7.29(1 H, s), 8.48-8.53(1 H, m) | 349 |
| 339 | CDCl₃ 1.00(6 H, s), 1.20-1.34(1 H, m), 1.38-1.50(2 H, m), 1.70-1.98(5 H, m), 2.12-2.21(2 H, m), 2.45(3 H, s), 3.17(2 H, d, J = 6.7 Hz), 3.43(2 H, s), 4.09-4.13(2 H, m), | 432 |

TABLE 113-continued

| | | | |
|---|---|---|---|
| | 4.17(1 H, tt, J = 3.8 and 11.8 Hz), 5.60(1 H, brs), 7.44(1 H, s), 7.83-7.89(1 H, m) | | |
| 340 | CDCl₃ 0.83-0.91(1 H, m), 0.94-1.00(1 H, m), 1.20-1.50(4 H, m), 1.70-1.97(5 H, m), 2.12-2.21(2 H, m), 2.42(3 H, s), 2.57-2.62(1 H, m), 3.05-3.19(2 H, m), 3.90-3.98(1 H, m), 4.16(1 H, tt, J = 3.9 and 11.8 Hz), 6.35(1 H, brs), 7.32(1 H, s) | 334 | |

TABLE 114

| Example No. | Chemical Structure | properties m.p.(° C.) (recryst. solvent) | ¹H-NMR | MS (FAB) (M + 1)⁺ |
|---|---|---|---|---|
| 341 | 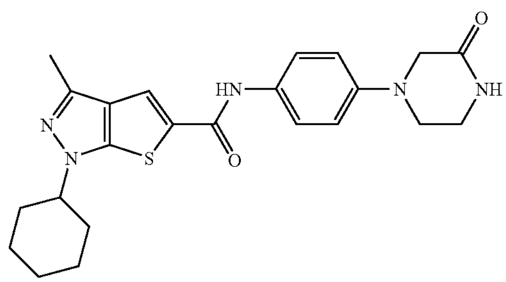 | pale brown solid 220(dec.) | DMSO-d₆ 1.16-1.32(1 H, m), 1.38-1.51(2 H, m), 1.63-1.87(5 H, m), 2.02-2.11(2 H, m), 2.39(3 H, s), 3.26-3.39(4 H, m), 3.67(2 H, s), 4.16-4.26(1 H, m), 6.91-6.96(2 H, m), 7.56-7.61(2 H, m), 8.00(1 H, s), 8.01-8.03(1 H, m), 10.06(1 H, brs) | 438 |
| 342 | 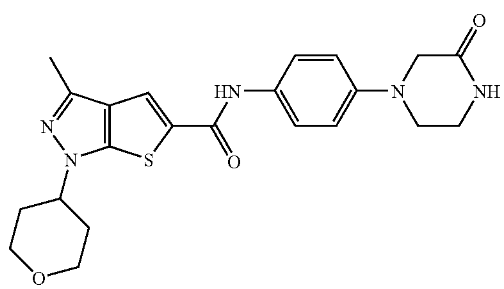 | pale brown solid 155(dec.) | CDCl₃ 2.11-2.38(4 H, m), 2.47(3 H, s), 3.45-3.49(2 H, m), 3.52-3.61(4 H, m), 3.87(2 H, s), 4.12-4.18(2 H, m), 4.39-4.49(1 H, m), 6.01(1 H, brs), 6.87-6.93(2 H, m), 7.47(1 H, s), 7.50-7.56(2 H, m), 7.58(1 H, brs) | 440 |
| 343 | 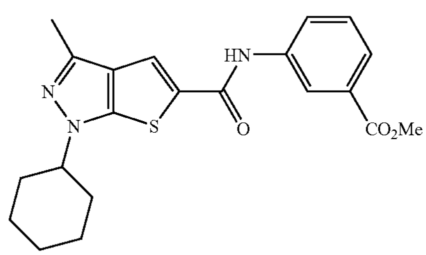 | colorless solid 155.5-157 | CDCl₃ 1.22-1.35(1 H, m), 1.39-1.52(2 H, m), 1.72-1.98(5 H, m), 2.16-2.24(2 H, m), 2.47(3 H, s), 3.93(3 H, s), 4.20(1 H, tt, J = 3.8 and 11.8 Hz), 7.45(1 H, t, J = 7.9 Hz), 7.50(1 H, s), 7.74(1 H, brs), 7.81(1 H, dt, J = 7.9 and 1.3 Hz), 7.98-8.04(1 H, m), 8.11-8.13(1 H, m) | 398 |
| 344 | 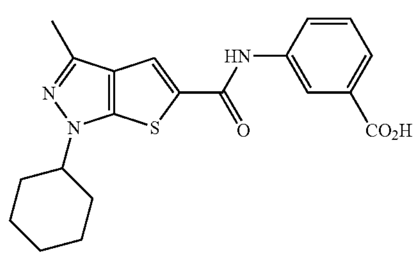 | colorless foamy solid | CDCl₃ 1.20-1.32(1 H, m), 1.36-1.50(2 H, m), 1.71-1.96(5 H, m), 2.15-2.22(2 H, m), 2.42(3 H, s), 4.18(1 H, tt, J = 3.8 and 11.8 Hz), 7.42(1 H, t, J = 7.9 Hz), 7.64(1 H, s), 7.80-7.85(1 H, m), 8.05-8.10(1 H, m), 8.13-8.16(1 H, m), 8.30(1 H, brs) | 384 |

TABLE 115

| Example No. | Chemical Structure | properties m.p.(° C.) (recryst. solvent) | ¹H-NMR | MS (FAB) (M + 1)⁺ |
|---|---|---|---|---|
| 345 | 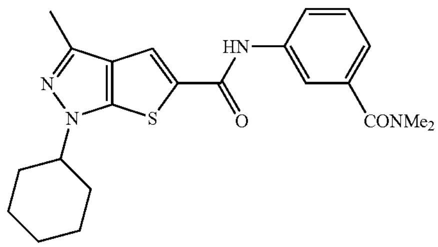 | colorless solid 226-228 | CDCl₃ 1.25-1.35(1 H, m), 1.39-1.52(2 H, m), 1.72-1.98(5 H, m), 2.16-2.24(2 H, m), 2.47(3 H, s), 3.02(3 H, brs), 3.13(3 H, brs), 4.19(1 H, tt, J = 3.9 and 11.8 Hz), 7.12-7.16(1 H, m), 7.34-7.39(1 H, m), 7.57(1 H, s), 7.60(1 H, brs), 7.84-7.68(1 H, m), 8.15(1 H, brs) | 411 |
| 346 | 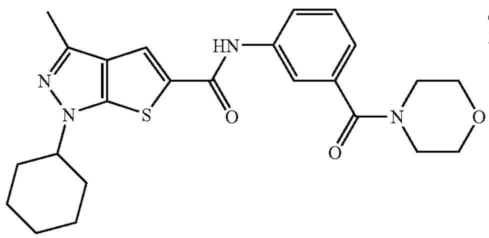 | colorless solid 218-220 | CDCl₃ 1.24-1.36(1 H, m), 1.39-1.52(2 H, m), 1.72-1.98(5 H, m), 2.17-2.25(2 H, m), 2.47(3 H, s), 3.45-3.89(8 H, m), 4.15-4.25(1 H, m), 7.15-7.20(1 H, m), 7.38-7.43(1 H, m), 7.51(1 H, s), 7.59-7.84(1 H, m), 7.71-7.74(1 H, m), 7.81(1 H, brs) | 453 |
| 347 | 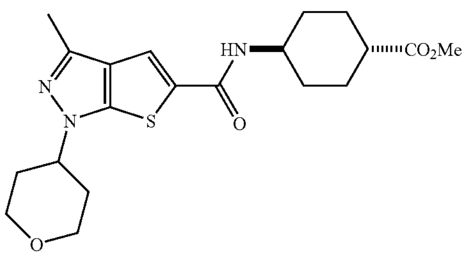 | colorless solid 185-187 | CDCl₃ 1.18-1.32(2 H, m), 1.55-1.67(2 H, m), 2.04-2.33(9 H, m), 2.43(3 H, s), 3.55(2 H, dt, J = 2.4 and 11.7 Hz), 3.69(3 H, s), 3.88-3.99(1 H, m), 4.09-4.16(2 H, m), 4.36-4.45(1 H, m), 5.69-5.74(1 H, m), 7.31(1 H, s) | 406 |
| 348 | 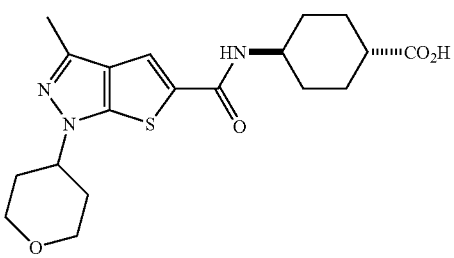 | colorless solid 267-270 | DMSO-d₆ 1.27-1.47(4 H, m), 1.85-2.04(8 H, m), 2.12-2.22(1 H, m), 2.33(3 H, s), 3.49(2 H, dt, J = 2.4 and 11.6 Hz), 3.63-3.72(1 H, m), 3.95-4.00(2 H, m), 4.43-4.52(1 H, m), 7.81(1 H, s), 8.25-8.29(1 H, m) | 392 |

TABLE 116

| Example No. | Chemical Structure | properties m.p.(° C.) (recryst. solvent) |
|---|---|---|
| 349 | 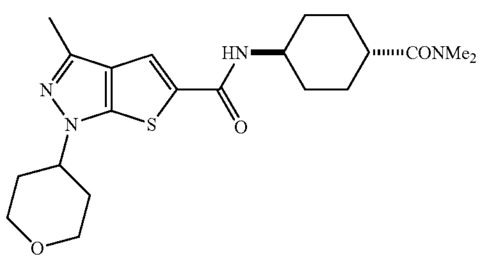 | colorless solid 232-234 |

TABLE 116-continued

| No. | Structure | Properties |
|-----|-----------|------------|
| 350 | (3-methyl-1-(tetrahydro-2H-pyran-4-yl)-1H-thieno[2,3-c]pyrazole-5-carboxamide with cyclohexyl-morpholine amide) | colorless solid 220-222 |
| 351 | (3-(tetrahydropyran-4-yloxy)-1-(tetrahydro-2H-pyran-4-yl)-1H-thieno[2,3-c]pyrazole-5-carboxamide with cyclohexyl-4-hydroxypiperidine amide) | colorless solid 255-260 |
| 352 | (3-methyl-1-(tetrahydro-2H-pyran-4-yl)-1H-thieno[2,3-c]pyrazole-5-carboxamide with cyclohexyl-4-methylpiperazine amide) | colorless solid 200-203 |

| Example No. | $^1$H-NMR | MS(FAB) $(M + 1)^+$ |
|---|---|---|
| 349 | CDCl$_3$ 1.22-1.34(2 H, m), 1.69-1.90(4 H, m), 2.08-2.26(6 H, m), 2.44(3 H, s), 2.49(1 H, tt, J = 3.6 and 11.6 Hz), 2.94(3 H, s), 3.06(3 H, s), 3.55(2 H, dt, J = 2.4 and 11.7 Hz), 3.90-4.03(1 H, m), 4.10-4.17(2 H, m), 4.36-4.46(1 H, m), 5.69-5.74(1 H, m), 7.31(1 H, s) | 419 |
| 350 | CDCl$_3$ 1.20-1.35(2 H, m), 1.71-1.89(4 H, m), 2.08-2.27(6 H, m), 2.40-2.48(1 H, m), 2.44(3 H, s), 3.47-3.72(10 H, m), 3.91-4.01(1 H, m), 4.09-4.17(2 H, m), 4.37-4.46(1 H, m), 5.67-5.72(1 H, m), 7.31(1 H, s) | 461 |
| 351 | DMSO-d$_6$ 1.17-1.53(6 H, m), 1.62-2.07(10 H, m), 2.36(3 H, s), 2.48-2.54(1 H, m), 2.91-3.03(1 H, m), 3.13-3.24(1 H, m), 3.47-3.55(2 H, m), 3.61-3.79(3 H, m), 3.88-4.00(3 H, m), 4.43-4.53(1 H, m), 4.72-7.75(1 H, m), 7.83(1 H, s), 8.26-8.29(1 H, m) | 475 |
| 352 | CDCl$_3$ 2.20-1.33(2 H, m), 1.70-1.88(4 H, m), 2.08-2.27(6 H, m), 2.31(3 H, s), 2.35-2.48(5 H, m), 2.43(3 H, s), 3.48-3.66(6 H, m), 3.90-4.02(1 H, m), 4.10-4.16(2 H, m), 4.36-4.47(1 H, m), 5.65-5.71(1 H, m), 7.31(1 H, s) | 474 |

TABLE 117

| Example No. | Chemical Structure | properties m.p.(° C.) (recryst. solvent) | $^1$H-NMR | MS (FAB) $(M + 1)^+$ |
|---|---|---|---|---|
| 353 | (3-methyl-1-cyclohexyl-1H-thieno[2,3-c]pyrazole-5-carboxamide with propyl-morpholine) | colorless solid 128-129 | CDCl$_3$ 1.21-1.35(1 H, m), 1.38-1.52(2 H, m), 1.71-2.96(7 H, m), 2.05-2.22(2 H, m), 2.44(3 H, s), 2.50-2.59(6 H, m), 3.52-3.57(2 H, m), 3.76-3.81(4 H, m), 4.14-4.24(1 H, m), 7.38(1 H, s), 7.67-7.73(1 H, m) | 391 |

TABLE 117-continued

| Example No. | Chemical Structure | properties m.p.(° C.) (recryst. solvent) | ¹H-NMR | MS (FAB) (M + 1)⁺ |
|---|---|---|---|---|
| 354 | 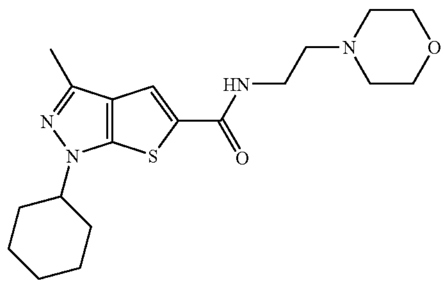 | colorless solid 138-138.5 | CDCl₃ 1.22-1.34(1 H, m), 1.37-1.51(2 H, m), 1.72-1.96(5 H, m), 2.14-2.21(2 H, m), 2.45(3 H, s), 2.49-2.54(4 H, m), 2.59(2 H, t, J = 5.9 Hz), 3.51-3.57(2 H, m), 3.74-3.78(4 H, m), 4.17(1 H, tt, J = 3.8 and 11.8 Hz), 6.50-6.55(1 H, m), 7.32(1 H, s) | 377 |
| 355 | 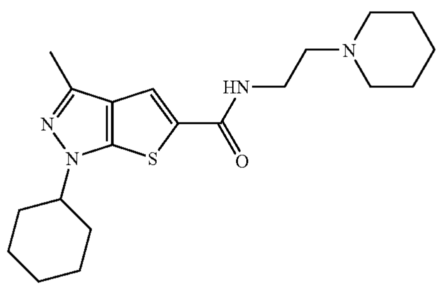 | colorless solid 122-123 | CDCl₃ 1.22-1.53(5 H, m), 1.59-1.66(4 H, m), 1.71-1.97(5 H, m), 2.14-2.22(2 H, m), 2.40-2.48(4 H, m), 2.45(3 H, s), 2.52-2.56(2 H, m), 3.47-3.54(2 H, m), 4.17(1 H, tt, J = 3.8 and 11.8 Hz), 6.73-6.79(1 H, m), 7.31(1 H, s) | 375 |
| 356 | 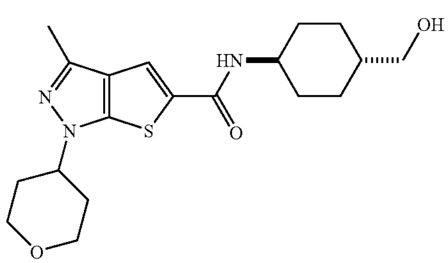 | colorless solid 175-178 | DMSO-d₆ 0.90-1.03(2 H, m), 1.23-1.37(3 H, m), 1.75-2.06(8 H, m), 2.36(3 H, s), 3.20-3.26(2 H, m), 3.46-3.54(2 H, m), 3.59-3.72(1 H, m), 3.94-4.01(2 H, m), 4.38-4.52(2 H, m), 7.81(1 H, s), 8.23-8.28(1 H, m) | 378 |

TABLE 118

| Example No. | Chemical Structure | properties m.p.(° C.) (recryst. solvent) |
|---|---|---|
| 357 | 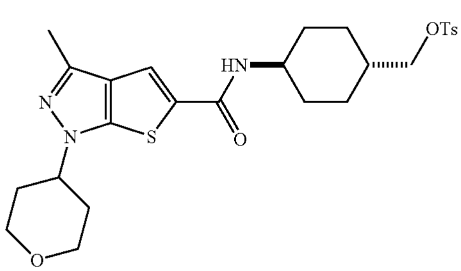 | colorless solid 193-195 |

TABLE 118-continued
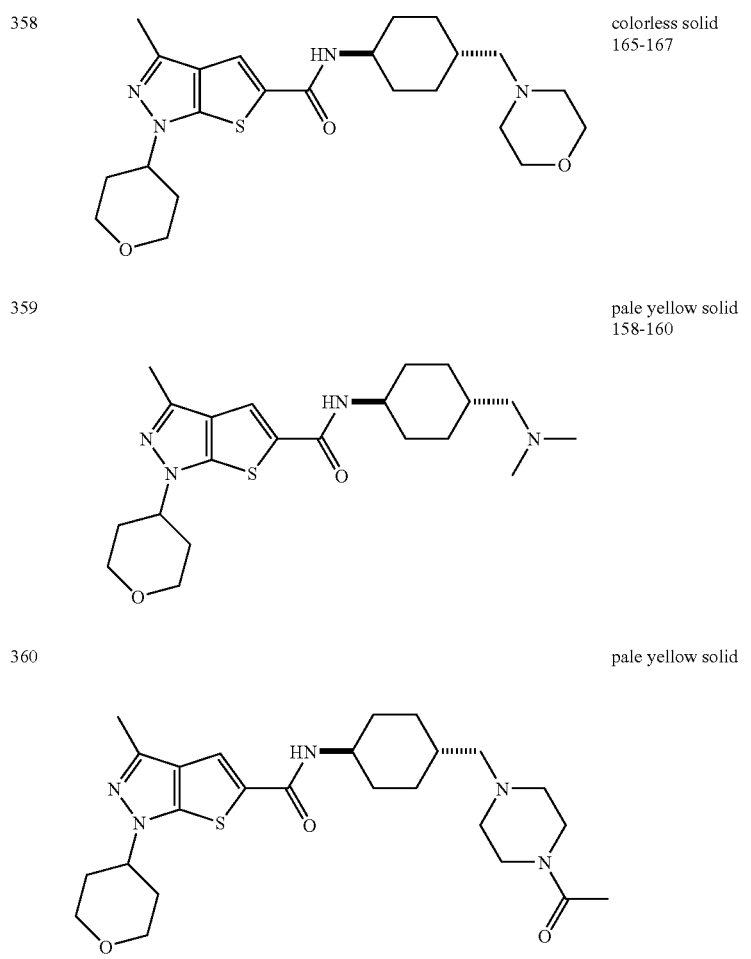
| 358 | | colorless solid 165-167 |
| 359 | | pale yellow solid 158-160 |
| 360 | | pale yellow solid |
| Example No. | ¹H-NMR | MS(FAB) (M + 1)⁺ |
|---|---|---|
| 357 | CDCl₃ 1.02-1.27(4 H, m), 1.62-1.87(3 H, m), 2.06-2.25(6 H, m), 2.43(3 H, s), 2.46(3 H, s), 3.55(2 H, dt, J = 2.5 and 11.7 Hz), 3.80-3.92(3 H, m), 4.10-4.16(2 H, m), 4.36-4.46(1 H, m), 5.67-5.72(1 H, m), 7.30(1 H, s), 7.34-7.39(2 H, m), 7.78-7.93(2 H, m) | 532 |
| 358 | CDCl₃ 1.01-1.28(4 H, m), 1.43-1.56(1 H, m), 1.84-1.95(2 H, m), 2.08-2.25(8 H, m), 2.38-2.42(4 H, m), 2.44(3 H, s), 3.55(2 H, dt, J = 2.4 and 11.8 Hz), 3.68-3.73(4 H, m), 3.85-3.95(1 H, m), 4.09-4.17(2 H, m), 4.35-4.46(1 H, m), 5.68-5.73(1 H, m), 7.31(1 H, s) | 447 |
| 359 | CDCl₃ 1.00-1.27(4 H, m), 1.36-1.50(1 H, m), 1.84-1.92(2 H, m), 2.06-2.17(8 H, m), 2.20(6 H, s), 2.44(3 H, s), 3.55(2 H, dt, J = 2.4 and 11.7 Hz), 3.83-3.98(1 H, m), 4.10-4.17(2 H, m), 4.36-4.47(1 H, m), 5.68-5.73(1 H, m), 7.31(1 H, s) | 405 |
| 360 | CDCl₃ 1.01-1.28(4 H, m), 1.42-1.55(1 H, m), 1.85-1.93(2 H, m), 2.08-2.25(8 H, m), 2.09(3 H, s), 2.33-2.42(4 H, m), 2.44(3 H, s), 3.43-3.48(2 H, m), 3.55(2 H, dt, J = 2.3 and 11.7 Hz), 3.59-3.63(2 H, m), 4.10-4.17(2 H, m), 4.37-4.47(1 H, m), 5.70-5.75(1 H, m), 7.32(1 H, s) | 488 |

TABLE 119

| Example No. | Chemical Structure | properties m.p.(° C.) (recryst. solvent) |
|---|---|---|
| 361 | 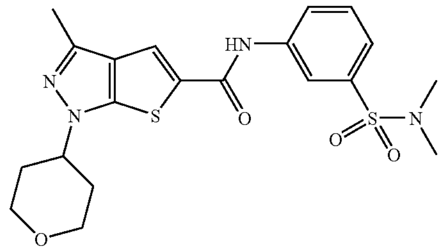 | colorless solid 224-225 |
| 362 | 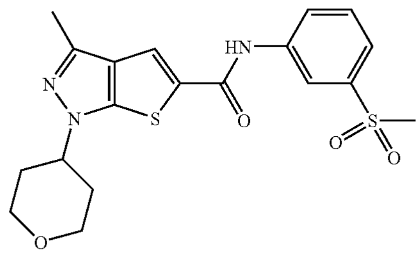 | colorless solid 226-227 |
| 363 | 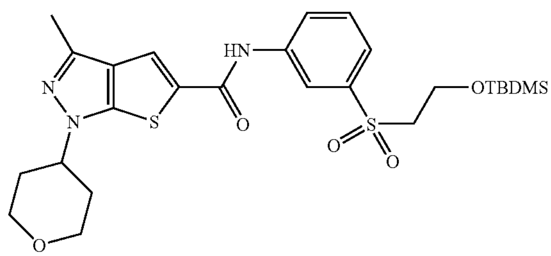 | colorless solid 181-182 |
| 364 | 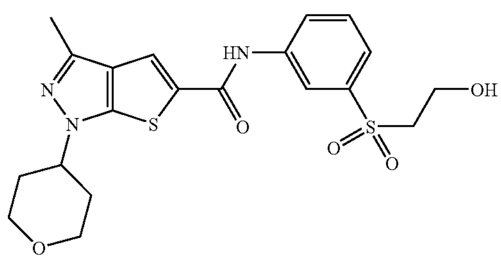 | colorless solid 229-232 |

| Example No. | $^1$H-NMR | MS(FAB) (M + 1)$^+$ |
|---|---|---|
| 361 | DMSO-d$_6$ 1.92-2.10(4 H, m), 2.42(3 H, s), 2.64(6 H, s), 3.51(2 H, dt, J = 2.4 and 11.5 Hz), 3.96-4.02(2 H, m), 4.50-4.60(1 H, m), 7.44-7.49(1 H, m), 7.62-7.67(1 H, m), 8.10-8.16(1 H, m), 8.17(1 H, s), 8.18-8.20(1 H, m), 10.57(1 H, brs) | 449 |
| 362 | DMSO-d$_6$ 1.91-2.10(4 H, m), 2.42(3 H, s), 3.22(3 H, s), 3.48-3.57(2 H, m), 3.96-4.03(2 H, m), 4.50-4.60(1 H, m), 7.64-7.68(2 H, m), 8.06-8.12(1 H, m), 8.14(1 H, s), 8.34(1 H, brs), 10.61(1 H, brs) | 420 |
| 363 | CDCl$_3$ −0.04(6 H, s), 0.77(9 H, s), 2.12-2.284 H, m), 2.50(3 H, s), 3.37-3.43(2 H, m), 3.57(2 H, dt, J = 2.5 and 11.7 Hz), 3.99-4.05(2 H, m), 4.12-4.18(2 H, m), 4.40-4.50(1 H, m), 7.55-7.61(1 H, m), 7.60(1 H, s), 7.67-7.71(1 H, m), 8.01-8.04(1 H, m), 8.09(1 H, br), 8.22-8.26(1 H, m) | 564 |
| 364 | DMSO-d$_6$ 1.92-2.09(4 H, m), 2.42(3 H, s), 3.43-3.48(2 H, m), 3.51(2 H, dt, J = 2.4 and 11.6 Hz), 3.66-3.74(2 H, m), 3.96-4.03(2 H, m), 4.49-4.60(1 H, m), 4.88-4.93(1 H, m), 7.59-7.67(2 H, m), 8.08-8.13(1 H, m), 8.14(1 H, s), 8.30-8.32(1 H, m), 10.61(1 H, brs) | 450 |

TABLE 120

| Example No. | Chemical Structure | properties m.p.(° C.) (recryst. solvent) |
|---|---|---|
| 365 | [3-methyl-1-cyclohexyl-thieno[2,3-c]pyrazole-5-carboxamide N-(3-fluoro-4-(4-hydroxypiperidin-1-yl)phenyl)] 2MsOH | colorless solid 201-206 (EtOH/(iso-Pr)₂O) |
| 366 | [3-methyl-1-cyclohexyl-thieno[2,3-c]pyrazole-5-carboxamide N-(3-fluoro-4-(4-hydroxypiperidin-1-yl)phenyl)] 1pTsOH | colorless solid 211-213 (iso-PrOH) |
| 367 | [3-methyl-1-cyclohexyl-thieno[2,3-c]pyrazole-5-carboxamide N-(4-(4-hydroxypiperidin-1-yl)phenyl)] MsOH | colorless solid 223-228 (Et₂O/AcOEt) |
| 368 | [3-methyl-1-cyclohexyl-thieno[2,3-c]pyrazole-5-carboxamide N-(4-(4-hydroxypiperidin-1-yl)phenyl)] 1pTsOH | colorless solid 255(dec.) (EtOH/H₂O) |

| Example No. | ¹H-NMR | MS(FAB) (M + 1)⁺ |
|---|---|---|
| 365 | DMSO-d₆ 1.16-1.30(1 H, m), 1.36-1.51(2 H, m), 1.54-1.92(9 H, m), 2.02-2.10(2 H, m), 2.34(6 H, s), 2.40(3 H, s), 2.82-2.92(2 H, m), 3.25-3.33(2 H, m), 3.62-3.70(1 H, m), 4.10-4.25(1 H, m), 7.12-7.21(1 H, m), 7.39-7.45(1 H, m), 7.62-7.70(1 H, m), 8.03(1 H, s), 10.29(1 H, brs) | 457 |
| 366 | DMSO-d₆ 1.16-1.31(1 H, m), 1.36-1.91(11 H, m), 2.02-2.10(2 H, m), 2.29(3 H, s), 2.40(3 H, s), 2.77-2.87(2 H, m), 3.22-3.30(2 H, m), 3.58-3.67(1 H, m), 4.15-4.26(1 H, m), 7.08-7.18(3 H, m), 7.38-7.44(1 H, m), 7.45-7.50(2 H, m), 7.61-7.69(1 H, m), 8.03(1 H, s), 10.29(1 H, brs) | 457 |
| 367 | CD₃OD 1.26-1.41(1 H, m), 1.46-1.60(2 H, m), 1.73-2.07(7 H, m), 2.12-2.28(4 H, m), 2.46(3 H, s), 2.70(3 H, s), 3.53-3.66(2 H, br), 3.74-3.91(2 H, br), 4.02-4.14(1 H, br), 4.22(1 H, tt, J = 3.9 and 11.8 Hz), 7.60-7.66(2 H, m), 7.89-7.96(2 H, m), 7.91(1 H, s), 10.26(1 H, brs) | 439 |
| 368 | DMSO-d₆ 1.19-1.31(1 H, m), 1.39-1.52(2 H, m), 1.65-1.89(7 H, m), 1.96-2.13(4 H, m), 2.29(3 H, s), | 439 |

TABLE 120-continued 2.40(3 H, s), 3.22-3.95(4 H, m), 4.23(1 H, tt, J = 3.8 and 11.6 Hz), 7.11(2 H, d, J = 8.0 Hz), 7.35-7.66(1 H, br), 7.47(2 H, d, J = 8.0 Hz), 7.72-7.91(2 H, br), 8.07(1 H, brs), 10.38(1 H, brs)

TABLE 121

| Example No. | Chemical Structure | properties m.p.(° C.) (recryst. solvent) |
|---|---|---|
| 369 | 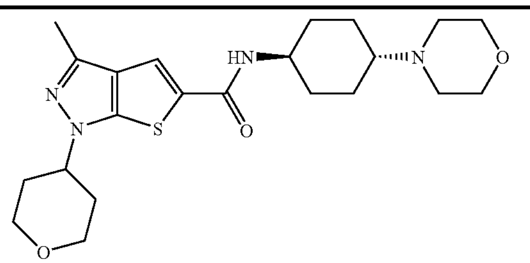 | colorless solid 226-227.5 (EtOH) |
| 370 | 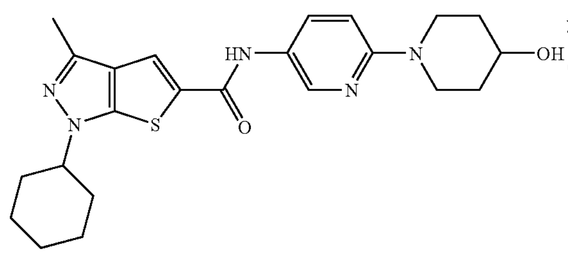 | yellow solid 189-190.5 (EtOH) |
| 371 | 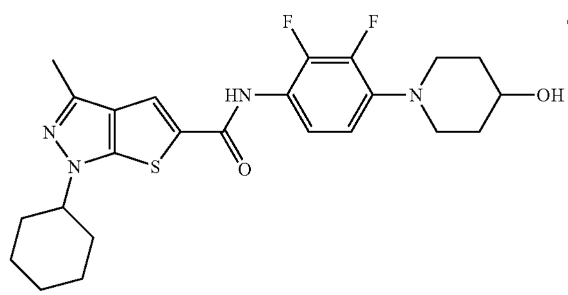 | colorless solid 191-193 |
| 372 | 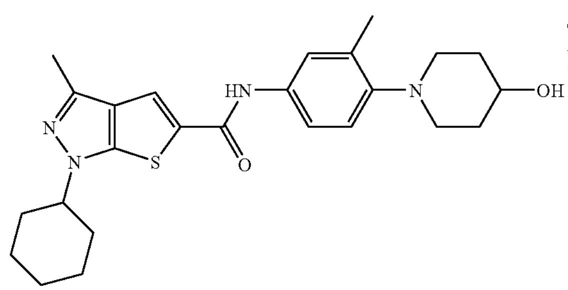 | colorless solid 232-233 (EtOH) |

| Example No. | ¹H-NMR | MS(FAB) (M + 1)⁺ |
|---|---|---|
| 369 | CDCl₃ 1.19-1.32(2 H, m), 1.36-1.48(2 H, m), 1.93-2.02(2 H, m), 2.07-2.28(7 H, m), 2.43(3 H, s), 2.53-2.60(4 H, m), 3.55(2 H, dt, J = 2.4 and 11.6 Hz), 3.70-3.77(4 H, m), 3.83-3.97(1 H, m), 4.10-4.18(2 H, m), 4.37-4.47(1 H, m), 5.70-5.77(1 H, m), 7.31(1 H, s) | 433 |
| 370 | CDCl₃ 1.21-1.33(1 H, m), 1.39-1.51(2 H, m), 1.53-2.03(10 H, m), 2.15-2.24(2 H, m), 2.44(3 H, s), 3.10-3.21(2 H, m), 3.88-3.96(1 H, m), 3.98-4.09(2 H, m), | 440 |

TABLE 121-continued

| | | | |
|---|---|---|---|
| | | 4.19(1 H, tt, J = 3.8 and 11.8 Hz), 6.69(1 H, d, J = 9.1 Hz), 7.49(1 H, s), 7.63(1 H, brs), 7.90(1 H, dd, J = 2.7 and 9.1 Hz), 8.19(1 H, d, J = 2.7 Hz) | |
| | 371 | CDCl$_3$ 1.22-1.37(1 H, m), 1.40-1.56(3 H, m), 1.71-2.10(9 H, m), 2.17-2.247(2 H, m), 2.47(3 H, s), 2.83-2.94(2 H, m), 3.31-3.41(2 H, m), 3.82-3.93(1 H, m), 4.19(1 H, tt, J = 3.8 and 11.8 Hz), 6.71-6.68(1 H, m), 7.48(1 H, s), 7.67(1 H, brs), 7.90-7.99(1 H, m) | 475 |
| | 372 | CDCl$_3$ 1.21-1.35(1 H, m), 1.39-1.52(3 H, m), 1.69-2.06(9 H, m), 2.13-2.23(2 H, m), 2.30(3 H, s), 2.45(3 H, s), 2.67-2.76(2 H, m), 3.02-3.11(2 H, m), 3.79-3.89(1 H, m), 4.19(1 H, tt, J = 3.8 and 11.8 Hz), 7.00(1 H, d, J = 8.4 Hz), 7.32-7.41(2 H, m), 7.44(1 H, s), 7.56(1 H, brs) | 453 |

TABLE 122

| Example No. | Chemical Structure | properties m.p.(° C.) (recryst. solvent) |
|---|---|---|
| 373 | 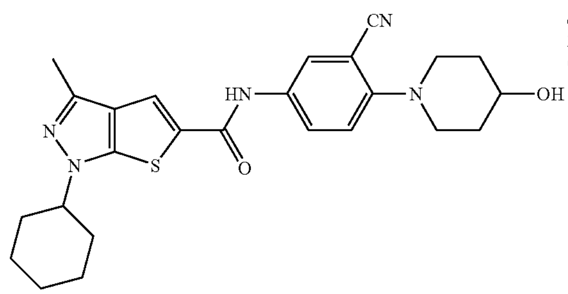 | colorless solid 255-256.5 (EtOH) |
| 374 | 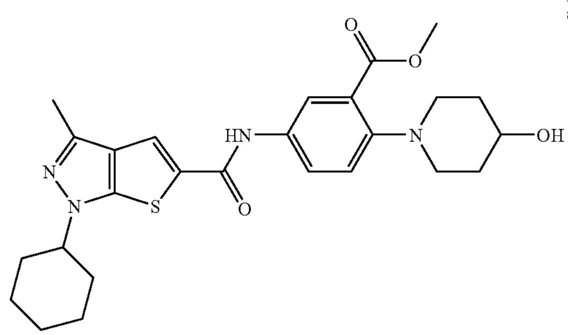 | pale yellow foamy solid |
| 375 | 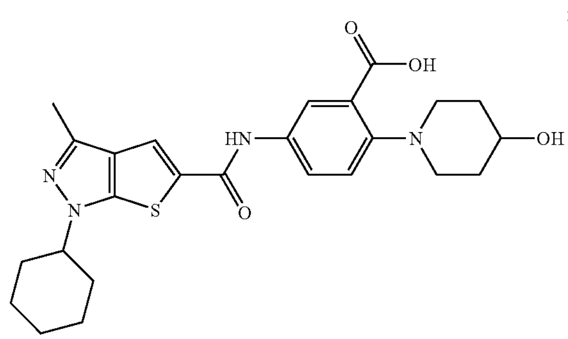 | colorless solid >300 |

TABLE 122-continued

| 376 | [chemical structure] | yellow solid 121-123 |

| Example No. | ¹H-NMR | MS(FAB) (M + 1)⁺ |
|---|---|---|
| 373 | CDCl₃ 1.21-1.35(1 H, m), 1.39-1.57(3 H, m), 1.71-1.98(7 H, m), 2.03-2.12(2 H, m), 2.16-2.23(2 H, m), 2.45(3 H, s), 2.94-3.03(2 H, m), 3.39-3.48(2 H, m), 3.88-3.97(1 H, m), 4.19(1 H, tt, J = 3.8 and 11.8 Hz), 7.02(1 H, d, J = 8.9 Hz), 7.50(1 H, s), 7.70-7.82(3 H, m) | 464 |
| 374 | CDCl₃ 1.22-1.34(1 H, m), 1.38-1.57(3 H, m), 1.69-2.08(9 H, m), 2.14-2.23(2 H, m), 2.45(3 H, s), 2.80-2.90(2 H, m), 3.21-3.31(2 H, m), 3.80-3.88(1 H, m), 3.89(3 H, s), 4.19(1 H, tt, J = 3.8 and 11.8 Hz), 7.05(1 H, d, J = 8.8 Hz), 7.48(1 H, s), 7.71(1 H, brs), 7.77(1 H, dd, J = 2.6 and 8.8 Hz) 7.84(1 H, d, J = 2.6 Hz) | 497 |
| 375 | DMSO-d₆ 1.19-1.32(1 H, m), 1.39-1.51(2 H, m), 1.59-1.88(7 H, m), 1.93-2.02(2 H, m), 2.03-2.11(2 H, m), 2.40(3 H, s), 2.98-3.09(2 H, m), 3.12-3.21(2 H, m), 3.76-3.85(1 H, m), 4.23(1 H, tt, J = 3.8 and 11.5 Hz), 4.92(1 H, d, J = 4.2 Hz), 7.70(1 H, d, J = 8.8 Hz), 8.08-8.14(2 H, m), 8.35(1 H, d, J = 2.6 Hz), 10.47(1 H, brs). | 483 |
| 376 | DMSO-d₆ 1.30-1.42(2 H, m), 1.73-1.83(2 H, m), 1.91-2.09(4 H, m), 2.41(3 H, s), 2.99-3.10(2 H, m), 3.51(2 H, dt, J = 2.3 and 11.6 Hz), 3.63-3.72(1 H, m), 3.91-4.03(4 H, m), 4.44-4.54(1 H, m), 4.67(1 H, d, J = 4.2 Hz), 6.85(1 H, d, J = 9.2 Hz), 7.82(1 H, dd, J = 2.7 and 9.2 Hz), 8.37(1 H, d, J = 2.7 Hz), 10.13(1 H, brs). brs). | 442 |

TABLE 123

| Example No. | Chemical Structure | propeties m.p.(° C.) (recryst. solvent) |
|---|---|---|
| 377 | [chemical structure] | colorless solid 194-195 (EtOH) |
| 378 | [chemical structure] | colorless solid 268-269.5 (EtOH) |

TABLE 123-continued

| 379 | 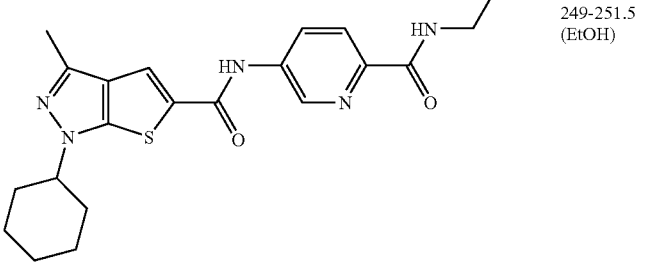 | —OH colorless solid 249-251.5 (EtOH) |

| 380 | 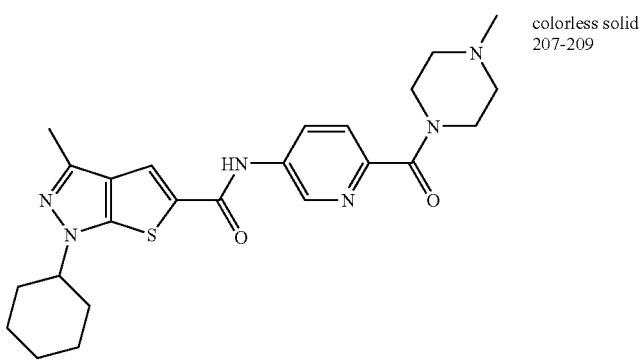 | colorless solid 207-209 |

| Example No. | ¹H-NMR | MS(FAB) $(M + 1)^+$ |
|---|---|---|
| 377 | CDCl₃ 1.53-1.69(4 H, m), 1.74-1.82(2 H, m), 1.97-2.25(6 H, m), 2.31-2.40(2 H, m), 2.44(3 H, s), 2.50-2.59(1 H, m), 2.94-3.03(2 H, m), 3.41(2 H, dt, J = 1.7 and 11.8 Hz), 3.55(2 H, dt, J = 2.4 and 11.6 Hz), 3.92-4.08(3 H, m), 4.10-4.18(2 H, m), 4.36-4.47(1 H, m), 5.82-5.90(1 H, m), 7.33(1 H, s) | 433 |
| 378 | DMSO-d₆ 1.19-1.50(5 H, m), 1.62-1.88(7 H, m), 2.03-2.12(2 H, m), 2.41(3 H, s), 3.14-3.28(2 H, m), 3.61-3.80(2 H, m), 3.99-4.09(1 H, m), 4.24(1 H, tt, J = 3.8 and 11.5 Hz), 4.77(1 H, d, J = 4.2 Hz), 7.58(1 H, d, J = 8.6 Hz), 8.10(1 H, s), 8.24(1 H, dd, J = 2.4 and 8.6 Hz), 8.88(1 H, d, J = 2.4 Hz), 10.58(1 H, brs). | 468 |
| 379 | DMSO-d₆ 1.19-1.32(1 H, m), 1.39-1.51(2 H, m), 1.63-1.89(5 H, m), 2.03-2.12(2 H, m), 2.41(3 H, s), 3.33-3.41(2 H, m), 3.50-3.58(2 H, m), 4.23(1 H, tt, J = 3.8 and 11.4 Hz), 4.79(1 H, d, J = 5.4 Hz), 8.04(1 H, d, J = 8.6 Hz), 8.12(1 H, s), 8.34(1 H, dd, J = 2.4 and 8.6 Hz), 8.55-8.63(1 H, m), 8.95(1 H, d, J = 2.4 Hz), 10.67(1 H, brs). | 428 |
| 380 | DMSO-d₆ 1.19-1.32(1 H, m), 1.39-1.51(2 H, m), 1.63-1.89(5 H, m), 2.03-2.12(2 H, m), 2.19(3 H, s), 2.24-2.40(4 H, m), 2.41(3 H, s), 3.42-3.51(2 H, m), 3.60-3.69(2 H, m), 4.24(1 H, tt, J = 3.9 and 11.5 Hz), 7.61(1 H, d, J = 8.6 Hz), 8.10(1 H, s), 8.25(1 H, dd, J = 2.5 and 8.6 Hz), 8.89(1 H, d, J = 2.5 Hz), 10.60(1 H, brs). | 467 |

TABLE 124

| Example No. | Chemical Structure | properties m.p. (° C.) (recryst. solvent) | ¹H-NMR | MS (FAB) (M + 1)⁺ |
|---|---|---|---|---|
| 381 | 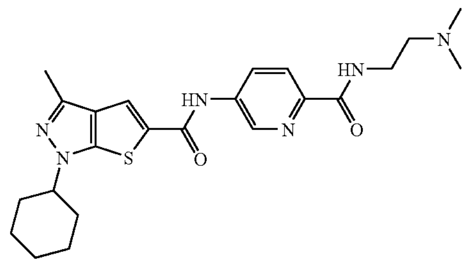 | colorless solid 214-215.5 | CDCl₃ 1.22-1.33(1 H, m), 1.38-1.51(2 H, m), 1.71-1.98(5 H, m), 2.15-23(2 H, m), 2.29(6 H, s), 2.43(3 H, s), 2.53(2 H, t, J = 6.2 Hz), 3.52-3.60(2 H, m), 4.19(1 H, tt, J = 3.8 and 11.8 Hz), 7.62(1 H, s), 8.12-8.34(4 H, m), 8.78-8.82(1 H, m) | 455 |
| 382 | 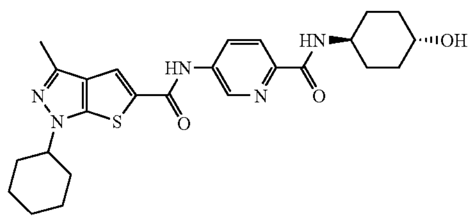 | colorless solid 252-254 | DMSO-d₆ 1.18-1.32(3 H, m), 1.39-1.53(4 H, m), 1.64-1.89(9 H, m), 2.02-2.12(2 H, m), 2.41(3 H, s), 3.36-3.46(1 H, m), 3.68-3.80(1 H, m), 4.24(1 H, tt, J = 3.8 and 11.5 Hz), 4.55(1 H, d, J = 4.4 Hz), 8.03(1 H, d, J = 8.6 Hz), 8.12(1 H, s), 8.30-8.38(2 H, m), 8.94(1 H, d, J = 2.4 Hz), 10.67(1 H, brs). | 482 |
| 383 | 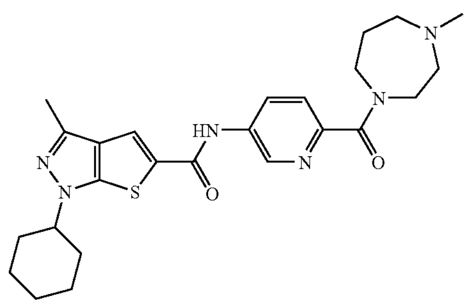 | colorless solid 197.5-199.5 | CDCl₃ 1.22-1.35(1 H, m), 1.39-1.51(2 H, m), 1.71-2.08(7 H, m), 2.13-2.25(2 H, m), 2.36(1.5 H, s), 2.40(1.5 H, s), 2.47(3 H, s), 2.56-2.2.70(3 H, m), 2.73-2.83(1 H, m), 3.52-3.68(2 H, m), 3.82-3.91(2 H, m), 4.20(1 H, tt, J = 3.8 and 11.8 Hz), 7.31-7.38(1 H, m), 7.76-7.87 (1 H, m), 7.95(1 H, s),8.48-8.58(1 H, m), 9.33(1 H, brs) | 481 |
| 384 | 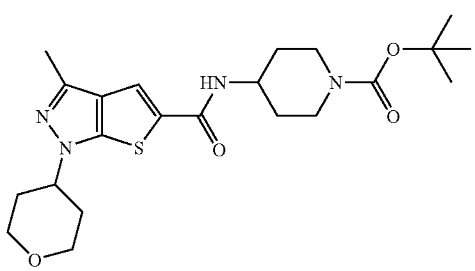 | colorless solid 175-180 | CDCl₃ 1.33-1.54(2 H, m), 1.45(9 H, s), 1.98-2.06(2 H, m), 2.09-2.25(4 H, m), 2.44(3 H, s), 2.83-2.97 (2 H, m), 3.51-3.61(2 H, m), 4.02-4.19(5 H, m), 4.35-4.48(1 H, m), 5.82-5.89(1 H, m), 7.35(1 H, s) | 449 |

TABLE 125

| Example No. | Chemical Structure | properties m.p. (° C.) (recryst. solvent) | ¹H-NMR | MS (FAB) (M + 1)⁺ |
|---|---|---|---|---|
| 385 | 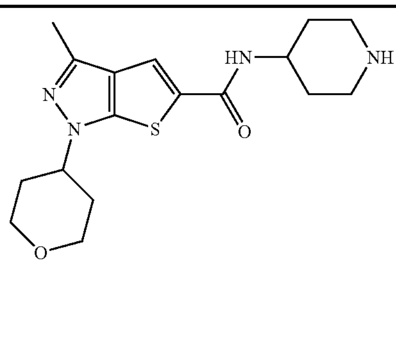 | colorless solid 205-214 | CDCl₃ 1.37-1.9(2 H, m), 2.00-2.25(6 H, m), 2.44(3 H, s), 2.70-2.80(2 H, m), 3.08-3.17(2 H, m), 3.55(2 H, dt, J = 2.4 and 11.6 Hz), 4.00-4.19(3 H, m), 4.36-4.48(1 H, m), 5.81-5.90(1 H, m), 7.34(1 H, s) | 349 |

TABLE 125-continued

| Example No. | Chemical Structure | propeties m.p. (° C.) (recryst. solvent) | ¹H-NMR | MS (FAB) (M + 1)⁺ |
|---|---|---|---|---|
| 386 | 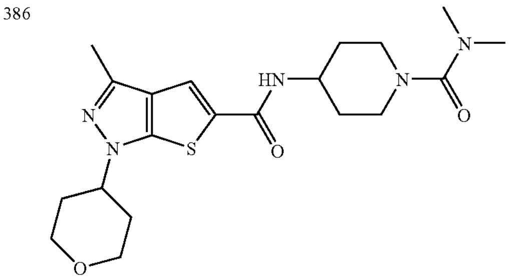 | colorless solid 239-240 (EtOH) | CDCl₃ 1.46-1.59(2 H, m), 2.00-2.25(6 H, m), 2.44(3 H, s), 2.83(6 H, s), 2.89-2.99(2 H, m), 3.55(2 H, dt, J = 2.4 and 11.6 Hz), 3.64-3.73(2 H, m), 4.08-4.19(3 H, m), 4.37-4.47(1 H, m), 5.91-5.98(1 H, m), 7.35(1 H, s) | 420 |
| 387 | 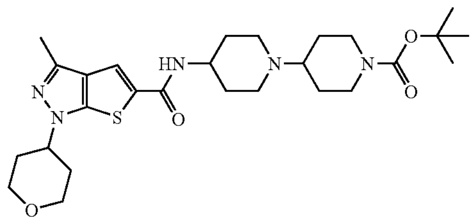 | colorless solid 214.5-217 | CDCl₃ 1.37-1.60(4 H, m), 1.46(9 H, s), 1.73-1.85(2 H. m), 2.01-2.25(6 H, m), 2.32-2.51(3 H, m), 2.44(3 H, s), 2.63-2.76(2 H, m), 2.89-2.97(2 H, m), 3.55(2 H, dt, J = 2.4 and 11.6 Hz), 3.90-4.01(1 H, m), 4.08-4.22(4 H, m), 4.36-4.48(1 H, m), 5.79-5.86(1 H, m), 7.33(1 H, s) | 532 |
| 388 | 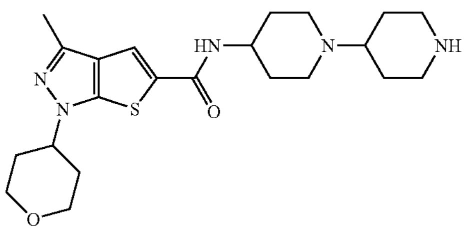 | colorless solid 180-182.5 | CDCl₃ 1.36-1.59(4 H, m), 1.78-1.88(2 H, m), 2.00-2.25(6 H, m), 2.31-2.50(3 H, m), 2.44(3 H, s), 2.55-2.65(2 H, m), 2.89-2.99(2 H, m), 3.11-3.20(2 H, m), 3.55(2 H, dt, J = 2.4 and 11.6 Hz), 3.90-4.01(1 H, m), 4.09-4.19(2 H, m), 4.37-4.48(1 H, m), 5.73-5.81(1 H, m), 7.32(1 H, s) | 432 |

TABLE 126

| Example No. | Chemical Structure | propeties m.p. (° C.) (recryst. solvent) | ¹H-NMR | MS (FAB) (M + 1)⁺ |
|---|---|---|---|---|
| 389 | 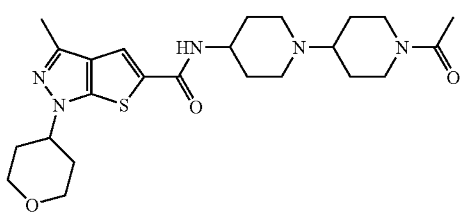 | colorless solid 235.5-237 (EtOH) | CDCl₃ 1.38-1.58(4 H, m), 1.80-1.91(2 H. m), 2.01-2.25(6 H, m), 2.09(3 H, s), 2.30-2.40(2 H, m), 2.44(3 H, s), 2.47-2.60(2 H, m), 2.87-2.94(2 H, m), 2.99-3.09(2 H, m), 3.55(2 H, dt, J = 2.4 and 11.6 Hz), 3.81-4.00(2 H, m), 4.09-4.18(2 H, m), 4.35-4.46(1 H, m), 4.62-4.70(1 H, m), 5.75-5.81(1 H, m), 7.33(1 H, s) | 474 |
| 390 | 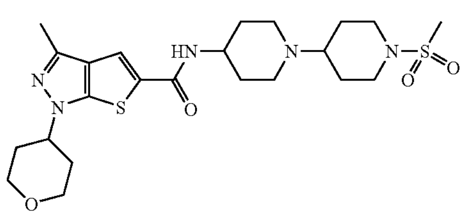 | colorless solid 273-275.5 | CDCl₃ 1.46-1.58(2 H, m), 1.60-1.72(2 H, m), 1.88-1.96(2 H. m), 2.02-2.24(6 H, m), 2.32-2.49(3 H, m), 2.44(3 H, s), 2.64-2.74(2 H, m), 2.78(3 H, s), 2.88-2.96(2 H, m), 3.55(2 H, dt, J = 2.4 and 11.6 Hz), 3.81-4.01(3 H, m), 4.10-4.18(2 H, m), 4.38-4.48(1 H, m), 5.73-5.80(1 H, m), 7.33(1 H, s) | 510 |

TABLE 126-continued

| Example No. | Chemical Structure | propeties m.p. (° C.) (recryst. solvent) | ¹H-NMR | MS (FAB) (M + 1)⁺ |
|---|---|---|---|---|
| 391 | 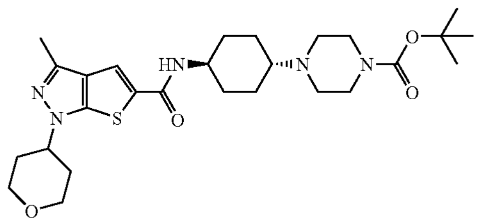 | colorless solid 141-145 | CDCl₃ 1.20-1.32(2 H, m), 1.38-1.52(2 H, m), 1.46(9 H, s), 1.89-1.98(2 H. m), 2.08-2.24(6 H, m), 2.28-2.38(1 H, m), 2.43(3 H, s), 2.49-2.55(4 H, m), 3.39-3.47(4 H, m), 3.55(2 H, dt, J = 2.4 and 11.6 Hz), 3.82-3.93(1 H, m), 4.09-4.16(2 H, m), 4.37-4.47(1 H, m), 5.71-5.78(1 H, m), 7.31(1 H, s) | 532 |
| 392 | 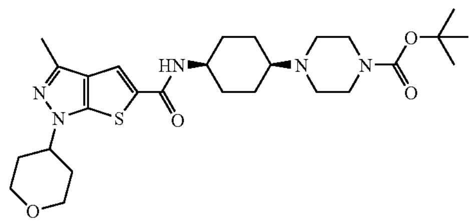 | colorless solid 209-210.5 | CDCl₃ 1.47(9 H, s), 1.54-1.80(6 H, m), 1.83-1.92(2 H, m), 2.09-2.28(5 H, m), 2.45(3 H, s), 2.48-2.56(4 H, m), 3.41-3.49(4 H, m), 3.56(2 H, dt, J = 2.4 and 11.6 Hz), 4.10-4.22(3 H, m), 4.37-4.48(1 H, m), 5.93-6.00(1 H, m), 7.33(1 H, s) | 532 |

TABLE 127

| Example No. | Chemical Structure | propeties m.p. (° C.) (recryst. solvent) | ¹H-NMR | MS (FAB) (M + 1)⁺ |
|---|---|---|---|---|
| 393 | 2HCl | colorless solid 270 (dec.) | DMSO-d₆ 1.31-1.48(2 H, m), 1.55-1.71(2 H, m), 1.88-2.08(6 H, m), 2.11-2.20(2 H, m), 2.36(3 H, s), 3.42-3.80(10 H, m), 3.93-4.00(2 H, m), 4.41-4.51(1 H, m), 7.84(1 H, s), 8.35-8.40(1 H, m), 9.40-9.74(2 H, m), 11.79-11.91(1 H, m) | 432 (free) |
| 394 | 2HCl | colorless solid 209-220 | DMSO-d₆ 1.56-1.69(2 H, m), 1.85-2.07(10 H, m), 2.38(3 H, s), 3.29-3.68(11 H, m), 3.92-4.09(3 H, m), 4.42-4.53(1 H, m), 8.04(1 H, s), 8.07-8.11(1 H, m), 9.37-10.00(2 H, m), 11.69-11.81(1 H, m) | 432 (free) |
| 395 | 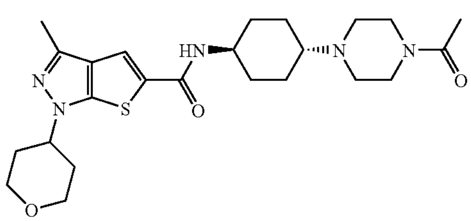 | colorless solid 255-256 (EtOH) | CDCl₃ 1.20-1.32(2 H, m), 1.36-1.49(2 H, m), 1.89-1.98(2 H, m), 2.07-2.24(6 H, m), 2.09(3 H, s), 2.28-2.40(1 H, m), 2.43(3 H, s), 2.50-2.60(4 H, m), 3.41-3.49(2 H, m), 3.55(2 H, dt, J = 2.4 and 11.6 Hz), 3.59-3.66(2 H, m), 3.82-3.95(1 H, m), 4.09-4.17(2 H, m), 4.35-4.47(1 H, m), 5.22-5.29(1 H, m), 7.32(1 H, s) | 474 |

TABLE 127-continued

| Example No. | Chemical Structure | propeties m.p. (° C.) (recryst. solvent) | ¹H-NMR | MS (FAB) (M + 1)⁺ |
|---|---|---|---|---|
| 396 | 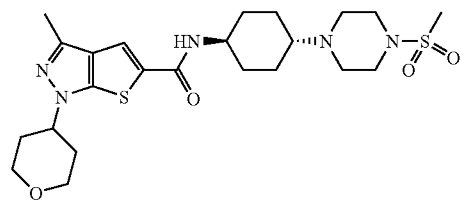 | colorless 245-246.5 (EtOH) | CDCl₃ 1.20-1.32(2 H, m), 1.37-1.49(2 H, m), 1.89-1.99(2 H. m), 2.08-2.25(6 H, m), 2.30-2.40(1 H, m), 2.43(3 H, s), 2.63-2.73(4 H, m), 2.77(3 H, s), 3.19-3.31(4 H, m), 3.55(2 H, dt, J = 2.4 and 11.6 Hz), 3.82-3.95(1 H, m), 4.09-4.19(2 H, m), 4.37-4.47(1 H, m), 5.69-5.78(1 H, m), 7.32(1 H, s) | 510 |

TABLE 128

| Example No. | Chemical Structure | propeties m.p. (° C.) (recryst. solvent) | ¹H-NMR | MS (FAB) (M + 1)⁺ |
|---|---|---|---|---|
| 397 | 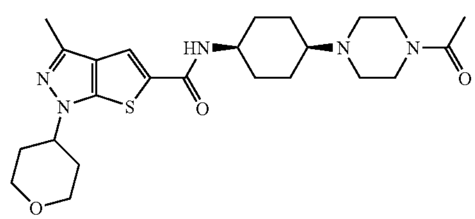 | colorless solid 226.5-227.5 (EtOH) | CDCl₃ 1.58-1.79(6 H, m), 1.81-1.92(2 H, m), 2.08-2.29(5 H. m), 2.09(3 H, s), 2.45(3 H, s), 2.48-2.60(4 H, m), 3.43-3.51(2 H, m), 3.56(2 H, dt, J = 2.4 and 11.6 Hz), 3.60-3.69(2 H, m), 4.09-4.22(3 H, m), 4.38-4.48(1 H, m), 5.90-5.99(1 H, m), 7.33(1 H, s) | 474 |
| 398 | 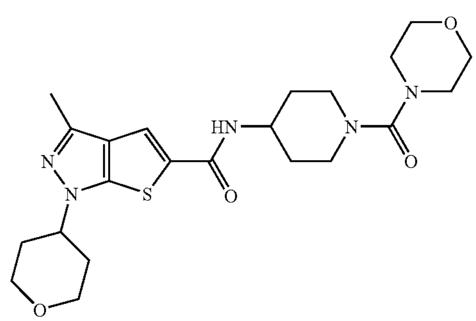 | colorless solid 198-199 (EtOH) | CDCl₃ 1.43-1.57(2 H, m), 2.00-2.25(6 H. m), 2.44(3 H, s), 2.90-3.01(2 H, m), 3.24-3.31(4 H, m), 3.55(2 H, dt, J = 2.5 and 11.6 Hz), 3.65-3.78(6 H, m), 4.08-4.20(3 H, m), 4.36-4.48(1 H, m), 5.80-5.87(1 H, m), 7.33(1 H, s) | 462 |
| 399 | 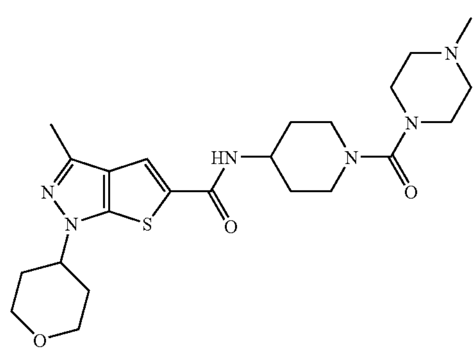 | colorless solid 211.5-213 (AcOEt) | CDCl₃ 1.431.59(2 H, m), 2.00-1.99-1.27(6 H. m), 2.30(3 H, s), 2.36-2.42(4 H, m), 2.44(3 H, s), 2.90-3.01(2 H, m), 3.25-3.34(4 H, m), 3.55(2 H, dt, J = 2.4 and 11.6 Hz), 3.67-3.78(2 H, m), 4.08-4.20(3 H, m), 4.36-4.47(1 H, m), 5.98-6.06(1 H, m), 7.36(1 H, s) | 475 |

TABLE 128-continued

| Example No. | Chemical Structure | propeties m.p. (° C.) (recryst. solvent) | ¹H-NMR | MS (FAB) (M + 1)⁺ |
|---|---|---|---|---|
| 400 | 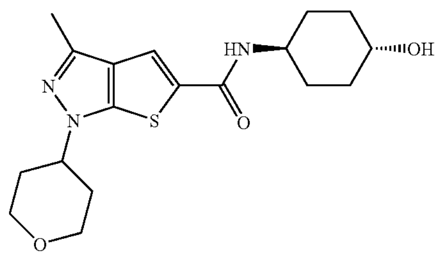 | pale reddish brown solid 199-204 | CDCl₃ 1.23-1.39(2 H, m), 1.41-1.53(3 H, m), 2.00-2.24(8 H, m), 2.43(3 H, s), 3.55(2 H, dt, J = 2.4 and 11.6 Hz), 3.60-3.71(1 H, m), 3.89-4.00(1 H, m), 4.09-4.17(2 H, m), 4.36-4.47(1 H, m), 5.69-5.75(1 H, m), 7.31(1 H, s) | 364 |

TABLE 129

| Example No. | Chemical Structure | propeties m.p. (° C.) (recryst. solvent) | ¹H-NMR | MS (FAB) (M + 1)⁺ |
|---|---|---|---|---|
| 401 | 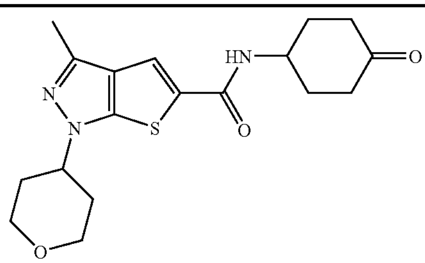 | colorless solid 177-178.5 | CDCl₃ 1.71-1.83(2 H, m), 2.09-2.25(4 H, m), 2.32-2.41(2 H, m), 2.44(3 H, s), 2.47-2.59(4 H, m), 3.56(2 H, dt, J = 2.5 and 11.6 Hz), 4.09-4.18(2 H, m), 4.38-4.50(2 H, m), 5.89-5.96(1 H, m), 7.37(1 H, s) | 362 |
| 402 | 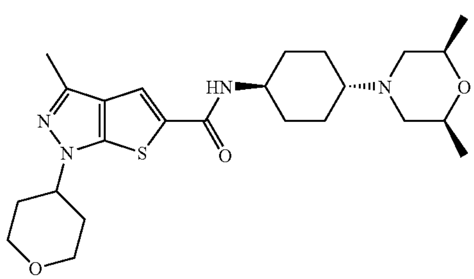 | colorless solid 199-200 (iso-PrOH) | CDCl₃ 1.17(6 H, d, J = 6.3 Hz), 1.19-1.31(2 H, m), 1.36-1.49(2 H, m), 1.90-2.00(4 H, m), 2.08-2.28(7 H, m), 2.43(3 H, s), 2.70-2.78(2 H, m), 3.55(2 H, dt, J = 2.4 and 11.7 Hz), 3.60-3.70(2 H, m), 3.82-3.95(1 H, m), 4.09-4.17(2 H, m), 4.35-4.46(1 H, m), 5.66-5.72(1 H, m), 7.31(1 H, s) | 461 |
| 403 | 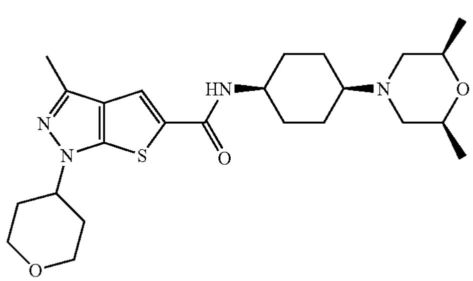 | colorless solid 202-208 | CDCl₃ 1.19(6 H, d, J = 6.2 Hz), 1.56-1.92(10 H, m), 2.09-2.27(5 H, m), 2.45(3 H, s), 2.83-2.90(2 H, m), 3.56(2 H, dt, J = 2.4 and 11.6 Hz), 3.61-3.71(2 H, m), 4.09-4.23(3 H, m), 4.37-4.48(1 H, m), 5.91-6.00(1 H, m), 7.33(1 H, s) | 461 |
| 404 | 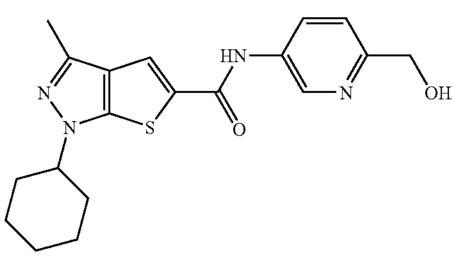 | colorless solid 170.5-172 (AcOEt) | CDCl₃ 1.21-1.35(1 H, m), 1.39-1.52(2 H, m), 1.71-1.99(5 H, m), 2.14-2.25(2 H, m), 2.45(3 H, s), 4.19(1 H, tt, J = 3.8 and 11.8 Hz), 4.75(2 H, s), 7.27(1 H, d, J = 8.5 Hz), 7.56(1 H, s), 7.88(1 H, brs), 8.19(1 H, dd, J = 2.4 and 8.5 Hz), 8.61(1 H, d, J = 2.4 Hz) | 371 |

TABLE 130

| Example No. | Chemical Structure | propeties m.p. (° C.) (recryst. solvent) | ¹H-NMR | MS (FAB) (M + 1)⁺ |
|---|---|---|---|---|
| 405 | 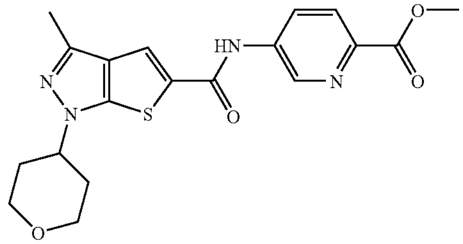 | colorless solid 232-233 | CDCl₃ 2.10-2.26(4 H, m), 2.45(3 H, s), 3.57(2 H, dt, J = 2.5 and 11.5 Hz), 4.00(3 H, s), 4.10-4.19(2 H, m), 4.39-4.49(1 H, m), 7.63(1 H, s), 8.17(1 H, d, J = 8.6 Hz), 8.20(1 H, brs), 8.53(1 H, dd, J = 2.7 and 8.6 Hz), 8.71(1 H, d, J = 2.7 Hz) | 401 |
| 406 | 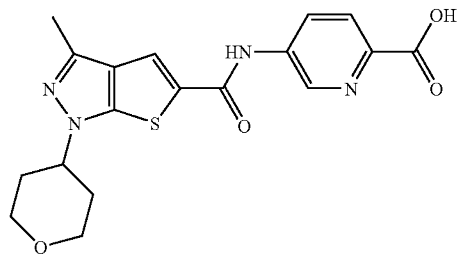 | colorless solid 262-264 | DMSO-d₆ 1.90-2.10(4 H, m), 2.43(3 H, s), 3.51(2 H, dt, J = 2.3 and 11.6 Hz), 3.39-4.03(2 H, m), 4.49-4.59(1 H, m), 8.07(1 H, d, J = 8.6 Hz), 8.16(1 H, s), 8.35(1 H, dd, J = 2.3 and 8.6 Hz), 9.00(1 H, d, J = 2.3 Hz), 10.74 (1 H, brs), | 387 |
| 407 | 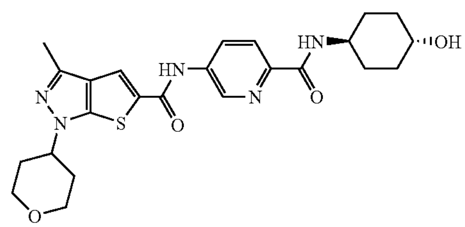 | colorless solid 258-259.5 (EtOH) | DMSO-d₆ 1.20-1.32(2 H, m), 1.40-1.54(2 H, m), 1.73-1.89(4 H, m), 1.91-2.10(4 H, m), 2.43(3 H, s), 3.34-3.45(1 H, m), 3.51(2 H, dt, J = 2.3 and 11.6 Hz), 3.69-3.80(1 H, m), 3.94-4.03(2 H, m), 4.49-4.58(2 H, m), 8.03(1 H, d, J = 8.7 Hz), 8.13(1 H, s), 8.29-8.38(1 H, m), 8.95(1 H, d, J = 2.4 Hz), 10.67(1 H, brs). | 484 |
| 408 | 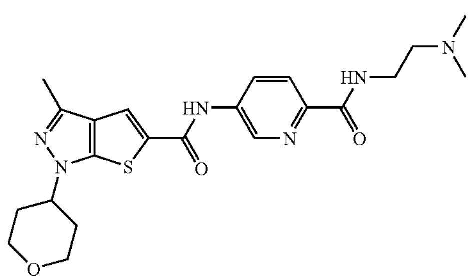 | colorless 185-186 (AcOEt) | CDCl₃ 2.10-2.27(4 H, m), 2.32(6 H, s), 2.45(3 H, s), 2.58(2 H, t, J = 6.2 Hz), 3.51-3.61(4 H, m), 4.10-4.19(2 H, m), 4.39-4.50(1 H, m), 7.66(1 H, s), 8.14-8.19(1 H, m), 8.20-8.31(3 H, m), 8.78(1 H, d, J = 2.3 Hz) | 457 |

TABLE 131

| Example No. | Chemical Structure | propeties m.p. (° C.) (recryst. solvent) | ¹H-NMR | MS (FAB) (M + 1)⁺ |
|---|---|---|---|---|
| 409 | 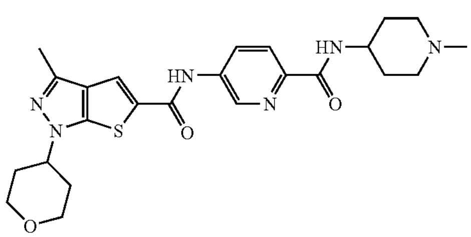 | colorless solid 240-242 (AcOEt) | CDCl₃ 1.60-1.73(2 H, m), 1.98-2.07(2 H, m), 2.10-2.29(6 H, m), 2.30(3 H, s), 2.46(3 H, s), 2.78-2.88(2 H, m), 3.57(2 H, dt, J = 2.5 and 11.6 Hz), 3.90-4.02(1 H, m), 4.10-4.19(2 H, m), 4.39-4.49(1 H, m), 7.62(1 H, s), 7.80-7.87(1 H, m), 8.12-8.29(3 H, m), 8.77(1 H, d, J = 2.3 Hz) | 483 |

TABLE 131-continued

| Example No. | Chemical Structure | propeties m.p. (° C.) (recryst. solvent) | ¹H-NMR | MS (FAB) (M + 1)⁺ |
|---|---|---|---|---|
| 410 | 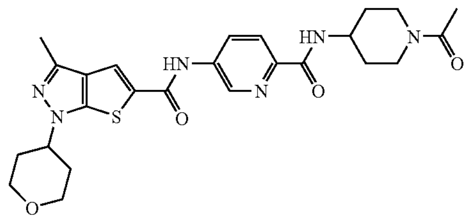 | colorlesds solid >300 | DMSO-d₆ 1.41-1.66(2 H, m), 1.71-1.87(2 H, m), 1.91-2.10(4 H, m), 2.01(3 H, s), 2.43(3 H, s), 2.60-2.71(1 H, m), 3.09-3.20(1 H, m), 3.51(2 H, dt, J = 2.3 and 11.6 Hz), 3.79-3.89(1 H, m), 3.96-4.10(3 H, m), 4.31-4.40(1 H, m), 4.47-4.59(1 H, m), 8.02-8.08(1 H, m), 8.14(1 H, s), 8.31-8.38(1 H, m), 8.52-8.59(1 H, m), 8.96(1 H, d, J = 2.4 Hz), 10.68(1 H, brs). | 511 |
| 411 | 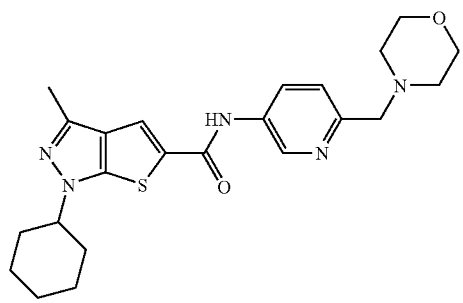 | pale brown foam | CDCl₃ 1.22-1.35(1 H, m), 1.39-1.51(2 H, m), 1.70-1.98(5 H, m), 2.14-2.25(2 H, m), 2.46(3 H, s), 2.49-2.57(4 H, m), 3.64(2 H, s), 3.70-3.79(4 H, m), 4.20(1 H, tt, J = 3.8 and 11.8 Hz), 7.42(1 H, d, J = 8.5 Hz), 7.53(1 H, s), 7.74(1 H, brs), 8.24(1 H, dd, J = 2.7 and 8.5 Hz), 8.58(1 H, d, J = 2.7 Hz) | 440 |
| 412 | 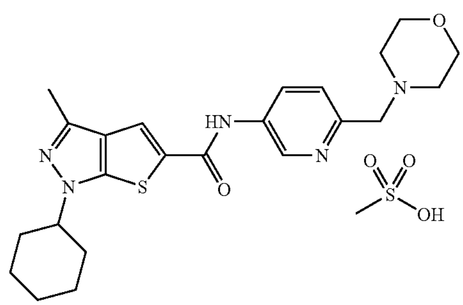 | pale brown solid 225.5-227.5 (iso-PrOH) | DMSO-d₆ 1.19-1.31(1 H, m), 1.39-1.52(2 H, m), 1.63-1.89(5 H, m), 2.03-2.13(2 H, m), 2.32(3 H, s), 2.41(3 H, s), 3.20-3.32(4 H, m), 3.79-3.91(4 H, m), 4.24(1 H, tt, J = 3.8 and 11.5 Hz), 4.41-4.51(2 H, m), 7.55(1 H, d, J = 8.5 Hz), 8.13(1 H, s), 8.26(1 H, dd, J = 2.4 and 8.5 Hz), 9.03(1 H, d, J = 2.4 Hz), 10.29(1 H, brs), 10.62(1 H, brs), | 440 (free) |

TABLE 132

| Example No. | Chemical Structure | propeties m.p. (° C.) (recryst. solvent) | ¹H-NMR | MS (FAB) (M + 1)⁺ |
|---|---|---|---|---|
| 413 | 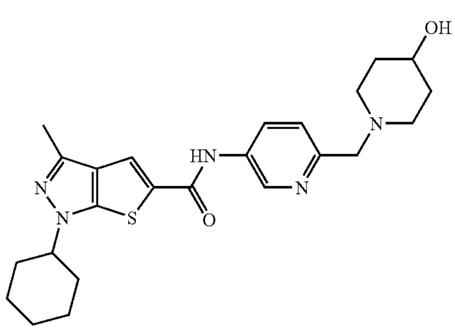 | pale yellow solid 214.5-216 (EtOH) | CDCl₃ 1.22-1.35(1 H, m), 1.39-1.51(3 H, m), 1.56-1.69(2 H, m), 1.71-1.99(7 H, m), 2.16-2.29(4 H, m), 2.46(3 H, s), 2.74-2.83(2 H, m), 3.63(2 H, s), 3.66-3.76(1 H, m), 4.20(1 H, tt, J = 3.8 and 11.8 Hz), 7.42(1 H, d, J = 8.5 Hz), 7.54(1 H, s), 7.79(1 H, brs), 8.22(1 H, dd, J = 2.5 and 8.5 Hz), 8.57(1 H, d, J = 2.5 Hz) | 454 |

TABLE 132-continued

| Example No. | Chemical Structure | propeties m.p. (° C.) (recryst. solvent) | ¹H-NMR | MS (FAB) (M + 1)⁺ |
|---|---|---|---|---|
| 414 | 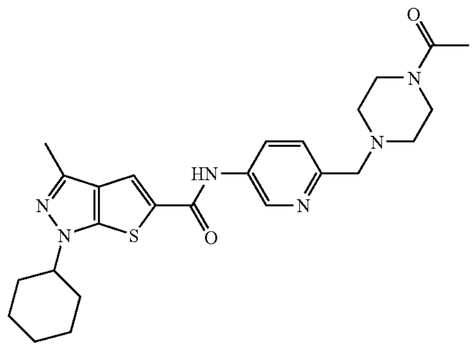 | colorless solid 229-230.5 (AcOEt) | CDCl₃ 1.22-1.35(1 H, m), 1.40-1.51(2 H, m), 1.71-1.99(5 H, m), 2.09(3 H, m), 2.16-2.22(2 H, m), 2.41-2.56(4 H, m), 2.46(3 H, s), 3.47-3.52(2 H, m), 3.61-3.69(2 H, m), 3.66(2 H, s), 4.20(1 H, tt, J = 3.8 and 11.8 Hz), 7.40(1 H, d, J = 8.5 Hz), 7.58(1 H, s), 8.00(1 H, brs), 8.25(1 H, dd,dd, J = 2.6 and 8.5 Hz), 8.60(1 H, d, J = 2.6 Hz) | 481 |
| 415 | 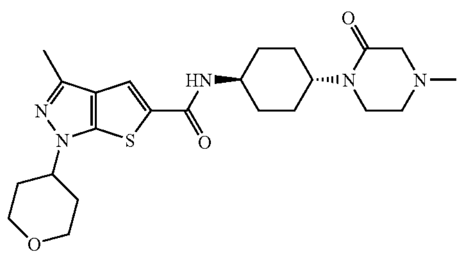 | colorless solid 266-268 (EtOH) | CDCl₃ 1.42-1.53(2 H, m), 1.58-1.80(4 H, m), 2.07-2.25(6 H. m), 2.33(3 H, s), 2.44(3 H, s), 2.61-2.69(2 H, m), 3.15(2 H, s), 3.23-3.31(2 H, m), 3.55(2 H, dt, J = 2.3 and 11.6 Hz), 3.88-4.00(1 H, m), 4.09-4.17(2 H, m), 4.37-4.46(1 H, m), 4.51-4.61(1 H, m), 6.48-6.56(1 H, m), 7.46(1 H, s) | 460 |
| 416 | 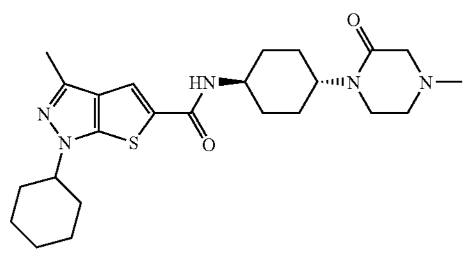 | colorless solid 263-265 (EtOH) | CDCl₃ 1.21-1.33(1 H, m), 1.37-1.52(4 H, m), 1.58-1.98(9 H, m), 2.11-2.21(4 H, m), 2.33(3 H, s), 2.44(3 H, s), 2.61-2.68(2 H, m), 3.14(2 H, s), 3.23-3.31(2 H, m), 3.88-3.99(1 H, m), 4.17(1 H, tt, J = 3.9 and 11.9 Hz), 4.49-4.60(1 H, m), 6.21-6.29(1 H, m), 7.41(1 H, s) | 458 |

TABLE 133

| Example No. | Chemical Structure | propeties m.p. (° C.) (recryst. solvent) | ¹H-NMR | MS (FAB) (M + 1)⁺ |
|---|---|---|---|---|
| 417 | 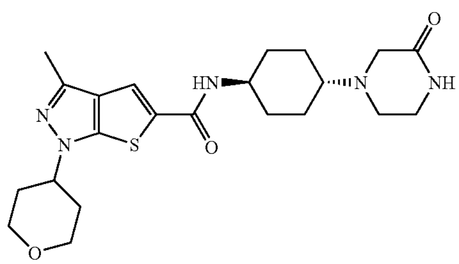 | colorless solid 229.5-232 | CDCl₃ 1.21-1.34(2 H, m), 1.38-1.50(2 H, m), 1.91-2.00(2 H, m), 2.09-2.26(6 H, m), 2.34-2.43(1 H, m), 2.44(3 H, s), 2.71-2.79(2 H, m), 3.29(2 H, s), 3.32-3.39(2 H, m), 3.55(2 H, dt, J = 2.4 and 11.6 Hz), 3.84-3.97(1 H, m), 4.09-4.18(2 H, m), 4.37-4.48(1 H, m), 5.71-5.79(1 H, m), 5.94(1 H, brs), 7.32(1 H, s) | 446 |

TABLE 133-continued

| Example No. | Chemical Structure | propeties m.p. (° C.) (recryst. solvent) | ¹H-NMR | MS (FAB) (M + 1)⁺ |
|---|---|---|---|---|
| 418 | 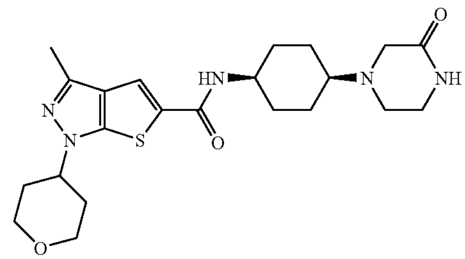 | colorless solid 109-118 | CDCl₃ 1.64-1.89(8 H, m), 2.09-2.26(4 H, m), 2.32-2.40(1 H, m), 2.45(3 H, s), 2.71-2.80(2 H, m), 3.26(2 H, s), 3.32-3.42(2 H, m), 3.56(2 H, dt, J = 2.4 and 11.7 Hz), 4.09-4.20(3 H, m), 4.37-4.49(1 H, m), 5.93-6.01(1 H, m), 6.14(1 H, brs), 7.56(1 H, s) | 446 |
| 419 | 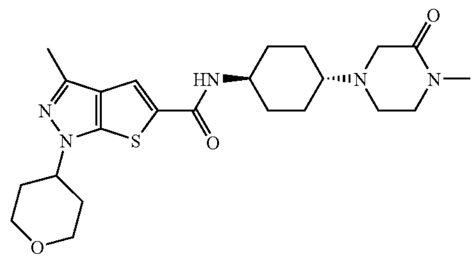 | colorless solid 242-244 (EtOH) | CDCl₃ 1.21-1.33(2 H, m), 1.36-1.49(2 H, m), 1.92-2.01(2 H, m), 2.08-2.25(6 H. m), 2.29-2.39(1 H, m), 2.43(3 H, s), 2.73-2.81(2 H, m), 2.95(3 H, s), 3.28(2 H, s), 3.29-3.34(2 H, m), 3.55(2 H, dt, J = 2.4 and 11.6 Hz), 3.83-3.97(1 H, m), 4.10-4.18(2 H, m), 4.36-4.47(1 H, m), 5.73-5.81(1 H, m), 7.33(1 H, s) | 460 |
| 420 | 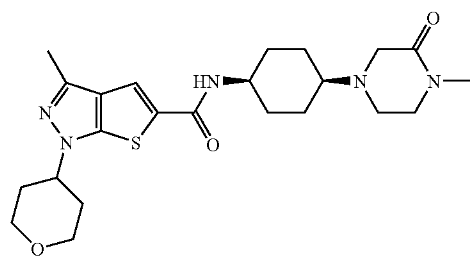 | colorless solid 181-182 | CDCl₃ 1.67-1.89(8 H, m), 2.09-2.25(4 H, m), 2.28-2.35(1 H, m), 2.45(3 H, s), 2.74-2.28(2 H, m), 2.98(3 H, s), 3.25(2 H, s), 3.30-3.39(2 H, m), 3.56(2 H, dt, J = 2.3 and 11.6 Hz), 4.09-4.21(3 H, m), 4.37-4.47(1 H, m), 5.88-5.94(1 H, m), 7.33(1 H, s) | 460 |

TABLE 134

| Example No. | Chemical Structure | propeties m.p. (° C.) (recryst. solvent) | ¹H-NMR | MS (FAB) (M + 1)⁺ |
|---|---|---|---|---|
| 421 | 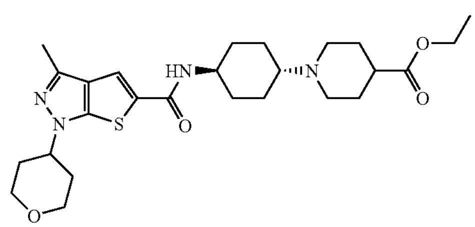 | colorless solid 206-208.5 | CDCl₃ 1.19-1.31(2 H, m), 1.25(3 H, t, J = 7.1 Hz), 1.39-1.51(2 H, m), 1.68-1.80(2 H, m), 1.88-1.98(4 H, m), 2.08-2.39(10 H, m), 2.43(3 H, s), 2.83-2.92(2 H, m), 3.55(2 H, dt, J = 2.4 and 11.7 Hz), 3.81-3.93(1 H, m), 4.09-4.18(4 H, m), 4.36-4.46(1 H, m), 5.67-5.73(1 H, m), 7.31(1 H, s) | 503 |
| 422 | 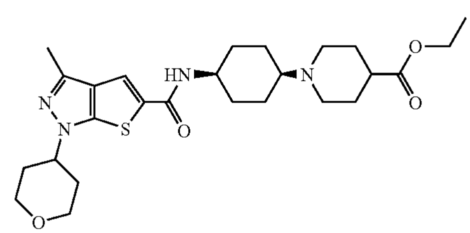 | colorless foam | CDCl₃ 1.26(3 H, t, J = 7.1 Hz), 1.54-4.81(8 H, m), 1.84-1.99(4 H, m), 2.05-2.34(8 H, m), 2.45(3 H, s), 2.99-3.08(2 H, m), 3.56(2 H, dt, J = 2.4 and 11.7 Hz), 4.10-4.24(5 H, m), 4.38-4.48(1 H, m), 5.95-6.01(1 H, m), 7.33(1 H, s) | 503 |

TABLE 134-continued

| Example No. | Chemical Structure | propeties m.p. (° C.) (recryst. solvent) | ¹H-NMR | MS (FAB) (M + 1)⁺ |
|---|---|---|---|---|
| 423 | 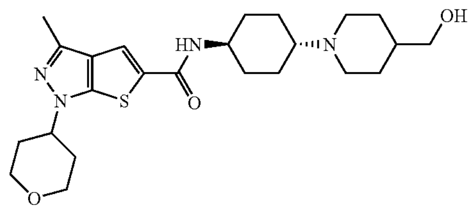 | colorless solid 201-202 | CDCl₃ 1.19-1.31(4 H, m), 1.33-1.57(4 H, m), 1.72-1.81(2 H, m), 1.90-1.99(2 H. m), 2.09-2.28(8 H, m), 2.30-2.39(1 H, m), 2.43(3 H, s), 2.88-2.98(2 H, m), 3.50(2 H, d, J = 6.4 Hz), 3.55(2 H, dt, J = 2.3 and 11.6 Hz), 3.81-3.94(1 H, m), 4.09-4.17(2 H, m), 4.37-4.48(1 H, m), 5.67-5.74(1 H, m), 7.31(1 H, s) | 461 |
| 424 | 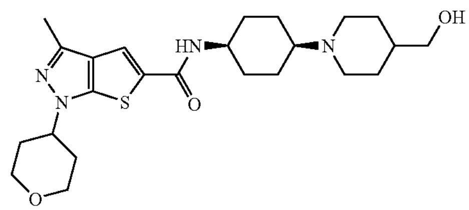 | colorless solid 119-122 | CDCl₃ 1.21-1.33(2 H, m), 1.40-1.71(6 H, m), 1.75-1.85(4 H, m), 1.87-1.97(2 H, m), 2.00-2.28(7 H, m), 2.45(3 H, s), 3.05-3.13(2 H, m), 3.48-3.60(4 H, m), 4.09-4.17(2 H, m), 4.19-4.27(1 H, m), 4.36-4.48(1 H, m), 5.99-6.07(1 H, m), 7.33(1 H, s) | 461 |

TABLE 135

| Example No. | Chemical Structure | propeties m.p. (° C.) (recryst. solvent) | ¹H-NMR | MS (FAB) (M + 1)⁺ |
|---|---|---|---|---|
| 425 | 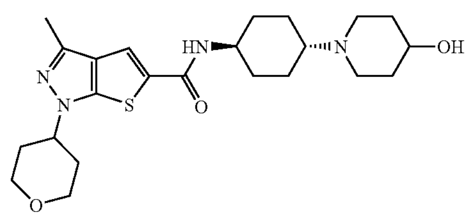 | colorless solid 211-213.5 | CDCl₃ 1.19-1.31(2 H, m), 1.39-1.69(5 H, m), 1.89-1.98(4 H, m), 2.08-2.25(6 H. m), 2.30-2.40(3 H, m), 2.43(3 H, s), 2.78-2.88(2 H, m), 3.55(2 H, dt, J = 2.4 and 11.7 Hz), 3.62-3.75(1 H, m), 3.82-3.93(1 H, m), 4.09-4.17(2 H, m), 4.37-4.47(1 H, m). 5.69-5.76(1 H, m), 7.31(1 H, s) | 447 |
| 426 | 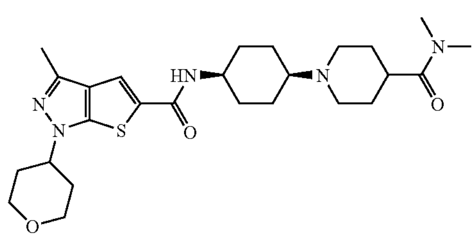 | colorless solid 234.5-237 (EtOH) | CDCl₃ 1.62-1.78(8 H, m), 1.79-1.91(4 H, m), 1.98-2.07(2 H, m), 2.09-2.26(5 H, m), 2.46(3 H, s), 2.47-2.55(1 H, m), 2.95(3 H, s), 3.06(3 H, s), 3.10-3.18(2 H, m), 3.56(2 H, dt, J = 2.4 and 11.7 Hz), 4.09-4.21(3 H, m), 4.38-4.46(1 H, m), 5.98-6.06(1 H, m), 7.36(1 H, s) | 502 |
| 427 | 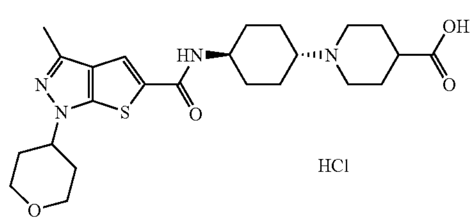 | colorless solid 211-218 | DMSO-d₆ 1.32-1.49(2 H, m), 1.53-1.69(2 H, m), 1.88-2.21(12 H, m), 2.36(3 H, s), 2.49-2.61(1 H, m), 2.89-3.06(2 H, m), 3.11-3.22(1 H, m), 3.30-3.54(4 H, m), 3.64-3.77(1 H, m), 3.91-4.00(2 H, m), 4.40-4.52(1 H, m), 7.87(1 H, s), 8.40-8.49(1 H, m), 10.50-10.74(1 H, m). | 475 (free) |

TABLE 135-continued

| Example No. | Chemical Structure | propeties m.p. (° C.) (recryst. solvent | ¹H-NMR | MS (FAB) (M + 1)⁺ |
|---|---|---|---|---|
| 428 | 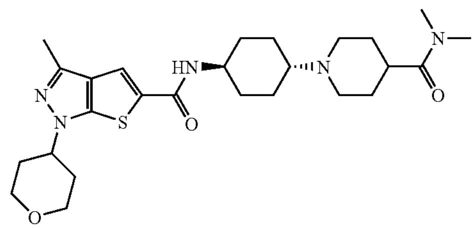 | colorless solid 233.5-234.5 (AcOEt/ EtOH) | CDCl₃ 1.19-1.31(2 H, m), 1.39-1.52(2 H, m), 1.68-1.98(6 H, m), 2.07-2.51(10 H. m), 2.43(3 H, s), 2.90-2.99(2 H, m), 2.94(3 H, s), 3.05(3 H, s), 3.55(2 H, dt, J = 2.3 and 11.6 Hz), 3.81-3.94(1 H, m), 4.09-4.18(2 H, m), 4.35-4.47(1 H, m), 5.71-5.79(1 H, m), 7.32(1 H, s) | 502 |

TABLE 136

| Example No. | Chemical Structure | propeties m.p. (° C.) (recryst. solvent | ¹H-NMR | MS(FAB) (M + 1)⁺ |
|---|---|---|---|---|
| 429 | 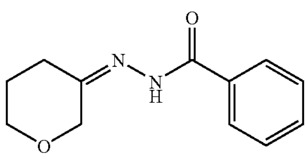 | pale reddish brown viscous solid | CDCl₃ 1.89-2.02(2 H, m), 2.49-2.61(2 H, m), 2.76-2.88(2 H, m), 4.21-4.40(2 H. m), 7.40-7.59(3 H, m), 7.71-7.90(2 H, m), 8.70-8.91(1 H, m) | 219 |
| 430 | 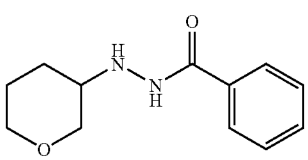 | colorless solid 127-130.5 | CDCl₃ 1.49-1.65(2 H, m), 1.76-1.88(1 H, m), 1.92-2.03(1 H, m), 3.05-3.13(1 H. m), 3.39-3.46(1 H, m), 3.49-3.58(1 H, m), 3.72-3.80(1 H, m), 3.87-3.95(1 H, m), 7.41-7.49(2 H, m), 7.50-7.59(1 H, m), 7.63(1 H, brs), 7.71-7.80(2 H, m) | 221 |
| 431 | 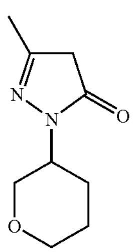 | pale brown solid 170-181 | CDCl₃ 1.71-1.81(2 H, m), 1.91-2.01(2 H, m), 2.09(3 H, s), 3.20(2 H. s), 3.33-3.42(1 H, m), 3.56(1 H, t, J = 10.7 Hz), 3.84-3.94(2 H, m), 4.15-4.25(1 H, m) | 183 |
| 432 | 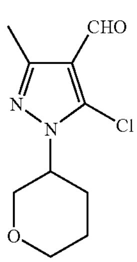 | colorless solid 124-129 | CDCl₃ 1.80-1.90(2 H, m), 2.07-2.15(1 H, m), 2.19-2.30(1 H, m), 2.45(3 H, s), 3.41-3.51(1 H, m), 3.72(1 H, t, J = 10.7 Hz), 3.94-4.01(2 H, m), 4.39-4.49(1 H, m), 9.89(1 H, s) | 229 |

TABLE 137

| Example No. | Chemical Structure | propeties m.p. (° C.) (recryst. solvent) | ¹H-NMR | MS (FAB) (M + 1)⁺ |
|---|---|---|---|---|
| 433 | 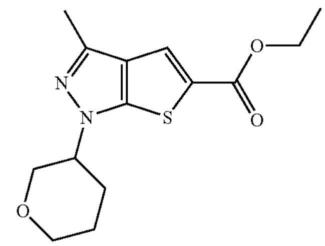 | pale yellow oil | CDCl₃ 1.38(3 H, t, J = 7.1 Hz), 1.72-1.90(2 H, m), 2.18-2.31(2 H, m), 2.45(3 H, s), 3.60(1 H, ddd, J = 3.4 and 9.6 and 11.5 Hz), 3.82(1 H, dd, J = 8.7 and 11.3 Hz), 3.89-3.96(1 H, m), 4.11-4.18(1 H, m), 4.32-4.40(3 H, m), 7.69(1 H, s) | 295 |
| 434 | 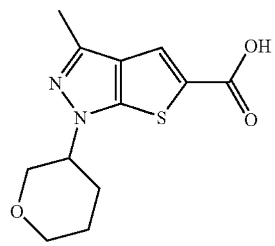 | colorless solid 174-176 | DMSO-d₆ 1.59-1.78(2 H, m), 2.05-2.22(2 H, m), 2.38(3 H, s), 3.49-3.58(1 H, m), 3.70-3.81(2 H, m), 4.00(1 H, dd, J = 3.4 and 11.4 Hz), 4.32-4.40(1 H, m), 7.76(1 H, s), 13.10(1 H, brs) | 267 |
| 435 | 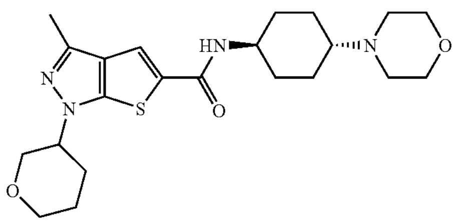 | colorless solid 211.5-212.5 (EtOH) | CDCl₃ 1.20-1.31(2 H, m), 1.36-1.49(2 H, m), 1.70-1.90(2 H, m), 1.93-2.02(2 H, m), 2.13-2.31(5 H, m), 2.43(3 H, s), 2.53-2.61(4 H, m), 3.54-3.63(1 H, m), 3.69-3.75(4 H, m), 3.81(1 H, dd, J = 8.7 and 11.3 Hz), 3.84-3.95(2 H, m), 4.10-4.16(1 H, m), 4.31-4.40(1 H, m), 5.69-5.76(1 H, m), 7.31(1 H, s) | 433 |
| 436 | 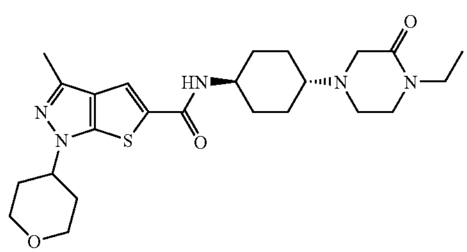 | colorless solid 223-225 (EtOH) | CDCl₃ 1.14(3 H, t, J = 7.2 Hz), 1.20-1.33(2 H, m), 1.35-1.49(2 H, m), 1.92-2.02(2 H, m), 2.08-2.38(7 H. m), 2.43(3 H, s), 2.72-2.81(2 H, m), 3.27(2 H, s), 3.29-3.36(2 H, m), 3.43(2 H, q, J = 7.2 Hz), 3.55(2 H, dt, J = 2.4 and 11.6 Hz), 3.83-3.97(1 H, m), 4.09-4.20(2 H, m), 4.37-4.48(1 H, m), 5.76-5.83(1 H, m), 7.33(1 H, s) | 474 |

TABLE 138

| Example No. | Chemical Structure | propeties m.p. (° C.) (recryst. solvent) | ¹H-NMR | MS (FAB) (M + 1)⁺ |
|---|---|---|---|---|
| 437 | 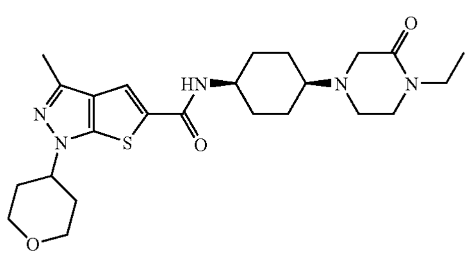 | colorless solid 187-190 | CDCl₃ 1.16(3 H, t, J = 7.2 Hz), 1.65-1.90(8 H, m), 2.08-2.35(5 H, m), 2.45(3 H, s), 2.72-2.83(2 H, m), 3.24(2 H, s), 3.30-3.39(2 H, m), 3.45(2 H, q, J = 7.2 Hz), 3.56(2 H, dt, J = 2.5 and 11.6 Hz), 4.08-4.21(3 H, m), 4.37-4.47(1 H, m), 5.37-5.94(1 H, m), 7.33(1 H, s) | 474 |

TABLE 138-continued

| Example No. | Chemical Structure | propeties m.p. (° C.) (recryst. solvent) | 1H-NMR | MS (FAB) (M + 1)+ |
|---|---|---|---|---|
| 438 | 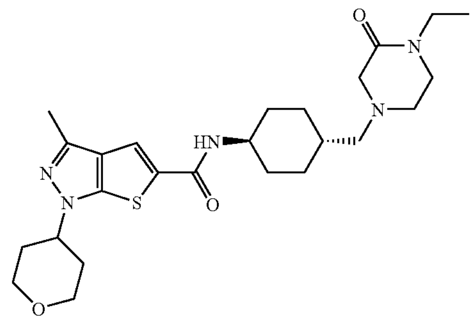 | colorless solid 180-186 | CDCl3 1.01-1.29(4 H, m), 1.14(3 H, t, J = 7.2 Hz), 1.40-1.53(1 H, m), 1.86-1.94(2 H, m), 2.07-2.27(8 H, m), 2.43(3 H, s), 2.62-2.69(2 H, m), 3.08(2 H, s), 3.29-3.33(2 H, m), 3.43(2 H, q, J = 7.2 Hz), 3.55(2 H, dt, J = 2.4 and 11.6 Hz), 3.82-3.98(1 H, m), 4.09-4.18(2 H, m), 4.36-4.47(1 H, m), 5.75-5.81(1 H, m), 7.33(1 H, s) | 488 |
| 439 | 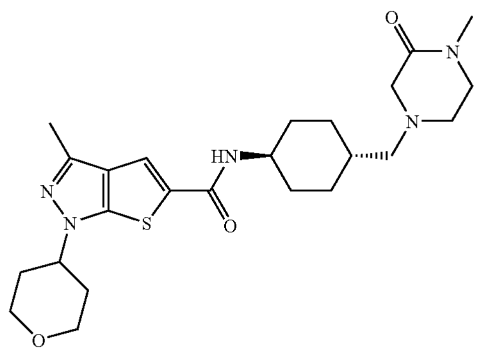 | colorless solid 194-197 | CDCl3 1.01-1.30(4 H, m), 1.40-1.54(1 H, m), 1.83-1.95(2 H,m), 2.07-2.29(8 H, m), 2.44(3 H, s), 2.51-2.60(2 H, m), 2.96(3 H, s), 3.09(2 H, s), 3.29-3.38(2 H, m), 3.55(2 H, dt, J = 2.3 and 11.6 Hz), 3.84-3.98(1 H, m), 4.09-4.19(2 H, m), 4.36-4.48(1 H, m), 5.78-5.86(1 H, m), 7.33(1 H, s) | 474 |
| 440 | 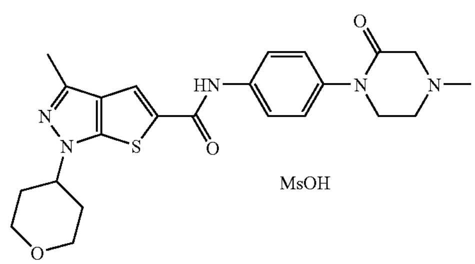 | pale yellow solid 255 (dec.) (iso-PrOH) | DMSO-d6 1.90-2.08(4 H, m), 2.30(3 H, s), 2.42(3 H, s), 2.93(3 H, brs), 3.51(2 H, dt, J = 2.3 and 11.7 Hz), 3.50-4.07(8 H, m), 4.47-4.57(1 H, m), 7.31-7.36(2 H, m), 7.76-7.81(2 H, m), 8.10(1 H, s), 10.36(1 H, brs) | 454 |

INDUSTRIAL APPLICABILITY

The present invention provides thienopyrazole derivatives having selective PDE 7 (phosphodiesterase VII) inhibiting effect. These compounds are effective compounds for treating various kinds of diseases such as allergic diseases, inflammatory diseases and immunologic diseases.

The invention claimed is:
1. Thienopyrazole compounds represented by the following formula (I):

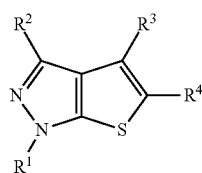

wherein
R$^1$ is a substituted or unsubstituted C$_3$-C$_8$ alkyl group, substituted, or unsubstituted cycloalkyl group or substituted or unsubstituted heterocycloalkyl group;
R$^2$ is a hydrogen atom or substituted or unsubstituted C$_1$-C$_3$ alkyl group;
R$^3$ is a hydrogen atom, substituted or unsubstituted C$_1$-C$_3$ alkyl group, or a halogen atom;
R$^4$ is a substituted or unsubstituted aryl group, substituted or unsubstituted heteroaryl group, or a group —CONR$^5$R$^6$ or —CO$_2$R$^7$;
R$^5$ and R$^6$ are, same or different from each other, a hydrogen atom; C$_1$-C$_6$ alkyl group which may be substituted by a halogen atom, substituted or unsubstituted aryl group, substituted or unsubstituted heteroaryl group, substituted or unsubstituted heterocycloalkyl group, substituted or unsubstituted cycloalkyl group, a group —NR$^7$COR$^8$, —COR$^8$, —NR$^9$R$^{10}$; substituted or unsubstituted cycloalkyl group; substituted or unsubstituted heterocycloalkyl group; substituted or unsubstituted aryl group; substituted or unsubstituted heteroaryl group; or substituted or unsubstituted heterocycloalkyl group in which the ring is formed together with the nitrogen atom binding $R^5$ and $R^6$;

$R^7$ is a hydrogen atom, or substituted or unsubstituted $C_1$-$C_3$ alkyl group;

$R^8$ is a substituted or unsubstituted heterocycloalkyl group, or a group —OH, —$OR^7$ or —$NR^9R^{10}$;

$R^9$ and $R^{10}$ are, same or different from each other, a hydrogen atom, substituted or unsubstituted $C_1$-$C_3$ alkyl group, substituted or unsubstituted heterocycloalkyl group; substituted or unsubstituted acyl group; a group —$SO_2R^7$, or substituted or unsubstituted heterocycloalkyl group in which the ring is formed together with the nitrogen atom binding $R^5$ and $R^6$ or pharmaceutically acceptable salts or solvates thereof.

2. The compound according to claim 1, wherein $R^1$ is a substituted or unsubstituted cycloalkyl group.

3. The compound according to claim 1, wherein $R^1$ is a substituted or unsubstituted heterocycloalkyl group.

4. The compound according to claim 1, wherein $R^1$ is a substituted or unsubstituted cyclohexyl group.

5. The compound according to claim 1, wherein $R^1$ is a substituted or unsubstituted tetrahydropyranyl group.

6. The compound according to claim 1, wherein $R^2$ is a methyl group.

7. The compound according to claim 1, wherein $R^3$ is a hydrogen atom.

8. The compound according to claim 1, wherein $R^4$ is —$CONR^5R^6$.

9. The compound according to claim 8, wherein any one of $R^5$ and $R^6$ is a hydrogen atom.

10. The compound according to claim 8, wherein any one of $R^5$ and $R^6$ is a substituted or unsubstituted cycloalkyl group.

11. The compound according to claim 8, wherein any one of $R^5$ and $R^6$ is a cycloalkyl group which is substituted by a heterocycloalkyl group which may be substituted.

12. The compound according to claim 8, wherein any one of $R^5$ and $R^6$ is an aryl group which may be substituted.

13. The compound according to claim 8, wherein any one of $R^5$ and $R^6$ is an aryl group which is substituted by a heterocycloalkyl group which may be substituted.

14. The compound according to claim 8, wherein any one of $R^5$ and $R^6$ is a substituted or unsubstituted heteroaryl group.

15. A pharmaceutical composition containing a compound according to claim 1, or a pharmaceutical acceptable salt thereof, as an active ingredient and a pharmaceutically acceptable diluent or exipient.

16. A method of inhibiting PDE 7 in a subject in need thereof comprising administering a compound according to claim 1, or a pharmaceutical acceptable salt thereof, to the subject to inhibit PDE 7.

17. A method for preparing the thienopyrazole compounds represented by the formula (I):

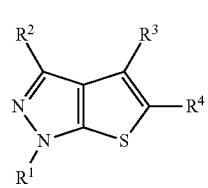

(I)

wherein
$R^1$ is a substituted or unsubstituted $C_3$-$C_8$ alkyl group substituted or unsubstituted cycloalkyl group or substituted or unsubstituted heterocycloalkyl group;

$R^2$ is a hydrogen atom or substituted or unsubstituted $C_1$-$C_3$ alkyl group;

$R^3$ is a hydrogen atom, substituted or unsubstituted $C_1$-$C_3$ alkyl group, or a halogen atom, $R^4$ is a substituted or unsubstituted aryl group, substituted or unsubstituted heteroaryl group, or a group —$CONR^5R^6$ or —$CO_2R^7$;

comprising chlorinating the pyrazole-5-one derivative represented by the formula (VI):

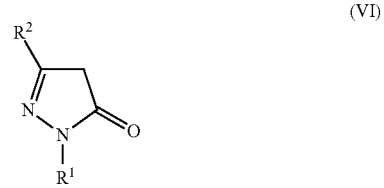

(VI)

wherein
$R^1$ is substituted or unsubstituted $C_3$-$C_8$ alkyl group, substituted or unsubstituted cycloalkyl group or substituted or unsubstituted heterocycloalkyl group;

$R^2$ is a hydrogen atom or substituted or unsubstituted $C_1$-$C_3$ alkyl group; and then, undergoing an electrophilic substitution reaction of the resulting compound without separation to give the pyrazole derivative of the formula (IV):

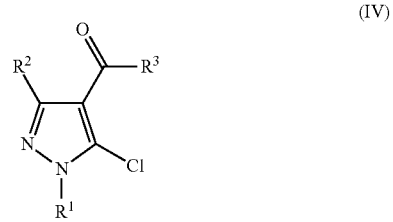

(IV)

wherein
$R^1$ is a substituted or unsubstituted $C_3$-$C_8$ alkyl group, substituted or unsubstituted cycloalkyl group or substituted or unsubstituted heterocycloalkyl group, $R^2$ is a hydrogen atom or substituted or unsubstituted $C_1$-$C_3$ alkyl group;

$R^3$ is a hydrogen atom, substituted or unsubstituted $C_1$-$C_3$ alkyl group, or a halogen atom;

then, reacting the resulting pyrazole derivative of formula (IV) with the compound of the formula (III) in the presence of base:

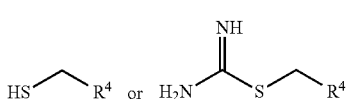

(III)

wherein
$R^4$ is a substituted or unsubstituted aryl group, substituted or unsubstituted heteroaryl group or a group —$CONR^5R^6$ or —$CO_2R^7$, to give the compound of the formula (II):

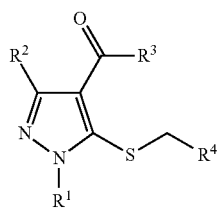

wherein
R¹ is a substituted or unsubstituted $C_3$-$C_8$ alkyl group, substituted or unsubstituted cycloalkyl group or substituted or unsubstituted heterocycloalkyl group;
R² is a hydrogen atom or substituted or unsubstituted $C_1$-$C_3$ alkyl group;
R³ is a hydrogen atom, substituted or unsubstituted $C_1$-$C_3$ alkyl group, or a halogen atom;
R⁴ is a substituted or unsubstituted aryl group, substituted or unsubstituted heteroaryl group, or a group —CONR⁵R⁶ or —CO₂R⁷;
and then, treating the resulting compound of formula (II) with base to give the thienopyrazole compound of the formula (I).

18. A method for preparing the thienopyrazole compounds represented by the formula (I):

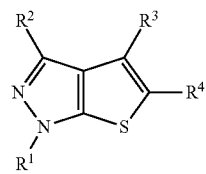

wherein
R¹ is a substituted or unsubstituted $C_3$-$C_8$ alkyl group, substituted or unsubstituted cycloalkyl group or substituted or unsubstituted heterocycloalkyl group;
R² is a hydrogen atom or substituted or unsubstituted $C_1$-$C_3$ alkyl group;
R³ is a hydrogen atom, substituted or unsubstituted $C_1$-$C_3$ alkyl group, or a halogen atom;
R⁴ is a substituted or unsubstituted aryl group, substituted or unsubstituted heteroaryl group, or a group —CONR⁵R⁶ or —CO₂R⁷;
comprising undergoing an electrophilic substitution reaction of the chloropyrazole derivative of the formula (V):

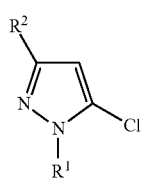

wherein
R¹ is a substituted or unsubstituted $C_3$-$C_8$ alkyl group, substituted or unsubstituted cycloalkyl group or substituted or unsubstituted heterocycloalkyl group;

R² is a hydrogen atom or substituted or unsubstituted $C_1$-$C_3$ alkyl group;
to give the pyrazole derivative of the formula (IV):

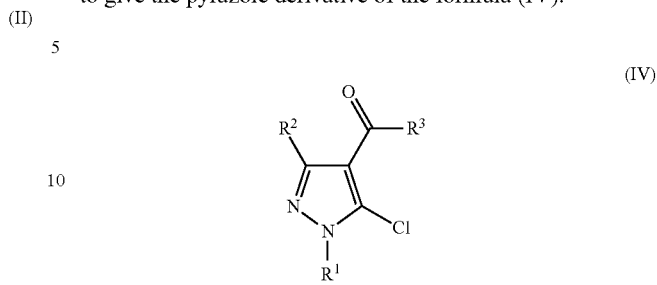

wherein
R¹ is a substituted or unsubstituted $C_3$-$C_8$ alkyl group substituted or unsubstituted cycloalkyl group or substituted or unsubstituted heterocycloalkyl group;
R² is a hydrogen atom or substituted or unsubstituted $C_1$-$C_3$ alkyl group;
R³ is a hydrogen atom, substituted or unsubstituted $C_1$-$C_3$ alkyl group, or a halogen atom;
then, reacting the resulting pyrazole derivative of formula (IV) with the compound of the formula (III) in the presence of base:

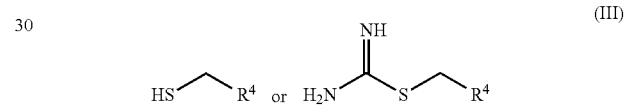

wherein
R⁴ is a substituted or unsubstituted aryl group substituted or unsubstituted heteroaryl group, or a group —CONR⁵R⁶ or —CO₂R⁷;
to give the compound of the formula (II):

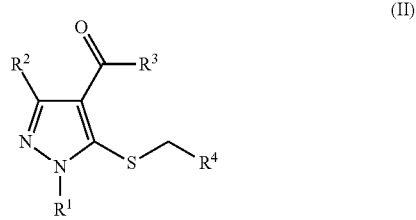

wherein
R¹ is a substituted or unsubstituted $C_3$-$C_8$ alkyl group, substituted or unsubstituted cycloalkyl group or substituted or unsubstituted heterocycloalkyl group;
R² is a hydrogen atom or substituted or unsubstituted $C_1$-$C_3$ alkyl group;
R³ is a hydrogen atom, substituted or unsubstituted $C_1$-$C_3$ alkyl group, or a halogen atom;
R⁴ is a substituted or unsubstituted aryl group, substituted or unsubstituted heteroaryl group, or a group —CONR⁵R⁶ or —CO₂R⁷;
and then, treating the resulting compound of formula (II) with base to give the thienopyrazole compound of the formula (I).

19. A method for preparing the thienopyrazole compounds represented by the formula (I):

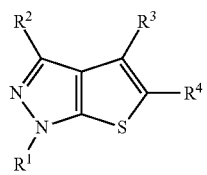

(I)

wherein
- $R^1$ is a substituted or unsubstituted $C_3$-$C_8$ alkyl group, substituted or unsubstituted cycloalkyl group or substituted or unsubstituted heterocycloalkyl group;
- $R^2$ is a hydrogen atom or substituted or unsubstituted $C_1$-$C_3$ alkyl group;
- $R^3$ is a hydrogen atom substituted or unsubstituted $C_1$-$C_3$ alkyl group, or a halogen atom;
- $R^4$ is a substituted or unsubstituted aryl group, substituted or unsubstituted heteroaryl group, or a group —$CONR^5R^6$ or —$CO_2R^7$;

comprising reacting the pyrazole derivative of formula (IV):

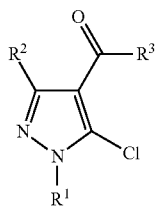

(IV)

wherein
- $R^1$ is a substituted or unsubstituted $C_3$-$C_8$ alkyl group, substituted or unsubstituted cycloalkyl group or substituted or unsubstituted heterocycloalkyl group;
- $R^2$ is a hydrogen atom or substituted or unsubstituted $C_1$-$C_3$ alkyl group;
- $R^3$ is a hydrogen atom, substituted or unsubstituted $C_1$-$C_3$ alkyl group, or a halogen atom;

with the compound of the formula (III) in the presence of base:

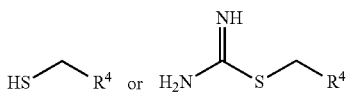

(III)

wherein
- $R^4$ is a substituted or unsubstituted aryl group, substituted or unsubstituted heteroaryl group, or a group —$CONR^5R^6$ or —$CO_2R^7$;

to give the compound of the formula (II):

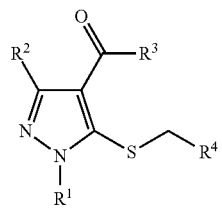

(II)

wherein
- $R^1$ is a substituted or unsubstituted $C_3$-$C_8$ alkyl group, substituted or unsubstituted cycloalkyl group or substituted or unsubstituted heterocycloalkyl group;
- $R^2$ is a hydrogen atom or substituted or unsubstituted $C_1$-$C_3$ alkyl group;
- $R^3$ is a hydrogen atom, substituted or unsubstituted $C_1$-$C_3$ alkyl group, or a halogen atom;
- $R^4$ is a substituted or unsubstituted aryl group, substituted or unsubstituted heteroaryl group, or a group —$CONR^5R^6$ or —$CO_2R^7$;

and then, treating the resulting compound of formula (II) with base to give the thienopyrazole compound of the formula (I).

20. The method for preparing thienopyrazole compound according to claim 19, wherein the conversion of the compound of formula (IV) to the compound of formula (I) is carried out in one pot synthesis without separation of the compound of the formula (II).

21. The method according to claim 17, wherein the group $R^3$ is a hydrogen atom.

* * * * *